US008949032B2

(12) United States Patent
Famili et al.

(10) Patent No.: US 8,949,032 B2
(45) Date of Patent: *Feb. 3, 2015

(54) MULTICELLULAR METABOLIC MODELS AND METHODS

(75) Inventors: Imandokht Famili, San Diego, CA (US); Christophe H. Schilling, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 1532 days.

This patent is subject to a terminal disclaimer.

(21) Appl. No.: 11/188,136

(22) Filed: Jul. 21, 2005

(65) Prior Publication Data

US 2006/0147899 A1   Jul. 6, 2006

Related U.S. Application Data

(63) Continuation-in-part of application No. 10/402,854, filed on Mar. 27, 2003, now Pat. No. 8,229,673.

(60) Provisional application No. 60/368,588, filed on Mar. 29, 2002.

(51) Int. Cl.
| | |
|---|---|
| *G01N 33/50* | (2006.01) |
| *G06F 19/12* | (2011.01) |
| *G06F 19/18* | (2011.01) |
| *G06F 19/28* | (2011.01) |

(52) U.S. Cl.
CPC .............. *G06F 19/12* (2013.01); *G06F 19/18* (2013.01); *G06F 19/28* (2013.01)
USPC .......................................................... 702/19

(58) Field of Classification Search
None
See application file for complete search history.

(56) References Cited

U.S. PATENT DOCUMENTS

| | | |
|---|---|---|
| 5,273,038 A | 12/1993 | Beavin et al. |
| 5,556,762 A | 9/1996 | Pinilla |
| 5,639,949 A | 6/1997 | Ligon et al. |

(Continued)

FOREIGN PATENT DOCUMENTS

| | | |
|---|---|---|
| JP | 2000-163398 | 6/2000 |
| WO | PCT/US91/08694 | 6/1992 |

(Continued)

OTHER PUBLICATIONS

Adamowicz et al., "Nutritional complementation of oxidative glucose metabolism in *Escherichia coli* via pyrroloquinoline quinone-dependent glucose dehydrogenase and the Entner-Doudoroff pathway," *Appl. Environ. Microbiol.* 57(7):2012-2015 (1991).

(Continued)

*Primary Examiner* — Jason Sims
(74) *Attorney, Agent, or Firm* — Jones Day

(57) ABSTRACT

The invention provides a computer readable medium or media, having: (a) a first data structure relating a plurality of reactants to a plurality of reactions from a first cell, each of said reactions comprising a reactant identified as a substrate of the reaction, a reactant identified as a product of the reaction and a stoichiometric coefficient relating said substrate and said product; (b) a second data structure relating a plurality of reactants to a plurality of reactions from a second cell, each of said reactions comprising a reactant identified as a substrate of the reaction, a reactant identified as a product of the reaction and a stoichiometric coefficient relating said substrate and said product; (c) a third data structure relating a plurality of intra-system reactants to a plurality of intra-system reactions between said first and second cells, each of said intra-system reactions comprising a reactant identified as a substrate of the reaction, a reactant identified as a product of the reaction and a stoichiometric coefficient relating said substrate and said product; (d) a constraint set for said plurality of reactions for said first, second and third data structures, and (e) commands for determining at least one flux distribution that minimizes or maximizes an objective function when said constraint set is applied to said first and second data structures, wherein said at least one flux distribution is predictive of a physiological function of said first and second cells. The first, second and third data structures also can include a plurality of data structures. Additionally provided is a method for predicting a physiological function of a multicellular organism. The method includes: (a) providing a first data structure relating a plurality of reactants to a plurality of reactions from a first cell, each of said reactions comprising a reactant identified as a substrate of the reaction, a reactant identified as a product of the reaction and a stoichiometric coefficient relating said substrate and said product; (b) providing a second data structure relating a plurality of reactants to a plurality of reactions from a second cell, each of said reactions comprising a reactant identified as a substrate of the reaction, a reactant identified as a product of the reaction and a stoichiometric coefficient relating said substrate and said product; (c) providing a third data structure relating a plurality of intra-system reactants to a plurality of intra-system reactions between said first and second cells, each of said intra-system reactions comprising a reactant identified as a substrate of the reaction, a reactant identified as a product of the reaction and a stoichiometric coefficient relating said substrate and said product; (d) providing a constraint set for said plurality of reactions for said first, second and third data structures; (e) providing an objective function, and (f) determining at least one flux distribution that minimizes or maximizes an objective function when said constraint set is applied to said first and second data structures, wherein said at least one flux distribution is predictive of a physiological function of said first and second cells.

47 Claims, 158 Drawing Sheets

(56) References Cited

U.S. PATENT DOCUMENTS

| | | | |
|---|---|---|---|
| 5,689,633 | A | 11/1997 | Cotner et al. |
| 5,914,891 | A | 6/1999 | Arkin et al. |
| 5,930,154 | A | 7/1999 | Thalhammer et al. |
| 5,947,899 | A | 9/1999 | Scollan et al. |
| 5,980,096 | A | 11/1999 | Thalhammer-Reyero |
| 6,132,969 | A | 10/2000 | Stoughton et al. |
| 6,165,709 | A | 12/2000 | Friend et al. |
| 6,200,803 | B1 | 3/2001 | Roberts |
| 6,221,597 | B1 | 4/2001 | Roberts |
| 6,302,302 | B1 | 10/2001 | Albisetti |
| 6,326,140 | B1 | 12/2001 | Rine et al. |
| 6,329,139 | B1 | 12/2001 | Nova et al. |
| 6,351,712 | B1 | 2/2002 | Stoughton et al. |
| 6,370,478 | B1 | 4/2002 | Stoughton et al. |
| 6,379,964 | B1 | 4/2002 | Del Cardayre |
| 6,983,227 | B1 * | 1/2006 | Thalhammer-Reyero ........ 703/2 |
| 7,127,379 | B2 | 10/2006 | Palsson et al. |
| 2002/0012939 | A1 * | 1/2002 | Palsson .............................. 435/6 |
| 2002/0168654 | A1 | 11/2002 | Maranas et al. |
| 2003/0059792 | A1 * | 3/2003 | Palsson et al. .................... 435/6 |
| 2003/0113761 | A1 | 6/2003 | Tan et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2006/0147899 | A1 | 7/2006 | Famili et al. |
| 2007/0111294 | A1 | 5/2007 | Burgard et al. |
| 2008/0176327 | A1 | 7/2008 | Palsson et al. |

FOREIGN PATENT DOCUMENTS

| | | |
|---|---|---|
| WO | WO 92/09300 | 6/1992 |
| WO | 96/22575 | 7/1996 |
| WO | WO 00/46405 | 8/2000 |
| WO | WO 01/36658 | 5/2001 |
| WO | WO 01/57775 | 8/2001 |
| WO | WO 01/57775 A2 | 8/2001 |
| WO | WO 02/055995 | 7/2002 |
| WO | WO 02/061115 | 8/2002 |
| WO | WO 03/082214 | 10/2003 |
| WO | WO 03/106998 | 12/2003 |

OTHER PUBLICATIONS

Akutsu, "Estimation Algorithm of Genetic Network," Mathmatical Science (Suri-Kagaku) Science 37(6):40-46 (1999). (Original and Translation submitted herewith).
Alberty, "Calculation of Biochemical Net Reactions and Pathways by Using Matrix Operations," Biophys. J. 71(1):507-515 (1996).
Alm et al., "Genomic-sequence comparison of two unrelated isolates of the human gastric pathogen Helicobacter pylori," Nature 397(6715):176-80 (1999).
Alon et al., "Broad patterns of gene expression revealed by clustering analysis of tumor and normal colon tissues probed by oligonucleotide arrays," Proc. Natl. Acad. Sci. USA 96(12):6745-6750 (1990).
Alter et al., "Singular value decomposition for genome-wide expression data processing and modeling," Proc. Natl. Acad. Sci. USA 97(18):10101-10106 (2000).
Altschul et al., "Gapped BLAST and PSI-BLAST: A New Generation of Protein Database Search Programs," Nucleic Acids Res. 25(17):3389-3402 (1997).
Alves et al., "Systemic properties of ensembles of metabolic networks: application of graphical and statistical methods to simple unbranched pathways," Bioinformatics 16(6):534-547 (2000).
Andre, "An overview of membrane transport proteins in Saccharomyces cerevisiae," Yeast 11(16):1575-1611 (1995).
Anonymous, "The yeast genome directory" Nature 387(6632 Suppl):5 (1997).
Appel et al., "A new generation of information retrieval tools for biologists: the example of the ExPASy WWW server," Trends Biochem. Sci. 19(6):258-260 (1994).

Arigoni et al., "A Genome-Based Approach for the Identification of Essential Bacterial Genes," Nature Biotechnol. 16(9):851-856 (1998).
Aristidou and Penttila, "Metabolic engineering applications to renewable resource utilization," Curr. Opin. Biotechnol. 11(2)187-198 (2000).
Attanoos et al., "Ileostomy polyps, adenomas, and adenocarcinomas," Gut., 37(6):840-844 (1995).
Baba et al., "Construction of Escherichia coli K-12 in-frame, single-gene knockout mutants: the Keio collection," Mol. Syst. Biol. 2:2006-2008 (2006).
Bailey and Elkan, "Fitting a mixture model by expectation maximization to discover motifs in biopolymers," Proc. Int. Conf. Intell. Syst. Mol. Biol. 2:28-36 (1994).
Bailey and Gribskov, "Combining evidence using p-values: application to sequence homology searches," Bioinformatics 14(1):48-54 (1998).
Bailey, "Complex Biology With No Parameters," Nat. Biotechnol. 19(6):503-504 (2001).
Bairoch and Apweiler, "The SWISS-PROT Protein Sequence database and its supplement TrEMBL in 2000," Nucleic Acids Res. 28(1):45-48 (2000).
Ball, et al., "Integrating functional genomic information into the Saccharomyces genome database," Nucleic Acids Res. 28(1):77-80 (2000).
Baltz et al., "DNA Sequence Sampling of the Streptococcus Pneumonia Genome to Identify Novel Targets for Antibiotic Development," Microbial. Drug Resist, 4(1):1-9 (1998).
Ban et al., "Thymine and uracil catabolism in Escherichia coli," J. Gen. Microbiol. 73(2):267-272 (1972).
Bansal, "Integrating co-regulated gene-groups and pair-wise genome comparisons to automate reconstruction of microbial pathways," Bioinformatics and Bioengineering Conference 209-216 (2001).
Bard et al., "Sterol mutants of Saccharomyces cerevisiae: chromatographic analyses," Lipids 12(8):645-654 (1977).
Baxevanis, "The Molecular Biology Database Collection: 2002 update," Nucleic Acids Res. 30:1-12 (2002).
Beard et al., "Energy Balance for Analysis of Complex Metabolic Networks," Biophys. J. 83(1):79-86 (2002).
Beckers et al., "Large-Scale Mutational Analysis for the Annotation of the Mouse Genome," Curr. Opin. Chem. Biol. 6(1)17-23 (2002).
Bell et al., "Composition and functional analysis of the Saccharomyces cerevisiae trehalose synthase complex," J. Biol. Chem. 273(50):33311-33319 (1998).
Benjamini and Hochberg, "Controlling the False Discovery Rate: A Practical and Powerful Approach to Multiple Testing," J.R Statist. Soc. B 57:289-300 (1995).
Benson et al., "GenBank," Nucleic Acids Res. 28(1):15-18 (2000).
Berry, "Improving production of aromatic compounds in Escherichia coli by metabolic engineering," Trends Biotechnol. 14(7):250-256 (1996).
Bialy, "Living on the Edges," Nat. Biotechnol. 19(2):111-112 (2001).
Bianchi and Zanella, "Hematologically important mutations: red cell pyruvate kinase (third update)," Blood Cells Molecules Diseases 15:47-53 (2000).
Birkholz, "Fumarate reductase of Helicobacter pylori—an immunogenic protein," J. Med. Microbiol. 41(1):56-62 (1994).
Birner et al., "Roles of phosphatidylethanolamine and of its several biosynthetic pathways in Saccharomyces cerevisiae," Mol. Biol. Cell. 12(4):997-1007 (2001).
Blackstock and Weir, "Proteomics: quantitative and physical mapping of cellular proteins," Trends Biotechnol. 17(3):121-127 (1999).
Blattner et al., "The Complete Genome Sequence of Escherichia coli K-12," Science 277(5331):1453-1474 (Sep. 1997).
Bochner, "New technologies to assess genotype-phenotype relationships," Nat. Rev. Genet. 4(4):309-314 (2003).
Boles et al., "A family of hexosephosphate mutases in Saccharomyces cerevisia," Eur. J. Biochem. 220(1):83-96 (1994).
Boles et al., "Characterization of a glucose-repressed pyruvate kinase (Pyk2p) in Saccharomyces cerevisiae that is catalytically insensitive to fructose-1,6-bisphosphate," J. Bacteriol. 179(9):2987-2993 (1997).

(56) References Cited

OTHER PUBLICATIONS

Boles et al., "Identification and characterization of MAE 1, the *Saccharomyces cerevisiae* structural gene encoding mitochondrial malic enzyme," *J. Bacteriol.* 180(11):2875-2882 (1998).
Bonarius et al., "Flux Analysis of Underdetermined Metabolic Networks: The Quest for the Missing Constraints," *Trends Biotechnol.* 15(8):308-314 (1997).
Bono et al., "Reconstruction of amino acid biosynthesis pathways from the complete genome sequence," *Genome Res.* 8(3):203-210 (1998).
Bottomley et al., "Cloning, sequencing, expression, purification characterization of a type II dehydroquinase from *Helicobacter pylori*," *Biochem J* 319(Pt 2):559-565 (1996).
Bourot and Karst, "Isolation and characterization of the *Saccharomyces cerevisiae* SUT1 gene involved in sterol uptake," *Genetics* 165(1):97-102 (1995).
Burgard and Maranas, "Probing the Performance Limits of the *Escherichia coli* Metabolic Network Subject to Gene Additions or Deletions," *Biotechnol. Bioeng.* 74(5):364-375 (2001).
Burgard and Maranas, "Review of the Enzymes and Metabolic Pathways (EMP) Database," *Metab. Eng*, 3(3):193-194(2) (2001).
Burgard et al., "Minimal reaction sets for *Escherichia coli* metabolism under different growth requirements and uptake environments," *Biotechnol. Prog.* 17(5):791-797 (2001).
Burgard et al., "Optknock: a bilevel programming framework for identifying gene knockout strategies for microbial strain optimization," *Biotechnol. Bioeng.* 84(6):647-657 (2003).
Burns, "Acetyl-CoA carboxylase activity in *Helicobacter pylori* and the requirement of increased CO2 for growth," *Microbiology* 141(Pt 12):3113-3118 (1995).
Callis, "Regulation of Protein Degradation," *The Plant Cell* 7:845-857 (1995).
Carrier and Keasling, "Investigating Autocatalytic Gene Expression Systems through Mechanistic Modeling," *J. Theor. Biol.* 201(1):25-36 (1999).
Chadha et al., "Hybrid process for ethanol production from rice straw," *Acta Microbiol. Immuno.l Hung.* 42(1):53-59 (1995).
Chadha et al., "Simultaneous saccharification and fermentation of rice straw into ethanol," *Acta Microbiol. Immunol. Hung.* 42(1):71-75 (1995).
Chalker et al., "Systematic identification of selective essential genes in *Helicobacter pylori* by genome prioritization and allelic replacement mutagenesis," *J. Bacteriol.* 183(4):1259-1268 (2001).
Chartrain et al., "Metabolic engineering and directed evotion for the production of pharmaceuticals," *Curr. Opin. Biotech.* 11(2):209-214 (2000).
Chen et al., "Characterization of the respiratory chain of *Helicobacter pylori*," *FEMS Immuol. Med. Microbiol.* 24(2):169-174 (1999).
Cherry et al., "SGD: *Saccharomyces* Genome Database," *Nucleic Acids Res.* 26(1):73-79 (1998).
Christensen and Nielsen, "Metabolic network analysis. A powerful tool in metabolic engineering," *Adv. Biochem. Eng. Biotechnol.* 66:209-231 (2000).
Ciriacy and Breitenbach, "Physiological effects of seven different blocks in glycolysis in *Saccharomyces cerevisiae*," *J. Bacteriol* 139(1):152-160 (1979).
Clarke, "Stability of Complex Reaction Networks," *Adv. Chem. Phys.* 43:1-125 (1980).
Clarke, "Complete set of steady states for the general stoichiometric dynamical system," *J. Chem. Phys.* 75(10):4970-4979 (1981).
Clarke, "Stoichiometric network analysis," *Cell Biophys.* 12:237-253 (1988).
Clifton and Fraenkel, "Mutant studies of yeast phosphofructokinase.," *Biochemistry* 21(8):1935-1942 (1982).
Clifton et al., "Glycolysis mutants in *Saccharomyces cerevisiae.*," *Genetics* 88(1):1-11 (1978).
Compan et al., "Anaerobic activation of arcA transcription in *Escherichia coli*: roles of Fnr and ArcA," *Mol. Microbiol.* 11(5):955-964 (1994).

Costanzo et al., "YPD, PombePD and WormPD: model organism volumes of the BioKnowledge library, an integrated resource for protein information," *Nucleic Acids Res.* 29(1):75-9 (2001).
Cotter et al., "Aerobic regulation of cytochrome d oxidase (cydAB) operon expression in *Escherichia coli*: roles of Fnr and ArcA in repression and activation," *Mol. Microbiol.* 25(3):605-615 (1997).
Cover and Blaser, "*Helicobacter pylori* infection, a paradigm for chronic mucosal inflammation: pathogenesis and implications for eradication and prevention," *Adv. Intern. Med.* 41:85-117 (1996).
Covert and Palsson, "Constraints-based models: Regulation of Gene Expression Reduces the Steady-state Solution Space," *J. Theor. Biol.* 221:309-325 (2003).
Covert and Palsson, "Transcriptional Regulation in Constraints-based Metabolic Models of *Escherchia coli*," *J. Biol. Chem.* 277(31):28058-28064 (2002).
Cupp and McAlister-Henn, "Cloning and Characterization of the gene encoding the IDH1 subunit of NAD(+)-dependent isocitrate dehydrogenase from *Saccharomyces cerevisiae*," *J. Biol. Chem.* 267(23):16417-16423 (1992).
D'Haeseleer et al., "Genetic network inference: from co-expression clustering to reverse engineering," *Bioinformatics*, 16(8):707-726 (2000).
Dafoe et al., "In Silico Knowledge Discovery Biomedical databases," Proceedings of the SPIE Fifth Workshop on Neural Networks, San Francisco, Nov. 7-10, 1993.
Danchin, "Comparison Between the *Escherichia coli* and *Bacillus subtilis* Genomes Suggests That a Major Function of Polynucleotide Phosphorylase is to Synthesize CDP," *DNA Res.* 4(1):9-18 (Feb 1997).
Dandekar et al., "Pathway Alignment: Application to the Comparative Analysis of Glycolytic Enzymes," *Biochem. J.* 343:115-124 (1999).
Dantigny et al., "Transition rate kinetics from ethanol oxidation to glucose utilisation within a structured model of baker's yeast," *Appl. Microbiol. Biotechnol.* 36:352-357 (1991).
Datsenko and Wanner, "One-step inactivation of chromosomal genes in *Escherichia coli* K-12 using PCR products," *Proc. Natl. Acad. Sci. USA*, 97(12):6640-6645 (2000).
Daum et al., "Biochemistry, cell biology and molecular biology of lipids of *Saccharomyces cerevisiae*," *Yeast* 14(16):1471-1510 (1998).
Daum et al., "Systematic analysis of yeast strains with possible defects in lipid metabolism," *Yeast* 15(7):601-614 (1999).
de Jong, "Modeling and simulation of genetic regulatory systems: a literature review," *J. Comput. Biol.* 9(1):67-103 (2002).
De Reuse, et al., "The *Helicobacter pylori* ureC gene codes for a phosphoglucosamine mutase," *J. Bacteriol.* 179(11):3488-3493 (1997).
Delgado and Liao, "Identifying Rate-Controlling Enzymes in Metabolic Pathways without Kinetic Parameters," *Biotechnol. Prog.* 7:15-20 (1991).
Demain et al., "Cellulase, clostridia, and ethanol," *Microbio.l Mol. Biol. Rev.* 69(1):124-154 (2005).
Department of Energy, *Breaking the Biological Barriers to Cellulosic Ethanol* (2006).
DeRisi et al., "Use of cDNA microarray to analyse gene expression patters in human cancer," *Nat. Gene.* 14:457-460 (1996).
DeRisi et al.,"Exploring the Metabolic and Genetic Control of Gene Expression on a Genomic Scale," *Science* 278(5338):680-686 (1997).
Dickson "Sphingolipid functions in *Saccharomyces cerevisiae*: comparison to mammals," *Annu. Rev. Biochem.* 67:27-48 (1998).
Dickson et al., "Serine palmitoyltransferase," *Methods Enzymol.* 311:3-9 (2000).
Edwards and Palsson, "How Will Bioinformatics Influence Metabolic Engineering," *Biotechnol. Bioeng.* 58(2-3):162-169 (1998).
Edwards and Palsson, "Metabolic flux balance analysis and the in silico analysis of *Escherichia colia* K-12 gene deletions," *BMC Bioinform.* 1:1-10 (2000).
Edwards and Palsson, "Robustness analysis of the *Escherichia coli* metabolic network," *Biotechnol. Prog.* 16(6):927-939 (2000).
Edwards et al., "Characterizing the Metabolic Phenotype: A Phenotype Phase Plane Analysis," *Biotech. Bioeng.* 77(1):27-36 (2002).

(56) References Cited

OTHER PUBLICATIONS

Edwards et al., "Genomically Based Comparative Flux Balance Analysis of *Escherichia coli* and *Haemophilus Influenza*," Abstract of Papers, *Am. Chem. Soc.* 213(1-3):BIOT 50. San Francisco (Apr. 13-17, 1997).
Eisen et al., "Cluster analysis and display of genome-wide expression patterns," *Proc. Natl. Acad. Sci. USA* 95:14863-14868 (1998).
Eisenberg et al., "Protein Function in the Post-Genomic Era," *Nature* 405(6788):823-826 (2000).
Ermolaeva, et al., "Prediction of Operons in Microbial Genomes," *Nucl. Acids Res.* 29(5):1216-1221 (2001).
Everett et al., "Pendred Syndrome is Caused by Mutations in a Putative Sulphate Transporter Gene (PDS)," *Nat. Genet.* 17:411-422 (1997).
Feist and Palsson, "The growing scope of applications of genome-scale metabolic reconstructions using *Escherichia coli*," *Natural Biotech.* 26(6):659-667 (2008).
Fiehn, "Metabolomics—the link between genotypes and phenotypes," *Plant Mol. Biol.* 48(1-2):155-171 (2002).
Finel, "Does NADH play a central role in energy metabolism in *Helicobacter pylori*?," *Trends Biochem. Sci.* 23(11):412-413 (1998).
Fiorelli et al., "Chronic non-spherocytic haemolytic disorders associated with glucose-6-phosphate dehydrogenase variats," *Bailliere's Clinical Haematology*, 13:39-55 (2000).
Fleischmann, "Whole-genome random sequencing and assembly of *Haemophilus influenzae* Rd," *Science* 269(5223):496-512 (1995).
Flikweert et al., "Pyruvate decarboxylase: an indispensable enzyme for growth of *Saccharomyces cerevisiae* on glucose.," *Yeast* 12(3):247-257 (1996).
Forst, "Network genomics—A Novel approach for the analysis of biological systems in the post-genomic era," *Mol. Biol. Rpts.* 29(3):265-280 (2002).
Forster et al., "Large-scale evaluation of in silico gene deletions in *Saccharomyces cerevisiae*," *Omics* 7(2)193-202 (2003).
Fotheringham, "Engineering biosynthetic pathways: new routes to chiral amino acids," *Curr. Opin. Chem. Biol.* 4(1):120-124 (2000).
Fraenkel, "The accumulation of glucose 6-phosphate from glucose and its effect in an *Escherichia coli* mutant lacking phosphoglucose isomerase and glucose 6-phosphate dehydrogenase," *J. Biol. Chem.* 243(24):6451-6457 (1968).
Fraser et al., "Microbial genome sequencing," *Nature* 406:799-803 (2000).
Fromont-Racine et al., "Toward a functional analysis of the yeast genome through exhaustive two-hybrid screens," *Nat. Genet.* 16(3):277-282 (1997).
Fukuchi et al., "Isolation, overexpression and disruption of a *Saccharomyces cerevisiae* YNK gene encoding nucleoside diphosphate kinase," *Genetics* 129(1):141-146 (1993).
Galperin and Brenner, "Using Metabolic Pathway Databases for Functional Annotation," *Trends Genet.* 14(8):332-333 (1998).
Gancedo and Delgado, "Isolation and characterization of a mutant from *Saccharomyces cerevisiae* lacking fructose 1,6-bisphosphatase," *Eur. J .Biochem.* 139:651-655 (1984).
Gangloff et al., "Molecular cloning of the yeast mitochondrial aconitase gene (ACO1) and evidence of a synergistic regulation of expression by glucose plus glutamate.," *Mol. Cell. Biol.* 10(7):3551-3561 (1990).
Ge et al., "Cloning and functional characterization of *Helicobacter pylori* fumarate reductase operon comprising three structural genes coding for subunits C, A and B," *Gene* 204(1-2):227-234 (1997).
Glasner et al., "ASAP, a systematic annotation package for community analysis of genomes," *Nucleic Acids Res.* 31(1):147-151 (2003).
Goffeau, "Four years of post-genomic life with 6000 yeast genes," *FEBS Lett* 480(1):37-41 (2000).
Gombert and Nielsen, "Mathematical modeling of metabolism," *Curr. Opin. Biotechnol.* 11(2):180-186 (2000).
Grewal, et al., "Computer Modelling of the Interaction Between Human Choriogonadotropin and Its Receptor," *Protein Eng.* 7(2):205-211 (1994).
Griffin, et al., "Complementary profiling of gene expression at the transcriptome and proteome levels in *Saccharomyces cerevisiae*," *Mol. Cell Proteomics* 1:323-333 (2002).
Grundy et al., "Regulation of the *Bacillus subtilis* acetate kinase gene by CcpA." *J. Bacteriol.* 175(22):7348-7355 (1993).
Guardia et al., "Cybernetic modeling and regulation of metabolic pathways in multiple steady states of hybridoma cells," *Biotech. Prog.* 16(5):847-853 (2000).
Guelzim et al., "Topological and causal structure of the yeast transcriptional regulatory network," *Nat. Genet.* 31(1):60-63 (2002).
Guetsova et al., "The isolation and characterization of *Saccharomyces cerevisiae* mutants that constitutively express purine biosynthetic genes," *Genetics* 147(2):383-397 (1997).
Hardison et al., "Globin Gene Server: A Prototype E-Mail Database Server Featuring Extensive Multiple Alignments and Data Compilation for Electronic Genetic Analysis," *Genomics*, 21(2):344-353 (1994).
Hartig et al., "Differentially regulated malate synthase genes participate in carbon and nitrogen metabolism of *S. cerevisiae*.," *Nucleic Acids Res*, 20(21):5677-5686 (1992).
Hasty et al., "Computational Studies of Gene Regulatory Networks: In Numero Molecular Biology," *Nat. Rev. Genet.* 2(4):268-279 (2001).
Hata et al., "Characterization of a *Saccharomyces cerevisiae* mutant, N22, defective in ergosterol synthesis and preparation of [28-14C]ergosta-5,7-dien-3 beta-ol with the mutant," *J. Biochem.* 94(2):501-510 (1983).
Hatzimanikatis et al., "Analysis and Design of Metabolic Reaction Networks Via Mixed-Interger linear Optimization," *AIChE Journal*, 42(5):1277-1292 (1996).
Hazell et al., "How *Helicobacter pylori* works: an overview of the metabolism of *Helicobacter pylori*," *Helicobacter* 2(1):1-12 (1997).
Heinisch et al., "Investigation of two yeast genes encoding putative isoenzymes of phosphoglycerate mutase.," *Yeast* 14(3):203-213 (1998).
Heinrich et al., "Metabolic regulation and mathematical models," *Prog. Biophys. Mol. Biol.* 32(1):1-82 (1977).
Henriksen et al., "Growth energetics and metabolism fluxes in continuous cultures of *Penicillium chrysogenum*," *J. Biotechnol.* 45(2):149-164 (1996).
Heyer et al., "Exploring expression data: identification and analysis of coexpressed genes," *Genome Res.* 9(11):1106-1115 (1999).
Holter et al., "Dynamic modeling of gene expression data," *Proc. Natl. Acad. Sci USA*, 98(4):1693-1698 (2001).
Holter et al., "Fundamental patterns underlying gene expression profiles: simplicity from complexity," *Proc Natl Acad Sci USA*, 97:8409-9414 (2000).
Hughes et al., "Functional discovery via a compendium of expression profiles," *Cell* 102(1):109-126 (2000).
Hughes et al., "*Helicobacter pylori* porCDAB and oorDABC genes encode distinct pyruvate: flavodoxin and 2-oxoglutarate:acceptor oxidoreductases which mediate electron transport to NADP," *J. Bacteriol.* 180(5):1119-1128 (1998).
Ideker et al., "Integrated Genomic and Proteomic Analyses of a Systematically Perturbed Metabolic Network," *Science* 292(5518):929-934 (2001).
Ince and Knowles, "Ethylene formation by cell-free extracts of *Escherichia coli*," *Arch. Microbiol.* 146(2):151-158 (1986).
Ishii et al., "DBTBS: a database of *Bacillus subtilis* promoters and transcription factors," *Nucleic Acids Res.* 29(1):278-280 (2001).
Iyer et al., "Genomic binding sites of the yeast cell-cycle transcription factors SBF and MBF," *Nature* 409(6819):533-538 (2001).
Jamshidi et al., "Dynamic simulation of the human red blood cell metabolic network," *Bioinformatics* 17(3):286-287 (2001).
Jamshidi et al., "In silico model-driven assessment of the effects of single nucleotide polymorphins (SNPs) on human red blood cell-metabolism," *Genome Res.* 12(11):1687-1692 (2002).
Jenkins and Nunn,"Genetic and molecular characterization of the genes involved in short-chain fatty acid degradation in *Escherichia coli*: the ato system," *J. Bacteriol.* 169(1):42-52 (1987).
Jenssen et al., "A Literature Network of Human Genes for High-Throughput Analysis of Gene Expression," *Nat. Gene.* 28(1):21-28 (2001).

(56) References Cited

OTHER PUBLICATIONS

Jorgensen et al., "Metabolic flux distributions in *Penicillium chrysogenum* during fed-batch cultivations." *Biotechnol. Bioeng.* 46(2):117-131 (1995).
Joshi and Palsson, "Metabolic dynamics in the human red cell. Part I—A comprehensive kinetic model," *J Theor Biol* 141(4):515-528 (1989).
Juty et al., "Simultaneous Modeling of Metabolic, Genetic, and Product-Interaction Networks," *Brief. Bioinform.* 2(3):223-232 (2001).
Kanehisa and Goto, "Kyoto Encyclopedia of Genes and Genomes database (KEGG)," *Nucleic Acids Res.* 28(1):27-30 (2000).
Karp et al., "Eco Cyc: encyclopedia of *Escherichia coli* genes and metabolism," *Nucleic Acids Res.* 27(1):55-58 (1999).
Karp et al., "HinCyc: A knowledge base of the complete genome and metabolic pathways of *H. influenzae*," *Proc. Int. Conf. Intel. Syst. Mol. Biol.* 4:116-124 (1996).
Karp et al., "The EcoCyc and MetaCyc databases," *Nucleic Acids Res.* 28(1):56-59 (2000).
Karp, "An ontology for biological function based on molecular interactions," *Bioinformatics* 16(3):269-285 (2000).
Karp, "Metabolic Databases," *Trends Biochem. Sci.* 23(3):114-116 (1998).
Kather et al., "Another unusual type of citric acid cycle enzyme in *Helicobacter pylori*: the malate:quinone oxidoreductase," *J. Bacteriol.* 182(11):3204-3209 (2000).
Kaufman et al., "Towards a logical analysis of the immune response," *J. Theor. Biol.* 114(4):527-561 (1985).
Keating et al., "An ethanologenic yeast exhibiting unusual metabolism in the fermentation of lignocellulosic hexose sugars," *J. Ind. Microbiol. Biotechnol.*, 31(5):235-244 (2004).
Kelly, "The physiology and metabolism of the human gastric pathogen *Helicobacter pylori*," *Adv. Microb. Physiol.* 40:137-189 (1998).
Kim et al., "*Saccharomyces cerevisiae* contains two functional citrate synthase genes.," *Mol. Cell Biol.* 6(6):1936-1942 (1986).
Kirkman et al., "Red cell NADP+ and NADPH in glucose-6-phosphate dehydrogenase deficiency," *J. Clin. Inv.* 55(4):875-878 (1975).
Kremling et al., "The organization of metabolic reaction networks. III. Application for diauxic growth on glucose and lactose," *Metab. Eng.* 3(4):362-379 (2001).
Kunst and Devine, "The project of sequencing the entire *Bacillus substilis* genome," *Res. Microb.* 142:905-912 (1991).
Lacroute, "Regulation of pyrimidine biosynthesis in *Saccharomyces cerevisiae*" *J. Bacteriol.* 95(3):824-832 (1968).
Latif and Rajoka, "Production of ethanol and xylitol from corn cobs by yeasts," *Bioresour. Technol.* 77(1):57-63 (2001).
Lee et al., "Incorporating qualitative knowledge in enzyme kinetic models using fuzzy logic," *Biotech. Bioeng.* 62(6):722-729 (1999).
Lendenmann and Egli, "Is *Escherichia coli* growing in glucose-limited chemostat culture able to utilize other sugars without lag?," *Microbiology*, 141(Pt 1):71-78 (1995).
Leyva-Vasquez and Setlow, "Cloning and nucleotide sequences of the genes encoding triose phosphate isomerase, phosphoglycerate mutase, and enolase from *Bacillus subtilis*," *J. Bacteriol.* 176(13):3903-3910 (1994).
Li and Wong, "Model-based analysis of oligonucleotide arrays: expression index computation and outlier detection," *Proc. Natl. Acad. Sci USA*, 98(1):31-36 (2001).
Liao and Oh, "Toward predicting metabolic fluxes in metabolically engineered strains," *Metab. Eng.*1(3):214-223 (1999).
Liao et al., "Pathway Analysis, Engineering, and Physiological Considerations for Redirecting Central Metabolism," *Biotechnol. Bioeng.* 52(1):129-140 (1996).
Link et al., "Methods for generating precise deletions and insertions in the genome of wild-type *Escherichia coli*: Application to open reading frame characterization," *J. Bacteriol.* 179(20):6228-6237 (1997).
Loftus et al., "Isolation, characterization, and disruption of the yeast gene encoding cytosolic NADP-specific isocitrate dehydrogenase," *Biochemistry* 33(32):9661-9667 (1994).
Lopez et al., "The yeast inositol monophosphatase is a lithium- and sodium-sensitive enzyme encoded by a non-essential gene pair," *Mol. Microbiol.* 31(4):1255-1264 (1999).
Lynd et al., "Biocommodity Enginering," *Biotech. Prog.* 15:777-793 (1999).
Mahadevan and Schilling, "The effects of alternate optimal solutions in constraint-based genome-scale metabolic models," *Metab. Eng.* 5(4):264-276 (2003).
Maier et al., "Hydrogen uptake hydrogenase in *Helicobacter pylori*," *FEMS Microbiol. Lett.* 141(1):71-76 (1996).
Marcelli et al., "The respiratory chain of *Helicobacter pylori*: identification of cytochromes and the effects of oxygen on cytochrome and menaquinone levels," *FEMS Microbiol. Lett.* 138(1):59-64 (1996).
Marshall and Warren, "Unidentified curved bacilli in the stomach of patients with gastritis and peptic ulceration," *Lancet.* 1(8390):1311-1315 (1984).
McAdams and Arkin, "It's a noisy business! Genetic regulation at the nanomolar scale," *Trends Genetics* 15(2):65-69 (1999).
McAdams and Arkin, "Simulation of Prokaryotic Genetic Circuits," *Ann. Rev. Biophysics Biomol. Structure* 27:199-224 (1998).
McAdams and Arkin, "Stochastic mechanisms in gene expression," *Proc. Natl. Acad. Sci. USA* 94(3):814-819 (1997).
McAdams and Shapiro, "Circuit simulation of genetic networks," *Science* 269:651-656 (1995).
McAlister-Henn and Thompson, "Isolation and expression of the gene encoding yeast mitochondrial malate dehydrogenase.," *J. Bacteriol.* 169(11):5157-5166 (1987).
McGee,"*Helicobacter pylori* rocF is required for arginase activity and acid protection in vitro but is not essential for colonization of mice or for urease activity," *J. Bacteriol.* 181(23):7314-7322 (1999).
Meldrum, "Automation for genomics, part one: preparation for sequencing," *Genome Res.* 10(8):1081-1092 (2000).
Mendes et al., "Non-linear optimization of biochemical pathways: Applications to metabolic engineering and parameter estimation," *Bioinformatics*, 14(10):869-883 (1998).
Mendz and Hazell "Aminoacid utilization by *Helicobacter pylori*," *Int. J. Biochem. Cell. Biol.* 27(10):1085-1093 (1995).
Mendz and Hazell, "Fumarate catabolism in *Helicobacter pylori*," *Biochem. Mol. Biol. Int.* 31(2):325-332 (1993).
Mendz and Hazell, "Glucose phosphorylation in *Helicobacter pylori*," *Arch Biochem Biophys* 300(1):522-525 (1993).
Mendz et al., "Glucose utilization and lactate production by *Helicobacter pylori*," *J. Gen. Microbiol.* 139(12):3023-3028 (1993).
Mendz et al., "Characterisation of glucose transport in *Helicobacter pylori*," *Biochim. Biophys. Acta* 1244(2-3):269-276 (1995).
Mendz et al., "Characterization of fumarate transport in *Helicobacter pylori*," *J. Membr. Biol.* 165(1):65-76 (1998).
Mendz et al., "De novo synthesis of pyrimidine nucleotides by *Helicobacter pylori*," *J. Appl. Bacteriol.* 77(1):1-8 (1994).
Mendz et al., "Fumarate reductase: a target for therapeutic intervention against *Helicobacter pylori*," *Arch. Biochem. Biophys.* 321(1):153-159 (1995).
Mendz et al., "In situ characterization of *Helicobacter pylori* arginase," *Biochim. Biophys. Acta* 1388(2):465-477 (1998).
Mendz et al., "Pyruvate metabolism in *Helicobacter pylori*," *Arch Microbiol*, 162(3):187-192 (1994).
Mendz et al., "Salvage synthesis of purine nucleotides by *Helicobacter pylori*," *J. Appl. Bacteriol.* 77(6):674-681 (1994).
Mendz et al., "The Entner-Doudoroff pathway in *Helicobacter pylori*," *Arch. Biochem. Biophys.* 312(2):349-356 (1994).
Mendz, et al., "Purine metabolism and the microaerophily of *Helicobacter pylori*," *Arch. Microbiol.* 168(6):448-456 (1997).
Mewes et al., "MIPS: A database for genomes and protein sequences," *Nucleic Acids Res.* 30(1):31-34 (2002).
Mitchell, "The GLN1 locus of *Saccharomyces cerevisiae* encodes glutamine synthetase," *Genetics* 111(2):243-258 (1985).
Moszer et al., "SubtiList: the reference database for the *Bacillus subtilis* genome," *Nucleic Acids Res.* 30(1):62-65 (2002).
Mulquiney and Kuchel, "Model of 2,3-bisphosphoglycerate metabolism in the human erythrocyte based on detailed enzyme kinetic equations: computer simulation and metabolic control analysis," *Biochem. J.* 342(Pt 3):597-604 (1999).

(56) References Cited

OTHER PUBLICATIONS

Murray and Greenberg, "Expression of yeast INM1 encoding inositol monophosphatase is regulated by inositol, carbon source and growth stage and is decreased by lithium and valproate," *Mol Microbiol* 36(3):651-661 (2000).

Nedenskov, "Nutritional requirements for growth of *Helicobacter pylori*," *Appl. Environ. Microbiol.* 60(9):3450-3453 (1994).

Nissen et al., "Expression of a cytoplasmic transhydrogenase in *Saccharomyces cerevisiae* results in formation of 2-oxoglutarate due to depletion of the NADPH pool," *Yeast* 18(1):19-32 (2001).

Nissen et al., "Flux distributions in anaerobic, glucose-limited continuous cultures of *Saccharomyces cerevisiae*," *Microbiology* 143(Pt 1):203-218 (1997).

Ogasawara, "Systematic function analysis of *Bacillus subtilis* genes," *Res. Microbiol.* 151(2):129-134 (2000).

Oh and Liao, "Gene expression profiling by DNA microarrays and metabolic fluxes in *Escherichia coli*," *Biotech. Prog.* 16:278-286 (2000).

Olsson et al., "Separate and simultaneous enzymatic hydrolysis and fermentation of wheat hemicellulose with recombinant xylose utilizing *Saccharomyces cerevisiae*," *Appl. Biochem. Biotechnol.* 129-132:117-129 (2006).

Ostergaard et al., "Increasing galactose consumption by *Saccharomyces cerevisiae* through metabolic engineering of the GAL gene regulatory network," *Nat. Biotech.* 18:1283-1286 (2000).

Otto et al., "A mathematical model for the influence of fructose 6-phosphate, ATP, potassium, ammonium and magnesium on the phosphofructokinase from rat erythrocytes," *Eur. J. Biochem.* 49(1):169-178 (1974).

Ouzounis and Karp, "Global Properties of the Metabolic Map of *Escherichia coli*," *Genome Res.* 10(4):568-576 (2000).

Overbeek et al., "WIT: Integrated System for High-Throughput Genome Sequence Analysis and Metabolic Reconstruction" *Nucleic Acids Res.* 28(1):123-125 (2000).

Overkamp et al., "In vivo analysis of the mechanisms for oxidation of cytosolic NADH by *Saccharomyces cerevisiae* mitochondria," *J. Bacteriol.* 182(10):2823-2830 (2000).

Ozcan et al., "Glucose uptake and catabolite repression in dominant HTR1 mutants of *Saccharomyces cerevisiae.*," *J. Bacteriol.* 175(17):5520-5528 (1993).

Pallotta et al., "*Saccharomyces cerevisiae* mitochondria can synthesise FMN and FAD from externally added riboflavin and export them to the extramitochondrial phase," *FEBS Lett.* 428(3):245-249 (1998).

Palmieri et al., "Identification and functions of new transporters in yeast mitochondria," *Biochim. Biophys. Acta* 1459(2-3):363-369 (2000).

Palmieri et al., "Identification of the yeast ACR1 gene product as a succinate-fumarate transporter essential for growth on ethanol or acetate," *FEBS Lett.* 417(1):114-118 (1997).

Palmieri et al., "Identification of the yeast mitochondrial transporter for oxaloacetate and sulfate," *J. Biol. Chem.* 274(32):22184-22190 (1999).

Palmieri et al., "Yeast mitochondrial carriers: bacterial expression, biochemical identification and metabolic significance," *J. Bioenerg. Biomem.*, 32(1):67-77 (2000).

Palsson, "What Lies Beyond Bioinformatics," *Nat. Biotechnol.* 15:3-4 (1997).

Papin et al., "The genome-scale metabolic extreme pathway structure in *Haemophilus influenzae* shows significant network redundancy," *J. Theor. Biol.* 215(1):67-82 (2002).

Parks et al., "Use of sterol mutants as probes for sterol functions in the yeast, *Saccharomyces cerevisiae*," *Crit. Rev. Biochem. Mol. Bio.* 34(6):399-404 (1999).

Parks, "Metabolism of sterols in yeast," *CRC Crit. Rev. Microbiol.* 6(4):301-341 (1978).

Patel and West, "Degradation of the pyrimidine bases uracil and thymine by *Escherichia coli* B" *Microbios*. 49(199):107-113 (1987).

Paulsen et al., "Unified inventory of established and putative transporters encoded within the complete genome of *Saccharomyces cerevisiae*," *FEBS Lett.* 430(1-2):116-125 (1998).

Pearson et al., "Comparison of DNA Sequences With Protein Sequences," *Genomics* 46(1):24-36 (1997).

Pennisi, "Laboratory Workhouse Decoded," *Science* 277(5331):1432-1434 (1997).

Persson et al., "Phosphate permeases of *Saccharomyces cerevisiae*: structure, function and regulation," *Biochim. Biophys. Acta* 1422(3):255-272 (1999).

Peterson et al., "The Comprehensive Microbial Resource," *Nucleic Acids Res.* 29(1):123-125 (2001).

Pharkya et al., "Exploring the overproduction of amino acids using the bilevel optimization framework OptKnock," *Biotechnol. Bioeng.* 84(7):887-899 (2003).

Phelps et al., "Metabolomics and microarrays for improved understanding of phenotypic characteristics controlled by both genomics and environmental constraints," *Curr. Opin. Biotechnol.* 13(1):20-24 (2002).

Pieper and Reineke, "Engineering bacteria for bioremediation," *Curr. Opin. Biotech.* 11(3):262-270 (2000).

Pitson et al., "The tricarboxylic acid cycle of *Helicobacter pylori*," *Eur. J. Biochem.* 260(1):258-267 (1999).

Pramanik and Keasling, "Stoichiometric Model of *Escherichia coli* Metabolism: Incorporation of Growth-Rate Dependent Biomass Composition and Mechanistic Energy Requirements," *Biotechnol. Bioeng.* 56(4):398-421 (1997).

Price et al., "Determination of redundancy and systems properties of the metabolic network of *Helicobacter pylori* using genome-scale extreme pathway analysis," *Genome Res.* 12(5):760-769 (2002).

Price et al., "Genome-scale models of microbial cells: evaluating the consequences of constraints," *Nat. Rev. Microbiol.* 2(11):886-897 (2004).

Price et al., "Network-based analysis of metabolic regulation in the human red blood cell," *J. Theor. Biol.* 225(2):185-194 (2003).

Przybyla-Zawislak et al., "Genes of succinyl-CoA ligase from *Saccharomyces cerevisiae.*," *Eur. J. Biochem.* 258(2):736-743 (1998).

Qian et al., "Ethanol production from dilute-Acid softwood hydrolysate by co-culture," *Appl. Biochem Biotechnol.* 134(3):273-284 (2006).

Rao and Arkin "Control motifs for intracellular regulatory networks," *Ann. Rev. Biomed. Eng.* 3:391-419 (2001).

Reed and Palsson, "Thirteen years of building constraint-based in silico models of *Escherichia coli*" *J. Bacteriol.* 185(9):2692-2699 (2003).

Reed et al., "An expanded genome-scale model of *Escherichia coli* K-12 (iJR904 GSM/GPR)," *Genome Biol.* 4(9):R54 (2003).

Regenberg et al., "Substrate specificity and gene expression of the amino-acid permeases in *Saccharomyces cerevisiae*," *Curr. Genet* .36(6):317-328 (1999).

Remize et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl. Environ. Microbiol.* 66(8):3151-3159 (2000).

Ren et al., "Genome-wide location and function of DNA binding proteins," *Science* 290(5500):2306-2309 (2000).

Repetto and Tzagoloff, "In vivo assembly of yeast mitochondrial alpha-ketoglutarate dehydrogenase complex," *Mol. Cell. Biol.* 11(8):3931-3939 (1991).

Reynolds and Penn, "Characteristics of *Helicobacter pylori* growth in a defined medium and determination of its amino acid requirements," *Microbiology* 140(Pt 10):2649-2656 (1994).

Rhee et al., "Activation of gene expression by a ligand-induced conformational change of a protein-DNA complex," *J. Biol. Chem.* 273(18):11257-11266 (1998).

Saier, "Genome sequencing and informatics: new tools for biochemical discoveries," *Plant Physiol.* 117(4):1129-1133 (1998).

Salgado et al., "RegulonDB (version 3.2): transcriptional regulation and operon organization in *Escherichia coli* K-12," *Nucleic Acids Res.* 29(1):72-74 (2001).

(56) References Cited

OTHER PUBLICATIONS

Salmon et al., "Global gene expression profiling in *Escherichia coli* K12. The effects of oxygen availability and FNR," *J. Biol. Chem.* 278(32):29837-29855 (2003).

Sauer et al., "Metabolic Capacity of *Bacillus subtilis* for the Production of Purine Nucleosides, Riboflavin, and Folic Acid," *Biotechnol. Bioeng.* 59(2):227-238 (1998).

Sauer et al., "Metabolic flux ratio analysis of genetic and environmental modulations of *Escherichia coli* central carbon metabolism," *J. Bacteriol.* 181(21):6679-6688 (1999).

Sauer, "Evolutionary Engineering of Industrially Important Microbial Phenotypes," *Adv.Biochem. Eng. Biotechnol.* 73:129-169 (2001).

Savageau, "Biochemical systems analysis. I. Some mathematical properties of the rate law for the component enzymatic reactions," *J Theor Biol*, 25(3):365-369 (1969).

Savageau, "Development of fractal kinetic theory for enzyme-catalysed reactions and implications for the design of biochemical pathways," *Biosys.* 47(1-2):9-36 (1998).

Savinelli and Palsson, "Network Analysis of Intermediary Metabolism using Linear Iptimization I. Development of Mathematical Formalism," J. Theor. Biol 154:421-454 (1992).

Savinell and Palsson, "Network Analysis of Intermediary Metabolism using Linear Optimization. II. Interpretation of Hybridoma Cell Metabolism," *J. Theor. Biol.* 154:455-473 (1992).

Schaaff-Gerstenschlager and Zimmermann, "Pentose-phosphate pathway in *Saccharomyces cerevisiae*: analysis of deletion mutants for transketolase, transaldolase, and glucose 6-phosphate dehydrogenase," *Curr. Genet* 24(5):373-376 (1993).

Schena et al., "Quantitative monitoring of gene expression patterns with a complementary DNA microarray," *Science* 270(5235):467-470 (1995).

Schilling et al., "Genome-scale metabolic model of *Helicobacter pylori* 26695," *J. Bacteriol.* 184(16):4582-4593 (2002).

Schilling, "On Systems Biology and the Pathway Analysis of Metabolic Networks," Department of bioengineering, University of California, San Diego, La Jolla 198-241 (2000).

Schneider, et al., "The *Escherichia coli* gabDTPC operon: specific gamma-aminobutyrate catabolism and nonspecific induction," *J. Bacteriol.* 184(24):6976-6986 (2002).

Schuster and Hilgetag "On elementary flux modes in biochemical reaction systems at steady state," *J. Biol. Syst.* 2(2):165-182 (1994).

Schuster et al., "Detection of elementary flux modes in biochemical networks: a promising tool for pathway analysis and metabolic engineering," *Trends Biotechnol.* 17(2):53-60 (1999).

Schuster et al., "Exploring the pathway structure of metabolism: decomposition into subnetworks and application to *Mycoplasma pneumoniae*," *Bioinformatics* 18(2):351-361 (2002).

Schwikowski et al., "A network of protein-protein interactions in yeast," *Nature Biotechnol.* 18(12):1257-1261 (2000).

Scott et al., "The Pendred Syndrome Gene Encodes a Chloride-Iodide Transport Protein," *Nat. Genet.* 21(4):440-443 (1999).

Sedivy and Fraenkel, "Fructose bisphosphatase of *Saccharomyces cerevisiae*. Cloning, disruption and regulation of the FBP1 structural gene.," *J. Mol. Biol.* 186(2):307-319 (1985).

Selkov et al., "A reconstruction of the metabolism of *Methanococcus jannaschii* from sequence data," *Genetics* 197(1-2):GC11-26 (1997).

Selkov et al., "Functional Analysis of Gapped Microbial Genomes: Amino Acid Metabolism of *Thiobacillus ferroxidans*," *Proc. Nat.l Acad. Sci. USA*, 97(7):3509-3514 (2000).

Selkov et al., "MPW: the metabolic 45 (1998) pathways database," *Nucleic Acids Res.* 26(1):43-45 (1998).

Selkov et al., "The metabolic pathway collection from EMP: the enzymes and metabolic pathways database," *Nucleic Acids Res.* 24(1):26-28 (1996).

Shen-Orr et al., "Network motifs in the transcriptional regulation network of *Escherichia coli*," *Nat. Genet.* 31(1):64-68 (2002).

Sherlock et al., "Analysis of large-scale gene expression data," *Curr. Opin. Immunol.* 12:201-205 (2000).

Shipston and Bunch, "The physiology of L-methionine catabolism to the secondary metabolite ethylene by *Escherichia coli*," *J. Gen. Microbiol.l* 135(6), 1489-1497 (1989).

Silve et al., "The immunosuppressant SR 31747 blocks cell proliferation by inhibiting a steroid isomerase in *Saccharomyces cerevisiae*," *Mol. Cell. Biol.* 16(6):2719-2727 (1996).

Skouloubris et al., "The *Helicobacter pylori* UreI protein is not involved in urease activity but is essential for bacterial survival in vivo," *Infect. Immun.* 66(9):4517-4521 (1998).

Smith et al., "Functional analysis of the genes of yeast chromosome V by genetic footprinting.," *Science* 274(5295):2069-2074 (1996).

Somogyi and Sniegoski, "Modeling the complexity of genetic networks: understanding the multigenic and pleitropic regulation," *Complexity* 1(6):45-63 (1996).

Stark et al., "Amino acid utilisation and deamination of glutamine and asparagine by *Helicobacter pylori*," *J. Med. Microbiol.* 46(9):793-800 (1997).

Stephanopoulos, "Metabolic Engineering," *Biotechnol. Bioeng.* 58(2-3):119-120 (1998).

Stephanopoulos, "Metabolic Engineering," *Curr. Opin. Biotechnol.* 5(2):196-200 (1994).

Summers et al., "*Saccharomyces cerevisiae* cho2 mutants are deficient in phospholipid methylation and cross-pathway regulation of inositol synthesis" *Genetics* 120(4):909-922 (1988).

Swartz, "A PURE approach to constructive biology.," *Nat. Biotechnol.* 19(8):732-733 (2001).

Syvanen, "Accessing genetic variation: Genotyping single nucleotide polymorphisms.," *Nat. Rev. Genet.* 2(12):930-942 (Dec. 2001).

Szambelan et al., "Use of *Zymomonas mobilis* and *Saccharomyces cerevisiae* mixed with *Kluyveromyces fragilis* for improved ethanol production from Jerusalem artichoke tubers," *Biotechnol. Lett.* 26(10):845-848 (2004).

Tamayo et al., "Interpreting patterns of gene expression with self-organizing maps: methods and application to hematopoietic differentiation," *Proc. Natl. Acad. Sci. USA*. 96(6):2907-2912 (1999).

Tanaka and Zerez, "Red cell enzymopathies of the glycolytic pathway," *Semin. Hematol.* 27(2):165-185 (1990).

Taniguchi and Tanaka, "Clarification of interactions among microorganisms and development of co-culture system for production of useful substances," *Adv. Biochem. Eng. Biotechnol*. 90:35-62 (2004).

Tao et al., "Engineering a homo-ethanol pathway in *Escherichia coli*: increased glycolytic flux and levels of expression of glycolytic genes during xylose fermentation," *J. Bacteriol.* 183(10):2979-2988 (2001).

ter Linde et al., "Genome-wide transcriptional analysis of aerobic and anaerobic chemostat cultures of *Saccharomyces cerevisiae*," *J Bacteriol.* 181(24):7409-7413 (Dec. 1999).

Thieffry and Thomas, "Dynamical behavior of biological regulatory networks II. Immunity control in bacteriophage lambda," *Bull. Math Biol.* 57(2):277-297 (1995).

Thomas and Surdin-Kerjan, "Metabolism of sulfur amino acids in *Saccharomyces cerevisiae*," *Microbiol. Mol. Biol. Rev.* 61(4):503-532 (1997).

Tomb et al., "The complete genome sequence of the gastric pathogen *Helicobacter pylori*," *Nature* 388(6642):539-547 (1997).

Tomita et al., "E-Cell: Software Environment for Whole-Cell Simulation," *Bioinformatics* 15(1):72-84 (1999).

Trotter et al., "A genetic screen for aminophospholipid transport mutants identifies the phosphatidylinositol 4-kinase, STT4p, as an essential component in phosphatidylserine metabolism," *J. Biol. Chem.* 273(21):13189-13196 (1998).

Uetz et al., "A comprehensive analysis of protein-protein interactions in *Saccharomyces cerevisiae*," *Nature* 403(6770):623-627 (2000).

Van den Berg,"ACS2, a *Saccharomyces cerevisiae* gene encoding acetyl-coenzyme A synthetase, essential for growth on glucose," *Eur. J. Biochem.* 231(3):704-713 (1995).

Van Dijken, et al., "Alcoholic fermentation by 'non-fermentative' yeasts," *Yeast* 2(2):123-127 (1986).

Van Dijken, et al., "Kinetics of growth and sugar consumption in yeasts," *Antonie Van Leeuwenhoek*, 63(3-4):343-352 (1993).

Varma and Palsson, "Metabolic capabilites of *Escherichia coli*. II: Optimal Growth Patterns.," *J. Theor. Biol.* 165:503-522 (1993).

(56) References Cited

OTHER PUBLICATIONS

Varma and Palsson, "Parametric sensitivity of stoichiometric flux balance models applied to wild-type *Eschericia coli* metabolism," *Biotechnol. Bioeng.* 45(1):69-79 (1995).

Varma and Palsson, "Predictions for Oxygen Supply Control to Enhance Population Stability of Engineered Production Strains," *Biotechnol. Bioeng.* 43(4):275-285 (1994).

Varma et al., "Biochemical Production Capabilities of *Eschericia coli*," *Biotechnol. Bioeng* 42(1):59-73 (1993).

Varma et al., "Stoichiometric Interpretation of *Escherichia coli* Glucose Catabolism Under Various Oxygenation Rates.," *Appl. Environ. Microbiol.* 59(8):2465-2473 (1993).

Varner and Ramkrishna, "Mathematical Models of Metabolic Pathways," *Curr. Opin. Biotechnol.* 10(2):146-150 (1999).

Varner, "Large-scale prediction of phenotype: concept," *Biotech. Bioeng.* 69(6):664-678 (2000).

Vaseghi et al., "In vivo Dynamics of the pentose phosphate pathway in *Saccharomyces cerevisiae*," *Meta Engin.* 1:128-140 (1999).

Velculescu et al., "Analysing uncharted transcriptomes with SAGE," *Trends Genet.* 16(10):423-425 (2000).

Venter et al., "Shotgun sequencing of the human genome," *Science* 280(5369):1540-1542 (1998).

Verduyn et al., "A theoretical evaluation of growth yields of yeasts," *Antonie Van Leeuwenhoek*, 59(1):49-63 (1991).

Verduyn et al., "Energetics of *Saccharomyces cerevisiae* in anaerobic glucose-limited chemostat cultures," *J. Gen. Microbiol.* 136:405-412 (1990).

Verduyn, "Physiology of yeasts in relation to biomass yields," *Antonie Van Leeuwenhoek* 60(3-4):325-353 (1991).

Vissing et al., "Paradoxically Enhanced Glucose Production During Exercise in Humans with Blocked Glycolysis Caused by Muscle Phosphofructokinase Deficiency," *Neurology* 47(3):766-771 (1996).

Wang, et al., "Computer-aided baker's yeast fermentations," *Biotechnol. Bioeng.* 19(1):69-86 (1977).

Wang et al., Computer Control of Bakers' Yeast Production, *Biotechnol. Bioeng.* 21:975-995 (1979).

Waterston and Sulston, "The Human Genome Project: reaching the finish line," *Science* 282(5386):53-54 (1998).

Wen et al., "Large-scale temporal gene expression mapping of central nervous system development," *Proc. Natl. Acad. Sci. USA*, 95(1):334-339 (1998).

Wiback and Palsson, "Extreme pathway analysis of human red blood cell metabolism," *Biophys. J.* 83:808-818 (2002).

Wieczorke et al., "Concurrent knock-out of at least 20 transporter genes is required to block uptake of hexoses in *Saccharomyces cerevisiae*," *FEBS Lett.* 46(3):123-128 (1999).

Wills and Melham, "Pyruvate carboxylase deficiency in yeast: a mutant affecting the interaction between the glyoxylate and Krebs cycles.," *Arch. Biochem. Biophys.* 236(2):782-791 (1985).

Wingender et al., "The TRANSFAC system on gene expression regulation," *Nucleic. Acids Res.* 29(1):281-283 (2001).

Winzeler et al., "Functional characterization of the *S. cerevisiae* genome by gene deletion and parallel analysis," *Science* 285(5429):901-906 (1999).

Wong et al., "Mathematical Model of the Lac Operon: Inducer Exclusion, Catabolite Repression, and Diauxic Growth on Glucose and Lactose," *Biotechnol. Prog.* 13(2):132-143 (1997).

Xie and Wang, "Energy Metabolism and ATP Balance in Animal Cell Cultivation Using a Stoichiometrically Based Reaction Network," *Biotech. Bioeng.* 52:591-601 (1996).

Xie and Wang, "Material Balance Studies on Animal Cell Metabolism Using a Stoichiometrically Based Reaction Network," *Biotech. Bioeng.* 52:579-590 (1996).

Xie and Wang, "Integrated Approaches to the Design of Media and Feeding Strategies for Fed-Batch Cultures of Animal Cells," *Trends Biotechnol.* 15(3):109-113 (1997).

Yamada et al., "Effects of common polymorphisms on the properties of recombinant human methylenetetrahydrofolate reductase," *Proc. Natl. Acad. Sci USA*, 98(26):14853-14858 (2001).

Yeung et al., "Model-based clustering and data transformations for gene expression data," *Bioinformatics* 17(10):977-987 (2001).

Yeung et al., "Reverse engineering gene networks using singular value decomposition and robust regression," *Proc Natl Acad Sci USA*, 99(9):6163-6168 (2002).

Yoshida et al., "Combined transcriptome and proteome analysis as a powerful approach to study genes under glucose repression in *Bacillus subtilis*," *Nucleic Acids. Res.* 29(3):683-692 (2001).

Zanella and Bianchi, "Red cell pyruvate kinase deficiency: from genetics to clinical manifestations," *Bailliere's Best Pract. Res. Clin. Haematol.* 13(1):57-81 (2000).

Zeng et al., "Use of respiratory quotient as a control parameter for optimum oxygen supply and scale-up of 2,3-butanediol production under microaerobic conditions," *Biotechnol. Bioeng.* 44(9):1107-1114 (1994).

Zhu and Zhang, "SCPD: a promoter database of the yeast *Saccharomyces cerevisiae*," *Bioinformatics* 15(7-8):607-611 (1999).

Zigova, "Effect of RQ and pre-seed conditions on biomass and galactosyl transferase production during fed-batch culture of *S. cerevisiae* BT150," *J. Biotechnol.* 80(1):55-62 (2000).

Zweytick et al., "Biochemical characterization and subcellular localization of the sterol C-24(28) reductase, erg4p, from the yeast *Saccharomyces cerevisiae*," *FEBS Lett.* 470(1):83-87 (2000).

URL affymetrix.com/index.affx (As printed on Sep. 18, 2009).

URL affymetrix.com/products_services/arrays/specific/ecoli_antisense.affx. (As printed on Sep. 18, 2009).

URL asap.ahabs.wisc.edu/annotation/php/logon.php, The ASAP website. (As printed on Sep. 17, 2009).

URL ca.expasy.org/sprot/ protein database SWISS-PROT. (As printed on Jun. 15, 2009).

Five pages from URL: web.archive.org/web/20050731094028/http://www.chem.qmw.ac.uk/iubmb/enzyme / EnzymeNomenclature database maintained by G. P. Moss of Queen Mary and Wesffield Colege in the United Kingdom; Date Obtained May 15, 2009.

URL dchip.org, dChip software. (As printed on Jun. 15, 2009).

URL Dictionary.com pp. 1-2 (2004), Matrix. (As printed on Nov. 12, 2004).

Three pages from URL: web.archive.org/web/19981206132808/http://ecocyc.panbio.com/ecocyc/ecocyc.html; Ecocyc; obtained on Sep. 18, 2009.

URL enzobio.com/lifesci_index.htm, Enzo BioArray Terminal Labeling Kit protocol. (As printed on Sep. 18, 2009).

URL genetics.wisc.edu/, *E. coli* Genome Project at the University of Wisconsin. As printed on Sep. 18, 2009.

URL genome.ad.jp/kegg/, Kyoto Encyclopedia of Genes and Genomes database (KEGG). (As printed on Sep. 18, 2009).

URL Genome.jp Website, KEGG *Bacillus subtillis*, 1-7 (2005). (As printed on Sep. 18, 2009).

URL genome.tugraz.at/Software/Genesis/Description.html, "Genesis" software. (As printed on Sep. 18, 2009).

Six pages from URL: web.archive.org/web/2005025215224/genome-www.stanford.edu/~sherlock/cluster.html, "XCluster" software: obtained on Sep. 18, 2009.

Home page from URL: web.archive.org/web/20050201083239/igweb.integratedgenomics.com/MPW/, Metabolic pathways database (MPW), obtained on Sep. 18, 2009.

URL integratedgenomics.com, ERGO from Integrated Genomics. (As printed on Sep. 18, 2009).

Three pages from URL: web.archive.org/web/2007001095540/http://mips.gsf.de/proj/yeast/pathways on Sep. 6, 2008. MIPS, website: Comprehensive Yeast Genome Database—Pathways; Date Obtained Sep. 18, 2009.

Two pages from URL: www.ncbi.nlm.nih.gov/sites/entrz?db=genome obtained on Jun. 15, 2009.

URL ncbi.nlm.nih.gov/LocusLink/LocusLink database maintained by the NCBI. (As printed on Jun. 15, 2009).

URL ncbi.nlm.nih.gov/Taxonomy/taxonomyhome.html/. (As printed on Sep. 18, 2009).

URL nslij-genetics.org/search_omim.html, Online Mendelian Inheritance in Man database, Center for Medical Genetics, Johns Hopkins University (Baltimore, MD) and National Center for

(56) References Cited

OTHER PUBLICATIONS

Biotechnology Information, National Library of Medicine (Bethesda, MD). (As printed on Sep. 18, 2009).
URL qiagen.com, Qiagen RNeasy Mini Kit. (As printed on Sep. 18, 2009).
URL rana.lbl.gov/EisenSoftware.htm, "Cluster" software. (As printed on Sep. 18, 2009).
Home page from URL: web.archive.org/web/20070228190312/http://systemsbiology.ucsd.edu, obtained on Sep. 18, 2009.
Two pages from URL: web.archive.org/web/20060712190022/http://www.tigr.org/. The Institute for Genome Research, J. Craig Venter Institute; obtained on Sep. 18, 2009.
Home page from URL: web.archive.org/web/20021126044821/http://tula.cifn.unam.mx:8850/regulondb/regulon_intro.frameset; obtained on Sep. 18, 2009.
Home page from URL: web.archive.org/web/20041125063300/http://wit.acs.anl.org; What is There (WIT), Obtained Nov. 23, 2008.
URL workbench.sdsc.edu/ Biology Workbench. (As printed on Sep. 18, 2009).
URL www.i-sis.org.uk/WITBRL.php; Hoppert, M. (2004) (As printed Jun. 23, 2008).
Biaudet, et al., "Micado—a network-oriented database for microbial genomes," *Comput. Appl. Biosci.*, 13:431-438 (1997).
Bronk, J.R., *Human Metabolism: Functional Diversity and Integration*, Addison Wesley Longman, Essex, England (1999).
Chvatal, *Linear Programming*, W.H. Freeman and Co., New York (1983).
Covert et al., "Metabolic modeling of microbial strains in silico," *Trends in Biochemical Sciences*, 26:179-186 (2001).
Covert et al., "Regulation of gene expression in flux balance models of metabolism," *J. Theor. Biol.* 213:73-88 (2001).
Dafoe, M.E., et al., "In Silico Knowledge Discovery in Biomedical Databases", *Proceedings of the SPIE*, SPIE, Bellingham, VA, US, pp. 239-243, XP000197711 (1993).
Dauner and Sauer, "Stoichiometric growth model for riboflavin-producing *Bacillus subtilis*," *Biotechnol. Bioeng.*, 76:132-143 (2001).
Dauner et al., "*Bacillus subtilis* metabolism and energetics in carbon-limited and excess-carbon chemostat culture," *J. Bact.*, 183:7308-7317 (2001).
Dauner et al., "Metabolic flux analysis with a comprehensive isotopomer model in *Bacillus subtilis*," *Biotechnol. Bioeng.*, 76:144-156 (2001).
Decamp et al., *Protein Engineering Principles and Practice*, Ed. Cleland and Crak, Wiley-Liss, New York, pp. 467-505 (1996).
Devine, K., "The *Bacillus subtilis* genome project: aims and progress," *TIBTECH*, 13:210-216 (1995).
Devlin, T.M., Ed., *Textbook of Biochemistry with Clinical Correlations*, 4th ed., John Wiley and Sons, New York, NY (1997).
Dirusso and Black, "Long-chain fatty acid transport in bacteria and yeast. Paradigms for defining the mechanism underlying this protein-mediated process," *Mol. Cell Biochem.* 192(1-2):41-52 (1999).
Dooley et al., "An all D-amino acid opioid peptide with central analgesic activity from a combinatorial library," *Science*, 266:2019-2022 (1994).
Duarte et al., "Reconstruction and validation of *Saccharomyces cerevisiae* iND750, a fully compartmentalized genome-scale metabolic model," *Genome Res.* 14(7):1298-1309 (2004).
Edwards and Palsson, "Systems properties of the haemophilus influenzae Rd metabolic genotype," *J. Biol. Chem.* 274:17410-17416 (1999).
Edwards and Palsson, "The *Escherichia coli* MG1655 in silico metabolic genotype: its definition, characteristics, and capabilities," *Proc. Natl. Acad. Sci. USA*, 97:5528-5533 (2000).
Edwards et al., "Characterizing the metabolic phenotype: a phenotype phase plane analysis," *Biotech Bioeng.*, 77:27-36 (2002).
Edwards et al., "In silico predictions of *Escherichia coli* metabolic capabilities are consistent with experimental data," *Nat. Biotech.*, 19:125-130 (2001).

Fell and Small, "Fat synthesis in adipose tissue an examination of stoichiometric constraints," *Biochem. J.* 238:781-786 (1986).
Goryanin et al., "Mathematical simulation and analysis of cellular metabolism and regulation", *Bioinformatics* 15(9):749-758 (1999).
Goto et al., "LIGAND: chemical database for enzyme reactions," *Bioinformatics*, 14:591-599 (1998).
Houghten et al., "Generation and use of synthetic peptide combinatorial libraries for basic research and discovery," *Nature* 354:84-86 (1991).
Kunst et al., "The complete genome sequence of the gram-positive bacterium *Bacillus subtilis*," *Nature*, 390:249-256 (1997).
Majewski and Domach, "Simple constrained-optimization view of acetate overflow in *E. coli*," *Biotech Bioeng.*, 35:732-738 (1990).
Maughan, R. et al., *Biochemistry of Exercise and Training*, Oxford University Press, Oxford, England (1997).
Moszer et al., "SubtiList: the references database for the *Bacillus subtilis* genome," *Nucl. Acids Res.*, 30(1):62-65 (2002).
Ogata et al., "KEGG: Kyoto Encyclopedia of Genes and Genomes," *Nucleic Acids Research*, 27(1):29-34 (1999).
Palsson, "The challenges of in silico biology," *Nat. Biotech*, 18:1147-1150 (2000).
Raclot et al., "Selective release of human adipocyte fatty acids according to molecular structure," *Biochem J.* 324 (Pt 3):911-915 (1997).
Ray, *Learning XML*, O'Reilly and Associates, Sebastopol, CA (2001).
Salway, *Metabolism at a Glance*, 2nd ed., Blackwell Science, Malden, MA 1999.
Sauer and Bailey, "Estimation of P-to-O ratio in *Bacillus subtilis* and its influence on maximum riboflavin yield," *Biotechnol. Bioeng.*, 64:750-754 (1999).
Schaff et al., *The Virtual Cell*, Proceedings of the Pacific Symposium on Biocomputing, pp. 228-239 (1999).
Schilling and Palsson, "Assessment of the metabolic capabilities *Haemophilus influenzae* Rd through a genome-scale pathway analysis," *J. Theor. Biol.*, 203:249-283 (2000).
Schilling and Palsson, "The underlying pathway structure of biochemical reaction networks," *Proc. Natl. Acad. Sci. USA*, 95:4193-4198 (1998).
Schilling et al., "Combining pathway analysis with flux balance analysis for the comprehensive study of metabolic systems," *Biotech Bioeng.*, 71:286-306 (2000).
Schilling et al., "Metabolic pathway analysis: basic concepts and scientific applications in the post-genomic era," *Biotech Prog.*, 15:296-303 (1999).
Schilling et al., "Theory for the systemic definition of metabolic pathways and their use in interpreting metabolic function from a pathway-oriented perspective," *J. Theor. Biol.*, 203:229-248 (2000).
Schilling et al., "Toward metabolic phenomics: analysis of genomic data using flux balances," *Biotech Prog.*, 15:288-295 (1999).
Schilling et al., "Assessment of the metabolic capabilities of *Haemophilus influenzae* Rd through a genome-scale pathway analysis," *J. Theor. Biol.*, 203:249-283 (2000).
Schuster et al., "Exploring the pathway structure of metabolism: decompostion into subnetworks and application to *Mycoplasma pneumoniae*," *Bioinformatics* 18:351-361 (2002).
Sorlie et al., "Gene expression patterns of breast carcinomas distinguish tumor subclasses with clinical implications," *Proc Natl., Acad. Sci. USA*, 98(19):10869-10874.
Stipanuk. *Biochemical and Physiological Aspects of Human Nutrition*, W.B. Saunders, Philadelphia, PA (2000).
Tandeitnik et al., "Modeling of biological neurons by artificial neural networks", Nineteenth Convention of Electrical and Electronics Engineers in Israel, Jerusalem, Israel, New York, NY USA, pp. 239-242 (1996).
Thomas et al., "Boolean formalization of genetic control circuits," *J. Theor. Biol..*, 42:563-585 (1973).
Thomas et al., "Logical Analysis of Systems Comprising Feedback Loops," *J. Theor. Biol.*, 73:631-656 (1978).
Vanrolleghem et al., "Validation of a metabolic network for *Saccharomyces cerevisiae* using mixed substrate studies," *Biotech Prog.*, 12:434-448 (1996).

(56) References Cited

OTHER PUBLICATIONS

Varma and Palsson, "Metabolic flux balancing: basic concepts, scientific and practical use," *Bio/Technology*, 12:994-998 (1994).
Varma and Palsson, "Stoichiometric flux balance models quantitiatively predict growth and metabolic by-product secretion in wild-type *Escherichia coli* W3110," *Appl. Env. Micro.*, 60;3724-3731 (1994).
Vo TD, et al. Reconstruction and functional characterization of the human mitochondrial metabolic network based on proteomic and biochemical data. *J Biol Chem*. 279(38):39532-39540 (2004).

\* cited by examiner

| Mass Balances | Flux Constraints |
|---|---|
| $G: R_1 - R_2 - R_4 = 0$<br>$B: R_2 - R_3 = 0$<br>$C: R_4 - R_5 = 0$<br>$D: R_5 - V_{growth} = 0$<br>$E: R_5 - R_6 = 0$<br>$F: 2R_3 - V_{growth} = 0$<br>$A_{external}: -A_{xt} - R_1 = 0$<br>$E_{external}: R_6 - E_{xt} = 0$ | $0 \leq R_1 \leq \infty$<br>$-\infty \leq R_2 \leq \infty$<br>$0 \leq R_3 \leq \infty$<br>$0 \leq R_4 \leq \infty$<br>$0 \leq R_5 \leq \infty$<br>$0 \leq R_6 \leq \infty$<br>$0 \leq V_{growth} \leq \infty$<br>$Y_1 \leq A_{xt} \leq Y_1$<br>$-\infty \leq E_{xt} \leq \infty$ |
| Objective Function<br>$Z = V_{growth}$ | |

Figure 2

$$\begin{bmatrix} R_1 & R_2 & R_3 & R_4 & R_5 & R_6 & V_{growth} & A_{xt} & E_{xt} \\ 0 & 0 & -1 & 0 & 0 & 0 & 0 & 0 & 0 \\ 0 & 0 & 0 & -1 & -1 & 0 & 0 & 0 & 0 \\ 0 & 0 & 0 & 0 & 1 & 0 & -1 & 0 & 0 \\ 0 & 0 & 0 & 0 & 1 & -1 & 0 & 0 & 0 \\ -1 & 0 & 2 & 0 & 0 & 0 & 0 & 0 & 0 \\ 1 & 0 & 0 & -1 & 0 & 0 & 0 & 0 & 0 \\ -1 & -1 & 0 & 0 & 0 & 1 & 0 & -1 & 0 \\ 0 & 0 & 0 & 0 & 0 & 0 & 0 & -1 & 0 \\ 0 & 0 & 0 & 0 & 0 & 0 & 0 & 0 & -1 \end{bmatrix} \begin{bmatrix} B \\ C \\ D \\ E \\ F \\ G \\ A_{external} \\ E_{external} \end{bmatrix} = \begin{bmatrix} 0 \\ 0 \\ 0 \\ 0 \\ 0 \\ 0 \\ 0 \\ 0 \end{bmatrix}$$

Figure 3

Even Chain Fatty Acid Biosynthesis

Odd Chain Fatty Acid Biosynthesis
C17:1, n-8

Malate Aspartate Shuttle

Electron Transport Chain

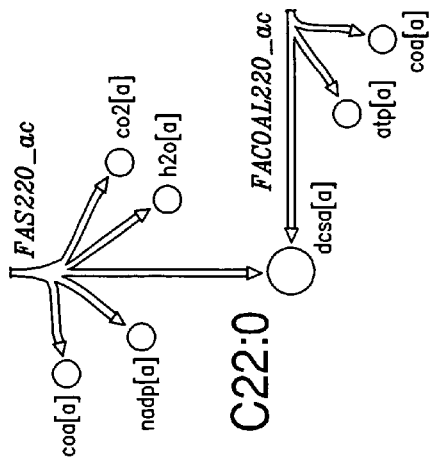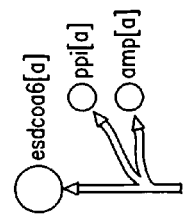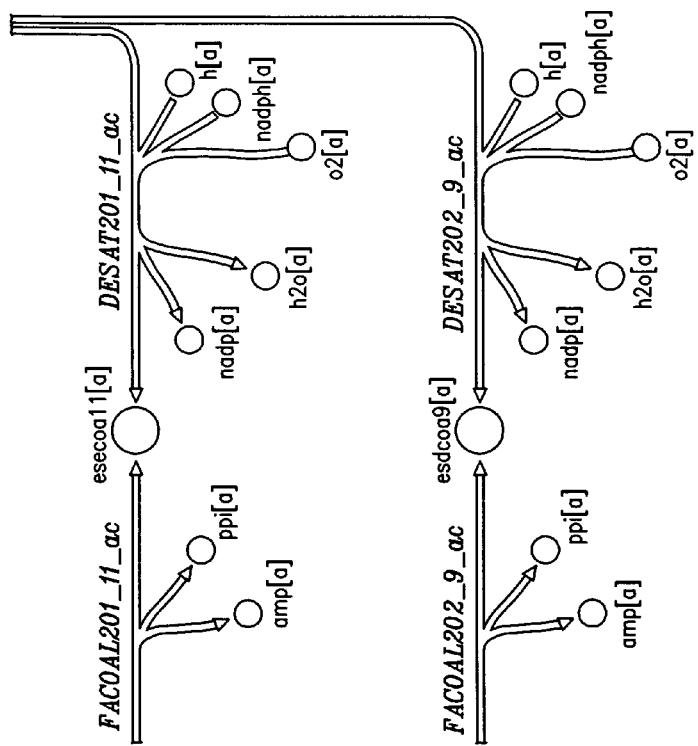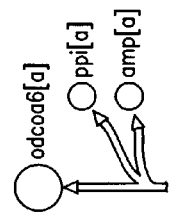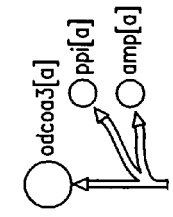
FIG. 7-27

FIG. 7-29
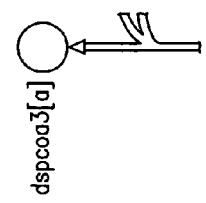
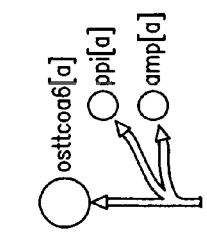
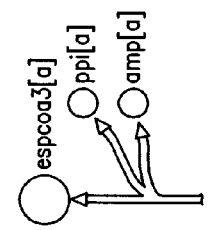
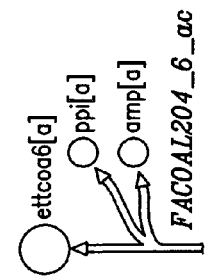

Net Reaction: ATP + H2O → ADP + Pi + H

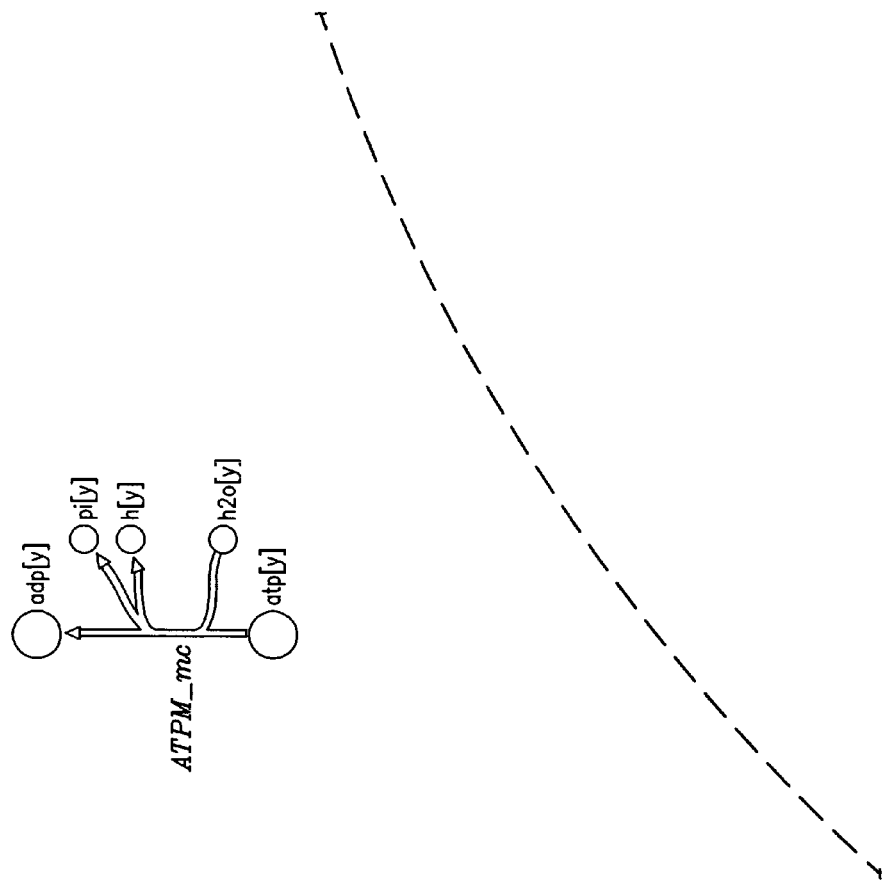
FIG. 9-8 Non-growth Associated Energy Maintainance

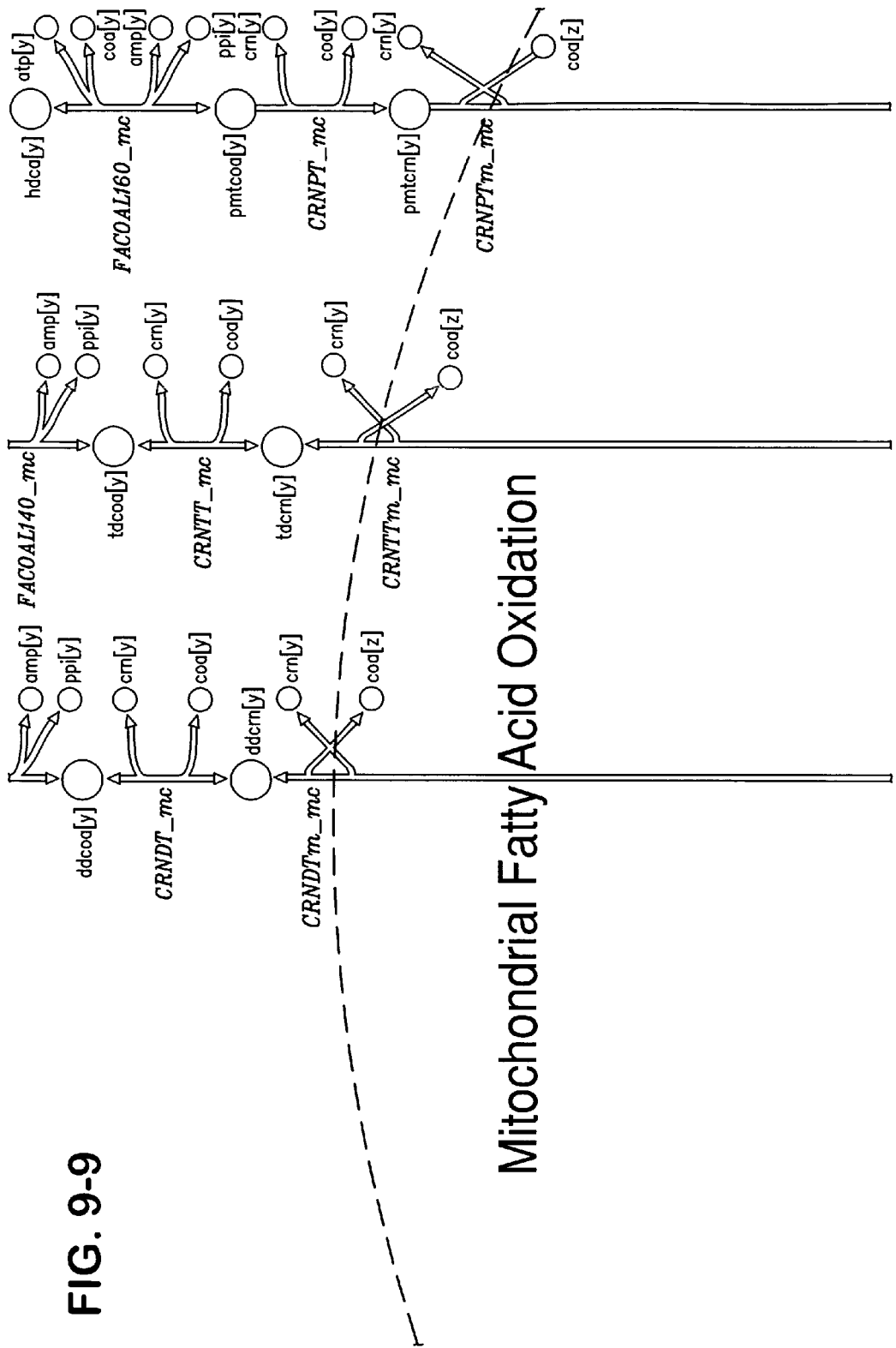
FIG. 9-9 Mitochondrial Fatty Acid Oxidation

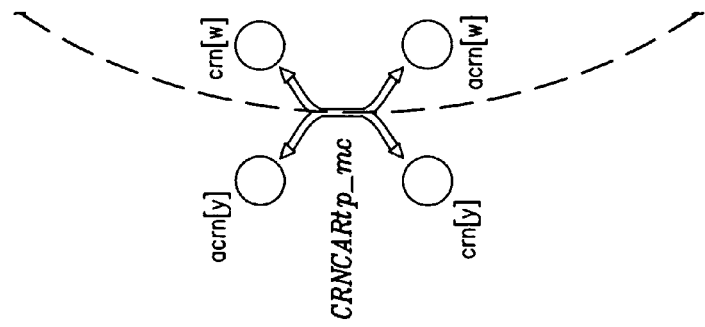
Phosphocreatine
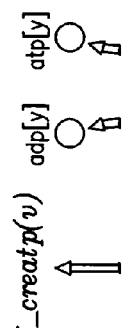
FIG. 9-27

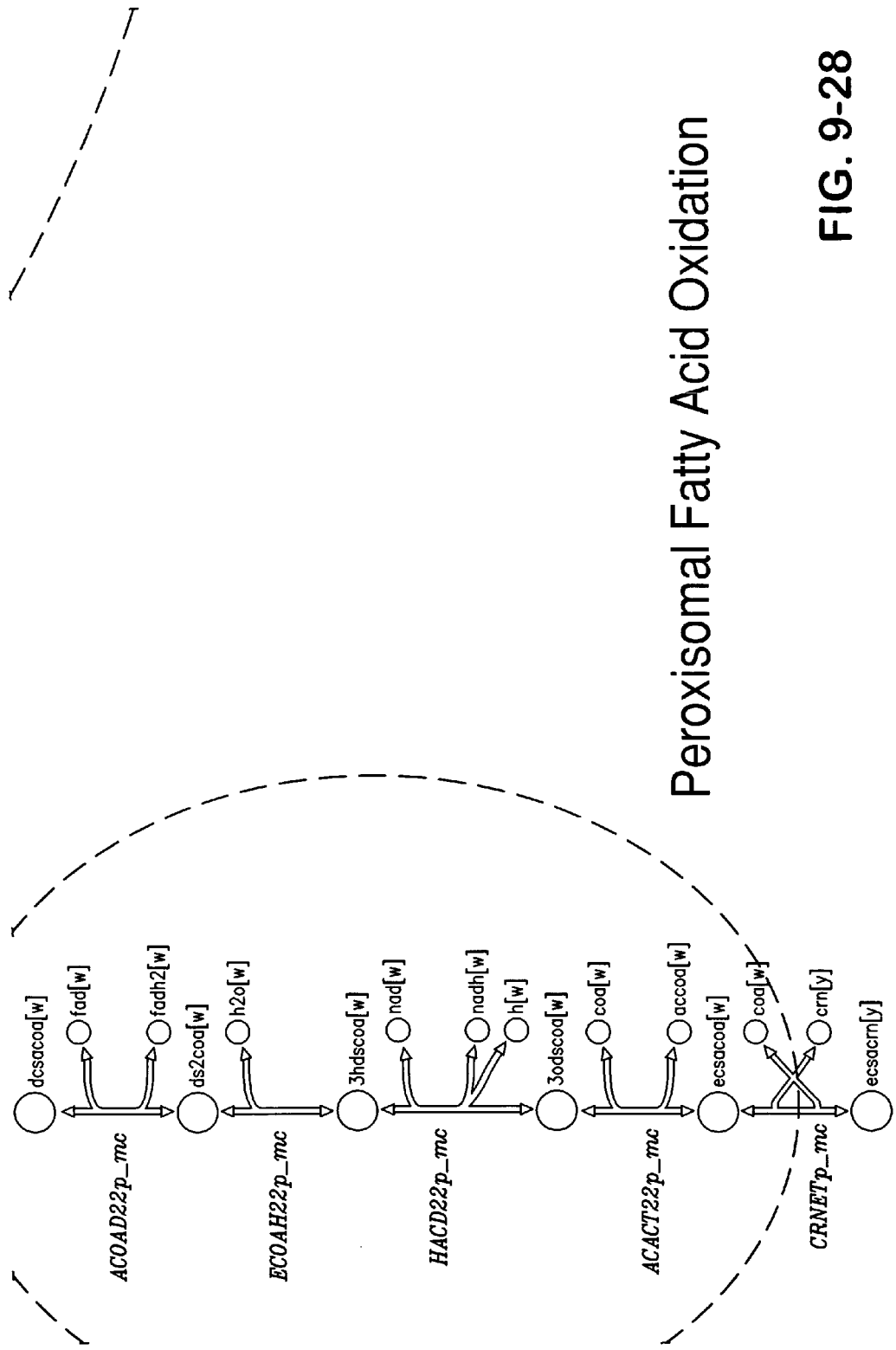
FIG. 9-28 Peroxisomal Fatty Acid Oxidation

FIG. 9-33

Bicarbonate Exchange via Kidneys

Mitochondrial Fatty Acid Oxidation

Unsaturated Fatty Acid Oxidation

Odd-chain Fatty Acid Oxidation

Odd Chain Fatty Acid Biosynthesis
C17:1, n-8

Glycerol Phosphate Shuttle

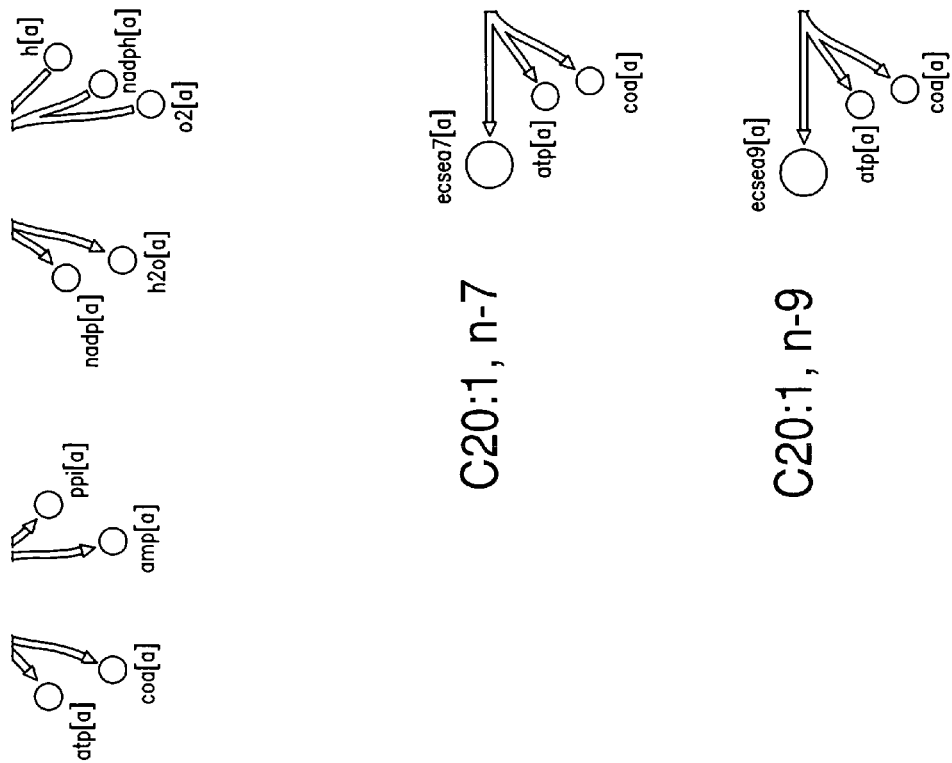
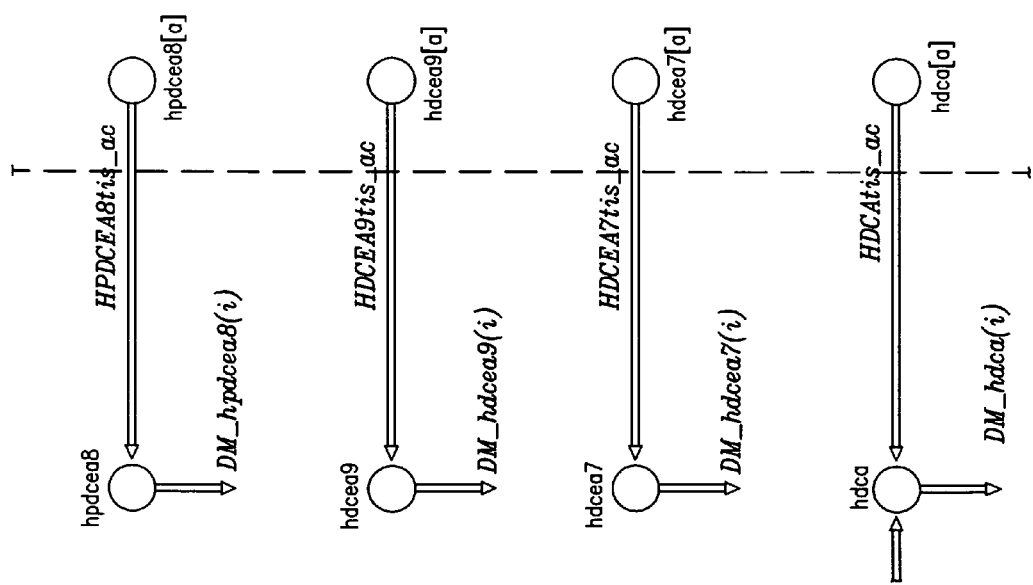
FIG. 10-46

Electron Transport Chain

FIG. 10-52
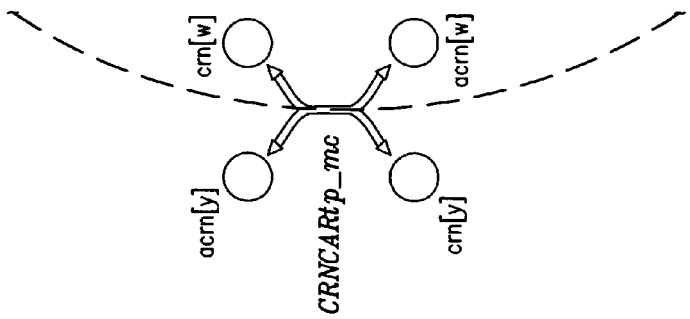
Phosphocreatine
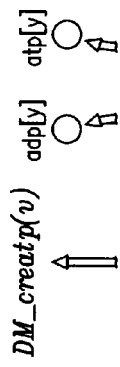

Peroxisomal Fatty Acid Oxidation

FIG. 10-56
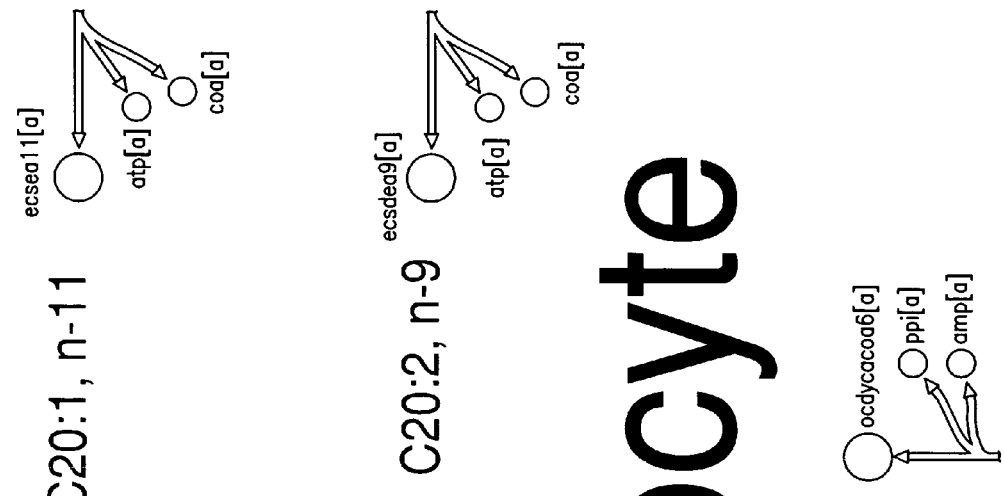
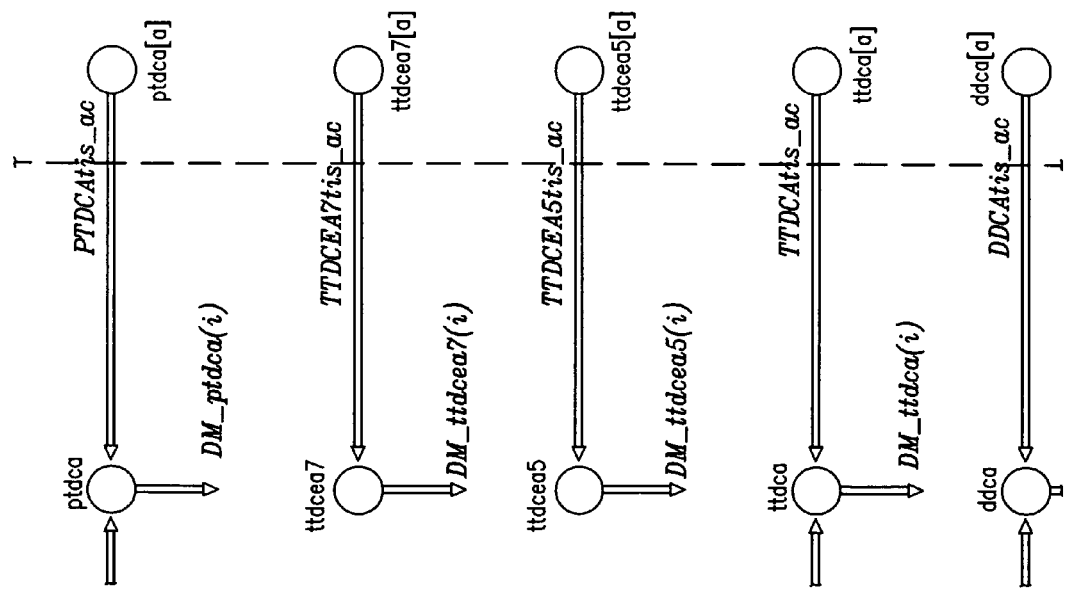

FIG. 10-59
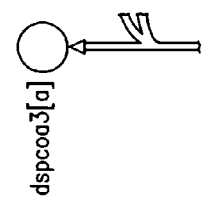
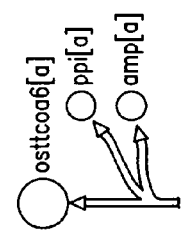
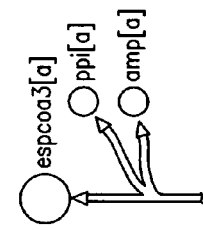
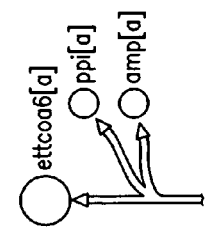

Essential Fatty Acids synthesized in kidney (Hunt, p.155)

Creatinine Secretion via Kidney

MULTICELLULAR METABOLIC MODELS AND METHODS

This application claims benefit of the filing date of U.S. Provisional Application No. 60/368,588, filed Mar. 29, 2002, and which is incorporated herein by reference.

This application is a continuation-in-part application of U.S. Ser. No. 10/402,854, filed Mar. 27, 2003, and which is incorporated herein by reference in its entirety.

BACKGROUND OF THE INVENTION

This invention relates generally to analysis of the activity of chemical reaction networks and, more specifically, to computational methods for simulating and predicting the activity of multiple interacting reaction networks.

Therapeutic agents, including drugs and gene-based agents, are being rapidly developed by the pharmaceutical industry with the goal of preventing or treating human disease. Dietary supplements, including herbal products, vitamins and amino acids, are also being developed and marketed by the nutraceutical industry. Because of the complexity of the biochemical reaction networks in and between human cells, even relatively minor perturbations caused by a therapeutic agent or a dietary component in the abundance or activity of a particular target, such as a metabolite, gene or protein, can affect hundreds of biochemical reactions. These perturbations can lead to desirable therapeutic effects, such as cell stasis or cell death in the case of cancer cells or other pathologically hyperproliferative cells. However, these perturbations can also lead to undesirable side effects, such as production of toxic byproducts, if the systemic effects of the perturbations are not taken into account.

Current approaches to drug and nutraceutical development do not take into account the effect of a perturbation in a molecular target on systemic cellular behavior. In order to design effective methods of repairing, engineering or disabling cellular activities, it is essential to understand human cellular behavior from an integrated perspective.

Cellular metabolism, which is an example of a process involving a highly integrated network of biochemical reactions, is fundamental to all normal cellular or physiological processes, including homeostatis, proliferation, differentiation, programmed cell death (apoptosis) and motility. Alterations in cellular metabolism characterize a vast number of human diseases. For example, tissue injury is often characterized by increased catabolism of glucose, fatty acids and amino acids, which, if persistent, can lead to organ dysfunction. Conditions of low oxygen supply (hypoxia) and nutrient supply, such as occur in solid tumors, result in a myriad of adaptive metabolic changes including activation of glycolysis and neovascularization. Metabolic dysfunctions also contribute to neurodegenerative diseases, cardiovascular disease, neuromuscular diseases, obesity and diabetes. Currently, despite the importance of cellular metabolism to normal and pathological processes, a detailed systemic understanding of cellular metabolism in human cells is currently lacking.

Thus, there exists a need for models that describe interacting reaction networks within and between cells, including core metabolic reaction networks and metabolic reaction networks in specialized cell types, which can be used to simulate different aspects of multicellular behavior under physiological, pathological and therapeutic conditions. The present invention satisfies this need, and provides related advantages as well.

SUMMARY OF THE INVENTION

The invention provides a computer readable medium or media, having: (a) a first data structure relating a plurality of reactants to a plurality of reactions from a first cell, each of said reactions comprising a reactant identified as a substrate of the reaction, a reactant identified as a product of the reaction and a stoichiometric coefficient relating said substrate and said product; (b) a second data structure relating a plurality of reactants to a plurality of reactions from a second cell, each of said reactions comprising a reactant identified as a substrate of the reaction, a reactant identified as a product of the reaction and a stoichiometric coefficient relating said substrate and said product; (c) a third data structure relating a plurality of intra-system reactants to a plurality of intra-system reactions between said first and second cells, each of said intra-system reactions comprising a reactant identified as a substrate of the reaction, a reactant identified as a product of the reaction and a stoichiometric coefficient relating said substrate and said product; (d) a constraint set for said plurality of reactions for said first, second and third data structures, and (e) commands for determining at least one flux distribution that minimizes or maximizes an objective function when said constraint set is applied to said first and second data structures, wherein said at least one flux distribution is predictive of a physiological function of said first and second cells. The first, second and third data structures also can include a plurality of data structures. Additionally provided is a method for predicting a physiological function of a multicellular organism. The method includes: (a) providing a first data structure relating a plurality of reactants to a plurality of reactions from a first cell, each of said reactions comprising a reactant identified as a substrate of the reaction, a reactant identified as a product of the reaction and a stoichiometric coefficient relating said substrate and said product; (b) providing a second data structure relating a plurality of reactants to a plurality of reactions from a second cell, each of said reactions comprising a reactant identified as a substrate of the reaction, a reactant identified as a product of the reaction and a stoichiometric coefficient relating said substrate and said product; (c) providing a third data structure relating a plurality of intra-system reactants to a plurality of intra-system reactions between said first and second cells, each of said intra-system reactions comprising a reactant identified as a substrate of the reaction, a reactant identified as a product of the reaction and a stoichiometric coefficient relating said substrate and said product; (d) providing a constraint set for said plurality of reactions for said first, second and third data structures; (e) providing an objective function, and (f) determining at least one flux distribution that minimizes or maximizes an objective function when said constraint set is applied to said first and second data structures, wherein said at least one flux distribution is predictive of a physiological function of said first and second cells.

DETAILED DESCRIPTION OF THE INVENTION

Figure 1:
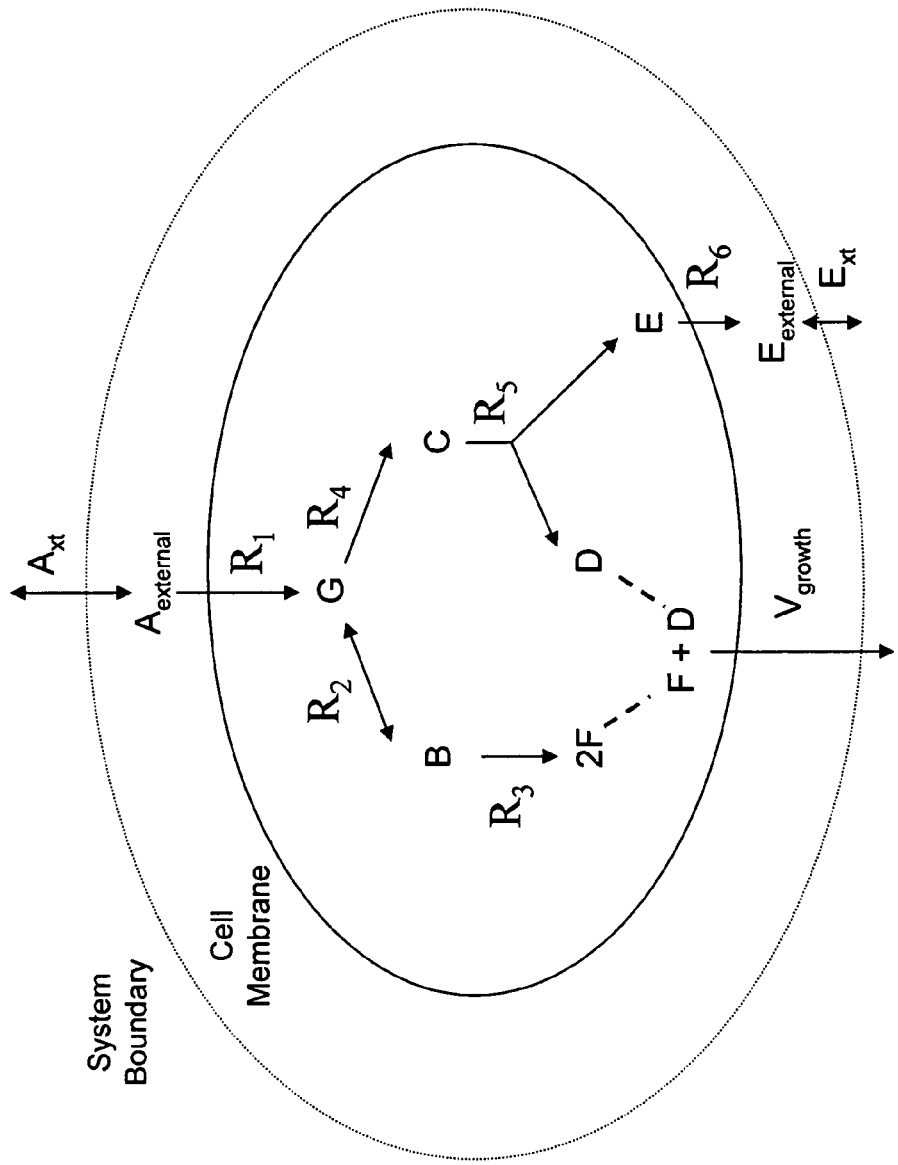
FIG. 1 shows a schematic representation of a hypothetical metabolic network.

The present invention provides in silico models that describe the interconnections between genes in the *Homo sapiens* genome and their associated reactions and reactants. The invention also provides in silico models that describe interconnections between different biochemical networks within a cell as well as between cells. The interconnections among different biochemical networks between cells can describe interactions between, for example, groups of cells including cells within different locations, tissues, organs or between cells carrying out different functions of a multicellular organism. Therefore, the models can be used to simulate different aspects of the cellular behavior of a cell derived from a multicellular organism, including a human cell, as well as be used to simulate different aspects of cellular behavioral interactions of groups of cells. Such groups of cells include, for example, eukaryotic cells, such as those of the same tissue type or colonies of prokaryotic cells, or different types of eukaryotic cells derived from the same or different tissue types from a multicellular organism. The different aspects of cellular behavior, including cellular behavioral interactions, can be simulated under different normal, pathological and therapeutic conditions, thereby providing valuable information for therapeutic, diagnostic and research applications. One advantage of the models of the invention is that they provide a holistic approach to simulating and predicting the activity of multicellular organisms, cellular interactions and individual cells, including the activity of *Homo sapiens* cells. Therefore, the models and methods can be used to simulate the activity of multiple interacting cells, including organs, physiological systems and whole body metabolism for practical diagnostic and therapeutic purposes.

In one embodiment, the invention is exemplified by reference to a metabolic model of a *Homo sapien* cell. This in silico model of an eukaryotic cell describes the cellular behavior resulting from two or more interacting networks because it can contain metabolic, regulatory and other network interactions, as described below. The models and methods of the invention applicable to the production and use of a cellular model containing two or more interacting networks also are applicable to the production and use of a multi-network model where the two or more networks are separated between compartments such as cells or tissues of a multicellular organism. Therefore, a *Homo sapien* or other eukaryotic cell model of the invention exemplifies application of the models and methods of the invention to models that describe the interaction of multiple biochemical networks between and among cells of a tissue, organ, physiological system or whole organism.

In another embodiment, the *Homo sapiens* metabolic models of the invention can be used to determine the effects of changes from aerobic to anaerobic conditions, such as occurs in skeletal muscles during exercise or in tumors, or to determine the effect of various dietary changes. The *Homo sapiens* metabolic models can also be used to determine the consequences of genetic defects, such as deficiencies in metabolic enzymes such as phosphofructokinase, phosphoglycerate kinase, phosphoglycerate mutase, lactate dehydrogenase and adenosine deaminase.

In a further embodiment, the invention provides a model of multicellular interactions that includes the network reconstruction, characteristics and simulation performance of an integrated two cell model of human adipocyte and myocyte cells. This multicellular model also included an intra-system biochemical network for extracellular physiological systems. The model was generated by reconstructing each of the component biochemical networks within the cells and combining them together with the addition of the intra-system biochemical network and achieved accurate predictive performance of the two cell types under different physiological conditions. Such multicellular metabolic models can be employed for the same determinations as described above for the *Homo sapiens* metabolic models. The determinations can be performed at the cellular, tissue, physiological system or organism level.

The multicellular and *Homo sapiens* metabolic models also can be used to choose appropriate targets for drug design. Such targets include genes, proteins or reactants, which when modulated positively or negatively in a simulation produce a desired therapeutic result. The models and methods of the invention can also be used to predict the effects of a therapeutic agent or dietary supplement on a cellular function of interest. Likewise, the models and methods can be used to predict both desirable and undesirable side effects of the therapeutic agent on an interrelated cellular function in the target cell, as well as the desirable and undesirable effects that may occur in other cell types. Thus, the models and methods of the invention can make the drug development process more rapid and cost effective than is currently possible.

The multicellular and *Homo sapiens* metabolic models also can be used to predict or validate the assignment of particular biochemical reactions to the enzyme-encoding genes found in the genome, and to identify the presence of reactions or pathways not indicated by current genomic data. Thus, the models can be used to guide the research and discovery process, potentially leading to the identification of new enzymes, medicines or metabolites of clinical importance.

The models of the invention are based on a data structure relating a plurality of reactants to a plurality of reactions, wherein each of the reactions includes a reactant identified as a substrate of the reaction, a reactant identified as a product of the reaction and a stoichiometric coefficient relating the substrate and the product. The reactions included in the data structure can be those that are common to all or most cells or to a particular type or species of cell, including *Homo sapiens* cells, such as core metabolic reactions, or reactions specific for one or more given cell type.

As used herein, the term "reaction" is intended to mean a conversion that consumes a substrate or forms a product that occurs in or by a cell. The term can include a conversion that occurs due to the activity of one or more enzymes that are genetically encoded by a genome of the cell. The term can also include a conversion that occurs spontaneously in a cell. When used in reference to a *Homo sapiens* reaction, the term is intended to mean a conversion that consumes a substrate or forms a product that occurs in or by a *Homo sapiens* cell.

Conversions included in the term include, for example, changes in chemical composition such as those due to nucleophilic or electrophilic addition, nucleophilic or electrophilic substitution, elimination, isomerization, deamination, phosphorylation, methylation, reduction, oxidation or changes in location such as those that occur due to a transport reaction that moves a reactant from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "reactant" is intended to mean a chemical that is a substrate or a product of a reaction that occurs in or by a cell. The term can include substrates or products of reactions performed by one or more enzymes encoded by a genome, reactions occurring in cells or organisms that are performed by one or more non-genetically encoded macromolecule, protein or enzyme, or reactions that occur spontaneously in a cell. When used in reference to a *Homo sapiens* reactant, the term is intended to mean a chemical that is a substrate or product of a reaction that occurs in or by a *Homo sapiens* cell. Metabolites are understood to be reactants within the meaning of the term. It will be understood that when used in reference to an in silico model or data structure, a reactant is intended to be a representation of a chemical that is a substrate or a product of a reaction that occurs in or by a cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to reactions or reactants including *Homo sapiens* reactions or reactants, is intended to mean at least 2 reactions or reactants. The term can include any number of reactions or reactants in the range from 2 to the number of naturally occurring reactants or reactions for a particular of cell or cells. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular cell or cells including a *Homo sapiens* cell or cells, such as at least 20%, 30%, 50%, 60%, 75%, 90%, 95% or 98% of the total number of naturally occurring reactions that occur in a particular *Homo sapiens* cell.

Similarly, the term "plurality," when used in reference to data structures, is intended to mean at least 2 data structures. The term can include any number of data structures in the range from 2 to the number of naturally occurring biochemical networks for a particular subsystem, system, intracellular system, cellular compartment, organelle, extra-cellular space, cytosol, mitochondrion, nucleus, endoplasmic reticulum, group of cells, tissue, organ or organism. Therefore, the term can include, for example, at least about 3, 4, 5, 6, 7, 8, 9, 10, 25, 20, 25, 50, 100 or more biochemical networks. The term also can be expressed as a portion of the total number of naturally occurring networks for any of the particular categories above occurring in prokaryotic or eukaryotic cells including *Homo sapiens*.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, or a stoichiometric coefficient.

As used herein, the term "constraint" is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer. Alternatively, a boundary can be a variable boundary value as set forth below.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "activity," when used in reference to a *Homo sapiens* cell or a multicellular interaction, is intended to mean the magnitude or rate of a change from an initial state to a final state. The term can include, for example, the amount of a chemical consumed or produced by a cell, the rate at which a chemical is consumed or produced by a cell, the amount or rate of growth of a cell or the amount of or rate at which energy, mass or electrons flow through a particular subset of reactions.

The invention provides a computer readable medium, having a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product.

Also provided is a computer readable medium or media, having: (a) a first data structure relating a plurality of reactants to a plurality of reactions from a first cell, each of said reactions comprising a reactant identified as a substrate of the reaction, a reactant identified as a product of the reaction and a stoichiometric coefficient relating said substrate and said product; (b) a second data structure relating a plurality of reactants to a plurality of reactions from a second cell, each of said reactions comprising a reactant identified as a substrate of the reaction, a reactant identified as a product of the reaction and a stoichiometric coefficient relating said substrate and said product; (c) a third data structure relating a plurality of intra-system reactants to a plurality of intra-system reactions between said first and second cells, each of said intra-system reactions comprising a reactant identified as a substrate of the reaction, a reactant identified as a product of the reaction and a stoichiometric coefficient relating said substrate and said product; (c) a constraint set for said plurality of reactions for said first, second and third data structures, and (d) commands for determining at least one flux distribution that minimizes or maximizes an objective function when said constraint set is applied to said first and second data structures, wherein said at least one flux distribution is predictive of a physiological function of said first and second cells.

Depending on the application, the plurality of reactions for any of a multicellular, multi-network or single cell model or method of the invention, including a *Homo sapiens* cell model or method, can include reactions selected from core metabolic reactions or peripheral metabolic reactions. As used herein, the term "core," when used in reference to a metabolic pathway, is intended to mean a metabolic pathway selected from glycolysis/gluconeogenesis, the pentose phosphate pathway (PPP), the tricarboxylic acid (TCA) cycle, glycogen storage, electron transfer system (ETS), the malate/aspartate shuttle, the glycerol phosphate shuttle, and plasma and mitochondrial membrane transporters. As used herein, the term "peripheral," when used in reference to a metabolic pathway, is intended to mean a metabolic pathway that includes one or more reactions that are not a part of a core metabolic pathway.

A plurality of reactants can be related to a plurality of reactions in any data structure that represents, for each reactant, the reactions by which it is consumed or produced. Thus, the data structure, which is referred to herein as a "reaction network data structure," serves as a representation of a biological reaction network or system. An example of a reaction network that can be represented in a reaction network data structure of the invention is the collection of reactions that constitute the core metabolic reactions of *Homo sapiens,* or the metabolic reactions of a skeletal muscle cell, as shown in the Examples. Further examples of reaction networks that can be represented in a reaction network data structure of the invention are the collection of reactions that constitute the core metabolic reactions and the triacylglycerol (TAG) biosynthetic pathways of an adipocyte cell; the core metabolic reactions and the energy and contractile reactions of a myocyte cell, and the intra-system reactions that supply buffering functions of the kidney.

The choice of reactions to include in a particular reaction network data structure, from among all the possible reactions that can occur in multicellular organisms or among multicellular interactions, including human cells, depends on the cell type or types and the physiological, pathological or therapeutic condition being modeled, and can be determined experimentally or from the literature, as described further below.

The reactions to be included in a particular network data structure of a multicellular interaction can be determined experimentally using, for example, gene or protein expression profiles, where the molecular characteristics of the cell can be correlated to the expression levels. The expression or lack of expression of genes or proteins in a cell type can be used in determining whether a reaction is included in the model by association to the expressed gene(s) and or protein(s). Thus, it is possible to use experimental technologies to determine which genes and/or proteins are expressed in a specific cell type, and to further use this information to determine which reactions are present in the cell type of interest. In this way a subset of reactions from all of those reactions that can occur in human cells are selected to comprise the set of reactions that represent a specific cell type. cDNA expression profiles have been demonstrated to be useful, for example, for classification of breast cancer cells (Sorlie et al., *Proc. Natl. Acad. Sci. U.S.A.* 98(19):10869-10874 (2001)).

The methods and models of the invention can be applied to any multicellular interaction as well as to any *Homo sapiens* cell type at any stage of differentiation, including, for example, embryonic stem cells, hematopoietic stem cells, differentiated hematopoietic cells, skeletal muscle cells, cardiac muscle cells, smooth muscle cells, skin cells, nerve cells, kidney cells, pulmonary cells, liver cells, adipocytes and endocrine cells (e.g. beta islet cells of the pancreas, mammary gland cells, adrenal cells, and other specialized hormone secreting cells). Similarly, the methods and models of the invention can be applied to any interaction between any of these cell types, including two or more of the same cell type or two or more different cell types. Described below in Example IV is an example of the interactions that occur between myocyte cells and adipocyte cells during different physiological conditions.

The methods and models of the invention can be applied to normal cells, pathological cells as well as to combinations of interactions between normal cells, interactions between pathological cells or interactions between normal and pathological cells. Normal cells that exhibit a variety of physiological activities of interest, including homeostasis, proliferation, differentiation, apoptosis, contraction and motility, can be modeled. Pathological cells can also be modeled, including cells that reflect genetic or developmental abnormalities, nutritional deficiencies, environmental assaults, infection (such as by bacteria, viral, protozoan or fungal agents), neoplasia, aging, altered immune or endocrine function, tissue damage, or any combination of these factors. The pathological cells can be representative of any type of pathology, such as a human pathology, including, for example, various metabolic disorders of carbohydrate, lipid or protein metabolism, obesity, diabetes, cardiovascular disease, fibrosis, various cancers, kidney failure, immune pathologies, neurodegenerative diseases, and various monogenetic metabolic diseases described in the Online Mendelian Inheritance in Man database (Center for Medical Genetics, Johns Hopkins University (Baltimore, Md.) and National Center for Biotechnology Information, National Library of Medicine (Bethesda, Md.)).

The methods and models of the invention can also be applied to cells or organisms undergoing therapeutic perturbations, such as cells treated with drugs that target participants in a reaction network or cause an effect on an interactive reaction network, cells or tissues treated with gene-based therapeutics that increase or decrease expression of an encoded protein, and cells or tissues treated with radiation. As used herein, the term "drug" refers to a compound of any molecular nature with a known or proposed therapeutic function, including, for example, small molecule compounds, peptides and other macromolecules, peptidomimetics and antibodies, any of which can optionally be tagged with cytostatic, targeting or detectable moieties. The term "gene-based therapeutic" refers to nucleic acid therapeutics, including, for example, expressible genes with normal or altered protein activity, antisense compounds, ribozymes, DNAzymes, RNA interference compounds (RNAi) and the like. The therapeutics can target any reaction network participant, in any cellular location, including participants in extracellular, cell surface, cytoplasmic, mitochondrial and nuclear locations. Experimental data that are gathered on the response of cells, tissues, or interactions thereof, to therapeutic treatment, such as alterations in gene or protein expression profiles, can be used to tailor a network or a combination of networks for a pathological state of a particular cell type.

The methods and models of the invention can be applied to cells, tissues and physiological systems, including *Homo sapiens* cells, tissues and physiological systems, as they exist in any form, such as in primary cell isolates or in established cell lines, or in the whole body, in intact organs or in tissue explants. Accordingly, the methods and models can take into account intercellular communications and/or inter-organ communications, the effect of adhesion to a substrate or neighboring cells (such as a stem cell interacting with mesenchymal cells or a cancer cell interacting with its tissue microenvironment, or beta-islet cells without normal stroma), and other interactions relevant to multicellular systems.

The reactants to be used in a reaction network data structure of the invention can be obtained from or stored in a compound database. As used herein, the term "compound database" is intended to mean a computer readable medium or media containing a plurality of molecules that includes substrates and products of biological reactions. The plurality of molecules can include molecules found in multiple organisms, thereby constituting a universal compound database. Alternatively, the plurality of molecules can be limited to those that occur in a particular organism, thereby constituting an organism-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space, the interior space of an organelle such as a mitochondrium, endoplasmic reticulum, Golgi apparatus, vacuole or nucleus; or any subcellular space that is separated from another by a membrane or other physical barrier. For example, a mitochondrial compartment is a subdivided region of the intracellular space of a cell, which in turn, is a subdivided region of a cell or tissue. A subdivided region also can include, for example, different regions or systems of a tissue, organ or physiological system of an organism. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of metabolic reactions of *Homo sapiens*, other multicellular organisms or single cell organisms that exhibit biochemical or physiological interactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced interconversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus a reaction that simply transports a metabolite from the extracellular environment to the cytosol, without changing its chemical composition is solely classified as a translocation, while a reaction that takes an extracellular substrate and converts it into a cytosolic product is both a translocation and a transformation. Further, intra-system reactions can include reactions representing one or more biochemical or physiological functions of an independent cell, tissue, organ or physiological system. For example, the buffering function of the kidneys for the hematopoietic system and intra-cellular environments can be represented as intra-system reactions and be included in a multicellular interaction model either as an independent reaction network or merged with one or more reaction networks of the constituent cells.

Exchange reactions are those which constitute sources and sinks, allowing the passage of metabolites into and out of a compartment or across a hypothetical system boundary. These reactions are included in a model for simulation purposes and represent the metabolic demands placed on *Homo sapiens*. While they may be chemically balanced in certain cases, they are typically not balanced and can often have only a single substrate or product. As a matter of convention the exchange reactions are further classified into demand exchange and input/output exchange reactions.

The metabolic demands placed on a multicellular or *Homo sapiens* metabolic reaction network can be readily determined from the dry weight composition of the cell, cells, tissue, organ or organism which is available in the published literature or which can be determined experimentally. The uptake rates and maintenance requirements for *Homo sapiens* cells can also be obtained from the published literature or determined experimentally.

Input/output exchange reactions are used to allow extracellular reactants to enter or exit the reaction network represented by a model of the invention. For each of the extracellular metabolites a corresponding input/output exchange reaction can be created. These reactions are always reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reactions can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion or muscle contraction; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular or organismic growth rate.

A specific reaction network is provided in FIG. 1 to exemplify the above-described reactions and their interactions. The reactions can be represented in the exemplary data structure shown in FIG. 3 as set forth below. The reaction network, shown in FIG. 1, includes intra-system reactions that occur entirely within the compartment indicated by the shaded oval such as reversible reaction $R_2$ which acts on reactants B and G and reaction $R_3$ which converts one equivalent of B to 2 equivalents of F. The reaction network shown in FIG. 1 also contains exchange reactions such as input/output exchange reactions $A_{xt}$ and $E_{xt}$, and the demand exchange reaction, $V_{growth}$, which represents growth in response to the one equivalent of D and one equivalent of F. Other intra-system reactions include $R_1$ which is a translocation and transformation reaction that translocates reactant A into the compartment and transforms it to reactant G and reaction $R_6$ which is a transport reaction that translocates reactant E out of the compartment.

A reaction network can be represented as a set of linear algebraic equations which can be presented as a stoichiometric matrix S, with S being an m×n matrix where m corresponds to the number of reactants or metabolites and n corresponds to the number of reactions taking place in the network. An example of a stoichiometric matrix representing the reaction network of FIG. 1 is shown in FIG. 3. As shown in FIG. 3, each column in the matrix corresponds to a particular reaction n, each row corresponds to a particular reactant m, and each $S_{mn}$ element corresponds to the stoichiometric coefficient of the reactant m in the reaction denoted n. The stoichiometric matrix includes intra-system reactions such as $R_2$ and $R_3$ which are related to reactants that participate in the respective reactions according to a stoichiometric coefficient having a sign indicative of whether the reactant is a substrate or product of the reaction and a value correlated with the number of equivalents of the reactant consumed or produced by the reaction. Exchange reactions such as $-E_{xt}$ and $-A_{xt}$ are similarly correlated with a stoichiometric coefficient. As exemplified by reactant E, the same compound can be treated separately as an internal reactant (E) and an external reactant ($E_{external}$) such that an exchange reaction ($R_6$) exporting the compound is correlated by stoichiometric coefficients of $-1$ and 1, respectively. However, because the compound is treated as a separate reactant by virtue of its compartmental location, a reaction, such as $R_5$, which produces the internal reactant (E) but does not act on the external reactant ($E_{external}$) is correlated by stoichiometric coefficients of 1 and 0, respectively. Demand reactions such as $V_{growth}$ can also be included in the stoichiometric matrix being correlated with substrates by an appropriate stoichiometric coefficient.

As set forth in further detail below, a stoichiometric matrix provides a convenient format for representing and analyzing a reaction network because it can be readily manipulated and used to compute network properties, for example, by using linear programming or general convex analysis. A reaction network data structure can take on a variety of formats so long as it is capable of relating reactants and reactions in the manner exemplified above for a stoichiometric matrix and in a manner that can be manipulated to determine an activity of one or more reactions using methods such as those exemplified below. Other examples of reaction network data structures that are useful in the invention include a connected graph, list of chemical reactions or a table of reaction equations.

A reaction network data structure can be constructed to include all reactions that are involved in metabolism occurring during the interaction of two or more cells, *Homo sapiens* cell metabolism or any portion thereof. A portion of an organisms metabolic reactions that can be included in a reaction network data structure of the invention includes, for example, a central metabolic pathway such as glycolysis, the TCA cycle, the PPP or ETS; or a peripheral metabolic pathway such as amino acid biosynthesis, amino acid degradation, purine biosynthesis, pyrimidine biosynthesis, lipid biosynthesis, fatty acid metabolism, vitamin or cofactor biosynthesis, transport processes and alternative carbon source catabolism. Examples of individual pathways within the peripheral pathways are set forth in Table 1. Other examples of portions of metabolic reactions that can be included in a reaction network data structure of the invention include, for example, TAG biosynthesis, muscle contraction requirements, bicarbonate buffer system and/or ammonia buffer system. Specific examples of these and other reactions are described further below and in the Examples.

Depending upon a particular application, a reaction network data structure can include a plurality of *Homo sapiens* reactions including any or all of the reactions listed in Table 1. Similarly, a reaction network data structure also can include the reaction set forth in Examples I-IV and include, for example, single reaction networks, multiple reaction networks that interact within a cell as well as multiple reaction networks that interact between cells or physiological systems.

For some applications, it can be advantageous to use a reaction network data structure that includes a minimal number of reactions to achieve a particular *Homo sapiens* activity or activity of a multicellular interaction under a particular set of environmental conditions. A reaction network data structure having a minimal number of reactions can be identified by performing the simulation methods described below in an iterative fashion where different reactions or sets of reactions are systematically removed and the effects observed. Accordingly, the invention provides a computer readable medium, containing a data structure relating a plurality of *Homo sapiens* reactants to a plurality of *Homo sapiens* reactions, wherein the plurality of *Homo sapiens* reactions contains at least 65 reactions. For example, the core metabolic reaction database shown in Tables 2 and 3 contains 65 reactions, and is sufficient to simulate aerobic and anaerobic metabolism on a number of carbon sources, including glucose. Similarly, the invention provides a computer readable medium containing a data structure relating a plurality of reactants of multicellular interactions to a plurality of reactions from multicellular interactions, wherein the reactions contain at least 430 for a two cell interaction. Such reactions between multicellular interactions are exemplified in Table 11, for example.

Depending upon the particular cell type or types, the physiological, pathological or therapeutic conditions being tested, the desired activity and the number of cellular interactions of a model or method of the invention, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in or by multicellular interactions, including *Homo sapiens*, or that are desired to simulate the activity of the full set of reactions occurring in multicellular interactions, including *Homo sapiens*. A reaction network data structure that is substantially complete with respect to the metabolic reactions of a multicellular organism, including *Homo sapiens*, provides an advantage of being relevant to a wide range of conditions to be simulated, whereas those with smaller numbers of metabolic reactions are specific to a particular subset of conditions to be simulated.

A *Homo sapiens* reaction network data structure can include one or more reactions that occur in or by *Homo sapiens* and that do not occur, either naturally or following manipulation, in or by another organism, such as *Saccharomyces cerevisiae*. It is understood that a *Homo sapiens* reaction network data structure of a particular cell type can also include one or more reactions that occur in another cell type. Addition of such heterologous reactions to a reaction network data structure of the invention can be used in methods to predict the consequences of heterologous gene transfer and protein expression, for example, when designing in vivo and ex vivo gene therapy approaches. Similarly, reaction networks for a multicellular interactions also can include one or more reactions that occur entirely within the species of origin of the cellular interactions or can contain one or more heterologous reactions from one or more different species.

The reactions included in a reaction network data structure of the invention can be metabolic reactions. A reaction network data structure can also be constructed to include other types of reactions such as regulatory reactions, signal transduction reactions, cell cycle reactions, reactions controlling developmental processes, reactions involved in apoptosis, reactions involved in responses to hypoxia, reactions involved in responses to cell-cell or cell-substrate interactions, reactions involved in protein synthesis and regulation thereof, reactions involved in gene transcription and translation, and regulation thereof, and reactions involved in assembly of a cell and its subcellular components.

A reaction network data structure or index of reactions used in the data structure such as that available in a metabolic reaction database, as described above, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction, a subset of reactions to which the reaction belongs, citations to references from which information was obtained, or a level of confidence with which a reaction is believed to occur in *Homo sapiens* or other organism. A computer readable medium or media of the invention can include a gene database containing annotated reactions. Such information can be obtained during the course of building a metabolic reaction database or model of the invention as described below.

As used herein, the term "gene database" is intended to mean a computer readable medium or media that contains at least one reaction that is annotated to assign a reaction to one or more macromolecules that perform the reaction or to assign one or more nucleic acid that encodes the one or more macromolecules that perform the reaction. A gene database can contain a plurality of reactions, some or all of which are annotated. An annotation can include, for example, a name for a macromolecule; assignment of a function to a macromolecule; assignment of an organism that contains the macromolecule or produces the macromolecule; assignment of a subcellular location for the macromolecule; assignment of conditions under which a macromolecule is regulated with respect to performing a reaction, being expressed or being degraded; assignment of a cellular component that regulates a macromolecule; an amino acid or nucleotide sequence for the macromolecule; a mRNA isoform, enzyme isoform, or any other desirable annotation or annotation found for a macromolecule in a genome database such as those that can be found in Genbank, a site maintained by the NCBI (ncbi.nlm.gov), the Kyoto Encyclopedia of Genes and Genomes (KEGG) (www.genome.ad.jp/kegg/), the protein database SWISS-PROT (ca.expasy.org/sprot/), the LocusLink database maintained by the NCBI (www.ncbi.nlm.nih.gov/LocusLink/), the Enzyme Nomenclature database maintained by G. P. Moss of Queen Mary and Westfield College in the United Kingdom (www.chem.qmw.ac.uk/iubmb/enzyme/).

A gene database of the invention can include a substantially complete collection of genes or open reading frames in a multicellular organism, including *Homo sapiens*, or a substantially complete collection of the macromolecules encoded by the organism's genome. Alternatively, a gene database can include a portion of genes or open reading frames in an organism or a portion of the macromolecules encoded by the organism's genome, such as the portion that includes substantially all metabolic genes or macromolecules. The portion can be at least 10%, 15%, 20%, 25%, 50%, 75%, 90% or 95% of the genes or open reading frames encoded by the organism's genome, or the macromolecules encoded therein. A gene database can also include macromolecules encoded by at least a portion of the nucleotide sequence for the organism's genome such as at least 10%, 15%, 20%, 25%, 50%, 75%, 90% or 95% of the organism's genome. Accordingly, a computer readable medium or media of the invention can include at least one reaction for each macromolecule encoded by a portion of an organism's genome, including a *Homo sapiens* genome.

An in silico model of multicellular interactions, including a *Homo sapiens* model, of the invention can be built by an iterative process which includes gathering information regarding particular reactions to be added to a model, representing the reactions in a reaction network data structure, and performing preliminary simulations wherein a set of constraints is placed on the reaction network and the output evaluated to identify errors in the network. Errors in the network such as gaps that lead to non-natural accumulation or consumption of a particular metabolite can be identified as described below and simulations repeated until a desired performance of the model is attained. An exemplary method for iterative model construction is provided in Example I. For multicellular interactions, an iterative process includes producing one or more component reaction networks followed by combining the components into a higher order multi-network system, as described in Example IV. For example, components can include the central metabolism reaction network and the cell specific reaction networks such as TAG biosynthesis for adipocytes or muscle contraction for myocytes. Combination of the central metabolism and the cell specific reaction networks into a single model produces, for example, a cell specific reaction network. Components also can include the individual cell types, tissues, physiological systems or intra-system reaction networks that are constituents of the larger multicellular system. Combining these components into a larger model produces, for example, a model describing the relationships and interactions of the multicellular system together with its various interactions.

Thus, the invention provides a method for making a data structure relating a plurality of reactants to a plurality of reactions in a computer readable medium or media. The method includes the steps of: (a) identifying a plurality of reactions and a plurality of reactants that are substrates and products of the reactions; (b) relating the plurality of reactants to the plurality of *Homo sapiens* reactions in a data structure, wherein each of the reactions includes a reactant identified as a substrate of the reaction, a reactant identified as a product of the reaction and a stoichiometric coefficient relating the substrate and the product; (c) making a constraint set for the plurality of reactions; (d) providing an objective function; (e) determining at least one flux distribution that minimizes or maximizes the objective function when the constraint set is applied to the data structure, and (f) if the at least one flux distribution is not predictive of physiology, then adding a reaction to or deleting a reaction from the data structure and repeating step (e), if the at least one flux distribution is predictive of physiology, then storing the data structure in a computer readable medium or media. The method can be applied to multicellular interactions within or among single or multicullar organisms, including *Homo sapiens*.

Information to be included in a data structure of the invention can be gathered from a variety of sources including, for example, annotated genome sequence information and biochemical literature.

Sources of annotated human genome sequence information include, for example, KEGG, SWISS-PROT, LocusLink, the Enzyme Nomenclature database, the International Human Genome Sequencing Consortium and commercial databases. KEGG contains a broad range of information, including a substantial amount of metabolic reconstruction. The genomes of 304 organisms can be accessed here, with gene products grouped by coordinated functions, often represented by a map (e.g., the enzymes involved in glycolysis would be grouped together). The maps are biochemical pathway templates which show enzymes connecting metabolites for various parts of metabolism. These general pathway templates are customized for a given organism by highlighting enzymes on a given template which have been identified in the genome of the organism. Enzymes and metabolites are active and yield useful information about stoichiometry, structure, alternative names and the like, when accessed.

SWISS-PROT contains detailed information about protein function. Accessible information includes alternate gene and gene product names, function, structure and sequence information, relevant literature references, and the like.

LocusLink contains general information about the locus where the gene is located and, of relevance, tissue specificity, cellular location, and implication of the gene product in various disease states.

The Enzyme Nomenclature database can be used to compare the gene products of two organisms. Often the gene names for genes with similar functions in two or more organisms are unrelated. When this is the case, the E.C. (Enzyme Commission) numbers can be used as unambiguous indicators of gene product function. The information in the Enzyme Nomenclature database is also published in Enzyme Nomenclature (Academic Press, San Diego, Calif., 1992) with 5 supplements to date, all found in the European Journal of Biochemistry (Blackwell Science, Malden, Mass.).

Sources of biochemical information include, for example, general resources relating to metabolism, resources relating specifically to human metabolism, and resources relating to the biochemistry, physiology and pathology of specific human cell types.

Sources of general information relating to metabolism, which were used to generate the human reaction databases and models described herein, were J. G. Salway, *Metabolism at a Glance*, $2^{nd}$ ed., Blackwell Science, Malden, Mass. (1999) and T. M. Devlin, ed., *Textbook of Biochemistry with Clinical Correlations*, $4^{th}$ ed., John Wiley and Sons, New York, N.Y. (1997). Human metabolism-specific resources included J. R. Bronk, *Human Metabolism: Functional Diversity and Integration*, Addison Wesley Longman, Essex, England (1999).

The literature used in conjunction with the skeletal muscle metabolic models and simulations described herein included R. Maughan et al., *Biochemistry of Exercise and Training*, Oxford University Press, Oxford, England (1997), as well as references on muscle pathology such as S. Carpenter et al., *Pathology of Skeletal Muscle*, $2^{nd}$ ed., Oxford University Press, Oxford, England (2001), and more specific articles on muscle metabolism as may be found in the Journal of Physiology (Cambridge University Press, Cambridge, England).

In the course of developing an in silico model of metabolism during or for multicellular interactions, the types of data that can be considered include, for example, biochemical information which is information related to the experimental characterization of a chemical reaction, often directly indicating a protein(s) associated with a reaction and the stoichiometry of the reaction or indirectly demonstrating the existence of a reaction occurring within a cellular extract; genetic information, which is information related to the experimental identification and genetic characterization of a gene(s) shown to code for a particular protein(s) implicated in carrying out a biochemical event; genomic information, which is information related to the identification of an open reading frame and functional assignment, through computational sequence analysis, that is then linked to a protein performing a biochemical event; physiological information, which is information related to overall cellular physiology, fitness characteristics, substrate utilization, and phenotyping results, which provide evidence of the assimilation or dissimilation of a compound used to infer the presence of specific biochemical event (in particular translocations); and modeling information, which is information generated through the course of simulating activity of cells, tissues or physiological systems using methods such as those described herein which lead to predictions regarding the status of a reaction such as whether or not the reaction is required to fulfill certain demands placed on a metabolic network. Additional information relevant to multicellular organisms that can be considered includes, for example, cell type-specific or condition-specific gene expression information, which can be determined experimentally, such as by gene array analysis or from expressed sequence tag (EST) analysis, or obtained from the biochemical and physiological literature.

The majority of the reactions occurring in a multicellular organism's reaction networks are catalyzed by enzymes/proteins, which are created through the transcription and translation of the genes found within the chromosome in the cell. The remaining reactions occur either spontaneously or through non-enzymatic processes. Furthermore, a reaction network data structure can contain reactions that add or delete steps to or from a particular reaction pathway. For example, reactions can be added to optimize or improve performance of a model for multicellular interactions in view of empirically observed activity. Alternatively, reactions can be deleted to remove intermediate steps in a pathway when the intermediate steps are not necessary to model flux through the pathway. For example, if a pathway contains 3 nonbranched steps, the reactions can be combined or added together to give a net reaction, thereby reducing memory required to store the reaction network data structure and the computational resources required for manipulation of the data structure.

The reactions that occur due to the activity of gene-encoded enzymes can be obtained from a genome database which lists genes identified from genome sequencing and subsequent genome annotation. Genome annotation consists of the locations of open reading frames and assignment of function from homology to other known genes or empirically determined activity. Such a genome database can be acquired through public or private databases containing annotated nucleic acid or protein sequences, including *Homo sapiens* sequences. If desired, a model developer can perform a network reconstruction and establish the model content associations between the genes, proteins, and reactions as described, for example, in Covert et al. *Trends in Biochemical Sciences* 26:179-186 (2001) and Palsson, WO 00/46405.

As reactions are added to a reaction network data structure or metabolic reaction database, those having known or putative associations to the proteins/enzymes which enable/catalyze the reaction and the associated genes that code for these proteins can be identified by annotation. Accordingly, the appropriate associations for all of the reactions to their related proteins or genes or both can be assigned. These associations can be used to capture the non-linear relationship between the genes and proteins as well as between proteins and reactions. In some cases one gene codes for one protein which then perform one reaction. However, often there are multiple genes which are required to create an active enzyme complex and often there are multiple reactions that can be carried out by one protein or multiple proteins that can carry out the same reaction. These associations capture the logic (i.e. AND or OR relationships) within the associations. Annotating a metabolic reaction database with these associations can allow the methods to be used to determine the effects of adding or eliminating a particular reaction not only at the reaction level, but at the genetic or protein level in the context of running a simulation or predicting a multicellular interaction activity, including *Homo sapiens* activity.

A reaction network data structure of the invention can be used to determine the activity of one or more reactions in a plurality of reactions occurring from multicellular interactions, including a plurality of *Homo sapiens* reactions, independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that can either occur spontaneously or are not protein-enabled reactions. Furthermore, the occurrence of a particular reaction in a cell for which no associated proteins or genetics have been currently identified can be indicated during the course of model building by the iterative model building methods of the invention.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J Theor. Biol.* 203:249-283 (2000), and in Schuster et al., *Bioinformatics* 18:351-361 (2002). The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

The reactions in a reaction network data structure or metabolic reaction database can be annotated with a value indicating the confidence with which the reaction is believed to occur in one or more cells of a multicellular interaction or in one or more reaction networks within a cell such as a *Homo sapiens* cell. The level of confidence can be, for example, a function of the amount and form of supporting data that is available. This data can come in various forms including published literature, documented experimental results, or results of computational analyses. Furthermore, the data can provide direct or indirect evidence for the existence of a chemical reaction in a cell based on genetic, biochemical, and/or physiological data.

The invention further provides a computer readable medium, containing (a) a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product, and (b) a constraint set for the plurality of *Homo sapiens* reactions. Similarly, the computer readable medium or media can relate a plurality of reactions to a plurality of reactions within first and second cells and for an intra-system between first and second interacting cells.

Constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure. Based on the in vivo environment where multiple cells interact, such as in a human organism, the metabolic resources available to the cell for biosynthesis of essential molecules for can be determined. Allowing the corresponding transport fluxes to be active provides the in silico interaction between cells with inputs and outputs for substrates and by-products produced by the metabolic network.

Returning to the hypothetical reaction network shown in FIG. 1, constraints can be placed on each reaction in the exemplary format shown in FIG. 2, as follows. The constraints are provided in a format that can be used to constrain the reactions of the stoichiometric matrix shown in FIG. 3. The format for the constraints used for a matrix or in linear programming can be conveniently represented as a linear inequality such as $$b_j \leq v_j \leq a_j : j = 1 \ldots n \qquad \text{(Eq. 1)}$$

where $v_j$ is the metabolic flux vector, $b_j$ is the minimum flux value and $a_j$ is the maximum flux value. Thus, $a_j$ can take on a finite value representing a maximum allowable flux through a given reaction or $b_j$ can take on a finite value representing minimum allowable flux through a given reaction. Additionally, if one chooses to leave certain reversible reactions or transport fluxes to operate in a forward and reverse manner the flux may remain unconstrained by setting $b_j$ to negative infinity and $a_j$ to positive infinity as shown for reaction $R_2$ in FIG. 2. If reactions proceed only in the forward reaction $b_j$ is set to zero while $a_j$ is set to positive infinity as shown for reactions $R_1$, $R_3$, $R_4$, $R_5$, and $R_6$ in FIG. 2. As an example, to simulate the event of a genetic deletion or non-expression of a particular protein, the flux through all of the corresponding metabolic reactions related to the gene or protein in question are reduced to zero by setting $a_j$ and $b_j$ to be zero. Furthermore, if one wishes to simulate the absence of a particular growth substrate one can simply constrain the corresponding transport fluxes that allow the metabolite to enter the cell to be zero by setting $a_j$ and $b_j$ to be zero. On the other hand if a substrate is only allowed to enter or exit the cell via transport mechanisms, the corresponding fluxes can be properly constrained to reflect this scenario.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism. Of particular importance in the regulation of human cell types is the implementation of paracrine and endocrine signaling pathways to control cellular activities. In these cases a cell secretes signaling molecules that may be carried far afield to act on distant targets (endocrine signaling), or act as local mediators (paracrine signaling). Examples of endocrine signaling molecules include hormones such as insulin, while examples of paracrine signaling molecules include neurotransmitters such as acetylcholine. These molecules induce cellular responses through signaling cascades that affect the activity of biochemical reactions in the cell. Regulation can be represented in an in silico *Homo sapiens* model by providing a variable constraint as set forth below.

Thus, the invention provides a computer readable medium or media, including (a) a data structure relating a plurality of *Homo sapiens* reactants to a plurality of *Homo sapiens* reactions, wherein each of the reactions includes a reactant identified as a substrate of the reaction, a reactant identified as a product of the reaction and a stoichiometric coefficient relating the substrate and the product, and wherein at least one of the reactions is a regulated reaction; and (b) a constraint set for the plurality of reactions, wherein the constraint set includes a variable constraint for the regulated reaction. Additionally, the invention provides a computer readable medium or media including data structures for two or more cells and for an intra-system and a constraint set for the plurality of reactions within the data structures that includes a variable constraint for a regulated reaction.

As used herein, the term "regulated," when used in reference to a reaction in a data structure, is intended to mean a reaction that experiences an altered flux due to a change in the value of a constraint or a reaction that has a variable constraint.

As used herein, the term "regulatory reaction" is intended to mean a chemical conversion or interaction that alters the activity of a protein, macromolecule or enzyme. A chemical conversion or interaction can directly alter the activity of a protein, macromolecule or enzyme such as occurs when the protein, macromolecule or enzyme is post-translationally modified or can indirectly alter the activity of a protein, macromolecule or enzyme such as occurs when a chemical conversion or binding event leads to altered expression of the protein, macromolecule or enzyme. Thus, transcriptional or translational regulatory pathways can indirectly alter a protein, macromolecule or enzyme or an associated reaction. Similarly, indirect regulatory reactions can include reactions that occur due to downstream components or participants in a regulatory reaction network. When used in reference to a data structure or in silico *Homo sapiens* model, for example, the term is intended to mean a first reaction that is related to a second reaction by a function that alters the flux through the second reaction by changing the value of a constraint on the second reaction.

As used herein, the term "regulatory data structure" is intended to mean a representation of an event, reaction or network of reactions that activate or inhibit a reaction, the representation being in a format that can be manipulated or analyzed. An event that activates a reaction can be an event that initiates the reaction or an event that increases the rate or level of activity for the reaction. An event that inhibits a reaction can be an event that stops the reaction or an event that decreases the rate or level of activity for the reaction. Reactions that can be represented in a regulatory data structure include, for example, reactions that control expression of a macromolecule that in turn, performs a reaction such as transcription and translation reactions, reactions that lead to post translational modification of a protein or enzyme such as phophorylation, dephosphorylation, prenylation, methylation, oxidation or covalent modification, reactions that process a protein or enzyme such as removal of a pre- or pro-sequence, reactions that degrade a protein or enzyme or reactions that lead to assembly of a protein or enzyme.

As used herein, the term "regulatory event" is intended to mean a modifier of the flux through a reaction that is independent of the amount of reactants available to the reaction. A modification included in the term can be a change in the presence, absence, or amount of an enzyme that performs a reaction. A modifier included in the term can be a regulatory reaction such as a signal transduction reaction or an environmental condition such as a change in pH, temperature, redox potential or time. It will be understood that when used in reference to an in silico *Homo sapiens* model. or data structure, or when used in reference to a model or data structure for a multicellular interaction, a regulatory event is intended to be a representation of a modifier of the flux through a *Homo sapiens* reaction or reaction occurring in one or more cells in a multicellular interaction that is independent of the amount of reactants available to the reaction.

Figure 4:
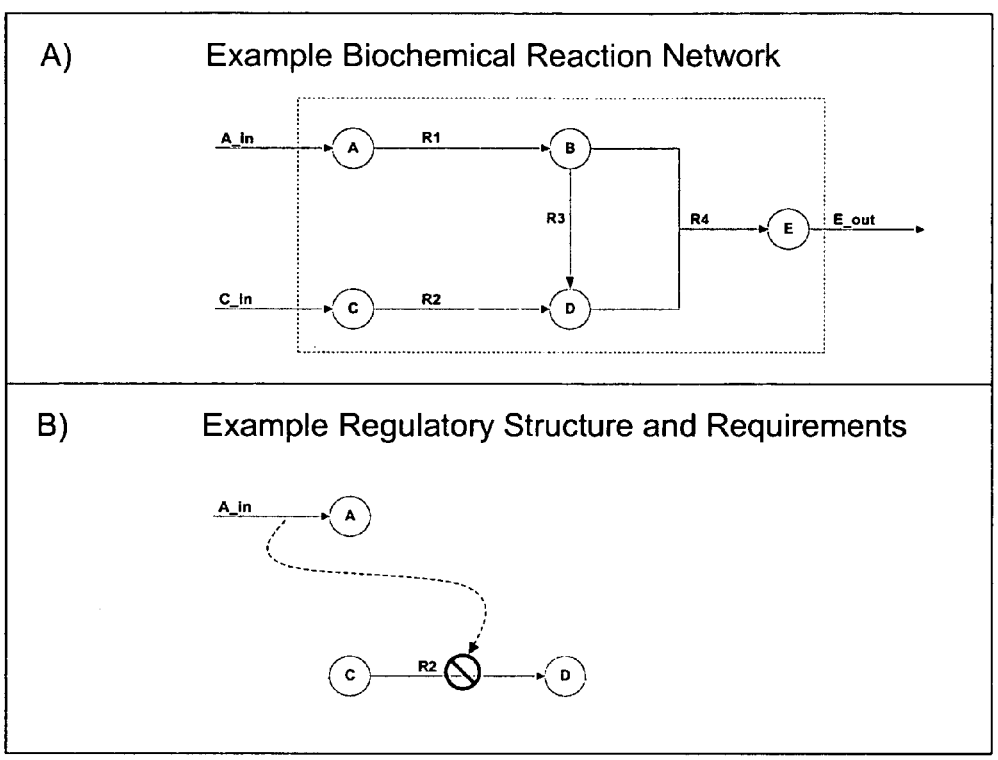
FIG. 4 shows, in Panel A, an exemplary biochemical reaction network and in Panel B, an exemplary regulatory control structure for the reaction network in panel A.

The effects of regulation on one or more reactions that occur in *Homo sapiens* can be predicted using an in silico *Homo sapiens* model or multicellular model of the invention. Regulation can be taken into consideration in the context of a particular condition being examined by providing a variable constraint for the reaction in an in silico *Homo sapiens* model or multicellular model. Such constraints constitute condition-dependent constraints. A data structure can represent regulatory reactions as Boolean logic statements (Reg-reaction). The variable takes on a value of 1 when the reaction is available for use in the reaction network and will take on a value of 0 if the reaction is restrained due to some regulatory feature. A series of Boolean statements can then be introduced to mathematically represent the regulatory network as described for example in Covert et al. *J. Theor. Biol.* 213:73-88 (2001). For example, in the case of a transport reaction (A_in) that imports metabolite A, where metabolite A inhibits reaction R2 as shown in FIG. 4, a Boolean rule can state that:

$$\text{Reg-}R2 = \text{IF NOT}(A\_in). \quad (\text{Eq. 2})$$

This statement indicates that reaction R2 can occur if reaction A_in is not occurring (i.e. if metabolite A is not present). Similarly, it is possible to assign the regulation to a variable A which would indicate an amount of A above or below a threshold that leads to the inhibition of reaction R2. Any function that provides values for variables corresponding to each of the reactions in the biochemical reaction network can be used to represent a regulatory reaction or set of regulatory reactions in a regulatory data structure. Such functions can include, for example, fuzzy logic, heuristic rule-based descriptions, differential equations or kinetic equations detailing system dynamics.

A reaction constraint placed on a reaction can be incorporated into an in silico *Homo sapiens* model or mulicellular model of interacting cells using the following general equation:

$$(\text{Reg-Reaction})^* b_j \leq v_j \leq a_j^* (\text{Reg-Reaction}), \forall$$

$$j = 1 \ldots n \quad (\text{Eq. 3})$$

For the example of reaction R2 this equation is written as follows:

$$(0)^* \text{Reg-}R2 \leq R2 \leq (\infty)^* \text{Reg-}R2. \quad (\text{Eq. 4})$$

Thus, during the course of a simulation, depending upon the presence or absence of metabolite A in the interior of the cell where reaction R2 occurs, the value for the upper boundary of flux for reaction R2 will change from 0 to infinity, respectively.

With the effects of a regulatory event or network taken into consideration by a constraint function and the condition-dependent constraints set to an initial relevant value, the behavior of the *Homo sapiens* reaction network or one or more reaction networks of a multicellular interaction can be simulated for the conditions considered as set forth below.

Although regulation has been exemplified above for the case where a variable constraint is dependent upon the outcome of a reaction in the data structure, a plurality of variable constraints can be included in an in silico *Homo sapiens* model or other model of multicellular interactions to represent regulation of a plurality of reactions. Furthermore, in the exemplary case set forth above, the regulatory structure includes a general control stating that a reaction is inhibited by a particular environmental condition. Using a general control of this type, it is possible to incorporate molecular mechanisms and additional detail into the regulatory structure that is responsible for determining the active nature of a particular chemical reaction within an organism.

Regulation can also be simulated by a model of the invention and used to predict a *Homo sapiens* physiological function without knowledge of the precise molecular mechanisms involved in the reaction network being modeled. Thus, the model can be used to predict, in silico, overall regulatory events or causal relationships that are not apparent from in vivo observation of any one reaction in a network or whose in vivo effects on a particular reaction are not known. Such overall regulatory effects can include those that result from overall environmental conditions such as changes in pH, temperature, redox potential, or the passage of time.

As described previously and further below, the models and method of the invention are applicable to a wide range of multicellular interactions. The multicellular interactions include, for example, interactions between prokaryotic cells such as colony growth and chemotaxis. The multicellular interactions include, for example, interactions between two or more eukaryotic cells such as the concerted action of two or more cells of the same or different cell type. A specific example of the concerted action of the same cell type includes the combined output of the contractile activity of myocytes. A specific example of the concerted action of different cell types includes the energy production of adipocyte cells and the contractile activity of myocyte cells based on the consumption of energy available from the adipocyte cells. Multicellular interactions also can include, for example, interactions between host cells and a pathogen, such as a bacteria, virus or worm, as well as symbiotic interactions between host cells and microbes, for example. A symbiotic microbe can include, for example, *E. coli*. Further examples of host and microbe interactions include bacterial communities that reside in the skin and mouth and the vagina flora, providing the host with a defense against infections. Moreover, the models and methods of the invention also can be used to reconstruction the reaction networks between a plurality of dynamic multicellular interactions including, for example, interactions between host cells or tissues, pathogen and symbiotic microbe.

Multicellular interactions also include, for example, interactions between cells of different tissues, different organs and/or physiological systems as well as interactions between some or all cells, tissues organs and/or physiological systems within a multicellular organism. Specific examples of such interactions include organismic homeostasis, signal transduction, the endocrine system, the exocrine system, sensory transduction, secretion, the hematopoietic system, the immune system, cell migration, cell adherence, cell invasion and neuronal and synaptic transduction. Numerous other multicellular interactions are well known in the art and can similarly be reconstructed and simulated to predict an activity thereof using the models and methods of the invention.

Given the teachings and guidance provided herein with respect to the construction and use of multiple reaction networks including, for example, the regulated and metabolic reaction networks of a *Homo sapiens* cell, those skilled in the art will know how to employ the models and methods of the invention for the construction and use of any multicellular interaction. Specific examples of such multicellular interactions are described above. Other examples of multicellular interactions include, for example, all interactions occurring between two or more cells such as those cells set forth in Table 5 below. Such multicellular interactions can occur between cells within the same or different physiological category or functional characterization. Similarly, such multicellular interactions also can occur between cells within the same and between different physiological categories or functional characterizations. The number and types of different cellular interactions will be determined by the multicellular model being produced using the methods of the invention.

Models of multicellular interactions also can include, for example, interactions between cells of one or more tissues and organs. The models and methods of the invention are applicable to predict the activity of interactions between some or all cell types of a tissue or organ. The models and methods of the invention also can include reaction networks that include interactions between some or all cell types of two or more tissues or organs. Specific examples of tissues or organs and their respective cell types and functions are shown below in Table 6. The models and methods of the invention can include, for example, some or all of these interactions to predict their respective activities. Similarly, Table 7 exemplifies the cell types of a liver. Given the teachings and guidance provided herein, the models and methods of the invention can be used to construct an in silico reconstruction of the reaction networks for some or all of these cell types to predict some or all of the activities of the liver. Further, an in silico reconstruction of reaction networks for some or all multicellular interactions exemplified in Tables 5-7, including those within and between tissues and organs, can be produced that can be used to predict some or all activities of one or more tissues or of an organism. Therefore, the invention provides for the in silico reconstruction of whole organisms, including human organisms, tissues, cells and physical or physiological functions performed by such cellular systems.

The invention also provides for the in silico reconstruction of a plurality of reaction networks that interact to perform the same or different activity. The plurality can be a small, medium or large plurality and can reside within the same cell, different cells or in different tissues or organisms. Specific examples of such pluralities residing within the same cell include the reaction networks exemplified below in Example IV for a myocyte or for an adipocyte. Specific examples of such pluralities residing in different cells or tissues include the reaction networks exemplified below in Example IV for coupled adipocyte-myocyte metabolism. Another example of interactions between different reaction networks within different networks includes interactions between pathogen and host cells.

Briefly, and as described previously, a computer readable medium or media can be produced that includes a plurality of data structures each relating a plurality of reactants to a plurality of reactions from each cell within the multicellular interaction. The reactions include a reactant identified as a substrate of the reaction, a reactant identified as a product of the reaction and a stoichiometric coefficient relating the substrate and said product In a two cell interaction, including populations of two cell types, the plurality of data structures can include a first data structure and a second data structure corresponding to the reactions within the two cells or populations of two cell types. The data structures will describe the reaction networks for each cell.

Figures 1, 7:
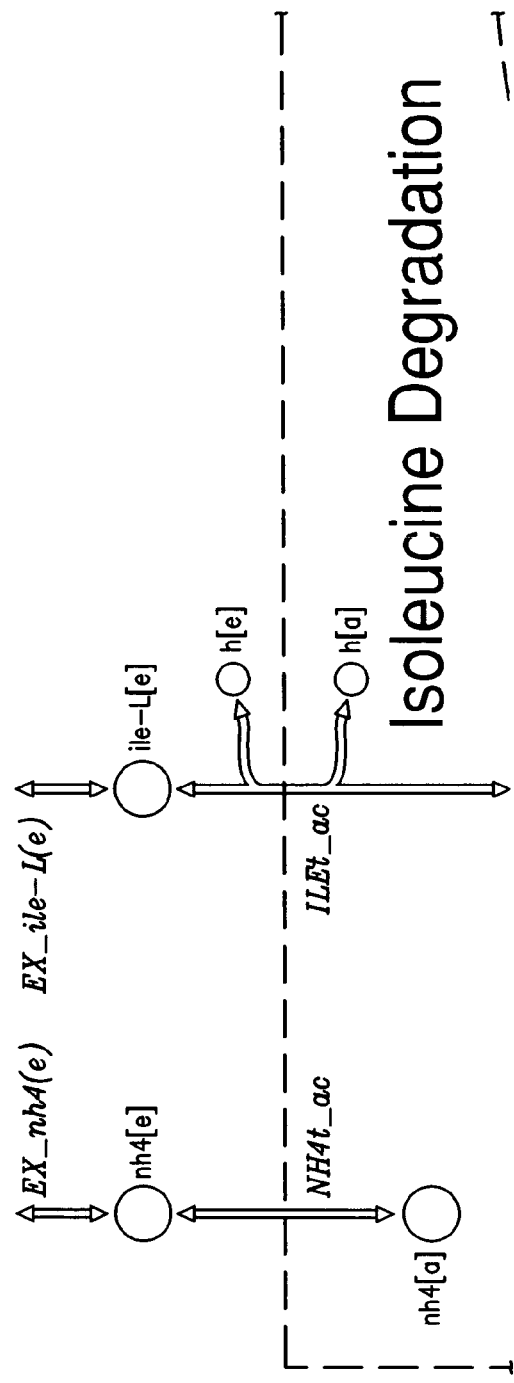
Figures 2, 7:
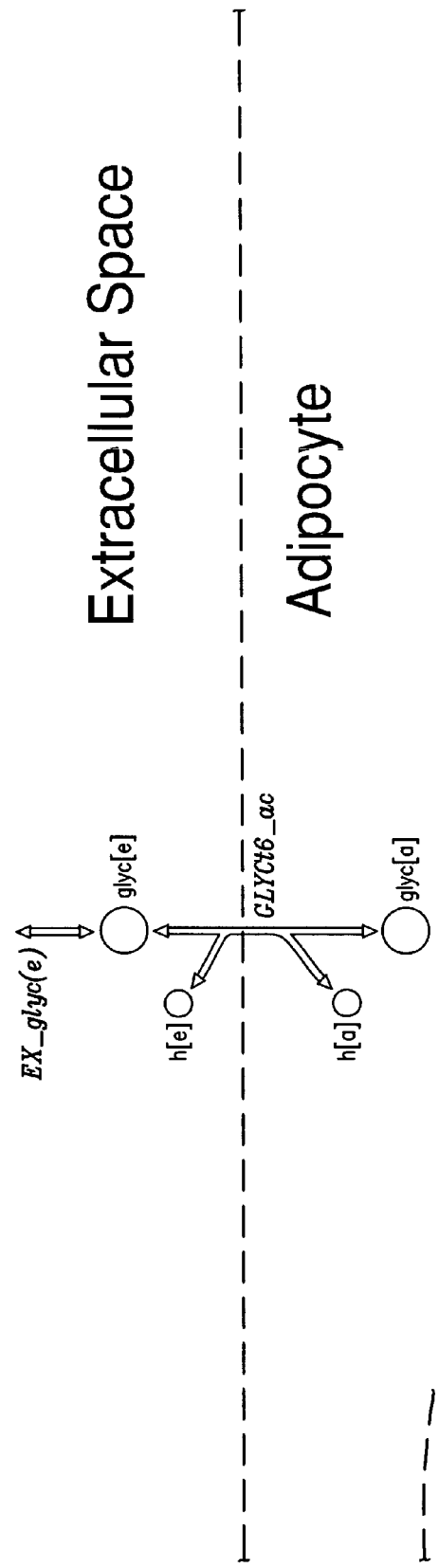
Figures 3, 7:
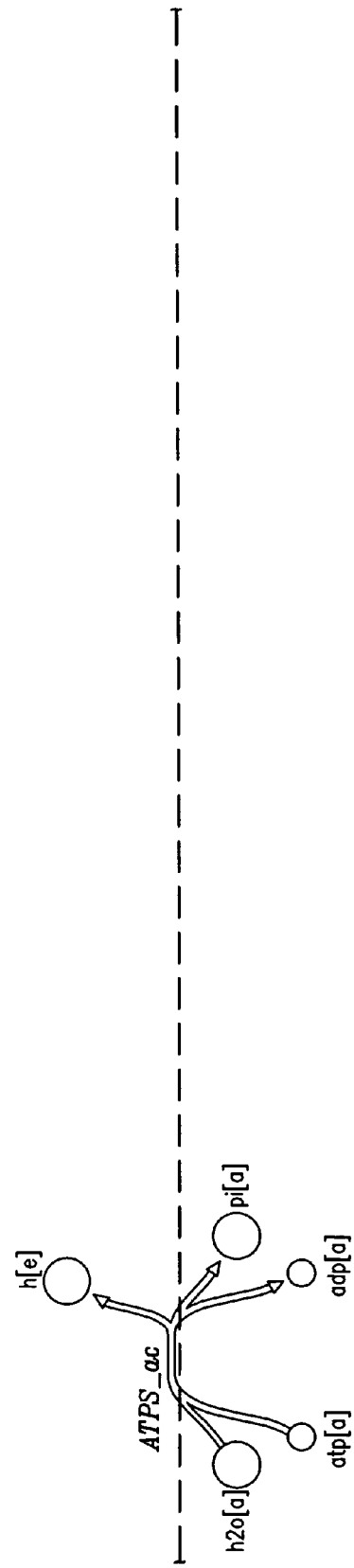
Figures 4, 7:
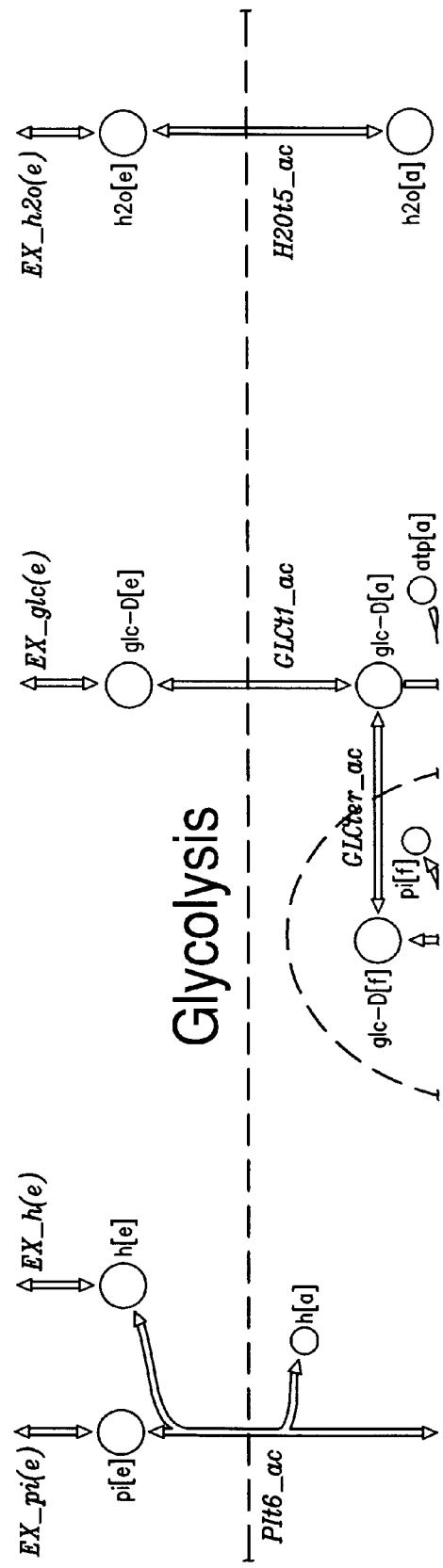
Figures 5, 7:
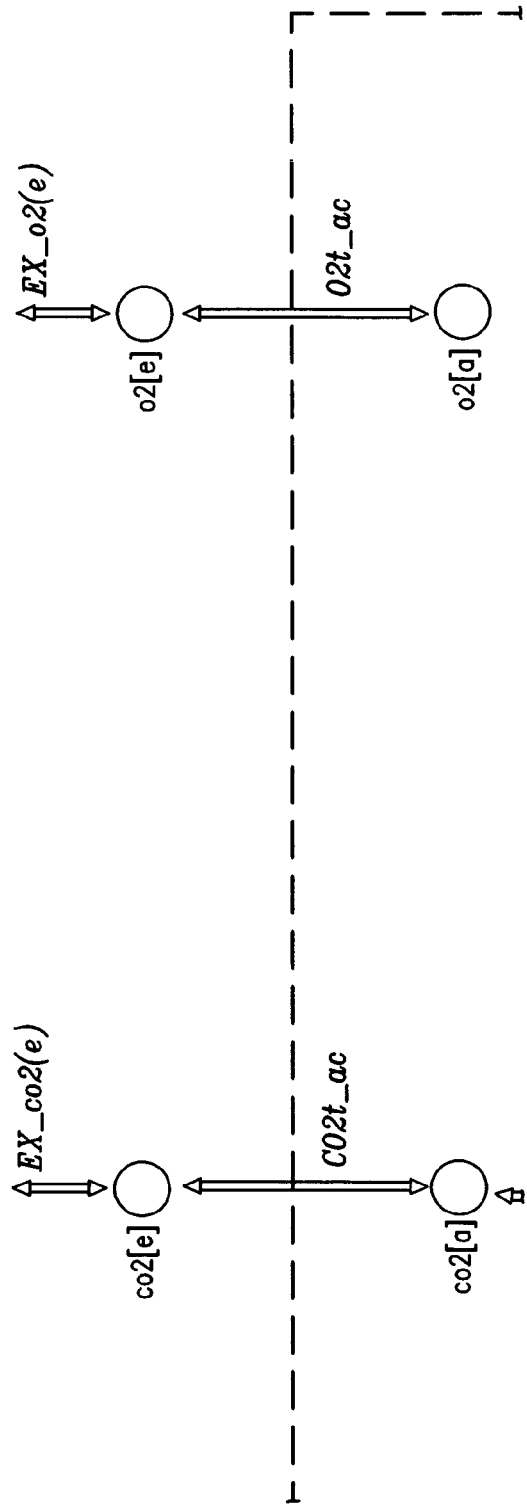
Figures 6, 7:
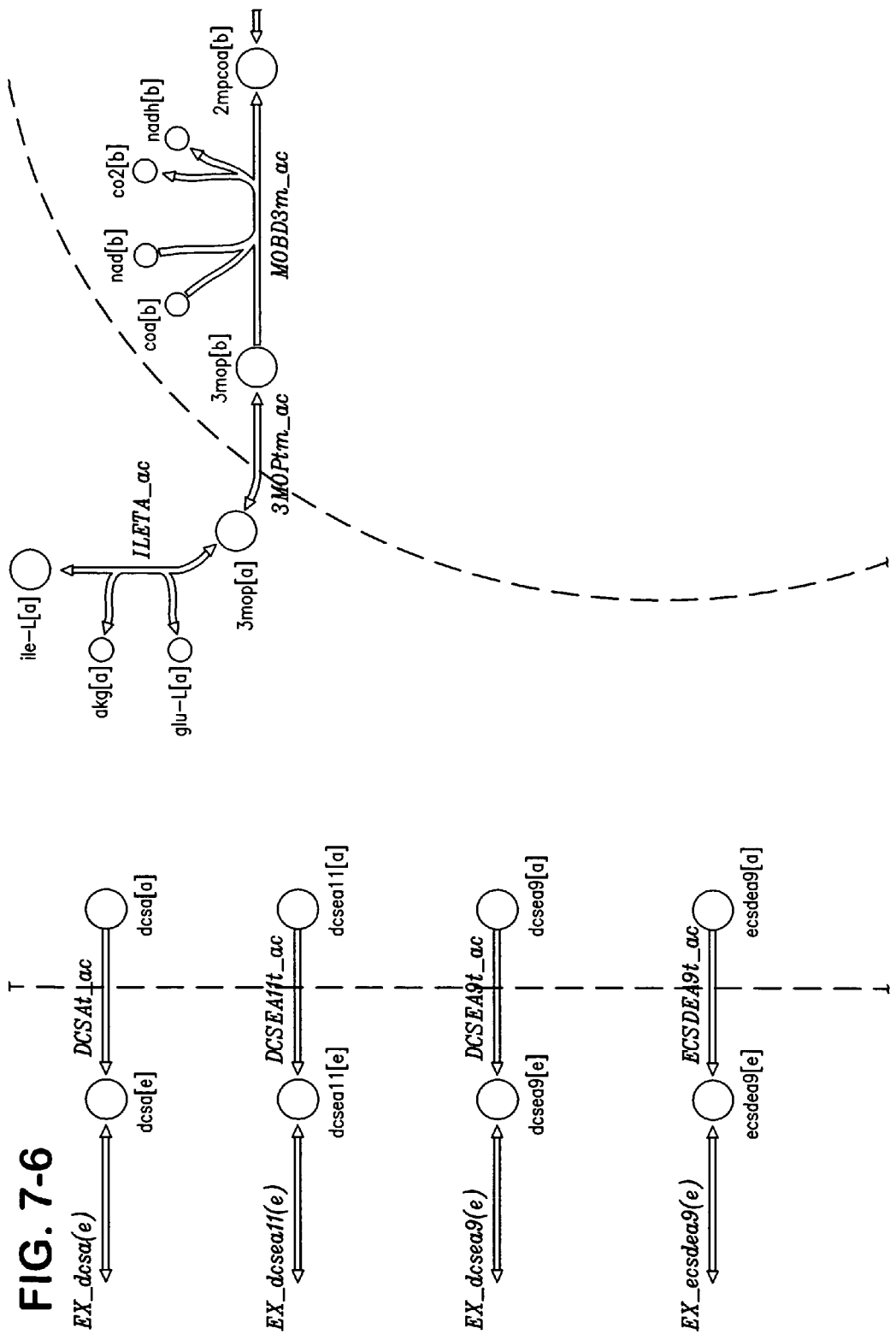
Figure 7:
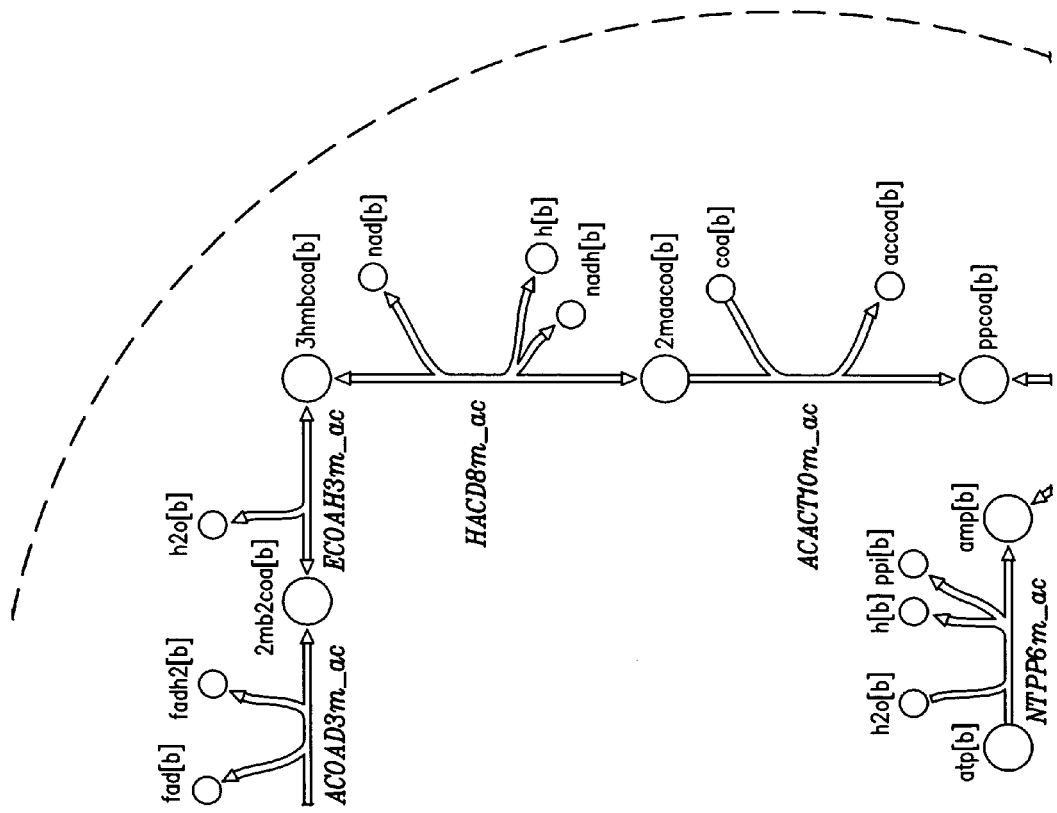
Figures 7, 8:
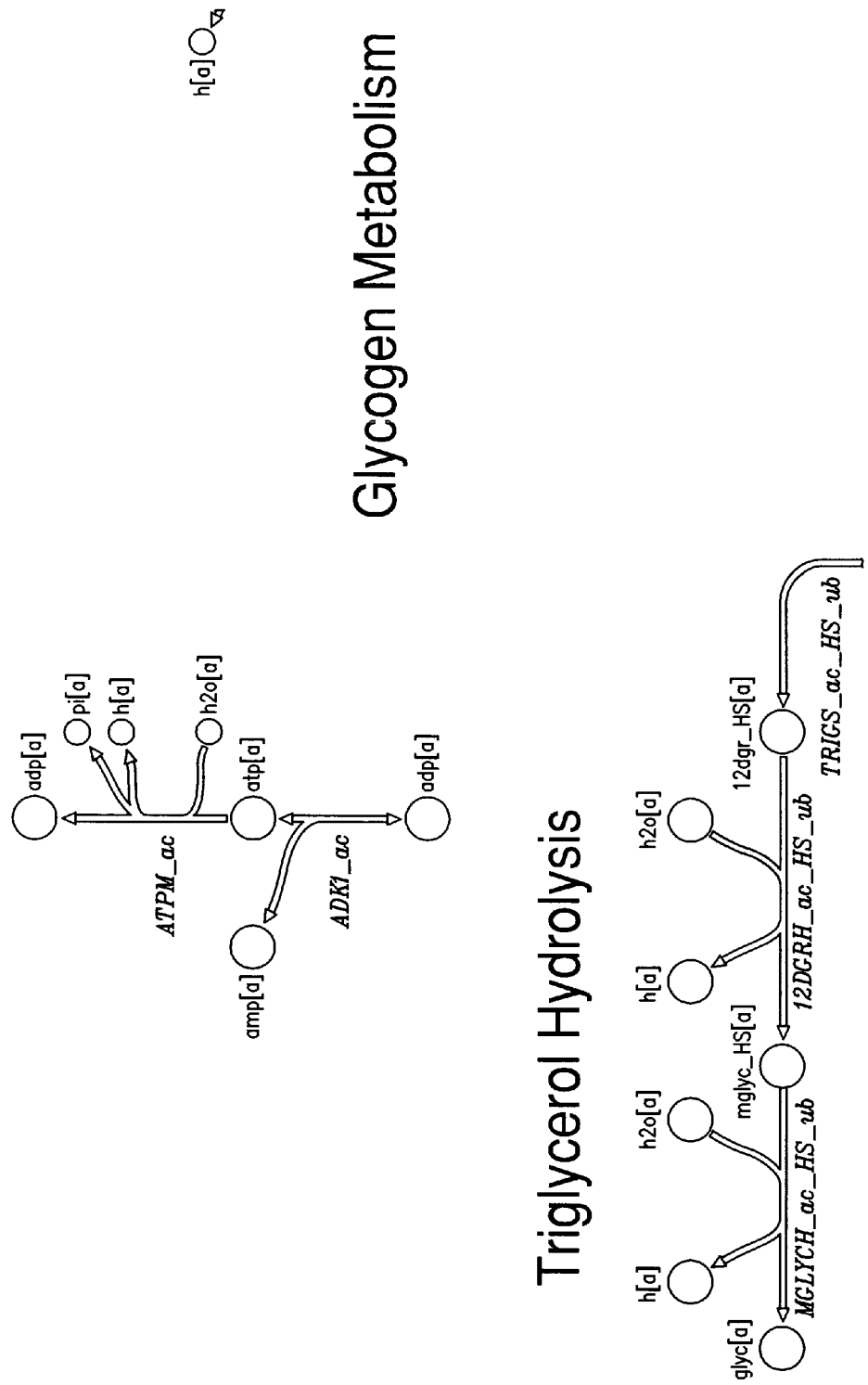
Figures 7, 8, 9:
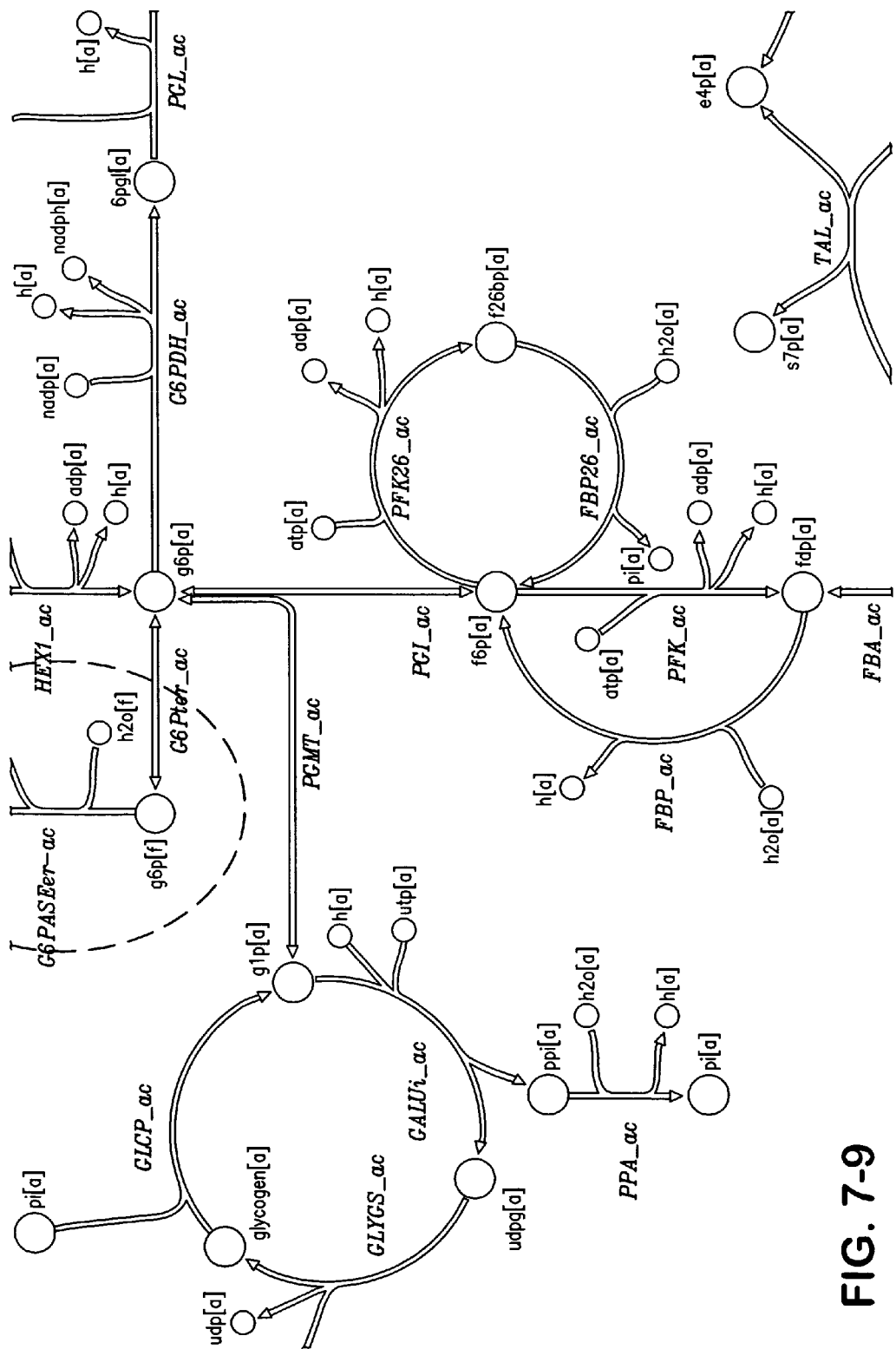
Figures 7, 8, 9, 10:
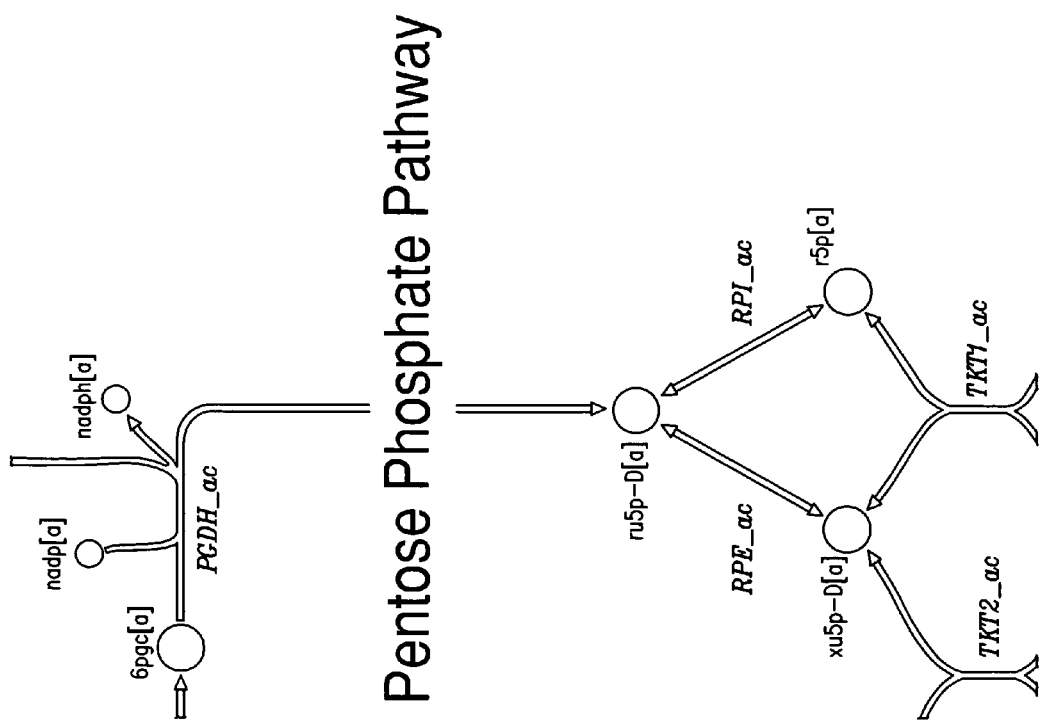
FIG. 10 shows a metabolic network of coupled adipoctye-myocyte metabolism.

For optimization of the multicellular interaction containing two cells, a third data structure is particularly useful for relating a plurality of intra-system reactants to a plurality of intra-system reactions between the first and second cells. Each of the intra-system reactions includes a reactant identified as a substrate of the reaction, a reactant identified as a product of the reaction and a stoichiometric coefficient relating the substrate and said product. The inta-system data structure can be included in the reconstruction as an independent data structure or as a component of one or more data structures for either or both cells within such a two cell interaction model. A specific example of intra-system reactions represented by a third data structure is shown in FIG. 10 for the bicarbonate and ammonia buffer systems employed in the two cell model describing adipocyte and myocyte interactions.

As with the models and methods of the invention described above and below, a computer readable medium or media describing a multicellular interaction also will contain a constraint set for the plurality of reactions for each of the first, second and third data structures as well as commands for determining at least one flux distribution that minimizes or maximizes an objective function when said constraint set is applied to said first and second data structures. The objective function can be, for example, those objective functions exemplified previously, those exemplified below or in the Examples as well as various other object functions well known to those skilled in the art given the teachings and guidance provided herein. Solving the optimization problem by determining one or more flux distribution will predict a physiological function of occurring as a result of the interaction between the first and second cells of the model.

Each of the first, second or third data structures can include one or more reaction networks. For example, and with reference to FIGS. 5-10, a reaction network for each of the cells exemplified therein can be defined as the different networks within each cell such as central metabolism and the cell specific reactions. Applying this view, the adipocyte and myocyte cells each contain at least two reaction networks. When combined together with the intra-cellular reaction network and the exchange reactions, the interactions of the two cells exemplified in FIG. 6 can be described by at least five different reaction networks. The interactions of this two cell model can therefore be described using at least five data structures. Alternatively, a reaction network can be defined as all the networks within each cell. When combined together with the intra-cellular reaction network and the exchange reactions, the interactions of the exemplified adipocyte and myocyte cells can be described by at least three different reaction networks. One reaction network for each cell and one reaction network for the intra-system reactions. Therefore, each of the first, second or third data structures can consist of a plurality of two or more reaction networks including, for example, 2, 3, 4, 5, 10, 20 or 25 or more as well as all integer numbers between and above these exemplary numbers. Similarly, given the teachings and guidance provided herein, the models and methods of the invention can be generated and used to predict an activity and/or physiological function of the intercellular network interactions or the intracellular network interaction. The latter interactions, for example, also predict an activity and/or a physiological function of the interactions between two or more cells including cells of different tissues, organs of a multicellular organism or of a whole organism.

As with the number of reaction networks within a data structure, the models and methods of the invention also can employ greater than three data structures as exemplified above. For example, the models and method of the invention can comprise one or more fourth data structures having one or more fourth constraint sets where each fourth data structure relates a plurality of reactants to a plurality of reactions from a cell already included in the model or from one or more third cells within the multicellular interaction. Use of one or more fourth data structures is particularly useful when reconstructing a interactions between three or more interacting cells including a large plurality of cells such as the cells within a tissue, organ, physiological system or organism. Each of the reactions within such fourth data structures include a reactant identified as a substrate of the reaction, a reactant identified as a product of the reaction and a stoichiometric coefficient relating the substrate and said product.

The number of fourth data structures can correspond to the number of cells greater than the first and second cells of the multicellular interaction and include, for example, a plurality of data structures. As with the specific embodiment of a two cell interaction, the plurality of data structures for three or more interacting cells can correspond to different cells within the cellular interaction as well as correspond to different cell types within the cellular interaction. The number of cells can include, for example, at least 4 cells, 5 cells, 6 cells, 7 cells, 8 cells, 9 cells, 10 cells, 100 cells, 1000 cells, 5000 cells, 10,000 cells or more. Therefore, the number of cells within a multicellular interaction model or used in a method of predicting a behavior of such multicellular interactions can include some or all cells which constitute a group of interacting cells, a tissue, organ, physiological system or whole organism. The multicellular interaction models and methods of the invention also can include some or all cells which constitute a group of interacting cells of different types or from different tissues, organs, physiological systems or organisms. The organism can be single cell prokaryotic or eukaryotic organism or multicellular eukaryotic organisms. Specific examples of different cell types include a mammary gland cell, hepatocyte, white fat cell, brown fat cell, liver lipocyte, red skeletal muscle cell, white skeletal muscle cell, intermediate skeletal muscle cell, smooth muscle cell, red blood cell, adipocyte, monocyte, reticulocyte, fibroblast, neuronal cell epithelial cell or one or more cells set forth in Table 5. Specific examples of physiological functions resulting from multicellular interactions that can be predicted include metabolite yield, ATP yield, biomass demand, growth, triacylglycerol storage, muscle contraction, milk secretion and oxygen transport capacity.

Intra-system reactions of a multicellular interaction model or method of the invention has been exemplified above and below with reference to the extracellular in vivo environment and, in particular, with reference to buffering this environment by supplying functions of the renal system. Given the teachings and guidance provided herein, those skilled in the art will understand that any extracellular reaction, plurality of reactions, function of the extracellular space or function supplied into the extracellular space by another cell, tissue or physiological system can be employed as an intra-system reaction network. Such reactions or activities can represent normal or pathological conditions or both conditions occurring within this intra-system environment. Specific examples of intra-system reactions include one or more reactions performed in the hematopoietic system, urine, connective tissue, contractile tissue or cells, lymphatic system, respiratory system or renal system. Reactions or reactants included in one or more intra-system data structures can be, for example, bicarbonate buffer system, an ammonia buffer system, a hormone, a signaling molecule, a vitamin, a mineral or a combination thereof.

The in silico models of multicellular or multi-network interactions, including *Homo sapiens* model and methods, described herein can be implemented on any conventional host computer system, such as those based on Intel® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement a method or model of the invention can be written in any well-known computer language, such as Java, C, C++, Visual Basic, FORTRAN or COBOL and compiled using any well-known compatible compiler. The software of the invention normally runs from instructions stored in a memory on a host computer system. A memory or computer readable medium can be a hard disk, floppy disc, compact disc, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

A database or data structure of the invention can be represented in a markup language format including, for example, Standard Generalized Markup Language (SGML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, "Learning XML" O'Reilly and Associates, Sebastopol, Calif. (2001).

A set of constraints can be applied to a reaction network data structure to simulate the flux of mass through the reaction network under a particular set of environmental conditions specified by a constraints set. Because the time constants characterizing metabolic transients and/or metabolic reactions are typically very rapid, on the order of milli-seconds to seconds, compared to the time constants of cell growth on the order of hours to days, the transient mass balances can be simplified to only consider the steady state behavior. Referring now to an example where the reaction network data structure is a stoichiometric matrix, the steady state mass balances can be applied using the following system of linear equations $$S \cdot v = 0 \quad (Eq. 5)$$

where S is the stoichiometric matrix as defined above and v is the flux vector. This equation defines the mass, energy, and redox potential constraints placed on the metabolic network as a result of stoichiometry. Together Equations 1 and 5 representing the reaction constraints and mass balances, respectively, effectively define the capabilities and constraints of the metabolic genotype and the organism's metabolic potential. All vectors, v, that satisfy Equation 5 are said to occur in the mathematical nullspace of S. Thus, the null space defines steady-state metabolic flux distributions that do not violate the mass, energy, or redox balance constraints. Typically, the number of fluxes is greater than the number of mass balance constraints, thus a plurality of flux distributions satisfy the mass balance constraints and occupy the null space. The null space, which defines the feasible set of metabolic flux distributions, is further reduced in size by applying the reaction constraints set forth in Equation 1 leading to a defined solution space. A point in this space represents a flux distribution and hence a metabolic phenotype for the network. An optimal solution within the set of all solutions can be determined using mathematical optimization methods when provided with a stated objective and a constraint set. The calculation of any solution constitutes a simulation of the model.

Objectives for activity of a human cell can be chosen. While the overall objective of a multi-cellular organism may be growth or reproduction, individual human cell types generally have much more complex objectives, even to the seemingly extreme objective of apoptosis (programmed cell death), which may benefit the organism but certainly not the individual cell. For example, certain cell types may have the objective of maximizing energy production, while others have the objective of maximizing the production of a particular hormone, extracellular matrix component, or a mechanical property such as contractile force. In cases where cell reproduction is slow, such as human skeletal muscle, growth and its effects need not be taken into account. In other cases, biomass composition and growth rate could be incorporated into a "maintenance" type of flux, where rather than optimizing for growth, production of precursors is set at a level consistent with experimental knowledge and a different objective is optimized.

Certain cell types, including cancer cells, can be viewed as having an objective of maximizing cell growth. Growth can be defined in terms of biosynthetic requirements based on literature values of biomass composition or experimentally determined values such as those obtained as described above. Thus, biomass generation can be defined as an exchange reaction that removes intermediate metabolites in the appropriate ratios and represented as an objective function. In addition to draining intermediate metabolites this reaction flux can be formed to utilize energy molecules such as ATP, NADH and NADPH so as to incorporate any maintenance requirement that must be met. This new reaction flux then becomes another constraint/balance equation that the system must satisfy as the objective function. Using the stoichiometric matrix of FIG. 3 as an example, adding such a constraint is analogous to adding the additional column $V_{growth}$ to the stoichiometric matrix to represent fluxes to describe the production demands placed on the metabolic system. Setting this new flux as the objective function and asking the system to maximize the value of this flux for a given set of constraints on all the other fluxes is then a method to simulate the growth of the organism.

Continuing with the example of the stoichiometric matrix applying a constraint set to a reaction network data structure can be illustrated as follows. The solution to equation 5 can be formulated as an optimization problem, in which the flux distribution that minimizes a particular objective is found. Mathematically, this optimization problem can be stated as:

$$\text{Minimize } Z \quad (Eq. 6)$$

$$\text{where } z = \Sigma c_i \cdot v_i \quad (Eq. 7)$$

where Z is the objective which is represented as a linear combination of metabolic fluxes $v_i$ using the weights $c_i$ in this linear combination. The optimization problem can also be stated as the equivalent maximization problem; i.e. by changing the sign on Z. Any commands for solving the optimazation problem can be used including, for example, linear programming commands.

A computer system of the invention can further include a user interface capable of receiving a representation of one or more reactions. A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to a multicellular organism's physiology, including *Homo sapiens* physiology. Also, the user interface can display a graphical representation of a reaction network or the results of a simulation using a model of the invention.

Once an initial reaction network data structure and set of constraints has been created, this model can be tested by preliminary simulation. During preliminary simulation, gaps in the network or "dead-ends" in which a metabolite can be produced but not consumed or where a metabolite can be consumed but not produced can be identified. Based on the results of preliminary simulations areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage the existing model is subjected to a series of functional tests to determine if it can perform basic requirements such as the ability to produce the required biomass constituents and generate predictions concerning the basic physiological characteristics of the particular cell type being modeled. The more preliminary testing that is conducted the higher the quality of the model that will be generated. Typically, the majority of the simulations used in this stage of development will be single optimizations. A single optimization can be used to calculate a single flux distribution demonstrating how metabolic resources are routed determined from the solution to one optimization problem. An optimization problem can be solved using linear programming as demonstrated in the Examples below. The result can be viewed as a display of a flux distribution on a reaction map. Temporary reactions can be added to the network to determine if they should be included into the model based on modeling/simulation requirements.

Once a model of the invention is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a phenotypic phase plane graph.

Thus, the invention provides a method for predicting a *Homo sapiens* physiological function. The method includes the steps of (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating said substrate and said product; (b) providing a constraint set for the plurality of *Homo sapiens* reactions; (c) providing an objective function, and (d) determining at least one flux distribution that minimizes or maximizes the objective function when the constraint set is applied to the data structure, thereby predicting a *Homo sapiens* physiological function.

A method for predicting a *Homo sapiens* physiological function can include the steps of (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product, and wherein at least one of the reactions is a regulated reaction; (b) providing a constraint set for the plurality of reactions, wherein the constraint set includes a variable constraint for the regulated reaction; (c) providing a condition-dependent value to the variable constraint; (d) providing an objective function, and (e) determining at least one flux distribution that minimizes or maximizes the objective function when the constraint set is applied to the data structure, thereby predicting a *Homo sapiens* physiological function.

Further, a method for predicting a physiological function of a multicellular organism also is provided. The method includes: (a) providing a first data structure relating a plurality of reactants to a plurality of reactions from a first cell, each of said reactions comprising a reactant identified as a substrate of the reaction, a reactant identified as a product of the reaction and a stoichiometric coefficient relating said substrate and said product; (b) providing a second data structure relating a plurality of reactants to a plurality of reactions from a second cell, each of said reactions comprising a reactant identified as a substrate of the reaction, a reactant identified as a product of the reaction and a stoichiometric coefficient relating said substrate and said product; (c) providing a third data structure relating a plurality of intra-system reactants to a plurality of intra-system reactions between said first and second cells, each of said intra-system reactions comprising a reactant identified as a substrate of the reaction, a reactant identified as a product of the reaction and a stoichiometric coefficient relating said substrate and said product; (d) providing a constraint set for said plurality of reactions for said first, second and third data structures; (e) providing an objective function, and (f) determining at least one flux distribution that minimizes or maximizes an objective function when said constraint set is applied to said first and second data structures, wherein said at least one flux distribution is predictive of a physiological function of said first and second cells.

As used herein, the term "physiological function," when used in reference to *Homo Sapiens*, is intended to mean an activity of an organism as a whole, including a multicellular organism and/or a *Homo sapiens* organism or cell as a whole. An activity included in the term can be the magnitude or rate of a change from an initial state of, for example, two or more interacting cells or a *Homo sapiens* cell to a final state of the two or more interacting cells or the *Homo sapiens* cell. An activity included in the term can be, for example, growth, energy production, redox equivalent production, biomass production, development, or consumption of carbon nitrogen, sulfur, phosphate, hydrogen or oxygen. An activity can also be an output of a particular reaction that is determined or predicted in the context of substantially all of the reactions that affect the particular reaction in two or more interacting cells or a *Homo sapiens* cell, for example, or substantially all of the reactions that occur in a plurality of interacting cells such as a tissue, organ or organism, or substantially all of the reactions that occur in a *Homo sapiens* cell (e.g. muscle contraction). Examples of a particular reaction included in the term are production of biomass precursors, production of a protein, production of an amino acid, production of a purine, production of a pyrimidine, production of a lipid, production of a fatty acid, production of a cofactor or transport of a metabolite. A physiological function can include an emergent property which emerges from the whole but not from the sum of parts where the parts are observed in isolation (see for example, Palsson, *Nat. Biotech* 18:1147-1150 (2000)).

A physiological function of reactions within two or more interacting cells, including *Homo sapiens* reactions, can be determined using phase plane analysis of flux distributions. Phase planes are representations of the feasible set which can be presented in two or three dimensions. As an example, two parameters that describe the growth conditions such as substrate and oxygen uptake rates can be defined as two axes of a two-dimensional space. The optimal flux distribution can be calculated from a reaction network data structure and a set of constraints as set forth above for all points in this plane by repeatedly solving the linear programming problem while adjusting the exchange fluxes defining the two-dimensional space. A finite number of qualitatively different metabolic pathway utilization patterns can be identified in such a plane, and lines can be drawn to demarcate these regions. The demarcations defining the regions can be determined using shadow prices of linear optimization as described, for example in Chvatal, *Linear Programming* New York, W. H. Freeman and Co. (1983). The regions are referred to as regions of constant shadow price structure. The shadow prices define the intrinsic value of each reactant toward the objective function as a number that is either negative, zero, or positive and are graphed according to the uptake rates represented by the x and y axes. When the shadow prices become zero as the value of the uptake rates are changed there is a qualitative shift in the optimal reaction network.

One demarcation line in the phenotype phase plane is defined as the line of optimality (LO). This line represents the optimal relation between respective metabolic fluxes. The LO can be identified by varying the x-axis flux and calculating the optimal y-axis flux with the objective function defined as the growth flux. From the phenotype phase plane analysis the conditions under which a desired activity is optimal can be determined. The maximal uptake rates lead to the definition of a finite area of the plot that is the predicted outcome of a reaction network within the environmental conditions represented by the constraint set. Similar analyses can be performed in multiple dimensions where each dimension on the plot corresponds to a different uptake rate. These and other methods for using phase plane analysis, such as those described in Edwards et al., *Biotech Bioeng.* 77:27-36(2002), can be used to analyze the results of a simulation using an in silico *Homo sapiens* model of the invention.

A physiological function of *Homo sapiens* can also be determined using a reaction map to display a flux distribution. A reaction map of *Homo sapiens* can be used to view reaction networks at a variety of levels. In the case of a cellular metabolic reaction network a reaction map can contain the entire reaction complement representing a global perspective. Alternatively, a reaction map can focus on a particular region of metabolism such as a region corresponding to a reaction subsystem described above or even on an individual pathway or reaction.

Thus, the invention provides an apparatus that produces a representation of a *Homo sapiens* physiological function, wherein the representation is produced by a process including the steps of: (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating said substrate and said product; (b) providing a constraint set for the plurality of *Homo sapiens* reactions; (c) providing an objective function; (d) determining at least one flux distribution that minimizes or maximizes the objective function when the constraint set is applied to the data structure, thereby predicting a *Homo sapiens* physiological function, and (e) producing a representation of the activity of the one or more *Homo sapiens* reactions. Similarly, the invention provides an apparatus that produces a representation of two or more interacting cells, including a tissue, organ, physiological system or whole organism wherein data structures are provided relating a plurality of reactants to a plurality of reactions for each type of interacting cell and for one or more intra-system functions. A constraint set is provided for the plurality of reactions for the plurality of data structures as well as an objective function that minimizes or maximizes an objective function when the constraint set is applied to predict a physiological function of the two or more interacting cells. The apparatus produces a representation of the activity of one or more reactions of the two or more interacting cells.

The methods of the invention can be used to determine the activity of a plurality of *Homo sapiens* reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, transport of a metabolite and metabolism of an alternative carbon source. In addition, the methods can be used to determine the activity of one or more of the reactions described above or listed in Table 1.

The methods of the invention can be used to determine a phenotype of a *Homo sapiens* mutant or aberrant cellular interaction between two or more cells. The activity of one or more reactions can be determined using the methods described above, wherein the reaction network data structure lacks one or more gene-associated reactions that occur in *Homo sapiens* or in a multicellular organism or multicellular interaction. Alternatively, the methods can be used to determine the activity of one or more reactions when a reaction that does not naturally occur in the model of multicellular interactions or in *Homo sapiens*, for example, is added to the reaction network data structure. Deletion of a gene can also be represented in a model of the invention by constraining the flux through the reaction to zero, thereby allowing the reaction to remain within the data structure. Thus, simulations can be made to predict the effects of adding or removing genes to or from one or more cells within a multicellular interaction, including *Homo sapiens* and/or a *Homo sapiens* cell. The methods can be particularly useful for determining the effects of adding or deleting a gene that encodes for a gene product that performs a reaction in a peripheral metabolic pathway.

A drug target or target for any other agent that affects a function of a multicellular interaction, including a *Homo sapiens* function can be predicted using the methods of the invention. Such predictions can be made by removing a reaction to simulate total inhibition or prevention by a drug or agent. Alternatively, partial inhibition or reduction in the activity a particular reaction can be predicted by performing the methods with altered constraints. For example, reduced activity can be introduced into a model of the invention by altering the $a_j$ or $b_j$ values for the metabolic flux vector of a target reaction to reflect a finite maximum or minimum flux value corresponding to the level of inhibition. Similarly, the effects of activating a reaction, by initiating or increasing the activity of the reaction, can be predicted by performing the methods with a reaction network data structure lacking a particular reaction or by altering the $a_j$ or $b_j$ values for the metabolic flux vector of a target reaction to reflect a maximum or minimum flux value corresponding to the level of activation. The methods can be particularly useful for identifying a target in a peripheral metabolic pathway.

Once a reaction has been identified for which activation or inhibition produces a desired effect on a function of a multicellular interaction, including a *Homo sapiens* function, an enzyme or macromolecule that performs the reaction in the multicellular system or a gene that expresses the enzyme or macromolecule can be identified as a target for a drug or other agent. A candidate compound for a target identified by the methods of the invention can be isolated or synthesized using known methods. Such methods for isolating or synthesizing compounds can include, for example, rational design based on known properties of the target (see, for example, DeCamp et al., *Protein Engineering Principles and Practice*, Ed. Cleland and Craik, Wiley-Liss, New York, pp. 467-506 (1996)), screening the target against combinatorial libraries of compounds (see for example, Houghten et al., *Nature*, 354, 84-86 (1991); Dooley et al., *Science*, 266, 2019-2022 (1994), which describe an iterative approach, or R. Houghten et al. PCT/US91/08694 and U.S. Pat. No. 5,556,762 which describe the positional-scanning approach), or a combination of both to obtain focused libraries. Those skilled in the art will know or will be able to routinely determine assay conditions to be used in a screen based on properties of the target or activity assays known in the art.

A candidate drug or agent, whether identified by the methods described above or by other methods known in the art, can be validated using an in silico model or method of multicellular interactions, including a *Homo sapiens* model or method of the invention. The effect of a candidate drug or agent on physiological function can be predicted based on the activity for a target in the presence of the candidate drug or agent measured in vitro or in vivo. This activity can be represented in an in silico model of the multicellular system by adding a reaction to the model, removing a reaction from the model or adjusting a constraint for a reaction in the model to reflect the measured effect of the candidate drug or agent on the activity of the reaction. By running a simulation under these conditions the holistic effect of the candidate drug or agent on the physiological function of the multicellular system, including *Homo sapiens* physiological function can be predicted.

The methods of the invention can be used to determine the effects of one or more environmental components or conditions on an activity of, for example, a multicellular interaction, a tissue, organ, physiological function or a *Homo sapiens* cell. As set forth above an exchange reaction can be added to a reaction network data structure corresponding to uptake of an environmental component, release of a component to the environment, or other environmental demand. The effect of the environmental component or condition can be further investigated by running simulations with adjusted $a_j$ or $b_j$ values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a multicellular system, organism or *Homo sapiens* cell can be taken up and metabolized. The environmental component can also be a combination of components present for example in a minimal medium composition. Thus, the methods can be used to determine an optimal or minimal medium composition that is capable of supporting a particular activity of a multicellular interaction or system, including a particular activity of *Homo sapiens*.

The invention further provides a method for determining a set of environmental components to achieve a desired activity for *Homo sapiens*. The method includes the steps of (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product; (b) providing a constraint set for the plurality of *Homo sapiens* reactions; (c) applying the constraint set to the data representation, thereby determining the activity of one or more *Homo sapiens* reactions (d) determining the activity of one or more *Homo sapiens* reactions according to steps (a) through (c), wherein the constraint set includes an upper or lower bound on the amount of an environmental component and (e) repeating steps (a) through (c) with a changed constraint set, wherein the activity determined in step (e) is improved compared to the activity determined in step (d). Similarly, a method for determining a set of environmental components to achieve a desired activity for a multicellular interaction also is provided. The method includes providing a plurality of data structures relating a plurality of reactants to a plurality of reactions for each type of interacting cell and for one or more intra-system functions; providing a constraint set for the plurality of reactions for the plurality of data structures as well as providing an objective function that minimizes or maximizes an objective function when the constraint set is applied to predict a physiological function of the two or more interacting cells; determining the activity of one or more reactions within two or more interacting cells using a constraint set having an upper or lower bound on the amount of an environmental component and repeating these steps until the activity is improved.

It is understood that modifications which do not substantially affect the activity of the various embodiments of this invention are also included within the definition of the invention provided herein. Accordingly, the following examples are intended to illustrate but not limit the present invention.

EXAMPLE I

This example shows the construction of a universal *Homo sapiens* metabolic reaction database, a *Homo sapiens* core metabolic reaction database and a *Homo sapiens* muscle cell metabolic reaction database. This example also shows the iterative model building process used to generate a *Homo sapiens* core metabolic model and a *Homo sapiens* muscle cell metabolic model.

A universal *Homo sapiens* reaction database was prepared from the genome databases and biochemical literature. The reaction database shown in Table 1 contains the following information:

Locus ID—the locus number of the gene found in the LocusLink website.

Gene Ab.—various abbreviations which are used for the gene.

Reaction Stoichiometry—includes all metabolites and direction of the reaction, as well as reversibility.

E.C.—The Enzyme Commission number.

Additional information included in the universal reaction database, although not shown in Table 1, included the chapter of Salway, surra (1999), where relevant reactions were found; the cellular location, if the reaction primarily occurs in a given compartment; the SWISS PROT identifier, which can be used to locate the gene record in SWISS PROT; the full name of the gene at the given locus; the chromosomal location of the gene; the Mendelian Inheritance in Man (MIM) data associated with the gene; and the tissue type, if the gene is primarily expressed in a certain tissue. Overall, 1130 metabolic enzyme- or transporter-encoding genes were included in the universal reaction database.

Fifty-nine reactions in the universal reaction database were identified and included based on biological data as found in Salway supra (1999), currently without genome annotation. Ten additional reactions, not described in the biochemical literature or genome annotation, were subsequently included in the reaction database following preliminary simulation testing and model content refinement. These 69 reactions are shown at the end of Table 1.

From the universal *Homo sapiens* reaction database shown in Table 1, a core metabolic reaction database was established, which included core metabolic reactions as well as some amino acid and fatty acid metabolic reactions, as described in Chapters 1, 3, 4, 7, 9, 10, 13, 17, 18 and 44 of J. G. Salway, *Metabolism at a Glance*, $2^{nd}$ ed., Blackwell Science, Malden, Mass. (1999). The core metabolic reaction database included 211 unique reactions, accounting for 737 genes in the *Homo sapiens* genome. The core metabolic reaction database was used, although not in its entirety, to create the core metabolic model described in Example II.

To allow for the modeling of muscle cells, the core reaction database was expanded to include 446 unique reactions, accounting for 889 genes in the *Homo sapiens* genome. This skeletal muscle metabolic reaction database was used to create the skeletal muscle metabolic model described in Example II.

Once the core and muscle cell metabolic reaction databases were compiled, the reactions were represented as a metabolic network data structure, or "stoichiometric input file." For example, the core metabolic network data structure shown in Table 2 contains 33 reversible reactions, 31 non-reversible reactions, 97 matrix columns and 52 unique enzymes. Each reaction in Table 2 is represented so as to indicate the substrate or substrates (a negative number) and the product or products (a positive number); the stoichiometry; the name of each reaction (the term following the zero); and whether the reaction is reversible (an R following the reaction name). A metabolite that appears in the mitochondria is indicated by an "m," and a metabolite that appears in the extracellular space is indicated by an "ex."

To perform a preliminary simulation or to simulate a physiological condition, a set of inputs and outputs has to be defined and the network objective function specified. To calculate the maximum ATP production of the *Homo sapiens* core metabolic network using glucose as a carbon source, a non-zero uptake value for glucose was assigned and ATP production was maximized as the objective function, using the representation shown in Table 2. The network's performance was examined by optimizing for the given objective function and the set of constraints defined in the input file, using flux balance analysis methods. The model was refined in an iterative manner by examining the results of the simulation and implementing the appropriate changes.

Using this iterative procedure, two metabolic reaction networks were generated, representing human core metabolism and human skeletal muscle cell metabolism.

EXAMPLE II

This example shows how human metabolism can be accurately simulated using a *Homo sapiens* core metabolic model.

The human core metabolic reaction database shown in Table 3 was used in simulations of human core metabolism. This reaction database contains a total of 65 reactions, covering the classic biochemical pathways of glycolysis, the pentose phosphate pathway, the tricitric acid cycle, oxidative phosphorylation, glycogen storage, the malate/aspartate shuttle, the glycerol phosphate shuttle, and plasma and mitochondrial membrane transporters. The reaction network was divided into three compartments: the cytosol, mitochondria, and the extracellular space. The total number of metabolites in the network is 50, of which 35 also appear in the mitochondria. This core metabolic network accounts for 250 human genes.

To perform simulations using the core metabolic network, network properties such as the P/O ratio were specified using Salway, supra (1999) as a reference. Oxidation of NADH through the Electron Transport System (ETS) was set to generate 2.5 ATP molecules (i.e. a P/O ratio of 2.5 for NADH), and that of $FADH_2$ was set to 1.5 ATP molecules (i.e. a P/O ratio of 1.5 for $FADH_2$).

Using the core metabolic network, aerobic and anaerobic metabolisms were simulated in silico. Secretion of metabolic by-products was in agreement with the known physiological parameters. Maximum yield of all 12 precursor-metabolites (glucose-6-phosphate, fructose-6-phosphate, ribose-5-phosphate, erythrose-4-phosphate, triose phosphate, 3-phosphoglycerate, phosphoenolpyruvate, pyruvate, acetyl CoA, α-ketoglutarate, succinyl CoA, and oxaloacetate) was examined and none found to exceed the values of its theoretical yield.

Maximum ATP yield was also examined in the cytosol and mitochondria. Salway, supra (1999) reports that in the absence of membrane proton-coupled transport systems, the energy yield is 38 ATP molecules per molecule of glucose and otherwise 31 ATP molecules per molecule of glucose. The core metabolic model demonstrated the same values as described by Salway supra (1999). Energy yield in the mitochondria was determined to be 38 molecules of ATP per glucose molecule. This is equivalent to production of energy in the absence of proton-couple transporters across mitochondrial membrane since all the protons were utilized only in oxidative phosphorylation. In the cytosol, energy yield was calculated to be 30.5 molecules of ATP per glucose molecule. This value reflects the cost of metabolite exchange across the mitochondrial membrane as described by Salway, supra (1999).

EXAMPLE III

This example shows how human muscle cell metabolism can be accurately simulated under various physiological and pathological conditions using a *Homo sapiens* muscle cell metabolic model.

As described in Example I, the core metabolic model was extended to also include all the major reactions occurring in the skeletal muscle cell, adding new functions to the classical metabolic pathways found in the core model, such as fatty acid synthesis and β-oxidation, triacylglycerol and phospholipid formation, and amino acid metabolism. Simulations were performed using the muscle cell reaction database shown in Table 4. The biochemical reactions were again compartmentalized into cytosolic and mitochondrial compartments.

To simulate physiological behavior of human skeletal muscle cells, an objective function had to be defined. Growth of muscle cells occurs in time scales of several hours to days. The time scale of interest in the simulation, however, was in the order of several to tens of minutes, reflecting the time period of metabolic changes during exercise. Thus, contraction (defined as, and related to energy production) was chosen to be the objective function, and no additional constraints were imposed to represent growth demands in the cell.

To study and test the behavior of the network, twelve physiological cases (Table 8) and five disease cases (Table 9) were examined. The input and output of metabolites were specified as indicated in Table 8, and maximum energy production and metabolite secretions were calculated and taken into account.

TABLE 8

| Metabolite Exchange | 1 | 2 | 3 | 4 | 5 | 6 | 7 | 8 | 9 | 10 | 11 | 12 |
|---|---|---|---|---|---|---|---|---|---|---|---|---|
| Glucose | I | I | — | — | I | I | — | — | — | — | — | — |
| O2 | I | — | I | — | I | — | I | — | I | — | I | — |
| Palmitate | I | I | — | — | — | — | — | — | I | I | — | — |
| Glycogen | I | I | I | I | — | — | — | — | — | — | — | — |
| Phosphocreatine | I | I | — | — | — | — | — | — | — | — | I | I |
| Triacylglycerol | I | I | — | — | — | — | I | I | — | — | — | — |
| Isoleucine | I | I | — | — | — | — | — | — | — | — | — | — |
| Valine | I | I | — | — | — | — | — | — | — | — | — | — |
| Hydroxybutyrate | — | — | — | — | — | — | — | — | — | — | — | — |
| Pyruvate | O | O | O | O | O | O | O | O | O | O | O | O |
| Lactate | O | O | O | O | O | O | O | O | O | O | O | O |
| Albumin | O | O | O | O | O | O | O | O | O | O | O | O |

TABLE 9

| Disease | Enzyme Deficiency | Reaction Constrained |
|---|---|---|
| McArdle's disease | phosphorylase | GBE1 |
| Tarui's disease | phosphofructokianse | PFKL |
| Phosphoglycerate kinase deficiency | phosphoglycerate kinase | PGK1R |
| Phosphoglycerate mutase deficiency | phosphoglycerate mutase | PGAM3R |
| Lactate dehydrogenase deficiency | Lactate dehyrogenase | LDHAR |

The skeletal muscle model was tested for utilization of various carbon sources available during various stages of exercise and food starvation (Table 8). The by-product secretion of the network in an aerobic to anaerobic shift was qualitatively compared to physiological outcome of exercise and found to exhibit the same general features such as secretion of fermentative by-products and lowered energy yield.

The network behavior was also examined for five disease cases (Table 9). The test cases were chosen based on their physiological relevance to the model's predictive capabilities. In brief, McArdle's disease is marked by the impairment of glycogen breakdown. Tarui's disease is characterized by a deficiency in phosphofructokinase. The remaining diseases examined are marked by a deficiency of metabolic enzymes phosphoglycerate kinase, phosphoglycerate mutase, and lactate dehydrogenase. In each case, the changes in flux and by-product secretion of metabolites were examined for an aerobic to anaerobic metabolic shift with glycogen and phosphocreatine as the sole carbon sources to the network and pyruvate, lactate, and albumin as the only metabolic by-products allowed to leave the system. To simulate the disease cases, the corresponding deficient enzyme was constrained to zero. In all cases, a severe reduction in energy production was demonstrated during exercise, representing the state of the disease as seen in clinical cases.

EXAMPLE IV

This Example shows the construction and simulation of a multi-cellular model demonstrating the interactions between human adipocytes and monocytes.

The specific examples described above demonstrate the use a constraint-based approach in modeling metabolism in microbial organisms including prokaryotes such as *E. coli* and eukaryotes such as *S. cerevisiae* as well as for complex multicellular organisms requiring regulatory interactions such as humans. Described below is the modeling procedure, network content, and simulation results including network characteristics and metabolic performance of an integrated two-cell model of human adipocyte (fatty cell) and myocyte (muscle cell) using the compositions and methods of the invention. Simulations were performed to exemplify the coupled function of the two cell types during distinct physiological conditions corresponding to the coupled function of adipocyes and myocytes during sprint and marathon physiological conditions.

A human metabolic network model was reconstructed using biochemical, physiological, and genomic data as described previously. Briefly, the central metabolic network was used as a template for the construction of cell-specific models by adding biochemical reactions known to occur in specific cell-types of interest based on genomic, biochemical, and/or physiological information. Other methods for reconstructing the cell-specific models included reconstructing all the biochemical pathways and biochemical reactions that occur in the human metabolism regardless of their tissue specificity and location within the cell in a database and then reconstructing cell-, tissue-, organ-specific models by separating reactions that occur in specified cells, tissues, and/or organs based on genomic, physiological, biochemical, and/or high throughput data such as gene expression, proteomics, metabolomics, and other types of "omic" data. In this latter approach, in addition to the cell-, tissue-, and/or organ-specific reactions, reactions can be added to balance metabolites and represent the biochemistry, physiology, and genetics of the cells, tissues, organs, and/or whole human body. In the approach described below, the initial reconstruction of a central metabolic network followed by development of cell-specific models, the reconstruction of a generic central metabolic network is not a necessary step in reconstructing and modeling human metabolism. Rather, it is performed to accelerate the reconstruction process.

Implementation of the multi-cellular adipocyte-myocyte model is described below with reference to the reconstruction of the constituent components. In this regard, the reconstruction of a central human metabolic network is described first followed by the reconstruction procedures for fatty cell and muscle cell specific networks. The reconstruction procedure by which the two cell-specific models were combined to generate a multi-cellular model for human metabolism is then described.

Metabolic Network of Central Human Metabolism

The metabolic network of the central human metabolism was constructed as a template and a starting point for reconstructing more specific cell models. To construct a central metabolic network for human metabolism, a compendium of 1557 annotated human genes obtained from Kyoto Encyclopedia of Genes and Genomes KEGG, National Center for Biotechnology Information or NCBI, and the Universal Protein Resource or UniProt databases was used. In addition to the genomic and proteomic data, several primary textbooks and publications on the biochemistry of human metabolism also were used and includedthe *Human Metabolism: Func-*

*tional Diversity and Integration,* Ed. by J. R. Bronk, Harlow, Addison, Wesley, Longman (1999); *Textbook of Biochemistry with Clinical Correlations,* Ed. by Thomas M. Devlin, New York, Wiley-Liss (2002), and *Metabolism at a Glance,* Ed. by J. G. Salway, Oxford, Malden, Mass., Blackwell Science (1999). The network reconstruction of human central metabolism included metabolic pathways for glycolysis, gluconeogenesis, citrate cycle (TCA cycle), pentose phosphate pathway, galactose, malonyl-CoA, lactate, and pyruvate metabolism. The methods described previously were similarly used for this reconstruction as well as those described below. Metabolic reactions were compartmentalized into extra-cellular space, cytosol, mitochondrion, and endoplasmic reticulum. In addition to the biochemical pathways, exchange reactions were included based on biochemical literature and physiological evidence to provide the transport of metabolites across different organelles and cytosolic membrane.

Figures 1, 5:
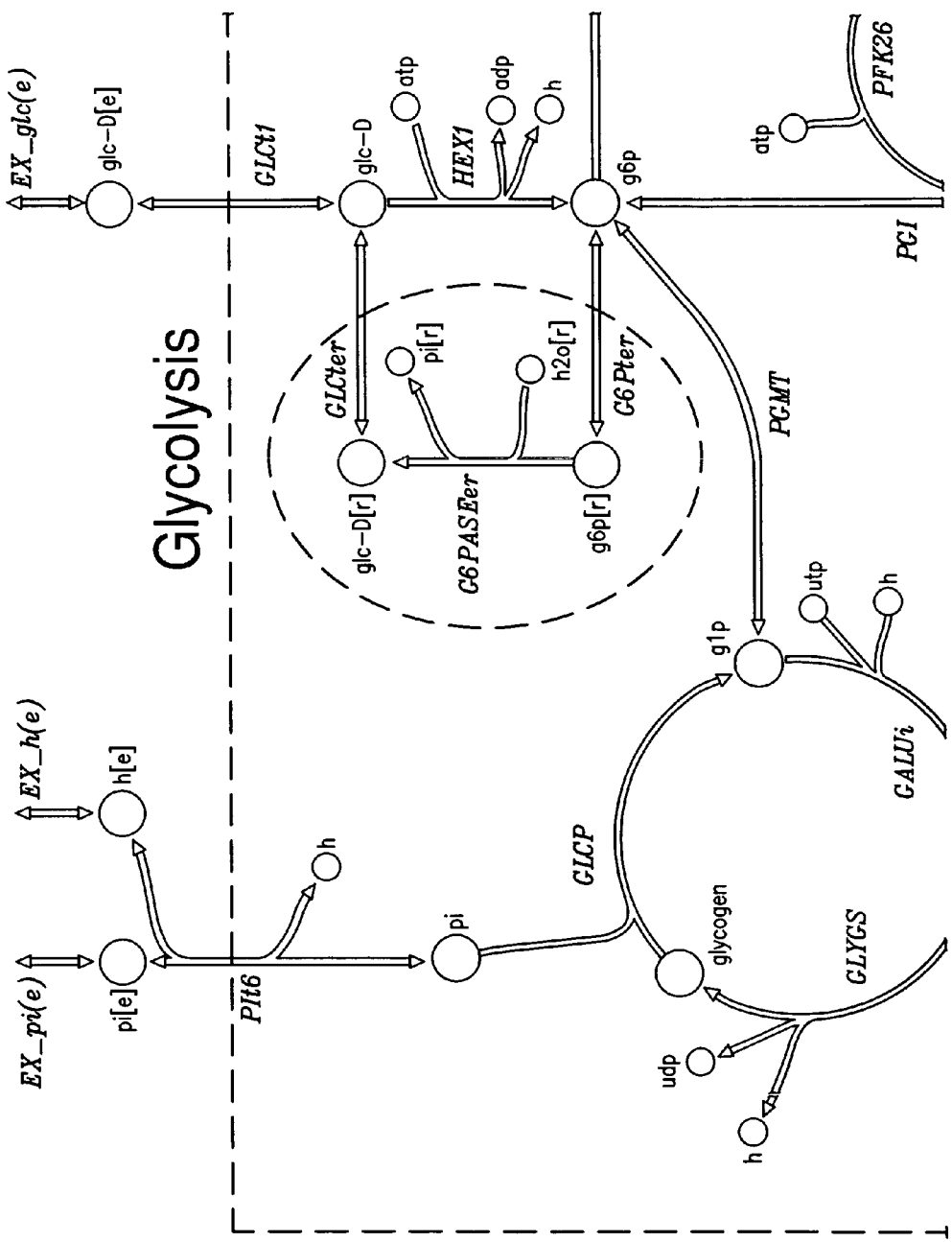
FIG. 5 shows a metabolic network of central human metabolism.
Figures 2, 5:
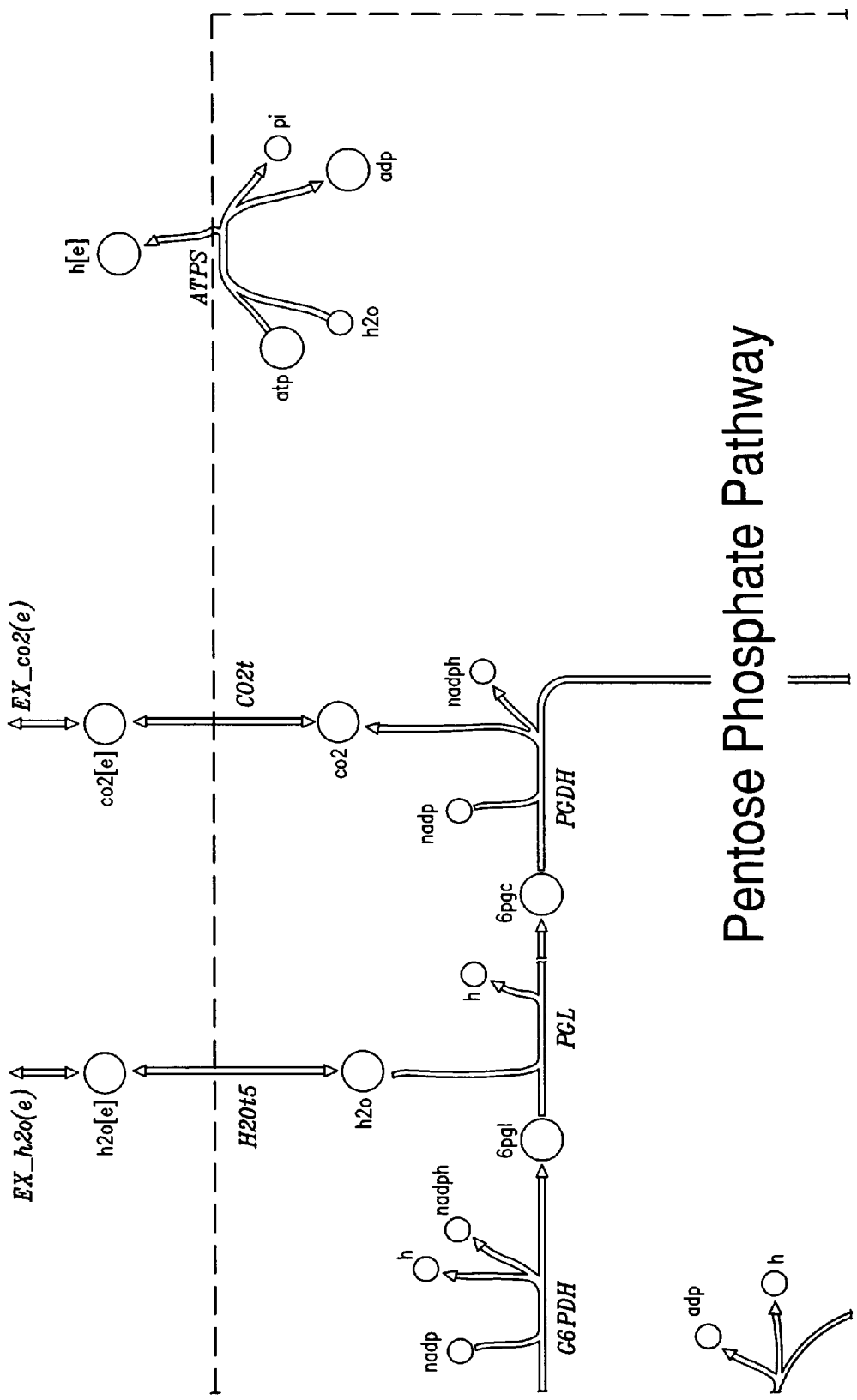
FIG. 2 shows mass balance constraints and flux constraints (reversibility constraints) that can be placed on the hypothetical metabolic network shown in FIG. 1.
Figures 3, 5:
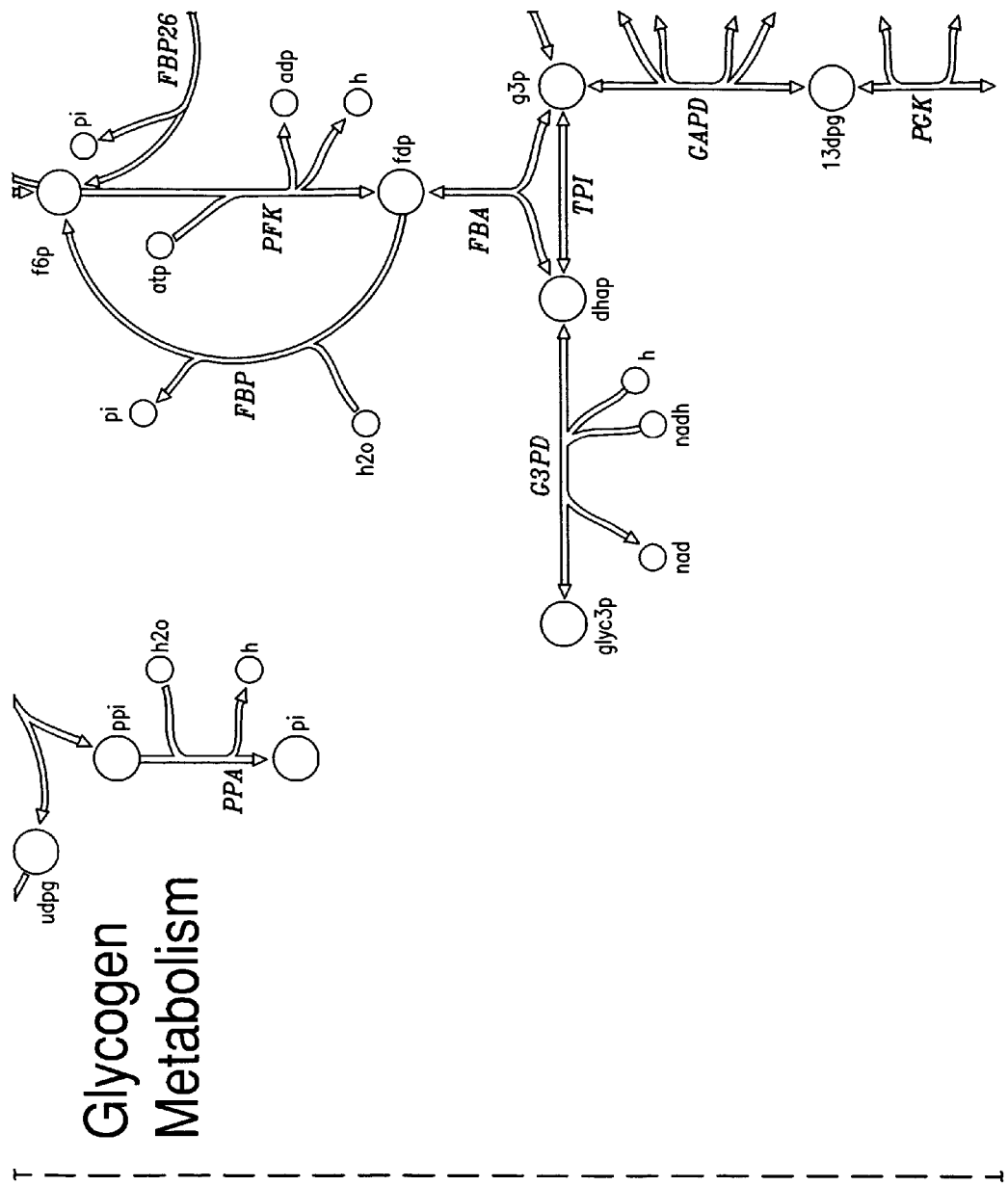
FIG. 3 shows the stoichiometric matrix (S) for the hypothetical metabolic network shown in FIG. 1.
Figures 4, 5:
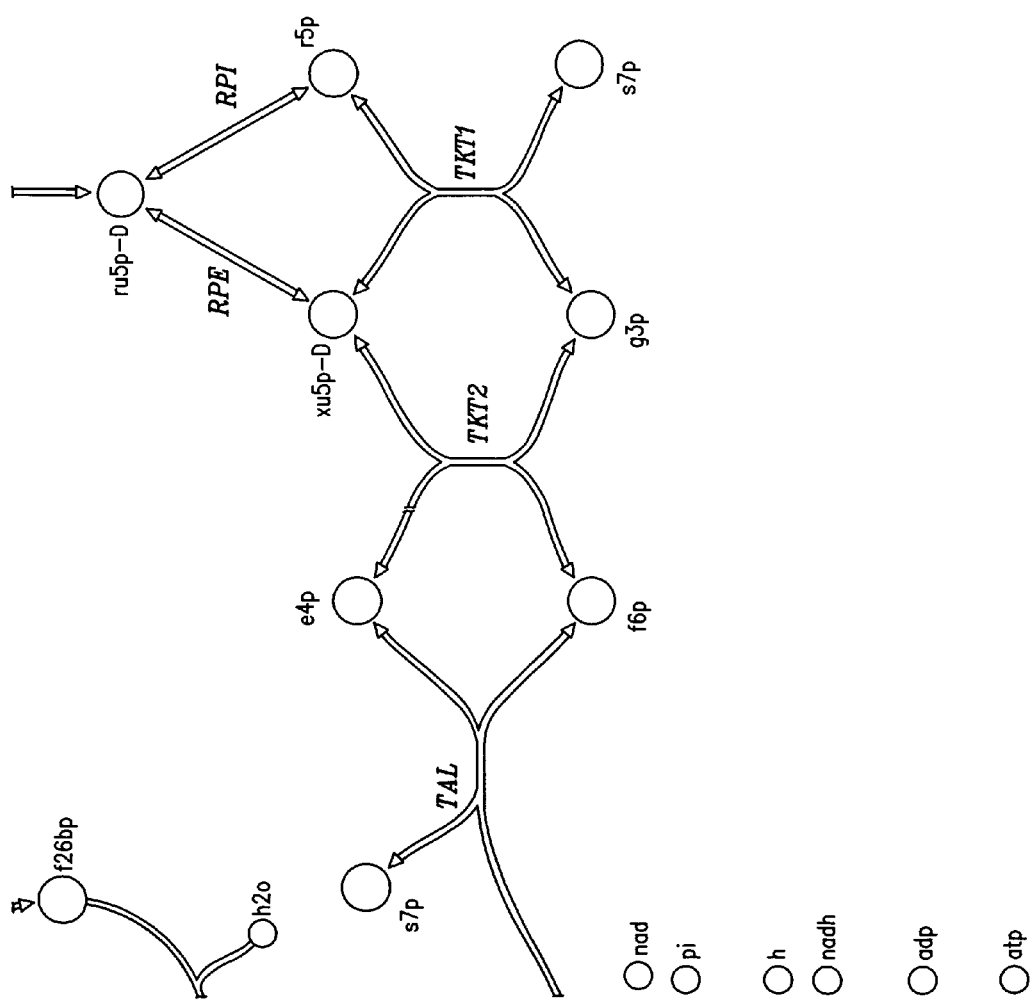
Figure 5:
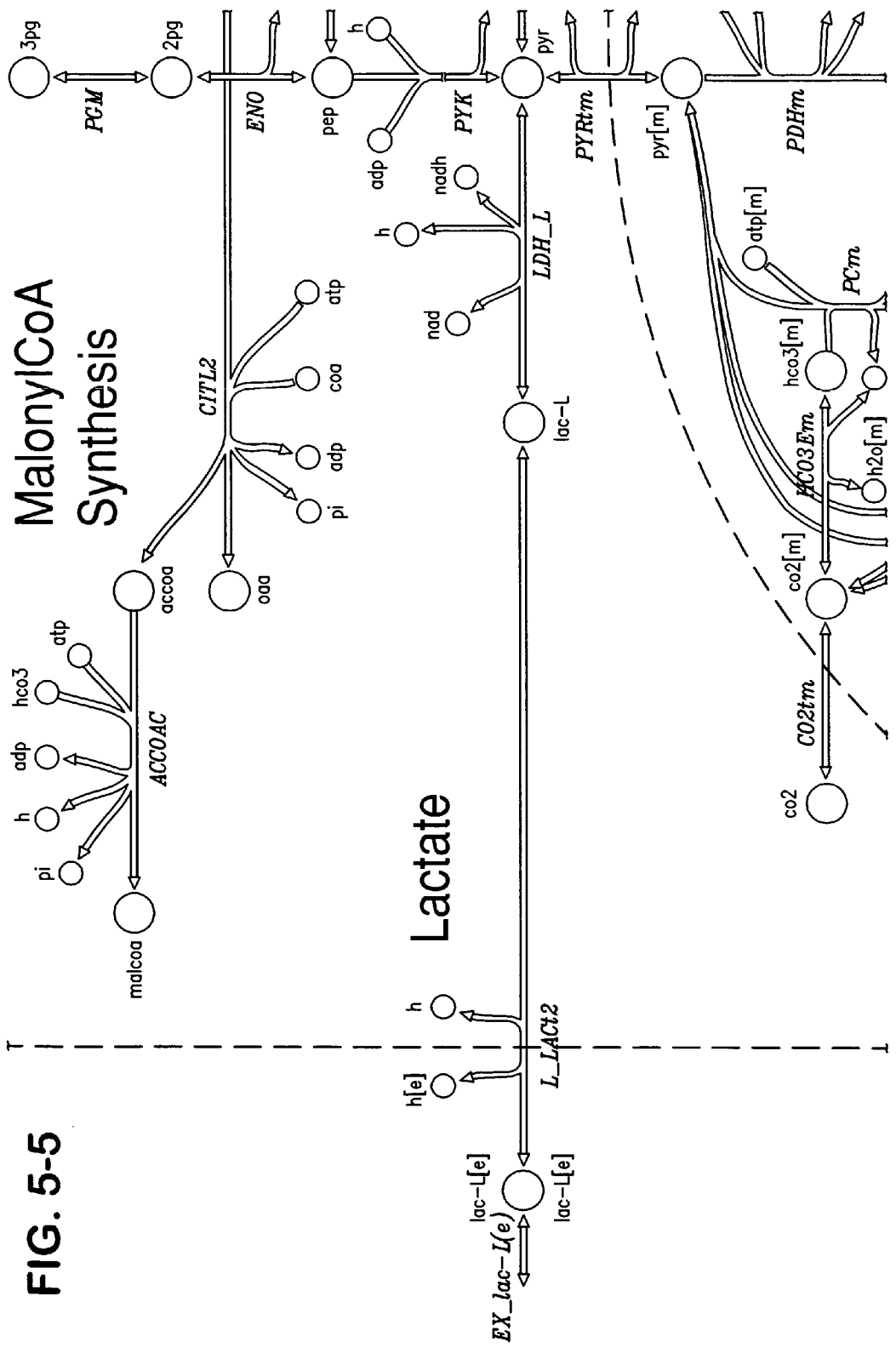
Figures 5, 6:
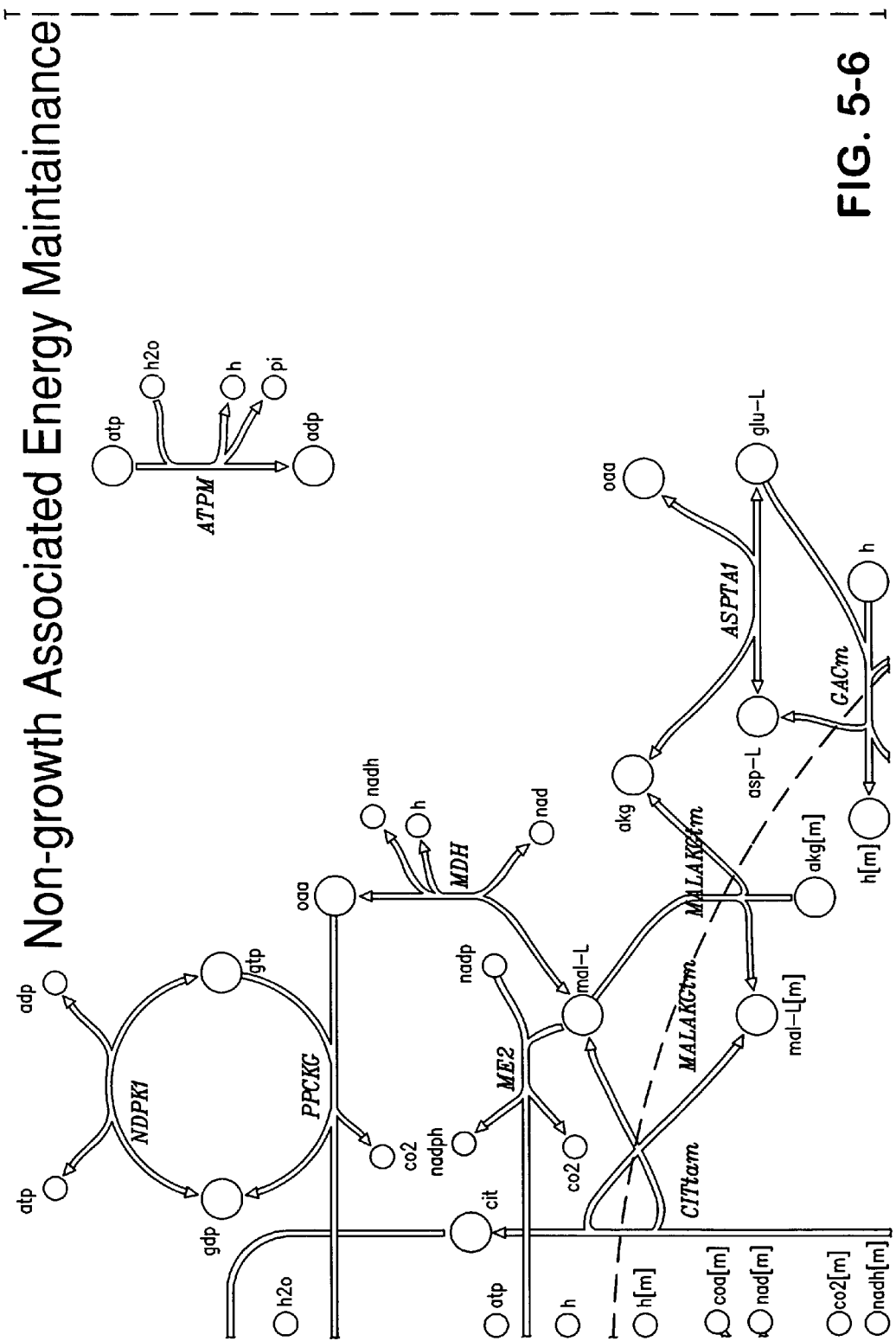
FIG. 6 shows an example of a gene-protein-reaction association for trios-phosphate isomerase.

The completed central metabolic network for human metabolism is shown in FIG. 5 where dashed lines indicate organelle, cell, or system boundary. The large dashed rectangle (black) represents the cytosolic membrane. The large dashed circle (red) represents the mitochondrial membrane and small dashed circle (green) represents the endoplasmic reticulum membrane. The human central metabolic network contains 80 reactions of which 25 are transporters and 60 unique metabolites 5. A representative example of a gene-protein-reaction association is shown in FIG. 6 where the open reading frame or ORF (7167) is associated to an mRNA transcript (TPI1). The transcript is then associated to a translated protein (TPi1) that catalyzes a corresponding reaction (TPI).

Adipocyte Metabolic Network

Adipocytes are specialized cells for synthesizing and storing triacylglycerol. Triacylglycerols (TAG's) are synthesized from dihydroxyacetone phosphate and fatty acids in white adipose tissue. Triacylglycerol synthesized in adipocytes can be hydrolyzed (or degraded) into fatty acids and glycerol via specialized pathways in the fat cells. The fatty acids that are released from triacylglycerol leave the cell and are transported to other cell types such as myocytes for energy production. The fatty acid composition of triacylglycerol in human mammary adipose tissue has been experimentally measured (Raclot et al., 324:911-5 (1997)) and includes essential, non-essential, saturated, unsaturated, even-, and odd-chain fatty acids (Table 10).

TABLE 10

Fatty acid composition of fat cell TAG in human, NEFA released by these cells in vitro, and relative mobilization (% NEFA/% TAG) of fatty acids.

| Fatty acid | TAG (weight %) | NEFA (weight %) | Relative mobilization |
|---|---|---|---|
| $C_{12:0}$ | 0.50 ± 0.07 | 0.45 ± 0.06 | 0.88 ± 0.02 |
| $C_{14:0}$ | 3.08 ± 0.13 | 2.94 ± 0.15 | 0.94 ± 0.01 |
| $C_{14:1,n-7}$ | 0.03 ± 0.00 | 0.03 ± 0.00 | 1.07 ± 0.14 |
| $C_{14:1,n-5}$ | 0.20 ± 0.01 | 0.19 ± 0.02 | 0.96 ± 0.03 |
| $C_{15:0}$ | 0.33 ± 0.02 | 0.35 ± 0.02 | 1.05 ± 0.02 |
| $C_{16:0}$ | 22.79 ± 0.56 | 23.51 ± 0.74 | 1.02 ± 0.01 |
| $C_{16:1,n-9}$ | 0.54 ± 0.01 | 0.42 ± 0.02*** | 0.77 ± 0.01 |
| $C_{16:1,n-7}$ | 2.77 ± 0.21 | 3.69 ± 0.34* | 1.31 ± 0.02 |
| $C_{17:1,n-8}$ | 0.29 ± 0.02 | 0.36 ± 0.02* | 1.21 ± 0.03 |
| $C_{18:0}$ | 6.67 ± 0.35 | 6.41 ± 1.39 | 0.95 ± 0.06 |
| $C_{18:1,n-9}$ | 40.79 ± 0.52 | 39.77 ± 0.57 | 0.96 ± 0.01 |
| $C_{18:1,n-7}$ | 1.90 ± 0.05 | 2.12 ± 0.10 | 1.10 ± 0.03 |
| $C_{18:1,n-5}$ | 0.27 ± 0.01 | 0.31 ± 0.03 | 1.12 ± 0.04 |
| $C_{18:2,n-6}$ | 16.23 ± 0.86 | 16.21 ± 0.62 | 0.99 ± 0.01 |
| $C_{18:3,n-6}$ | 0.04 ± 0.00 | 0.05 ± 0.01 | 1.27 ± 0.07 |

TABLE 10-continued

Fatty acid composition of fat cell TAG in human, NEFA released by these cells in vitro, and relative mobilization (% NEFA/% TAG) of fatty acids.

| Fatty acid | TAG (weight %) | NEFA (weight %) | Relative mobilization |
|---|---|---|---|
| $C_{18:3,n-3}$ | 0.51 ± 0.02 | 0.75 ± 0.03*** | 1.43 ± 0.03 |
| $C_{20:0}$ | 0.21 ± 0.02 | 0.10 ± 0.01*** | 0.47 ± 0.04 |
| $C_{20:1,n-11}$ | 0.17 ± 0.01 | 0.11 ± 0.01*** | 0.66 ± 0.03 |
| $C_{20:1,n-9}$ | 0.84 ± 0.02 | 0.53 ± 0.02*** | 0.62 ± 0.01 |
| $C_{20:1,n-7}$ | 0.03 ± 0.00 | 0.02 ± 0.00* | 0.67 ± 0.03 |
| $C_{20:2,n-9}$ | 0.04 ± 0.00 | 0.02 ± 0.00** | 0.63 ± 0.06 |
| $C_{20:2,n-6}$ | 0.31 ± 0.02 | 0.26 ± 0.01* | 0.82 ± 0.04 |
| $C_{20:3,n-6}$ | 0.26 ± 0.03 | 0.24 ± 0.03 | 0.90 ± 0.05 |
| $C_{20:3,n-3}$ | 0.03 ± 0.00 | 0.03 ± 0.00 | 0.90 ± 0.06 |
| $C_{20:4,n-6}$ | 0.35 ± 0.03 | 0.57 ± 0.04*** | 1.60 ± 0.04 |
| $C_{20:4,n-3}$ | 0.03 ± 0.01 | 0.04 ± 0.01 | 1.13 ± 0.16 |
| $C_{20:5,n-3}$ | 0.04 ± 0.01 | 0.10 ± 0.01*** | 2.25 ± 0.08 |
| $C_{22:0}$ | 0.04 ± 0.01 | 0.02 ± 0.01* | 0.42 ± 0.05 |
| $C_{22:1,n-11}$ | 0.03 ± 0.01 | 0.01 ± 0.00* | 0.37 ± 0.02 |
| $C_{22:1,n-9}$ | 0.07 ± 0.01 | 0.03 ± 0.00** | 0.45 ± 0.03 |
| $C_{22:4,n-6}$ | 0.17 ± 0.02 | 0.10 ± 0.01** | 0.58 ± 0.03 |
| $C_{22:5,n-6}$ | 0.02 ± 0.01 | 0.01 ± 0.00 | 0.59 ± 0.05 |
| $C_{22:5,n-3}$ | 0.20 ± 0.03 | 0.11 ± 0.01** | 0.55 ± 0.02 |
| $C_{22:6,n-3}$ | 0.21 ± 0.04 | 0.14 ± 0.02* | 0.65 ± 0.04 |

*$P < 0.05$;
** $P < 0.01$;
***$P < 0.001$

The adipocyte metabolic model was constructed by adding the non-essential saturated, unsaturated, even- and odd-chain fatty acid biosynthetic pathways to the central metabolic network for 21 of the fatty acids listed in Table 10. The remaining 13 essential fatty acids were supplied to the cell via the extra-cellular space, representing the nutritional intake from the environment. Pathway for biosynthesis of triacylglycerol (TAG) from all 34 fatty acids was included to account for the formation and storage of TAG in adipocytes. Reactions for hydrolysis of TAG into fatty acids were also included to represent TAG degradation. In addition to fatty acid synthesis and TAG biosynthesis and degradation, transport reactions were included to allow for the release of fatty acids from intra-cellular space to the environment.

Figures 5, 6, 7:
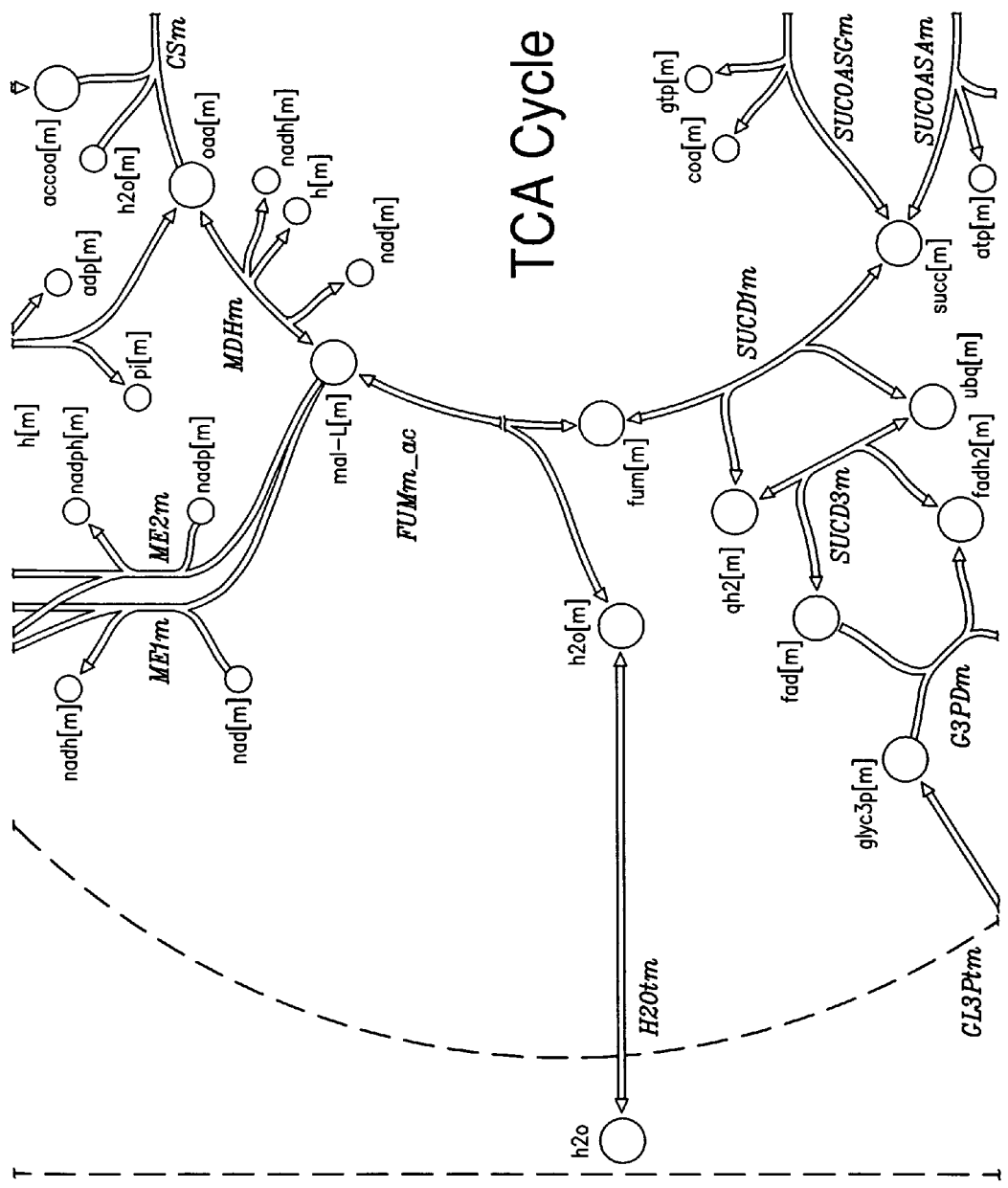
FIG. 7 shows a metabolic network of adipocyte metabolism.

The metabolic model of an adipocyte cell contains a total of 198 reactions of which 63 are transporters. The adipocyte cell model is shown in FIG. 7 where dashed lines indicate organelle, cell, or system boundary. The large dashed rectangle (yellow) represents the adipocyte cytosolic membrane. The two large dashed circles (red) represent the mitochondrial membrane and the small dashed circle at the top (green) represents the endoplasmic reticulum membrane. As shown, metabolic reactions were compartmentalized into extra-cellular, cytosolic, mitochondrial, and endoplasmic reticulum. As described above, the extra-cellular space represents the environment outside the cell, which can include the space outside the body, connective tissues, and interstitial space between cells.

Myocyte Metabolic Network

Figures 5, 6, 7, 8:
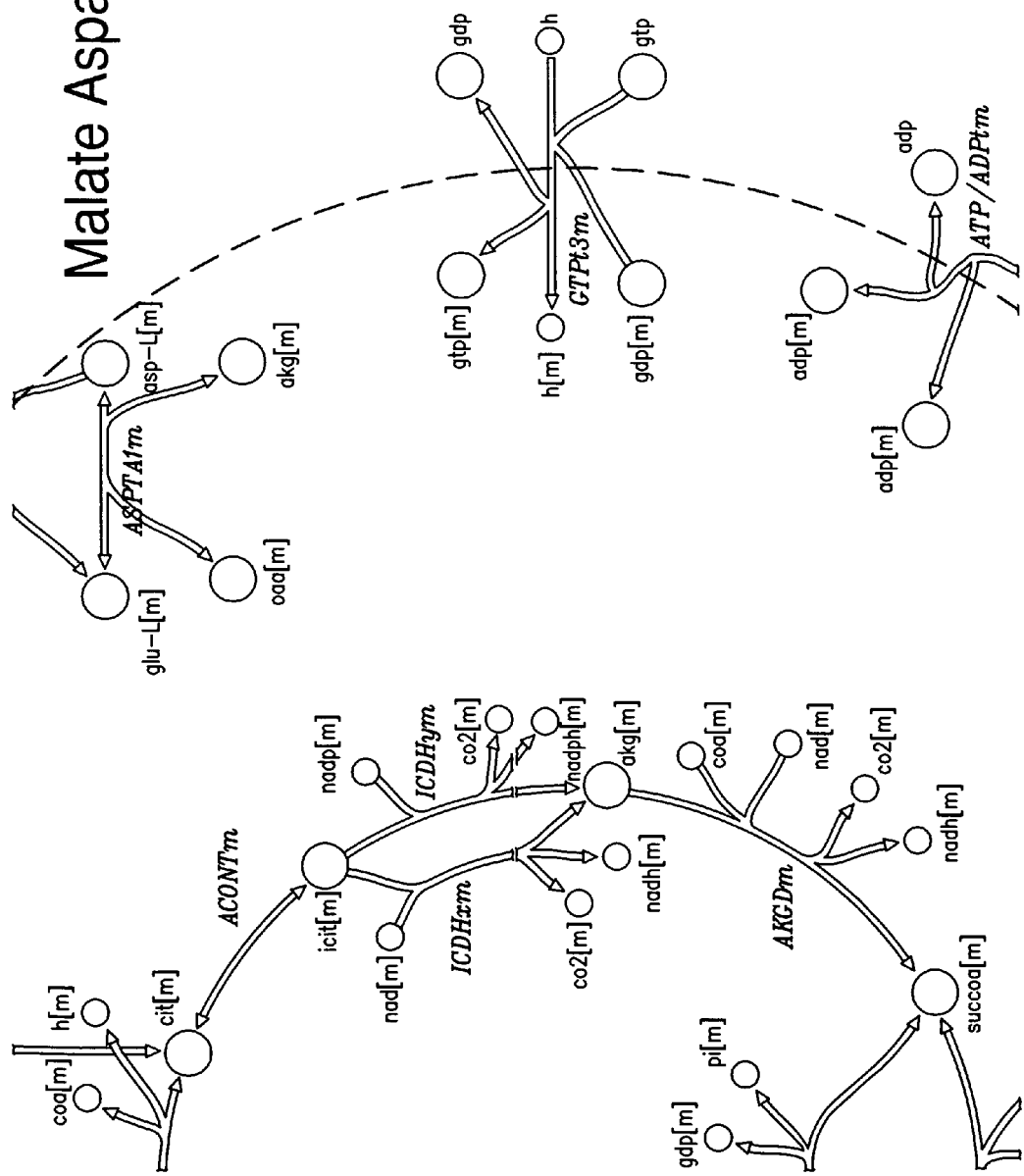
FIG. 8 shows muscle contraction in a myocyte metabolic model.

The energy required for muscle contraction is generally supplied by glucose, stored glycogen, phosphocreatine, and fatty acids. The myocyte model was constructed by adding phosphocreatine kinase reaction, myosin-actin activation mechanism, and β-oxidation pathway to the central metabolic network. Muscle contraction was represented by a sequential conversion of myoactin to myosin-ATP, myosin-ATP to myosin-ADP-P, myosin-ADP-P to myosin-actin-ADP-P complex, myosin-actin-ADP-P to myoactin, and subsequently the formation of muscle contraction as shown in FIG. 8.

The conversion of myoactin to myosin-actin-ADP-P complex and muscle contraction results in a net conversion of ATP and $H_2O$ to ADP, $H^+$, and $P_i$.

Figures 5, 6, 7, 8, 9:
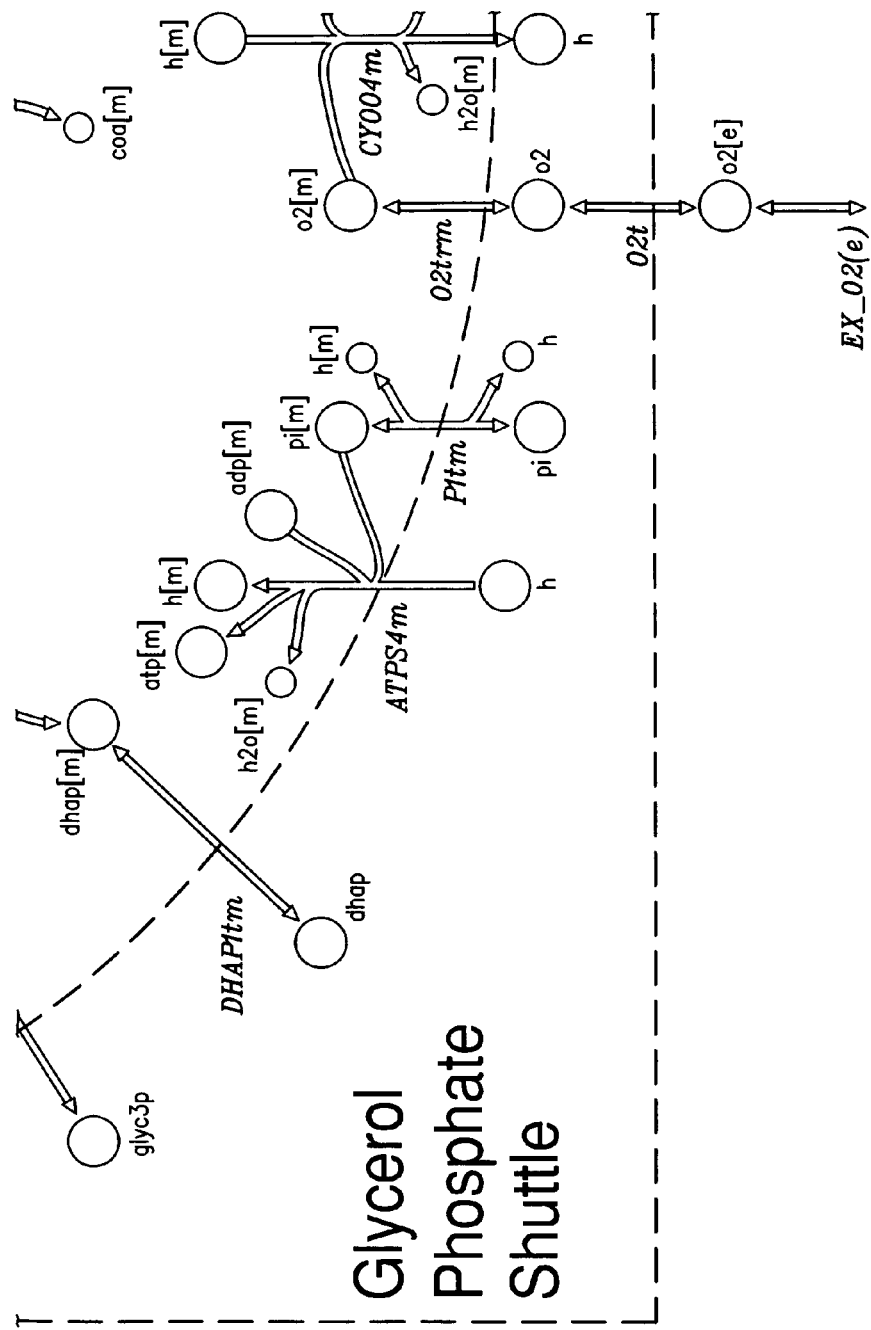
FIG. 9 shows a metabolic network of myocyte metabolism.
Figure 6:
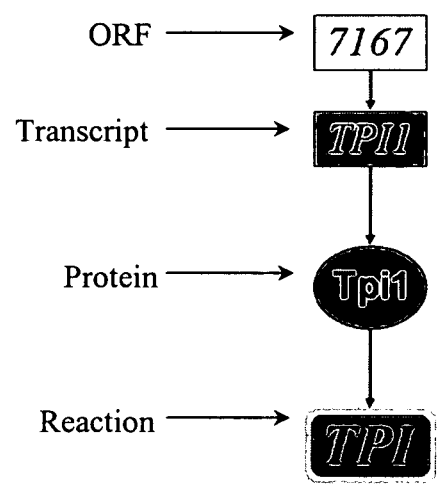

The complete reconstructed metabolic model for myocyte cell metabolism is shown in FIG. 9 where dashed lines indicate organelle, cell, or system boundary. The large dashed rectangle (brown) represents the myocyte cytosolic membrane. The two large dashed circles (red) represent the mitochondrial membrane. The medium sized dashed circle (purple) represents the peroxisomal membrane and the small dashed circle (green) represents the endoplasmic reticulum membrane. The myocyte network contains a total of 205 reactions of which 46 are transport reactions. Reactions for utilizing phosphcreatine as well as selected pathways for β-oxidation of saturated, unsaturated, even- and odd-chain fatty acids and their intermediates were also included in the model and are shown in FIG. 9. As with the previous network models, metabolic reactions were compartmentalized into extra-cellular, cytosolic, mitochondrial, peroxisomal, and endoplasmic reticulum.

Multi-Cellular Adipocyte-Myocyte Reconstruction

To generate a multi-cellular model for human metabolism, the metabolic function of the two models of adipocyte and myocyte were integrated by reconstructing a model that includes all the metabolic reactions in the two individual cell types. The interaction of the two cell types were then represented within an "intra-system" space, which represents the connective tissues such as blood, urine, and interstitial space, and an outside environment or "extra-system" space. To represent the uptake of metabolites and essential fatty acids from the environment, appropriate transport reactions were added to exchange metabolites across the extra-system boundary. Additional reactions also were added to balance metabolites in the intra-system space by including the bicarbonate and ammonia buffer systems as they function in the kidneys. These reactions were initially omitted but were added to improve the model once the requirement for the integrated system to buffer extracellular protons in the interstitial space became apparent once simulation testing began. The combined adipocyte-myocyte model contains 430 reactions and 240 unique metabolites. The complete reconstruction is shown in FIG. 10 and a summary of the reactions is set forth in Table 11. A substantially complete listing of all the reactions set forth in FIG. 10 is set forth below in Table 15.

TABLE 11

Network properties of central metabolic network, adipocyte, myocyte, and multi-cell adipocyte-myocyte models.

| Model | Reactions | Transporters | Compounds |
|---|---|---|---|
| Central Metabolism | 80 | 25 | 60 |
| Adipocyte | 198 | 63 | 150 |
| Myocyte | 205 | 46 | 167 |
| Adipocyte-Myocyte | 430 | 135 | 240 |

In FIG. 10, dashed lines again indicate organelle, cell, or system boundaries. The outer most large dashed rectangle (black) separates the environment inside and outside the human body. The two interior dashed rectangles represents the adipocyte cytosolic membrane (top, yellow) and the myocyte cytosolic membrane (bottom, brown). The pair of larger dashed circles within the adipocyte and myocyte cytosol (red) represent the mitochondrial membrane. The medium sized dashed circle in the myocyte cytosol (purple) represents the peroxisomal membrane and small dashed circle within the adipocyte and myocyte cytosol (green) represent the endoplasmic reticulum membrane.

Metabolic Simulations

The computational and infrastructure requirements for producing the integrated multi-cellular model were assessed by examining the network properties of first, the cell-specific models, and then the integrated multi-cellular reconstruction.

Metabolic Model of Central Human Metabolism

The metabolic capabilities of the central human model was determined through computation of maximum yield of the 12 precursor metabolites per glucose. The results are shown in Table 12. In all cases, the network's yield was less or equal to the maximum theoretical values except for succinyl-CoA. In the case of succinyl-CoA, a higher yield was possible by incorporating $CO_2$ via pyruvate carboxylase reaction, PCm. In addition to precursor metabolite yields, the maximum ATP yield per mole of glucose was computed in the network. The maximum ATP yield for the central human metabolism was computed to be 31.5 mol ATP/mol glucose, which is consistent with previously calculated values (Vo et al., *J. Biol. Chem.* 279:39532-40. (2004)).

TABLE 12

Maximum theoretical and central human metabolic network yields for the precursor metabolites per glucose. Units are in mol/mol glucose.

| Precursor Metabolites | Theoretical | Central Metabolism |
|---|---|---|
| Glucose 6-P | 1 | 0.94 |
| Fructose 6-P | 1 | 0.94 |
| Ribose 5-P | 1.2 | 1.115 |
| Erythrose 4-P | 1.5 | 1.37 |
| Glyceraldehyde 3-P | 2 | 1.775 |
| 3-P Glycerate | 2 | 2 |
| Phosphoenolpyruvate | 2 | 2 |
| Pyruvate | 2 | 2 |
| Oxaloacetate, mitochondrial | 2 | 1.969 |
| Acetyl-CoA, mitochondrial | 2 | 2 |
| aKeto-glutarate, mitochondrial | 1 | 1 |
| Succinyl-CoA, mitochondrial | 1 | 1.595 |

The biomass demand in living cells is a requirement for the production of biosynthetic components such as amino acids, lipids and other molecules that are needed to provide cell integrity, maintenance, and growth. All the biosynthetic components were made from the 12 precursor metabolites in the central metabolism shown in Table 12. The rate of growth and biomass maintenance in mammalian cells however is typically much lower than the rate of metabolic activities. Thus to represent the cells' biosynthetic requirement, a small flux demand was imposed for the production of the 12 precursor metabolites while maximizing for ATP. In the absence of experimental measurements, the capability of the network to meet the biosynthetic requirements was examined by constructing a reaction in which all the precursor metabolites were made simultaneously with stoichiometric coefficients of one as set forth in the reaction below:

Precursor Demand: 3pg[c]+accoa[m]+akg[m]+e4p[c]+f6p[c]+g3p[c]+g6p[c]+oaa[m]+pep[c]+pyr[c]+r5p[c]+succoa[m]→(2) coa[m]

In the absence of quantitative measurement, the above reaction serves to demonstrate the ability of the network to meet both biomass and energy requirements in the cell simultaneously. The maximum ATP yield for the central metabolism with a demand of 0.01 mmol/gDW of precursor metabolites was computed to be 29.0, demonstrating that the energy and carbon requirements for precursor metabolite generation, as expected, reduce the maximum energy production in the cell and this amount can be quantified using the reconstructed model.

Triacylglycerol Storage and Utilization in Adipocyte Tissue

As described previously, a main function of adipocyte is to synthesize, store, and hydrolyze triacylglycerols. The stored TAG can be used to generate ATP during starvation or under high-energy demand conditions. TAG hydrolysis results in the formation of fatty acids and glycerol in adipocyte. Fatty acids are transported to other tissues such as the muscle tissue where they can be utilized to generate energy. Glycerol is utilized further by the liver and other tissues where it is converted into glycerol phosphate and enters glycolytic pathway.

Figures 7, 8, 9, 10, 11:
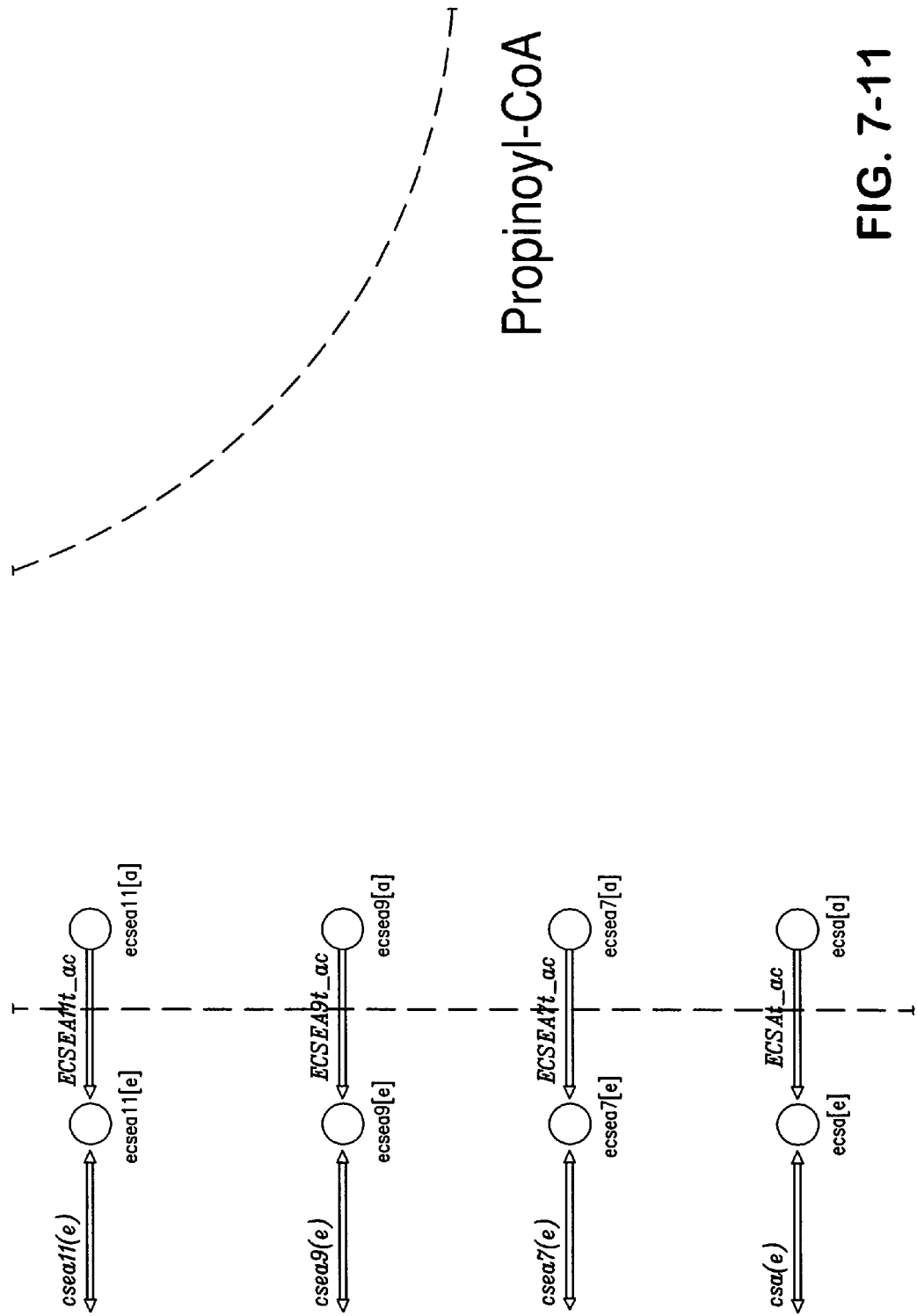
FIG. 11 shows triacylglycerol degradation in an adipocyte model.

To simulate the storage of triacylglycerol from glucose in adipocyte, TAG synthesis was simulated by maximizing an internal demand for cytosolic triacylglycerol. The maximum yield of triacylglycerol per glucose was computed to be 0.06 mol TAG/mol glucose, without any biomass demand. To demonstrate how the stored TAG can be reutilized to produce fatty acids, the influx of all other carbon sources including glucose was constrained to zero and glycerol secretion, which is assumed to be taken up by the liver, was maximized. When 2 mol of cytosolic proton was allowed to leave the system, a glycerol yield of 1 mol glycerol/mol TAG or 100% was computed. The excess two protons were formed in TAG degradation pathway. As shown in FIG. 11, degradation of TAG was performed in the following three steps: (1) TRIGH_ac_HS_ub; (2) 12DGRH_ac_HS_ub, and (3) MGLYCH_ac_HS_ub). Glycerol generated as an end product of this pathway was transported out of the cell via a proton-coupled symport mechanism. TAG was hydrolyzed completely to fatty acids and glycerol in three steps and in each step one proton is released. Glycerol transport was coupled to one proton. Thus, a net amount of two protons were generated per mol TAG degraded.

To balance protons, an ATPase reaction across the cytosolic membrane was used. However, since the β-oxidative pathways were not included in this adipocyte model, this network is unable to use membrane bound ATPase to balance the internal protons. When β-oxidative pathways are added to the adipocyte model, the model can completely balance protons.

In addition to triacylglycerol synthesis and hydrolysis, the maximum ATP yield on glucose (YATP/glucose) was computed in the adipocyte model. As for the central human metabolic network, YATP/glucose was 31.5 mol ATP/mol glucose.

Muscle Contraction During Aerobic and Anaerobic Exercise

The required energy in muscle tissue is generally supplied by glucose, stored glycogen, and phosphocreatine. During anaerobic exercise such as a sprint, for example, the blood vessels in the muscle tissue are compressed and the cells are isolated from the rest of the body (Devlin, supra). This compression restricts the oxygen supply to the tissue and enforces anaerobic energy metabolism in the cell. As a result, lactate is generated to balance the redox potential and must be secreted out of the cell. In the liver, lactate is converted into glucose. However, rapid muscle contraction and decreased blood flow to the muscle tissue cause lactate accumulation during anaerobic exercise and quickly impairs muscle contraction. During starvation or under high-energy demands, the glucose and glycogen storage of the muscle tissue quickly depletes and the energy storage in triacylglycerol molecules supplied by fatty cells is used to generate ATP.

To simulate the muscle physiology at steady state, phosphocreatine kinase reaction, myosin-actin activation mechanism, and β-oxidation pathway were included in the central metabolic network. The physiological function of muscle tissue was simulated by determining the maximum amount of contraction that is generated from the energy supplied by glucose, stored glycogen, phosphocreatine, and supplied fatty acids.

The metabolic capabilities of the myocyte model were assessed by first computing the maximum ATP yield on glucose. As for the central human metabolic network, YATP/glucose was 31.5 mol ATP/mol glucose. The muscle contraction was also examined with glucose as the sole carbon source. Maximum muscle contraction with glucose was computed to be 31.5 mol/mol glucose in aerobic and 2 mol/mol glucose in anaerobic condition. Lactate was secreted as a byproduct during anaerobic contraction (Yieldlactate/glucose=2 mol/mol).

Figures 7, 8, 9, 10, 11, 12:
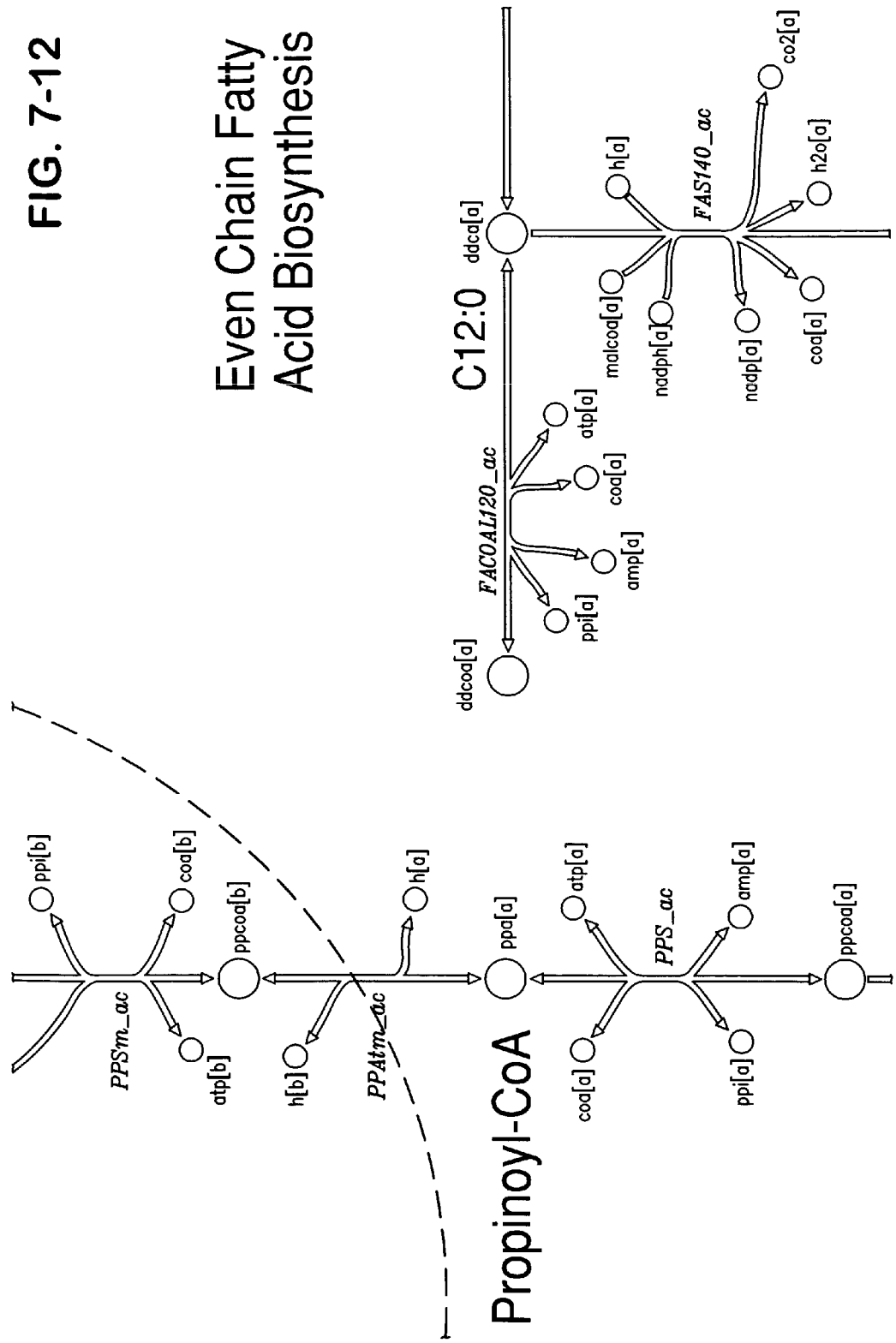
FIG. 12 shows the impairment of muscle contraction as a result of lactate accumulation during anaerobic exercise. Time is in arbitrary unit. Concentration and yield of lactate ($Y_{Lac}$) production are in mol/mol glucose.

As lactate accumulates during anaerobic metabolism, its secretion rate quickly fails to meet the demand to release lactate into the blood. To simulation the impairment of muscle contraction in anaerobic exercise, the maximum lactate secretion rate was constrained to 75%, 50%, 25%, and 0% of its maximum value under anaerobic condition. The results using these different constraints are shown in FIG. 12 where the time is shown as an arbitrary unit, rate of contraction and lactate secretion are in mols per cell mass per unit time, r corresponds to rate and lac corresponds to lactate. The results show that as more lactate accumulates in anaerobic metabolism, the maximum allowable lactate secretion decreases and maximum muscle contraction decreased proportionally.

Figures 7, 8, 9, 10, 11, 12, 13:
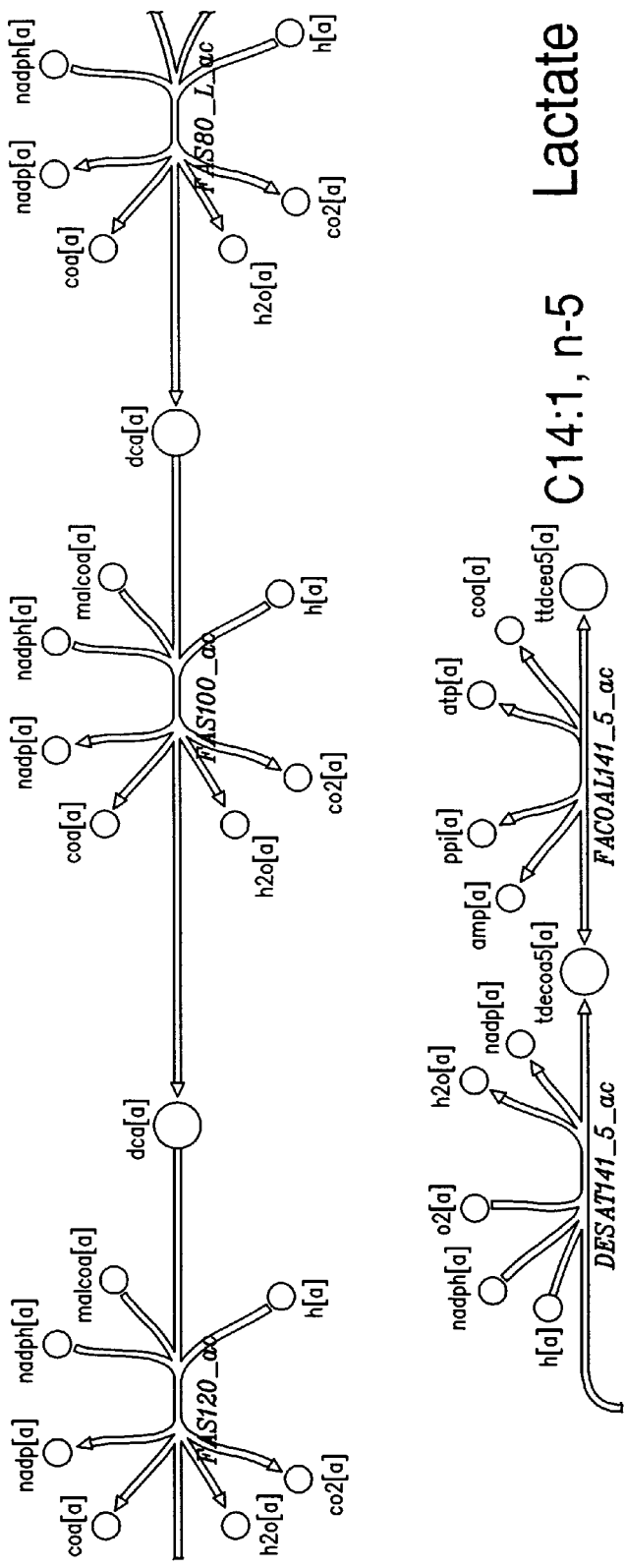
FIG. 13 shows glycogen utilization versus (highlighted on the left) glucose utilization (highlighted on the right) in myocyte.
Figures 7, 8, 9, 10, 11, 12, 13, 14:
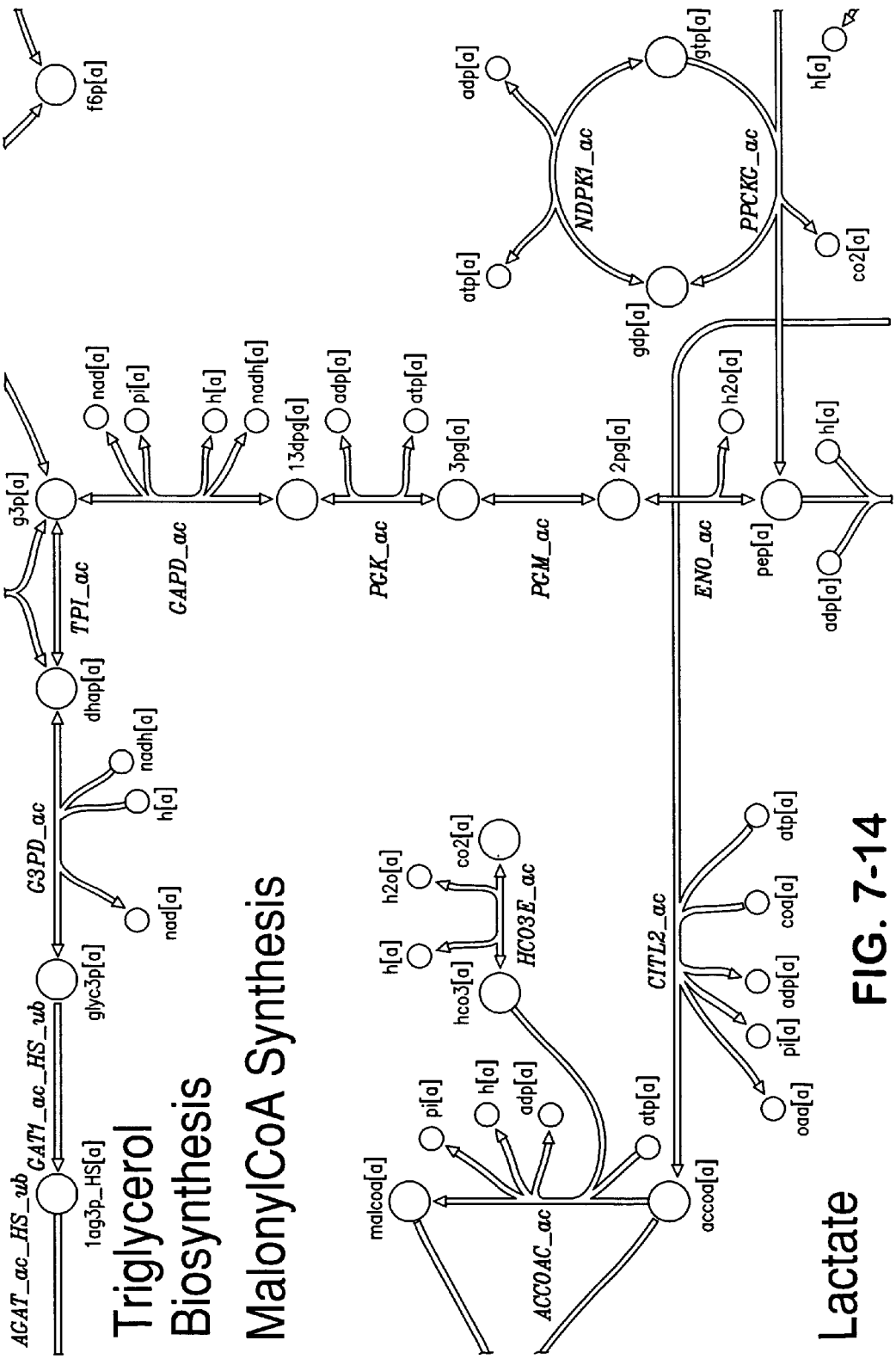
Figures 7, 8, 9, 10, 11, 12, 13, 14, 15:
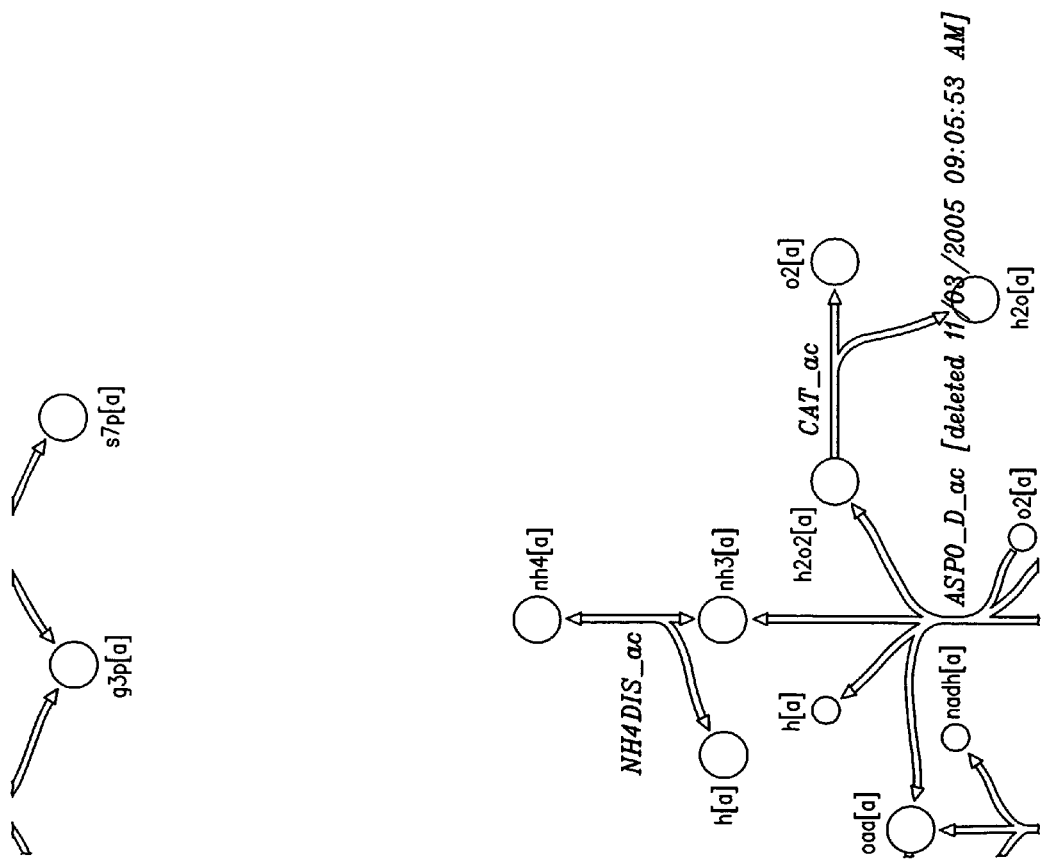
Figures 7, 8, 9, 10, 11, 12, 13, 14, 15, 16:
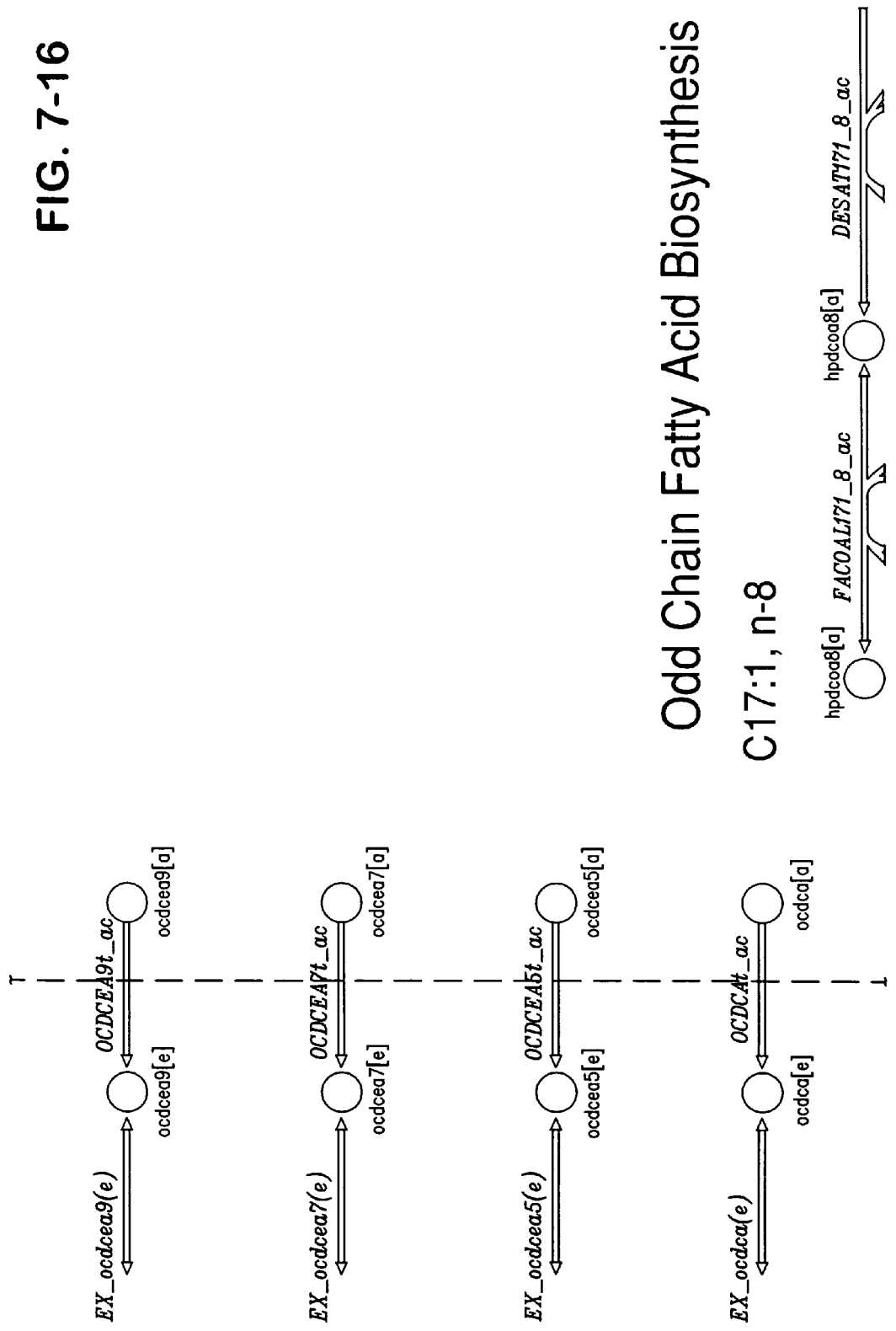
Figures 7, 8, 9, 10, 11, 12, 13, 14, 15, 16, 17:
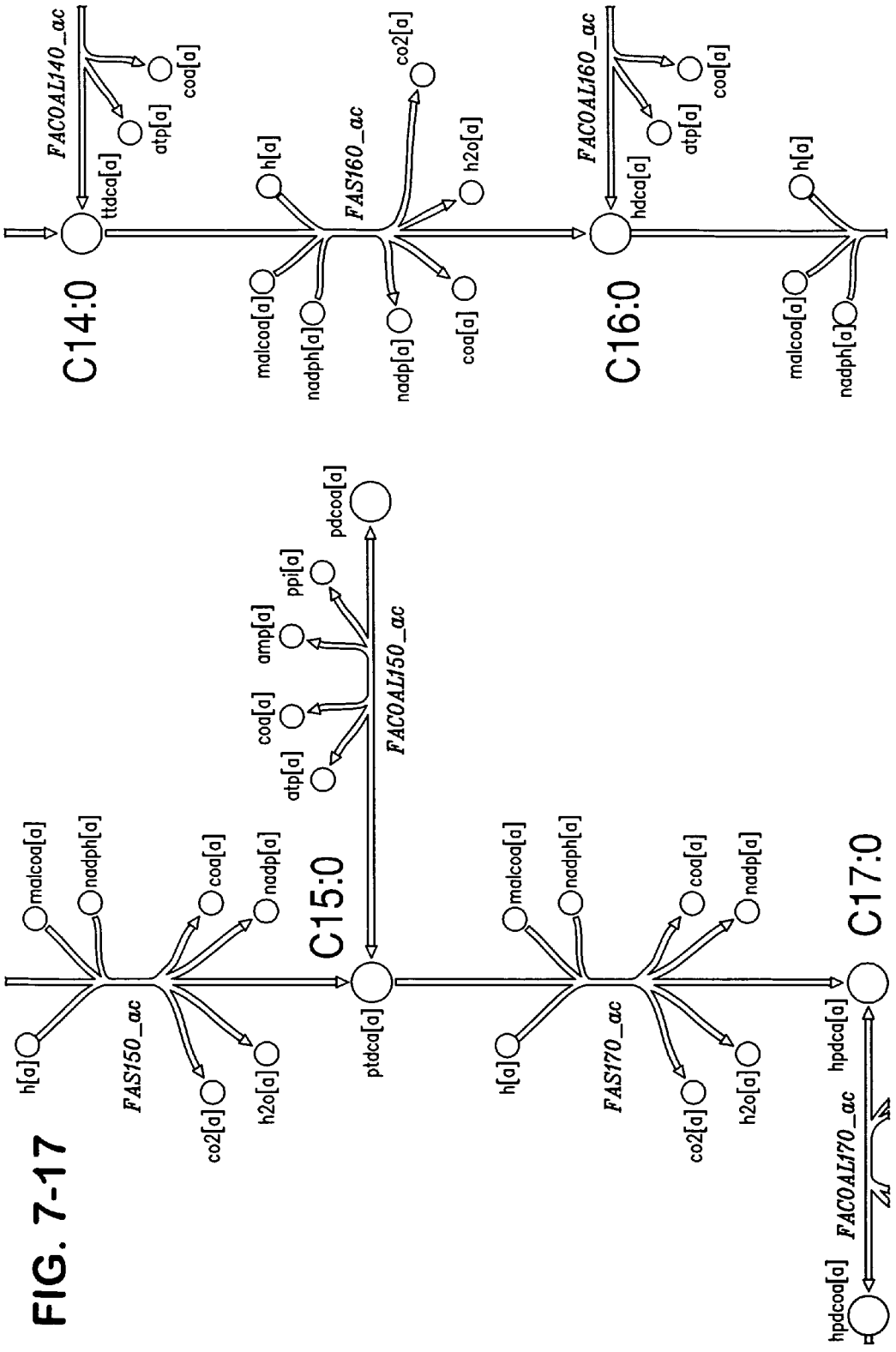
Figures 7, 8, 9, 10, 11, 12, 13, 14, 15, 16, 17, 18:
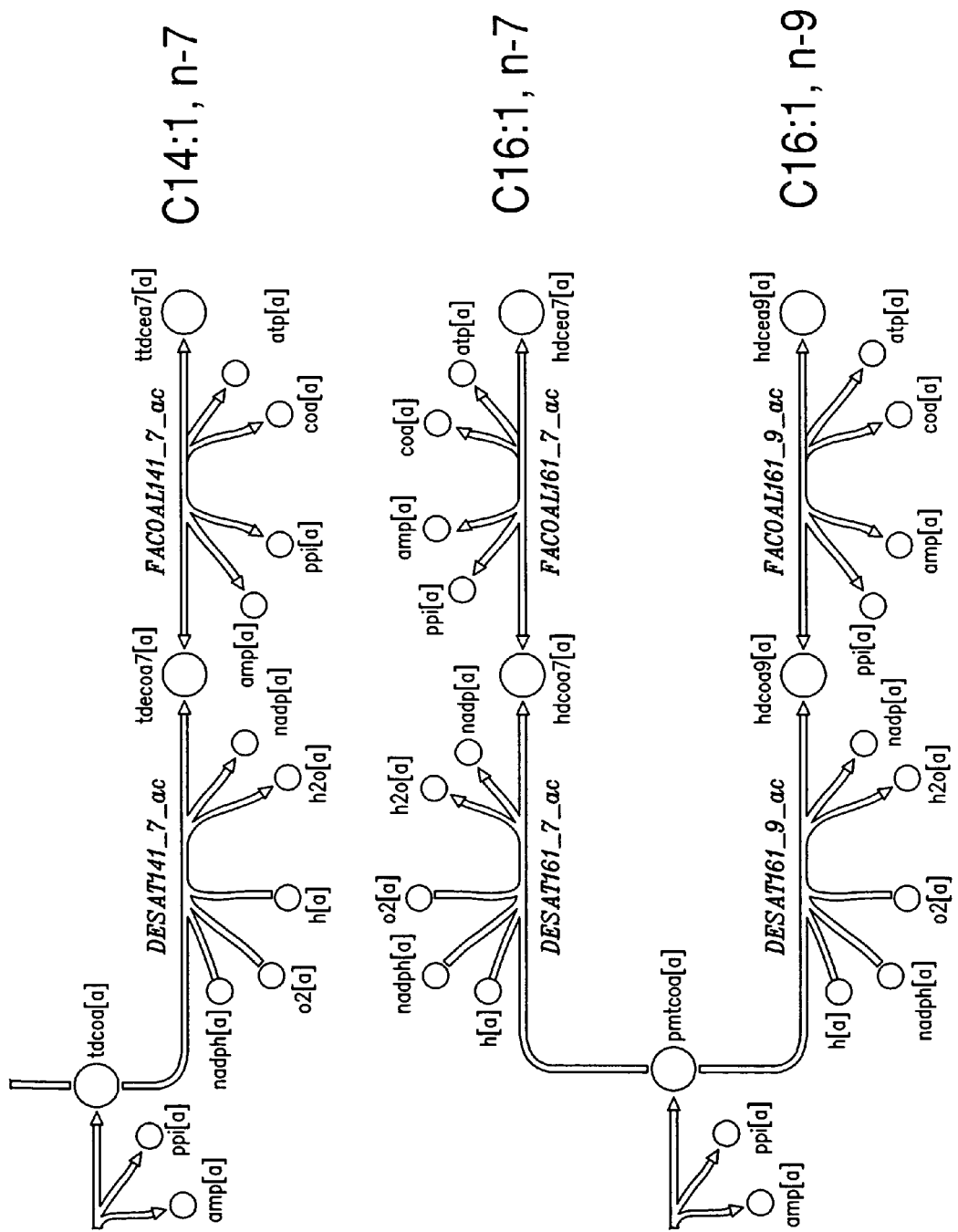
Figures 7, 8, 9, 10, 11, 12, 13, 14, 15, 16, 17, 18, 19:
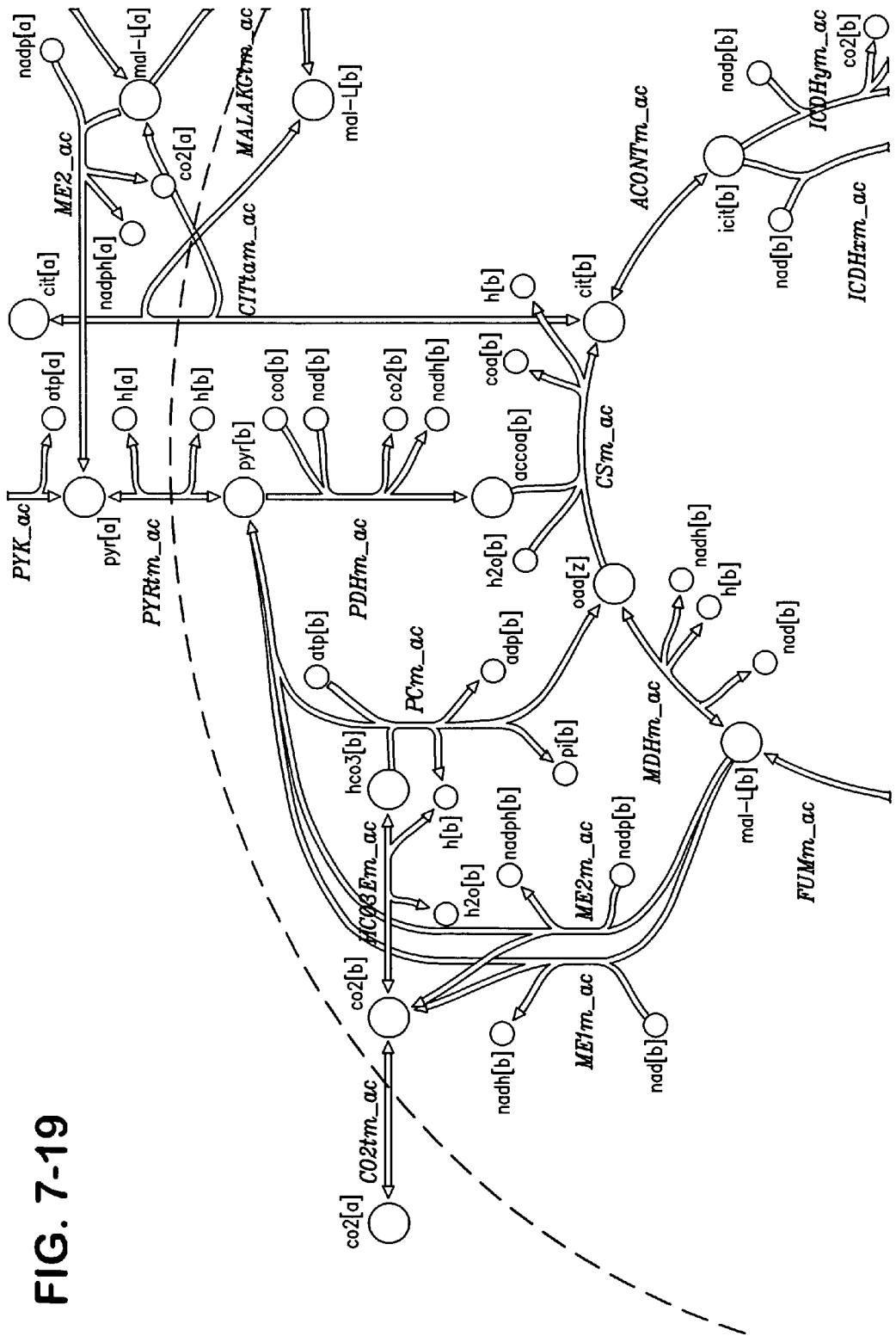
Figures 7, 8, 9, 10, 11, 12, 13, 14, 15, 16, 17, 18, 19, 20:
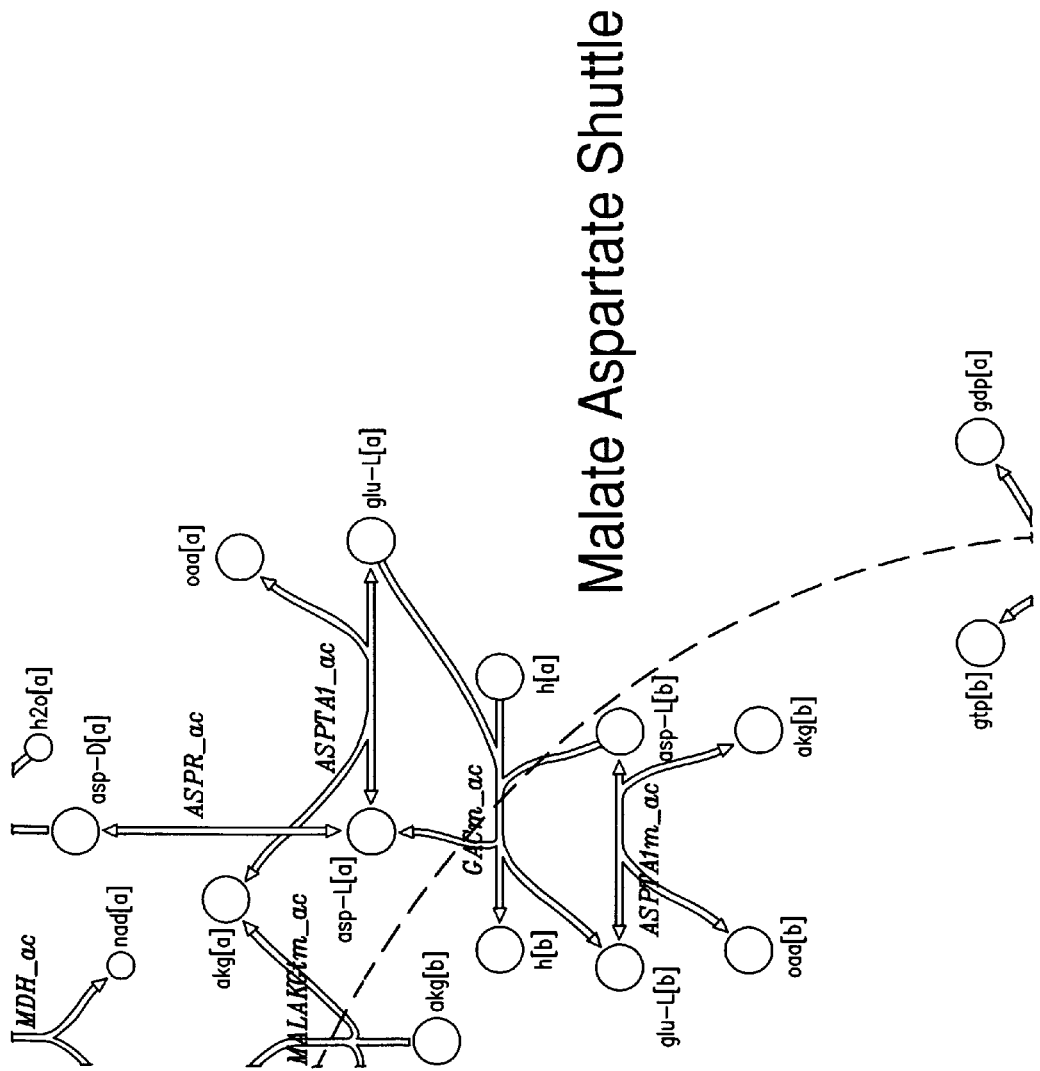
Figures 7, 8, 9, 10, 11, 12, 13, 14, 15, 16, 17, 18, 19, 20, 21:
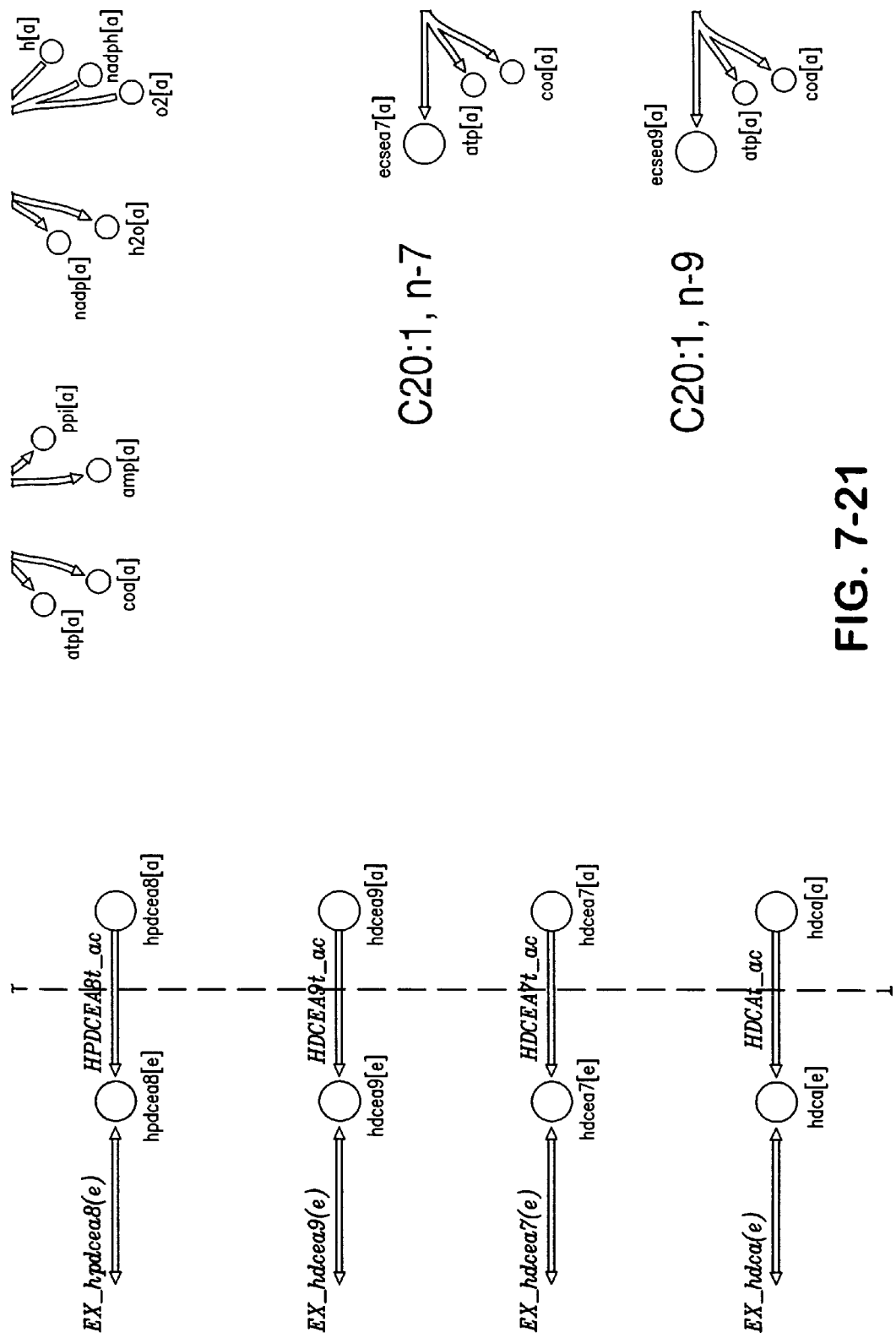
Figures 7, 8, 9, 10, 11, 12, 13, 14, 15, 16, 17, 18, 19, 20, 21, 22:
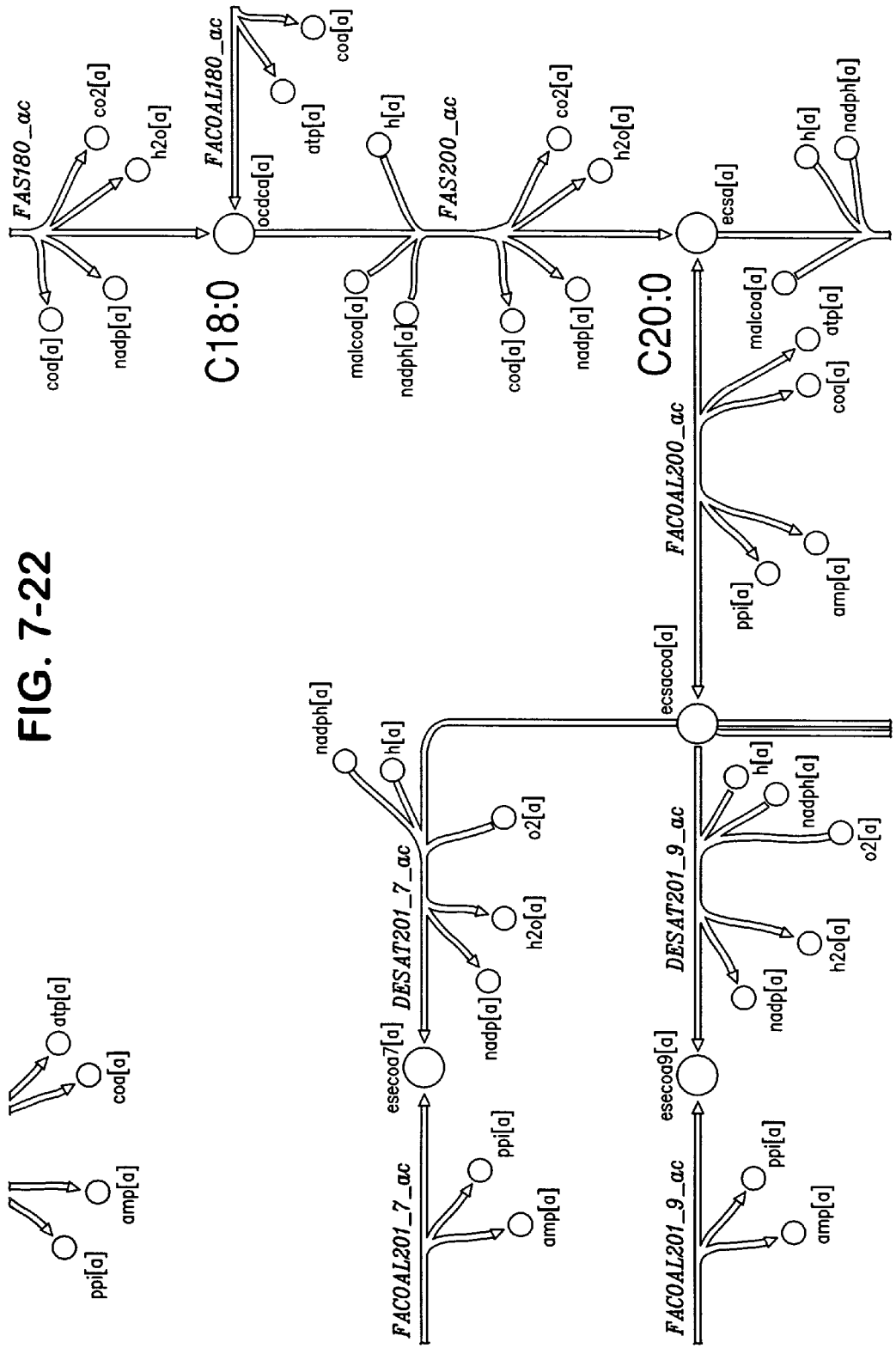
Figures 7, 8, 9, 10, 11, 12, 13, 14, 15, 16, 17, 18, 19, 20, 21, 22, 23:
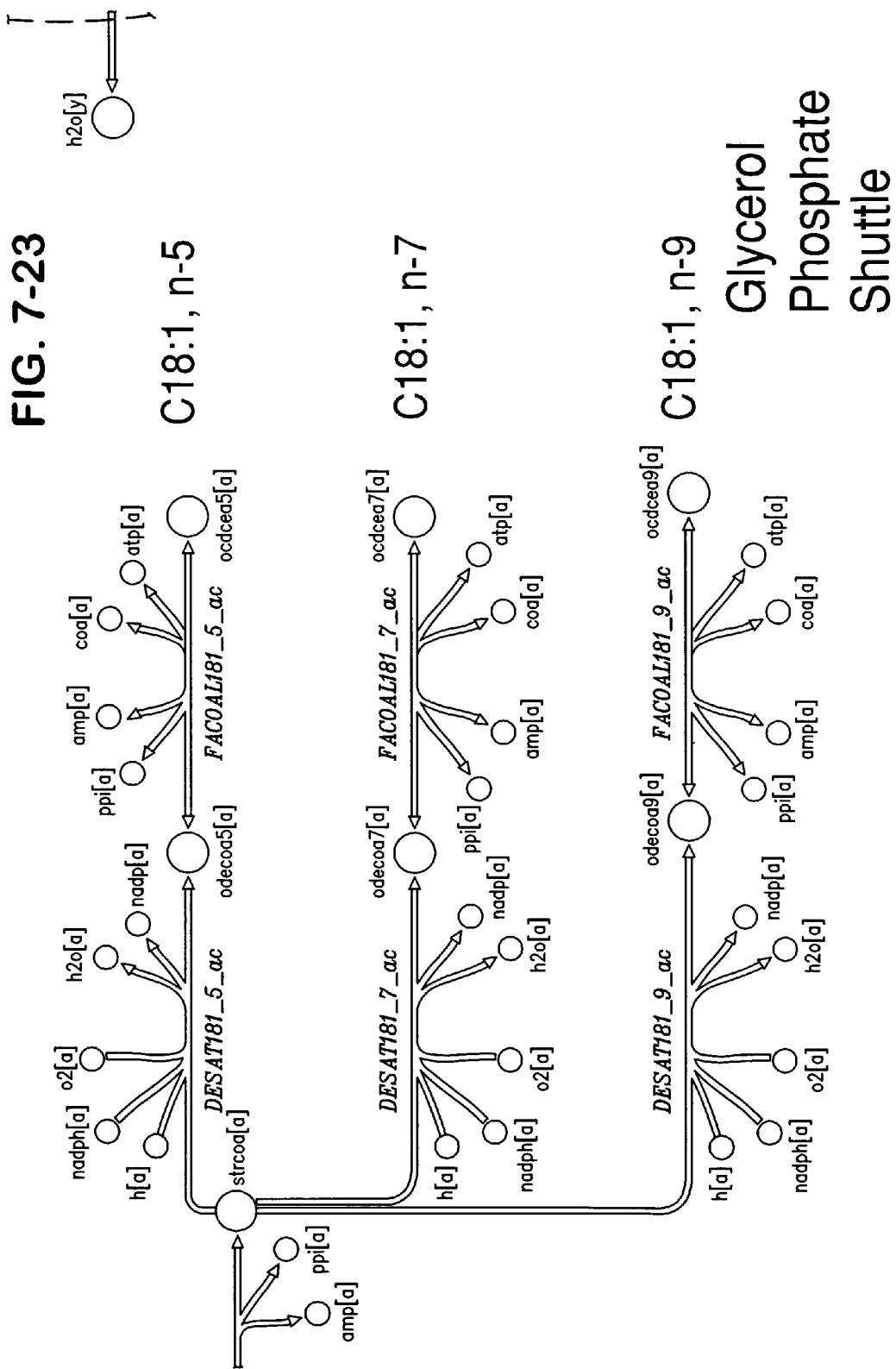
Figures 7, 8, 9, 10, 11, 12, 13, 14, 15, 16, 17, 18, 19, 20, 21, 22, 23, 24:
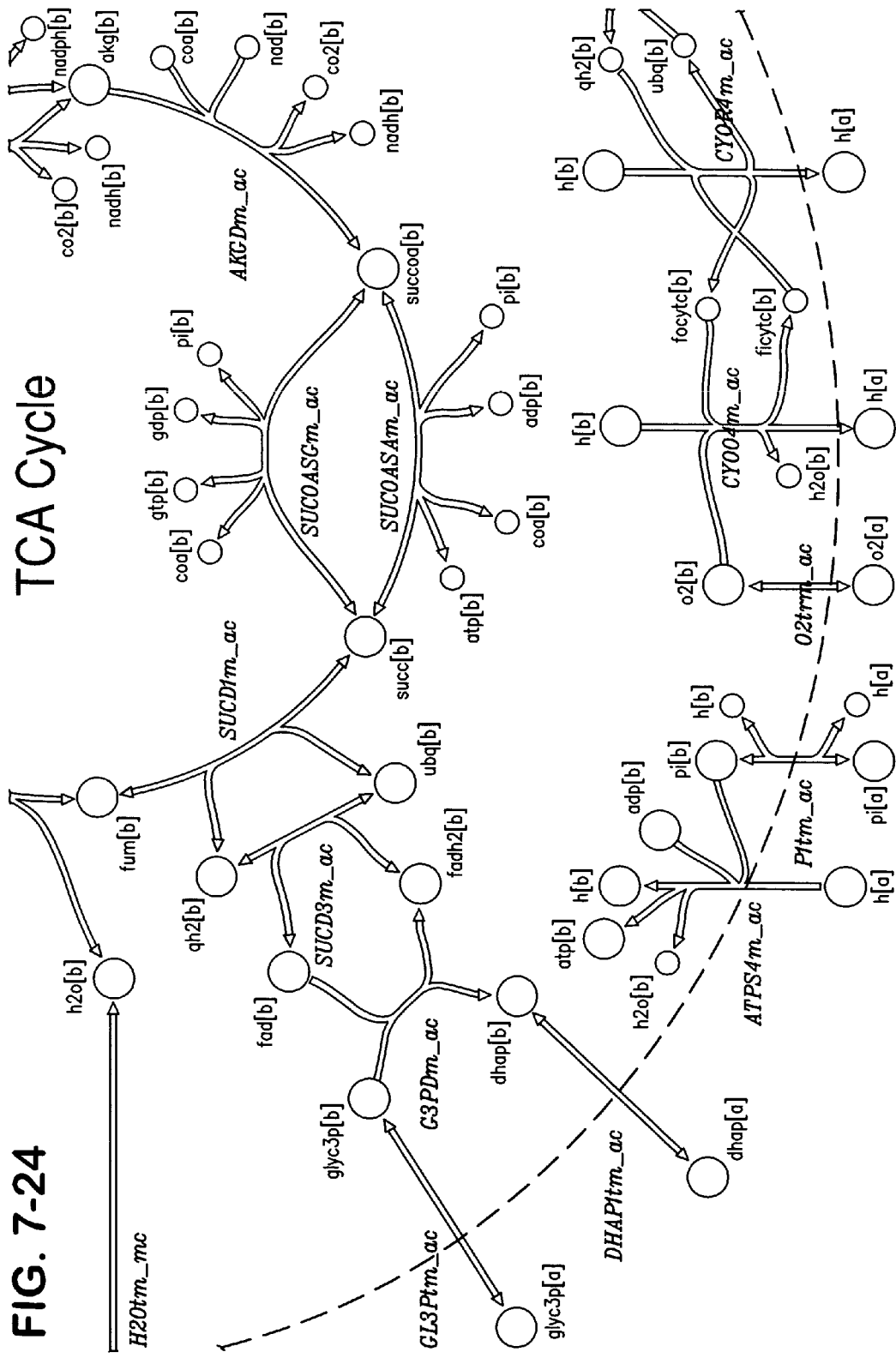
Figures 7, 8, 9, 10, 11, 12, 13, 14, 15, 16, 17, 18, 19, 20, 21, 22, 23, 24, 25:
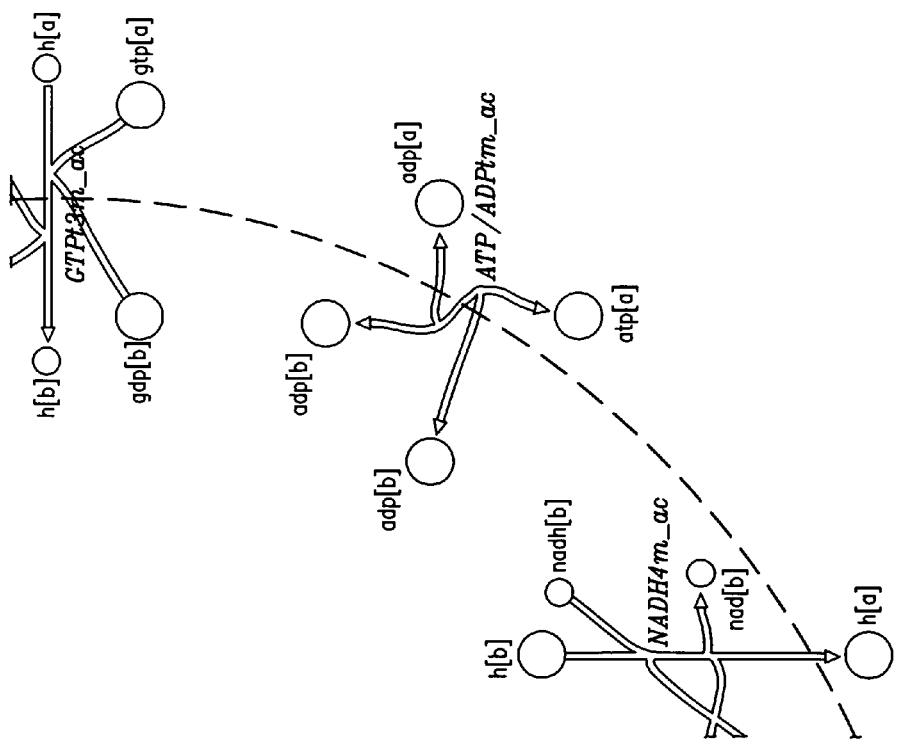
Figures 7, 8, 9, 10, 11, 12, 13, 14, 15, 16, 17, 18, 19, 20, 21, 22, 23, 24, 25, 26:
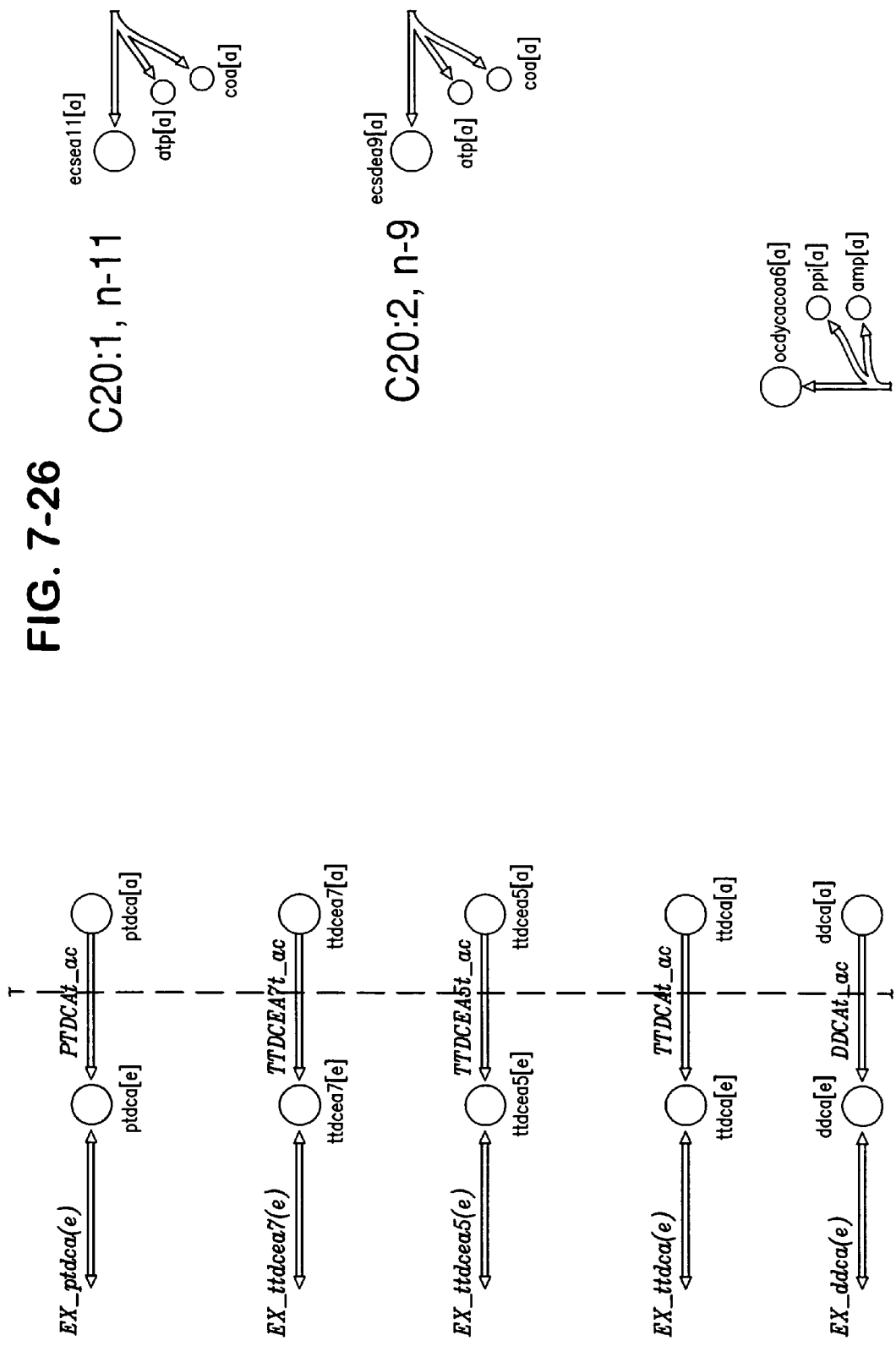
Figures 7, 8, 9, 10, 11, 12, 13, 14, 15, 16, 17, 18, 19, 20, 21, 22, 23, 24, 25, 26, 27, 28:
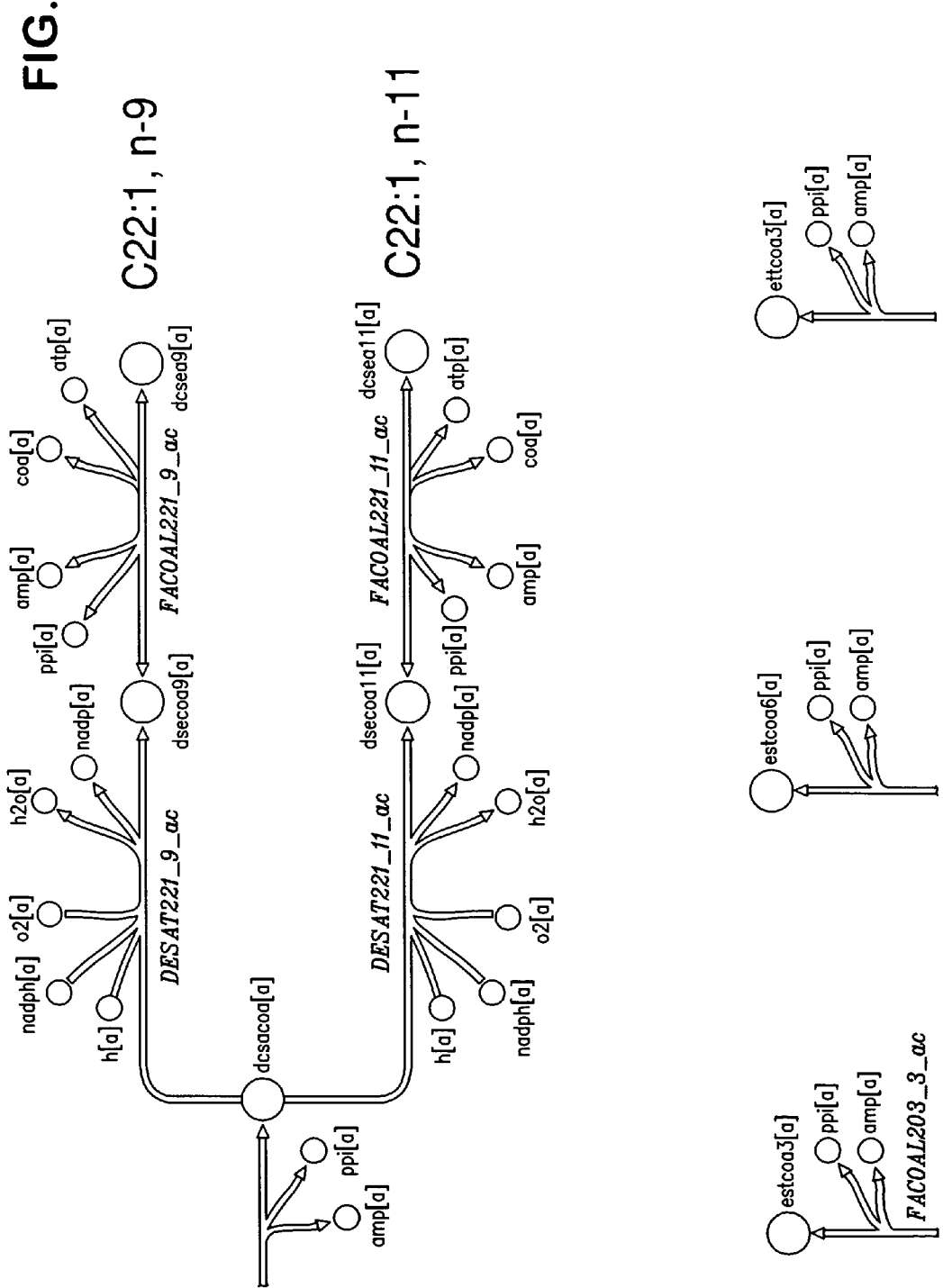
Figures 7, 8, 9, 10, 11, 12, 13, 14, 15, 16, 17, 18, 19, 20, 21, 22, 23, 24, 25, 26, 27, 28, 29, 30:
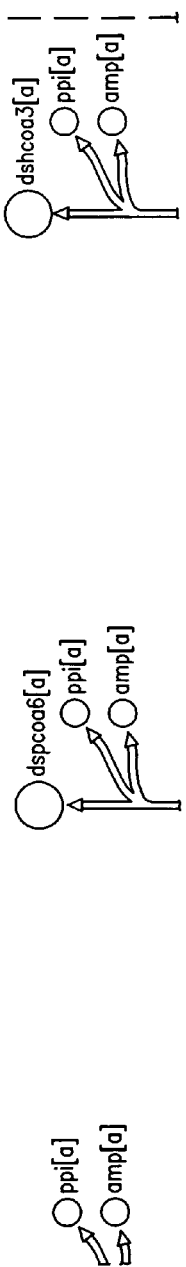
Figures 7, 8, 9, 10, 11, 12, 13, 14, 15, 16, 17, 18, 19, 20, 21, 22, 23, 24, 25, 26, 27, 28, 29, 30, 31:
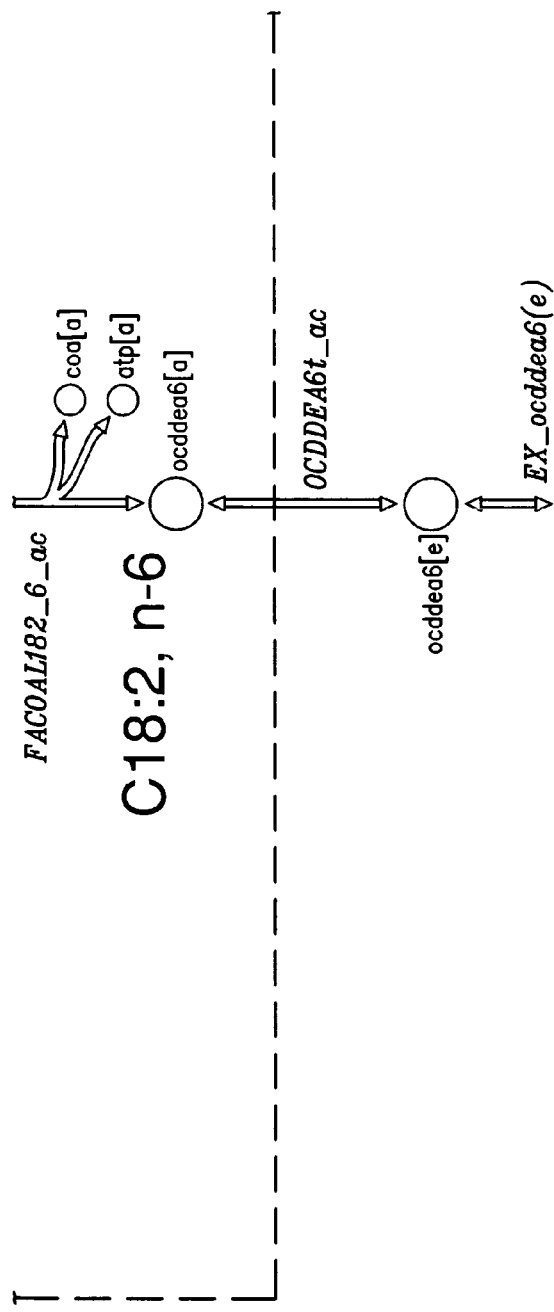
Figures 7, 8, 9, 10, 11, 12, 13, 14, 15, 16, 17, 18, 19, 20, 21, 22, 23, 24, 25, 26, 27, 28, 29, 30, 31, 32:
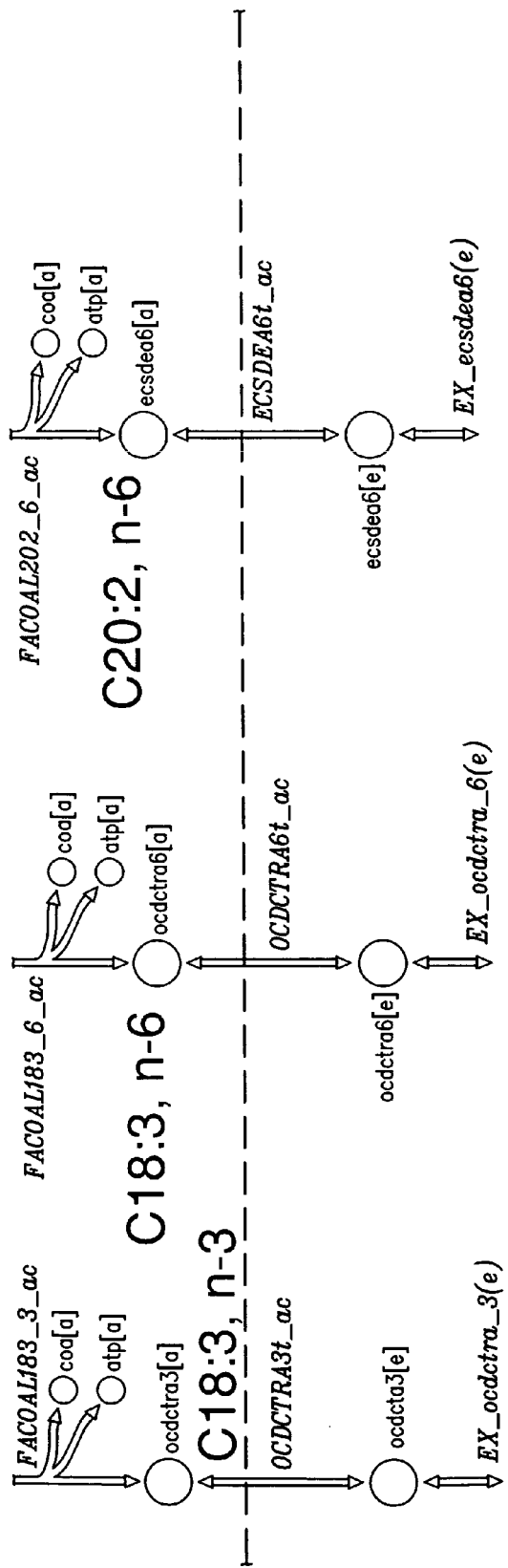
Figures 7, 8, 9, 10, 11, 12, 13, 14, 15, 16, 17, 18, 19, 20, 21, 22, 23, 24, 25, 26, 27, 28, 29, 30, 31, 32, 33:
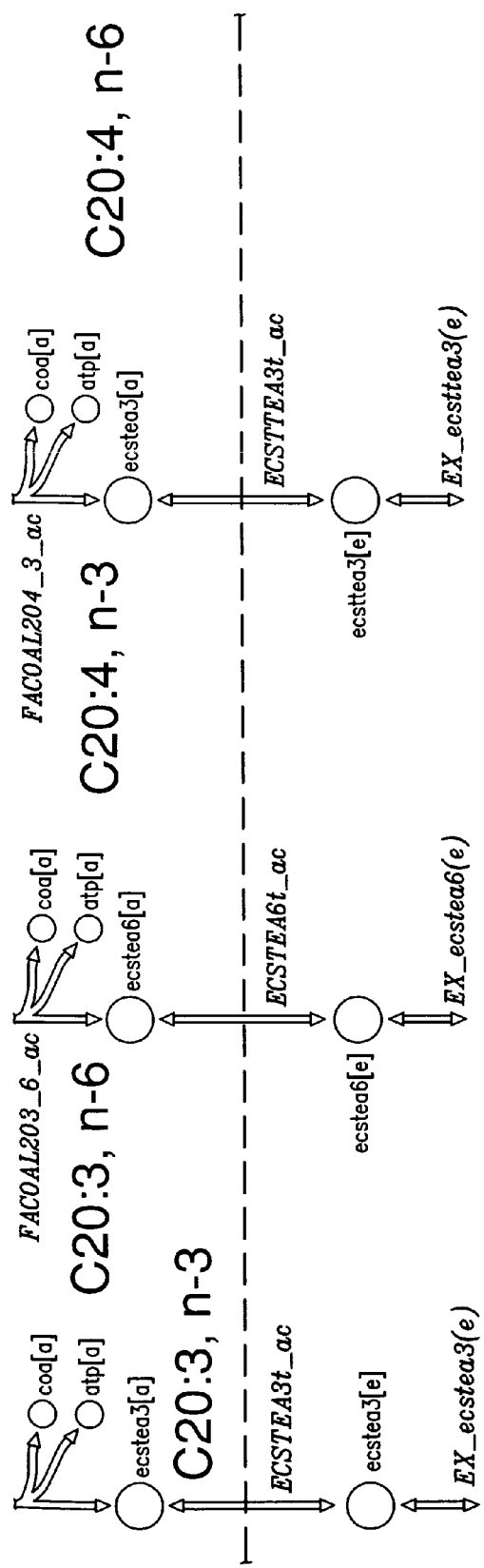
Figures 7, 8, 9, 10, 11, 12, 13, 14, 15, 16, 17, 18, 19, 20, 21, 22, 23, 24, 25, 26, 27, 28, 29, 30, 31, 32, 33, 34:
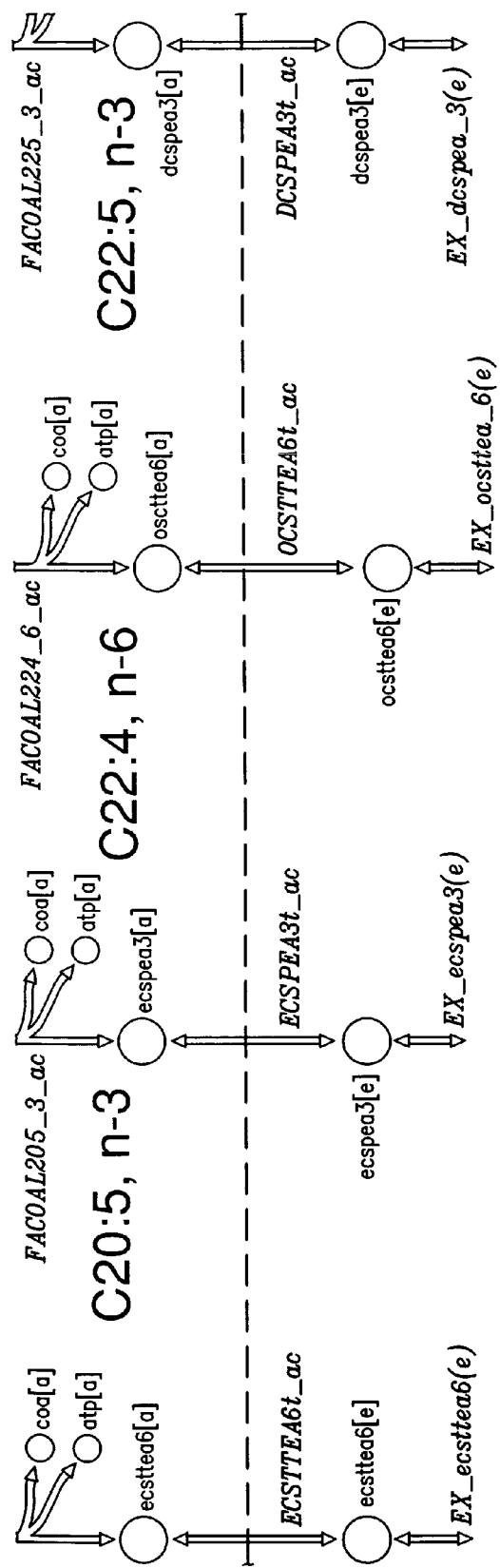
Figures 7, 8, 9, 10, 11, 12, 13, 14, 15, 16, 17, 18, 19, 20, 21, 22, 23, 24, 25, 26, 27, 28, 29, 30, 31, 32, 33, 34, 35:
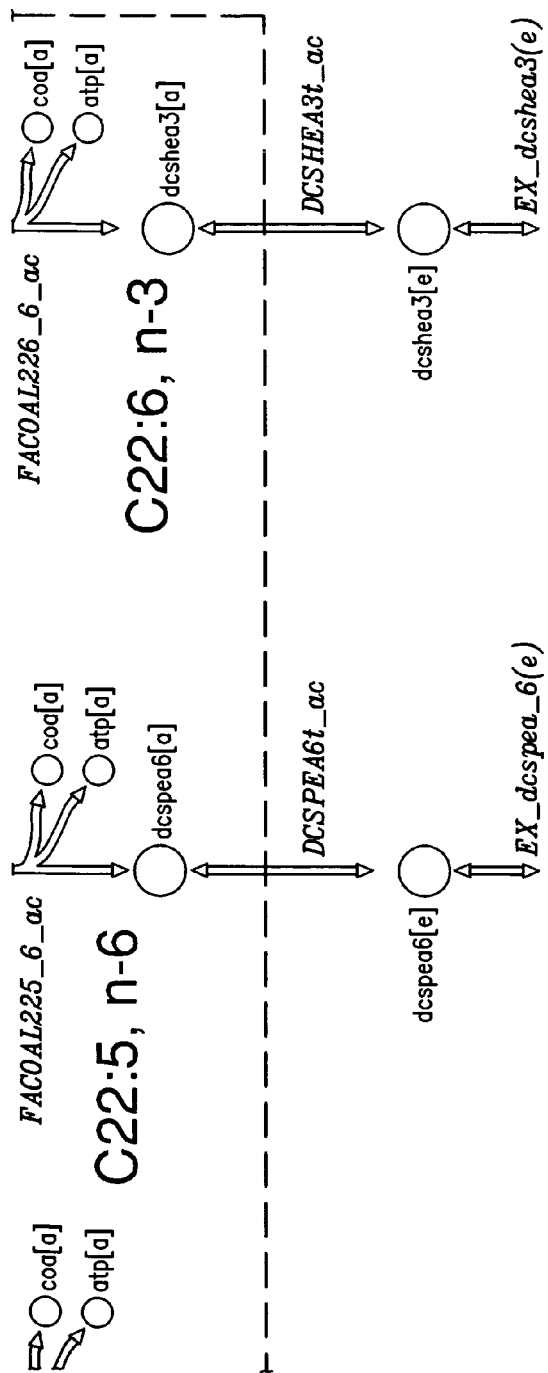
Figure 8:
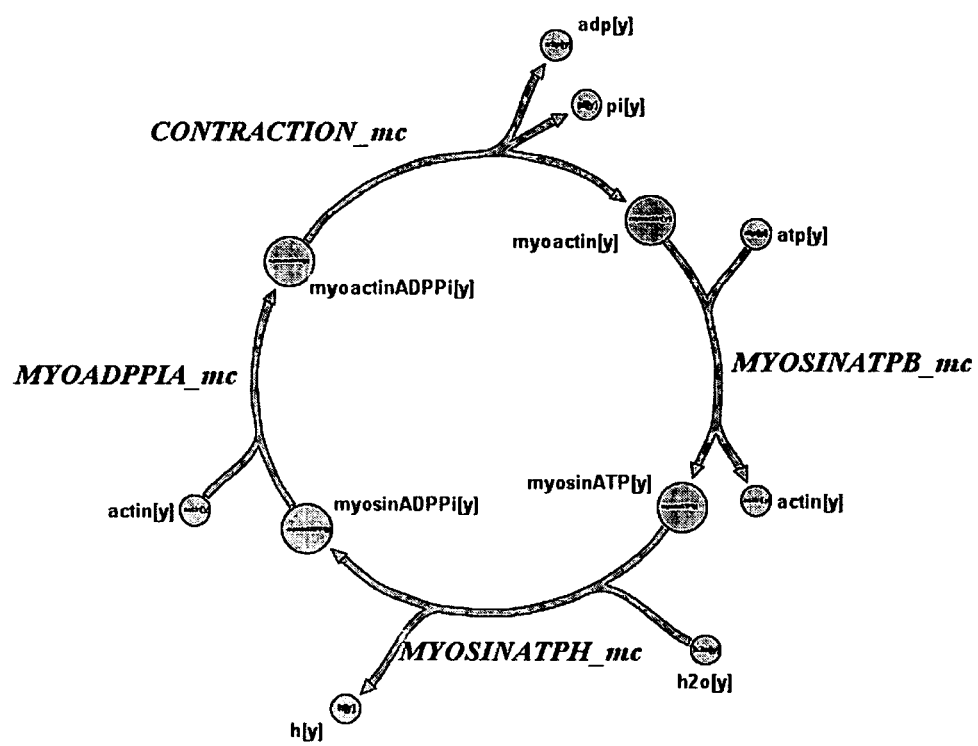
Figures 1, 9:
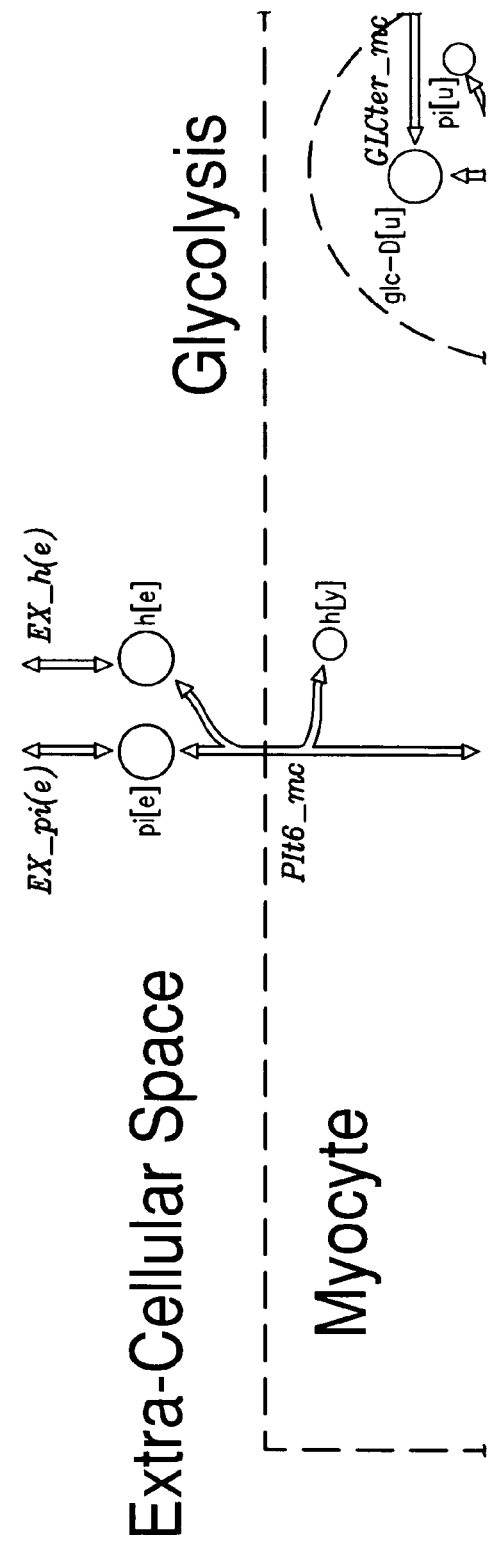
Figures 2, 9:
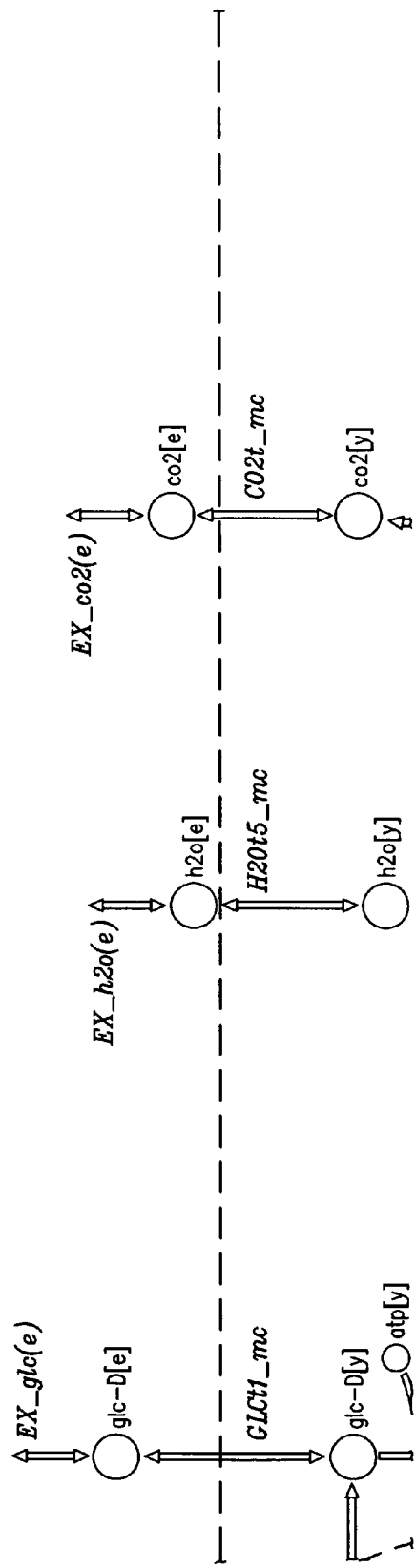
Figures 3, 9:
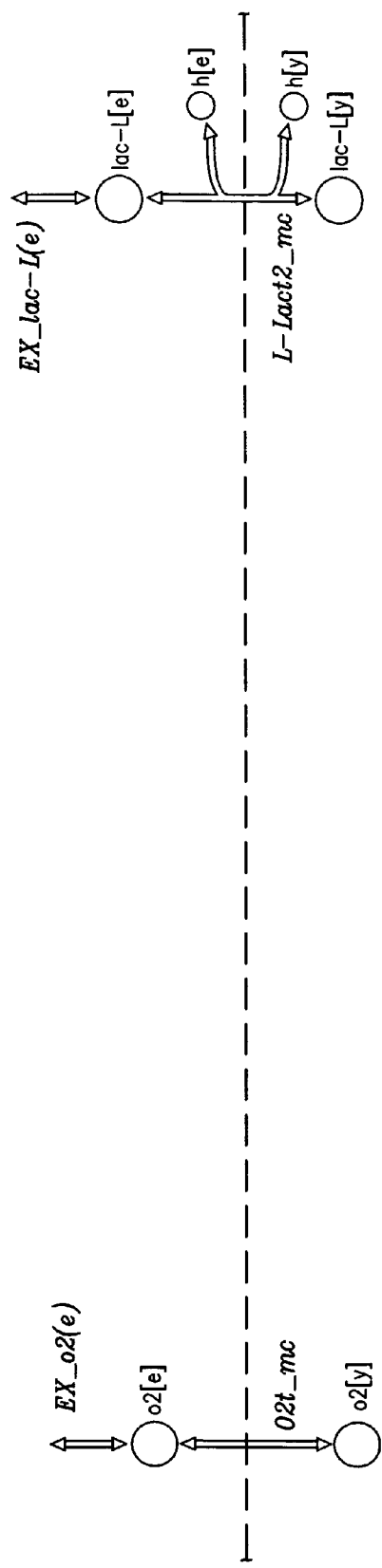
Figures 4, 9:
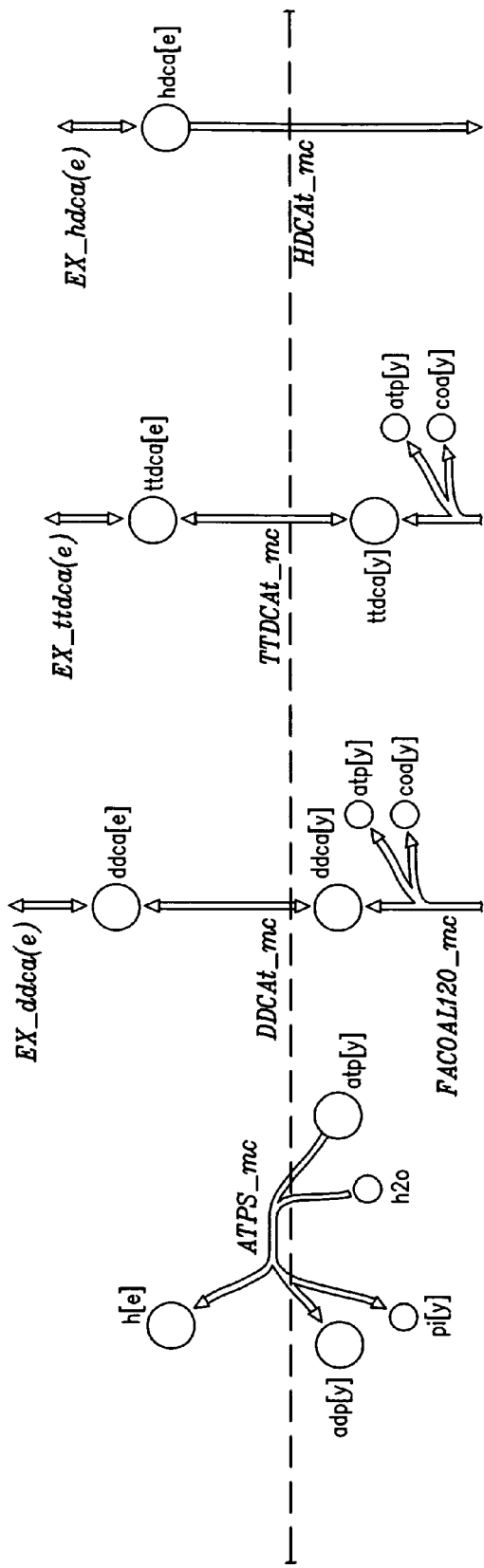
Figures 5, 9:
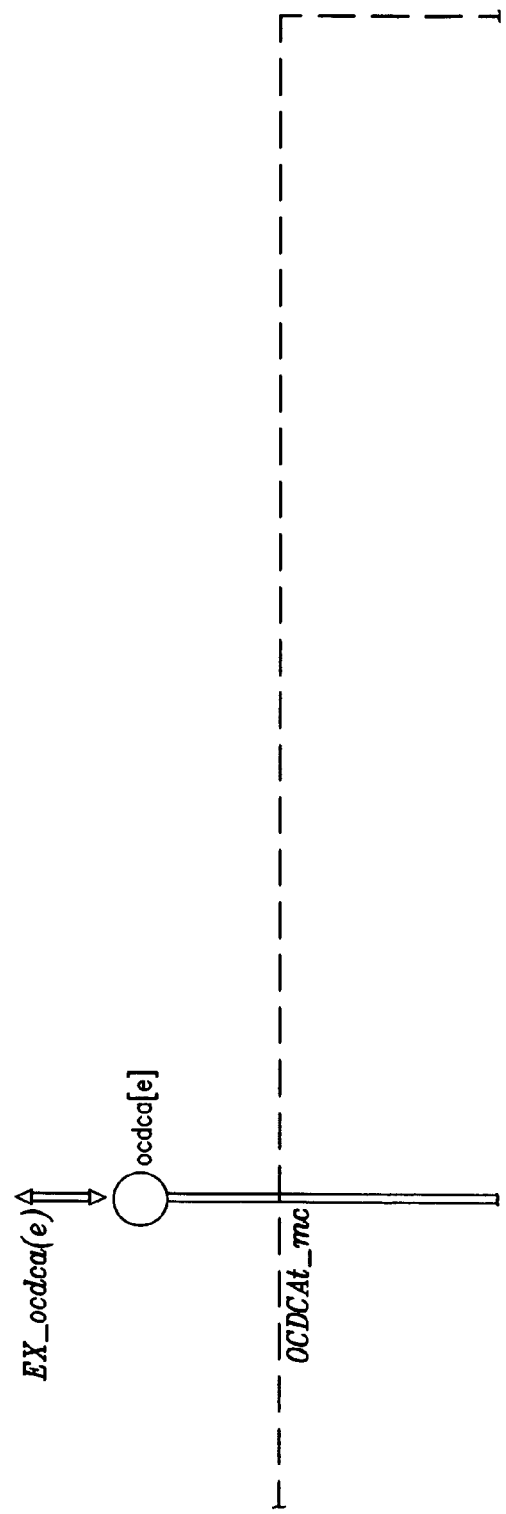
Figures 6, 9:
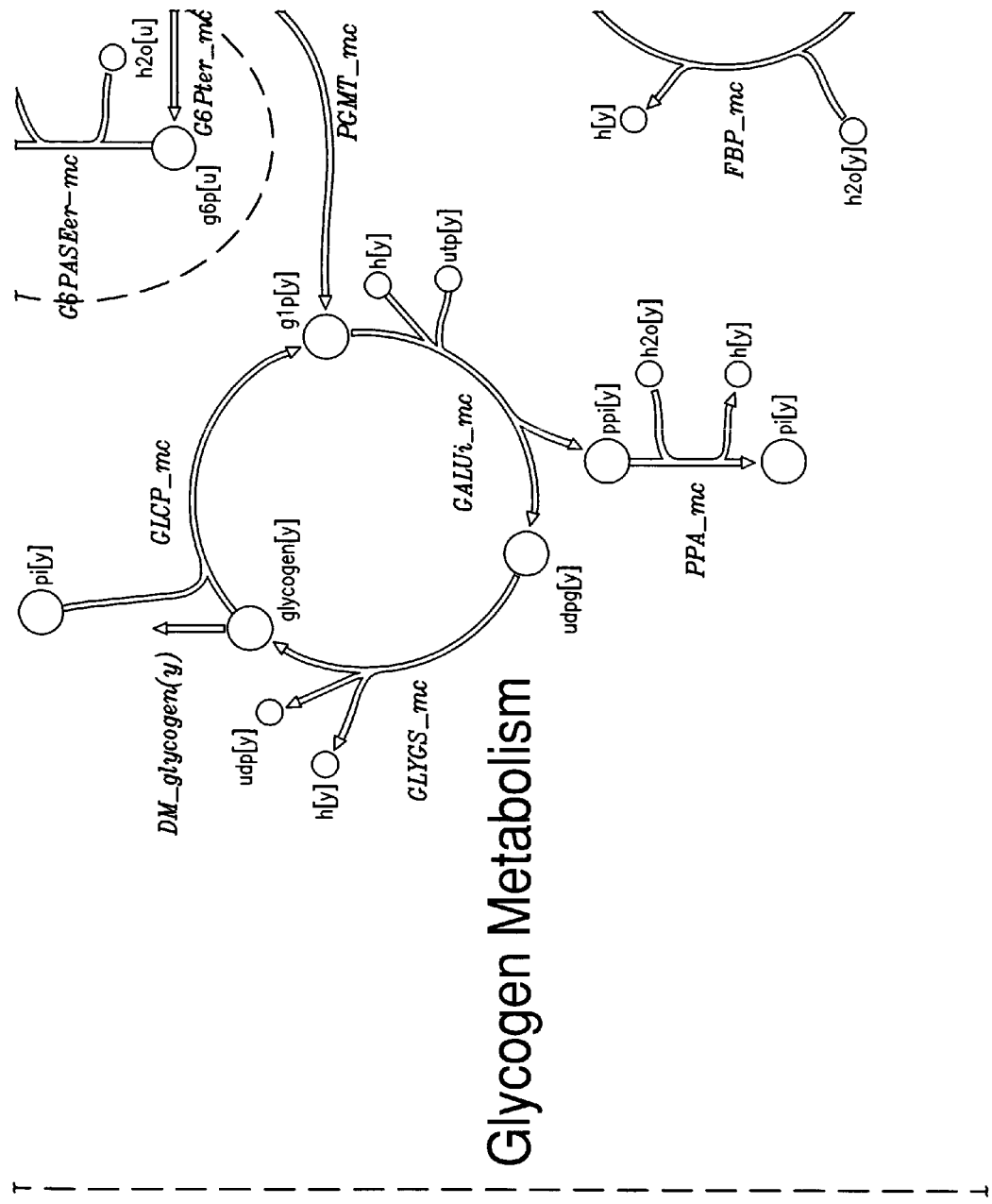
Figures 7, 9:
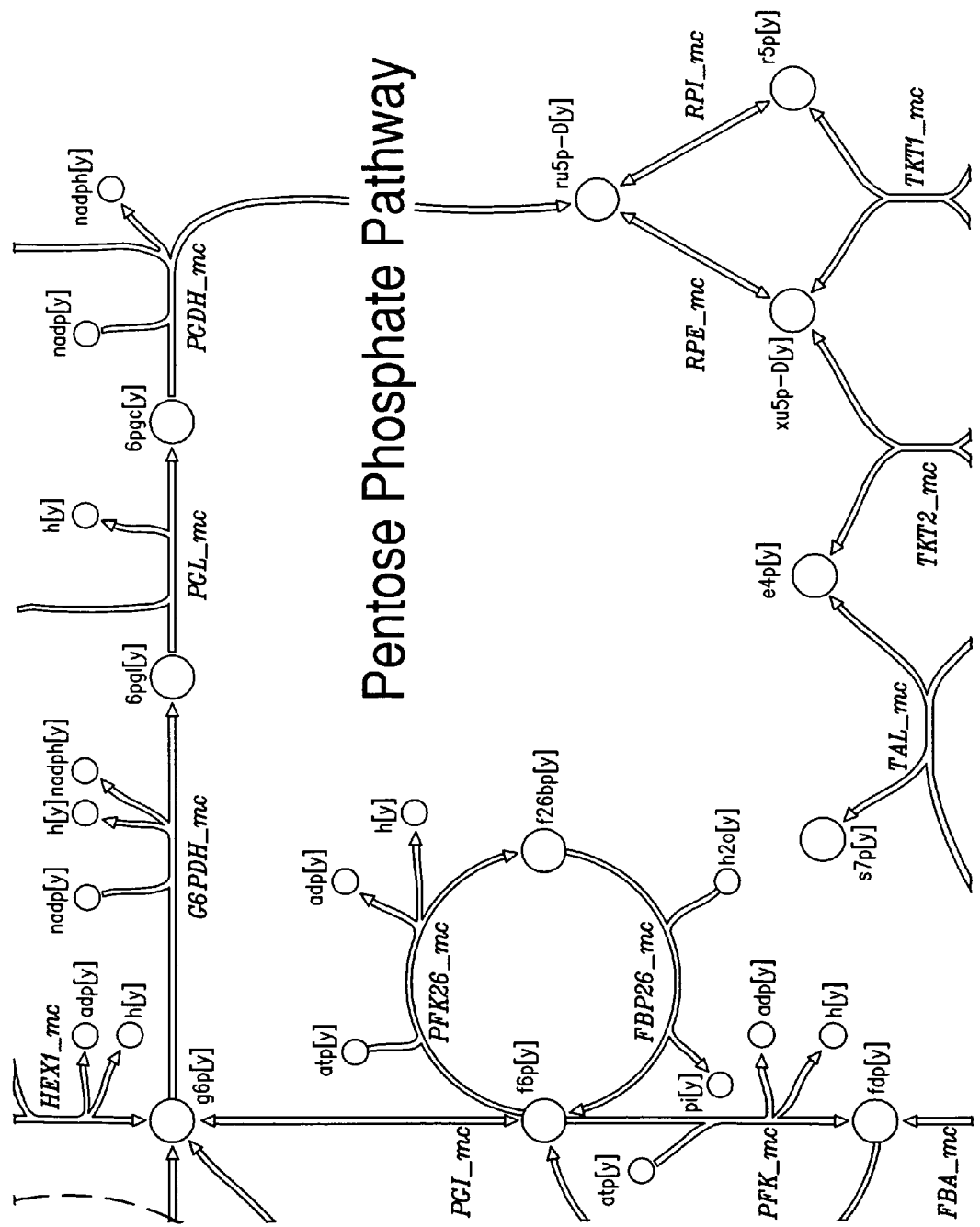
Figures 9, 10:
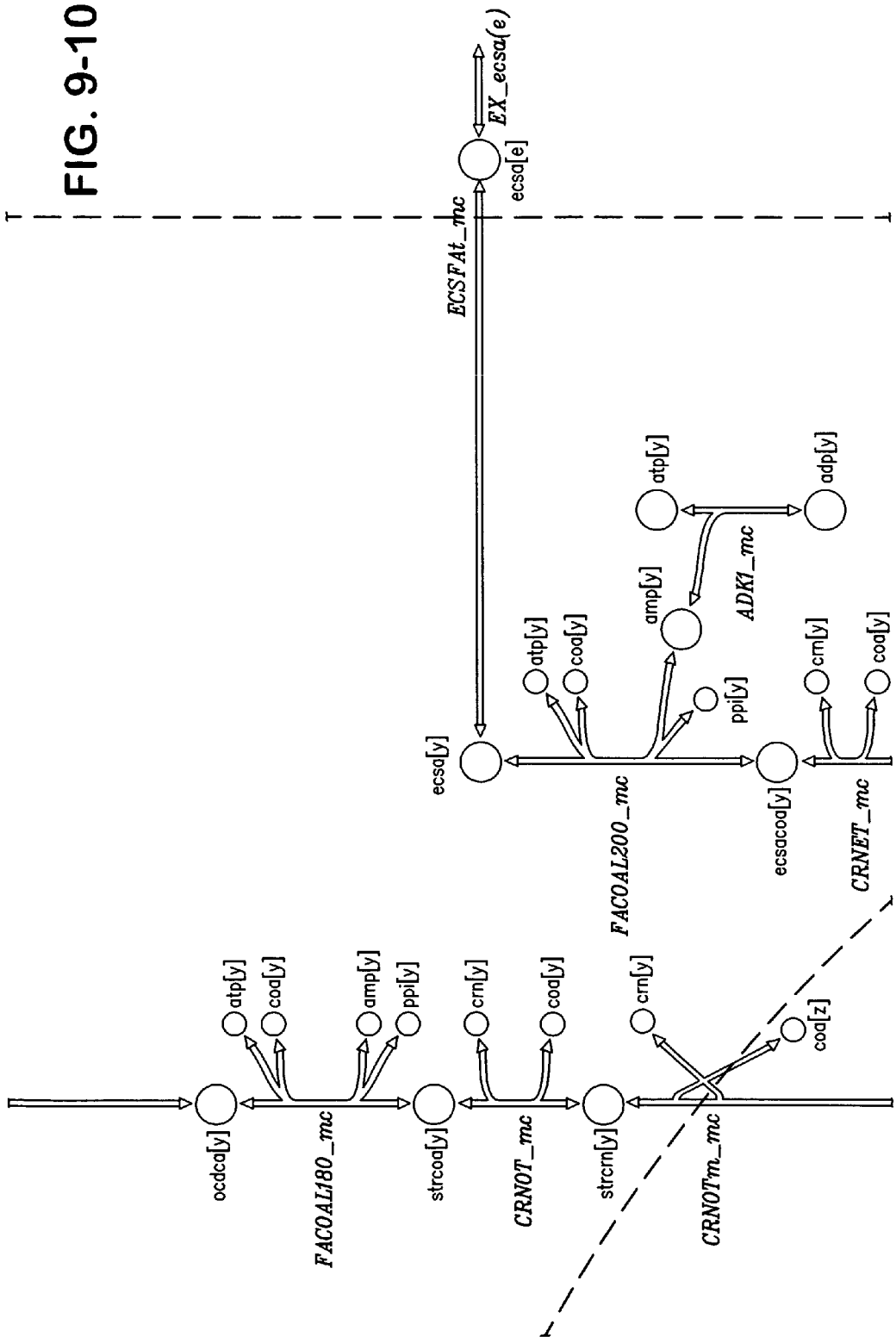
Figures 9, 10, 11:
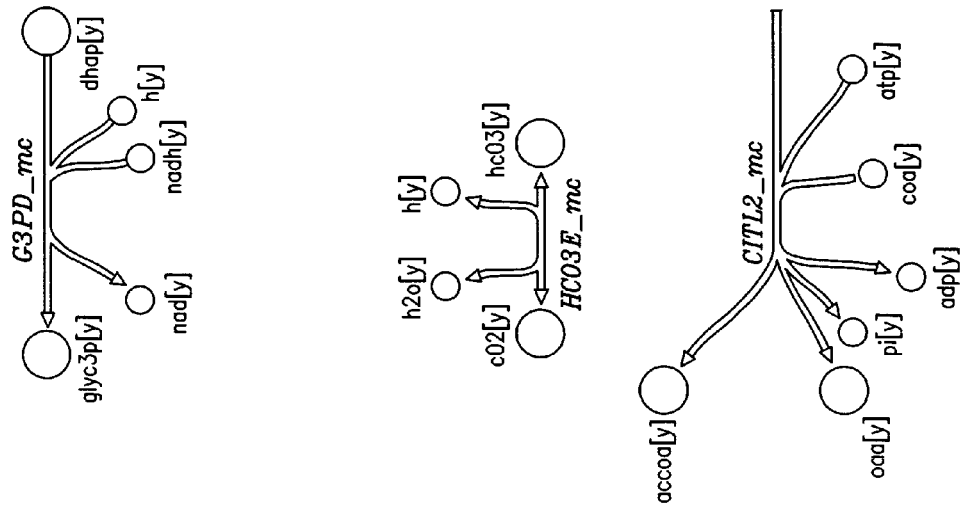
Figures 9, 10, 11, 12:
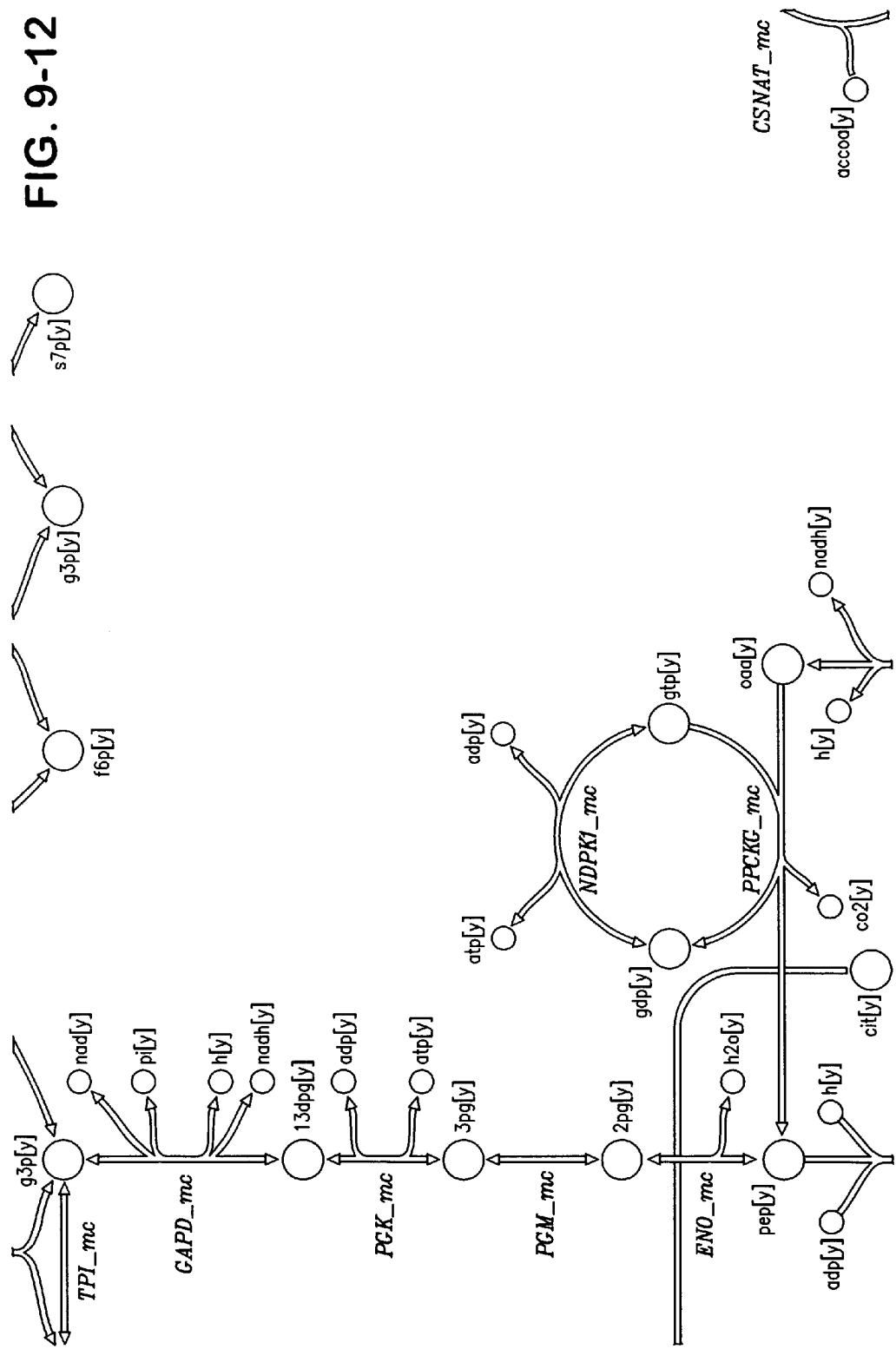
Figures 9, 10, 11, 12, 13:
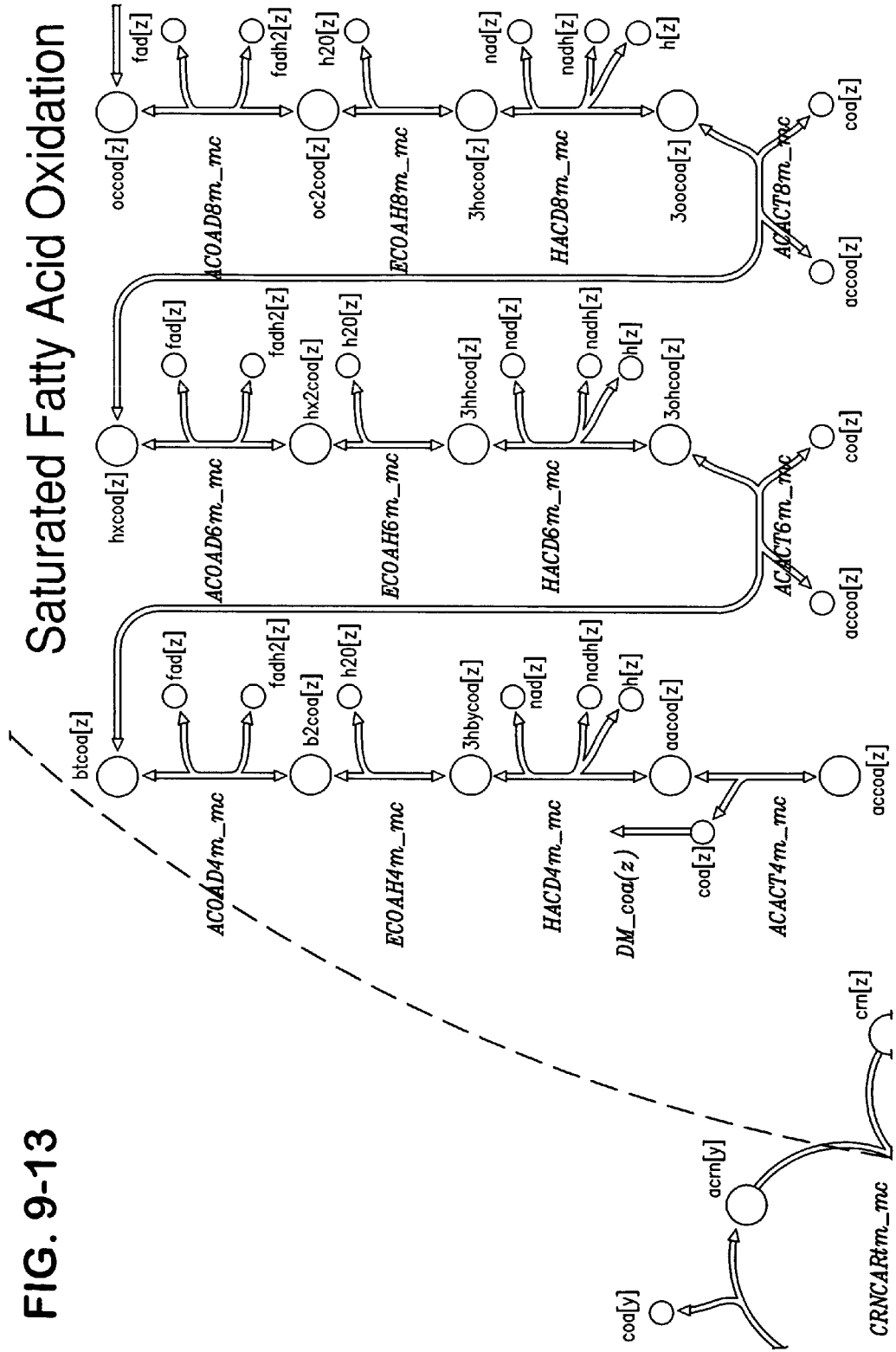
Figures 9, 10, 11, 12, 13, 14:
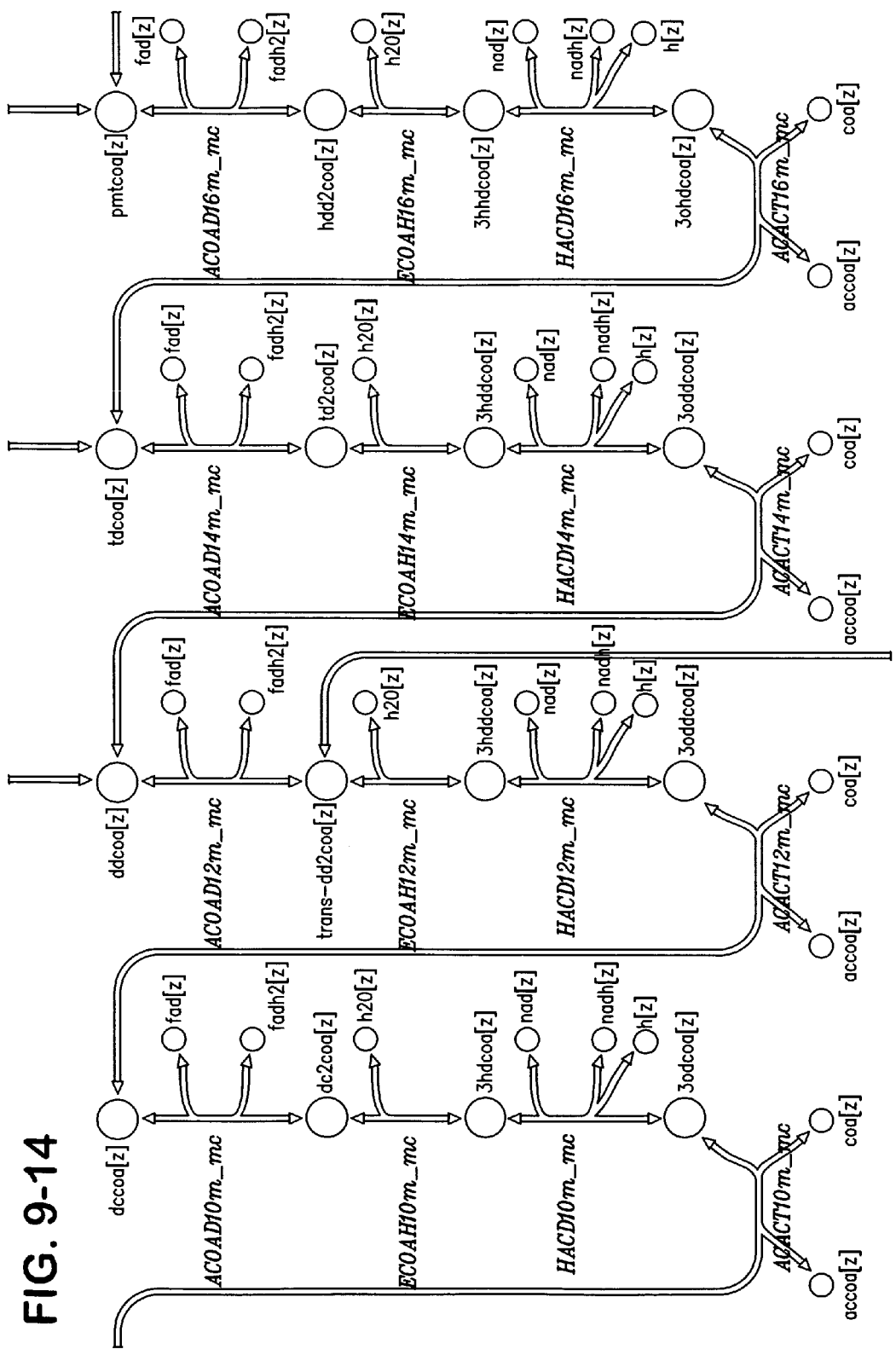
Figures 9, 10, 11, 12, 13, 14, 15:
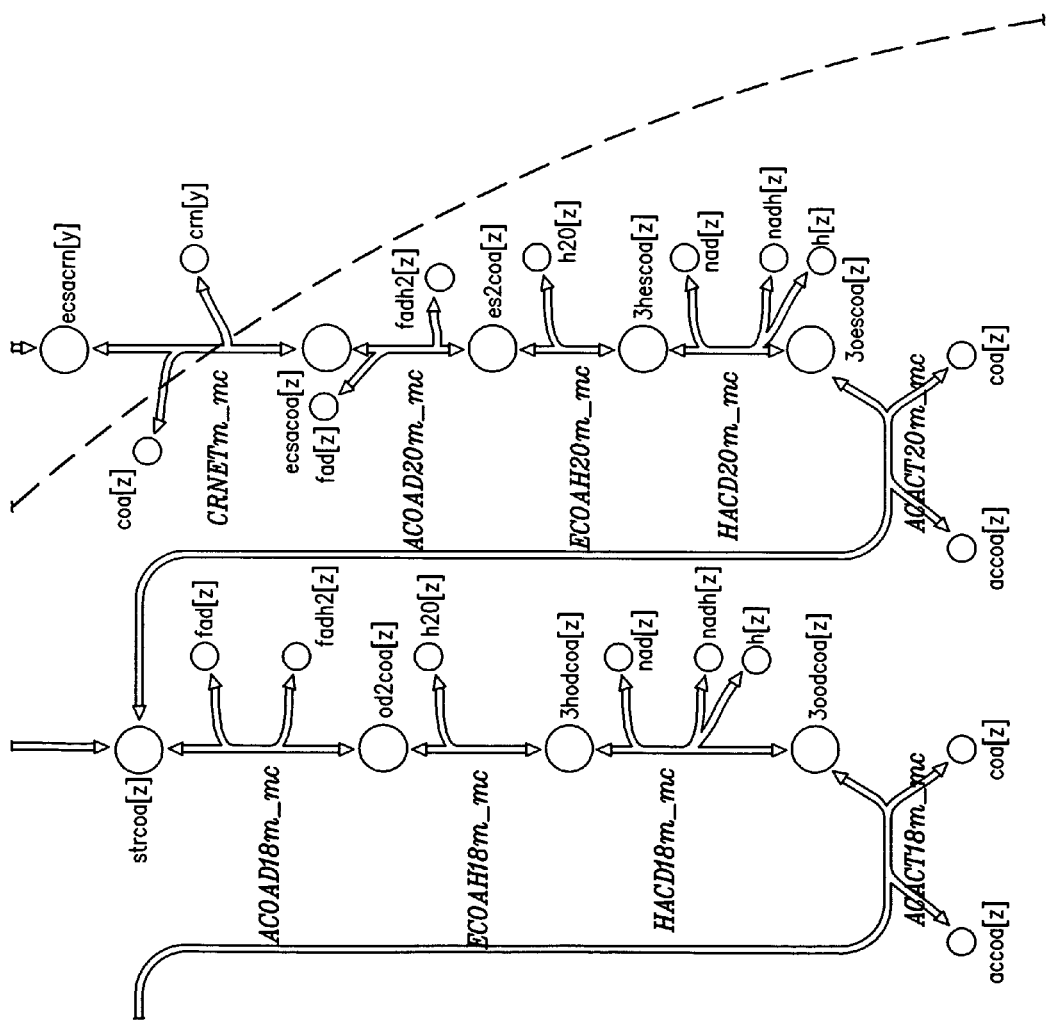
Figures 9, 10, 11, 12, 13, 14, 15, 16:
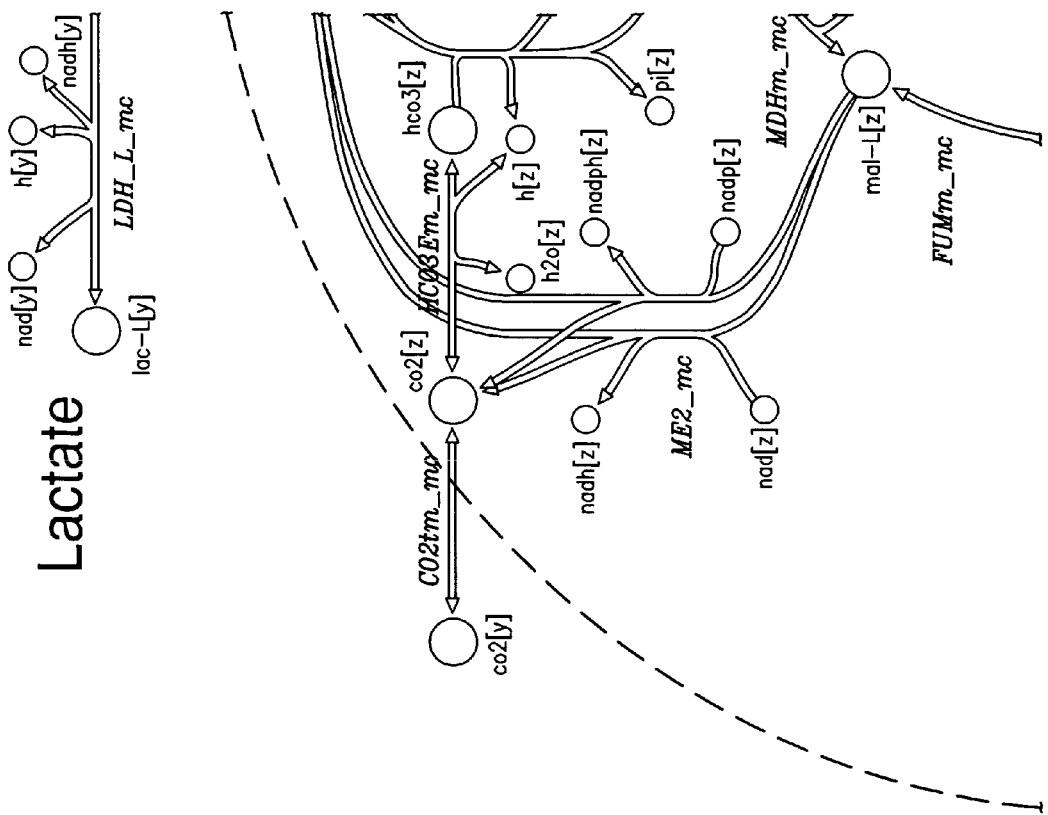
Figures 9, 10, 11, 12, 13, 14, 15, 16, 17:
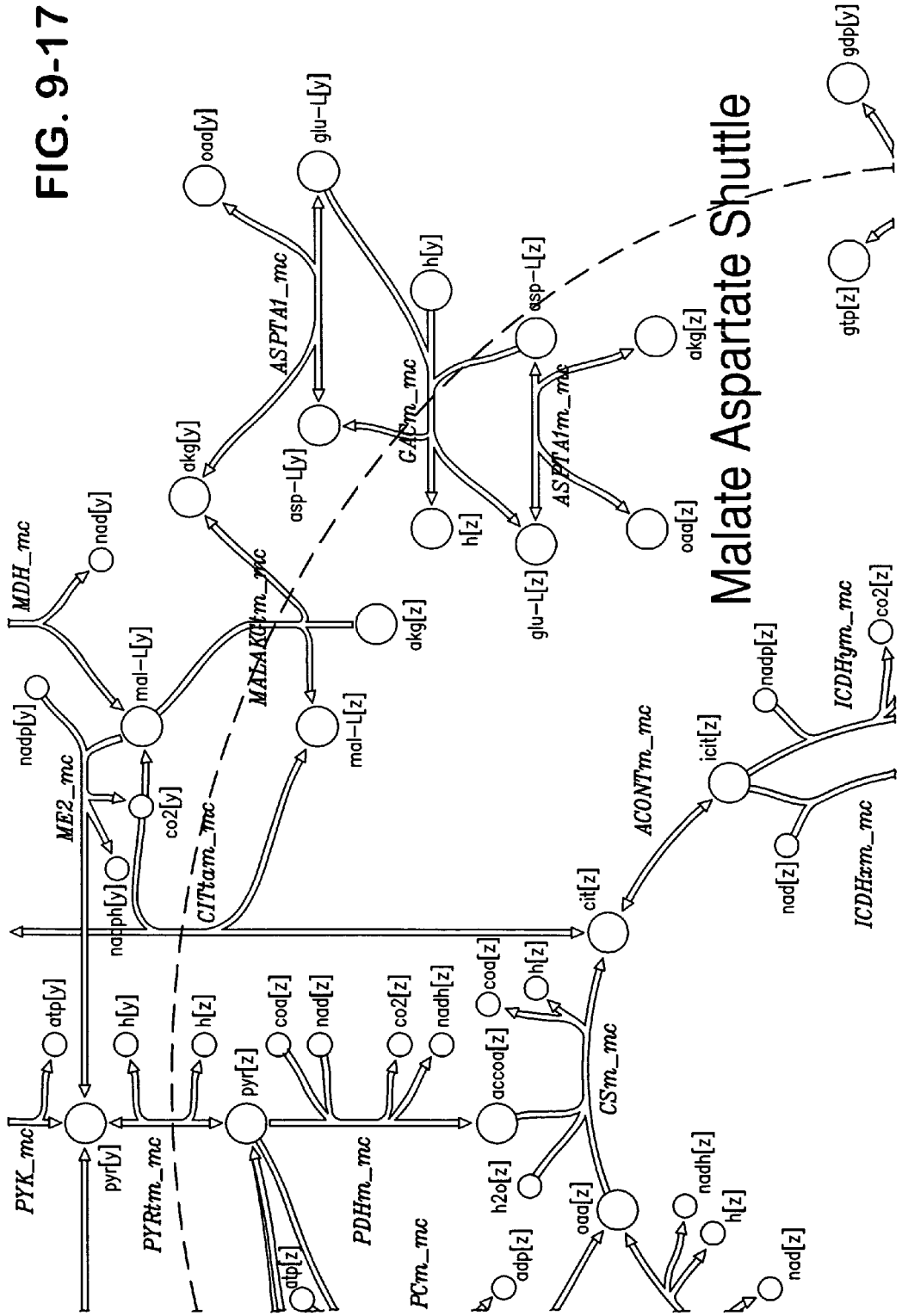
Figures 9, 10, 11, 12, 13, 14, 15, 16, 17, 18:
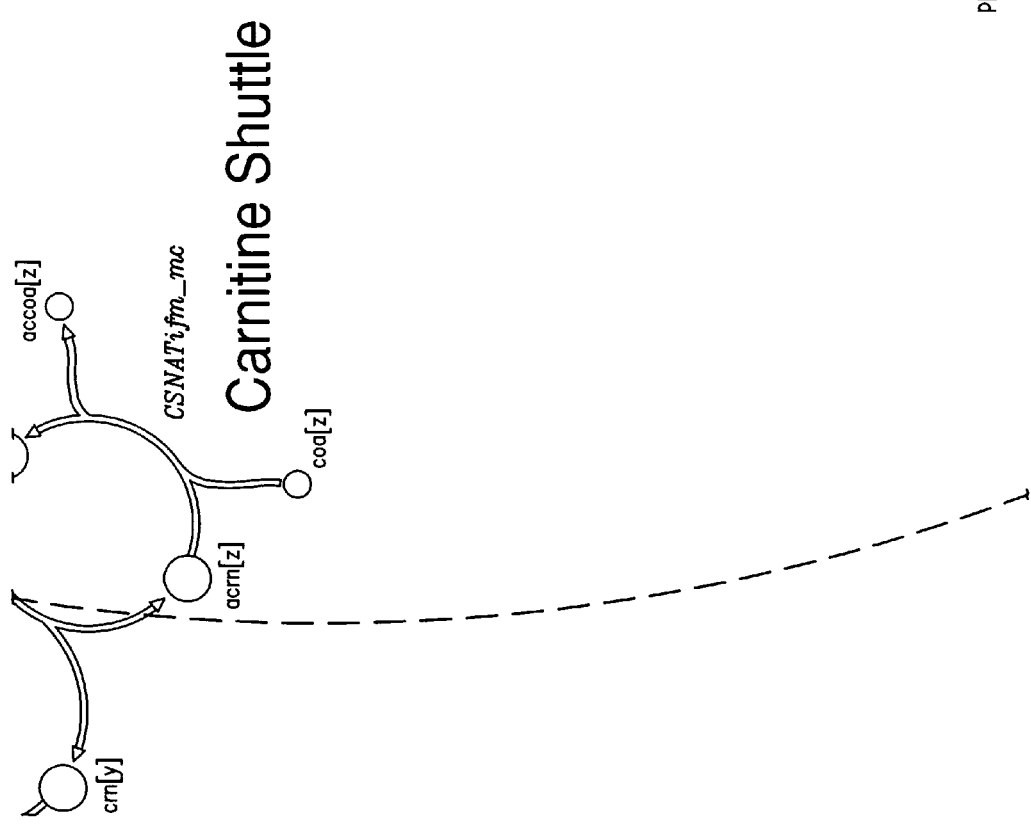
Figures 9, 10, 11, 12, 13, 14, 15, 16, 17, 18, 19:
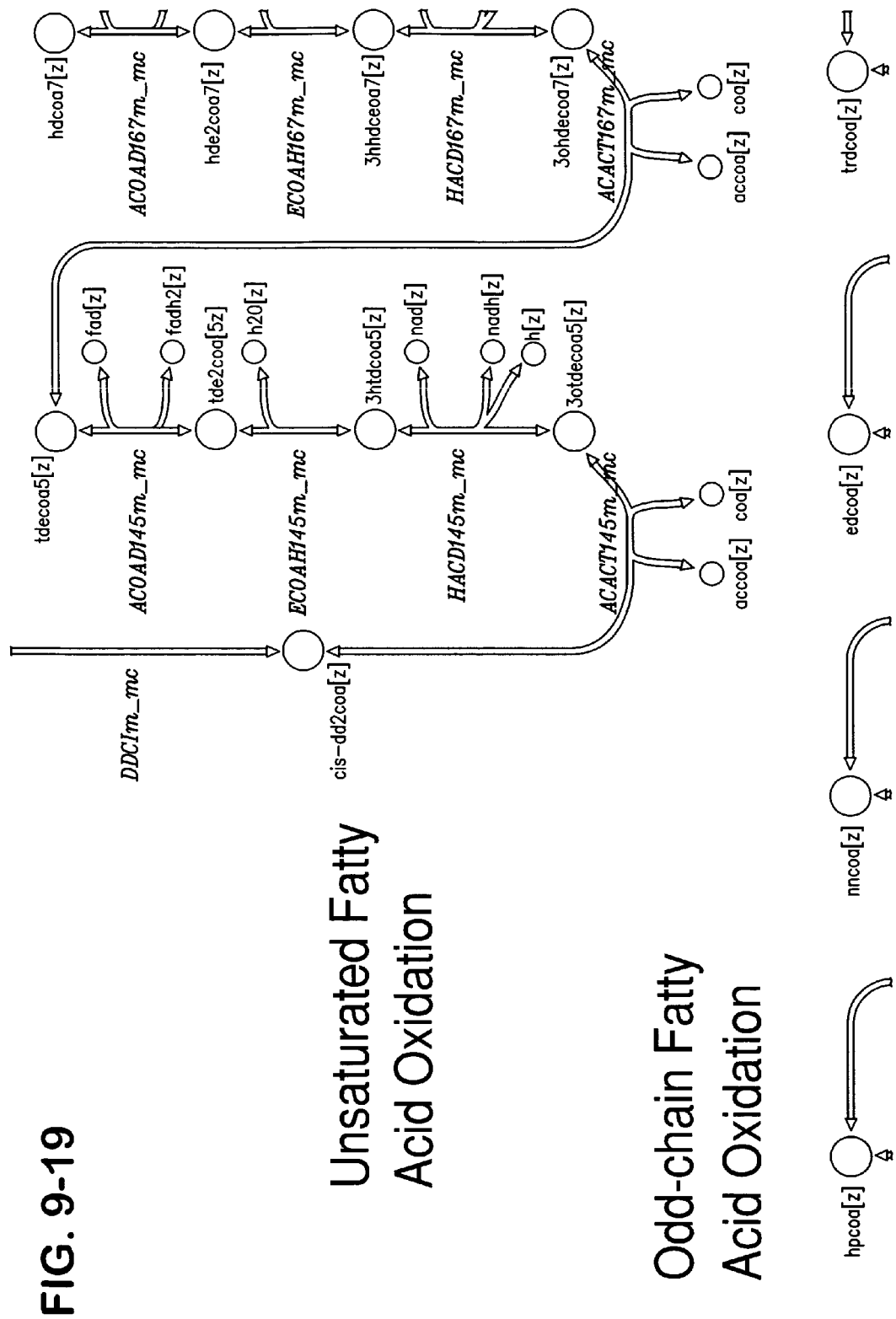
Figures 9, 10, 11, 12, 13, 14, 15, 16, 17, 18, 19, 20:
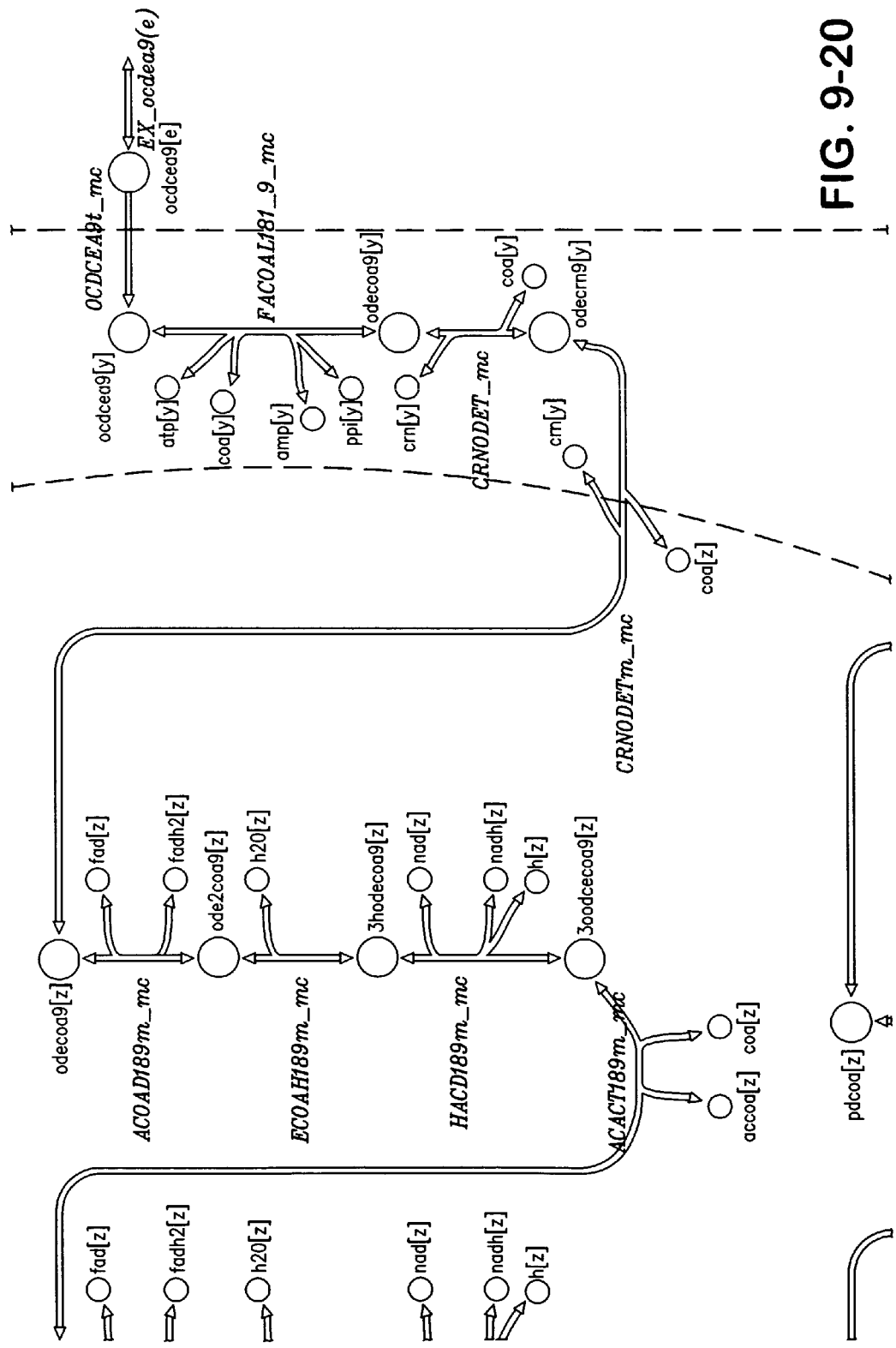
Figures 9, 10, 11, 12, 13, 14, 15, 16, 17, 18, 19, 20, 21:
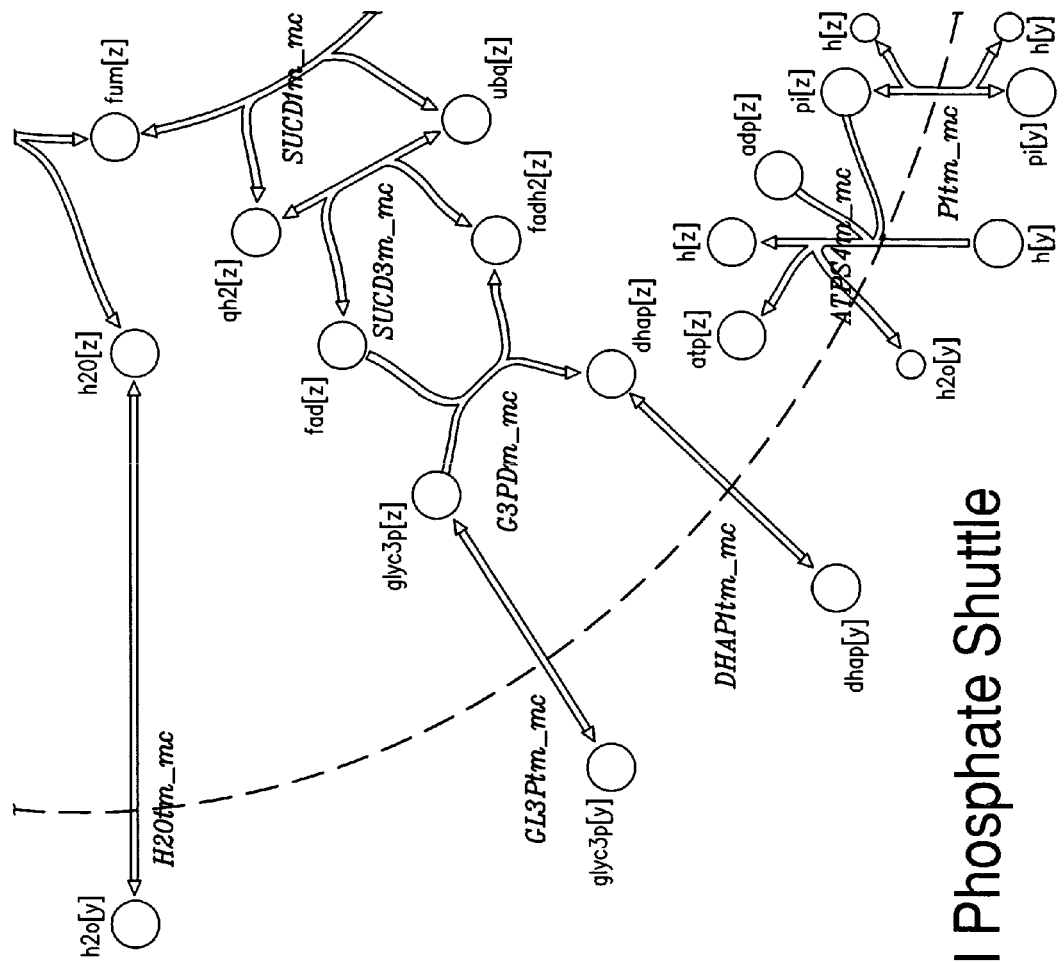
Figures 9, 10, 11, 12, 13, 14, 15, 16, 17, 18, 19, 20, 21, 22:
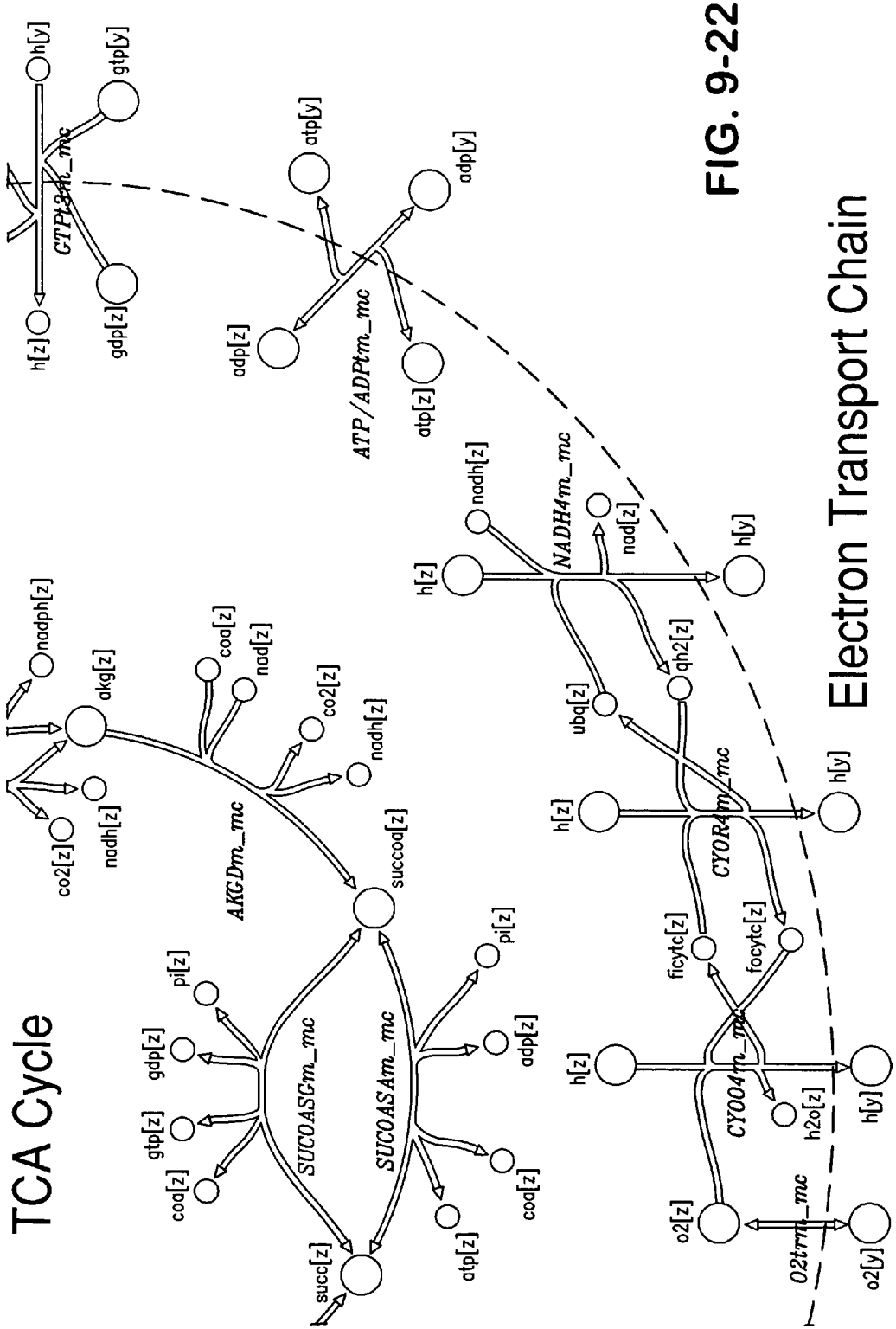
Figures 9, 10, 11, 12, 13, 14, 15, 16, 17, 18, 19, 20, 21, 22, 23:
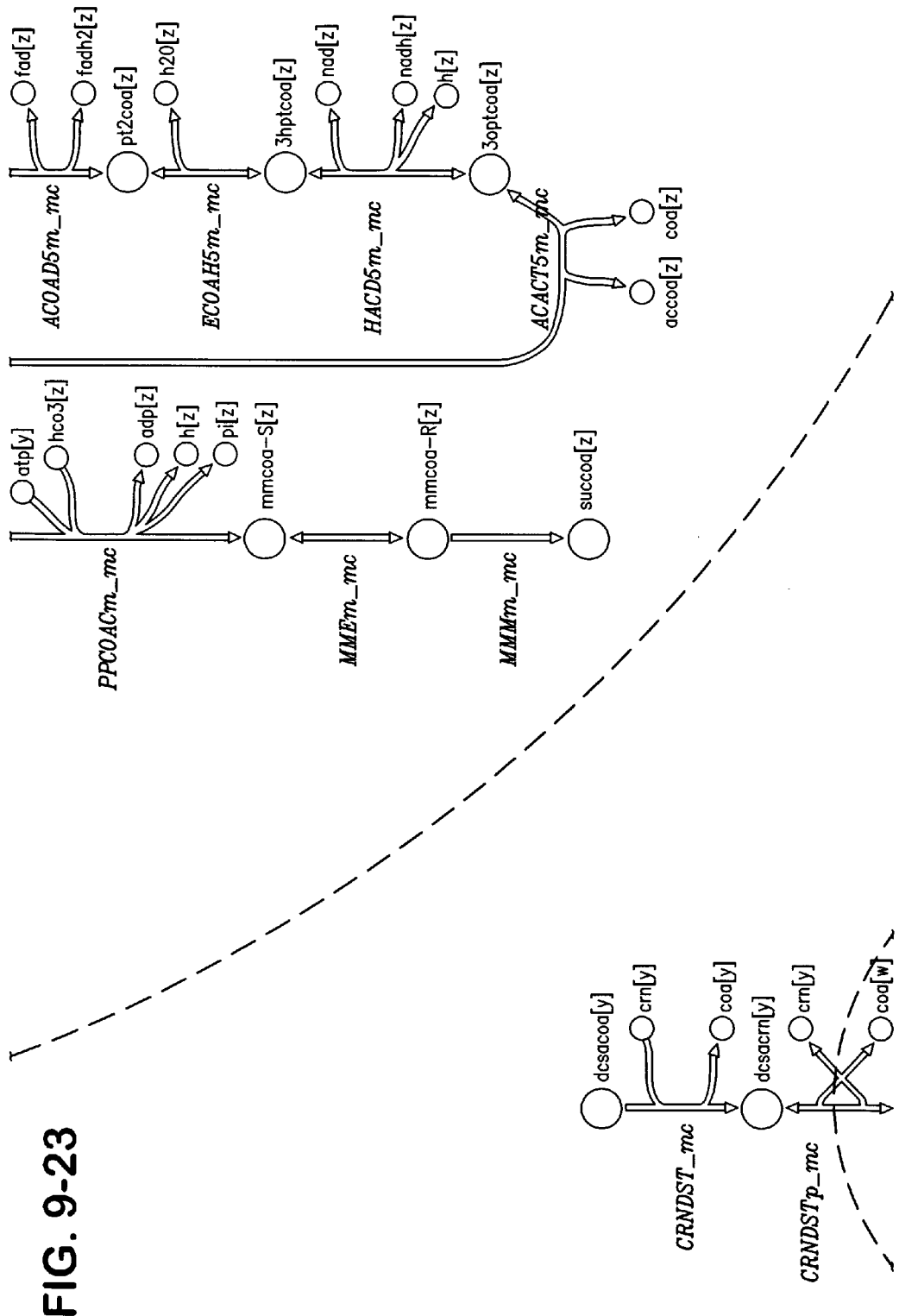
Figures 9, 10, 11, 12, 13, 14, 15, 16, 17, 18, 19, 20, 21, 22, 23, 24:
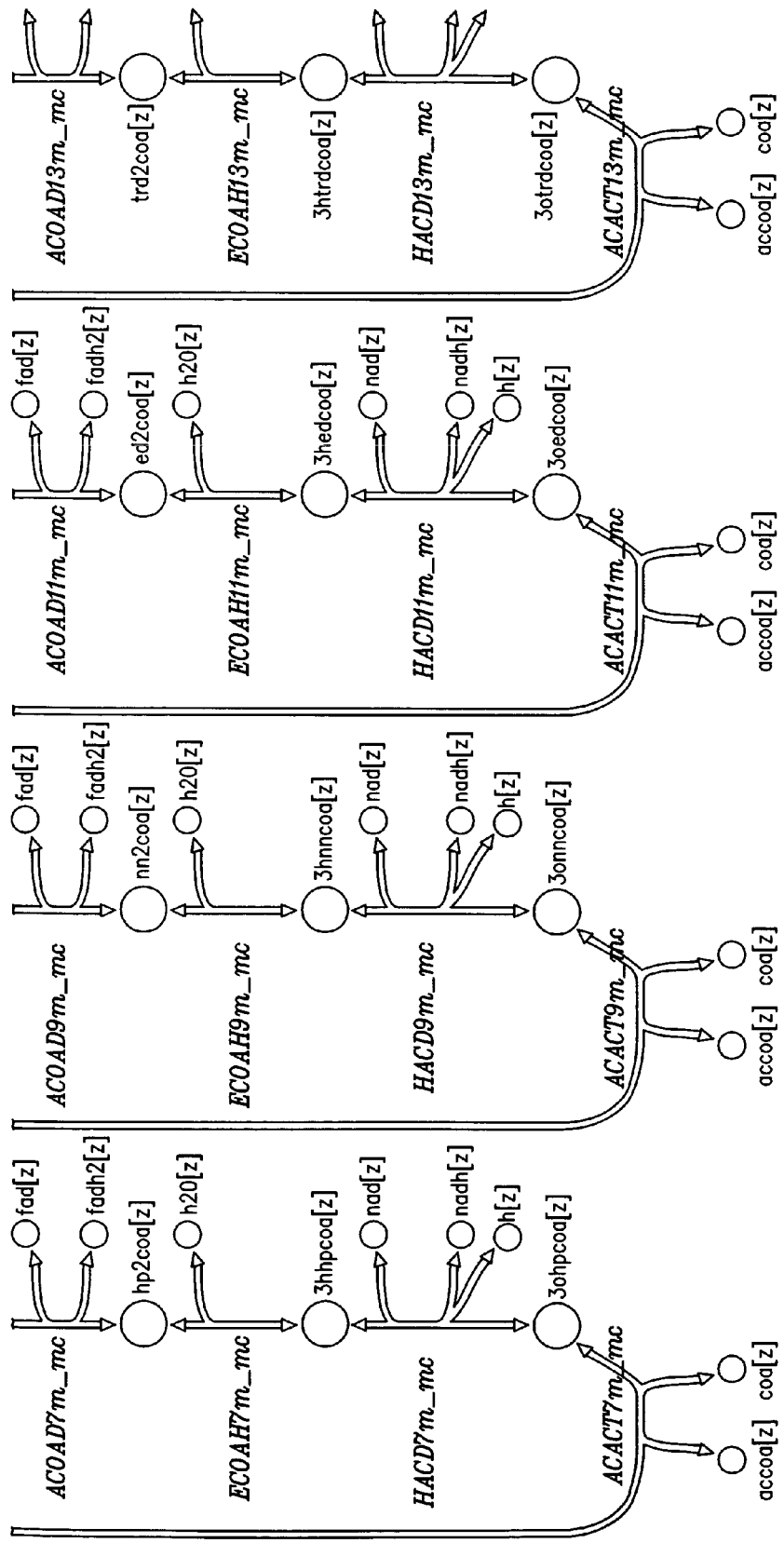
Figures 9, 10, 11, 12, 13, 14, 15, 16, 17, 18, 19, 20, 21, 22, 23, 24, 25:
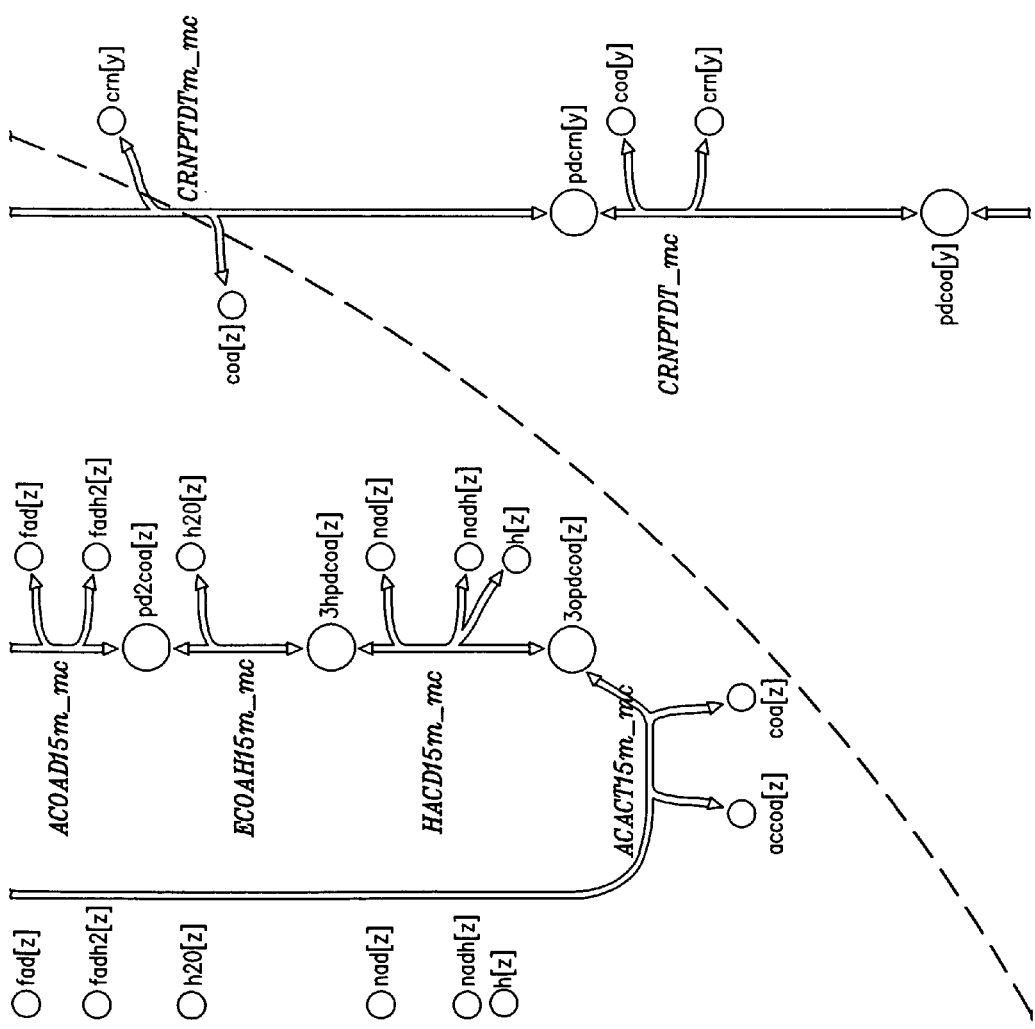
Figures 9, 10, 11, 12, 13, 14, 15, 16, 17, 18, 19, 20, 21, 22, 23, 24, 25, 26:
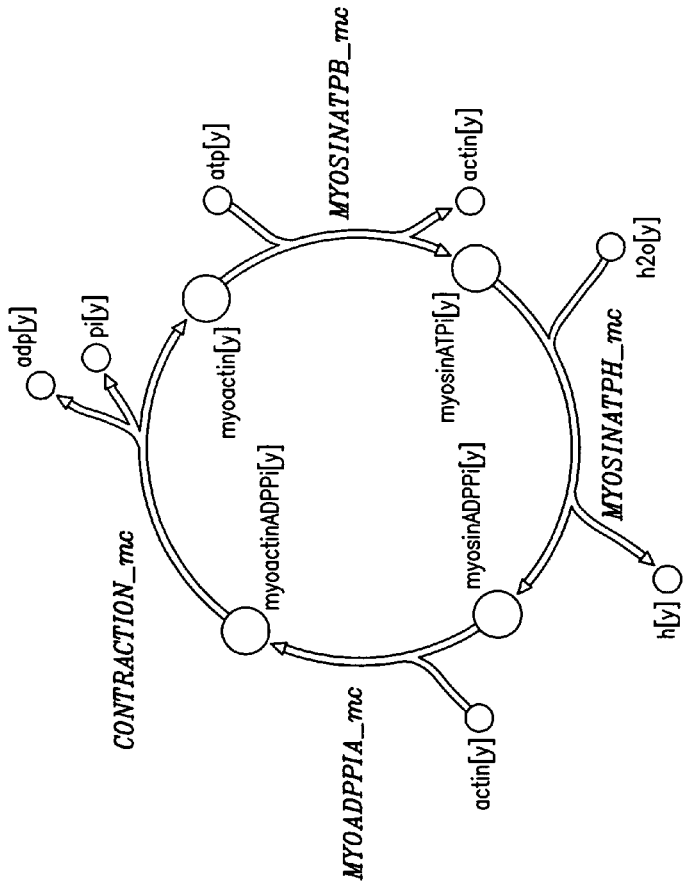
Figures 9, 10, 11, 12, 13, 14, 15, 16, 17, 18, 19, 20, 21, 22, 23, 24, 25, 26, 27, 28, 29:
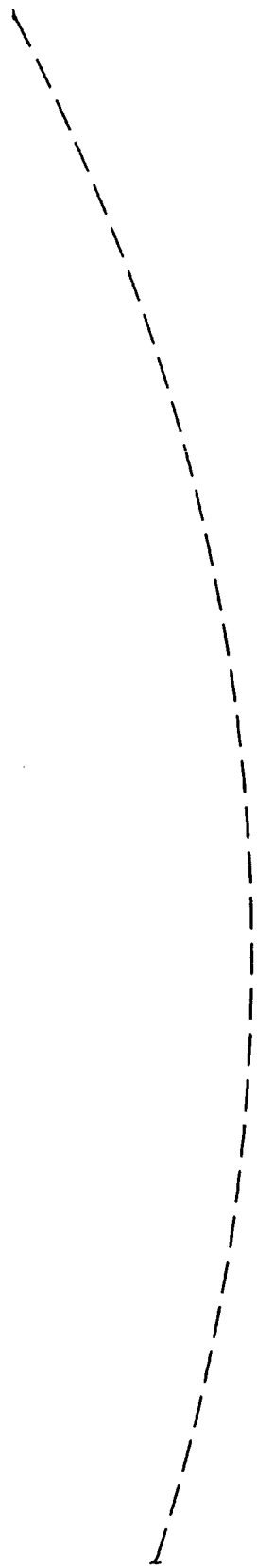
Figures 9, 10, 11, 12, 13, 14, 15, 16, 17, 18, 19, 20, 21, 22, 23, 24, 25, 26, 27, 28, 29, 30:
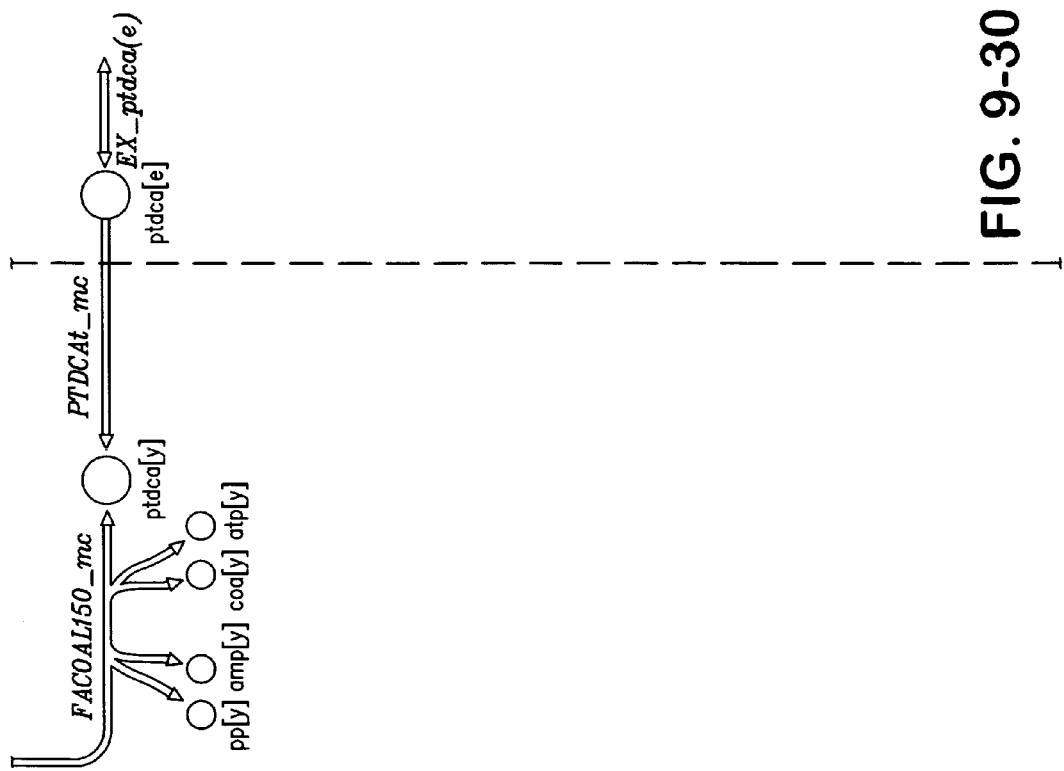
Figures 9, 10, 11, 12, 13, 14, 15, 16, 17, 18, 19, 20, 21, 22, 23, 24, 25, 26, 27, 28, 29, 30, 31:
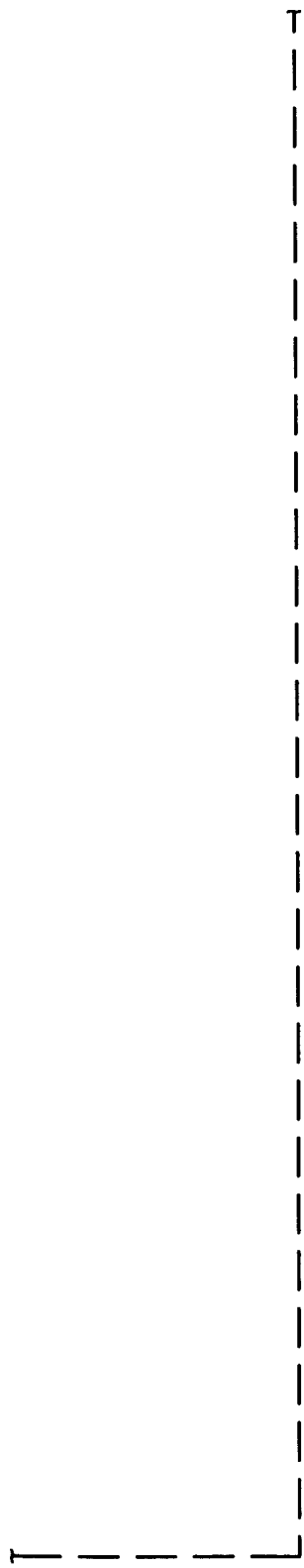
Figures 9, 10, 11, 12, 13, 14, 15, 16, 17, 18, 19, 20, 21, 22, 23, 24, 25, 26, 27, 28, 29, 30, 31, 32:
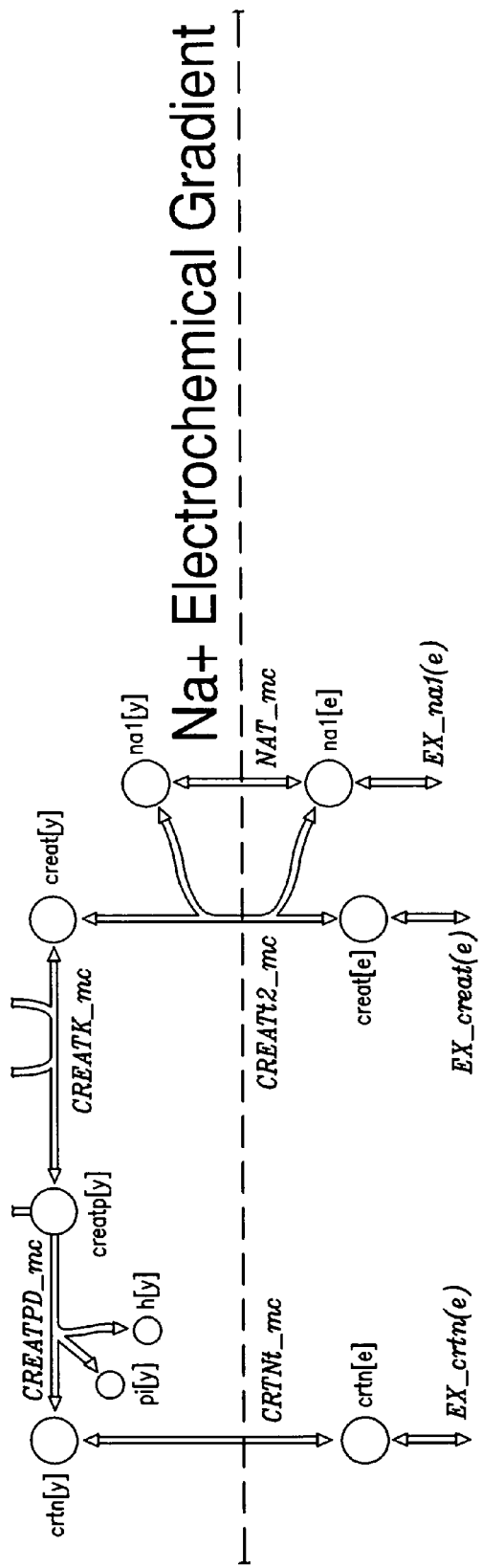
Figures 9, 10, 11, 12, 13, 14, 15, 16, 17, 18, 19, 20, 21, 22, 23, 24, 25, 26, 27, 28, 29, 30, 31, 32, 33, 34:
Figures 9, 10, 11, 12, 13, 14, 15, 16, 17, 18, 19, 20, 21, 22, 23, 24, 25, 26, 27, 28, 29, 30, 31, 32, 33, 34, 35:
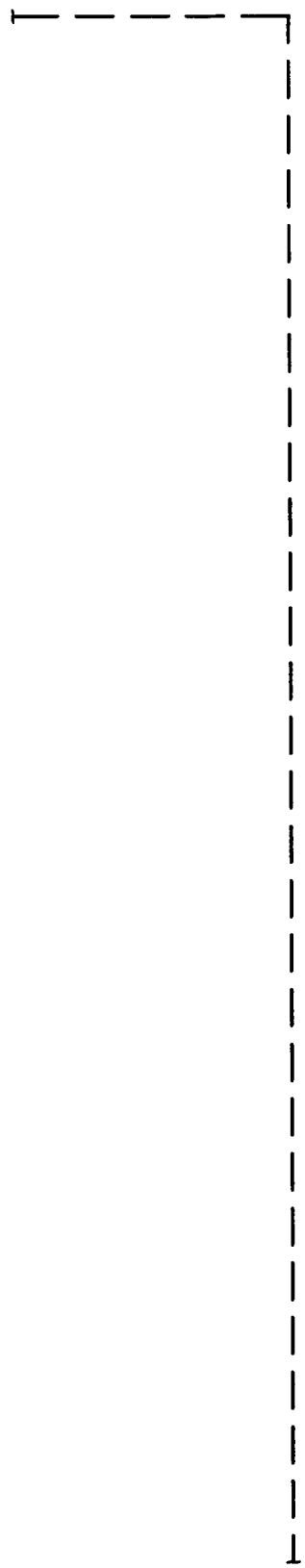
Figures 1, 10:
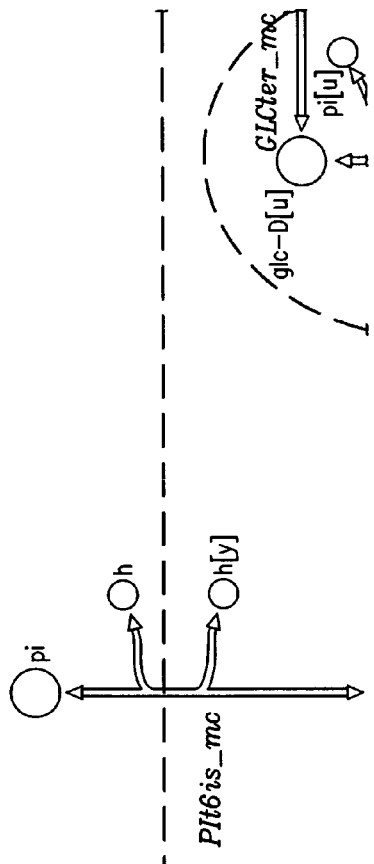
Figures 2, 10:
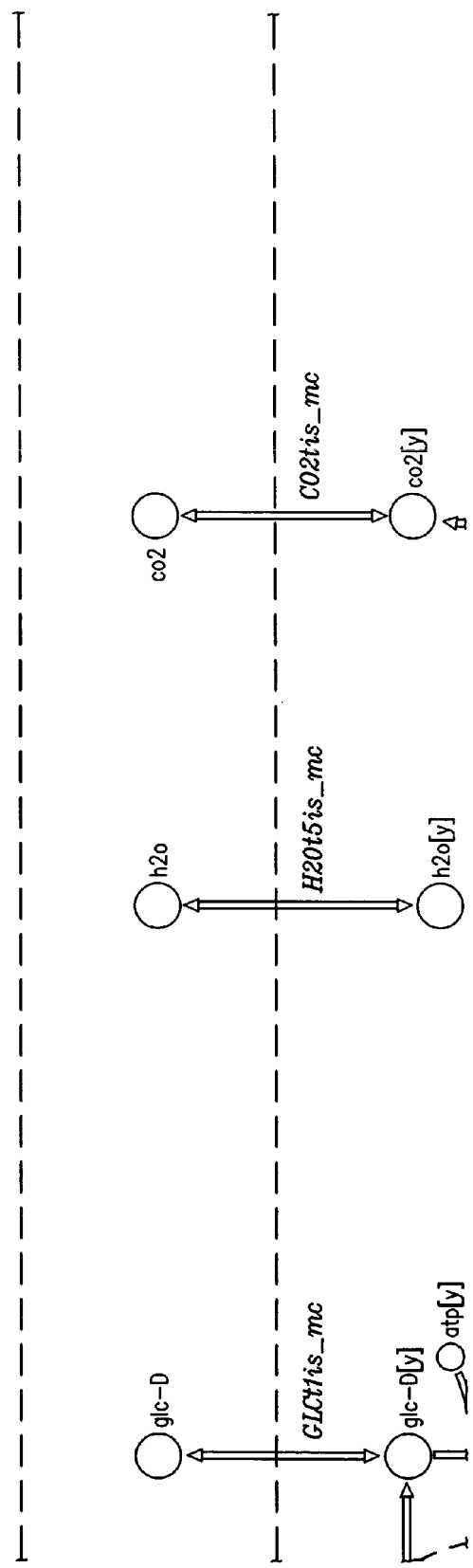
Figures 3, 10:
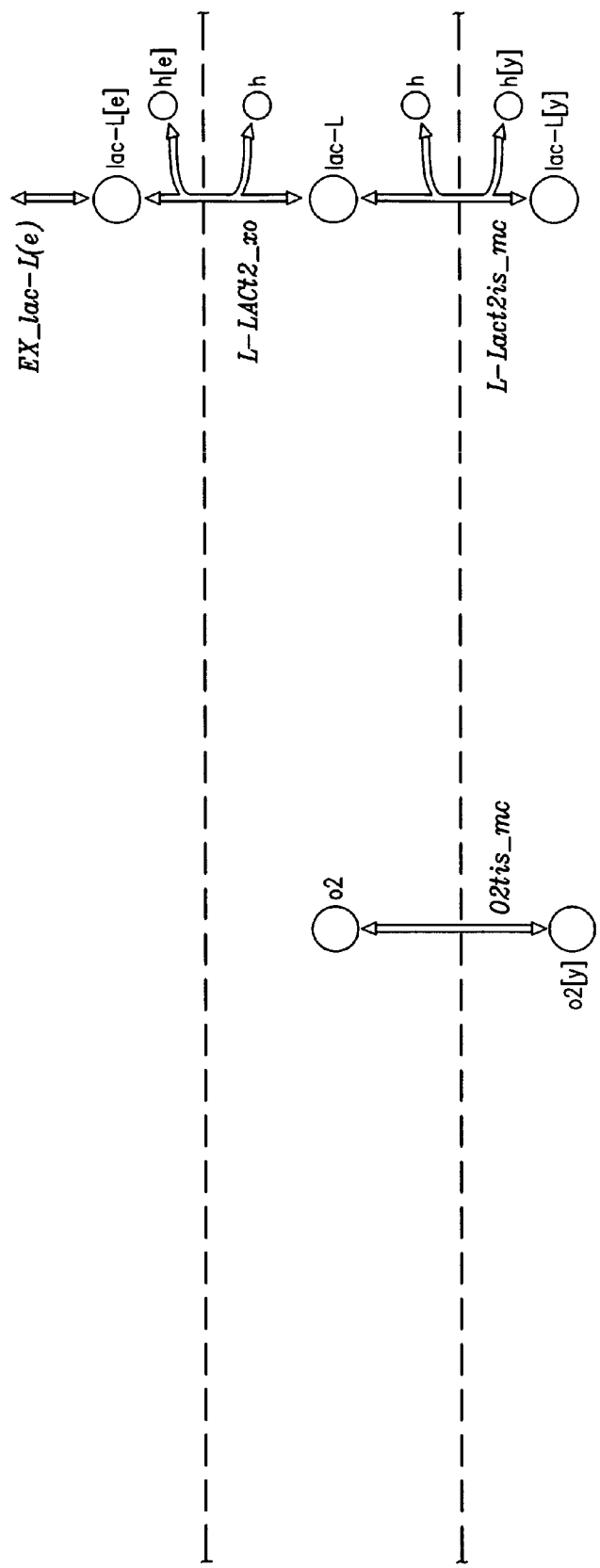
Figures 4, 10:
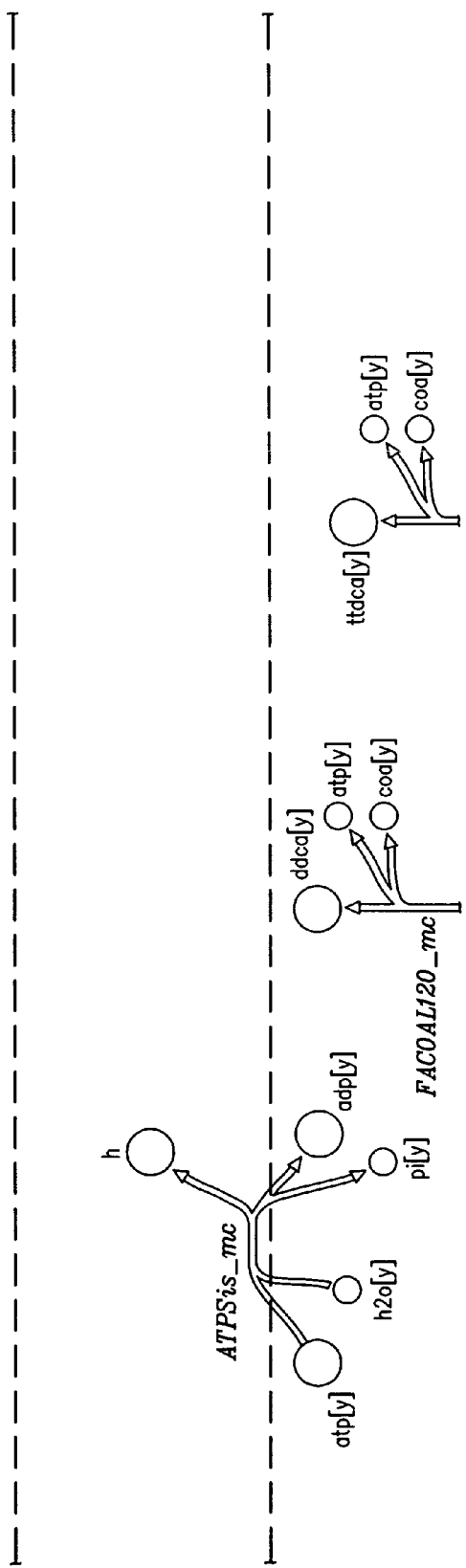
Figures 5, 10:
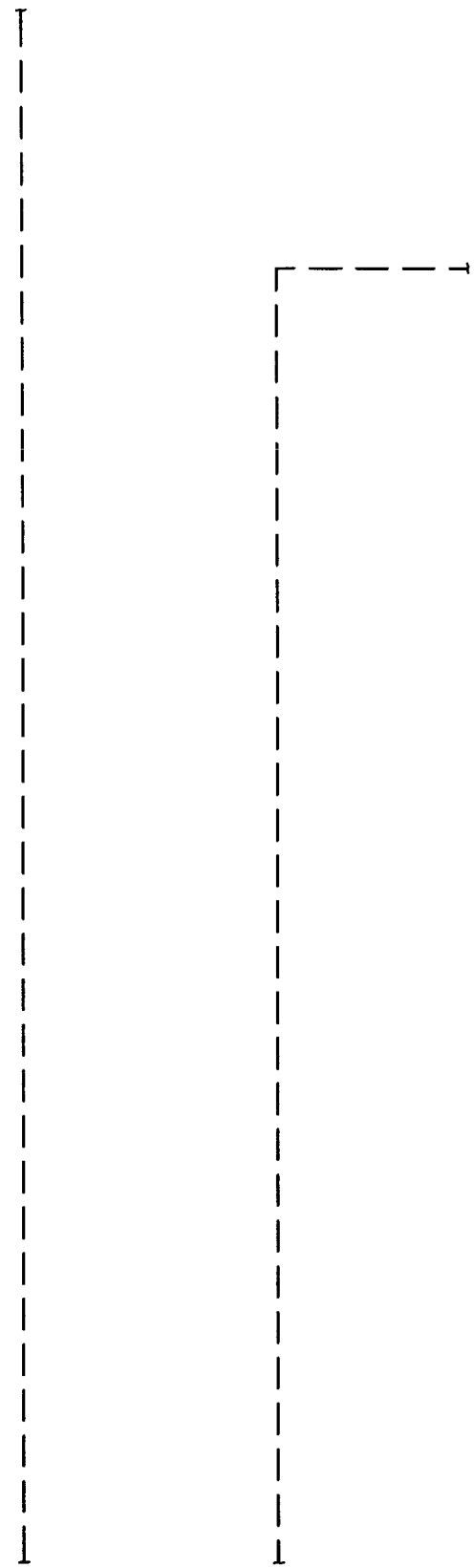
Figures 6, 10:
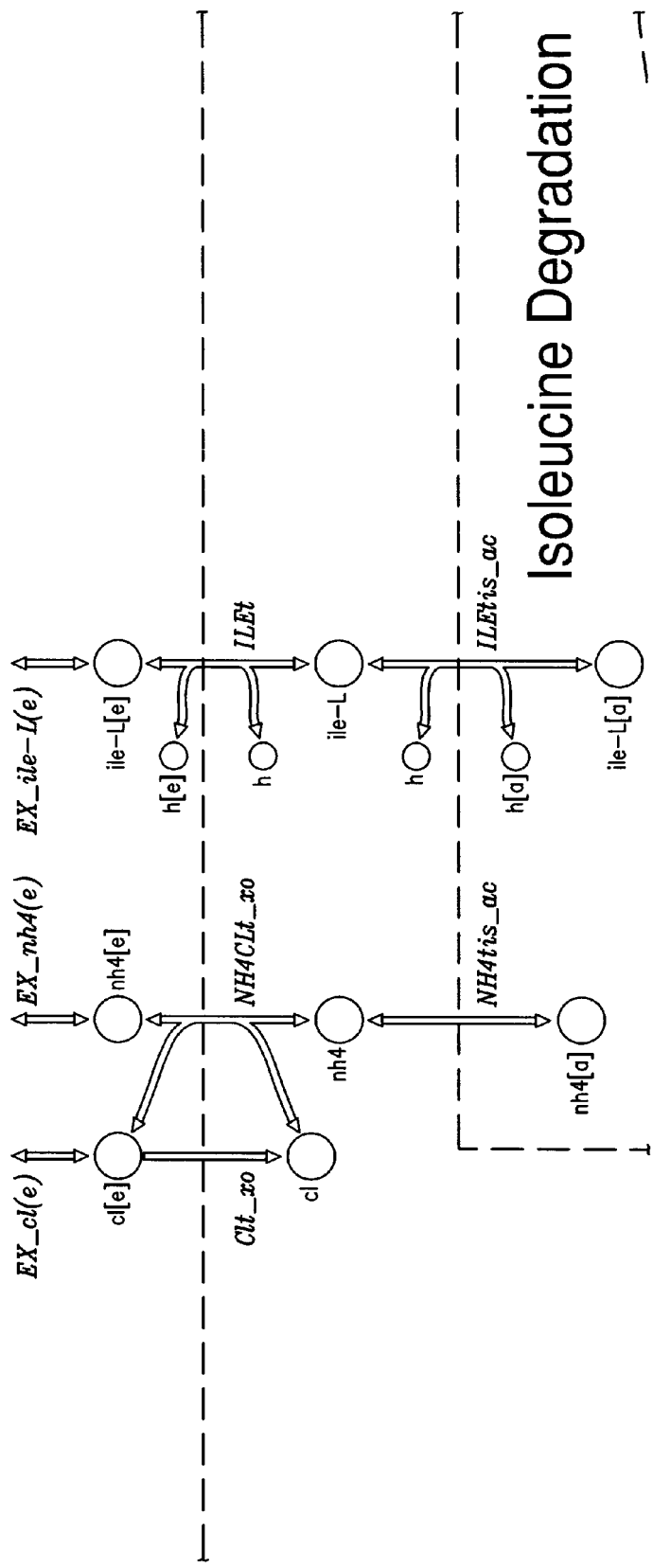
Figures 7, 10:
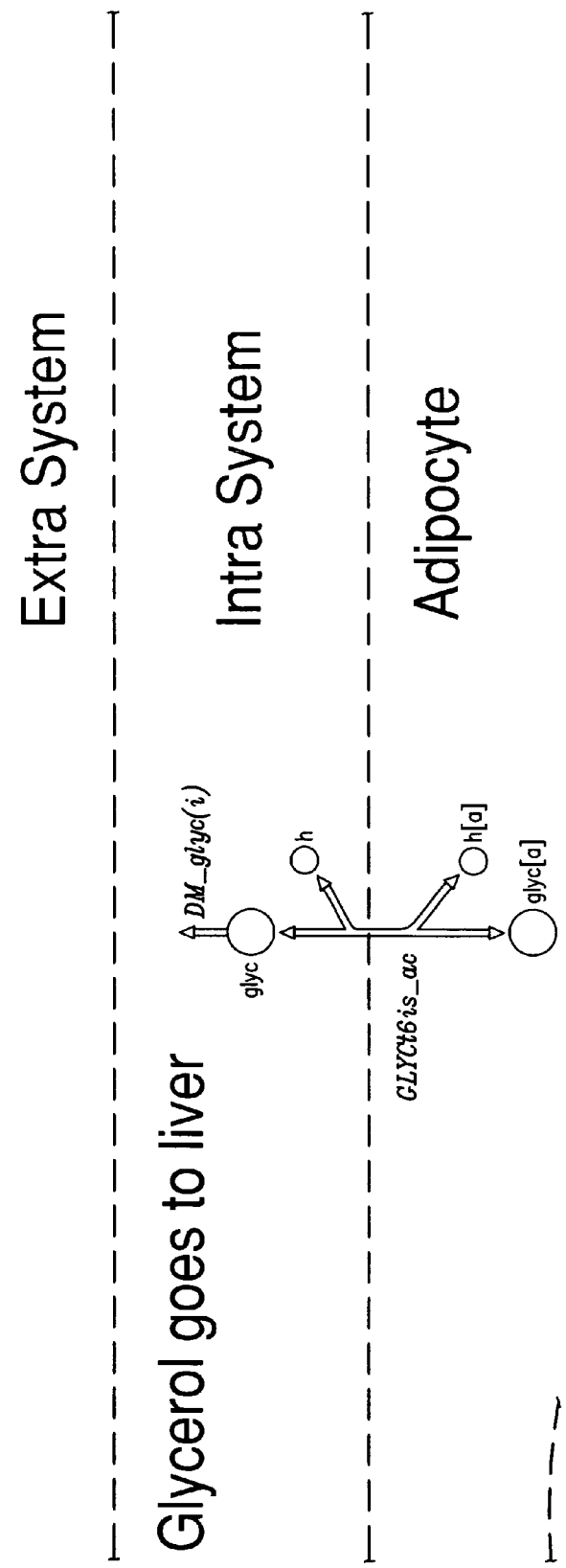
Figures 8, 10:
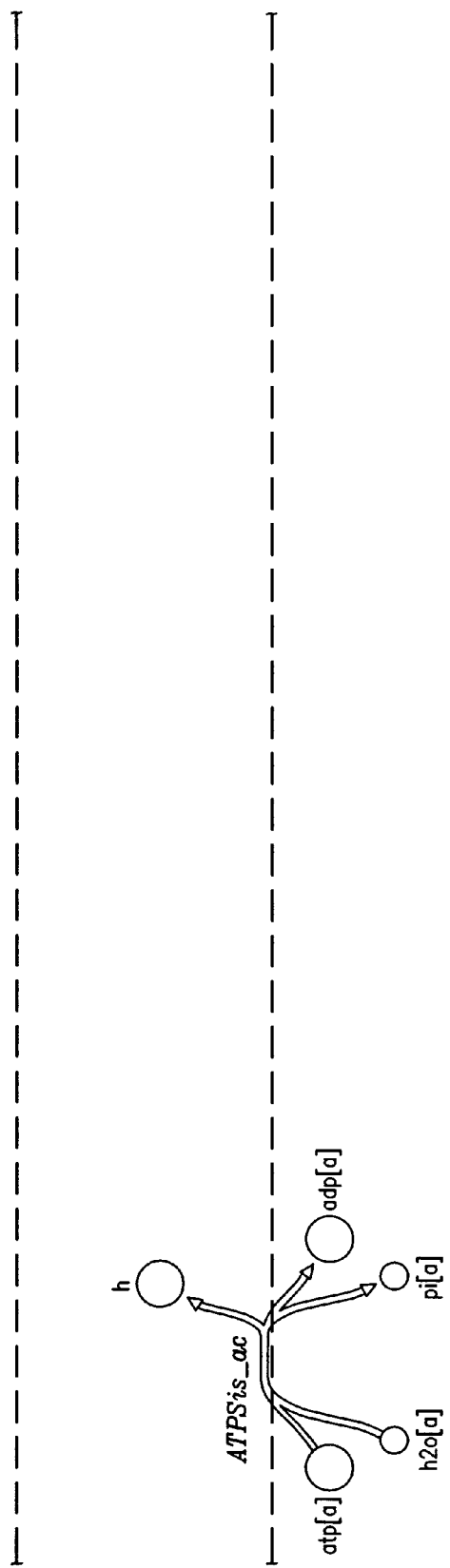
Figures 9, 10:
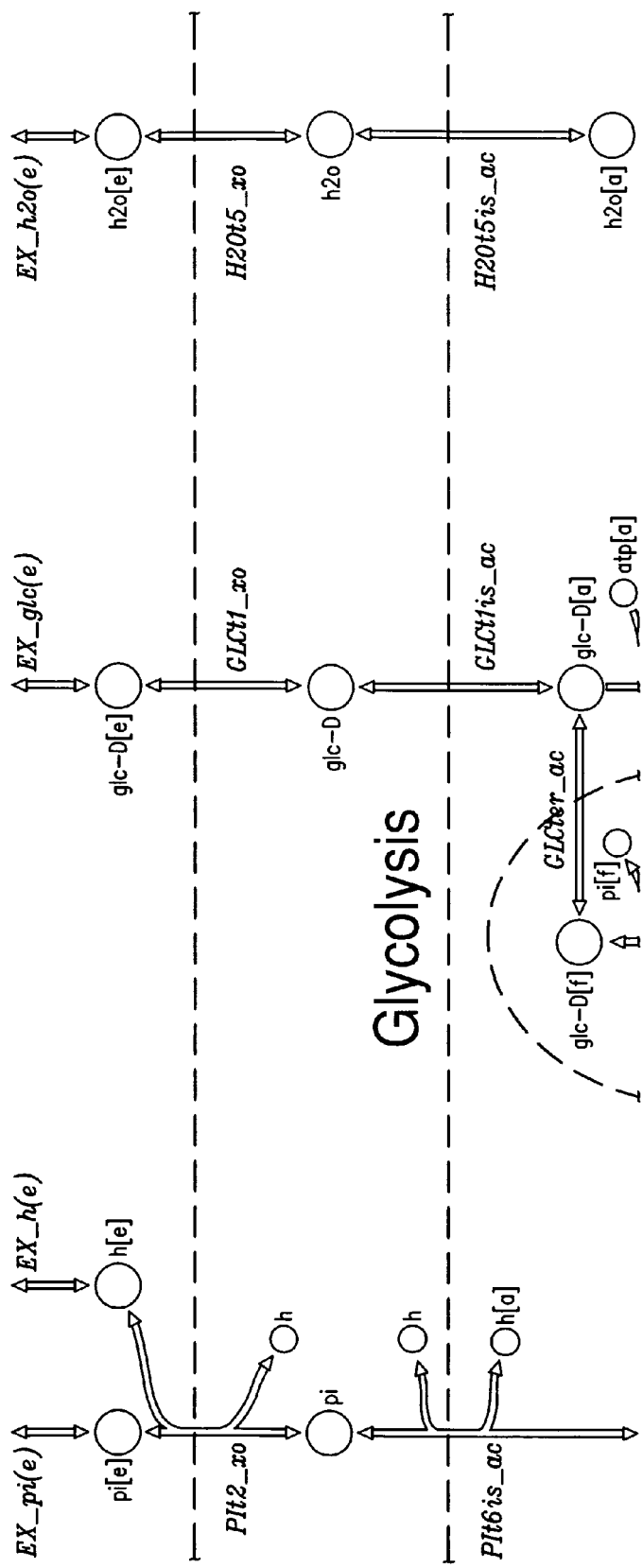
Figure 10:
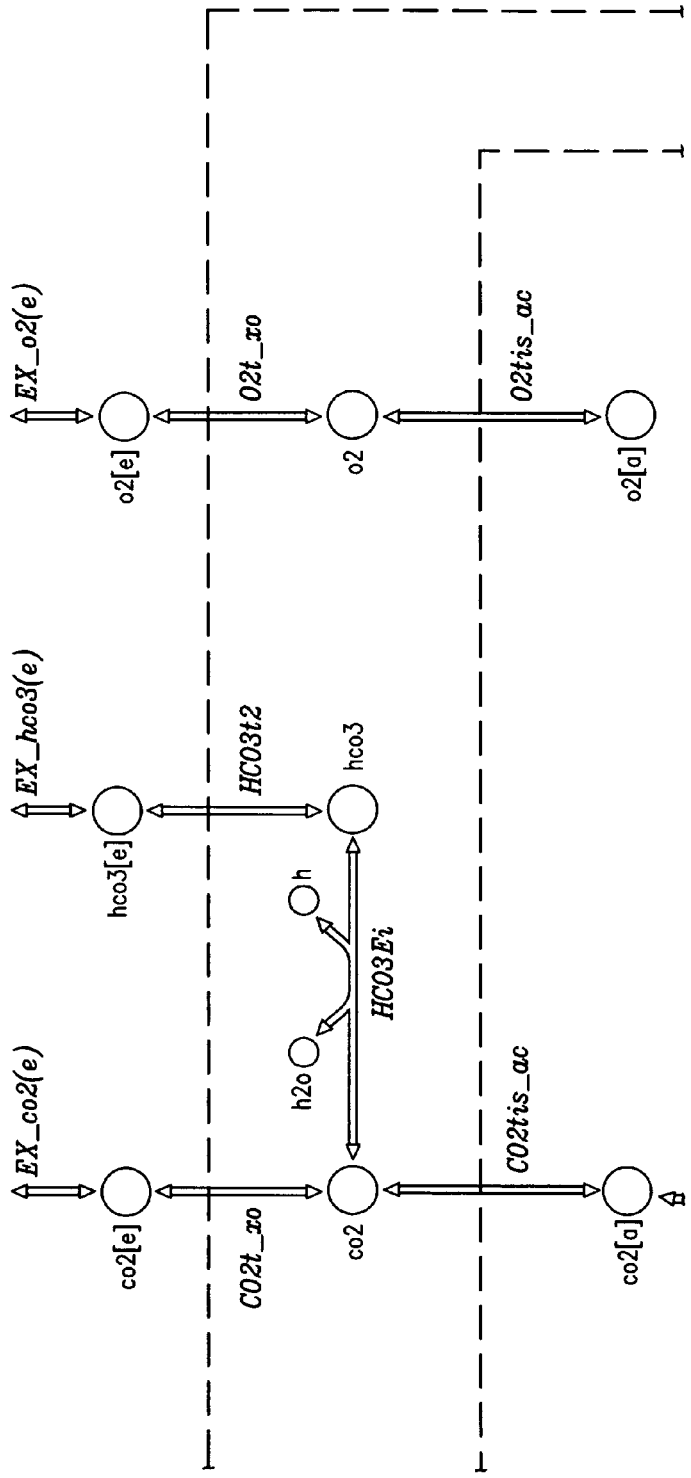
Figures 10, 11:
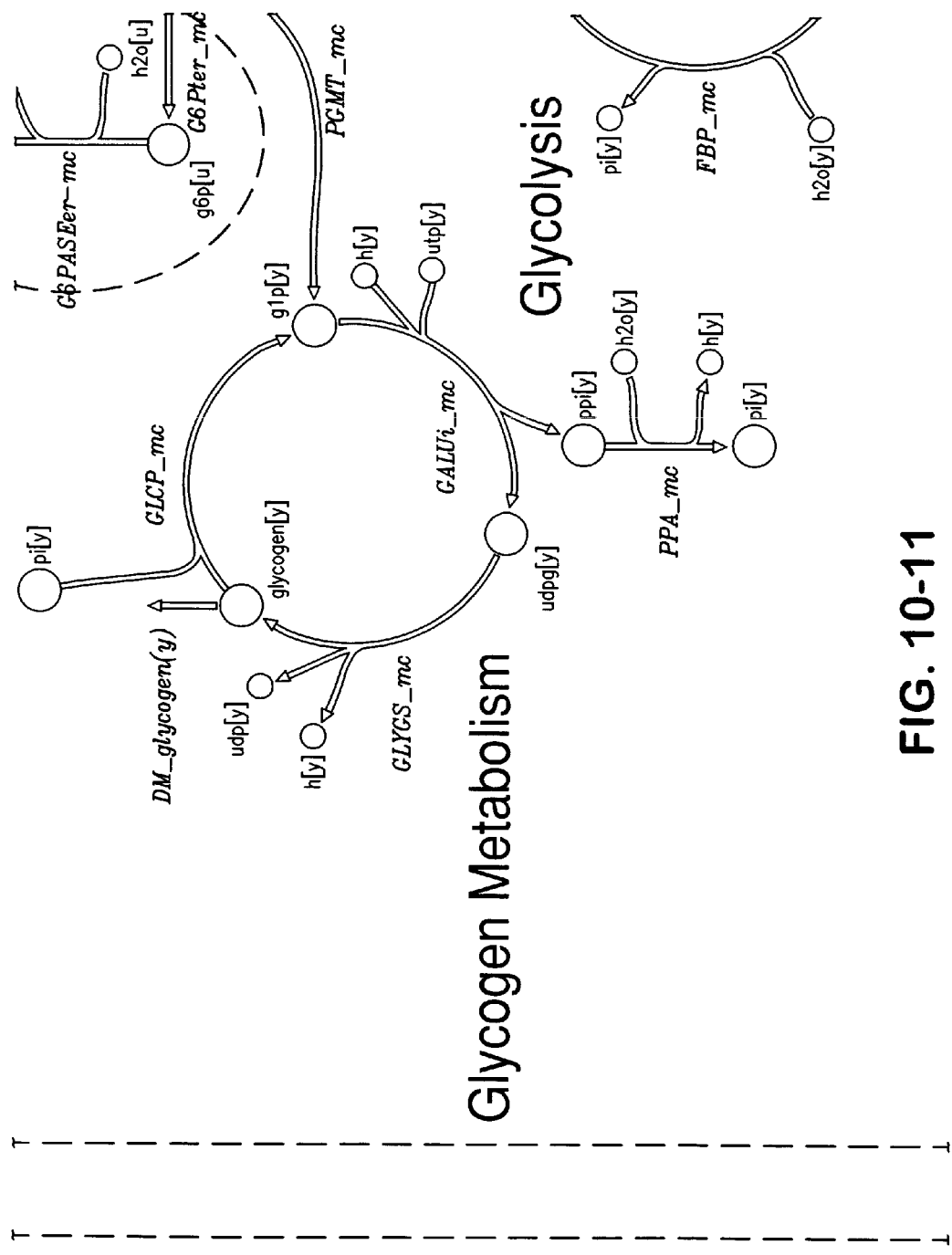
Figures 10, 11, 12:
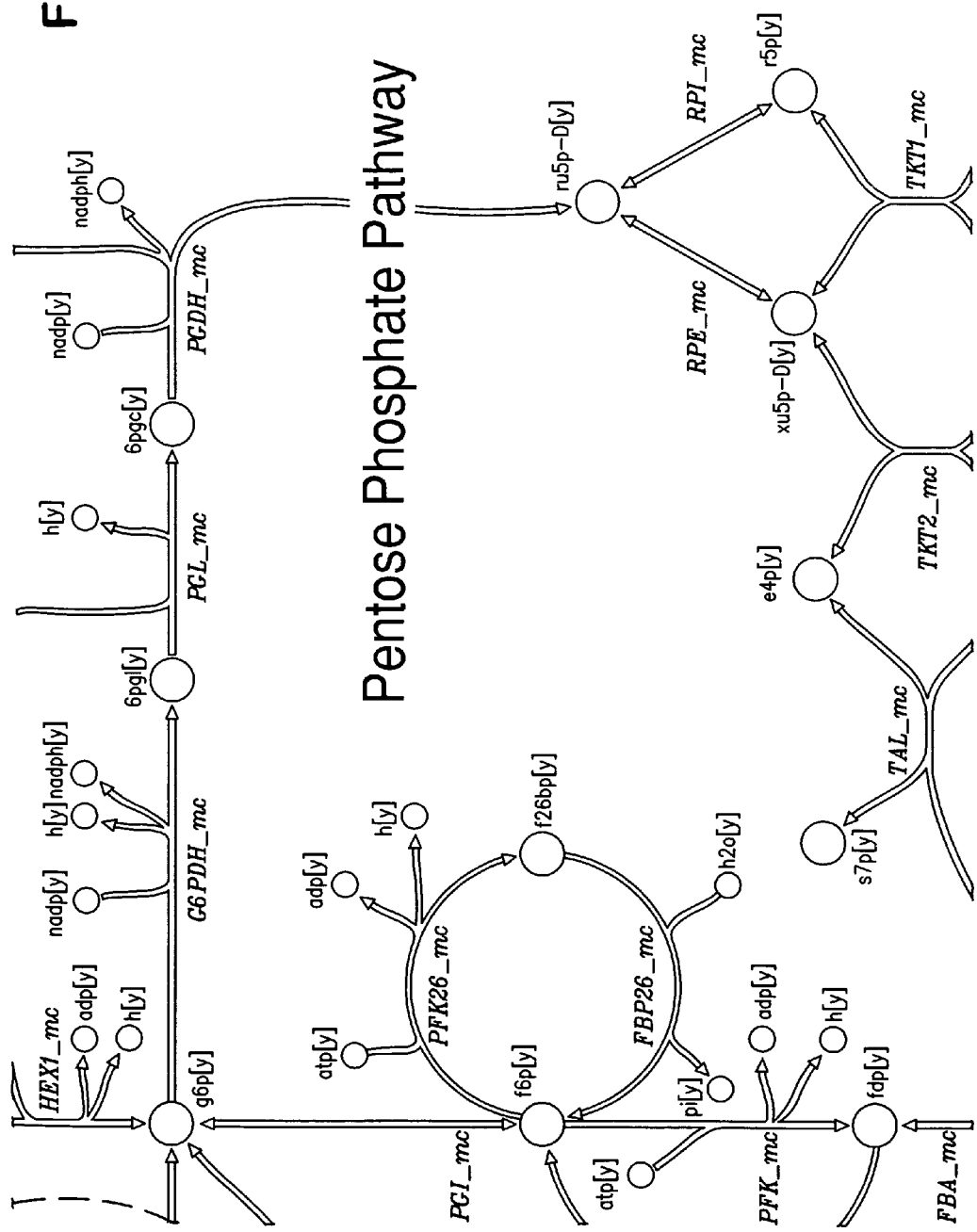
Figures 10, 11, 12, 13:
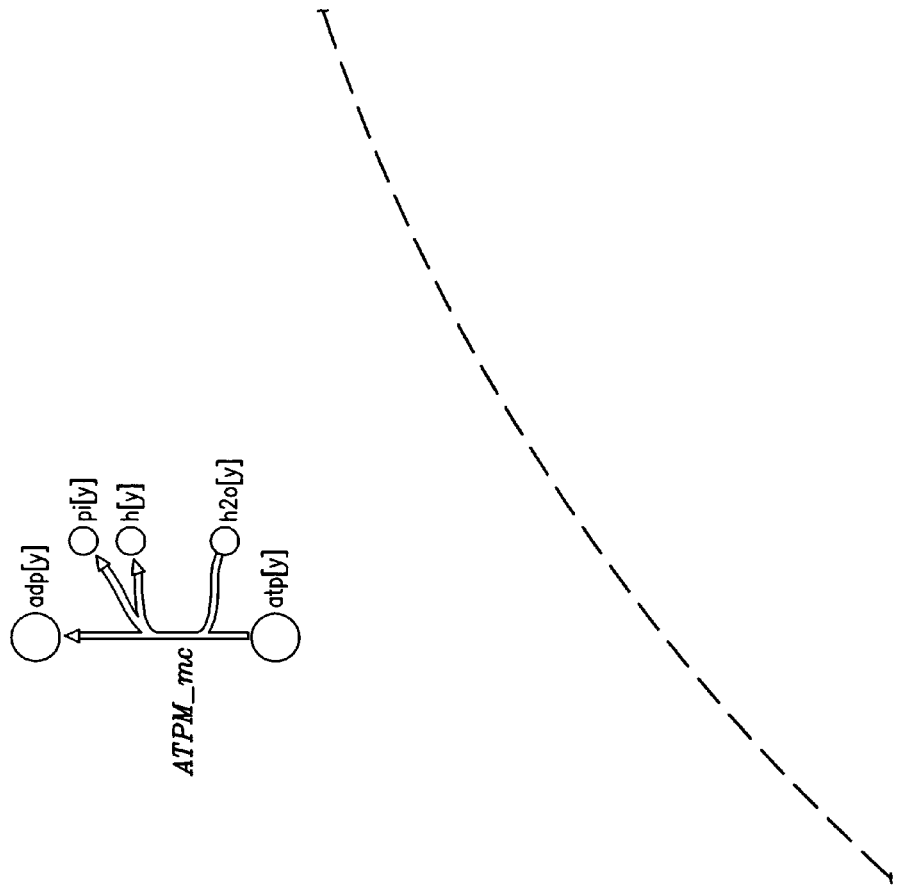
Figures 10, 11, 12, 13, 14:
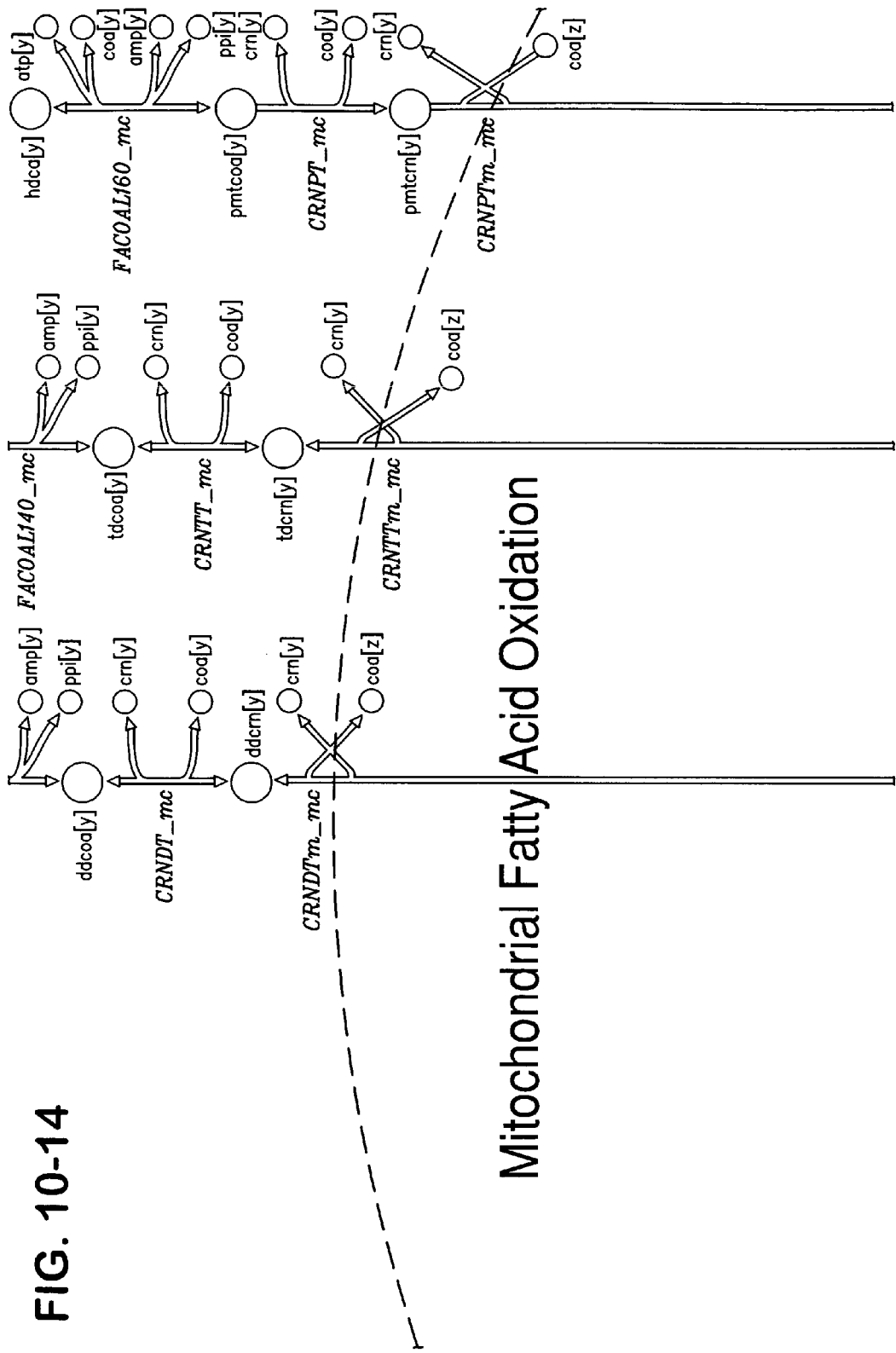
Figures 10, 11, 12, 13, 14, 15:
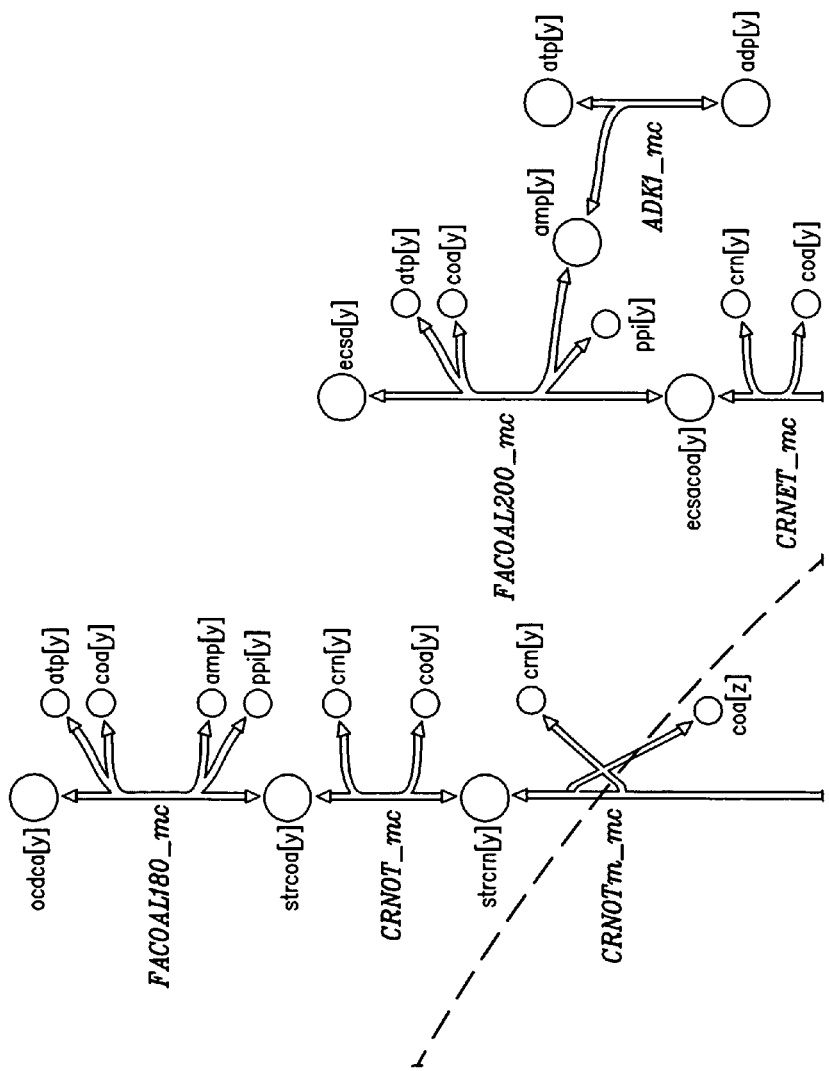
Figures 10, 11, 12, 13, 14, 15, 16:
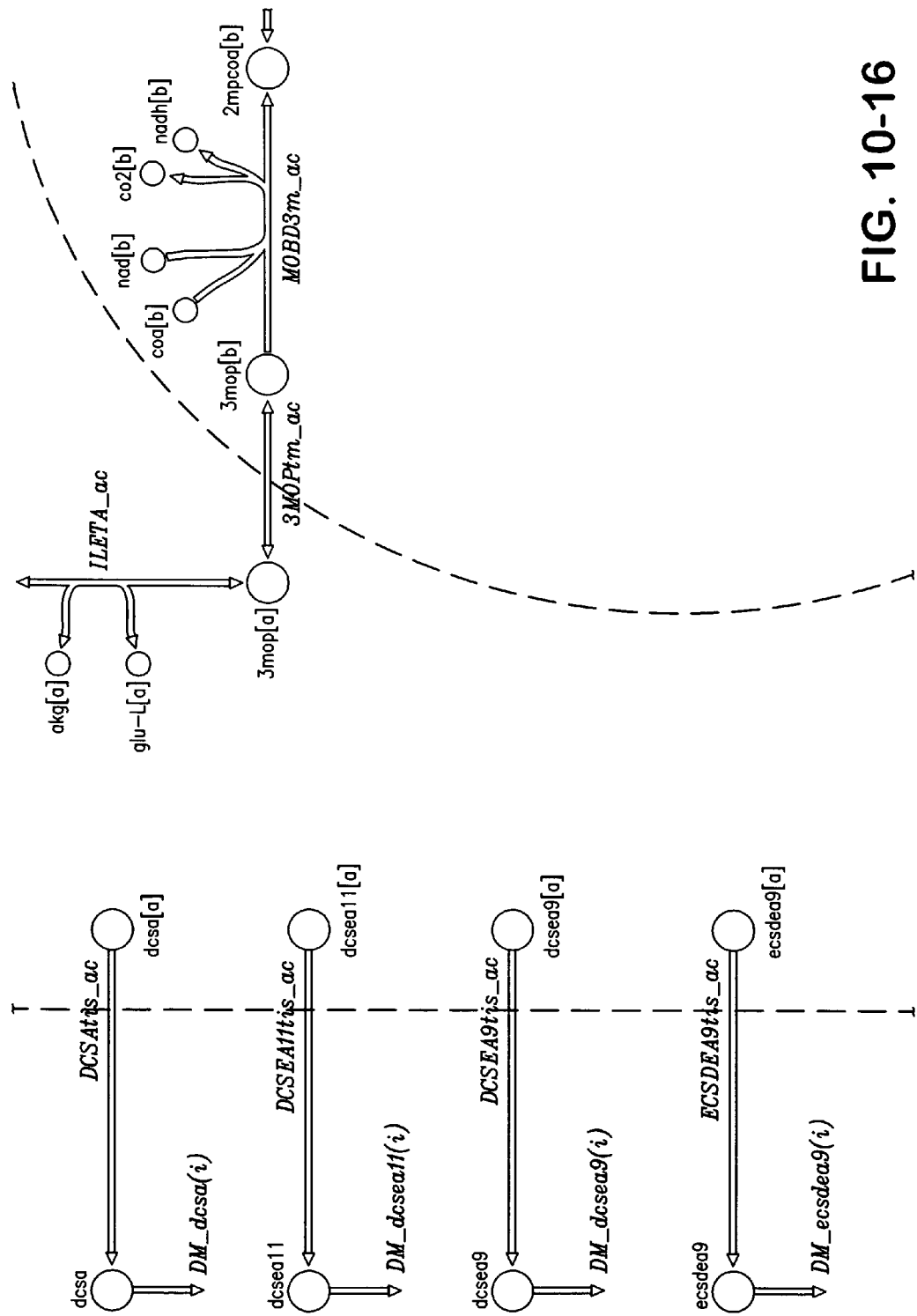
Figures 10, 11, 12, 13, 14, 15, 16, 17:
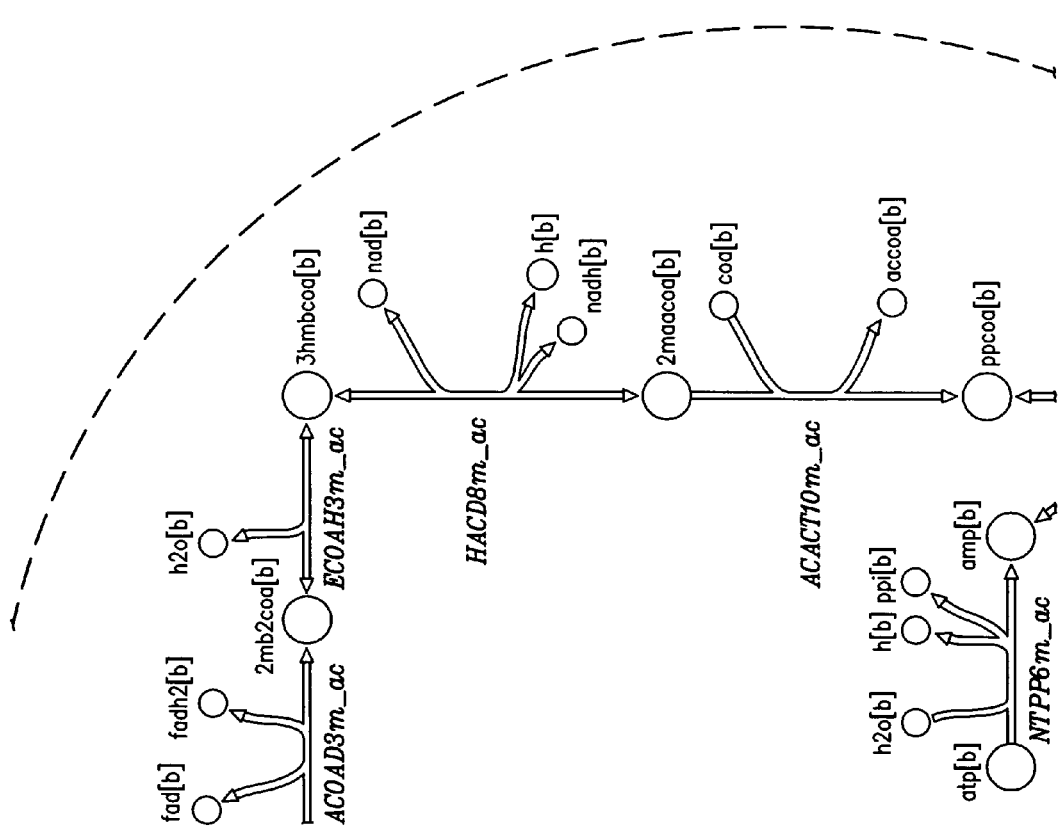
Figures 10, 11, 12, 13, 14, 15, 16, 17, 18:
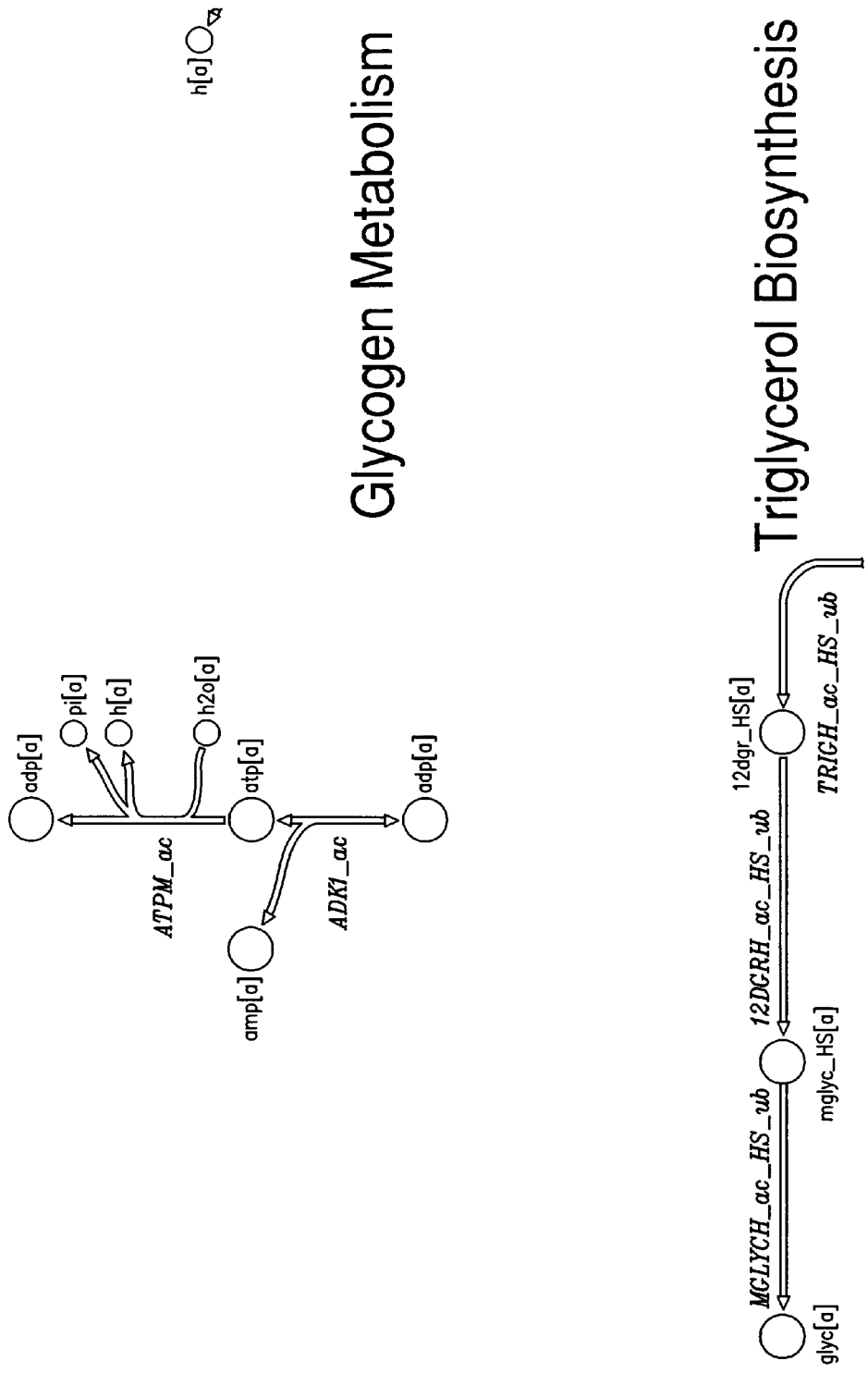
Figures 10, 11, 12, 13, 14, 15, 16, 17, 18, 19:
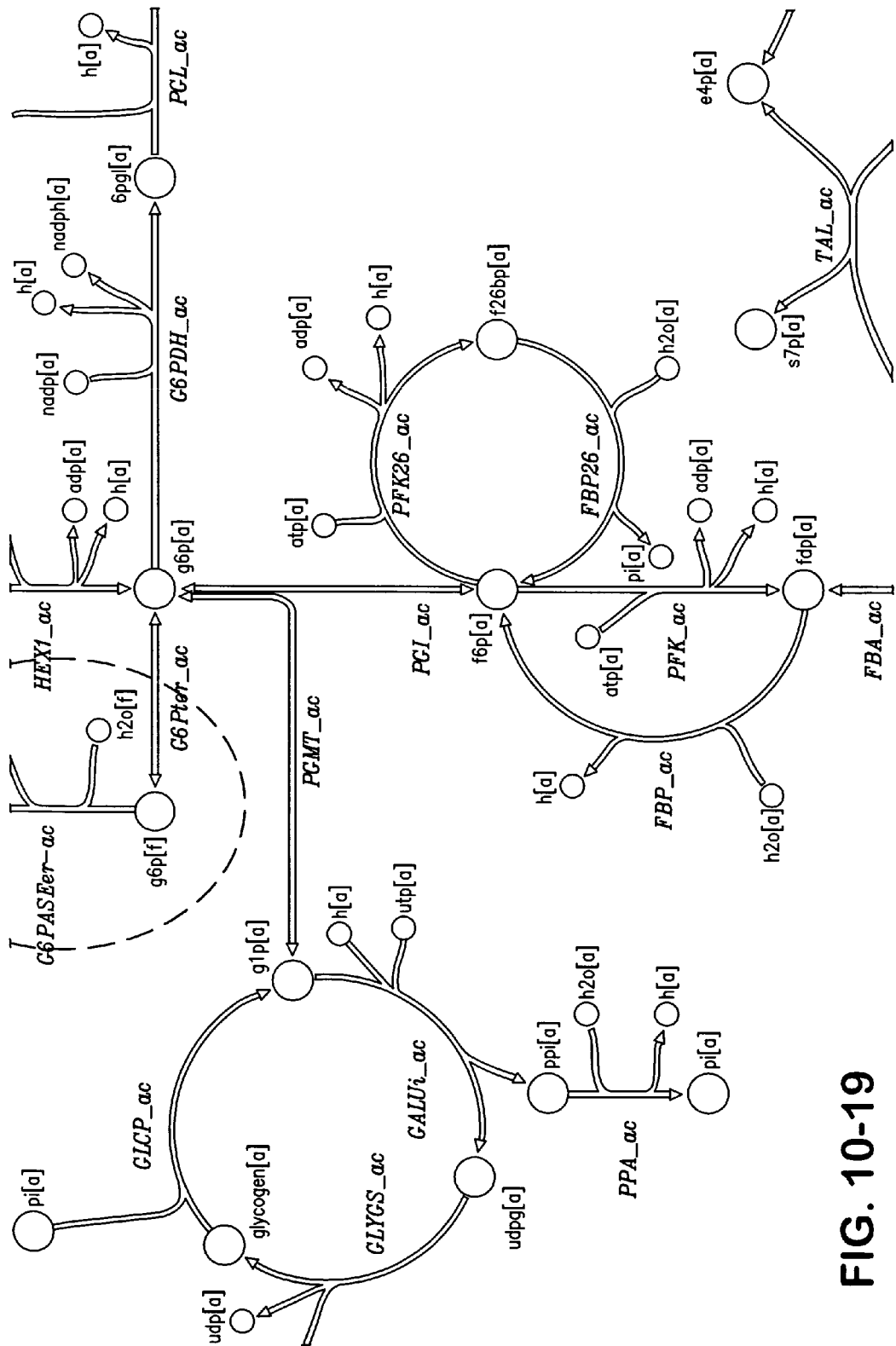
Figures 10, 11, 12, 13, 14, 15, 16, 17, 18, 19, 20:
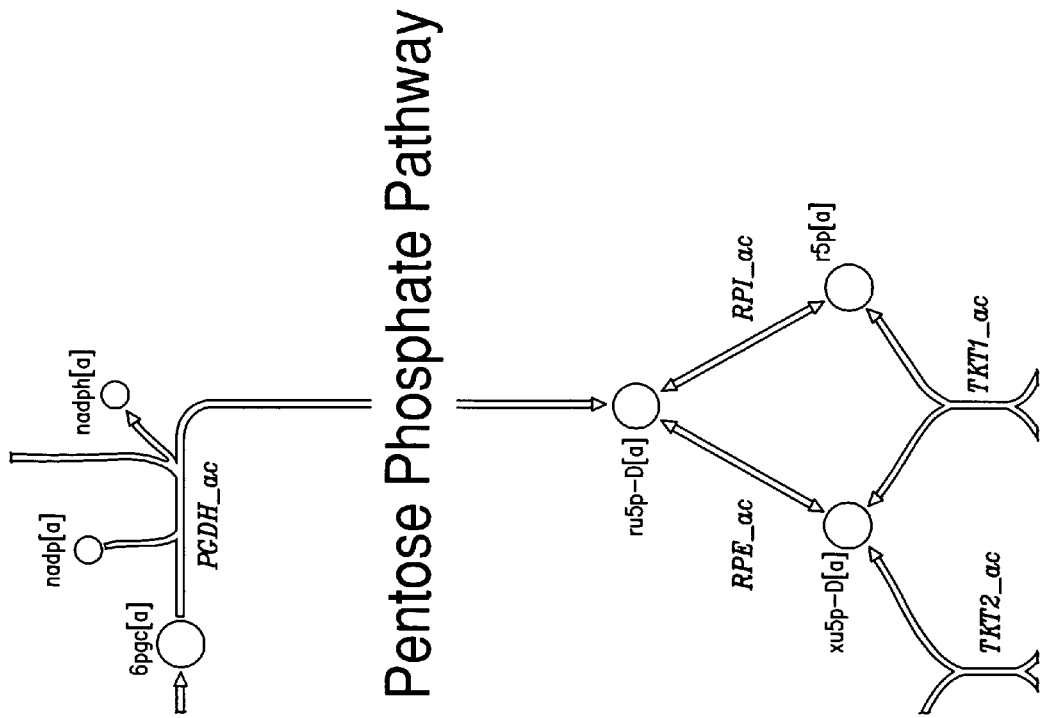
Figures 10, 11, 12, 13, 14, 15, 16, 17, 18, 19, 20, 21:
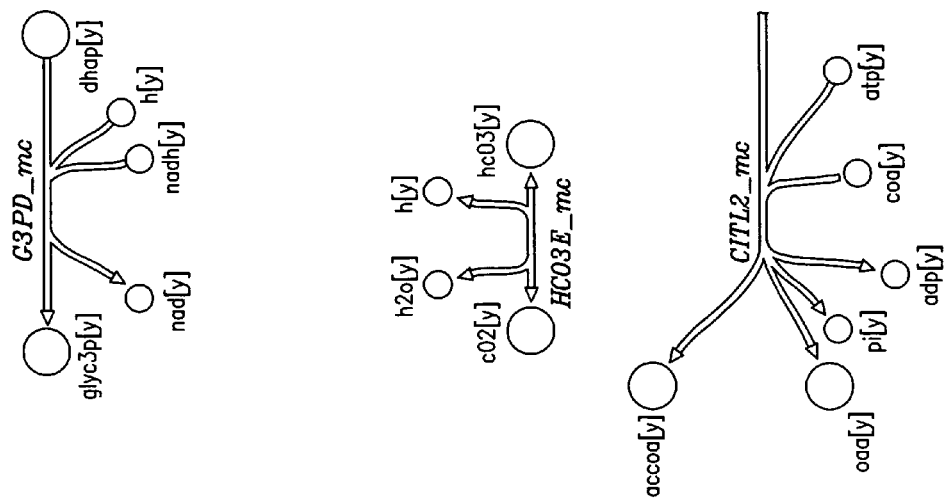
Figures 10, 11, 12, 13, 14, 15, 16, 17, 18, 19, 20, 21, 22:
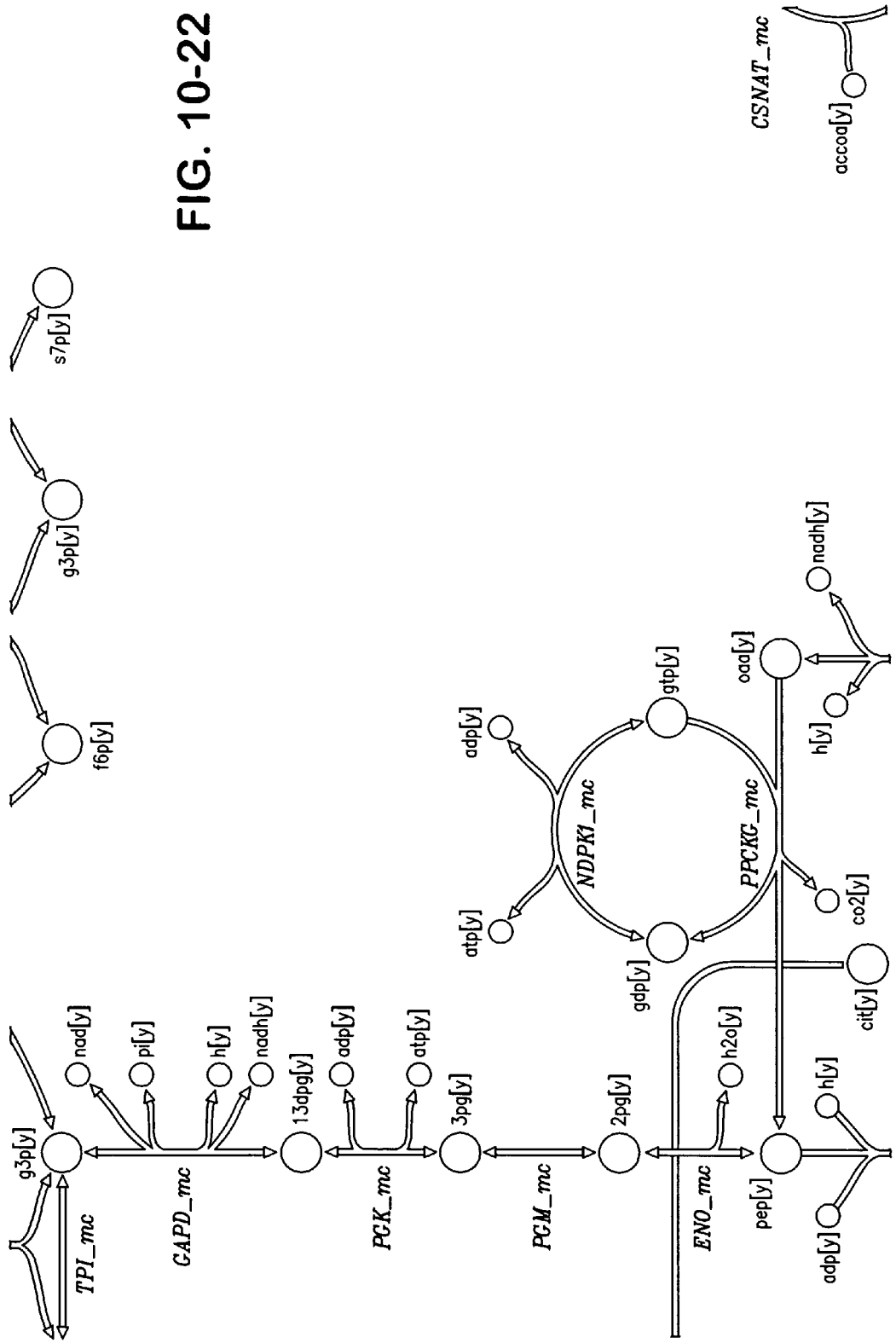
Figures 10, 11, 12, 13, 14, 15, 16, 17, 18, 19, 20, 21, 22, 23:
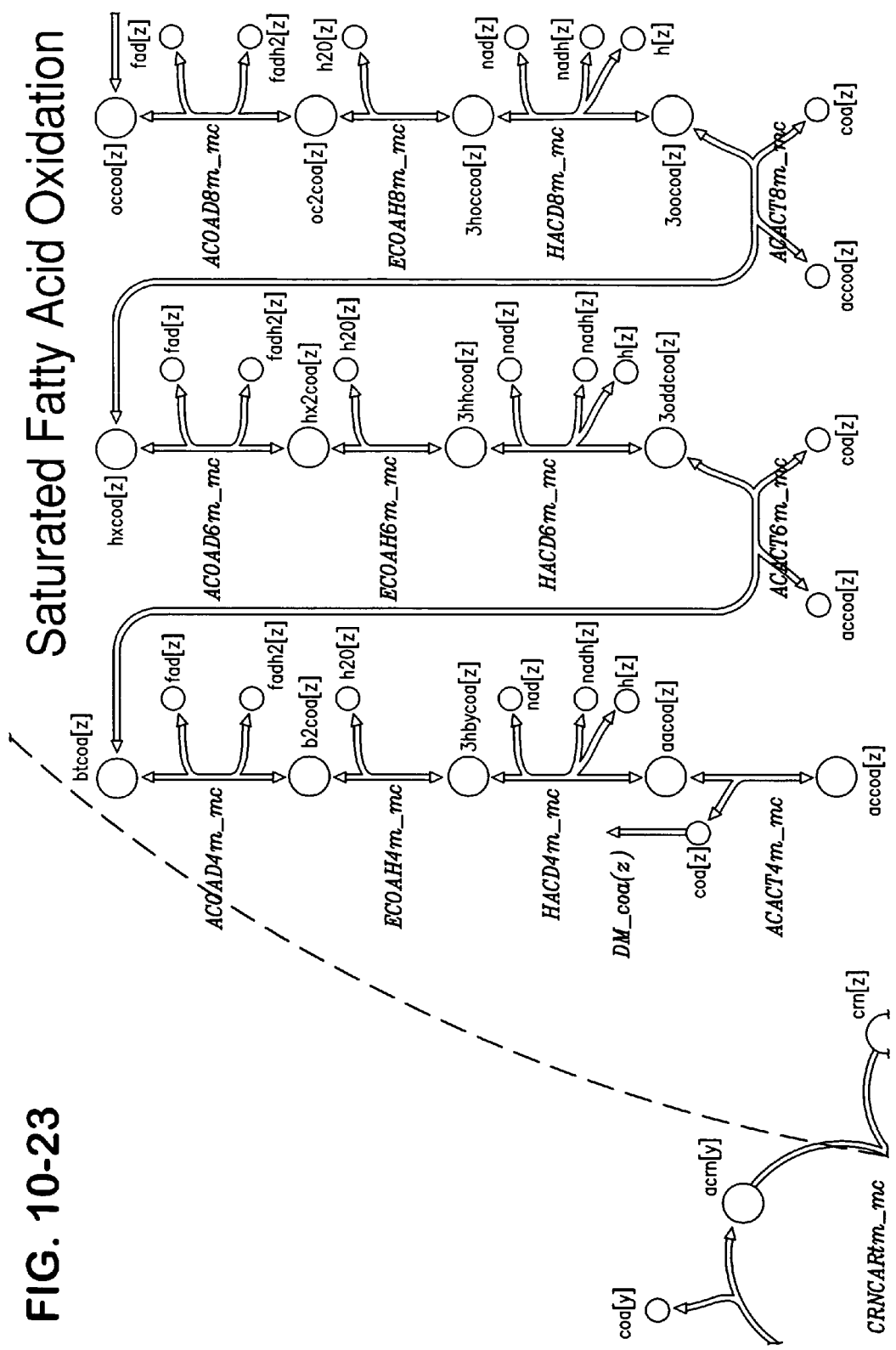
Figures 10, 11, 12, 13, 14, 15, 16, 17, 18, 19, 20, 21, 22, 23, 24:
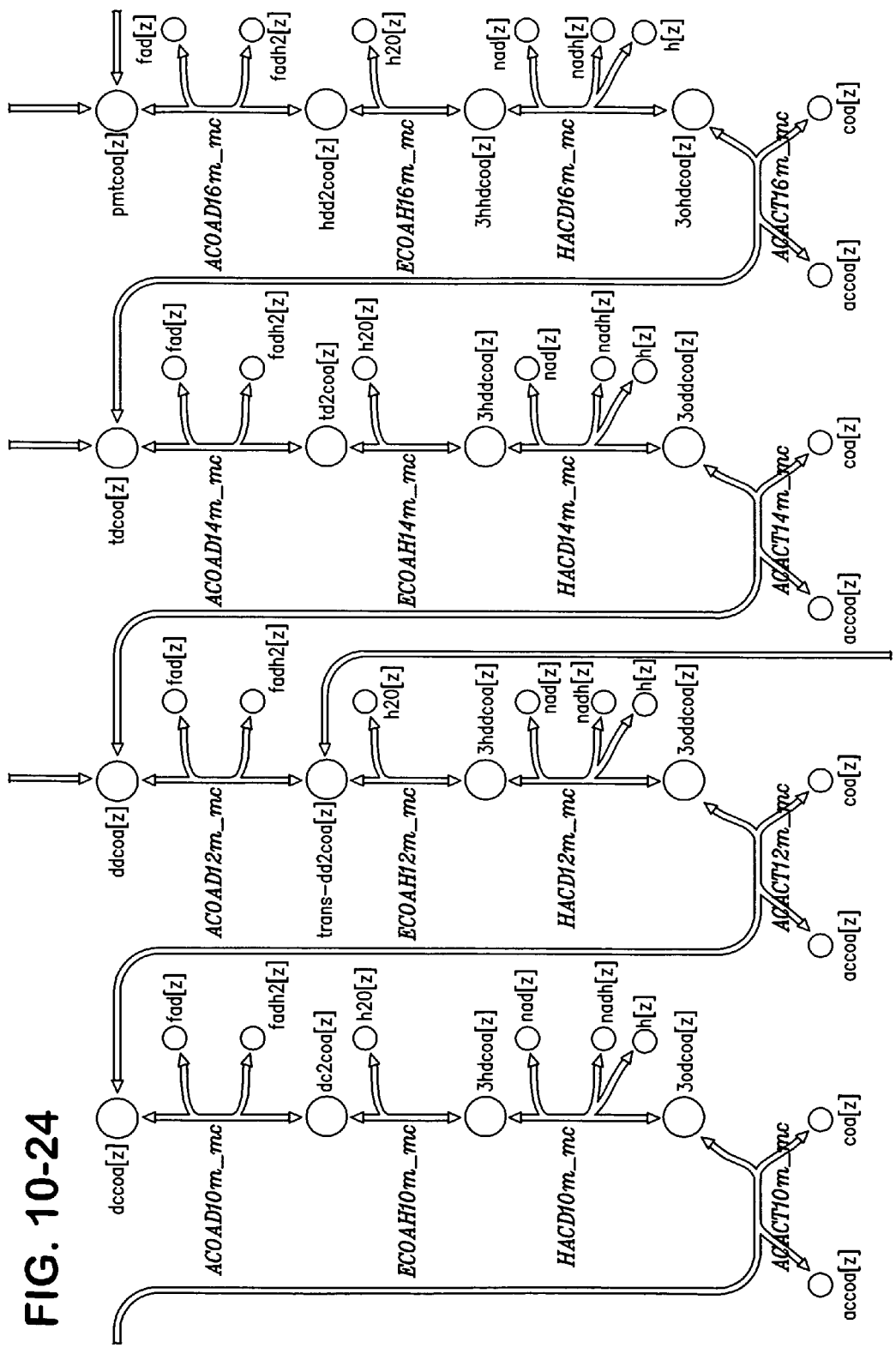
Figures 10, 11, 12, 13, 14, 15, 16, 17, 18, 19, 20, 21, 22, 23, 24, 25:
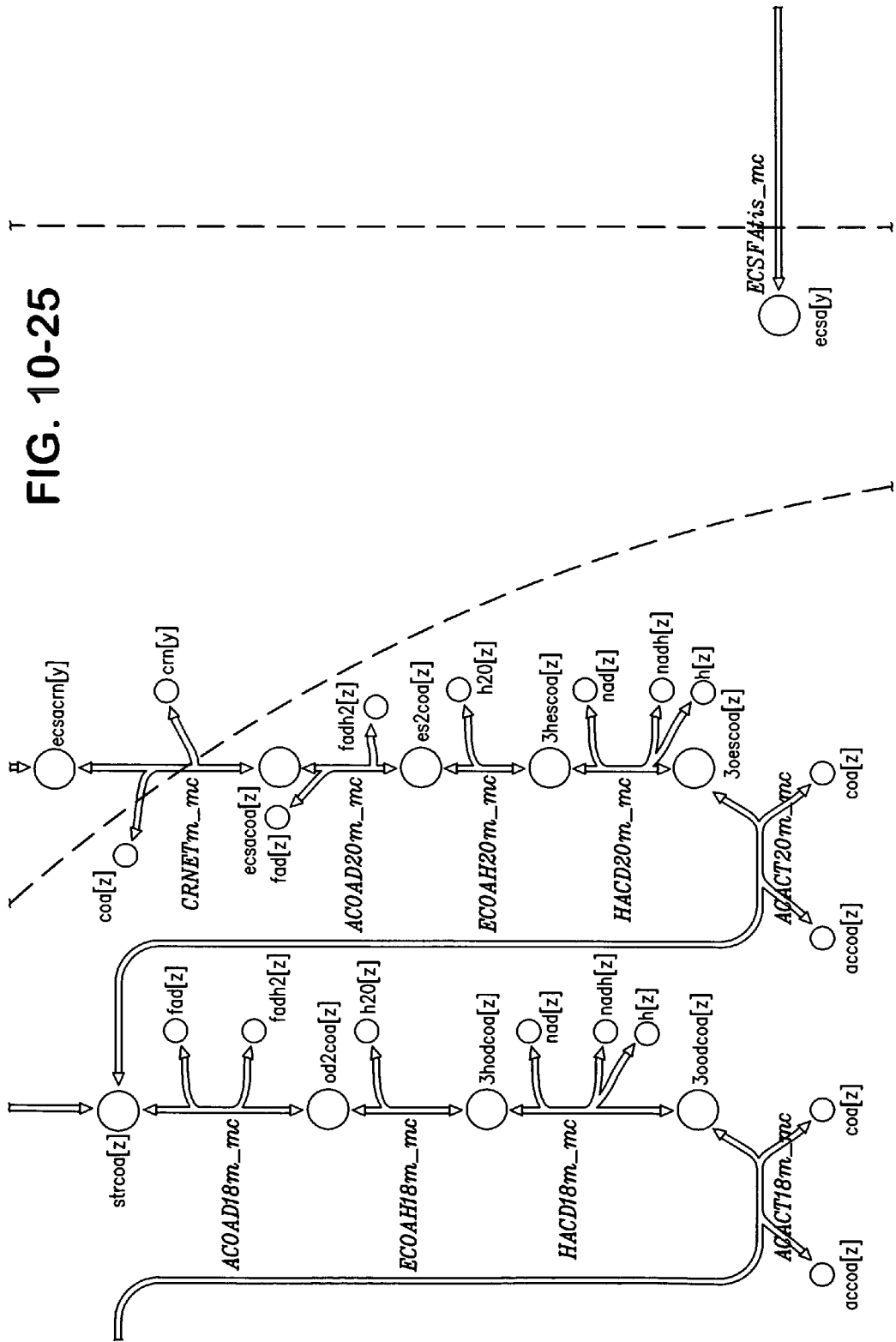
Figures 10, 11, 12, 13, 14, 15, 16, 17, 18, 19, 20, 21, 22, 23, 24, 25, 26:
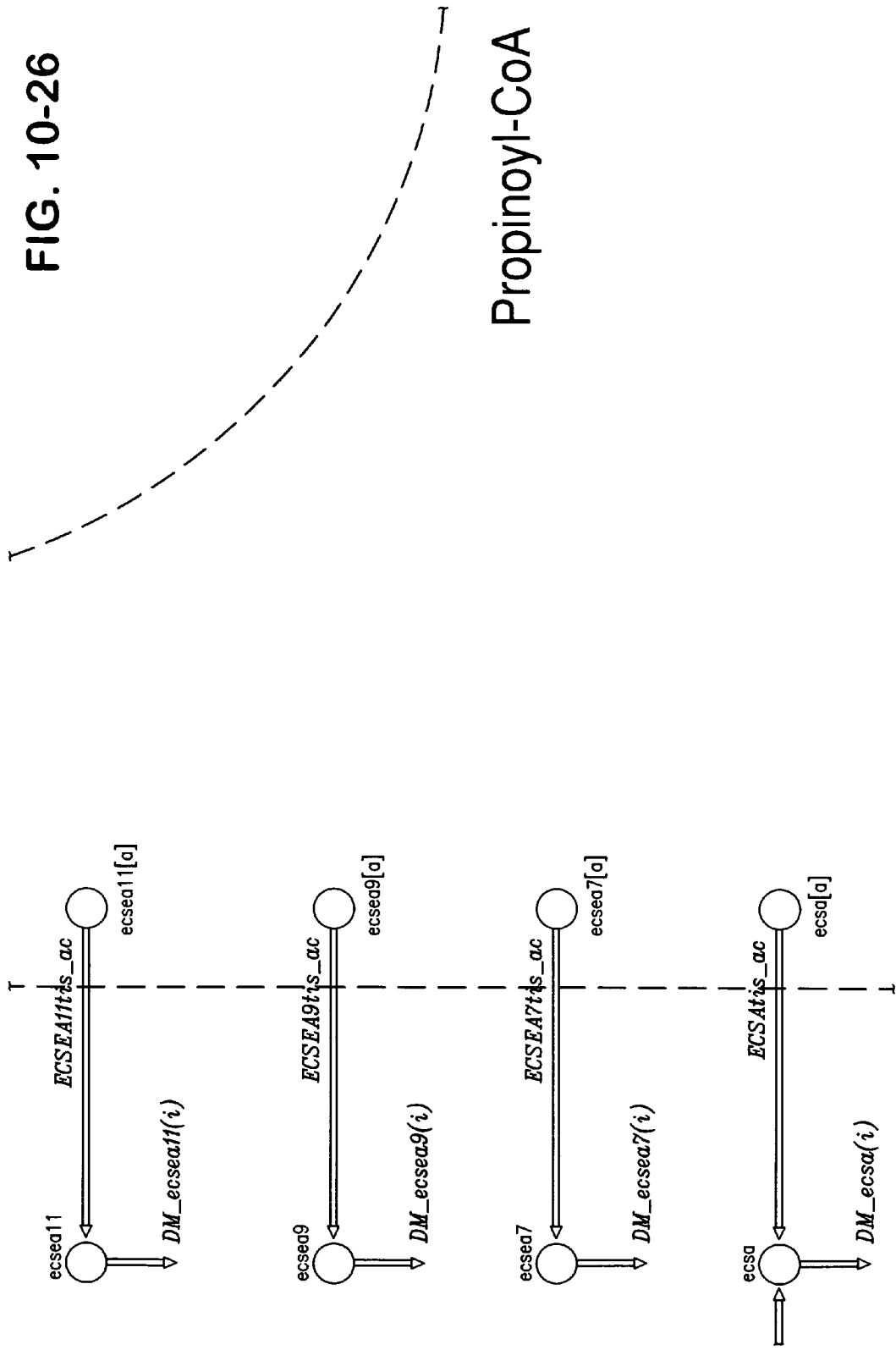
Figures 10, 11, 12, 13, 14, 15, 16, 17, 18, 19, 20, 21, 22, 23, 24, 25, 26, 27:
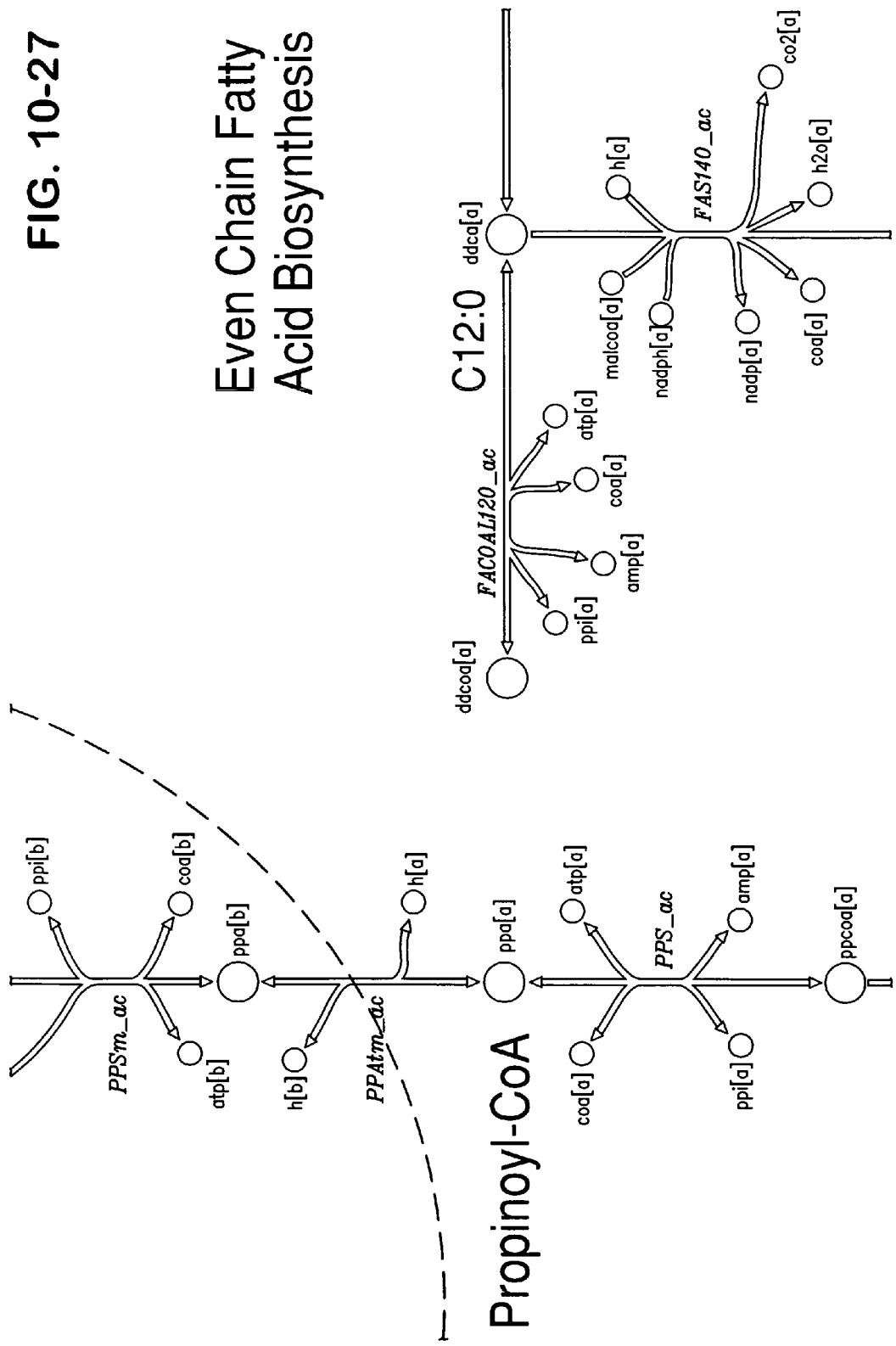
Figures 10, 11, 12, 13, 14, 15, 16, 17, 18, 19, 20, 21, 22, 23, 24, 25, 26, 27, 28:
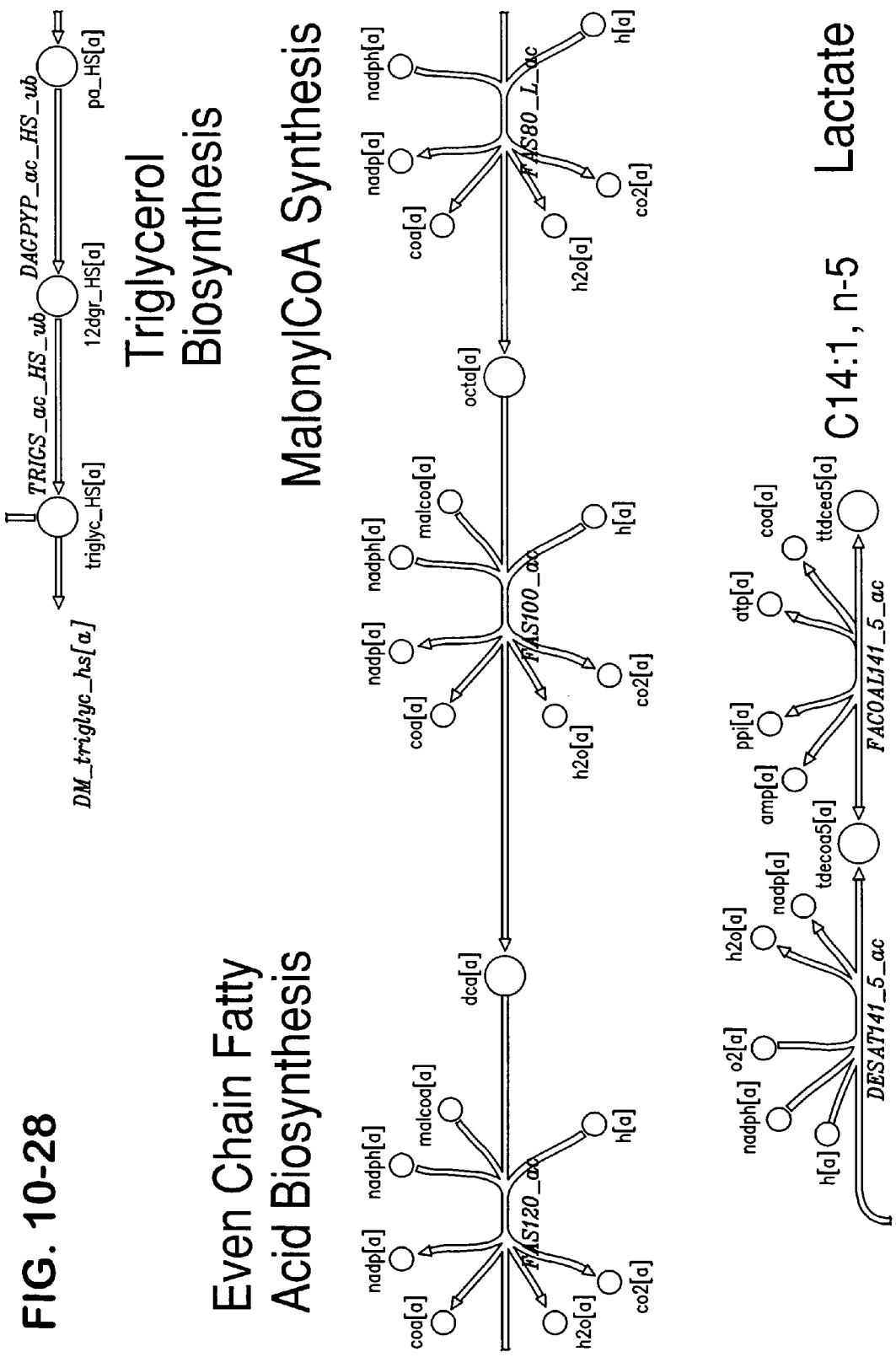
Figures 10, 11, 12, 13, 14, 15, 16, 17, 18, 19, 20, 21, 22, 23, 24, 25, 26, 27, 28, 29:
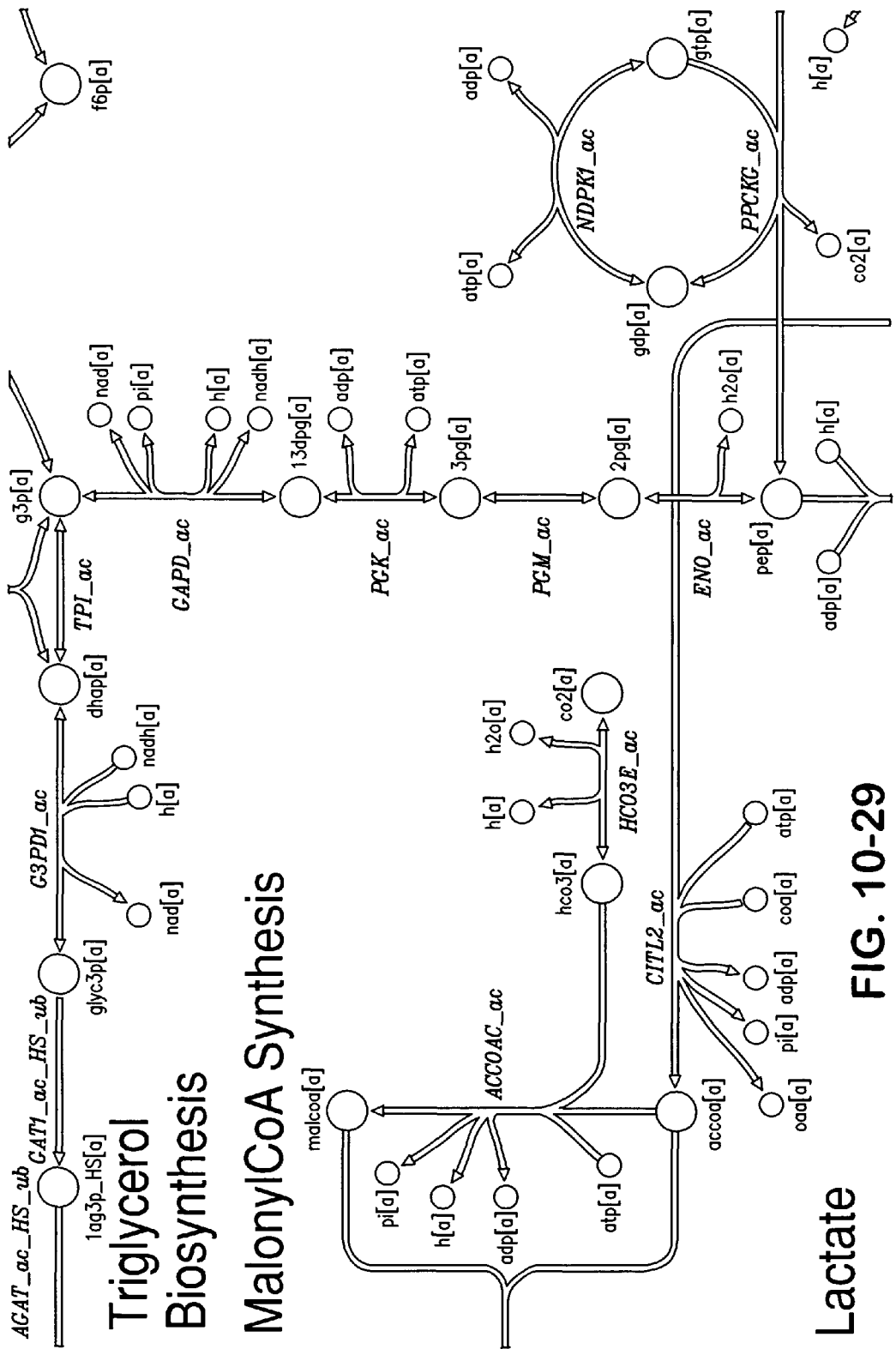
Figures 10, 11, 12, 13, 14, 15, 16, 17, 18, 19, 20, 21, 22, 23, 24, 25, 26, 27, 28, 29, 30:
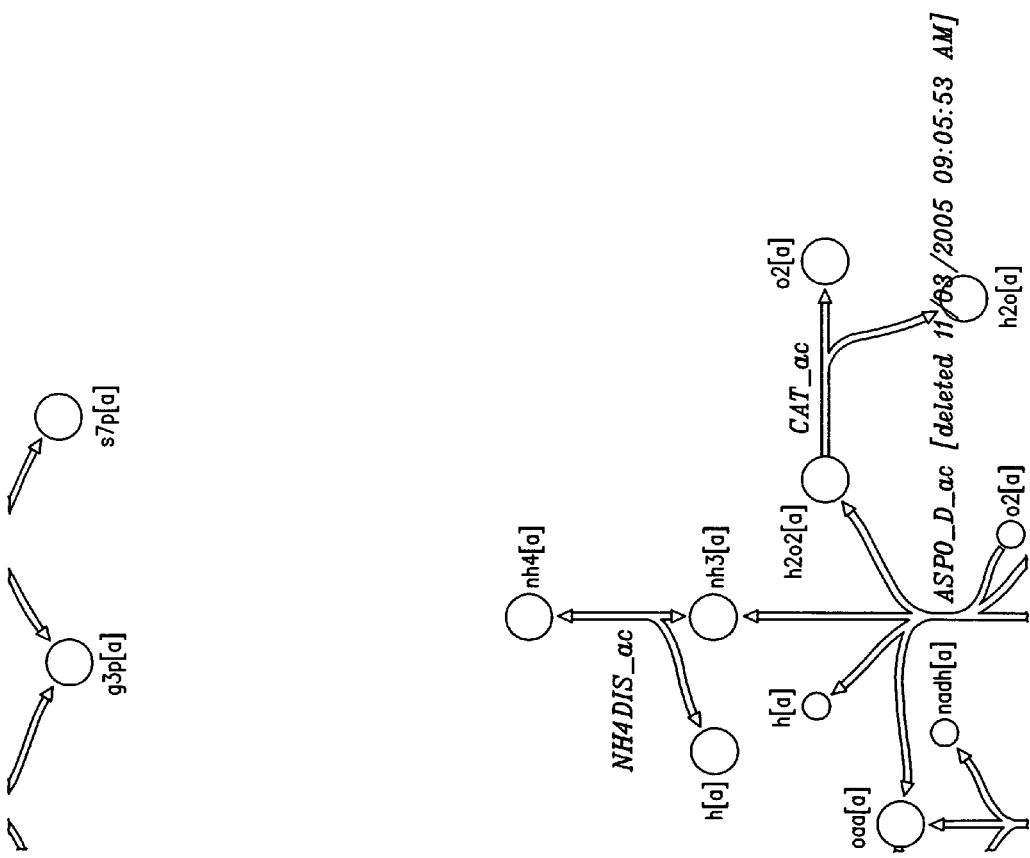
Figures 10, 11, 12, 13, 14, 15, 16, 17, 18, 19, 20, 21, 22, 23, 24, 25, 26, 27, 28, 29, 30, 31:
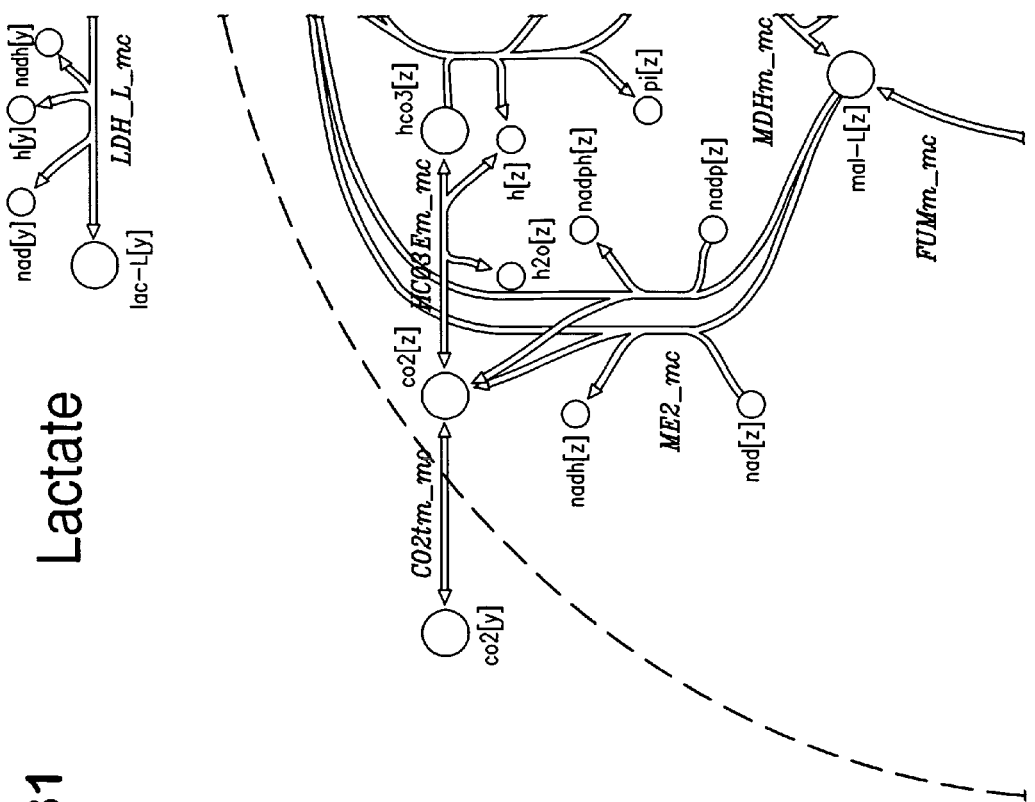
Figures 10, 11, 12, 13, 14, 15, 16, 17, 18, 19, 20, 21, 22, 23, 24, 25, 26, 27, 28, 29, 30, 31, 32:
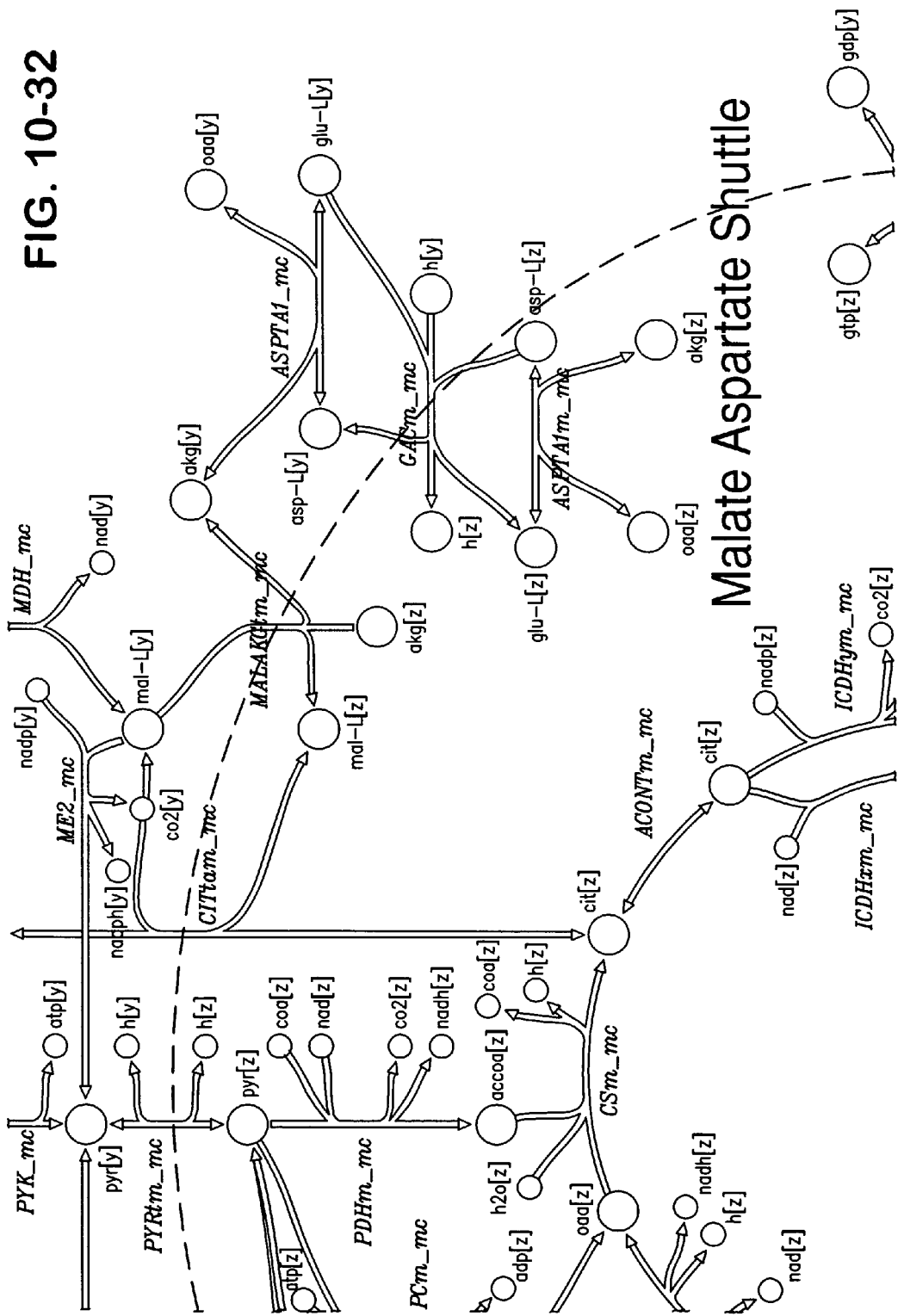
Figures 10, 11, 12, 13, 14, 15, 16, 17, 18, 19, 20, 21, 22, 23, 24, 25, 26, 27, 28, 29, 30, 31, 32, 33:
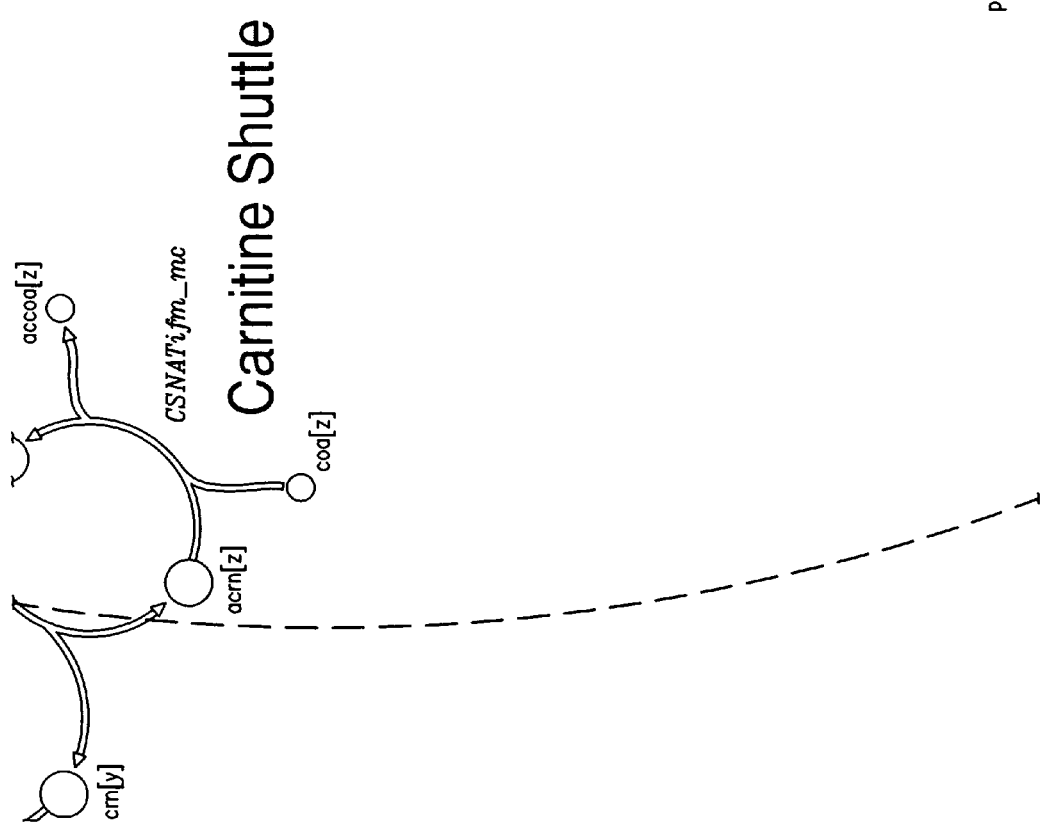
Figures 10, 11, 12, 13, 14, 15, 16, 17, 18, 19, 20, 21, 22, 23, 24, 25, 26, 27, 28, 29, 30, 31, 32, 33, 34:
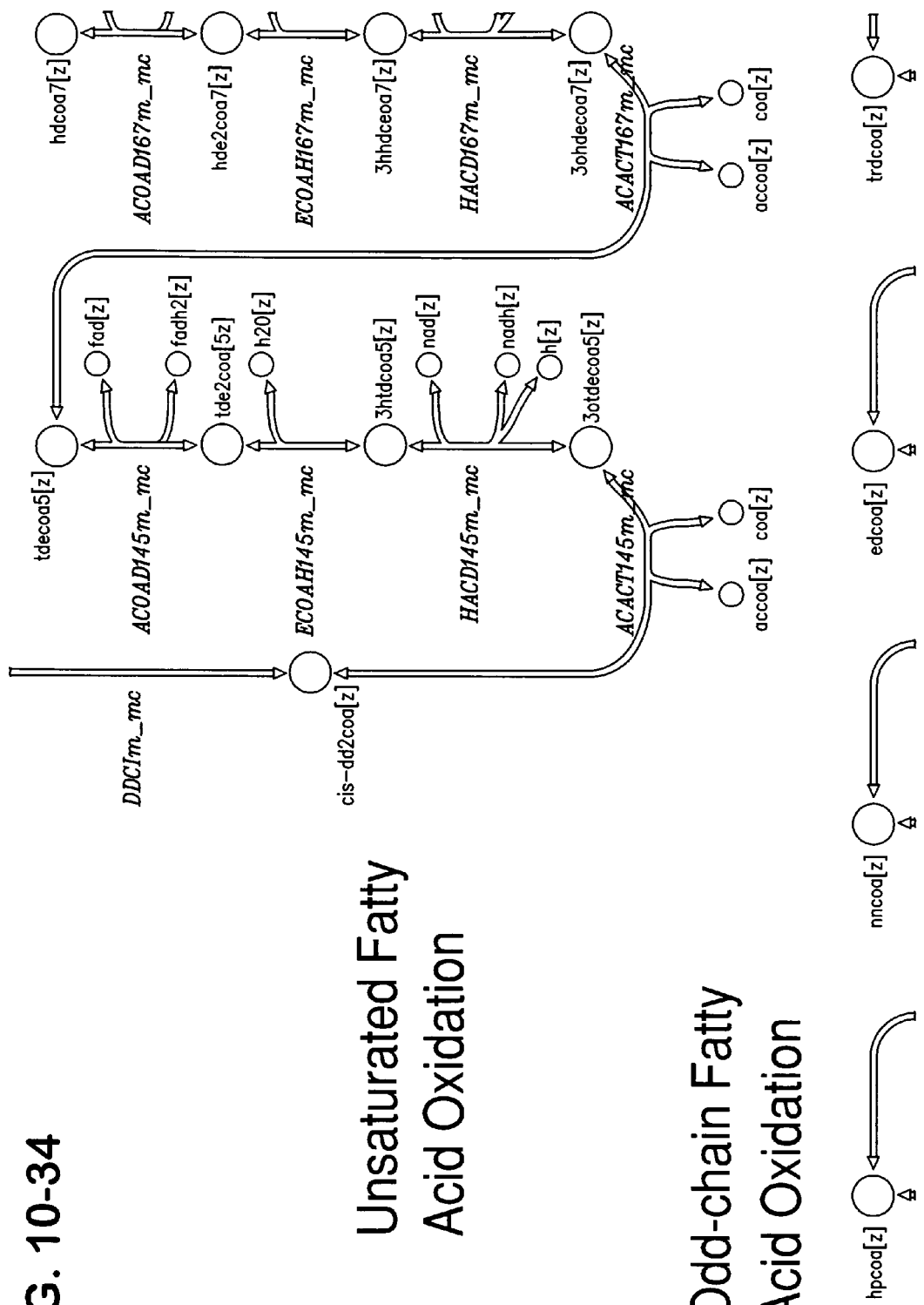
Figures 10, 11, 12, 13, 14, 15, 16, 17, 18, 19, 20, 21, 22, 23, 24, 25, 26, 27, 28, 29, 30, 31, 32, 33, 34, 35:
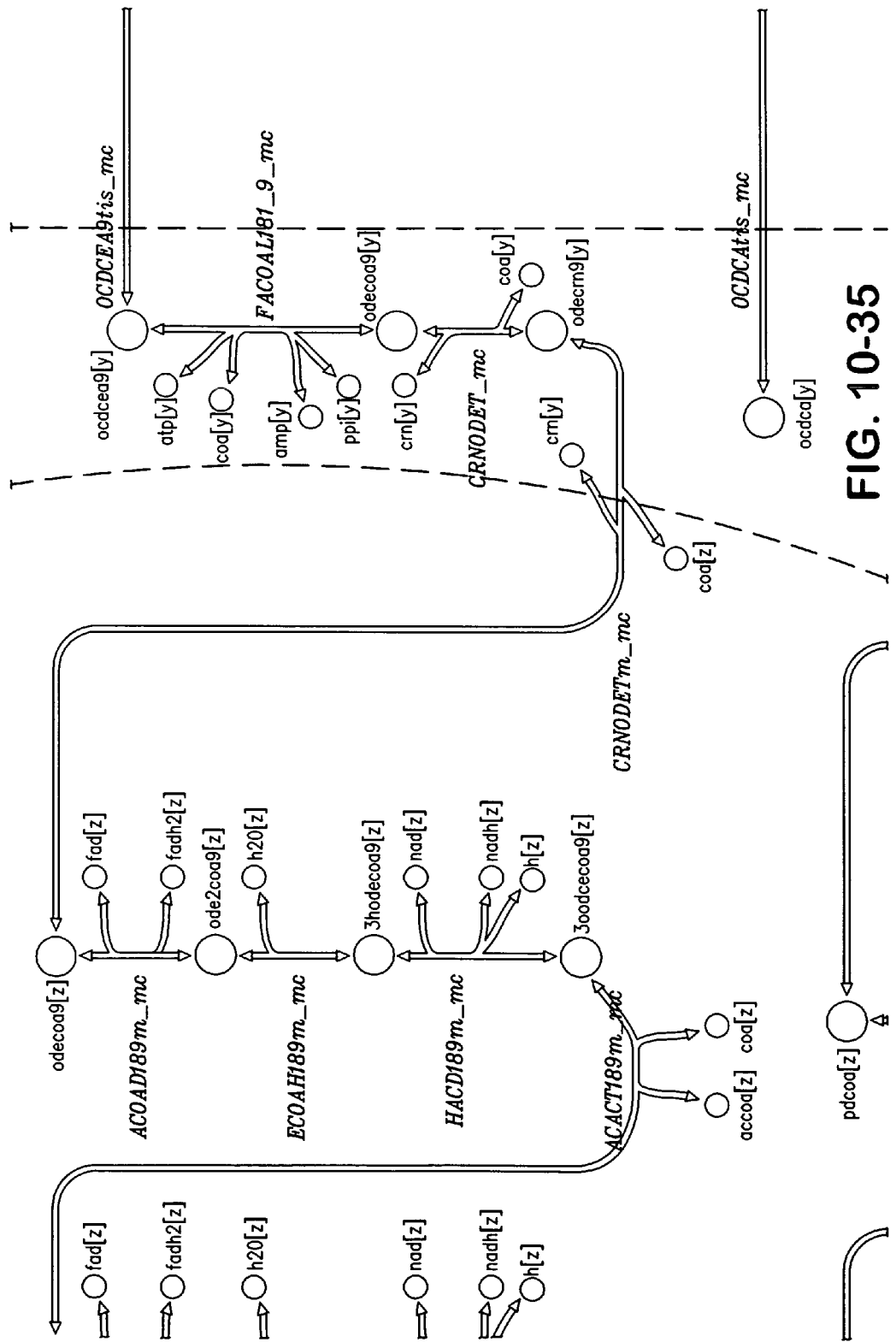
Figures 10, 11, 12, 13, 14, 15, 16, 17, 18, 19, 20, 21, 22, 23, 24, 25, 26, 27, 28, 29, 30, 31, 32, 33, 34, 35, 36:
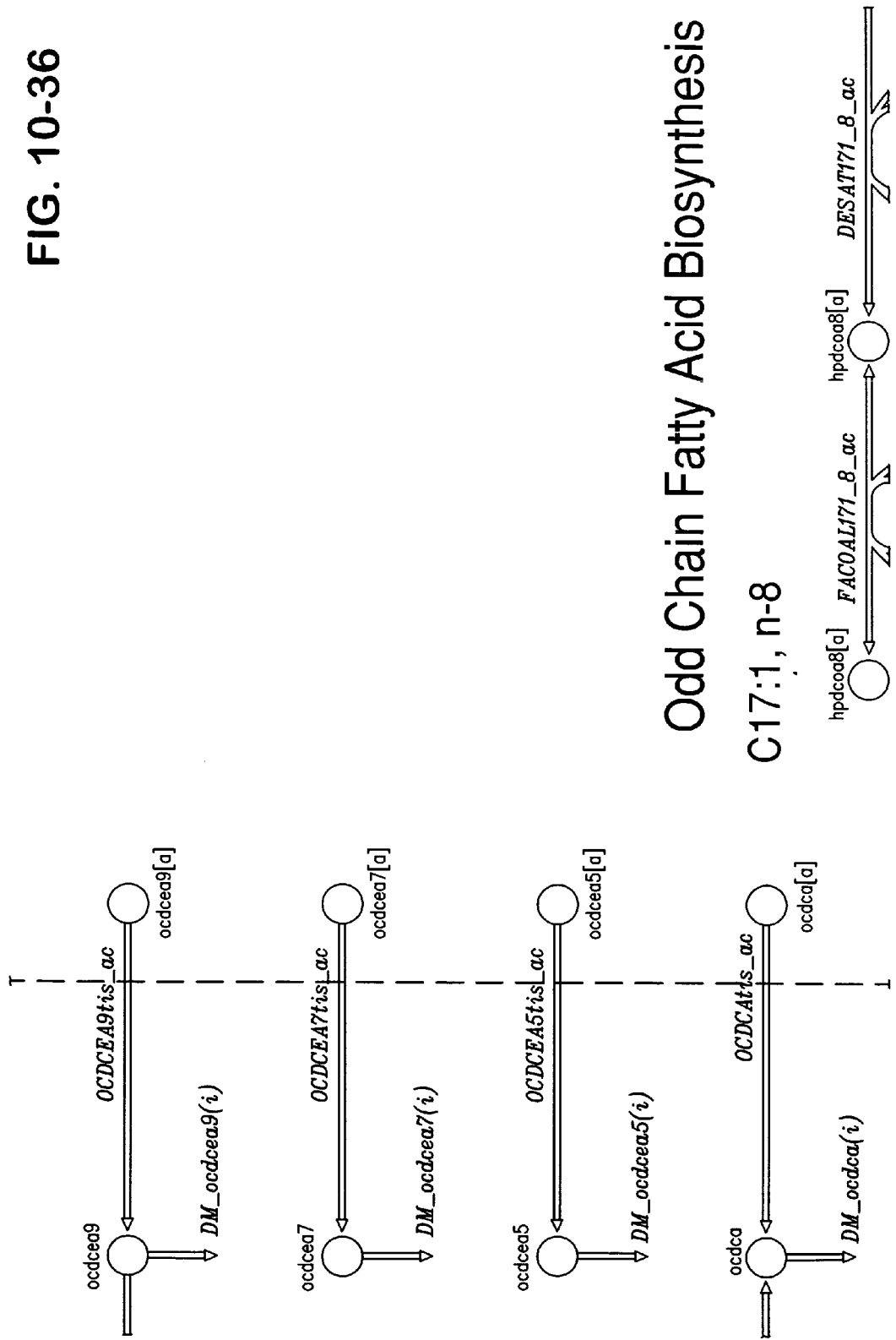
Figures 10, 11, 12, 13, 14, 15, 16, 17, 18, 19, 20, 21, 22, 23, 24, 25, 26, 27, 28, 29, 30, 31, 32, 33, 34, 35, 36, 37:
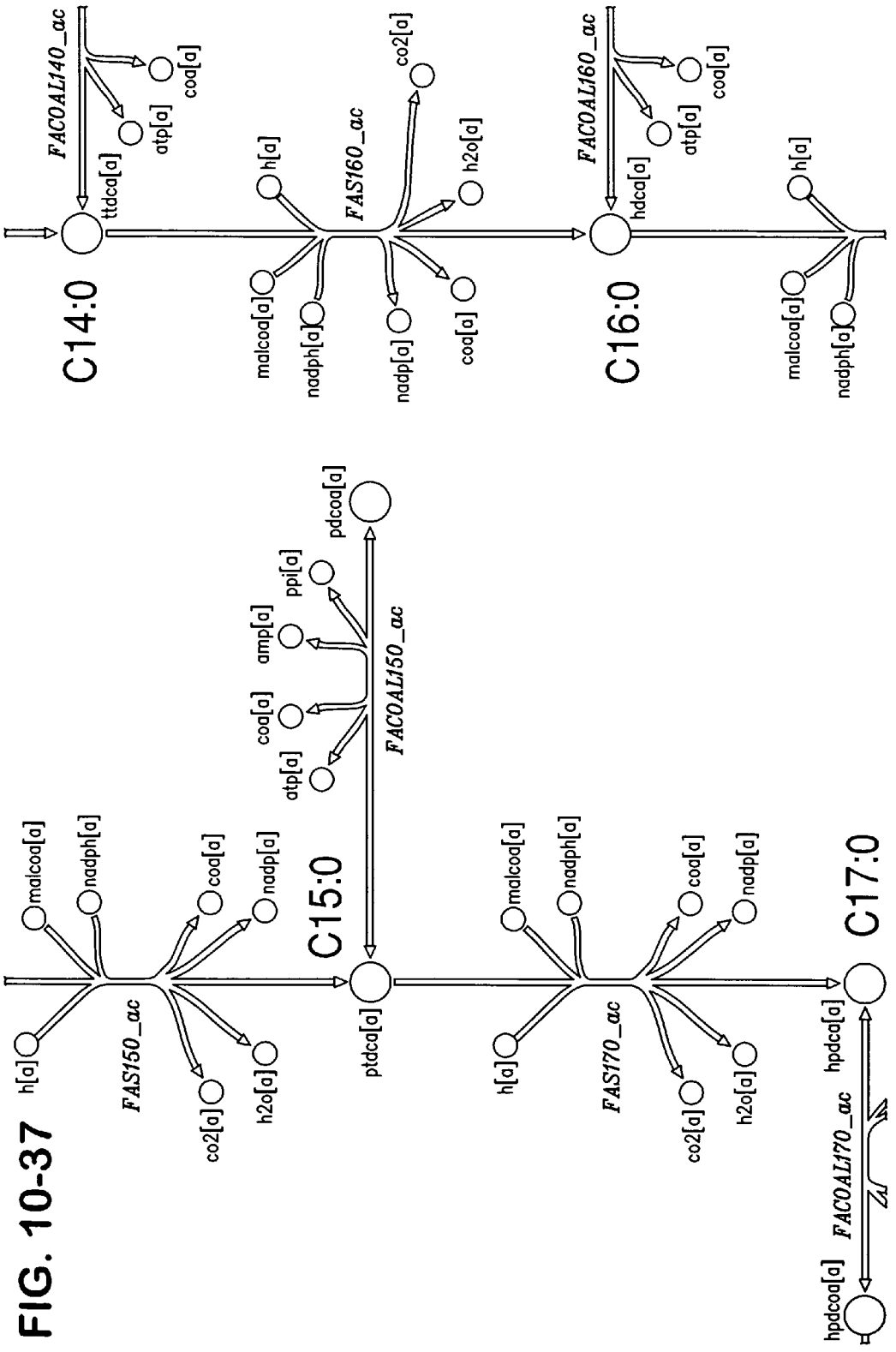
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38:
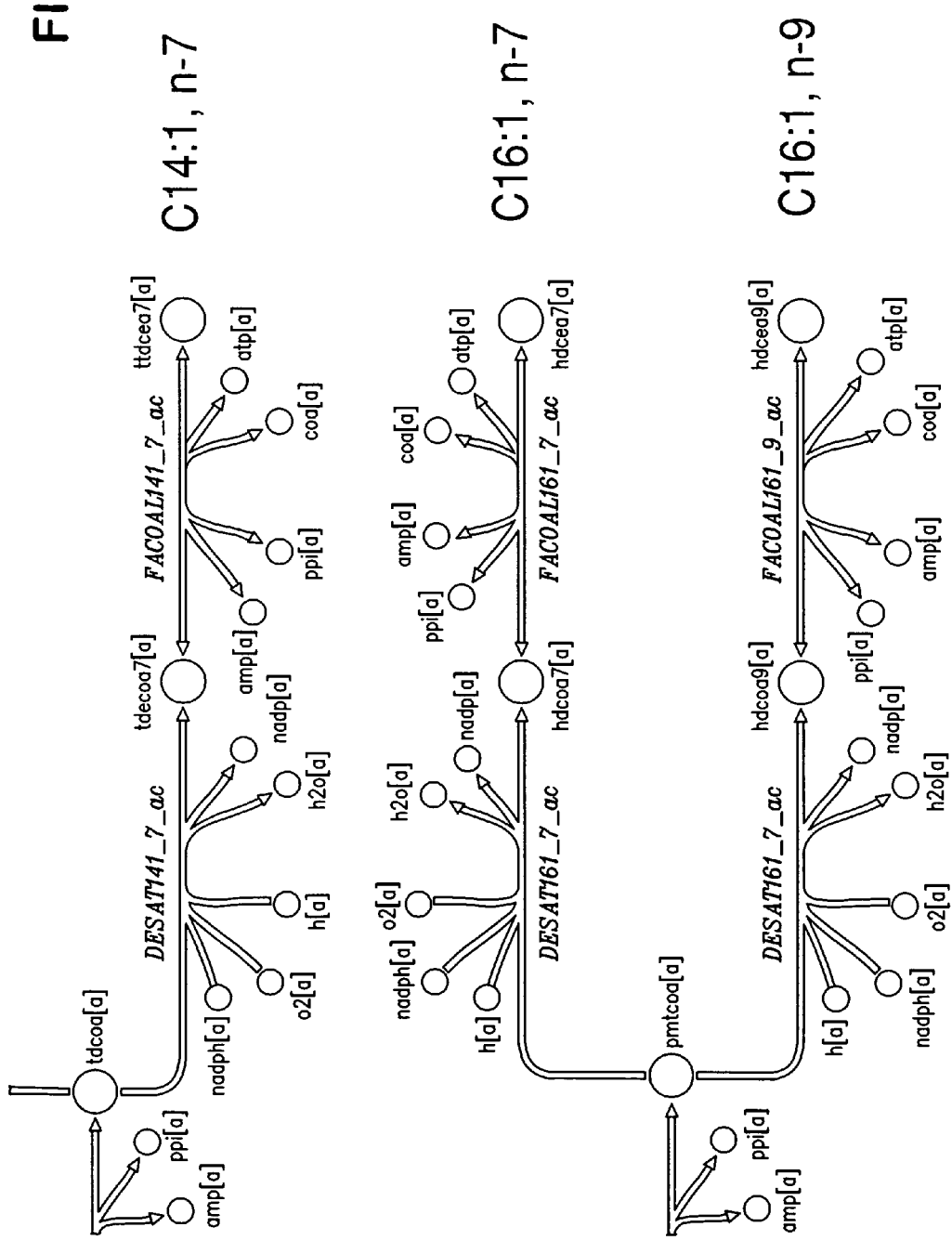
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
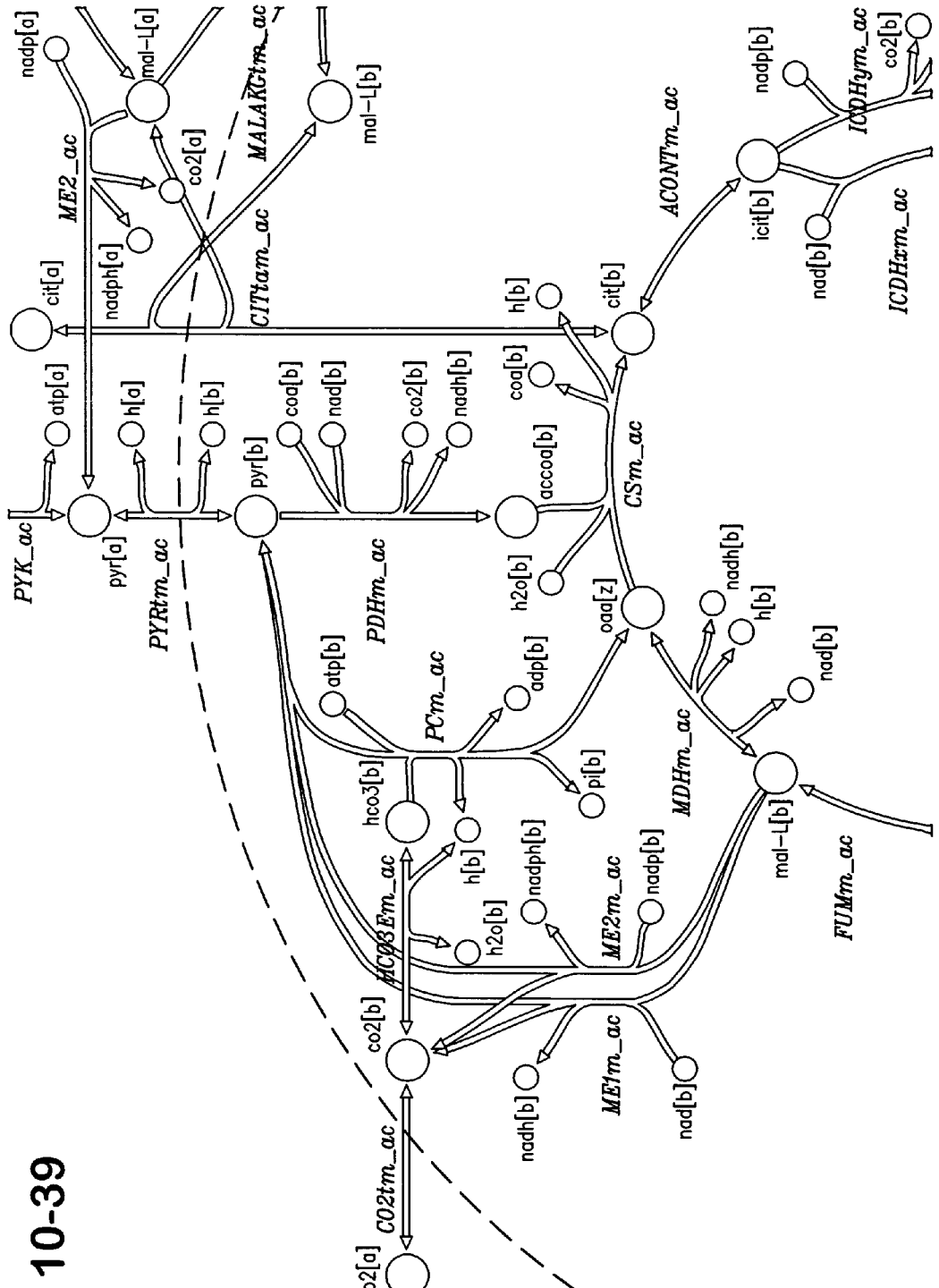
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
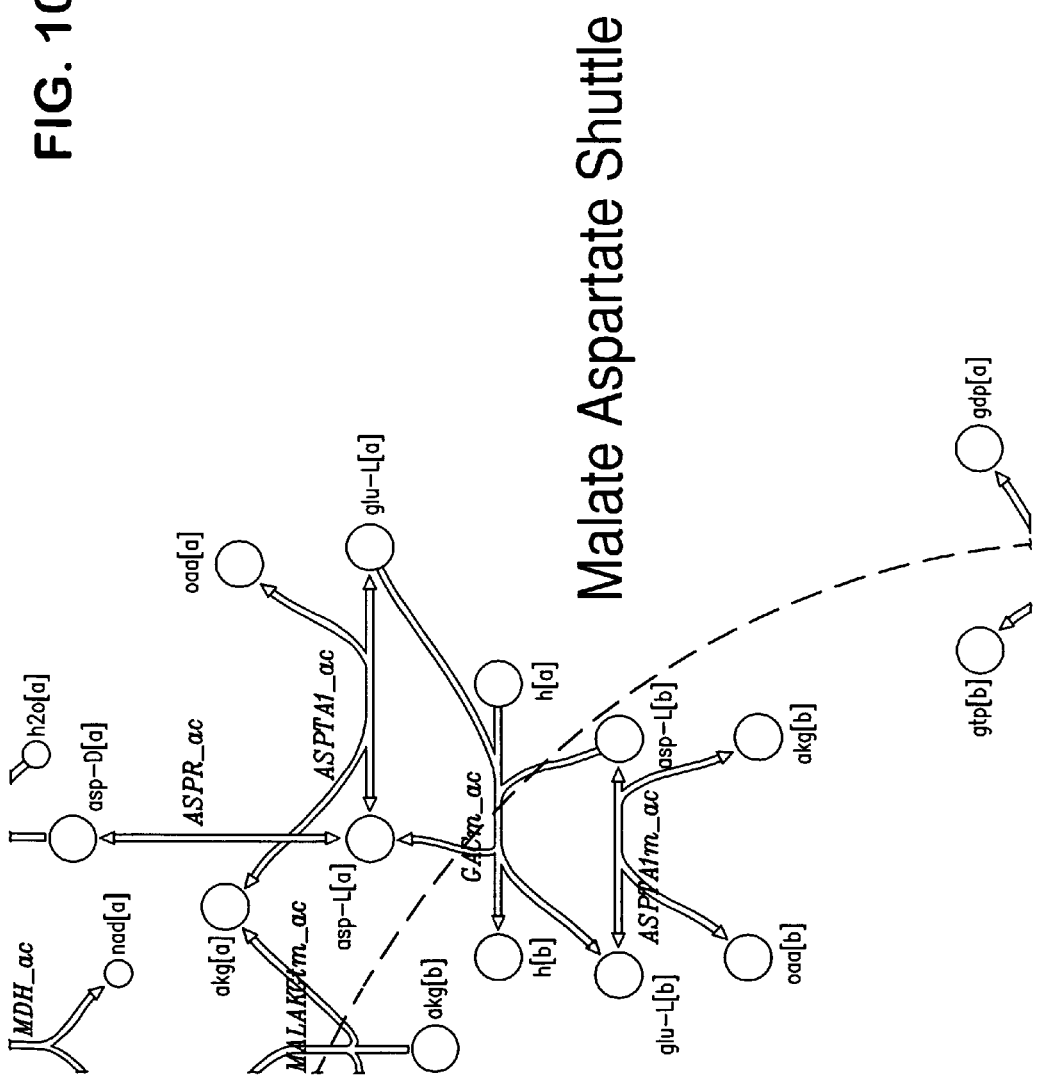
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
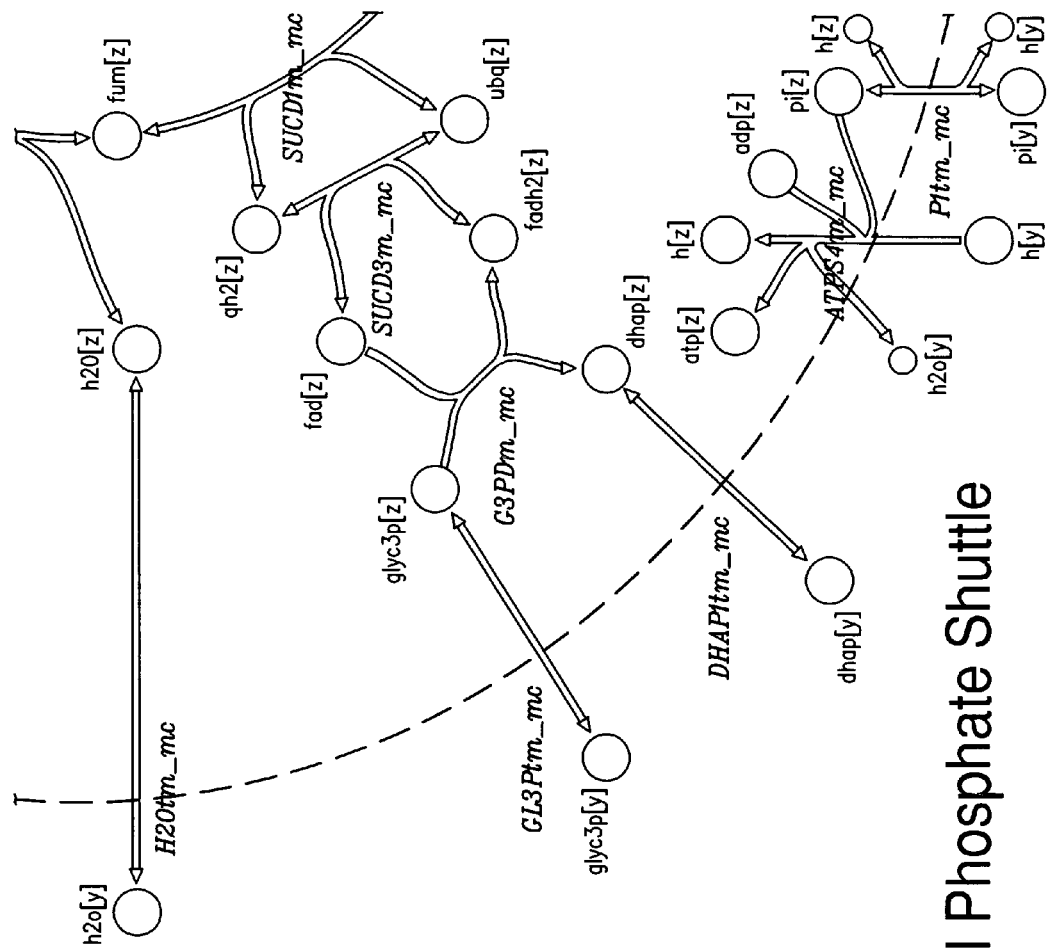
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
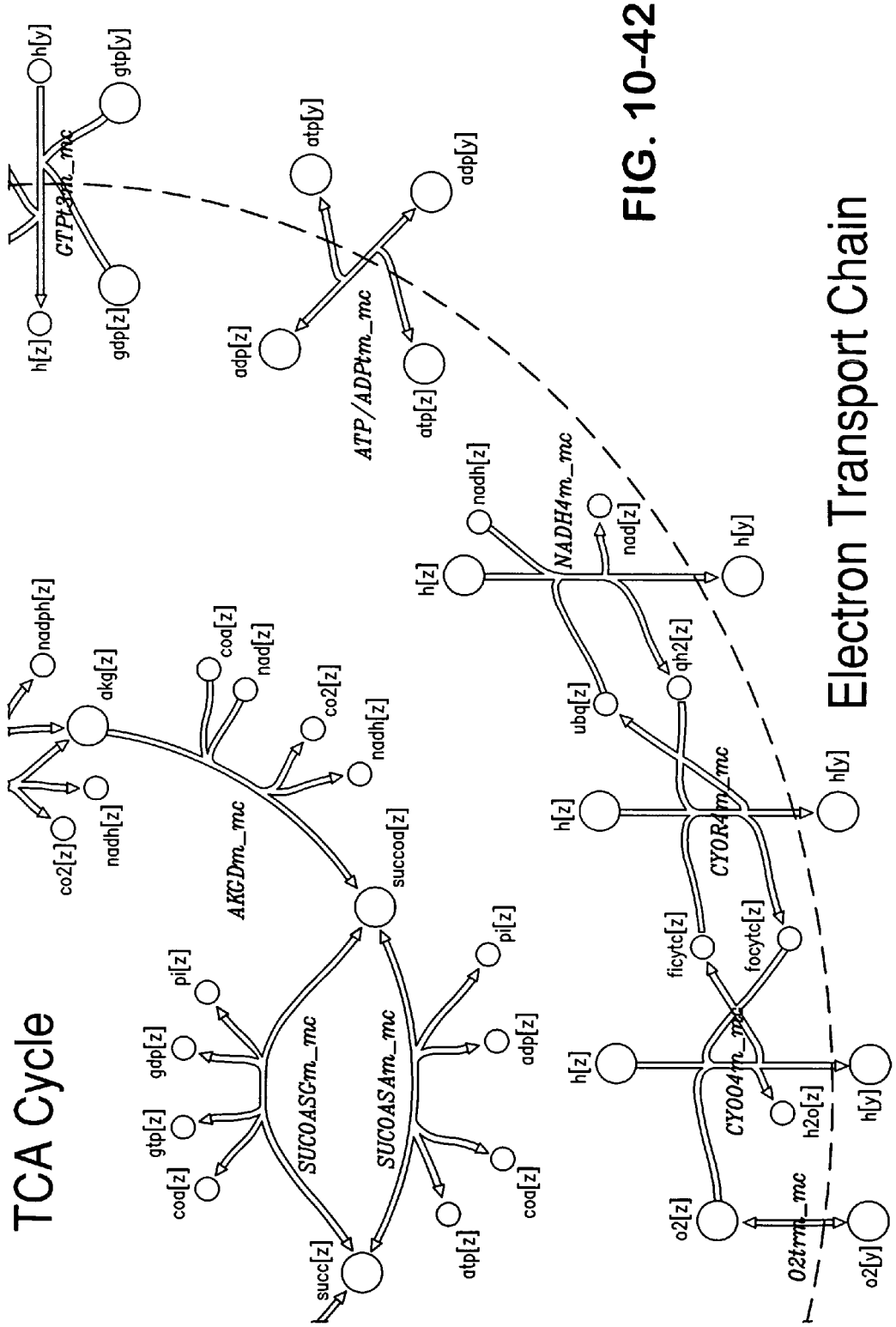
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
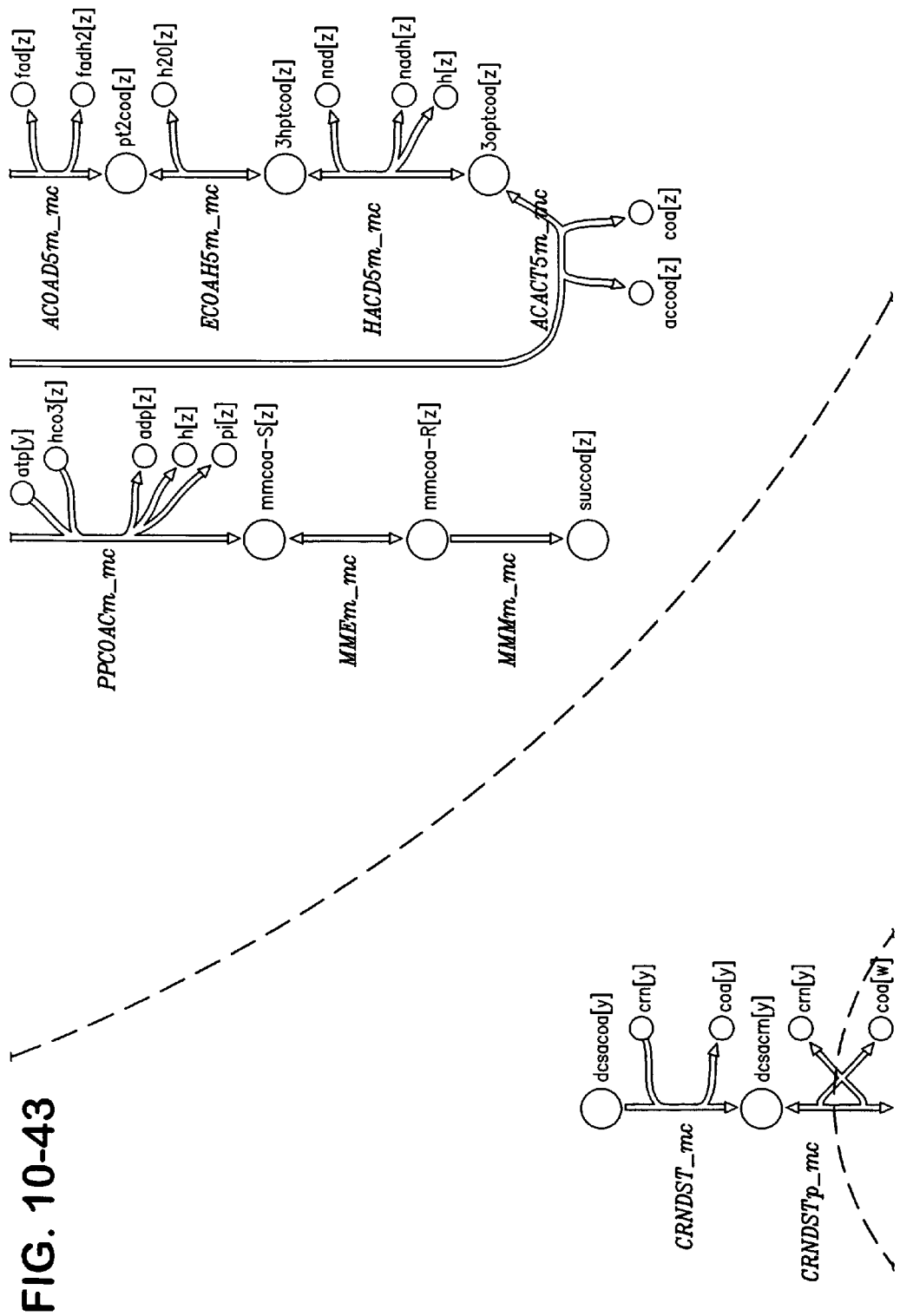
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
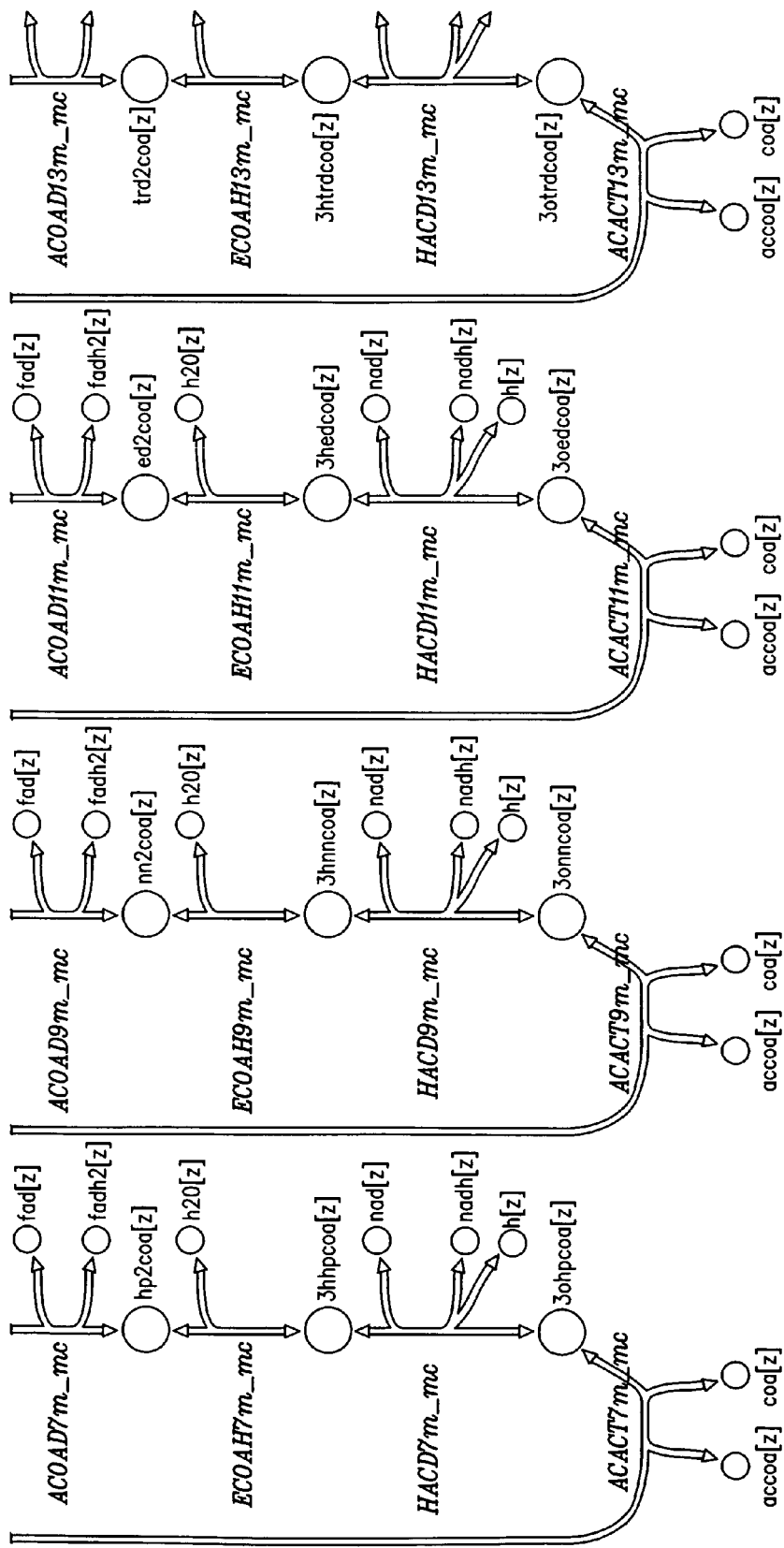
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
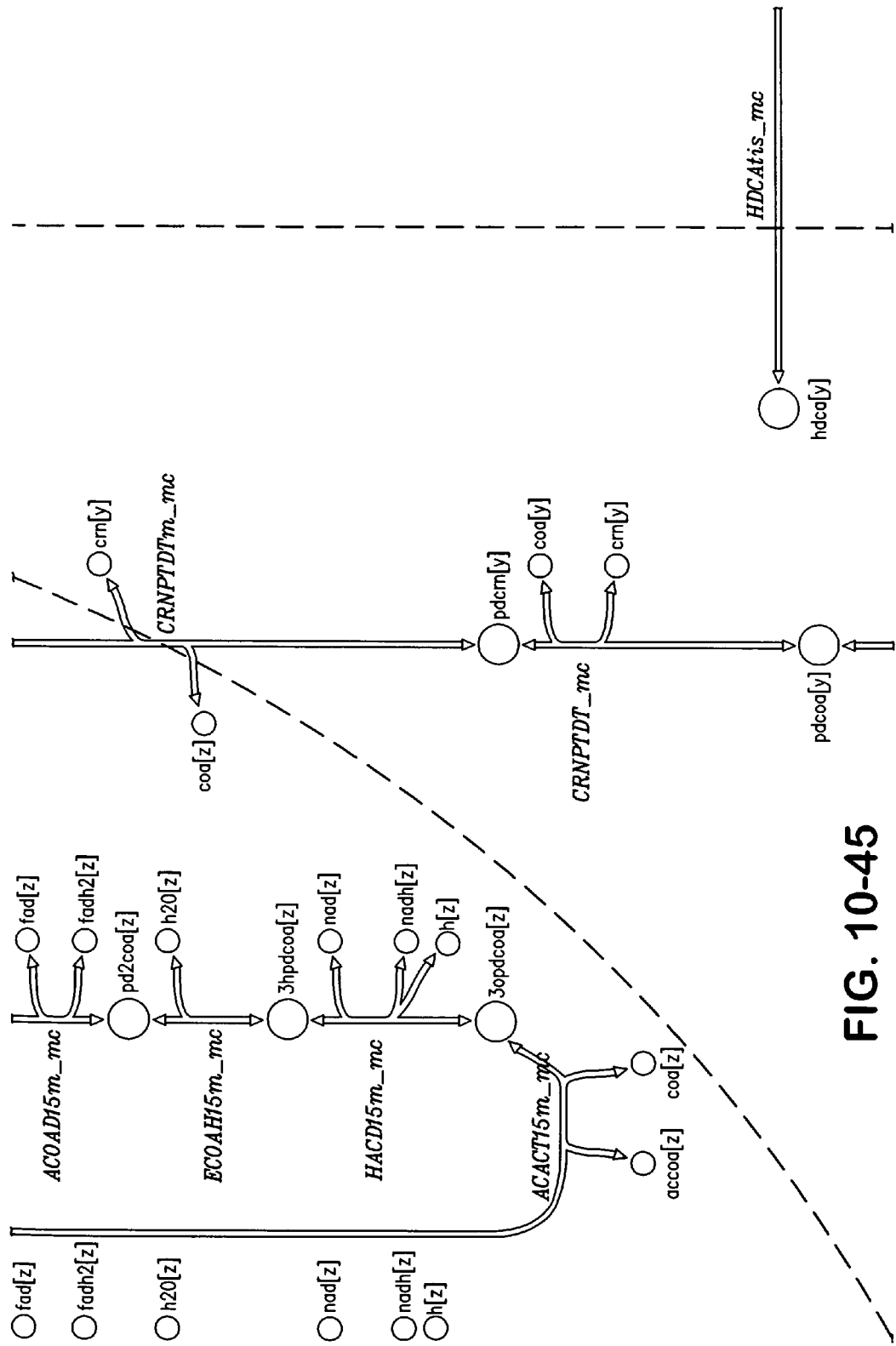
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
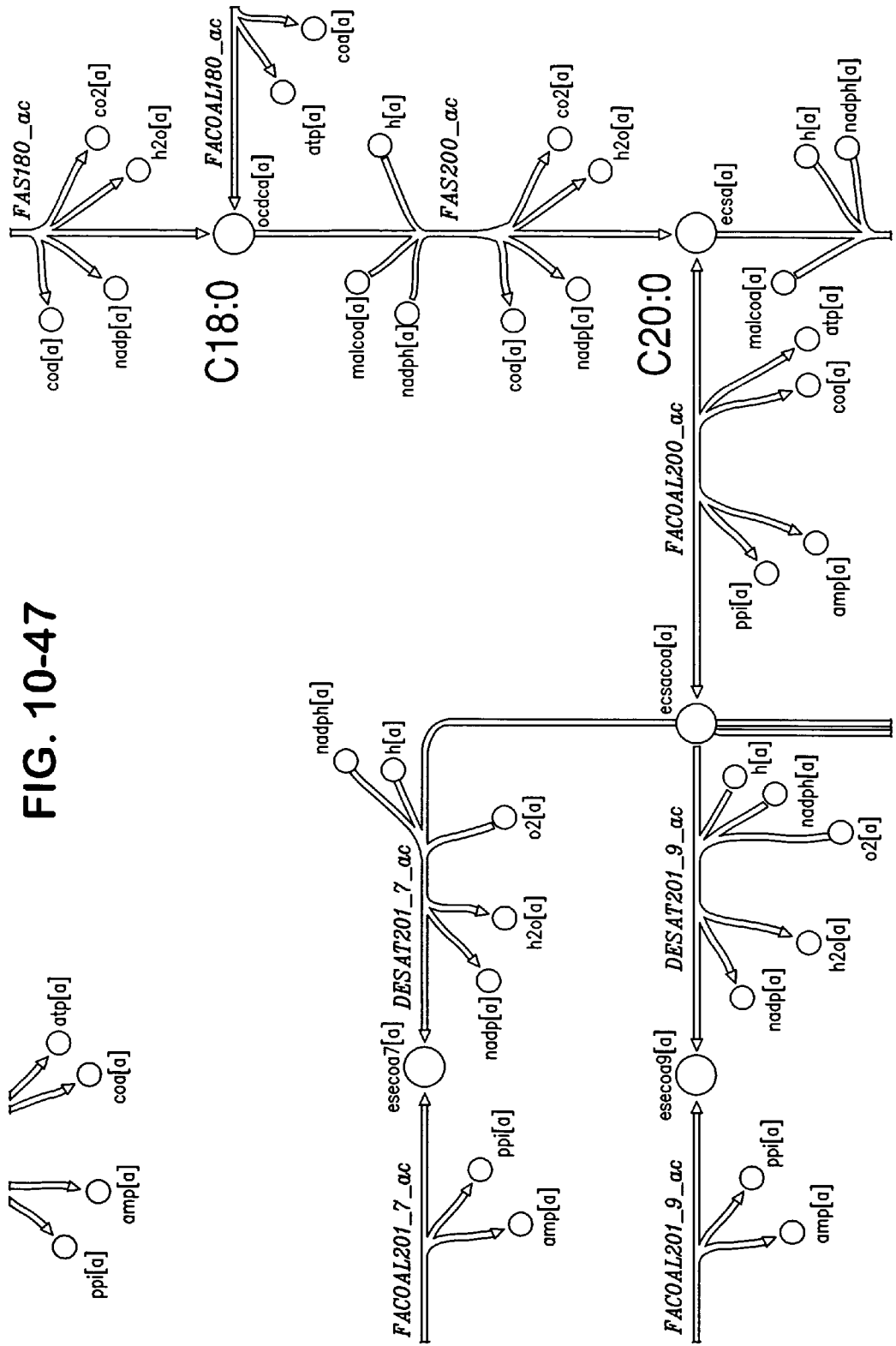
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
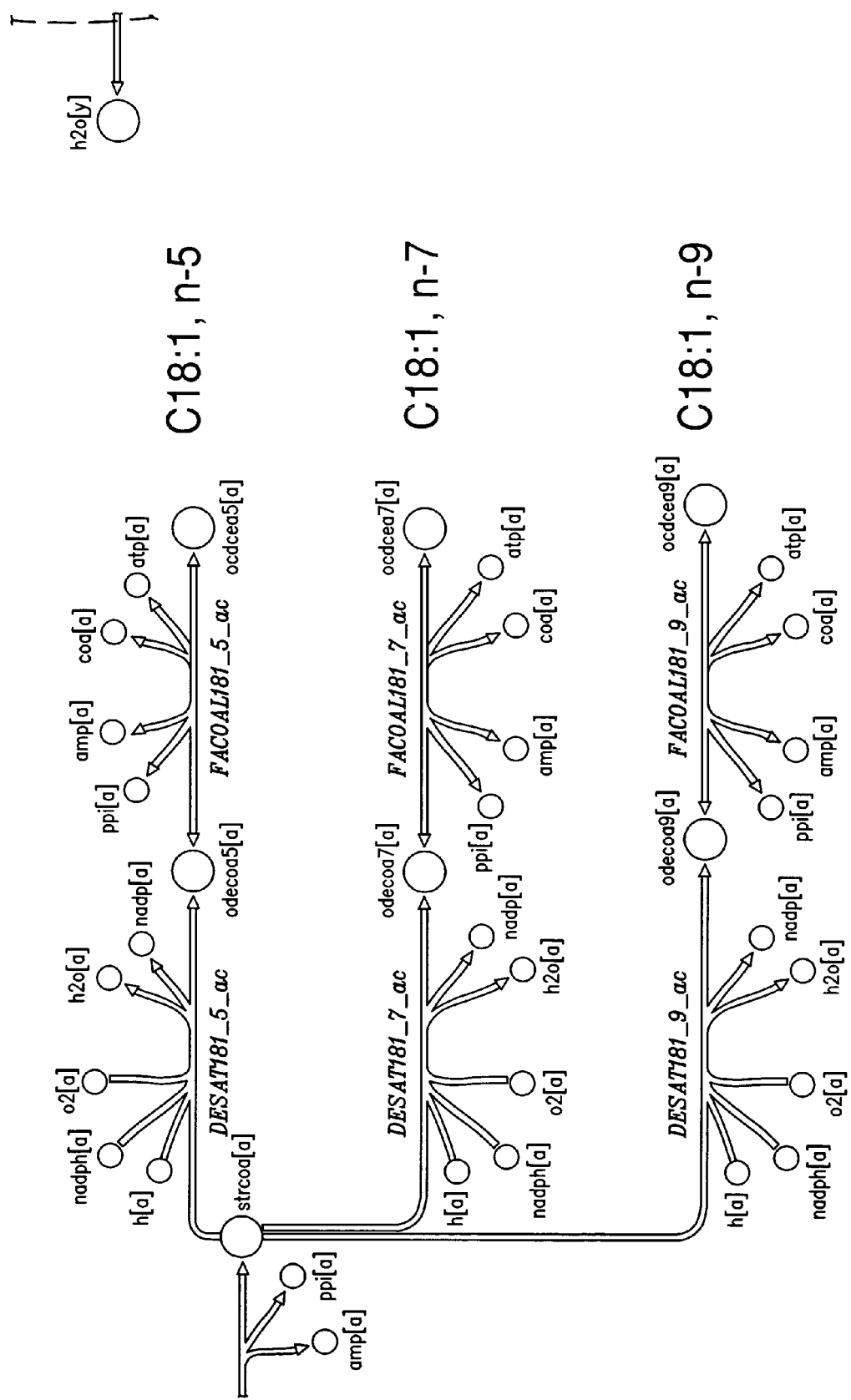
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
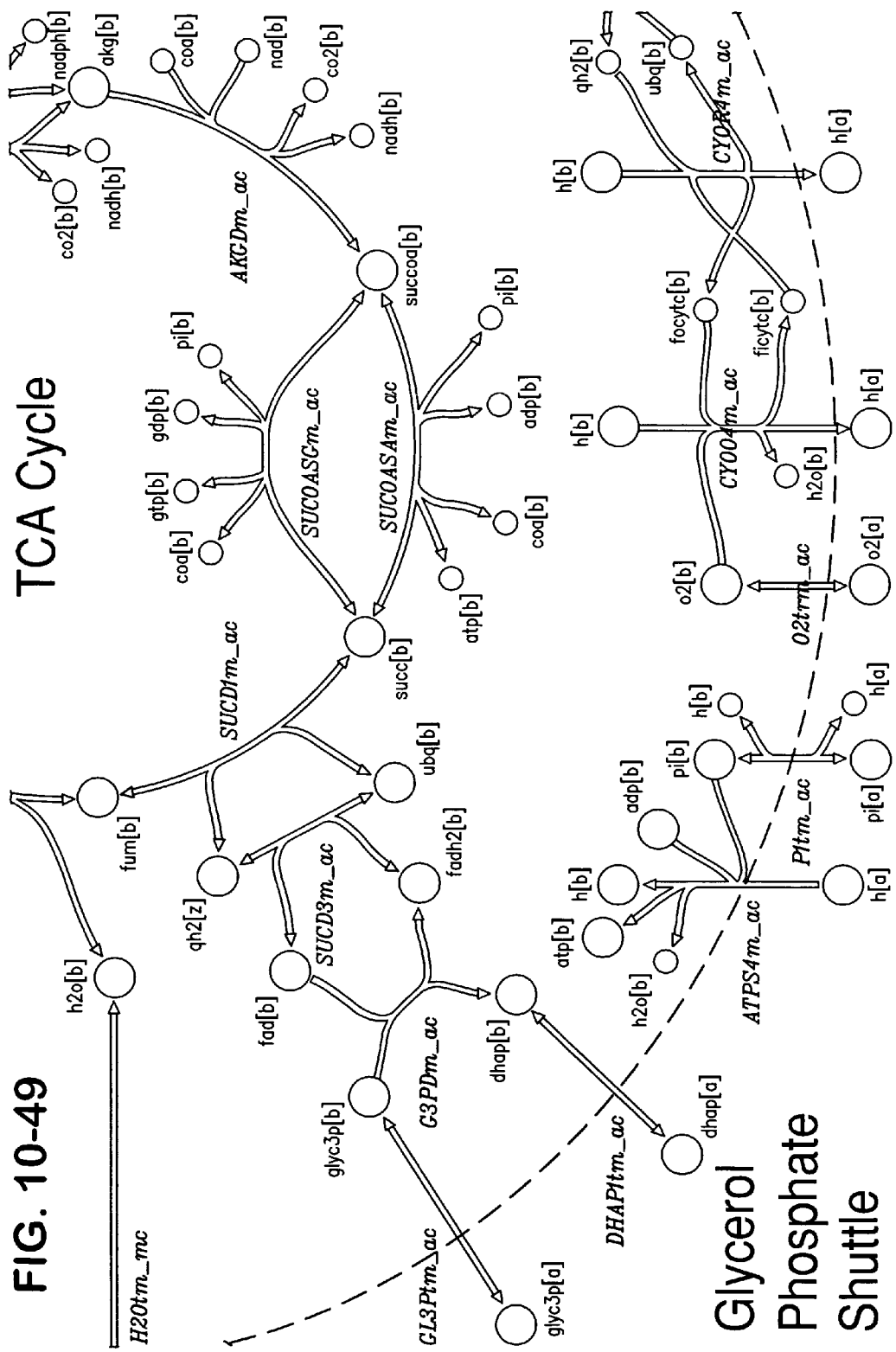
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
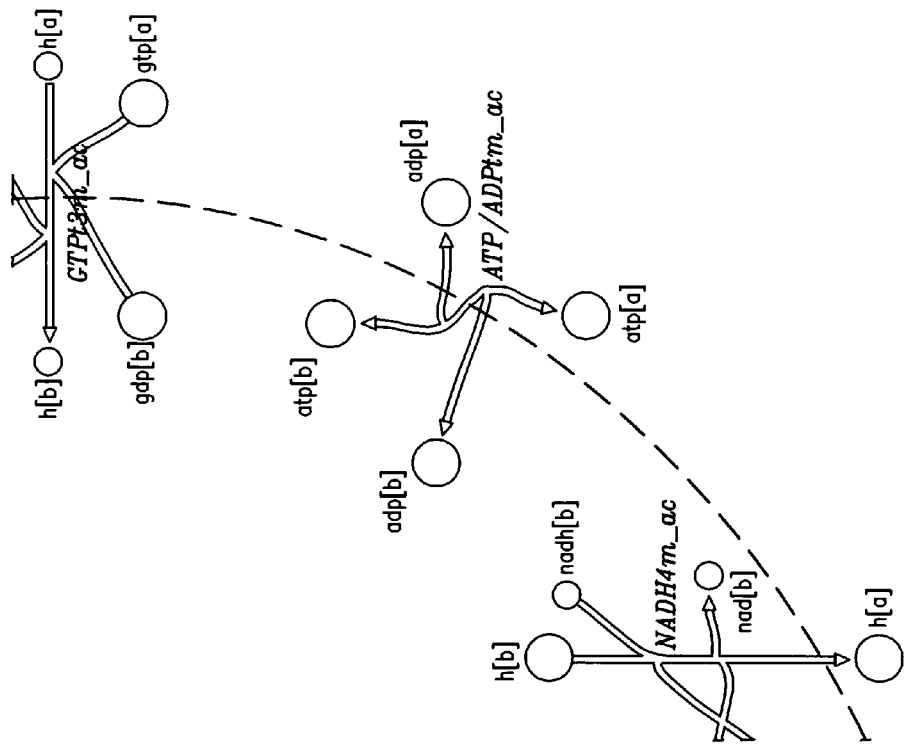
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
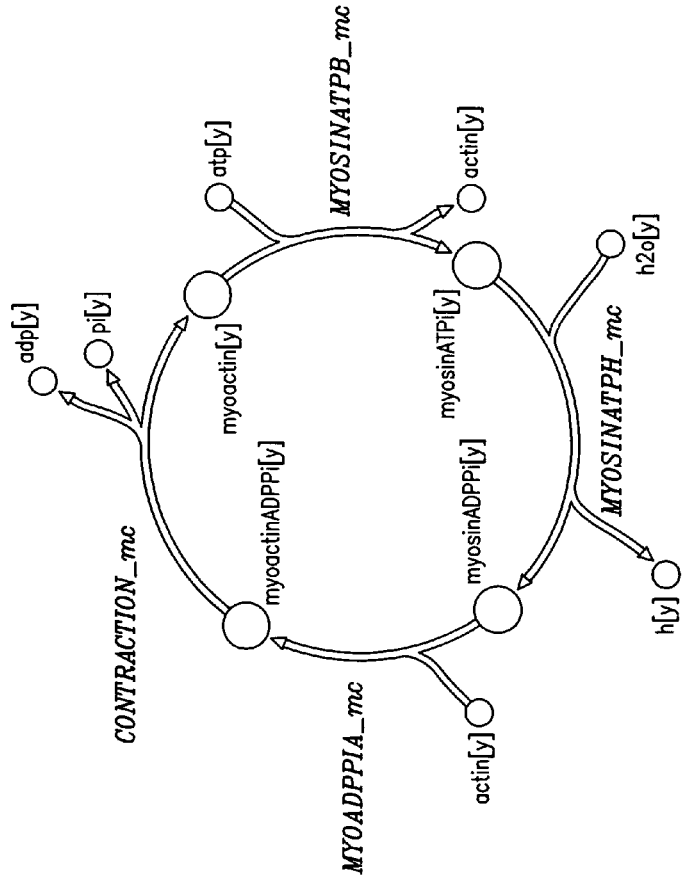
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
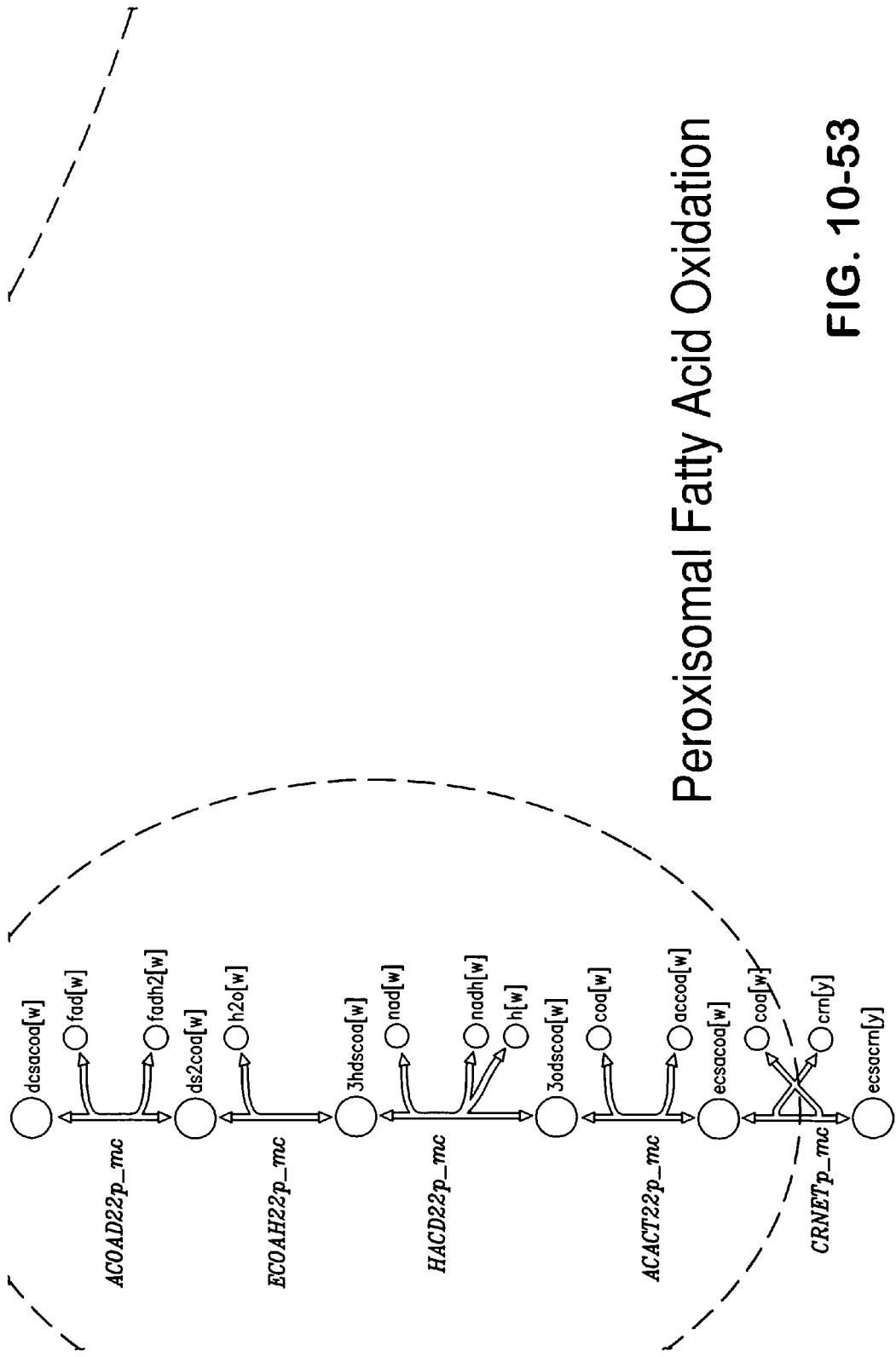
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
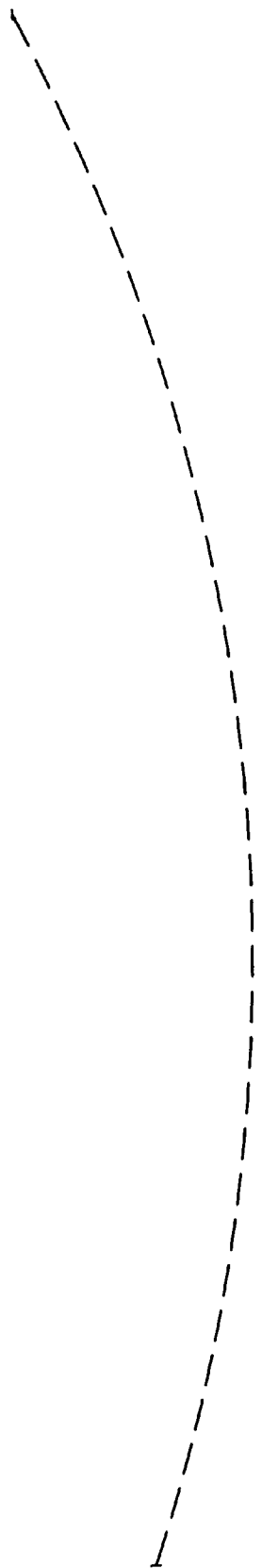
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55:
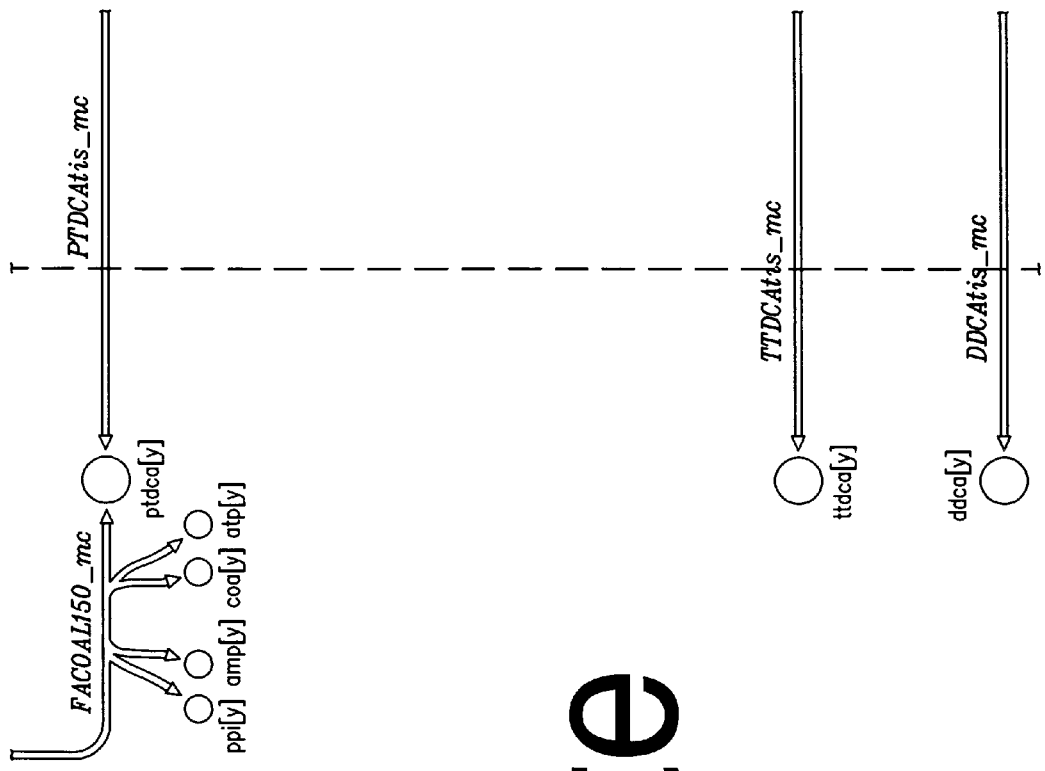
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57:
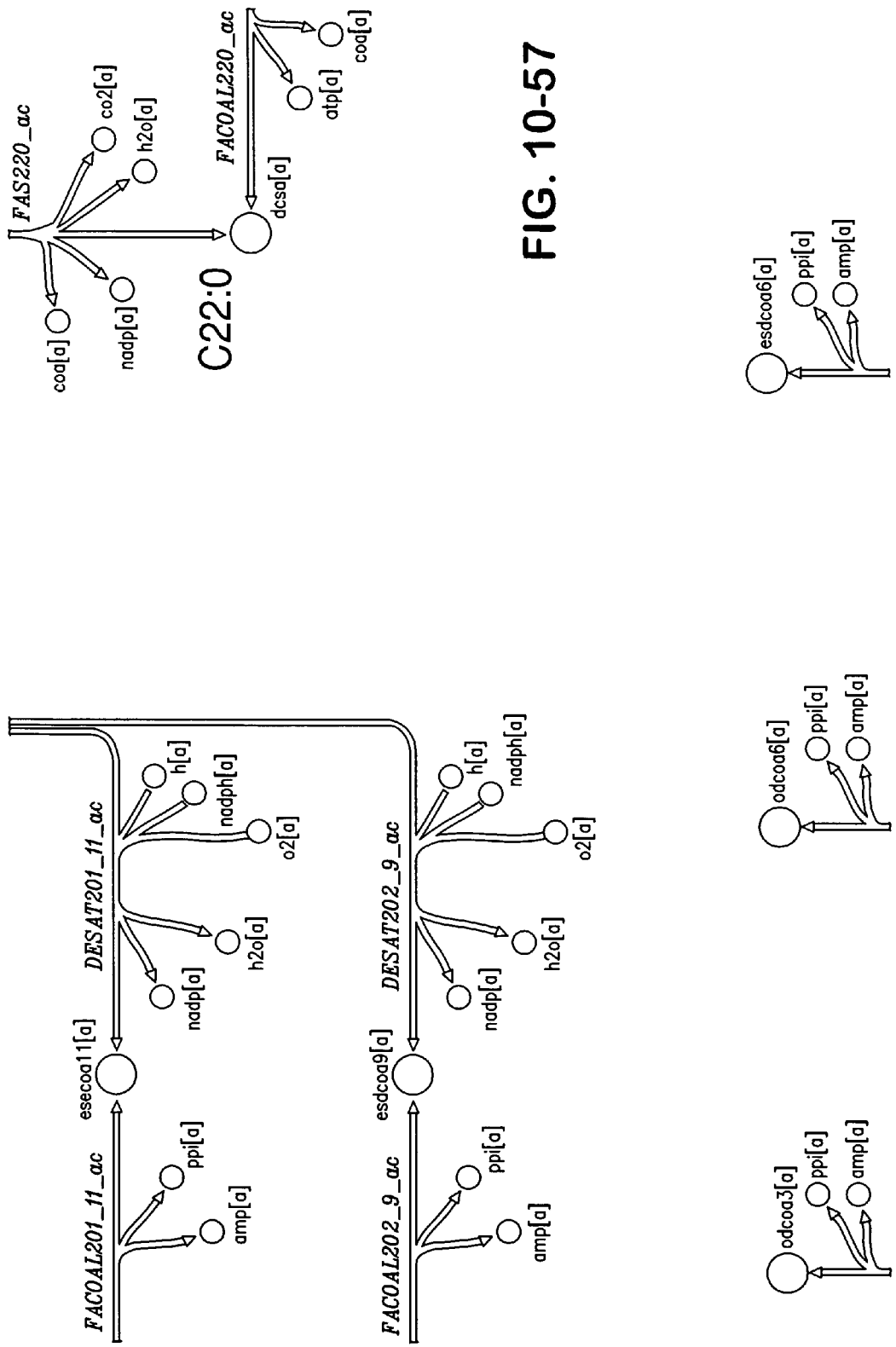
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58:
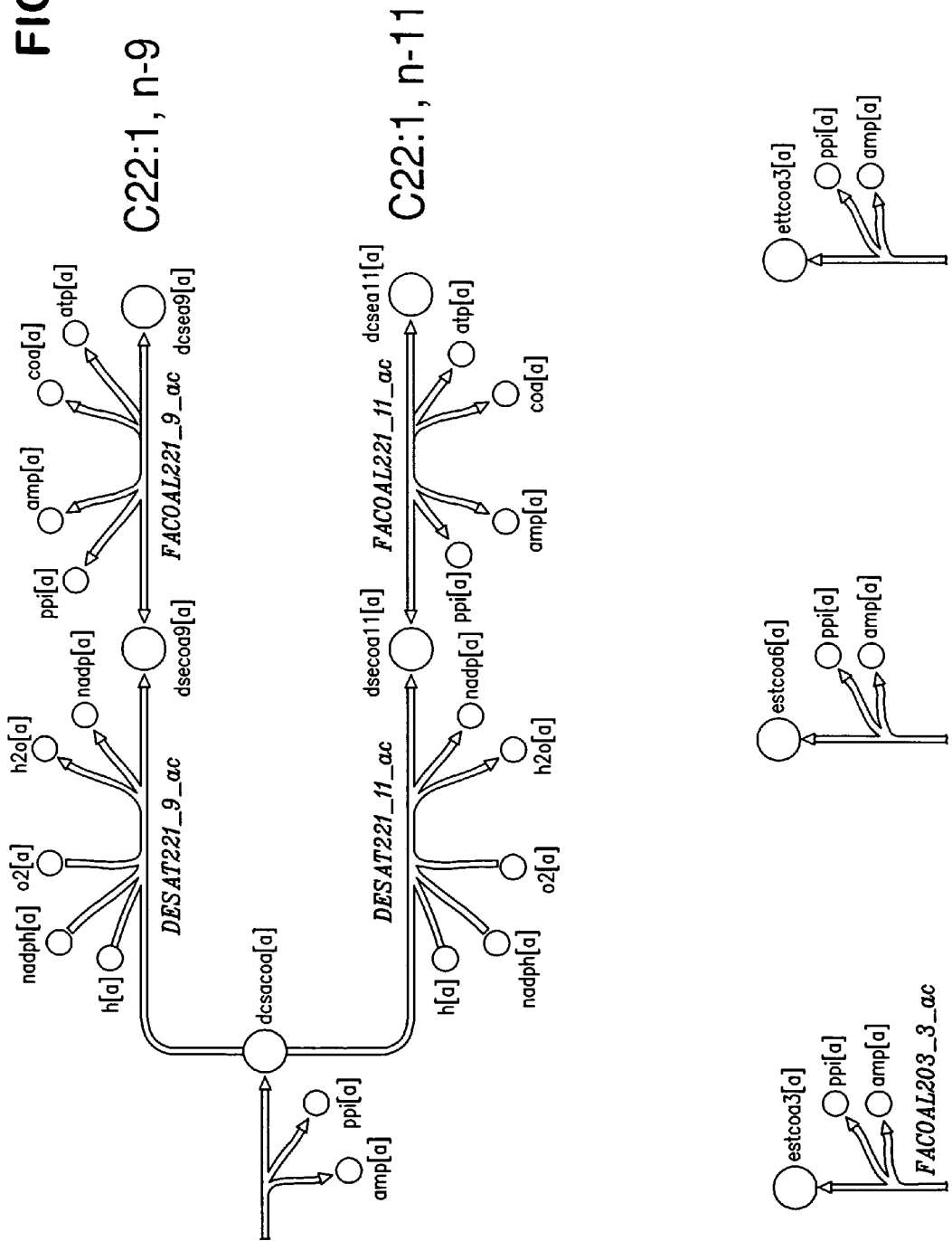
Figures 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60:
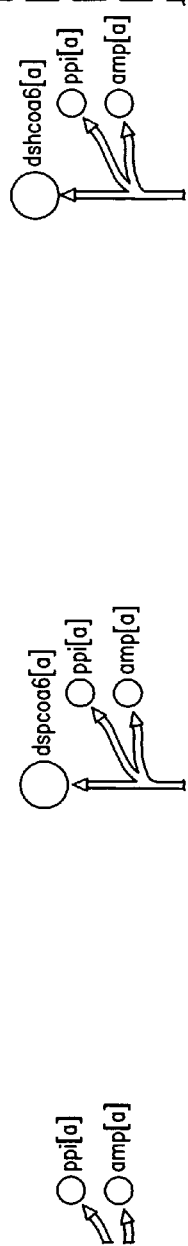
Figures 10, 62:
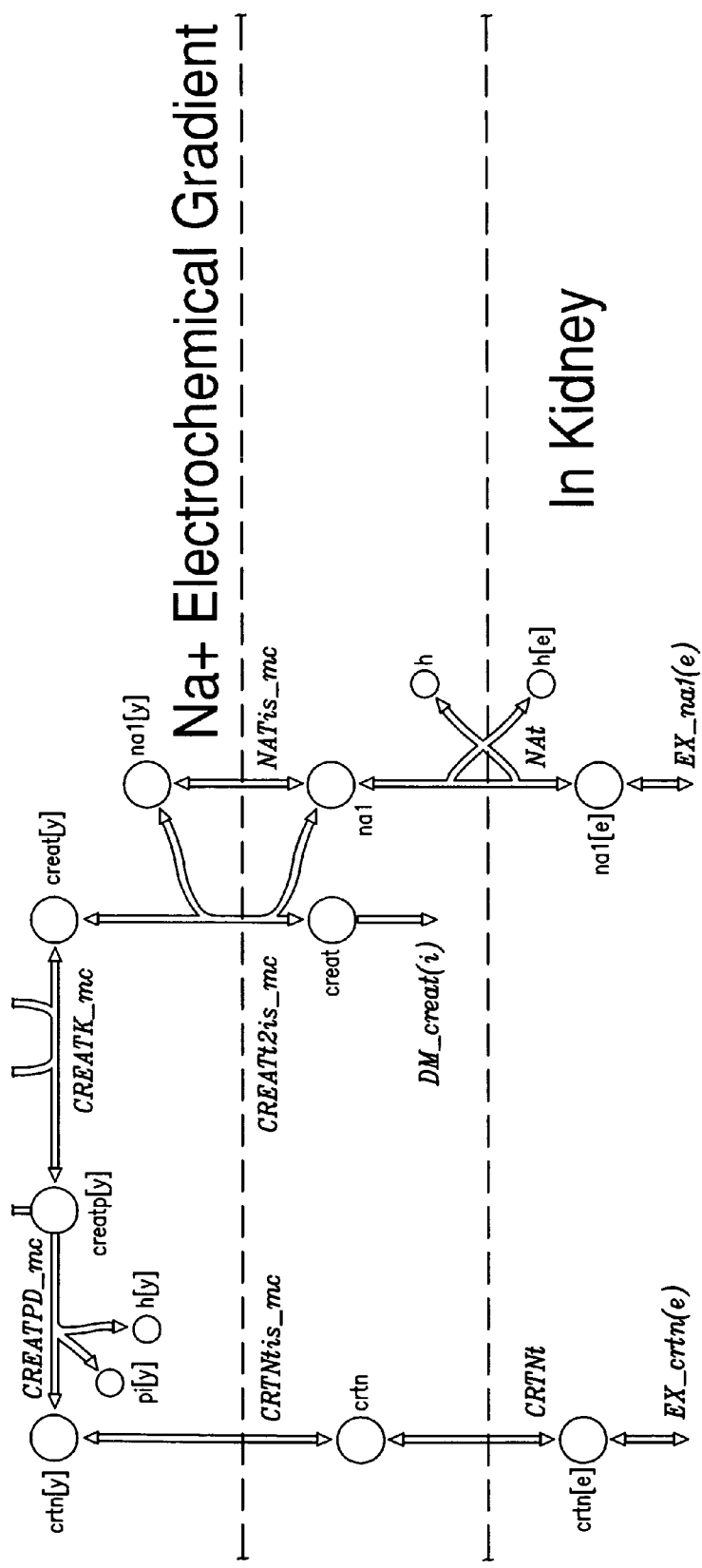
Figures 10, 63:
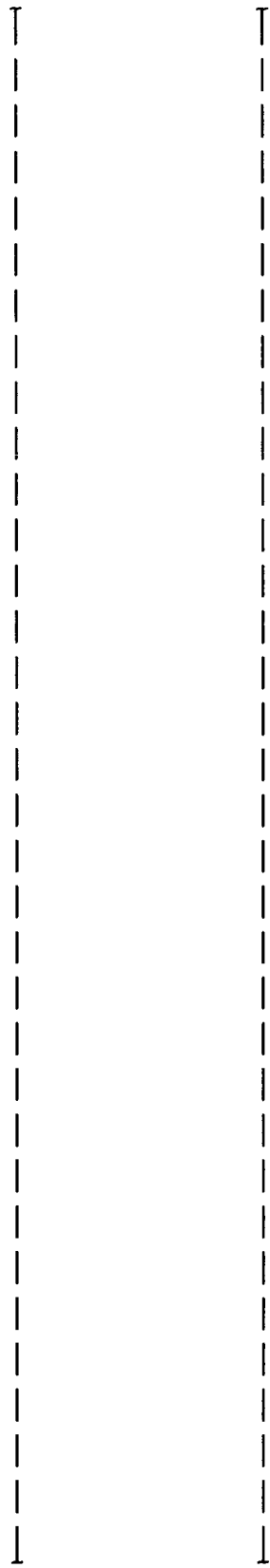
Figures 10, 64:
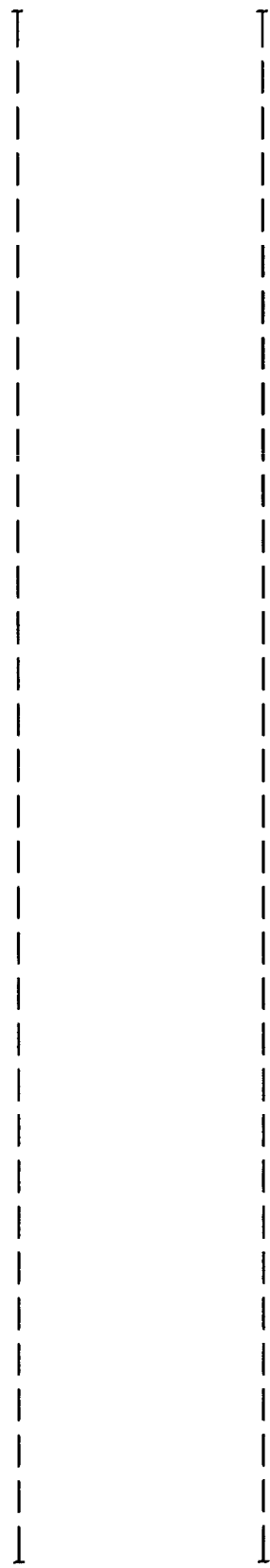
Figures 10, 65:
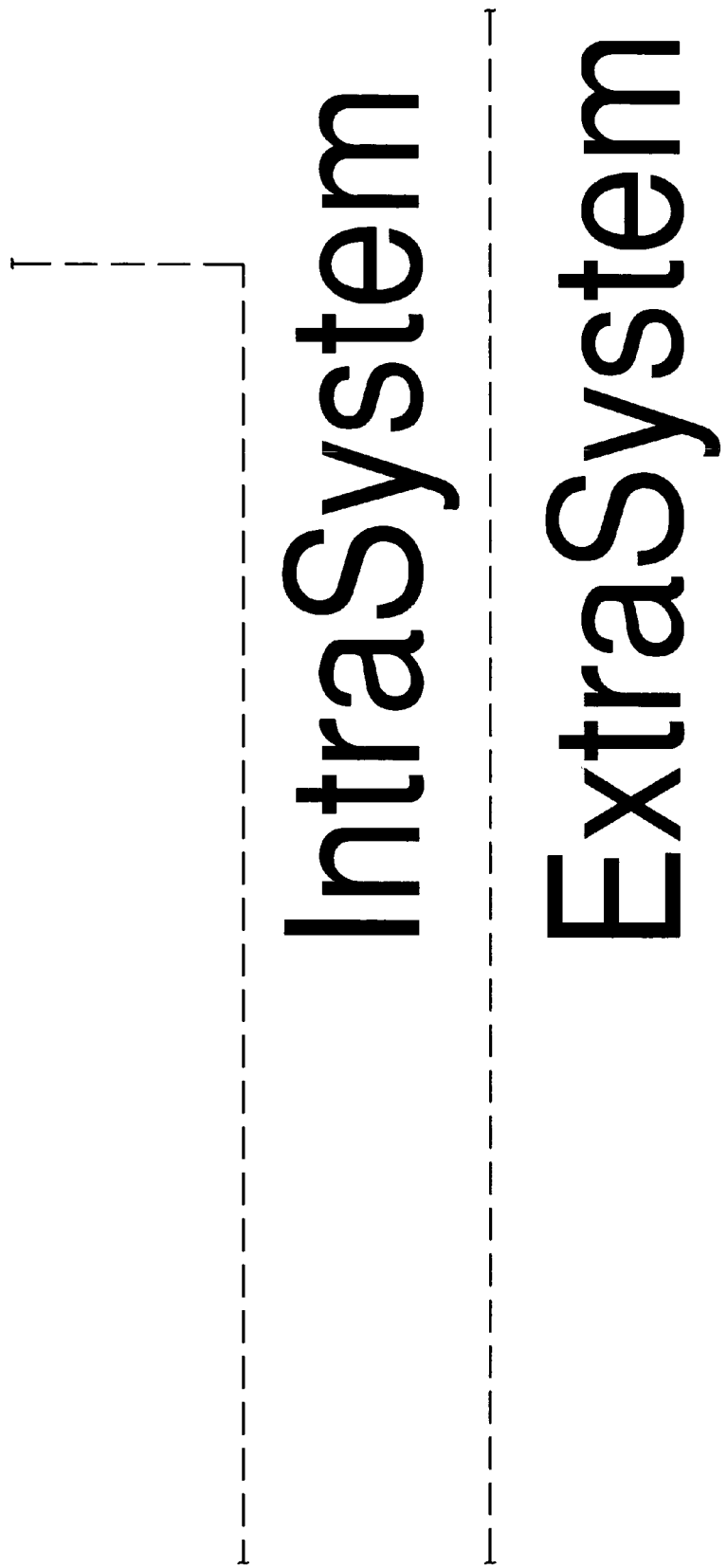
Figures 10, 66:
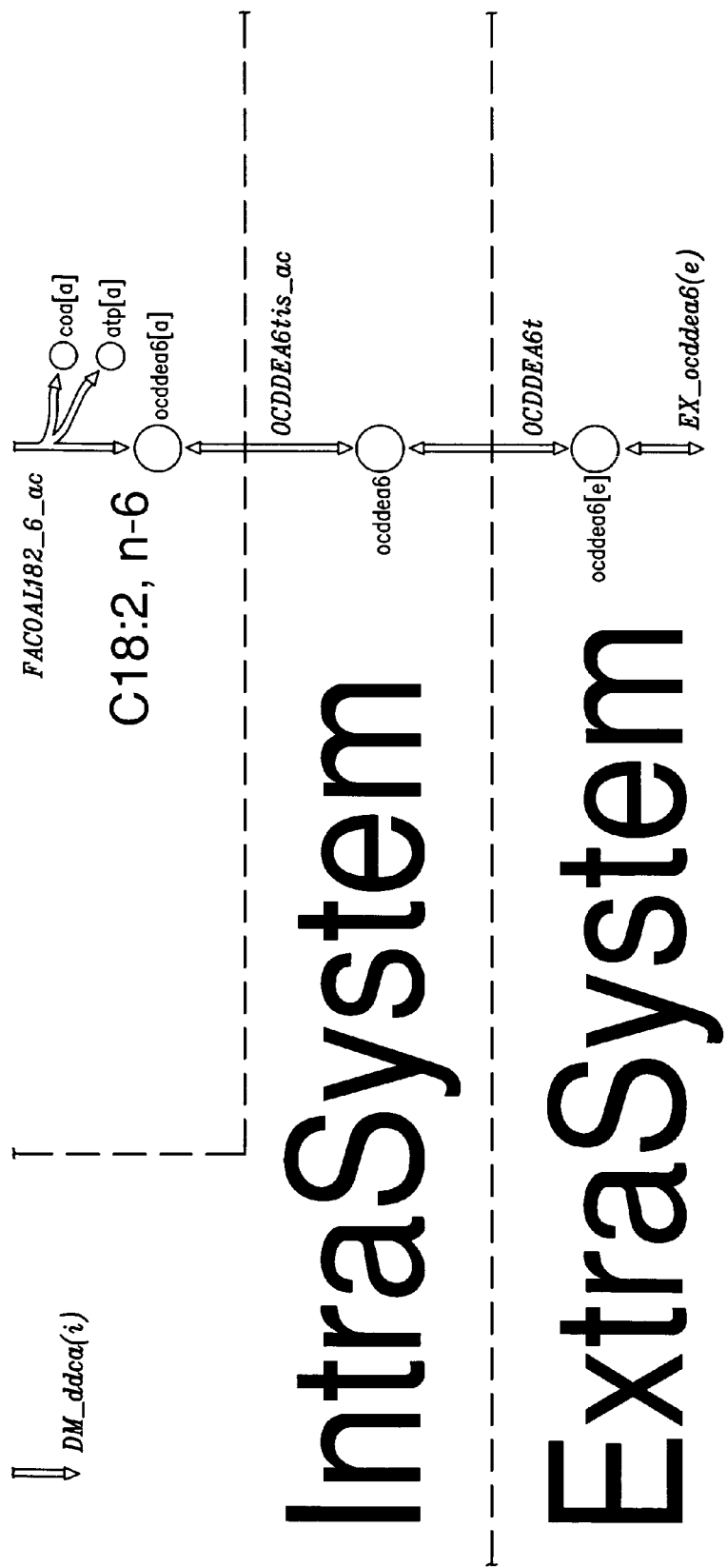
Figures 10, 67:
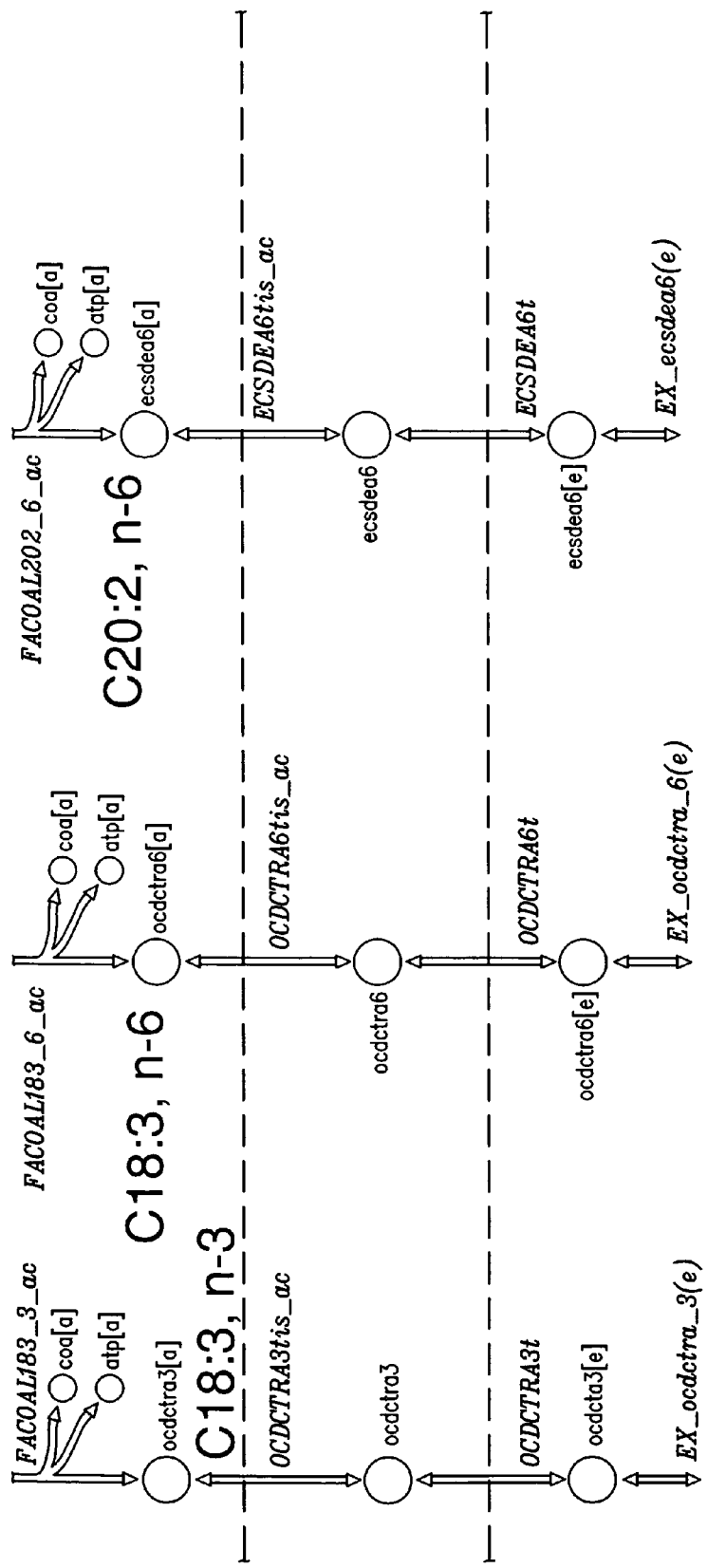
Figures 10, 68:
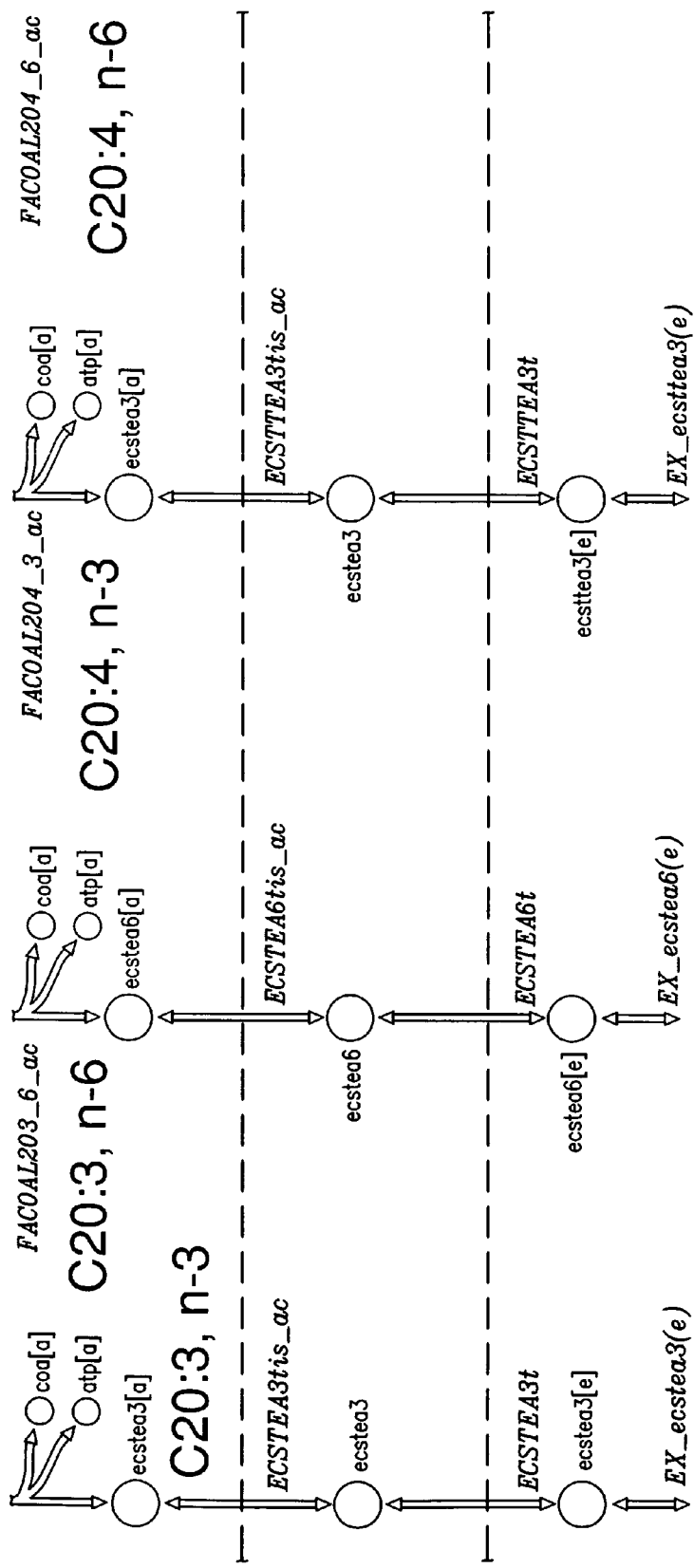
Figures 10, 69:
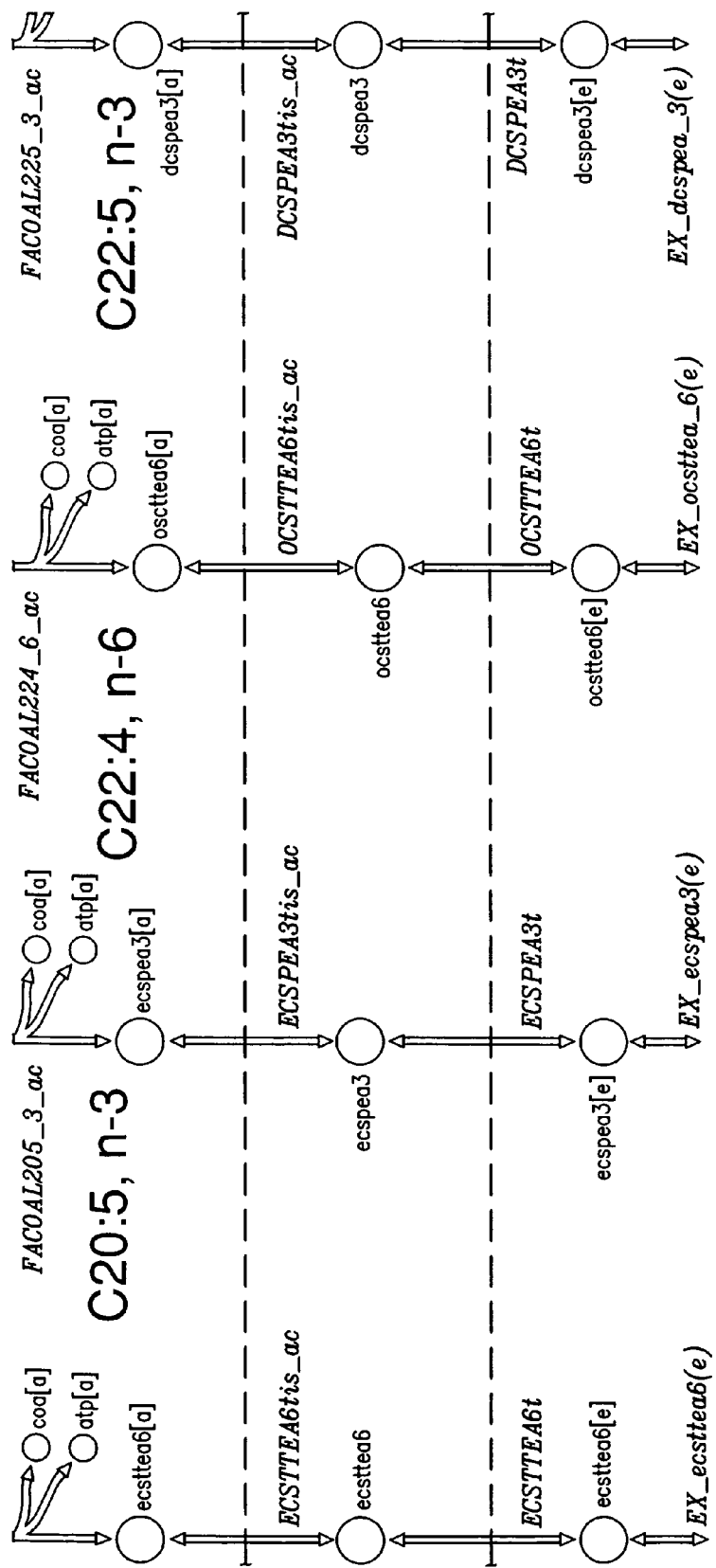
Figures 10, 70:
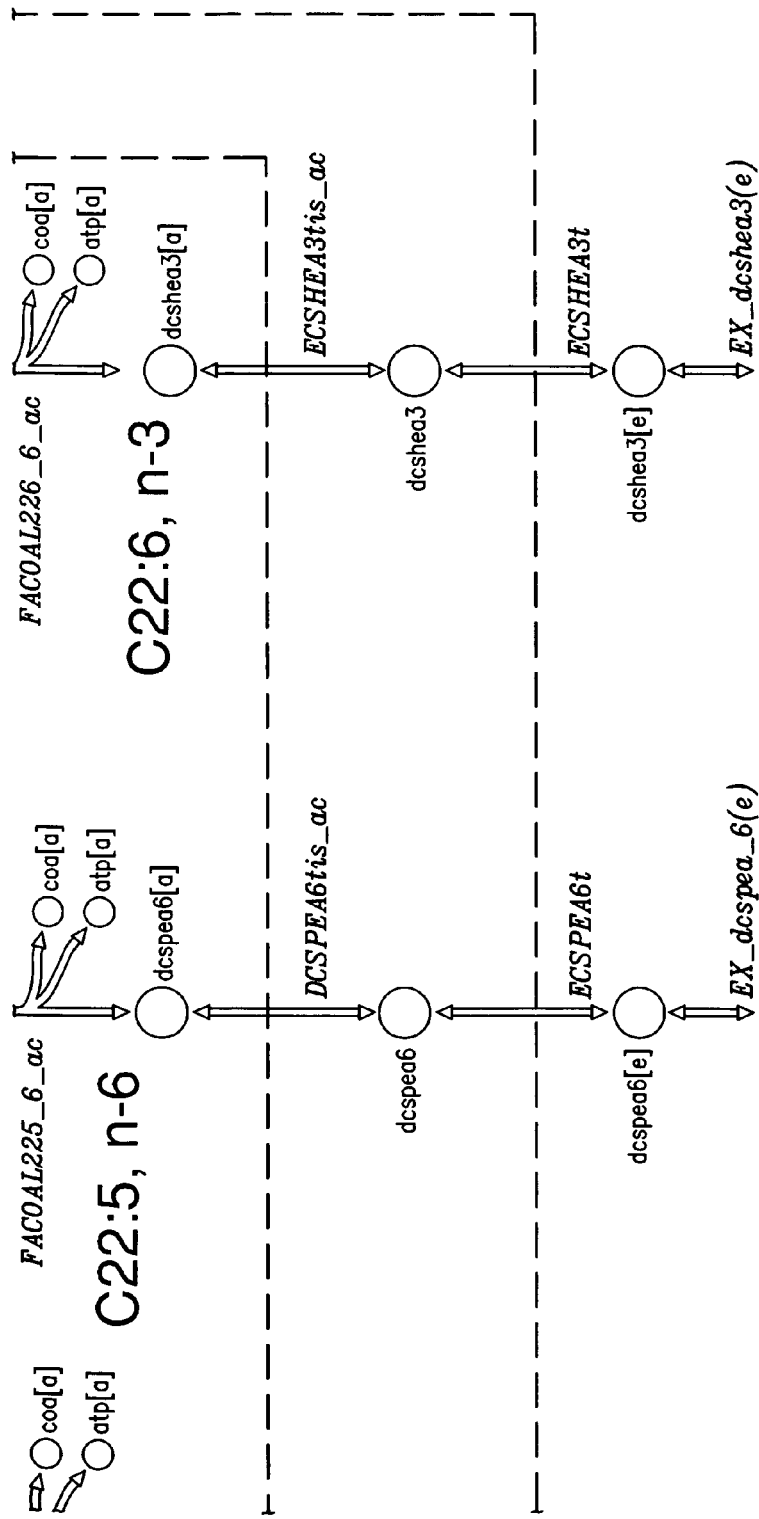
Figure 11:
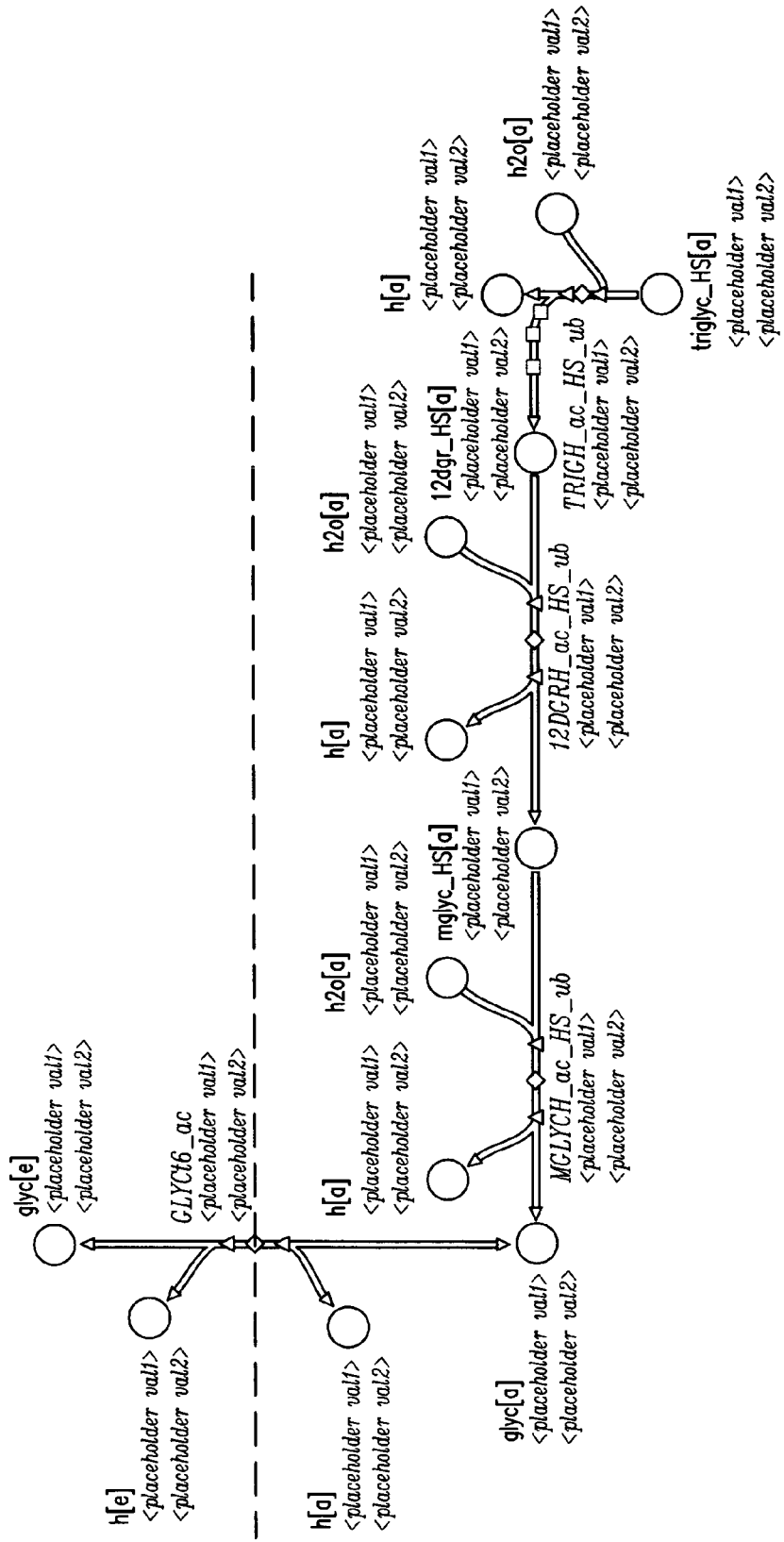
Figure 12:
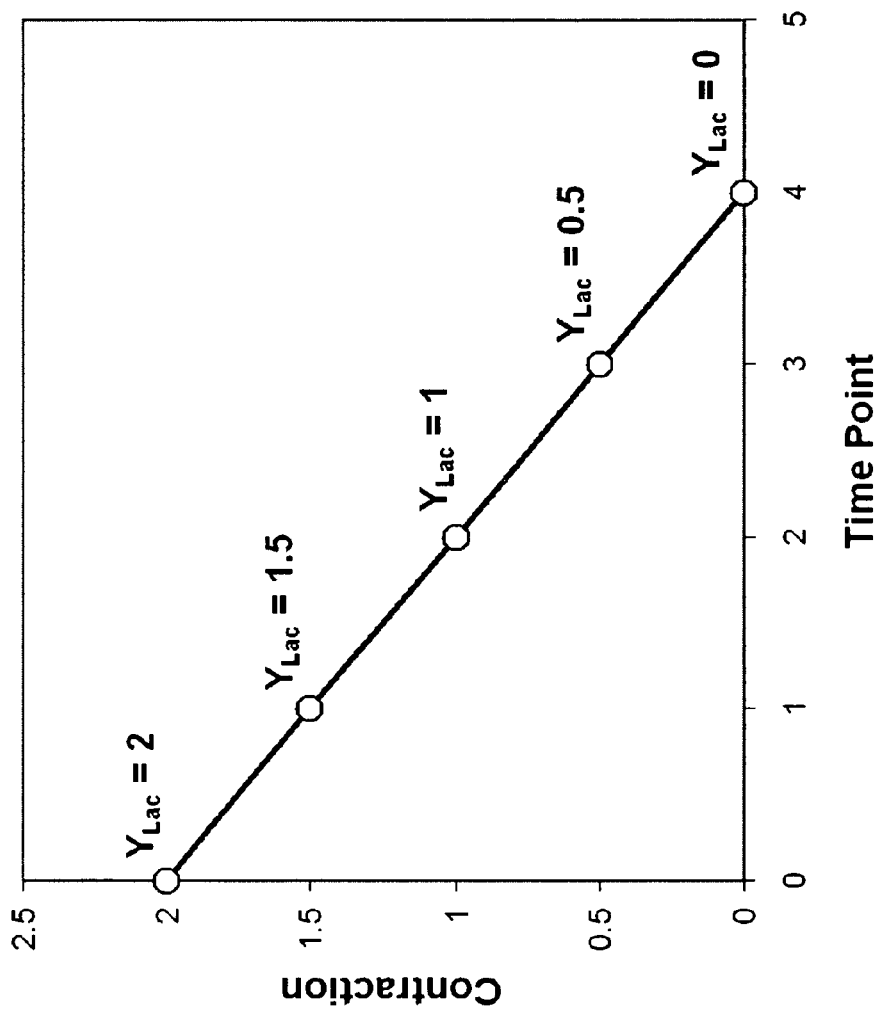
Figure 13:
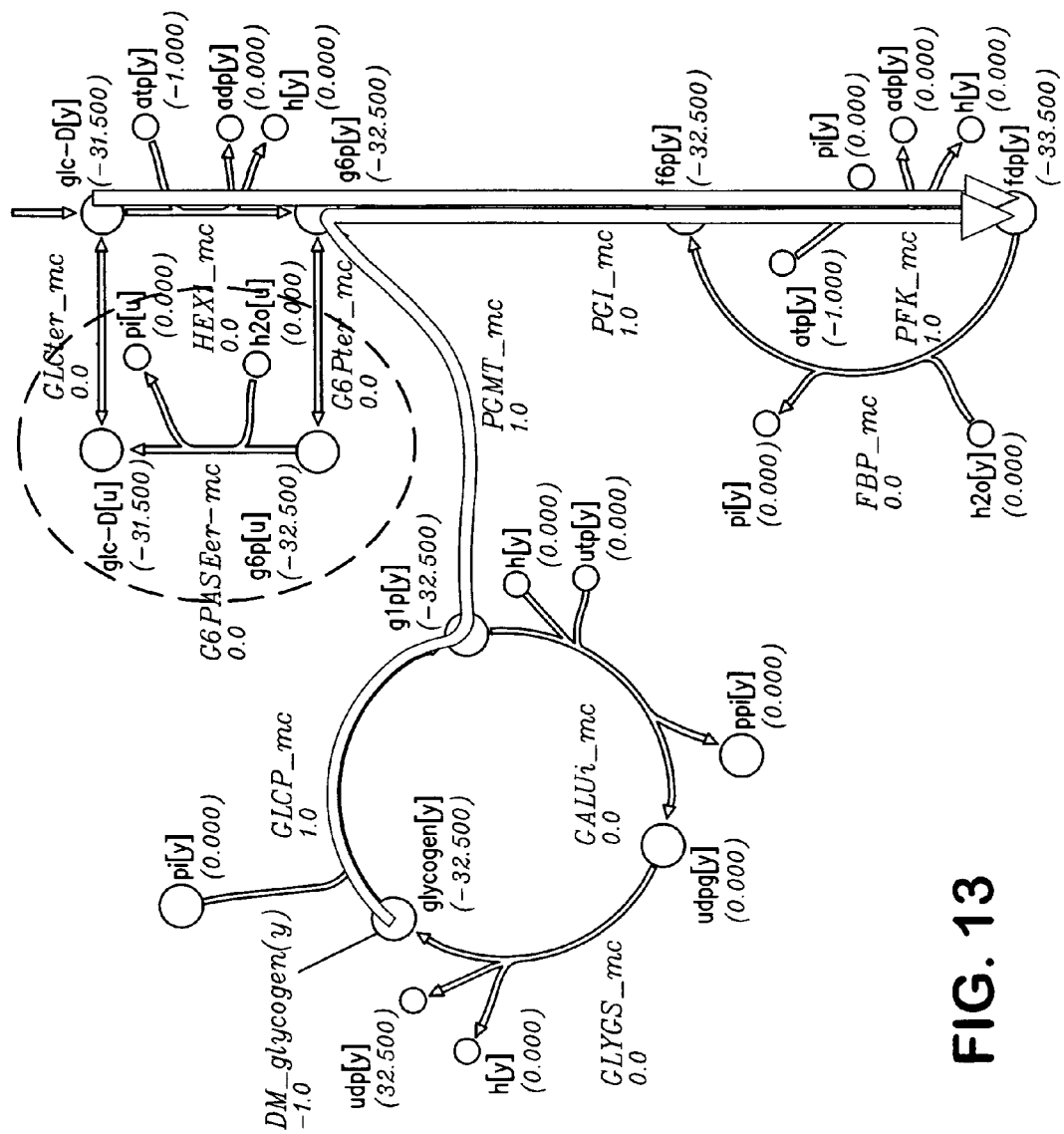

The muscle contraction was simulated also with stored glycogen and phosphocreatine as the energy source. The maximum contraction for glycogen was computed to be 32.5 mol/mol glycogen in aerobic and 3 mol/mol glycogen in anaerobic condition. The observed difference between the maximum contraction generated by glycogen in comparison to glucose arises from the absence of the phosphorylation or glucokinase step in the first step of glycolysis. The results of glycogen versus glucose utilization are illustrated in FIG. 13 where the glycogen utilization pathway is shown as the thick bent arrow on the left (red) and the glucose utilization pathway is shown as the thick straight arrow on the right (blue). The dashed circle (green) represents the endoplasmic reticulum membrane. The maximum contraction from phosphocreatine under both aerobic and anaerobic conditions was computed to be 1 mol/mol phosphocreatine. The energy generated from phosphocreatine is independent of the energy produced through oxidative phosphorylation and thus was computed to be the same in both aerobic and anaerobic conditions.

In addition, β-oxidative pathways in the myocyte tissue were examined by supplying the network with eicosanoate (n-C20:0), octadecenoate (C18:1, n-9), and pentadecanoate (C15:0) as examples of fatty acid oxidation of odd- and even-chain, and saturated and unsaturated fatty acids. The results are shown in Table 13 and demonstrate that maximum contraction in the myocyte model was 134 mol/mol for eicosanoate, 118.5 mol/mol for octadecenoate, and 98.5 mol/mol for pentadecanoate. The results also show that on a carbon-mole basis, all the fatty acids yielded approximately the same contraction, which was equivalent to ATP yield. Contraction was observed to be larger in terms of carbon yield than that generated from glucose (i.e. ~6.6 mol ATP/C-mol fatty acid in comparison to 5.3 mol ATP/C-mol glucose). The maximum ATP yield for palmitate (C16:0) was also computed to be 106 mol ATP/mol palmitate, which was consistent with the previously calculated values (Vo et al, supra). One mol of cytosolic protons per mol of fatty acid was supplied to the network for fatty acid oxidation.

TABLE 13

Maximum contraction in the myocyte model given different fatty acids

| Fatty Acid | Abbreviation* | Maximum Contraction (mol/mol fatty acid) | Maximum Contraction (mol/C-mol) |
|---|---|---|---|
| Eicosanoate | C20:0 | 134 | 6.7 |
| Octadecenoate | C18:1, n-9 | 118.5 | 6.6 |
| Palmitate | C16:0 | 106 | 6.6 |
| Pentadecanoate | C15:0 | 98.5 | 6.6 |

*Abbreviation indicates: number of carbons in the fatty acid, number of double bonds, carbon number where the 1st double bond appears if the fatty acid is unsaturated.

A unit of proton per fatty acid is required in the network to balance fatty acyl CoA formation in the cell as illustrated in the following reaction:

| | |
|---|---|
| Fatty Acid CoA Ligase: | Fatty Acid + ATP + CoA → Fatty Acyl-CoA + AMP + PPi |
| Adenylate Kinase: | AMP + ATP ↔ (2) ADP |
| Inorganic Diphosphatase: | PPi + $H_2O$ → $H^+$ + (2) Pi |
| Net: | Fatty Acid + CoA + (2) ATP + $H_2O$ → Fatty Acyl-CoA + (2)O ADP + (2) Pi + $H^+$ |

With respect to ATP balance (i.e. ATP+$H_2O$→ADP+$P_i$+$H^+$), the net reaction has one mol less $H_2O$ and $H^+$. Water can freely diffuse through the membrane. However, cell membrane is impermeable to free protons and thus protons were balanced in all compartments. The proton requirement in the cell can be fulfilled with a proton-coupled fatty acid transporter. It has been observed that the proton electrochemical gradient across the inner membrane plays a crucial role in energizing the long-chain fatty acid transport apparatus in *E. coli* and the proton electrochemical gradient across the inner membrane is required for optimal fatty acid transport (Di-Russo et al., *Mol. Cell. Biochem.* 192:41-52 (1999)). Fatty acid transporters in *S. cerevisiae* have also been studied, however, no evidence is currently available on the mechanism of transport. When a proton coupled fatty acid transporter was used in the model, the requirement for supplying a mol of proton to the system was eliminated.

Adipocyte-Myoctye Coupled Functions

Muscle cells largely rely on their stored glycogen and phosphocreatine content. During aerobic exercise, however, glucose, glycogen, and phosphcreatine storage of muscle cells are depleted and energy generation in myocytes is achieved by fatty acid oxidation. Lipolysis or lipid degradation proceeds in muscle cells following the transfer of fatty acids from adipocytes to myocytes via blood.

Modeling of multi-cellular metabolism was performed using a constraint-based approach as described herein where the metabolic networks of adipocyte and myocyte were combined into a multi-cellular metabolic model as shown in FIG. 10. The integrated model was assessed by computing the network energy requirements during anaerobic exercise such as that corresponding to a sprint and aerobic exercise such as that corresponding to a marathon. From a purely additive perspective, combining all of the reactions from the adipocyte model with those from the myocyte model was initially performed as a sufficient indicator for the combined network to compute integrated physiological results. However, with the two models strictly combined in this manner they were deficient at computing integrated functions such as those described below and, in particular, the results described in the "Muscle Contraction in a Marathon" section below. Addition of buffer systems for bicarbonate and ammonia allowed the combined model to function more efficiently and predictably.

In retrospect, the inclusion of intra-system reactions is consistent with the role that, for example, the kidney plays in integrated metabolic physiology.

Simulation of an Integrated Model for Muscle Contraction During a Sprint: The energy requirements of myocytes in a sprint are extremely high and supplied primarily from the fuel present in the muscle. In addition, oxygen cannot be transported to the cells fast enough to trigger an aerobic metabolism. It has been estimated that only 5% of the energy in a sprint is supplied via oxidative phosphorylation and the remaining ATP is generated from anaerobic metabolism from stored glycogen and phosphocreatine (*Biochemical and Physiological Aspects of Human Nutrition*, Philadelphia, Ed. by M. H. Stipanuk, W. B. Saunders, (2000)).

To simulate the metabolic activity of the muscle in a sprint, the maximum muscle contraction in an aerobic condition was computed by supplying the multi-cellular model with glucose, glycogen, and phosphocreatine as shown in Table 14. In addition, muscle contraction was simulated under anaerobic condition by constraining the oxygen supply to zero. Maximum contraction was computed to be the same as in the isolated myocyte model, as expected, demonstrating that the integrated model retains the functionalities observed in the single-cell model.

TABLE 14

Simulation results in the adipocyte-myocyte integrated model.[1]

| Carbon Source | Objective (Cell Type) | Aerobic mol/mol | Anaerobic carbon source |
|---|---|---|---|
| Glucose | Contraction (M) | 31.5 | 2 |
| Glycogen | Contraction (M) | 32.5 | 3 |
| Phosphocreatine | Contraction (M) | 1 | 1 |
| Glucose | ATP synthesis (A) | 32.5 | — |
| Glucose | TAG synthesis (A) | 0.06 | — |
| TAG | Glycerol (I) | 1* | — |
| TAG supplying C12:0, C14:0, C15:0, C16:0, C18:0, C18:1 n-9, and C20:0 | Contraction (M) | 253.9 | — |

*Two protons were allowed to leave the cytosol (see section "Triacylglycerol Storage and Utilization in Adipocyte Tissue")
— Not relevant
[1]M, myocyte; A, adipocyte; I, intra-system; TAG, triacylglycerol; C12:0, dodecanoate; C14:0, tetradecanoate; C15:0, pentadecanoate; C16:0, palmitate; C18:0, octadecanoate; C18:1 n-9, octadecenoate; C20:0, eicosanoate Simulation of an Integrated Model for Muscle Contraction During a Marathon: The total energy expenditure in a marathon is about 12,000 kJ or 2868 kcal, which is equivalent to burning about 750 g of carbohydrate or 330 g of fat (Stipanuk, supra). Since the total stored carbohydrate in the body is only about 400 to 900 g, the mobilized fatty acids from adipose tissue provide an important part of the supplied energy to the muscle cells in an aerobic metabolism and especially in a marathon.

To simulate the aerobic oxidation of fatty acid in the muscle cells, the integrated model was first demonstrated to be able to synthesize and store triacylglycerol in the adipocyte compartment when supplied by glucose. As for the single cell model, the integrated adipocyte-myocyte network was able to store TAG in adipocyte compartment. The results are shown in Table 14. In addition, TAG degradation and fatty acid mobilization to the blood was simulated by maximizing glycerol secretion in the intra-system space generated from the stored TAG in adipocyte. As with the single cell model, TAG hydrolysis was simulated with the integrated adipocyte-myocyte model and maximum glycerol secretion rate was shown to be the same.

To demonstrate the coupled function of the two cell types, muscle contraction in an aerobic exercise was simulated by constraining all other alternative carbon sources including glucose, stored glycogen, and phosphocreatine to zero and supplying adipocyte with stored triacylglycerol as an energy source. Exchange fluxes were included to ensure the proper transfer of fatty acids between the two models. The maximum muscle contraction in the network that contains β-oxidative pathways for fatty acids C12:0, C14:0, C15:0, C16:0, C18:0, C18:1 n-9, and C20:0 was simulated and computed to be 253.9 mol/mol TAG. The total contraction in this simulation is the sum of maximum contraction that is generated if the model was supplied with each fatty acid individually. The results from using the integrated model demonstrated that energy generated in the muscle cell from triacylglycerol is produced in an additive fashion and metabolite balance in the two cell types does not reduce the energy production in the cell.

These studies further demonstrate the the application of a constraint-based approach to modeling multi-cellular integrated metabolic models. The results also indicate that modeling multi-cellular networks can be optimized by incorporating intra-system reactions such as the bicarbonate and ammonia buffer systems into the integrated adipocyte-myocyte model. The reconstructed models and simulation results also demonstrated that metabolic functions of various cell types can be studied, understood and reproduced using the methods of the invention. Furthermore, coupling of the functions of multiple cell types in a system was demonstrated through the transport of various metabolites and the coupled function of different cell types were studied by imposing biologically appropriate objective function. Finally, the ability to predict further network modifications, such as the transport mechanism of fatty acids into myocyte, using the reconstructed models also was demonstrated. These results also indicate that multi-cellular modeling can be extended to the modeling of more than two cells and which correspond to various cell types including the same specie or among multiple different species, tissues, organs, and whole body by including additional genomic, biochemical, physiological, and high throughput datasets.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

TABLE 1

| Locus ID | Gene Ab. | Reaction Stoichiometry | E.C. |
|---|---|---|---|
| 1. Carbohydrate Metabolism | | | |
| 1.1 Glycolysis/Gluconeogenesis [PATH:hsa00010] | | | |
| 3098 | HK1 | GLC + ATP -> G6P + ADP | 2.7.1.1 |
| 3099 | HK2 | GLC + ATP -> G6P + ADP | 2.7.1.1 |
| 3101 | HK3 | GLC + ATP -> G6P + ADP | 2.7.1.1 |
| 2645 | GCK, HK4, MODY2, NIDDM | GLC + ATP -> G6P + ADP | 2.7.1.2 |
| 2538 | G6PC, G6PT | G6P + H2O -> GLC + PI | 3.1.3.9 |
| 2821 | GPI | G6P <-> F6P | 5.3.1.9 |
| 5211 | PFKL | F6P + ATP -> FDP + ADP | 2.7.1.11 |
| 5213 | PFKM | F6P + ATP -> FDP + ADP | 2.7.1.11 |
| 5214 | PFKP, PFK-C | F6P + ATP -> FDP + ADP | 2.7.1.11 |
| 5215 | PFKX | F6P + ATP -> FDP + ADP | 2.7.1.11 |
| 2203 | FBP1, FBP | FDP + H2O -> F6P + PI | 3.1.3.11 |
| 8789 | FBP2 | FDP + H2O -> F6P + PI | 3.1.3.11 |
| 226 | ALDOA | FDP <-> T3P2 + T3P1 | 4.1.2.13 |
| 229 | ALDOB | FDP <-> T3P2 + T3P1 | 4.1.2.13 |
| 230 | ALDOC | FDP <-> T3P2 + T3P1 | 4.1.2.13 |
| 7167 | TPI1 | T3P2 <-> T3P1 | 5.3.1.1 |
| 2597 | GAPD, GAPDH | T3P1 + PI + NAD <-> NADH + 13PDG | 1.2.1.12 |
| 26330 | GAPDS, GAPDH-2 | T3P1 + PI + NAD <-> NADH + 13PDG | 1.2.1.12 |
| 5230 | PGK1, PGKA | 13PDG + ADP <-> 3PG + ATP | 2.7.2.3 |
| 5233 | PGK2 | 13PDG + ADP <-> 3PG + ATP | 2.7.2.3 |
| 5223 | PGAM1, PGAMA | 13PDG -> 23PDG | 5.4.2.4 |
| | | 23PDG + H2O -> 3PG + PI | 3.1.3.13 |
| | | 3PG <-> 2PG | 5.4.2.1 |
| 5224 | PGAM2, PGAMM | 13PDG <-> 23PDG | 5.4.2.4 |
| | | 23PDG + H2O -> 3PG + PI | 3.1.3.13 |
| | | 3PG <-> 2PG | 5.4.2.1 |
| 669 | BPGM | 13PDG <-> 23PDG | 5.4.2.4 |
| | | 23PDG + H2O <-> 3PG + PI | 3.1.3.13 |
| | | 3PG <-> 2PG | 5.4.2.1 |
| 2023 | ENO1, PPH, ENO1L1 | 2PG <-> PEP + H2O | 4.2.1.11 |
| 2026 | ENO2 | 2PG <-> PEP + H2O | 4.2.1.11 |
| 2027 | ENO3 | 2PG <-> PEP + H2O | 4.2.1.11 |
| 26237 | ENO1B | 2PG <-> PEP + H2O | 4.2.1.11 |
| 5313 | PKLR, PK1 | PEP + ADP -> PYR + ATP | 2.7.1.40 |
| 5315 | PKM2, PK3, THBP1, OIP3 | PEP + ADP -> PYR + ATP | 2.7.1.40 |
| 5160 | PDHA1, PHE1A, PDHA | PYRm + COAm + NADm -> + NADHm + CO2m + ACCOAm | 1.2.4.1 |
| 5161 | PDHA2, PDHAL | PYRm + COAm + NADm -> + NADHm + CO2m + ACCOAm | 1.2.4.1 |
| 5162 | PDHB | PYRm + COAm + NADm -> + NADHm + CO2m + ACCOAm | 1.2.4.1 |
| 1737 | DLAT, DLTA, PDC-E2 | PYRm + COAm + NADm -> + NADHm + CO2m + ACCOAm | 2.3.1.12 |
| 8050 | PDX1, E3BP | PYRm + COAm + NADm -> + NADHm + CO2m + ACCOAm | 2.3.1.12 |
| 3939 | LDHA, LDH1 | NAD + LAC <-> PYR + NADH | 1.1.1.27 |
| 3945 | LDHB | NAD + LAC <-> PYR + NADH | 1.1.1.27 |

TABLE 1-continued

| Locus ID | Gene Ab. | Reaction Stoichiometry | E.C. |
|---|---|---|---|
| 3948 | LDHC, LDH3 | NAD + LAC <-> PYR + NADH | 1.1.1.27 |
| 5236 | PGM1 | G1P <-> G6P | 5.4.2.2 |
| 5237 | PGM2 | G1P <-> G6P | 5.4.2.2 |
| 5238 | PGM3 | G1P <-> G6P | 5.4.2.2 |
| 1738 | DLD, LAD, PHE3, DLDH, E3 | DLIPOm + FADm <-> LIPOm + FADH2m | 1.8.1.4 |
| 124 | ADH1 | ETH + NAD <-> ACAL + NADH | 1.1.1.1 |
| 125 | ADH2 | ETH + NAD <-> ACAL + NADH | 1.1.1.1 |
| 126 | ADH3 | ETH + NAD <-> ACAL + NADH | 1.1.1.1 |
| 127 | ADH4 | ETH + NAD <-> ACAL + NADH | 1.1.1.1 |
| 128 | ADH5 | FALD + RGT + NAD <-> FGT + NADH | 1.2.1.1 |
|  |  | ETH + NAD <-> ACAL + NADH | 1.1.1.1 |
| 130 | ADH6 | ETH + NAD <-> ACAL + NADH | 1.1.1.1 |
| 131 | ADH7 | ETH + NAD <-> ACAL + NADH | 1.1.1.1 |
| 10327 | AKR1A1, ALR, ALDR1 |  | 1.1.1.2 |
| 97 | ACYP1 |  | 3.6.1.7 |
| 98 | ACYP2 |  | 3.6.1.7 |
| 1.2 Citrate cycle (TCA cycle) PATH:hsa00020 | | | |
| 1431 | CS | ACCOAm + OAm + H2Om -> COAm + CITm | 4.1.3.7 |
| 48 | ACO1, IREB1, IRP1 | CIT <-> ICIT | 4.2.1.3 |
| 50 | ACO2 | CITm <-> ICITm | 4.2.1.3 |
| 3417 | IDH1 | ICIT + NADP -> NADPH + CO2 + AKG | 1.1.1.42 |
| 3418 | IDH2 | ICITm + NADPm -> NADPHm + CO2m + AKGm | 1.1.1.42 |
| 3419 | IDH3A | ICITm + NADm -> CO2m + NADHm + AKGm | 1.1.1.41 |
| 3420 | IDH3B | ICITm + NADm -> CO2m + NADHm + AKGm | 1.1.1.41 |
| 3421 | IDH3G | ICITm + NADm -> CO2m + NADHm + AKGm | 1.1.1.41 |
| 4967 | OGDH | AKGm + NADm + COAm -> CO2m + NADHm + SUCCOAm | 1.2.4.2 |
| 1743 | DLST, DLTS | AKGm + NADm + COAm -> CO2m + NADHm + SUCCOAm | 2.3.1.61 |
| 8802 | SUCLG1, SUCLA1 | GTPm + SUCCm + COAm <-> GDPm + PIm + SUCCOAm | 6.2.1.4 |
| 8803 | SUCLA2 | ATPm + SUCCm + COAm <-> ADPm + PIm + SUCCOAm | 6.2.1.4 |
| 2271 | FH | FUMm + H2Om <-> MALm | 4.2.1.2 |
| 4190 | MDH1 | MAL + NAD <-> NADH + OA | 1.1.1.37 |
| 4191 | MDH2 | MALm + NADm <-> NADHm + OAm | 1.1.1.37 |
| 5091 | PC, PCB | PYRm + ATPm + CO2m -> ADPm + OAm + PIm | 6.4.1.1 |
| 47 | ACLY, ATPCL, CLATP | ATP + CIT + COA + H2O -> ADP + PI + ACCOA + OA | 4.1.3.8 |
| 3657 |  |  |  |
| 5105 | PCK1 | OA + GTP -> PEP + GDP + CO2 | 4.1.1.32 |
| 5106 | PCK2, PEPCK | OAm + GTPm -> PEPm + GDPm + CO2m | 4.1.1.32 |
| 1.3 Pentose phosphate cycle PATH:hsa00030 | | | |
| 2539 | G6PD, G6PD1 | G6P + NADP <-> D6PGL + NADPH | 1.1.1.49 |
| 9563 | H6PD |  | 1.1.1.47 |
|  |  | D6PGL + H2O -> D6PGC | 3.1.1.31 |
| 25796 | PGLS, 6PGL | D6PGL + H2O -> D6PGC | 3.1.1.31 |
| 5226 | PGD | D6PGC + NADP -> NADPH + CO2 + RL5P | 1.1.1.44 |
| 6120 | RPE | RL5P <-> X5P | 5.1.3.1 |
| 7086 | TKT | R5P + X5P <-> T3P1 + S7P | 2.2.1.1 |
|  |  | X5P + E4P <-> F6P + T3P1 |  |
| 8277 | TKTL1, TKR, TKT2 | R5P + X5P <-> T3P1 + S7P | 2.2.1.1 |
|  |  | X5P + E4P <-> F6P + T3P1 |  |
| 6888 | TALDO1 | T3P1 + S7P <-> E4P + F6P | 2.2.1.2 |
| 5631 | PRPS1, PRS I, PRS, I | R5P + ATP <-> PRPP + AMP | 2.7.6.1 |
| 5634 | PRPS2, PRS II, PRS, II | R5P + ATP <-> PRPP + AMP | 2.7.6.1 |
| 2663 | GDH |  | 1.1.1.47 |
| 1.4 Pentose and glucuronate interconversions PATH:hsa00040 | | | |
| 231 | AKR1B1, AR, ALDR, ADR |  | 1.1.1.21 |
| 7359 | UGP1 | G1P + UTP -> UDPG + PPI | 2.7.7.9 |
| 7360 | UGP2, UGPP2 | G1P + UTP -> UDPG + PPI | 2.7.7.9 |
| 7358 | UGDH, UDPGDH |  | 1.1.1.22 |
| 10720 | UGT2B11 |  | 2.4.1.17 |
| 54658 | UGT1A1, UGT1A, GNT1, UGT1 |  | 2.4.1.17 |
| 7361 | UGT1A, UGT1, UGT1A |  | 2.4.1.17 |
| 7362 | UGT2B, UGT2, UGT2B |  | 2.4.1.17 |
| 7363 | UGT2B4, UGT2B11 |  | 2.4.1.17 |
| 7364 | UGT2B7, UGT2B9 |  | 2.4.1.17 |
| 7365 | UGT2B10 |  | 2.4.1.17 |
| 7366 | UGT2B15, UGT2B8 |  | 2.4.1.17 |
| 7367 | UGT2B17 |  | 2.4.1.17 |
| 13 | AADAC, DAC |  | 3.1.1.— |
| 3991 | LIPE, LHS, HSL |  | 3.1.1.— |
| 1.5 Fructose and mannose metabolism PATH:hsa00051 | | | |
| 4351 | MPI, PMI1 | MAN6P <-> F6P | 5.3.1.8 |
| 5372 | PMM1 | MAN6P <-> MAN1P | 5.4.2.8 |
| 5373 | PMM2, CDG1, CDGS | MAN6P <-> MAN1P | 5.4.2.8 |
| 2762 | GMDS |  | 4.2.1.47 |
| 8790 | FPGT, GFPP |  | 2.7.7.30 |
| 5207 | PFKFB1, PFRX | ATP + F6P -> ADP + F26P | 2.7.1.105 |
|  |  | F26P -> F6P + PI | 3.1.3.46 |
| 5208 | PFKFB2 | ATP + F6P -> ADP + F26P | 2.7.1.105 |
|  |  | F26P -> F6P + PI | 3.1.3.46 |

TABLE 1-continued

| Locus ID | Gene Ab. | Reaction Stoichiometry | E.C. |
|---|---|---|---|
| 5209 | PFKFB3 | ATP + F6P -> ADP + F26P | 2.7.1.105 |
| | | F26P -> F6P + PI | 3.1.3.46 |
| 5210 | PFKFB4 | ATP + F6P -> ADP + F26P | 2.7.1.105 |
| | | F26P -> F6P + PI | 3.1.3.46 |
| 3795 | KHK | | 2.7.1.3 |
| 6652 | SORD | DSOT + NAD -> FRU + NADH | 1.1.1.14 |
| 2526 | FUT4, FCT3A, FUC-TIV | | 2.4.1.— |
| 2529 | FUT7 | | 2.4.1.— |
| 3036 | HAS1, HAS | | 2.4.1.— |
| 3037 | HAS2 | | 2.4.1.— |
| 8473 | OGT, O-GLCNAC | | 2.4.1.— |
| 51144 | LOC51144 | | 1.1.1.— |
| 1.6 Galactose metabolism PATH:hsa00052 | | | |
| 2584 | GALK1, GALK | GLAC + ATP -> GAL1P + ADP | 2.7.1.6 |
| 2585 | GALK2, GK2 | GLAC + ATP -> GAL1P + ADP | 2.7.1.6 |
| 2592 | GALT | UTP + GAL1P <-> PPI + UDPGAL | 2.7.7.10 |
| 2582 | GALE | UDPGAL <-> UDPG | 5.1.3.2 |
| 2720 | GLB1 | | 3.2.1.23 |
| 3938 | LCT, LAC | | 3.2.1.62 |
| | | | 3.2.1.108 |
| 2683 | B4GALT1, GGTB2, BETA4GAL-T1, GT1, GTB | | 2.4.1.90 |
| | | | 2.4.1.38 |
| | | | 2.4.1.22 |
| 3906 | LALBA | | 2.4.1.22 |
| 2717 | GLA, GALA | MELI -> GLC + GLAC | 3.2.1.22 |
| 2548 | GAA | MLT -> 2 GLC | 3.2.1.20 |
| | | 6DGLC -> GLAC + GLC | |
| 2594 | GANAB | MLT -> 2 GLC | 3.2.1.20 |
| | | 6DGLC -> GLAC + GLC | |
| 2595 | GANC | MLT -> 2 GLC | 3.2.1.20 |
| | | 6DGLC -> GLAC + GLC | |
| 8972 | MGAM, MG, MGA | MLT -> 2 GLC | 3.2.1.20 |
| | | 6DGLC -> GLAC + GLC | |
| | | | 3.2.1.3 |
| 1.7 Ascorbate and aldarate metabolism PATH:hsa00053 | | | |
| 216 | ALDH1, PUMB1 | ACAL + NAD -> NADH + AC | 1.2.1.3 |
| 217 | ALDH2 | ACALm + NADm -> NADHm + ACm | 1.2.1.3 |
| 219 | ALDH5, ALDHX | | 1.2.1.3 |
| 223 | ALDH9, E3 | | 1.2.1.3 |
| | | | 1.2.1.19 |
| 224 | ALDH10, FALDH, SLS | | 1.2.1.3 |
| 8854 | RALDH2 | | 1.2.1.3 |
| 1591 | CYP24 | | 1.14.—.— |
| 1592 | CYP26A1, P450RAI | | 1.14.—.— |
| 1593 | CYP27A1, CTX, CYP27 | | 1.14.—.— |
| 1594 | CYP27B1, PDDR, VDD1, VDR, CYP1, VDDR, I, P450C1 | | 1.14.—.— |
| 1.8 Pyruvate metabolism PATH:hsa00620 | | | |
| 54988 | FLJ20581 | ATP + AC + COA -> AMP + PPI + ACCOA | 6.2.1.1 |
| 31 | ACACA, ACAC, ACC | ACCOA + ATP + CO2 <-> MALCOA + ADP + PI + H | 6.4.1.2 |
| | | | 6.3.4.14 |
| 32 | ACACB, ACCB, HACC275, ACC2 | ACCOA + ATP + CO2 <-> MALCOA + ADP + PI + H | 6.4.1.2 |
| | | | 6.3.4.14 |
| 2739 | GLO1, GLYI | RGT + MTHGXL <-> LGT | 4.4.1.5 |
| 3029 | HAGH, GLO2 | LGT -> RGT + LAC | 3.1.2.6 |
| 2223 | FDH | FALD + RGT + NAD <-> FGT + NADH | 1.2.1.1 |
| 9380 | GRHPR, GLXR | | 1.1.1.79 |
| 4200 | ME2 | MALm + NADm -> CO2m + NADHm + PYRm | 1.1.1.38 |
| 10873 | ME3 | MALm + NADPm -> CO2m + NADPHm + PYRm | 1.1.1.40 |
| 29897 | HUMNDME | MAL + NADP -> CO2 + NADPH + PYR | 1.1.1.40 |
| 4199 | ME1 | MAL + NADP -> CO2 + NADPH + PYR | 1.1.1.40 |
| 38 | ACAT1, ACAT, T2, THIL, MAT | 2 ACCOAm <-> COAm + AACCOAm | 2.3.1.9 |
| 39 | ACAT2 | 2 ACCOAm <-> COAm + AACCOAm | 2.3.1.9 |
| 1.9 Glyoxylate and dicarboxylate metabolism PATH:hsa00630 | | | |
| 5240 | PGP | | 3.1.3.18 |
| 2758 | GLYD | 3HPm + NADHm -> NADm + GLYAm | 1.1.1.29 |
| 10797 | MTHFD2, NMDMC | METHF <-> FTHF | 3.5.4.9 |
| | | METTHF + NAD -> METHF + NADH | 1.5.1.15 |
| 4522 | MTHFD1 | METTHF + NADP -> METHF + NADPH | 1.5.1.15 |
| | | METHF <-> FTHF | 3.5.4.9 |
| | | THF + FOR + ATP -> ADP + PI + FTHF | 6.3.4.3 |
| 1.10 Propanoate metabolism PATH:hsa00640 | | | |
| 34 | ACADM, MCAD | MBCOAm + FADm -> MCCOAm + FADH2m | 1.3.99.3 |
| | | IBCOAm + FADm -> MACOAm + FADH2m | |
| | | IVCOAm + FADm -> MCRCOAm + FADH2m | |
| 36 | ACADSB | MBCOAm + FADm -> MCCOAm + FADH2m | 1.3.99.3 |
| | | IBCOAm + FADm -> MACOAm + FADH2m | |
| | | IVCOAm + FADm -> MCRCOAm + FADH2m | |

TABLE 1-continued

| Locus ID | Gene Ab. | Reaction Stoichiometry | E.C. |
|---|---|---|---|
| 1892 | ECHS1, SCEH | MACOAm + H2Om -> HIBCOAm | 4.2.1.17 |
| | | MCCOAm + H2Om -> MHVCOAm | |
| 1962 | EHHADH | MHVCOAm + NADm -> MAACOAm + NADHm | 1.1.1.35 |
| | | HIBm + NADm -> MMAm + NADHm | |
| | | MACOAm + H2Om -> HIBCOAm | 4.2.1.17 |
| | | MCCOAm + H2Om -> MHVCOAm | |
| 3030 | HADHA, MTPA, GBP | MHVCOAm + NADm -> MAACOAm + NADHm | 1.1.1.35 |
| | | HIBm + NADm -> MMAm + NADHm | |
| | | MACOAm + H2Om -> HIBCOAm | 4.2.1.17 |
| | | MCCOAm + H2Om -> MHVCOAm | |
| | | C160CARm + COAm + FADm + NADm -> FADH2m + | 1.1.1.35 |
| | | NADHm + C140COAm + ACCOAm | 4.2.1.17 |
| 23417 | MLYCD, MCD | | 4.1.1.9 |
| 18 | ABAT, GABAT | GABA + AKG -> SUCCSAL + GLU | 2.6.1.19 |
| 5095 | PCCA | PROPCOAm + CO2m + ATPm -> ADPm + PIm + DMMCOAm | 6.4.1.3 |
| 5096 | PCCB | PROPCOAm + CO2m + ATPm -> ADPm + PIm + DMMCOAm | 6.4.1.3 |
| 4594 | MUT, MCM | LMMCOAm -> SUCCOAm | 5.4.99.2 |
| 4329 | MMSDH | MMAm + COAm + NADm -> NADHm + CO2m + PROPCOAm | 1.2.1.27 |
| 8523 | FACVL1, VLCS, VLACS | | 6.2.1.— |
| 1.11 Butanoate metabolism PATH:hsa00650 | | | |
| 3028 | HADH2, ERAB | C140COAm + 7 COAm + 7 FADm + 7 NADm -> 7 FADH2m + 7 NADHm + 7 ACCOAm | 1.1.1.35 |
| 3033 | HADHSC, SCHAD | | 1.1.1.35 |
| 35 | ACADS, SCAD | MBCOAm + FADm -> MCCOAm + FADH2m | 1.3.99.2 |
| | | IBCOAm + FADm -> MACOAm + FADH2m | |
| 7915 | ALDH5A1, SSADH, SSDH | | 1.2.1.24 |
| 2571 | GAD1, GAD, GAD67, GAD25 | GLU -> GABA + CO2 | 4.1.1.15 |
| 2572 | GAD2 | GLU -> GABA + CO2 | 4.1.1.15 |
| 2573 | GAD3 | GLU -> GABA + CO2 | 4.1.1.15 |
| 3157 | HMGCS1, HMGCS | H3MCOA + COA <-> ACCOA + AACCOA | 4.1.3.5 |
| 3158 | HMGCS2 | H3MCOA + COA <-> ACCOA + AACCOA | 4.1.3.5 |
| 3155 | HMGCL, HL | H3MCOAm -> ACCOAm + ACTACm | 4.1.3.4 |
| 5019 | OXCT | | 2.8.3.5 |
| 622 | BDH | 3HBm + NADm -> NADHm + Hm + ACTACm | 1.1.1.30 |
| 1629 | DBT, BCATE2 | OMVALm + COAm + NADm -> MBCOAm + NADHm + CO2m | 2.3.1.— |
| | | OIVALm + COAm + NADm -> IBCOAm + NADHm + CO2m | |
| | | OICAPm + COAm + NADHm -> IVCOAm + NADHm + CO2m | |
| 1.13 Inositol metabolism PATH:hsa00031 | | | |
| 2. Energy Metabolism | | | |
| 2.1 Oxidative phosphorylation PATH:hsa00190 | | | |
| 4535 | MTND1 | NADHm + Qm + 4 Hm -> QH2m + NADm + 4 H | 1.6.5.3 |
| 4536 | MTND2 | NADHm + Qm + 4 Hm -> QH2m + NADm + 4 H | 1.6.5.3 |
| 4537 | MTND3 | NADHm + Qm + 4 Hm -> QH2m + NADm + 4 H | 1.6.5.3 |
| 4538 | MTND4 | NADHm + Qm + 4 Hm -> QH2m + NADm + 4 H | 1.6.5.3 |
| 4539 | MTND4L | NADHm + Qm + 4 Hm -> QH2m + NADm + 4 H | 1.6.5.3 |
| 4540 | MTND5 | NADHm + Qm + 4 Hm -> QH2m + NADm + 4 H | 1.6.5.3 |
| 4541 | MTND6 | NADHm + Qm + 4 Hm -> QH2m + NADm + 4 H | 1.6.5.3 |
| 4694 | NDUFA1, MWFE | NADHm + Qm + 4 Hm -> QH2m + NADm + 4 H | 1.6.5.3 |
| 4695 | NDUFA2, B8 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4696 | NDUFA3, B9 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4697 | NDUFA4, MLRQ | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4698 | NDUFA5, UQOR13, B13 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4700 | NDUFA6, B14 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4701 | NDUFA7, B14.5a, B14.5A | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4702 | NDUFA8, PGIV | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4704 | NDUFA9, NDUFS2L | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4705 | NDUFA10 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4706 | NDUFAB1, SDAP | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4707 | NDUFB1, MNLL, CI-SGDH | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4708 | NDUFB2, AGGG | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4709 | NDUFB3, B12 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4710 | NDUFB4, B15 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4711 | NDUFB5, SGDH | NADHm + Qm + 4 Hm -> QH2m + NADm + 4 H | 1.6.5.3 |
| | | NADHm + Qm + 4 Hm -> QH2m + NADm + 4 H | 1.6.99.3 |

TABLE 1-continued

| Locus ID | Gene Ab. | Reaction Stoichiometry | E.C. |
|---|---|---|---|
| 4712 | NDUFB6, B17 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4713 | NDUFB7, B18 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4714 | NDUFB8, ASHI | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4715 | NDUFB9, UQOR22, B22 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4716 | NDUFB10, PDSW | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4717 | NDUFC1, KFYI | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4718 | NDUFC2, B14.5b, B14.5B | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4724 | NDUFS4, AQDQ | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4725 | NDUFS5 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4726 | NDUFS6 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4731 | NDUFV3 | NADHm + Qm + 4 Hm -> QH2m + NADm + 4 H | 1.6.5.3 |
| 4727 | NDUFS7, PSST | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4722 | NDUFS3 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4720 | NDUFS2 | NADHm + Qm + 4 Hm -> QH2m + NADm + 4 H | 1.6.5.3 |
| 4729 | NDUFV2 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4723 | NDUFV1, UQOR1 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4719 | NDUFS1, PRO1304 | NADHm + Qm + 4 Hm -> QH2m + NADm + 4 H | 1.6.99.3 |
| | | NADHm + Qm + 4 Hm -> QH2m + NADm + 4 H | 1.6.5.3 |
| 4728 | NDUFS8 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 6391 | SDHC | SUCCm + FADm <-> FUMm + FADH2m | 1.3.5.1 |
| | | FADH2m + Qm <-> FADm + QH2m | |
| 6392 | SDHD, CBT1, PGL, PGL1 | SUCCm + FADm <-> FUMm + FADH2m | 1.3.5.1 |
| | | FADH2m + Qm <-> FADm + QH2m | |
| 6389 | SDHA, SDH2, SDHF, FP | SUCCm + FADm <-> FUMm + FADH2m | 1.3.5.1 |
| | | FADH2m + Qm <-> FADm + QH2m | |
| 6390 | SDHB, SDH1, IP, SDH | SUCCm + FADm <-> FUMm + FADH2m | 1.3.5.1 |
| | | FADH2m + Qm <-> FADm + QH2m | |
| 7386 | UQCRFS1, RIS1 | O2m + 4 FEROm + 4 Hm -> 4 FERIm + 2 H2Om + 4 H | 1.10.2.2 |
| 4519 | MTCYB | O2m + 4 FEROm + 4 Hm -> 4 FERIm + 2 H2Om + 4 H | 1.10.2.2 |
| 1537 | CYC1 | O2m + 4 FEROm + 4 Hm -> 4 FERIm + 2 H2Om + 4 H | 1.10.2.2 |
| 7384 | UQCRC1, D3S3191 | O2m + 4 FEROm + 4 Hm -> 4 FERIm + 2 H2Om + 4 H | 1.10.2.2 |
| 7385 | UQCRC2 | O2m + 4 FEROm + 4 Hm -> 4 FERIm + 2 H2Om + 4 H | 1.10.2.2 |
| 7388 | UQCRH | O2m + 4 FEROm + 4 Hm -> 4 FERIm + 2 H2Om + 4 H | 1.10.2.2 |
| 7381 | UQCRB, QPC, UQBP, QP-C | O2m + 4 FEROm + 4 Hm -> 4 FERIm + 2 H2Om + 4 H | 1.10.2.2 |
| 27089 | QP-C | O2m + 4 FEROm + 4 Hm -> 4 FERIm + 2 H2Om + 4 H | 1.10.2.2 |
| 10975 | UQCR | O2m + 4 FEROm + 4 Hm -> 4 FERIm + 2 H2Om + 4 H | 1.10.2.2 |
| 1333 | COX5BL4 | QH2m + 2 FERIm + 4 Hm -> Qm + 2 FEROm + 4 H | 1.9.3.1 |
| 4514 | MTCO3 | QH2m + 2 FERIm + 4 Hm -> Qm + 2 FEROm + 4 H | 1.9.3.1 |
| 4512 | MTCO1 | QH2m + 2 FERIm + 4 Hm -> Qm + 2 FEROm + 4 H | 1.9.3.1 |
| 4513 | MTCO2 | QH2m + 2 FERIm + 4 Hm -> Qm + 2 FEROm + 4 H | 1.9.3.1 |
| 1329 | COX5B | QH2m + 2 FERIm + 4 Hm -> Qm + 2 FEROm + 4 H | 1.9.3.1 |
| 1327 | COX4 | QH2m + 2 FERIm + 4 Hm -> Qm + 2 FEROm + 4 H | 1.9.3.1 |
| 1337 | COX6A1, COX6A | QH2m + 2 FERIm + 4 Hm -> Qm + 2 FEROm + 4 H | 1.9.3.1 |
| 1339 | COX6A2 | QH2m + 2 FERIm + 4 Hm -> Qm + 2 FEROm + 4 H | 1.9.3.1 |
| 1340 | COX6B | QH2m + 2 FERIm + 4 Hm -> Qm + 2 FEROm + 4 H | 1.9.3.1 |
| 1345 | COX6C | QH2m + 2 FERIm + 4 Hm -> Qm + 2 FEROm + 4 H | 1.9.3.1 |
| 9377 | COX5A, COX, VA, COX-VA | QH2m + 2 FERIm + 4 Hm -> Qm + 2 FEROm + 4 H | 1.9.3.1 |
| 1346 | COX7A1, COX7AM, COX7A | QH2m + 2 FERIm + 4 Hm -> Qm + 2 FEROm + 4 H | 1.9.3.1 |
| 1347 | COX7A2, COX VIIa-L | QH2m + 2 FERIm + 4 Hm -> Qm + 2 FEROm + 4 H | 1.9.3.1 |
| 1348 | COX7A3 | QH2m + 2 FERIm + 4 Hm -> Qm + 2 FEROm + 4 H | 1.9.3.1 |
| 1349 | COX7B | QH2m + 2 FERIm + 4 Hm -> Qm + 2 FEROm + 4 H | 1.9.3.1 |
| 9167 | COX7A2L, COX7RP, EB1 | QH2m + 2 FERIm + 4 Hm -> Qm + 2 FEROm + 4 H | 1.9.3.1 |
| 1350 | COX7C | QH2m + 2 FERIm + 4 Hm -> Qm + 2 FEROm + 4 H | 1.9.3.1 |
| 1351 | COX8, COX VIII | QH2m + 2 FERIm + 4 Hm -> Qm + 2 FEROm + 4 H | 1.9.3.1 |
| 4508 | MTATP6 | ADPm + Pim + 3 H -> ATPm + 3 Hm + H2Om | 3.6.1.34 |
| 4509 | MTATP8 | ADPm + Pim + 3 H -> ATPm + 3 Hm + H2Om | 3.6.1.34 |
| 499 | ATP5A2 | ADPm + Pim + 3 H -> ATPm + 3 Hm + H2Om | 3.6.1.34 |
| 507 | ATP5BL1, ATP5BL1 | ADPm + Pim + 3 H -> ATPm + 3 Hm + H2Om | 3.6.1.34 |
| 508 | ATP5BL2, ATP5BL2 | ADPm + Pim + 3 H -> ATPm + 3 Hm + H2Om | 3.6.1.34 |
| 519 | ATP5H | ADPm + Pim + 3 H -> ATPm + 3 Hm + H2Om | 3.6.1.34 |
| 537 | ATP6S1, ORF, VATPS1, XAP-3 | ADPm + Pim + 3 H -> ATPm + 3 Hm + H2Om | 3.6.1.34 |
| 514 | ATP5E | ADPm + Pim + 3 H -> ATPm + 3 Hm + H2Om | 3.6.1.34 |
| 513 | ATP5D | ADPm + Pim + 3 H -> ATPm + 3 Hm + H2Om | 3.6.1.34 |

TABLE 1-continued

| Locus ID | Gene Ab. | Reaction Stoichiometry | E.C. |
|---|---|---|---|
| 506 | ATP5B, ATPSB | ADPm + Pim + 3 H -> ATPm + 3 Hm + H2Om | 3.6.1.34 |
| 509 | ATP5C1, ATP5C | ADPm + Pim + 3 H -> ATPm + 3 Hm + H2Om | 3.6.1.34 |
| 498 | ATP5A1, ATP5A, ATPM, OMR, HATP1 | ADPm + Pim + 3 H -> ATPm + 3 Hm + H2Om | 3.6.1.34 |
| 539 | ATP5O, ATPO, OSCP | ADPm + Pim + 3 H -> ATPm + 3 Hm + H2Om | 3.6.1.34 |
| 516 | ATP5G1, ATP5G | ADPm + Pim + 3 H -> ATPm + 3 Hm + H2Om | 3.6.1.34 |
| 517 | ATP5G2 | ADPm + Pim + 3 H -> ATPm + 3 Hm + H2Om | 3.6.1.34 |
| 518 | ATP5G3 | ADPm + Pim + 3 H -> ATPm + 3 Hm + H2Om | 3.6.1.34 |
| 515 | ATP5F1 | ADPm + Pim + 3 H -> ATPm + 3 Hm + H2Om | 3.6.1.34 |
| 521 | ATP5I | ADPm + Pim + 3 H -> ATPm + 3 Hm + H2Om | 3.6.1.34 |
| 522 | ATP5J, ATP5A, ATPM, ATP5 | ADPm + Pim + 3 H -> ATPm + 3 Hm + H2Om | 3.6.1.34 |
| 9551 | ATP5J2, ATP5JL, F1FO-ATPASE | ADPm + Pim + 3 H -> ATPm + 3 Hm + H2Om | 3.6.1.34 |
| 10476 | ATP5JD | ADPm + Pim + 3 H -> ATPm + 3 Hm + H2Om | 3.6.1.34 |
| 10632 | ATP5JG | ADPm + Pim + 3 H -> ATPm + 3 Hm + H2Om | 3.6.1.34 |
| 9296 | ATP6S14 | ADPm + Pim + 3 H -> ATPm + 3 Hm + H2Om | 3.6.1.34 |
| 528 | ATP6D | ADPm + Pim + 3 H -> ATPm + 3 Hm + H2Om | 3.6.1.34 |
| 523 | ATP6A1, VPP2 | ADPm + Pim + 3 H -> ATPm + 3 Hm + H2Om | 3.6.1.34 |
| 524 | ATP6A2, VPP2 | ADPm + Pim + 3 H -> ATPm + 3 Hm + H2Om | 3.6.1.34 |
| 525 | ATP6B1, VPP3, VATB | ADPm + Pim + 3 H -> ATPm + 3 Hm + H2Om | 3.6.1.34 |
| 526 | ATP6B2, VPP3 | ADPm + Pim + 3 H -> ATPm + 3 Hm + H2Om | 3.6.1.34 |
| 529 | ATP6E | ADPm + Pim + 3 H -> ATPm + 3 Hm + H2Om | 3.6.1.34 |
| 527 | ATP6C, ATPL | ADPm + Pim + 3 H -> ATPm + 3 Hm + H2Om | 3.6.1.34 |
| 533 | ATP6F | ADPm + Pim + 3 H -> ATPm + 3 Hm + H2Om | 3.6.1.34 |
| 10312 | TCIRG1, TIRC7, OC-116, OC-116 kDa, OC-116 KDA, ATP6N1C | ADPm + Pim + 3 H -> ATPm + 3 Hm + H2Om | 3.6.1.34 |
| 23545 | TJ6 | ADPm + Pim + 3 H -> ATPm + 3 Hm + H2Om | 3.6.1.34 |
| 50617 | ATP6N1B | ADPm + Pim + 3 H -> ATPm + 3 Hm + H2Om | 3.6.1.34 |
| 535 | ATP6N1 | ADPm + Pim + 3 H -> ATPm + 3 Hm + H2Om | 3.6.1.34 |
| 51382 | VATD | ADPm + Pim + 3 H -> ATPm + 3 Hm + H2Om | 3.6.1.34 |
| 8992 | ATP6H | ADPm + Pim + 3 H -> ATPm + 3 Hm + H2Om | 3.6.1.34 |
| 9550 | ATP6J | ADPm + Pim + 3 H -> ATPm + 3 Hm + H2Om | 3.6.1.34 |
| 51606 | LOC51606 | ADPm + Pim + 3 H -> ATPm + 3 Hm + H2Om | 3.6.1.34 |
| 495 | ATP4A, ATP6A | ATP + H + Kxt + H2O <-> ADP + PI + Hext + K | 3.6.1.36 |
| 496 | ATP4B, ATP6B | ATP + H + Kxt + H2O <-> ADP + PI + Hext + K | 3.6.1.36 |
| 476 | ATP1A1 | ATP + 3 NA + 2 Kxt + H2O <-> ADP + 3 NAxt + 2 K + PI | 3.6.1.37 |
| 477 | ATP1A2 | ATP + 3 NA + 2 Kxt + H2O <-> ADP + 3 NAxt + 2 K + PI | 3.6.1.37 |
| 478 | ATP1A3 | ATP + 3 NA + 2 Kxt + H2O <-> ADP + 3 NAxt + 2 K + PI | 3.6.1.37 |
| 479 | ATP1AL1 | ATP + 3 NA + 2 Kxt + H2O <-> ADP + 3 NAxt + 2 K + PI | 3.6.1.37 |
| 23439 | ATP1B4 | ATP + 3 NA + 2 Kxt + H2O <-> ADP + 3 NAxt + 2 K + PI | 3.6.1.37 |
| 481 | ATP1B1, ATP1B | ATP + 3 NA + 2 Kxt + H2O <-> ADP + 3 NAxt + 2 K + PI | 3.6.1.37 |
| 482 | ATP1B2, AMOG | ATP + 3 NA + 2 Kxt + H2O <-> ADP + 3 NAxt + 2 K + PI | 3.6.1.37 |
| 483 | ATP1B3 | ATP + 3 NA + 2 Kxt + H2O <-> ADP + 3 NAxt + 2 K + PI | 3.6.1.37 |
| 27032 | ATP2C1, ATP2C1A, PMR1 | ATP + 2 CA + H2O <-> ADP + PI + 2 CAxt | 3.6.1.38 |
| 487 | ATP2A1, SERCA1, ATP2A | ATP + 2 CA + H2O <-> ADP + PI + 2 CAxt | 3.6.1.38 |
| 488 | ATP2A2, ATP2B, SERCA2, DAR, DD | ATP + 2 CA + H2O <-> ADP + PI + 2 CAxt | 3.6.1.38 |
| 489 | ATP2A3, SERCA3 | ATP + 2 CA + H2O <-> ADP + PI + 2 CAxt | 3.6.1.38 |
| 490 | ATP2B1, PMCA1 | ATP + 2 CA + H2O <-> ADP + PI + 2 CAxt | 3.6.1.38 |
| 491 | ATP2B2, PMCA2 | ATP + 2 CA + H2O <-> ADP + PI + 2 CAxt | 3.6.1.38 |
| 492 | ATP2B3, PMCA3 | ATP + 2 CA + H2O <-> ADP + PI + 2 CAxt | 3.6.1.38 |
| 493 | ATP2B4, ATP2B2, PMCA4 | ATP + 2 CA + H2O <-> ADP + PI + 2 CAxt | 3.6.1.38 |
| 538 | ATP7A, MK, MNK, OHS | ATP + H2O + Cu2 -> ADP + PI + Cu2xt | 3.6.3.4 |
| 540 | ATP7B, WND | ATP + H2O + Cu2 -> ADP + PI + Cu2xt | 3.6.3.4 |
| 5464 | PP, SID6-8061 | PPI -> 2 PI | 3.6.1.1 |
| 2.2 Photosynthesis PATH:hsa00195 | | | |
| 2.3 Carbon fixation PATH:hsa00710 | | | |
| 2805 | GOT1 | OAm + GLUm <-> ASPm + AKGm | 2.6.1.1 |
| 2806 | GOT2 | OA + GLU <-> ASP + AKG | 2.6.1.1 |
| 2875 | GPT | PYR + GLU <-> AKG + ALA | 2.6.1.2 |
| 2.4 Reductive carboxylate cycle (CO2 fixation) PATH:hsa00720 | | | |
| 2.5 Methane metabolism PATH:hsa00680 | | | |
| 847 | CAT | 2 H2O2 -> O2 | 1.11.1.6 |
| 4025 | LPO, SPO | | 1.11.1.7 |
| 4353 | MPO | | 1.11.1.7 |
| 8288 | EPX, EPX-PEN, EPO, EPP | | 1.11.1.7 |
| 9588 | KIAA0106, AOP2 | | 1.11.1.7 |
| 6470 | SHMT1, CSHMT | THF + SER <-> GLY + METTHF | 2.1.2.1 |
| 6472 | SHMT2, GLYA, SHMT | THFm + SERm <-> GLYm + METTHFm | 2.1.2.1 |
| 51004 | LOC51004 | 2OPMPm + O2m -> 2OPMBm<br>2OPMMBm + O2m -> 2OMHMBm | 1.14.13.— |
| 9420 | CYP7B1 | 2OPMPm + O2m -> 2OPMBm<br>2OPMMBm + O2m -> 2OMHMBm | 1.14.13.— |
| 2.6 Nitrogen metabolism PATH:hsa00910 | | | |
| 11238 | CA5B | | 4.2.1.1 |
| 23632 | CA14 | | 4.2.1.1 |
| 759 | CA1 | | 4.2.1.1 |
| 760 | CA2 | | 4.2.1.1 |
| 761 | CA3, CAIII | | 4.2.1.1 |
| 762 | CA4, CAIV | | 4.2.1.1 |
| 763 | CA5A, CA5, CAV, CAVA | | 4.2.1.1 |

TABLE 1-continued

| Locus ID | Gene Ab. | Reaction Stoichiometry | E.C. |
|---|---|---|---|
| 765 | CA6 | | 4.2.1.1 |
| 766 | CA7 | | 4.2.1.1 |
| 767 | CA8, CALS, CARP | | 4.2.1.1 |
| 768 | CA9, MN | | 4.2.1.1 |
| 770 | CA11, CARP2 | | 4.2.1.1 |
| 771 | CA12 | | 4.2.1.1 |
| 1373 | CPS1 | GLUm + CO2m + 2 ATPm -> 2 ADPm + 2 PIm + CAPm | 6.3.4.16 |
| 275 | AMT | GLYm + THFm + NADm <-> METTHFm + NADHm + CO2m + NH3m | 2.1.2.10 |
| 3034 | HAL, HSTD, HIS | HIS -> NH3 + URO | 4.3.1.3 |
| 2746 | GLUD1, GLUD | AKGm + NADHm + NH3m <-> NADm + H2Om + GLUm | 1.4.1.3 |
| | | AKGm + NADPHm + NH3m <-> NADPm + H2Om + GLUm | |
| 8307 | GLUD2 | AKGm + NADHm + NH3m <-> NADm + H2Om + GLUm | 1.4.1.3 |
| | | AKGm + NADPHm + NH3m <-> NADPm + H2Om + GLUm | |
| 2752 | GLUL, GLNS | GLUm + NH3m + ATPm -> GLNm + ADPm + Pim | 6.3.1.2 |
| 22842 | KIAA0838 | GLN -> GLU + NH3 | 3.5.1.2 |
| 27165 | GA | GLN -> GLU + NH3 | 3.5.1.2 |
| 2744 | GLS | GLNm -> GLUm + NH3m | 3.5.1.2 |
| 440 | ASNS | ASPm + ATPm + GLNm -> GLUm + ASNm + AMPm + PPIm | 6.3.5.4 |
| 1491 | CTH | LLCT + H2O -> CYS + HSER | 4.4.1.1 |
| | | OBUT + NH3 <-> HSER | 4.4.1.1 |
| 2.7 Sulfur metabolism PATH:hsa00920 | | | |
| 9060 | PAPSS2, ATPSK2, SK2 | APS + ATP -> ADP + PAPS | 2.7.1.25 |
| | | SLF + ATP -> PPI + APS | 2.7.7.4 |
| 9061 | PAPSS1, ATPSK1, SK1 | APS + ATP -> ADP + PAPS | 2.7.1.25 |
| | | SLF + ATP -> PPI + APS | 2.7.7.4 |
| 10380 | BPNT1 | PAP -> AMP + PI | 3.1.3.7 |
| 6799 | SULT1A2 | | 2.8.2.1 |
| 6817 | SULT1A1, STP1 | | 2.8.2.1 |
| 6818 | SULT1A3, STM | | 2.8.2.1 |
| 6822 | SULT2A1, STD | | 2.8.2.2 |
| 6783 | STE, EST | | 2.8.2.4 |
| 6821 | SUOX | | 1.8.3.1 |
| 3. Lipid Metabolism | | | |
| 3.1 Fatty acid biosynthesis (path 1) PATH:hsa00061 | | | |
| 2194 | FASN | | 2.3.1.85 |
| 3.2 Fatty acid biosynthesis (path 2) PATH:hsa00062 | | | |
| 10449 | ACAA2, DSAEC | MAACOAm -> ACCOAm + PROPCOAm | 2.3.1.16 |
| 30 | ACAA1, ACAA | MAACOA -> ACCOA + PROPCOA | 2.3.1.16 |
| 3032 | HADHB | MAACOA -> ACCOA + PROPCOA | 2.3.1.16 |
| 3.3 Fatty acid metabolism PATH:hsa00071 | | | |
| 51 | ACOX1, ACOX | | 1.3.3.6 |
| 33 | ACADL, LCAD | | 1.3.99.13 |
| 2639 | GCDH | | 1.3.99.7 |
| 2179 | FACL1, LACS | ATP + LCCA + COA <-> AMP + PPI + ACOA | 6.2.1.3 |
| 2180 | FACL2, FACL1, LACS2 | ATP + LCCA + COA <-> AMP + PPI + ACOA | 6.2.1.3 |
| 2182 | FACL4, ACS4 | ATP + LCCA + COA <-> AMP + PPI + ACOA | 6.2.1.3 |
| 1374 | CPT1A, CPT1, CPT1-L | | 2.3.1.21 |
| 1375 | CPT1B, CPT1-M | | 2.3.1.21 |
| 1376 | CPT2, CPT1, CPTASE | | 2.3.1.21 |
| 1632 | DCI | | 5.3.3.8 |
| 11283 | CYP4F8 | | 1.14.14.1 |
| 1543 | CYP1A1, CYP1 | | 1.14.14.1 |
| 1544 | CYP1A2 | | 1.14.14.1 |
| 1545 | CYP1B1, GLC3A | | 1.14.14.1 |
| 1548 | CYP2A6, CYP2A3 | | 1.14.14.1 |
| 1549 | CYP2A7 | | 1.14.14.1 |
| 1551 | CYP3A7 | | 1.14.14.1 |
| 1553 | CYP2A13 | | 1.14.14.1 |
| 1554 | CYP2B | | 1.14.14.1 |
| 1555 | CYP2B6 | | 1.14.14.1 |
| 1557 | CYP2C19, CYP2C, P450IIC19 | | 1.14.14.1 |
| 1558 | CYP2C8 | | 1.14.14.1 |
| 1559 | CYP2C9, P450IIC9, CYP2C10 | | 1.14.14.1 |
| 1562 | CYP2C18, P450IIC17, CYP2C17 | | 1.14.14.1 |
| 1565 | CYP2D6 | | 1.14.14.1 |
| 1571 | CYP2E, CYP2E1, P450C2E | | 1.14.14.1 |
| 1572 | CYP2F1, CYP2F | | 1.14.14.1 |
| 1573 | CYP2J2 | | 1.14.14.1 |
| 1575 | CYP3A3 | | 1.14.14.1 |
| 1576 | CYP3A4 | | 1.14.14.1 |
| 1577 | CYP3A5, PCN3 | | 1.14.14.1 |
| 1580 | CYP4B1 | | 1.14.14.1 |
| 1588 | CYP19, ARO | | 1.14.14.1 |
| 1595 | CYP51 | | 1.14.14.1 |
| 194 | AHHR, AHH | | 1.14.14.1 |

TABLE 1-continued

| Locus ID | Gene Ab. | Reaction Stoichiometry | E.C. |
|---|---|---|---|
| 3.4 Synthesis and degradation of ketone bodies PATH:hsa00072 | | | |
| 3.5 Sterol biosynthesis PATH:hsa00100 | | | |
| 3156 | HMGCR | MVL + COA + 2 NADP <-> H3MCOA + 2 NADPH | 1.1.1.34 |
| 4598 | MVK, MVLK | ATP + MVL -> ADP + PMVL | 2.7.1.36 |
| | | CTP + MVL -> CDP + PMVL | |
| | | GTP + MVL -> GDP + PMVL | |
| | | UTP + MVL -> UDP + PMVL | |
| 10654 | PMVK, PMKASE, PMK, HUMPMKI | ATP + PMVL -> ADP + PPMVL | 2.7.4.2 |
| 4597 | MVD, MPD | ATP + PPMVL -> ADP + PI + IPPP + CO2 | 4.1.1.33 |
| 3422 | IDI1 | IPPP <-> DMPP | 5.3.3.2 |
| 2224 | FDPS | GPP + IPPP -> FPP + PPI | 2.5.1.10 |
| | | DMPP + IPPP -> GPP + PPI | 2.5.1.1 |
| 9453 | GGPS1, GGPPS | DMPP + IPPP -> GPP + PPI | 2.5.1.1 |
| | | GPP + IPPP -> FPP + PPI | 2.5.1.10 |
| | | | 2.5.1.29 |
| 2222 | FDFT1, DGPT | 2 FPP + NADPH -> NADP + SQL | 2.5.1.21 |
| 6713 | SQLE | SQL + O2 + NADP -> S23E + NADPH | 1.14.99.7 |
| 4047 | LSS, OSC | S23E -> LNST | 5.4.99.7 |
| 1728 | DIA4, NMOR1, NQO1, NMORI | | 1.6.99.2 |
| 4835 | NMOR2, NQO2 | | 1.6.99.2 |
| 37 | ACADVL, VLCAD, LCACD | | 1.3.99.— |
| 3.6 Bile acid biosynthesis PATH:hsa00120 | | | |
| 1056 | CEL, BSSL, BAL | | 3.1.1.3 |
| | | | 3.1.1.13 |
| 3988 | LIPA, LAL | | 3.1.1.13 |
| 6646 | SOAT1, ACAT, STAT, SOAT, ACAT1, ACACT | | 2.3.1.26 |
| 1581 | CYP7A1, CYP7 | | 1.14.13.17 |
| 6715 | SRD5A1 | | 1.3.99.5 |
| 6716 | SRD5A2 | | 1.3.99.5 |
| 6718 | AKR1D1, SRD5B1, 3o5bred | | 1.3.99.6 |
| 570 | BAAT, BAT | | 2.3.1.65 |
| 3.7 C21-Steroid hormone metabolism PATH:hsa00140 | | | |
| 1583 | CYP11A, P450SCC | IMZYMST -> IIMZYMST + CO2 | 1.14.15.6 |
| 3283 | HSD3B1, HSD3B, HSDB3 | IMZYMST -> IIMZYMST + CO2 | 5.3.3.1 |
| | | IMZYMST -> IIZYMST + CO2 | 1.1.1.145 |
| 3284 | HSD3B2 | IMZYMST -> IIMZYMST + CO2 | 5.3.3.1 |
| | | IMZYMST -> IIZYMST + CO2 | 1.1.1.145 |
| 1589 | CYP21A2, CYP21, P450C21B, CA21H, CYP21B, P450c21B | | 1.14.99.10 |
| 1586 | CYP17, P450C17 | | 1.14.99.9 |
| 1584 | CYP11B1, P450C11, CYP11B | | 1.14.15.4 |
| 1585 | CYP11B2, CYP11B | | 1.14.15.4 |
| 3290 | HSD11B1, HSD11, HSD11L, HSD11B | | 1.1.1.146 |
| 3291 | HSD11B2, HSD11K | | 1.1.1.146 |
| 3.8 Androgen and estrogen metabolism PATH:hsa00150 | | | |
| 3292 | HSD17B1, EDH17B2, EDHB17, HSD17 | | 1.1.1.62 |
| 3293 | HSD17B3, EDH17B3 | | 1.1.1.62 |
| 3294 | HSD17B2, EDH17B2 | | 1.1.1.62 |
| 3295 | HSD17B4 | | 1.1.1.62 |
| 3296 | HSD17BP1, EDH17B1, EDHB17, HSD17 | | 1.1.1.62 |
| 51478 | HSD17B7, PRAP | | 1.1.1.62 |
| 412 | STS, ARSC, ARSC1, SSDD | | 3.1.6.2 |
| 414 | ARSD | | 3.1.6.1 |
| 415 | ARSE, CDPX1, CDPXR, CDPX | | 3.1.6.1 |
| 11185 | INMT | | 2.1.1.— |
| 24140 | JM23 | | 2.1.1.— |
| 29104 | N6AMT1, PRED28 | | 2.1.1.— |
| 29960 | FJH1 | | 2.1.1.— |
| 3276 | HRMT1L2, HCP1, PRMT1 | | 2.1.1.— |
| 51628 | LOC51628 | | 2.1.1.— |
| 54743 | HASJ4442 | | 2.1.1.— |
| 27292 | HSA9761 | | 2.1.1.— |
| 4. Nucleotide Metabolism | | | |
| 4.1 Purine metabolism PATH:hsa00230 | | | |
| 11164 | NUDT5, HYSAH1, YSA1H | | 3.6.1.13 |
| 5471 | PPAT, GPAT | PRPP + GLN -> PPI + GLU + PRAM | 2.4.2.14 |
| 2618 | GART, PGFT, PRGS | PRAM + ATP + GLY <-> ADP + PI + GAR | 6.3.4.13 |
| | | FGAM + ATP -> ADP + PI + AIR | 6.3.3.1 |
| | | GAR + FTHF -> THF + FGAR | 2.1.2.2 |
| 5198 | PFAS, FGARAT, KIAA0361, PURL | FGAR + ATP + GLN -> GLU + ADP + PI + FGAM | 6.3.5.3 |
| 10606 | ADE2H1 | CAIR + ATP + ASP <-> ADP + PI + SAICAR | 6.3.2.6 |
| | | CAIR <-> AIR + CO2 | 4.1.1.21 |
| 5059 | PAICS, AIRC, PAIS | CAIR + ATP + ASP <-> ADP + PI + SAICAR | 6.3.2.6 |

TABLE 1-continued

| Locus ID | Gene Ab. | Reaction Stoichiometry | E.C. |
|---|---|---|---|
| 158 | ADSL | ASUC <-> FUM + AMP | 4.3.2.2 |
| 471 | ATIC, PURH | AICAR + FTHF <-> THF + PRFICA | 2.1.2.3 |
|  |  | PRFICA <-> IMP | 3.5.4.10 |
| 3251 | HPRT1, HPRT, HGPRT | HYXAN + PRPP -> PPI + IMP | 2.4.2.8 |
|  |  | GN + PRPP -> PPI + GMP |  |
| 3614 | IMPDH1 | IMP + NAD -> NADH + XMP | 1.1.1.205 |
| 3615 | IMPDH2 | IMP + NAD -> NADH + XMP | 1.1.1.205 |
| 8833 | GMPS |  | 6.3.5.2 |
| 14923 |  |  |  |
| 2987 | GUK1 | GMP + ATP <-> GDP + ADP | 2.7.4.8 |
|  |  | DGMP + ATP <-> DGDP + ADP |  |
|  |  | GMP + DATP <-> GDP + DADP |  |
| 2988 | GUK2 | GMP + ATP <-> GDP + ADP | 2.7.4.8 |
|  |  | DGMP + ATP <-> DGDP + ADP |  |
|  |  | GMP + DATP <-> GDP + DADP |  |
| 10621 | RPC39 |  | 2.7.7.6 |
| 10622 | RPC32 |  | 2.7.7.6 |
| 10623 | RPC62 |  | 2.7.7.6 |
| 11128 | RPC155 |  | 2.7.7.6 |
| 25885 | DKFZP586M0122 |  | 2.7.7.6 |
| 30834 | ZNRD1 |  | 2.7.7.6 |
| 51082 | LOC51082 |  | 2.7.7.6 |
| 51728 | LOC51728 |  | 2.7.7.6 |
| 5430 | POLR2A, RPOL2, POLR2, POLRA |  | 2.7.7.6 |
| 5431 | POLR2B, POL2RB |  | 2.7.7.6 |
| 5432 | POLR2C |  | 2.7.7.6 |
| 5433 | POLR2D, HSRBP4, HSRPB4 |  | 2.7.7.6 |
| 5434 | POLR2E, RPB5, XAP4 |  | 2.7.7.6 |
| 5435 | POLR2F, RPB6, HRBP14.4 |  | 2.7.7.6 |
| 5436 | POLR2G, RPB7 |  | 2.7.7.6 |
| 5437 | POLR2H, RPB8, RPB17 |  | 2.7.7.6 |
| 5438 | POLR2I |  | 2.7.7.6 |
| 5439 | POLR2J |  | 2.7.7.6 |
| 5440 | POLR2K, RPB7.0 |  | 2.7.7.6 |
| 5441 | POLR2L, RPB7.6, RPB10 |  | 2.7.7.6 |
| 5442 | POLRMT, APOLMT |  | 2.7.7.6 |
| 54479 | FLJ10816, Rpo1-2 |  | 2.7.7.6 |
| 55703 | FLJ10388 |  | 2.7.7.6 |
| 661 | BN51T |  | 2.7.7.6 |
| 9533 | RPA40, RPA39 |  | 2.7.7.6 |
| 10721 | POLQ |  | 2.7.7.7 |
| 11232 | POLG2, MTPOLB, HP55, POLB |  | 2.7.7.7 |
| 23649 | POLA2 |  | 2.7.7.7 |
| 5422 | POLA |  | 2.7.7.7 |
| 5423 | POLB |  | 2.7.7.7 |
| 5424 | POLD1, POLD |  | 2.7.7.7 |
| 5425 | POLD2 |  | 2.7.7.7 |
| 5426 | POLE |  | 2.7.7.7 |
| 5427 | POLE2 |  | 2.7.7.7 |
| 5428 | POLG |  | 2.7.7.7 |
| 5980 | REV3L, POLZ, REV3 |  | 2.7.7.7 |
| 7498 | XDH |  | 1.1.3.22 |
|  |  |  | 1.1.1.204 |
| 9615 | GDA KIAA1258, CYPIN, NEDASIN |  | 3.5.4.3 |
| 2766 | GMPR |  | 1.6.6.8 |
| 51292 | LOC51292 |  | 1.6.6.8 |
| 7377 | UOX |  | 1.7.3.3 |
| 6240 | RRM1 | ADP + RTHIO -> DADP + OTHIO | 1.17.4.1 |
|  |  | GDP + RTHIO -> DGDP + OTHIO |  |
|  |  | CDP + RTHIO -> DCDP + OTHIO |  |
|  |  | UDP + RTHIO -> DUDP + OTHIO |  |
| 6241 | RRM2 | ADP + RTHIO -> DADP + OTHIO | 1.17.4.1 |
|  |  | GDP + RTHIO -> DGDP + OTHIO |  |
|  |  | CDP + RTHIO -> DCDP + OTHIO |  |
|  |  | UDP + RTHIO -> DUDP + OTHIO |  |
| 4860 | NP, PNP | AND + PI <-> AD + R1P | 2.4.2.1 |
|  |  | GSN + PI <-> GN + R1P |  |
|  |  | DA + PI <-> AD + R1P |  |
|  |  | DG + PI <-> GN + R1P |  |
|  |  | DIN + PI <-> HYXAN + R1P |  |
|  |  | INS + PI <-> HYXAN + R1P |  |
|  |  | XTSINE + PI <-> XAN + R1P |  |
| 1890 | ECGF1, hPD-ECGF | DU + PI <-> URA + DR1P | 2.4.2.4 |
|  |  | DT + PI <-> THY + DR1P |  |
| 353 | APRT | AD + PRPP -> PPI + AMP | 2.4.2.7 |
| 132 | ADK | ADN + ATP -> AMP + ADP | 2.7.1.20 |
| 1633 | DCK |  | 2.7.1.74 |
| 1716 | DGUOK |  | 2.7.1.113 |

TABLE 1-continued

| Locus ID | Gene Ab. | Reaction Stoichiometry | E.C. |
|---|---|---|---|
| 203 | AK1 | ATP + AMP <-> 2 ADP<br>GTP + AMP <-> ADP + GDP<br>ITP + AMP <-> ADP + IDP | 2.7.4.3 |
| 204 | AK2 | ATP + AMP <-> 2 ADP<br>GTP + AMP <-> ADP + GDP<br>ITP + AMP <-> ADP + IDP | 2.7.4.3 |
| 205 | AK3 | ATP + AMP <-> 2 ADP<br>GTP + AMP <-> ADP + GDP<br>ITP + AMP <-> ADP + IDP | 2.7.4.3 |
| 26289 | AK5 | ATP + AMP <-> 2 ADP<br>GTP + AMP <-> ADP + GDP<br>ITP + AMP <-> ADP + IDP | 2.7.4.3 |
| 4830 | NME1, NM23, NM23-H1 | UDP + ATP <-> UTP + ADP<br>CDP + ATP <-> CTP + ADP<br>GDP + ATP <-> GTP + ADP<br>IDP + ATP <-> ITP + IDP<br>DGDP + ATP <-> DGTP + ADP<br>DUDP + ATP <-> DUTP + ADP<br>DCDP + ATP <-> DCTP + ADP<br>DTDP + ATP <-> DTTP + ADP<br>DADP + ATP <-> DATP + ADP | 2.7.4.6 |
| 4831 | NME2, NM23-H2 | UDP + ATP <-> UTP + ADP<br>CDP + ATP <-> CTP + ADP<br>GDP + ATP <-> GTP + ADP<br>IDP + ATP <-> ITP + IDP<br>DGDP + ATP <-> DGTP + ADP<br>DUDP + ATP <-> DUTP + ADP<br>DCDP + ATP <-> DCTP + ADP<br>DTDP + ATP <-> DTTP + ADP<br>DADP + ATP <-> DATP + ADP | 2.7.4.6 |
| 4832 | NME3, DR-nm23, DR-NM23 | UDP + ATP <-> UTP + ADP<br>CDP + ATP <-> CTP + ADP<br>GDP + ATP <-> GTP + ADP<br>IDP + ATP <-> ITP + IDP<br>DGDP + ATP <-> DGTP + ADP<br>DUDP + ATP <-> DUTP + ADP<br>DCDP + ATP <-> DCTP + ADP<br>DTDP + ATP <-> DTTP + ADP<br>DADP + ATP <-> DATP + ADP | 2.7.4.6 |
| 4833 | NME4 | UDPm + ATPm <-> UTPm + ADPm<br>CDPm + ATPm <-> CTPm + ADPm<br>GDPm + ATPm <-> GTPm + ADPm<br>IDPm + ATPm <-> ITPm + IDPm<br>DGDPm + ATPm <-> DGTPm + ADPm<br>DUDPm + ATPm <-> DUTPm + ADPm<br>DCDPm + ATPm <-> DCTPm + ADPm<br>DTDPm + ATPm <-> DTTPm + ADPm<br>DADPm + ATPm <-> DATPm + ADPm | 2.7.4.6 |
| 22978 | NT5B, PNT5, NT5B-PENDING | AMP + H2O -> PI + ADN<br>GMP -> PI + GSN<br>CMP -> CYTD + PI<br>UMP -> PI + URI<br>IMP -> PI + INS<br>DUMP -> DU + PI<br>DTMP -> DT + PI<br>DAMP -> DA + PI<br>DGMP -> DG + PI<br>DCMP -> DC + PI<br>XMP -> PI + XTSINE | 3.1.3.5 |
| 4877 | NT3 | AMP -> PI + ADN<br>GMP -> PI + GSN<br>CMP -> CYTD + PI<br>UMP -> PI + URI<br>IMP -> PI + INS<br>DUMP -> DU + PI<br>DTMP -> DT + PI<br>DAMP -> DA + PI<br>DGMP -> DG + PI<br>DCMP -> DC + PI<br>XMP -> PI + XTSINE | 3.1.3.5 |
| 4907 | NT5, CD73 | AMP -> PI + ADN<br>GMP -> PI + GSN<br>CMP -> CYTD + PI<br>UMP -> PI + URI<br>IMP -> PI + INS<br>DUMP -> DU + PI<br>DTMP -> DT + PI<br>DAMP -> DA + PI | 3.1.3.5 |

TABLE 1-continued

| Locus ID | Gene Ab. | Reaction Stoichiometry | E.C. |
|---|---|---|---|
| | | DGMP -> DG + PI | |
| | | DCMP -> DC + PI | |
| | | XMP -> PI + XTSINE | |
| 7370 | UMPH2 | AMP -> PI + ADN | 3.1.3.5 |
| | | GMP -> PI + GSN | |
| | | CMP -> CYTD + PI | |
| | | UMP -> PI + URI | |
| | | IMP -> PI + INS | |
| | | DUMP -> DU + PI | |
| | | DTMP -> DT + PI | |
| | | DAMP -> DA + PI | |
| | | DGMP -> DG + PI | |
| | | DCMP -> DC + PI | |
| | | XMP -> PI + XTSINE | |
| 10846 | PDE10A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 27115 | PDE7B | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5136 | PDE1A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5137 | PDE1C, HCAM3 | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5138 | PDE2A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5139 | PDE3A, CGI-PDE | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5140 | PDE3B | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5141 | PDE4A, DPDE2 | cAMP -> AMP | 3.1.4.17 |
| 5142 | PDE4B, DPDE4, PDEIVB | cAMP -> AMP | 3.1.4.17 |
| 5143 | PDE4C, DPDE1 | cAMP -> AMP | 3.1.4.17 |
| 5144 | PDE4D, DPDE3 | cAMP -> AMP | 3.1.4.17 |
| 5145 | PDE6A, PDEA, CGPR-A | cGMP -> GMP | 3.1.4.17 |
| 5146 | PDE6C, PDEA2 | cGMP -> GMP | 3.1.4.17 |
| 5147 | PDE6D | cGMP -> GMP | 3.1.4.17 |
| 5148 | PDE6G, PDEG | cGMP -> GMP | 3.1.4.17 |
| 5149 | PDE6H | cGMP -> GMP | 3.1.4.17 |
| 5152 | PDE9A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5153 | PDES1B | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |

TABLE 1-continued

| Locus ID | Gene Ab. | Reaction Stoichiometry | E.C. |
|---|---|---|---|
| 5158 | PDE6B, CSNB3, PDEB | cGMP -> GMP | 3.1.4.17 |
| 8654 | PDE5A | cGMP -> GMP | 3.1.4.17 |
| 100 | ADA | ADN -> INS + NH3 | 3.5.4.4 |
|  |  | DA -> DIN + NH3 |  |
| 270 | AMPD1, MADA | AMP -> IMP + NH3 | 3.5.4.6 |
| 271 | AMPD2 | AMP -> IMP + NH3 | 3.5.4.6 |
| 272 | AMPD3 | AMP -> IMP + NH3 | 3.5.4.6 |
| 953 | ENTPD1, CD39 |  | 3.6.1.5 |
| 3704 | ITPA |  | 3.6.1.19 |
| 107 | ADCY1 | ATP -> cAMP + PPI | 4.6.1.1 |
| 108 | ADCY2, HBAC2 | ATP -> cAMP + PPI | 4.6.1.1 |
| 109 | ADCY3, AC3, KIAA0511 | ATP -> cAMP + PPI | 4.6.1.1 |
| 110 | ADCY4 | ATP -> cAMP + PPI | 4.6.1.1 |
| 111 | ADCY5 | ATP -> cAMP + PPI | 4.6.1.1 |
| 112 | ADCY6 | ATP -> cAMP + PPI | 4.6.1.1 |
| 113 | ADCY7, KIAA0037 | ATP -> cAMP + PPI | 4.6.1.1 |
| 114 | ADCY8, ADCY3, HBAC1 | ATP -> cAMP + PPI | 4.6.1.1 |
| 115 | ADCY9 | ATP -> cAMP + PPI | 4.6.1.1 |
| 2977 | GUCY1A2, GUC1A2, GC-SA2 |  | 4.6.1.2 |
| 2982 | GUCY1A3, GUC1A3, GUCSA3, GC-SA3 |  | 4.6.1.2 |
| 2983 | GUCY1B3, GUC1B3, GUCSB3, GC-SB3 |  | 4.6.1.2 |
| 2984 | GUCY2C, GUC2C, STAR |  | 4.6.1.2 |
| 2986 | GUCY2F, GUC2F, GC-F, GUC2DL, RETGC-2 |  | 4.6.1.2 |
| 3000 | GUCY2D, CORD6, GUC2D, LCA1, GUC1A4, LCA, retGC |  | 4.6.1.2 |
| 4881 | NPR1, ANPRA, GUC2A, NPRA |  | 4.6.1.2 |
| 4882 | NPR2, ANPRB, GUC2B, NPRB, NPRBi |  | 4.6.1.2 |
| 159 | ADSS | IMP + GTP + ASP -> GDP + PI + ASUC | 6.3.4.4 |
| 318 | NUDT2, APAH1 |  | 3.6.1.17 |
| 5167 | ENPP1, M6S1, NPPS, PCA1, PC-1, PDNP1 |  | 3.6.1.9 |
| 5168 | ENPP2, ATX, PD-IALPHA, PDNP2 |  | 3.6.1.9 |
| 5169 | ENPP3, PD-IBETA, PDNP3 |  | 3.6.1.9 |
|  |  |  | 3.1.4.1 |
| 2272 | FHIT |  | 3.6.1.29 |
| 4.2 Pyrimidine metabolism PATH:hsa00240 |  |  |  |
| 790 | CAD | GLN + 2 ATP + CO2 -> GLU + CAP + 2 ADP + PI | 6.3.5.5 |
|  |  | CAP + ASP -> CAASP + PI | 2.1.3.2 |
|  |  | CAASP <-> DOROA | 3.5.2.3 |
| 1723 | DHODH | DOROA + O2 <-> H2O2 + OROA | 1.3.3.1 |
| 7372 | UMPS, OPRT | OMP -> CO2 + UMP | 4.1.1.23 |
|  |  | OROA + PRPP <-> PPI + OMP | 2.4.2.10 |
| 51727 | LOC51727 | ATP + UMP <-> ADP + UDP | 2.7.4.14 |
|  |  | CMP + ATP <-> ADP + CDP |  |
|  |  | DCMP + ATP <-> ADP + DCDP |  |
| 50808 | AKL3L |  | 2.7.4.10 |
| 1503 | CTPS | UTP + GLN + ATP -> GLU + CTP + ADP + PI | 6.3.4.2 |
|  |  | ATP + UTP + NH3 -> ADP + PI + CTP |  |
| 7371 | UMPK, TSA903 | URI + ATP -> ADP + UMP | 2.7.1.48 |
|  |  | URI + GTP -> UMP + GDP |  |
|  |  | CYTD + GTP -> GDP + CMP |  |
| 7378 | UP | URI + PI <-> URA + R1P | 2.4.2.3 |
| 1806 | DPYD, DPD |  | 1.3.1.2 |
| 1807 | DPYS, DHPase, DHPASE, DHP |  | 3.5.2.2 |
| 51733 | LOC51733 |  | 3.5.1.6 |
| 7296 | TXNRD1, TXNR | OTHIO + NADPH -> NADP + RTHIO | 1.6.4.5 |
| 1854 | DUT | DUTP -> PPI + DUMP | 3.6.1.23 |
| 7298 | TYMS, TMS, TS | DUMP + METTHF -> DHF + DTMP | 2.1.1.45 |
| 978 | CDA, CDD | CYTD -> URI + NH3 | 3.5.4.5 |
|  |  | DC -> NH3 + DU |  |
| 1635 | DCTD | DCMP <-> DUMP + NH3 | 3.5.4.12 |
| 7083 | TK1 | DU + ATP -> DUMP + ADP | 2.7.1.21 |
|  |  | DT + ATP -> ADP + DTMP |  |
| 7084 | TK2 | DUm + ATPm -> DUMPm + ADPm | 2.7.1.21 |
|  |  | DTm + ATPm -> ADPm + DTMPm |  |
| 1841 | DTYMK, TYMK, CDC8 | DTMP + ATP <-> ADP + DTDP | 2.7.4.9 |
| 4.3 Nucleotide sugars metabolism PATH:hsa00520 |  |  |  |
| 23483 | TDPGD |  | 4.2.1.46 |
| 1486 | CTBS, CTB |  | 3.2.1.— |

TABLE 1-continued

| Locus ID | Gene Ab. | Reaction Stoichiometry | E.C. |
|---|---|---|---|
| 5. Amino Acid Metabolism | | | |
| 5.1 Glutamate metabolism PATH:hsa00251 | | | |
| 8659 | ALDH4, P5CDH | P5C + NAD + H2O -> NADH + GLU | 1.5.1.12 |
| 2058 | EPRS, QARS, QPRS | GLU + ATP -> GTRNA + AMP + PPI | 6.1.1.17 |
| | | | 6.1.1.15 |
| 2673 | GFPT1, GFA, GFAT, GFPT | F6P + GLN -> GLU + GA6P | 2.6.1.16 |
| 9945 | GFPT2, GFAT2 | F6P + GLN -> GLU + GA6P | 2.6.1.16 |
| 5859 | QARS | | 6.1.1.18 |
| 2729 | GLCLC, GCS, GLCL | CYS + GLU + ATP -> GC + PI + ADP | 6.3.2.2 |
| 2730 | GLCLR | CYS + GLU + ATP -> GC + PI + ADP | 6.3.2.2 |
| 2937 | GSS, GSHS | GLY + GC + ATP -> RGT + PI + ADP | 6.3.2.3 |
| 2936 | GSR | NADPH + OGT -> NADP + RGT | 1.6.4.2 |
| 5188 | PET112L, PET112 | | 6.3.5.— |
| 5.2 Alanine and aspartate metabolism PATH:hsa00252 | | | |
| 4677 | NARS, ASNRS | ATP + ASP + TRNA -> AMP + PPI + ASPTRNA | 6.1.1.22 |
| 435 | ASL | ARGSUCC -> FUM + ARG | 4.3.2.1 |
| 189 | AGXT, SPAT | SERm + PYRm <-> ALAm + 3HPm | 2.6.1.51 |
| | | ALA + GLX <-> PYR + GLY | 2.6.1.44 |
| 16 | AARS | | 6.1.1.7 |
| 1615 | DARS | | 6.1.1.12 |
| 445 | ASS, CTLN1, ASS1 | CITR + ASP + ATP <-> AMP + PPI + ARGSUCC | 6.3.4.5 |
| 443 | ASPA, ASP, ACY2 | | 3.5.1.15 |
| 1384 | CRAT, CAT1 | ACCOA + CAR -> COA + ACAR | 2.3.1.7 |
| 8528 | DDO | | 1.4.3.1 |
| 5.3 Glycine, serine and threonine metabolism PATH:hsa00260 | | | |
| 5723 | PSPH, PSP | 3PSER + H2O -> PI + SER | 3.1.3.3 |
| 29968 | PSA | PHP + GLU <-> AKG + 3PSER | 2.6.1.52 |
| | | OHB + GLU <-> PHT + AKG | |
| 26227 | PHGDH, SERA, PGDH, PGD, PGAD | 3PG + NAD <-> NADH + PHP | 1.1.1.95 |
| 23464 | GCAT, KBL | | 2.3.1.29 |
| 211 | ALAS1, ALAS | SUCCOA + GLY -> ALAV + COA + CO2 | 2.3.1.37 |
| 212 | ALAS2, ANH1, ASB | SUCCOA + GLY -> ALAV + COA + CO2 | 2.3.1.37 |
| 4128 | MAOA | AMA + H2O + FAD -> NH3 + FADH2 + MTHGXL | 1.4.3.4 |
| 4129 | MAOB | AMA + H2O + FAD -> NH3 + FADH2 + MTHGXL | 1.4.3.4 |
| 26 | ABP1, AOC1, DAO | | 1.4.3.6 |
| 314 | AOC2, DAO2, RAO | | 1.4.3.6 |
| 8639 | AOC3, VAP-1, VAP1, HPAO | | 1.4.3.6 |
| 2731 | GLDC | GLY + LIPO <-> SAP + CO2 | 1.4.4.2 |
| 1610 | DAO, DAMOX | | 1.4.3.3 |
| 2617 | GARS | | 6.1.1.14 |
| 2628 | GATM | | 2.1.4.1 |
| 2593 | GAMT | | 2.1.1.2 |
| 23761 | PISD, PSSC, DKFZP566G2246, DJ858B16 | PS -> PE + CO2 | 4.1.1.65 |
| 635 | BHMT | | 2.1.1.5 |
| 29958 | DMGDH | | 1.5.99.2 |
| 875 | CBS | SER + HCYS -> LLCT + H2O | 4.2.1.22 |
| 6301 | SARS, SERS | | 6.1.1.11 |
| 10993 | SDS, SDH | SER -> PYR + NH3 + H2O | 4.2.1.13 |
| 6897 | TARS | | 6.1.1.3 |
| 5.4 Methionine metabolism PATH:hsa00271 | | | |
| 4143 | MAT1A, MATA1, SAMS1, MAT, SAMS | MET + ATP + H2O -> PPI + PI + SAM | 2.5.1.6 |
| 4144 | MAT2A, MATA2, SAMS2, MATII | MET + ATP + H2O -> PPI + PI + SAM | 2.5.1.6 |
| 1786 | DNMT1, MCMT, DNMT | SAM + DNA -> SAH + DNA5MC | 2.1.1.37 |
| 10768 | AHCYL1, XPVKONA | SAH + H2O -> HCYS + ADN | 3.3.1.1 |
| 191 | AHCY, SAHH | SAH + H2O -> HCYS + ADN | 3.3.1.1 |
| 4141 | MARS, METRS, MTRNS | | 6.1.1.10 |
| 4548 | MTR | HCYS + MTHF -> THF + MET | 2.1.1.13 |
| 5.5 Cysteine metabolism PATH:hsa00272 | | | |
| 833 | CARS | | 6.1.1.16 |
| 1036 | CDO1 | CYS + O2 <-> CYSS | 1.13.11.20 |
| 8509 | NDST2, HSST2, NST2 | | 2.8.2.— |
| 5.6 Valine, leucine and isoleucine degradation PATH:hsa00280 | | | |
| 586 | BCAT1, BCT1, ECA39, MECA39 | AKG + ILE -> OMVAL + GLU | 2.6.1.42 |
| | | AKG + VAL -> OIVAL + GLU | |
| | | AKG + LEU -> OICAP + GLU | |
| 587 | BCAT2, BCT2 | OICAPm + GLUm <-> AKGm + LEUm | 2.6.1.42 |
| | | OMVALm + GLUm <-> AKGm + ILEm | |
| 5014 | OVD1A | | 1.2.4.4 |
| 593 | BCKDHA, MSUD1 | OMVALm + COAm + NADm -> MBCOAm + NADHm + CO2m | 1.2.4.4 |
| | | OIVALm + COAm + NADm -> IBCOAm + NADHm + CO2m | |
| | | OICAPm + COAm + NADm -> IVCOAm + NADHm + CO2m | |
| 594 | BCKDHB, E1B | OMVALm + COAm + NADm -> MBCOAm + NADHm + CO2m | 1.2.4.4 |
| | | OIVALm + COAm + NADm -> IBCOAm + NADHm + CO2m | |
| | | OICAPm + COAm + NADH -> IVCOAm + NADHm + CO2m | |

TABLE 1-continued

| Locus ID | Gene Ab. | Reaction Stoichiometry | E.C. |
|---|---|---|---|
| 3712 | IVD | IVCOAm + FADm -> MCRCOAm + FADH2m | 1.3.99.10 |
| 316 | AOX1, AO | | 1.2.3.1 |
| 4164 | MCCC1 | MCRCOAm + ATPm + CO2m + H2Om -> MGCOAm + ADPm + Pim | 6.4.1.4 |
| 4165 | MCCC2 | MCRCOAm + ATPm + CO2m + H2Om -> MGCOAm + ADPm + Pim | 6.4.1.4 |
| 5.7 Valine, leucine and isoleucine biosynthesis PATH:hsa00290 | | | |
| 23395 | KIAA0028, LARS2 | | 6.4.1.4 |
| 3926 | LARS | | 6.4.1.4 |
| 3376 | IARS, ILRS | | 6.1.1.5 |
| 7406 | VARS1, VARS | | 6.1.1.9 |
| 7407 | VARS2, G7A | | 6.1.1.9 |
| 5.8 Lysine biosynthesis PATH:hsa00300 | | | |
| 3735 | KARS, KIAA0070 | ATP + LYS + LTRNA -> AMP + PPI + LLTRNA | 6.1.1.6 |
| 5.9 Lysine degradation PATH:hsa00310 | | | |
| 8424 | BBOX, BBH, GAMMA-BBH, G-BBH | | 1.14.11.1 |
| 5351 | PLOD, LLH | | 1.14.11.4 |
| 5352 | PLOD2 | | 1.14.11.4 |
| 8985 | PLOD3, LH3 | | 1.14.11.4 |
| 10157 | LKR/SDH, AASS | LYS + NADPH + AKG -> NADP + H2O + SAC | 1.5.1.9 |
|  |  | SAC + H2O + NAD -> GLU + NADH + AASA | |
| 5.10 Arginine and proline metabolism PATH:hsa00330 | | | |
| 5009 | OTC | ORNm + CAPm -> CITRm + Pim + Hm | 2.1.3.3 |
| 383 | ARG1 | ARG -> ORN + UREA | 3.5.3.1 |
| 384 | ARG2 | ARG -> ORN + UREA | 3.5.3.1 |
| 4842 | NOS1, NOS | | 1.14.13.39 |
| 4843 | NOS2A, NOS2 | | 1.14.13.39 |
| 4846 | NOS3, ECNOS | | 1.14.13.39 |
| 4942 | OAT | ORN + AKG <-> GLUGSAL + GLU | 2.6.1.13 |
| 5831 | PYCR1, P5C, PYCR | P5C + NADPH -> PRO + NADP | 1.5.1.2 |
|  |  | P5C + NADH -> PRO + NAD | |
|  |  | PHC + NADPH -> HPRO + NADP | |
|  |  | PHC + NADH -> HPRO + NAD | |
| 5033 | P4HA1, P4HA | | 1.14.11.2 |
| 5917 | RARS | ATP + ARG + ATRNA -> AMP + PPI + ALTRNA | 6.1.1.19 |
| 1152 | CKB, CKBB | PCRE + ADP -> CRE + ATP | 2.7.3.2 |
| 1156 | CKBE | | 2.7.3.2 |
| 1158 | CKM, CKMM | | 2.7.3.2 |
| 1159 | CKMT1, CKMT, UMTCK | | 2.7.3.2 |
| 1160 | CKMT2, SMTCK | | 2.7.3.2 |
| 6723 | SRM, SPS1, SRML1 | PTRSC + SAM -> SPRMD + 5MTA | 2.5.1.16 |
| 262 | AMD1, ADOMETDC | SAM <-> DSAM + CO2 | 4.1.1.50 |
| 263 | AMDP1, AMD, AMD2 | SAM <-> DSAM + CO2 | 4.1.1.50 |
| 1725 | DHPS | SPRMD + Qm -> DAPRP + QH2m | 1.5.99.6 |
| 6611 | SMS | DSAM + SPRMD -> 5MTA + SPRM | 2.5.1.22 |
| 4953 | ODC1 | ORN -> PTRSC + CO2 | 4.1.1.17 |
| 6303 | SAT, SSAT | | 2.3.1.57 |
| 5.11 Histidine metabolism PATH:hsa00340 | | | |
| 10841 | FTCD | FIGLU + THF -> NFTHF + GLU | 2.1.2.5 |
|  |  |  | 4.3.1.4 |
| 3067 | HDC | | 4.1.1.22 |
| 1644 | DDC, AADC | | 4.1.1.28 |
| 3176 | HNMT | | 2.1.1.8 |
| 218 | ALDH3 | ACAL + NAD -> NADH + AC | 1.2.1.5 |
| 220 | ALDH6 | ACAL + NAD -> NADH + AC | 1.2.1.5 |
| 221 | ALDH7, ALDH4 | ACAL + NAD -> NADH + AC | 1.2.1.5 |
| 222 | ALDH8 | ACAL + NAD -> NADH + AC | 1.2.1.5 |
| 3035 | HARS | ATP + HIS + HTRNA -> AMP + PPI + HHTRNA | 6.1.1.21 |
| 5.12 Tyrosine metabolism PATH:hsa00350 | | | |
| 6898 | TAT | AKG + TYR -> HPHPYR + GLU | 2.6.1.5 |
| 3242 | HPD, PPD | HPHPYR + O2 -> HGTS + CO2 | 1.13.11.27 |
| 3081 | HGD, AKU, HGO | HGTS + O2 -> MACA | 1.13.11.5 |
| 2954 | GSTZ1, MAAI | MACA -> FACA | 5.2.1.2 |
|  |  |  | 2.5.1.18 |
| 2184 | FAH | FACA + H2O -> FUM + ACA | 3.7.1.2 |
| 7299 | TYR, OCAIA | | 1.14.18.1 |
| 7054 | TH, TYH | | 1.14.16.2 |
| 1621 | DBH | | 1.14.17.1 |
| 5409 | PNMT, PENT | | 2.1.1.28 |
| 1312 | COMT | | 2.1.1.6 |
| 7173 | TPO, TPX | | 1.11.1.8 |
| 5.13 Phenylalanine metabolism PATH:hsa00360 | | | |
| 501 | ATQ1 | | 1.2.1.— |
| 5.14 Tryptophan metabolism PATH:hsa00380 | | | |
| 6999 | TDO2, TPH2, TRPO, TDO | TRP + O2 -> FKYN | 1.13.11.11 |
| 8564 | KMO | KYN + NADPH + O2 -> HKYN + NADP + H2O | 1.14.13.9 |
| 8942 | KYNU | KYN -> ALA + AN | 3.7.1.3 |
|  |  | HKYN + H2O -> HAN + ALA | |
| 23498 | HAAO, HAO, 3-HAO | HAN + O2 -> CMUSA | 1.13.11.6 |
| 7166 | TPH, TPRH | | 1.14.16.4 |

TABLE 1-continued

| Locus ID | Gene Ab. | Reaction Stoichiometry | E.C. |
|---|---|---|---|
| 438 | ASMT, HIOMT, ASMTY | | 2.1.1.4 |
| 15 | AANAT, SNAT | | 2.3.1.87 |
| 3620 | INDO, IDO | | 1.13.11.42 |
| 10352 | WARS2 | ATPm + TRPm + TRNAm -> AMPm + PPIm + TRPTRNAm | 6.1.1.2 |
| 7453 | WARS, IFP53, IFI53, GAMMA-2 | ATP + TRP + TRNA -> AMP + PPI + TRPTRNA | 6.1.1.2 |
| 4734 | NEDD4, KIAA0093 | | 6.3.2.— |
| 5.15 Phenylalanine, tyrosine and tryptophan biosynthesis PATH:hsa00400 | | | |
| 5053 | PAH, PKU1 | PHE + THBP + O2 -> TYR + DHBP + H2O | 1.14.16.1 |
| 10667 | FARS1 | | 6.1.1.20 |
| 2193 | FARSL, CML33 | | 6.1.1.20 |
| 10056 | PheHB | | 6.1.1.20 |
| 8565 | YARS, TYRRS, YTS, YRS | | 6.1.1.1 |
| 5.16 Urea cycle and metabolism of amino groups PATH:hsa00220 | | | |
| 5832 | PYCS | | 2.7.2.11 |
| | | GLUP + NADH -> NAD + PI + GLUGSAL | 1.2.1.41 |
| | | GLUP + NADPH -> NADP + PI + GLUGSAL | |
| 95 | ACY1 | | 3.5.1.14 |
| 6. Metabolism of Other Amino Acids | | | |
| 6.1 beta-Alanine metabolism PATH:hsa00410 | | | |
| 6.2 Taurine and hypotaurine metabolism PATH:hsa00430 | | | |
| 2678 | GGT1, GTG, D22S672, D22S732, GGT | RGT + ALA -> CGLY + ALAGLY | 2.3.2.2 |
| 2679 | GGT2, GGT | RGT + ALA -> CGLY + ALAGLY | 2.3.2.2 |
| 2680 | GGT3 | RGT + ALA -> CGLY + ALAGLY | 2.3.2.2 |
| 2687 | GGTLA1, GGT-REL, DKFZP566O011 | RGT + ALA -> CGLY + ALAGLY | 2.3.2.2 |
| 6.3 Aminophosphonate metabolism PATH:hsa00440 | | | |
| 5130 | PCYT1A, CTPCT, CT, PCYT1 | PCHO + CTP -> CDPCHO + PPI | 2.7.7.15 |
| 9791 | PTDSS1, KIAA0024, PSSA | CDPDG + SER <-> CMP + PS | 2.7.8.— |
| 6.4 Selenoamino acid metabolism PATH:hsa00450 | | | |
| 22928 | SPS2 | | 2.7.9.3 |
| 22929 | SPS, SELD | | 2.7.9.3 |
| 6.5 Cyanoamino acid metabolism PATH:hsa00460 | | | |
| 6.6 D-Glutamine and D-glutamate metabolism PATH:hsa00471 | | | |
| 6.7 D-Arginine and D-ornithine metabolism PATH:hsa00472 | | | |
| 6.9 Glutathione metabolism PATH:hsa00480 | | | |
| 5182 | PEPB | | 3.4.11.4 |
| 2655 | GCTG | | 2.3.2.4 |
| 2876 | GPX1, GSHPX1 | 2 RGT + H2O2 <-> OGT | 1.11.1.9 |
| 2877 | GPX2, GSHPX-GI | 2 RGT + H2O2 <-> OGT | 1.11.1.9 |
| 2878 | GPX3 | 2 RGT + H2O2 <-> OGT | 1.11.1.9 |
| 2879 | GPX4 | 2 RGT + H2O2 <-> OGT | 1.11.1.9 |
| 2880 | GPX5 | 2 RGT + H2O2 <-> OGT | 1.11.1.9 |
| 2881 | GPX6 | 2 RGT + H2O2 <-> OGT | 1.11.1.9 |
| 2938 | GSTA1 | | 2.5.1.18 |
| 2939 | GSTA2, GST2 | | 2.5.1.18 |
| 2940 | GSTA3 | | 2.5.1.18 |
| 2941 | GSTA4 | | 2.5.1.18 |
| 2944 | GSTM1, GST1, MU | | 2.5.1.18 |
| 2946 | GSTM2, GST4 | | 2.5.1.18 |
| 2947 | GSTM3, GST5 | | 2.5.1.18 |
| 2948 | GSTM4 | | 2.5.1.18 |
| 2949 | GSTM5 | | 2.5.1.18 |
| 2950 | GSTP1, FAEES3, DFN7, GST3, PI | | 2.5.1.18 |
| 2952 | GSTT1 | | 2.5.1.18 |
| 2953 | GSTT2 | | 2.5.1.18 |
| 4257 | MGST1, GST12, MGST, MGST-I | | 2.5.1.18 |
| 4258 | MGST2, GST2, MGST-II | | 2.5.1.18 |
| 4259 | MGST3, GST-III | | 2.5.1.18 |
| 7. Metabolism of Complex Carbohydrates | | | |
| 7.1 Starch and sucrose metabolism PATH:hsa00500 | | | |
| 6476 | SI | | 3.2.1.10 |
| | | | 3.2.1.48 |
| 11181 | TREH, TRE, TREA | TRE -> 2 GLC | 3.2.1.28 |
| 2990 | GUSB | | 3.2.1.31 |
| 2632 | GBE1 | GLYCOGEN + PI -> G1P | 2.4.1.18 |
| 5834 | PYGB | GLYCOGEN + PI -> G1P | 2.4.1.1 |
| 5836 | PYGL | GLYCOGEN + PI -> G1P | 2.4.1.1 |
| 5837 | PYGM | GLYCOGEN + PI -> G1P | 2.4.1.1 |
| 2997 | GYS1, GYS | UDPG -> UDP + GLYCOGEN | 2.4.1.11 |
| 2998 | GYS2 | UDPG -> UDP + GLYCOGEN | 2.4.1.11 |
| 276 | AMY1A, AMY1 | | 3.2.1.1 |
| 277 | AMY1B, AMY1 | | 3.2.1.1 |
| 278 | AMY1C, AMY1 | | 3.2.1.1 |
| 279 | AMY2A, AMY2 | | 3.2.1.1 |
| 280 | AMY2B, AMY2 | | 3.2.1.1 |
| 178 | AGL, GDE | | 2.4.1.25 |
| | | | 3.2.1.33 |
| 10000 | AKT3, PKBG, RAC-GAMMA, PRKBG | | 2.7.1.— |

TABLE 1-continued

| Locus ID | Gene Ab. | Reaction Stoichiometry | E.C. |
|---|---|---|---|
| 1017 | CDK2 | | 2.7.1.— |
| 1018 | CDK3 | | 2.7.1.— |
| 1019 | CDK4, PSK-J3 | | 2.7.1.— |
| 1020 | CDK5, PSSALRE | | 2.7.1.— |
| 1021 | CDK6, PLSTIRE | | 2.7.1.— |
| 1022 | CDK7, CAK1, STK1, CDKN7 | | 2.7.1.— |
| 1024 | CDK8, K35 | | 2.7.1.— |
| 1025 | CDK9, PITALRE, CDC2L4 | | 2.7.1.— |
| 10298 | PAK4 | | 2.7.1.— |
| 10746 | MAP3K2, MEKK2 | | 2.7.1.— |
| 1111 | CHEK1, CHK1 | | 2.7.1.— |
| 11200 | RAD53, CHK2, CDS1, HUCDS1 | | 2.7.1.— |
| 1195 | CLK1, CLK | | 2.7.1.— |
| 1326 | MAP3K8, COT, EST, ESTF, TPL-2 | | 2.7.1.— |
| 1432 | MAPK14, CSBP2, CSPB1, PRKM14, PRKM15, CSBP1, P38, MXI2 | | 2.7.1.— |
| 1452 | CSNK1A1 | | 2.7.1.— |
| 1453 | CSNK1D, HCKID | | 2.7.1.— |
| 1454 | CSNK1E, HCKIE | | 2.7.1.— |
| 1455 | CSNK1G2 | | 2.7.1.— |
| 1456 | CSNK1G3 | | 2.7.1.— |
| 1612 | DAPK1, DAPK | | 2.7.1.— |
| 1760 | DMPK, DM, DMK, DM1 | | 2.7.1.— |
| 1859 | DYRK1A, DYRK1, DYRK, MNB, MNBH | | 2.7.1.— |
| 208 | AKT2, RAC-BETA, PRKBB, PKBBETA | | 2.7.1.— |
| 269 | AMHR2, AMHR | | 2.7.1.— |
| 27330 | RPS6KA6, RSK4 | | 2.7.1.— |
| 2868 | GPRK2L, GPRK4 | | 2.7.1.— |
| 2869 | GPRK5, GRK5 | | 2.7.1.— |
| 2870 | GPRK6, GRK6 | | 2.7.1.— |
| 29904 | HSU93850 | | 2.7.1.— |
| 30811 | HUNK | | 2.7.1.— |
| 3611 | ILK, P59 | | 2.7.1.— |
| 3654 | IRAK1, IRAK | | 2.7.1.— |
| 369 | ARAF1, PKS2, RAFA1 | | 2.7.1.— |
| 370 | ARAF2P, PKS1, ARAF2 | | 2.7.1.— |
| 3984 | LIMK1, LIMK | | 2.7.1.— |
| 3985 | LIMK2 | | 2.7.1.— |
| 4117 | MAK | | 2.7.1.— |
| 4140 | MARK3, KP78 | | 2.7.1.— |
| 4215 | MAP3K3, MAPKKK3, MEKK3 | | 2.7.1.— |
| 4216 | MAP3K4, MAPKKK4, MTK1, MEKK4, KIAA0213 | | 2.7.1.— |
| 4217 | MAP3K5, ASK1, MAPKKK5, MEKK5 | | 2.7.1.— |
| 4293 | MAP3K9, PRKE1, MLK1 | | 2.7.1.— |
| 4294 | MAP3K10, MLK2, MST | | 2.7.1.— |
| 4342 | MOS | | 2.7.1.— |
| 4751 | NEK2, NLK1 | | 2.7.1.— |
| 4752 | NEK3 | | 2.7.1.— |
| 5058 | PAK1, PAKalpha | | 2.7.1.— |
| 5062 | PAK2, PAK65, PAKgamma | | 2.7.1.— |
| 5063 | PAK3, MRX30, PAK3beta | | 2.7.1.— |
| 5127 | PCTK1, PCTGAIRE | | 2.7.1.— |
| 5128 | PCTK2 | | 2.7.1.— |
| 5129 | PCTK3, PCTAIRE | | 2.7.1.— |
| 5292 | PIM1, PIM | | 2.7.1.— |
| 5347 | PLK, PLK1 | | 2.7.1.— |
| 5562 | PRKAA1 | | 2.7.1.— |
| 5563 | PRKAA2, AMPK, PRKAA | | 2.7.1.— |
| 5578 | PRKCA, PKCA | | 2.7.1.— |
| 5579 | PRKCB1, PKCB, PRKCB, PRKCB2 | | 2.7.1.— |
| 5580 | PRKCD | | 2.7.1.— |
| 5581 | PRKCE | | 2.7.1.— |
| 5582 | PRKCG, PKCC, PKCG | | 2.7.1.— |
| 5583 | PRKCH, PKC-L, PRKCL | | 2.7.1.— |
| 5584 | PRKCI, DXS1179E, PKCI | | 2.7.1.— |
| 5585 | PRKCL1, PAK1, PRK1, DBK, PKN | | 2.7.1.— |
| 5586 | PRKCL2, PRK2 | | 2.7.1.— |
| 5588 | PRKCQ | | 2.7.1.— |
| 5590 | PRKCZ | | 2.7.1.— |
| 5594 | MAPK1, PRKM1, P41MAPK, P42MAPK, ERK2, ERK, MAPK2, PRKM2 | | 2.7.1.— |
| 5595 | MAPK3, ERK1, PRKM3, P44ERK1, P44MAPK | | 2.7.1.— |
| 5597 | MAPK6, PRKM6, P97MAPK, ERK3 | | 2.7.1.— |
| 5598 | MAPK7, BMK1, ERK5, PRKM7 | | 2.7.1.— |
| 5599 | MAPK8, JNK, JNK1, SAPK1, PRKM8, | | 2.7.1.— |

TABLE 1-continued

| Locus ID | Gene Ab. | Reaction Stoichiometry | E.C. |
|---|---|---|---|
| | JNK1A2 | | |
| 5601 | MAPK9, JNK2, PRKM9, P54ASAPK, JUNKINASE | | 2.7.1.— |
| 5602 | MAPK10, JNK3, PRKM10, P493F12, P54BSAPK | | 2.7.1.— |
| 5603 | MAPK13, SAPK4, PRKM13, P38DELTA | | 2.7.1.— |
| 5604 | MAP2K1, MAPKK1, MEK1, MKK1, PRKMK1 | | 2.7.1.— |
| 5605 | MAP2K2, MEK2, PRKMK2 | | 2.7.1.— |
| 5606 | MAP2K3, MEK3, MKK3, PRKMK3 | | 2.7.1.— |
| 5607 | MAP2K5, MEK5, PRKMK5 | | 2.7.1.— |
| 5608 | MAP2K6, MEK6, MKK6, SAPKK3, PRKMK6 | | 2.7.1.— |
| 5609 | MAP2K7, MAPKK7, MKK7, PRKMK7, JNKK2 | | 2.7.1.— |
| 5610 | PRKR, EIF2AK1, PKR | | 2.7.1.— |
| 5613 | PRKX, PKX1 | | 2.7.1.— |
| 5894 | RAF1 | | 2.7.1.— |
| 613 | BCR, CML, PHL, BCR1, D22S11, D22S662 | | 2.7.1.— |
| 6195 | RPS6KA1, HU-1, RSK, RSK1, MAPKAPK1A | | 2.7.1.— |
| 6196 | RPS6KA2, HU-2, MAPKAPK1C, RSK, RSK3 | | 2.7.1.— |
| 6197 | RPS6KA3, RSK2, HU-2, HU-3, RSK, MAPKAPK1B, ISPK-1 | | 2.7.1.— |
| 6198 | RPS6KB1, STK14A | | 2.7.1.— |
| 6199 | RPS6KB2, P70-BETA, P70S6KB | | 2.7.1.— |
| 6300 | MAPK12, ERK6, PRKM12, SAPK3, P38GAMMA, SAPK-3 | | 2.7.1.— |
| 6416 | MAP2K4, JNKK1, MEK4, PRKMK4, SERK1, MKK4 | | 2.7.1.— |
| 6446 | SGK | | 2.7.1.— |
| 658 | BMPR1B, ALK-6, ALK6 | | 2.7.1.— |
| 659 | BMPR2, BMPR-II, BMPR3, BRK-3 | | 2.7.1.— |
| 673 | BRAF | | 2.7.1.— |
| 6792 | STK9 | | 2.7.1.— |
| 6794 | STK11, LKB1, PJS | | 2.7.1.— |
| 6885 | MAP3K7, TAK1 | | 2.7.1.— |
| 699 | BUB1 | | 2.7.1.— |
| 701 | BUB1B, BUBR1, MAD3L | | 2.7.1.— |
| 7016 | TESK1 | | 2.7.1.— |
| 7272 | TTK, MPS1L1 | | 2.7.1.— |
| 7867 | MAPKAPK3, 3PK, MAPKAP3 | | 2.7.1— |
| 8408 | ULK1 | | 2.7.1.— |
| 8558 | CDK10, PISSLRE | | 2.7.1.— |
| 8621 | CDC2L5, CDC2L, CHED | | 2.7.1.— |
| 8737 | RIPK1, RIP | | 2.7.1.— |
| 8814 | CDKL1, KKIALRE | | 2.7.1.— |
| 8899 | PRP4, PR4H | | 2.7.1.— |
| 9064 | MAP3K6, MAPKKK6 | | 2.7.1.— |
| 9149 | DYRK1B | | 2.7.1.— |
| 92 | ACVR2, ACTRII | | 2.7.1.— |
| 9201 | DCAMKL1, KIAA0369 | | 2.7.1.— |
| 93 | ACVR2B | | 2.7.1.— |
| 983 | CDC2 | | 2.7.1.— |
| 984 | CDC2L1 | | 2.7.1.— |
| 5205 | FIC1, BRIC, PFIC1, PFIC, ATP8B1 | DHPP -> DHP + PI<br>GTP -> GSN + 3 PI<br>DGTP -> DG + 3 PI | 3.6.1.— |
| 7.2 Glycoprotein biosynthesis PATH:hsa00510 | | | |
| 1798 | DPAGT1, DPAGT, UGAT, UAGT, D11S366, DGPT, DPAGT2, GPT | | 2.7.8.15 |
| 29880 | ALG5 | | 2.4.1.117 |
| 8813 | DPM1 | GDPMAN + DOLP -> GDP + DOLMANP | 2.4.1.83 |
| 1650 | DDOST, OST, OST48, KIAA0115 | | 2.4.1.119 |
| 6184 | RPN1 | | 2.4.1.119 |
| 6185 | RPN2 | | 2.4.1.119 |
| 10130 | P5 | | 5.3.4.1 |
| 10954 | PDIR | | 5.3.4.1 |
| 11008 | PDI | | 5.3.4.1 |
| 2923 | GRP58, ERp57, ERp60, ERp61, GRP57, P58, PI-PLC, ERP57, ERP60, ERP61 | | 5.3.4.1 |
| 5034 | P4HB, PROHB, PO4DB, ERBA2L | | 5.3.4.1 |
| 7841 | GCS1 | | 3.2.1.106 |

TABLE 1-continued

| Locus ID | Gene Ab. | Reaction Stoichiometry | E.C. |
|---|---|---|---|
| 4121 | MAN1A1, MAN9, HUMM9 | | 3.2.1.113 |
| 4245 | MGAT1, GLYT1, GLCNAC-TI, GNT-I, MGAT | | 2.4.1.101 |
| 4122 | MAN2A2, MANA2X | | 3.2.1.114 |
| 4124 | MAN2A1, MANA2 | | 3.2.1.114 |
| 4247 | MGAT2, CDGS2, GNT-II, GLONACTII, GNT2 | | 2.4.1.143 |
| 4248 | MGAT3, GNT-III | | 2.4.1.144 |
| 6487 | SIAT6, ST3GALII | | 2.4.99.6 |
| 6480 | SIAT1 | | 2.4.99.1 |
| 2339 | FNTA, FPTA, PGGT1A | | 2.5.1.— |
| 2342 | FNTB, FPTB | | 2.5.1.— |
| 5229 | PGGT1B, BGGI, GGTI | | 2.5.1.— |
| 5875 | RABGGTA | | 2.5.1.— |
| 5876 | RABGGTB | | 2.5.1.— |
| 1352 | COX10 | | 2.5.1.— |
| 7.3 Glycoprotein degradation PATH:hsa00511 | | | |
| 4758 | NEU1, NEU | | 3.2.1.18 |
| 3073 | HEXA, TSD | | 3.2.1.52 |
| 3074 | HEXB | | 3.2.1.52 |
| 4123 | MAN2C1, MANA, MANA1, MAN6A8 | | 3.2.1.24 |
| 4125 | MAN2B1, MANB, LAMAN | | 3.2.1.24 |
| 4126 | MANBA, MANB1 | | 3.2.1.25 |
| 2517 | FUCA1 | | 3.2.1.51 |
| 2519 | FUCA2 | | 3.2.1.51 |
| 175 | AGA, AGU | | 3.5.1.26 |
| 7.4 Aminosugars metabolism PATH:hsa005300 | | | |
| 6675 | UAP1, SPAG2, AGX1 | UTP + NAGA1P <-> UDPNAG + PPI | 2.7.7.23 |
| 10020 | GNE, GLCNE | | 5.1.3.14 |
| 22951 | CMAS | | 2.7.7.43 |
| 1727 | DIA1 | | 1.6.2.2 |
| 4669 | NAGLU, NAG | | 3.2.1.50 |
| 7.5 Lipopolysaccharide biosynthesis PATH:hsa00540 | | | |
| 6485 | SIAT5, SAT3, STZ | | 2.4.99.— |
| 7903 | SIAT8D, PST, PST1, ST8SIA-IV | | 2.4.99.— |
| 8128 | SIAT8B, STX, ST8SIA-II | | 2.4.99.— |
| 7.7 Glycosaminoglycan degradation PATH:hsa00531 | | | |
| 3423 | IDS, MPS2, SIDS | | 3.1.6.13 |
| 3425 | IDUA, IDA | | 3.2.1.76 |
| 411 | ARSB | | 3.1.6.12 |
| 2799 | GNS, G6S | | 3.1.6.14 |
| 2588 | GALNS, MPS4A, GALNAC6S, GAS | | 3.1.6.4 |
| 8. Metabolism of Complex Lipids | | | |
| 8.1 Glycerolipid metabolism PATH:hsa00561 | | | |
| 10554 | AGPAT1, LPAAT-ALPHA, G15 | AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | 2.3.1.51 |
| 10555 | AGPAT2, LPAAT-BETA | AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | 2.3.1.51 |
| 1606 | DGKA, DAGK, DAGK1 | | 2.7.1.107 |
| 1608 | DGKG, DAGK3 | | 2.7.1.107 |
| 1609 | DGKQ, DAGK4 | | 2.7.1.107 |
| 8525 | DGKZ, DAGK5, HDGKZETA | | 2.7.1.107 |
| 8526 | DGKE, DAGK6, DGK | | 2.7.1.107 |
| 8527 | DGKD, DGKDELTA, KIAA0145 | | 2.7.1.107 |
| 1120 | CHKL | ATP + CHO -> ADP + PCHO | 2.7.1.32 |
| | EKI1 | ATP + ETHM -> ADP + PETHM | 2.7.1.82 |
| 1119 | CHK, CKI | ATP + CHO -> ADP + PCHO | 2.7.1.32 |
| 43 | ACHE, YT | | 3.1.1.7 |
| 1103 | CHAT | | 2.3.1.6 |
| 5337 | PLD1 | | 3.1.4.4 |
| 26279 | PLA2G2D, SPLA2S | | 3.1.1.4 |
| 30814 | PLA2G2E | | 3.1.1.4 |
| 5319 | PLA2G1B, PLA2, PLA2A, PPLA2 | | 3.1.1.4 |
| 5320 | PLA2G2A, MOM1, PLA2B, PLA2L | | 3.1.1.4 |
| 5322 | PLA2G5 | | 3.1.1.4 |
| 8398 | PLA2G6, IPLA2 | | 3.1.1.4 |
| 8399 | PLA2G10, SPLA2 | | 3.1.1.4 |
| 1040 | CDS1 | PA + CTP <-> CDPDG + PPI | 2.7.7.41 |
| 10423 | PIS | CDPDG + MYOI -> CMP + PINS | 2.7.8.11 |
| 2710 | GK | GL + ATP -> GL3P + ADP | 2.7.1.30 |
| 2820 | GPD2 | GL3Pm + FADm -> T3P2m + FADH2m | 1.1.99.5 |
| 2819 | GPD1 | T3P2 + NADH <-> GL3P + NAD | 1.1.1.8 |
| 248 | ALPI | AHTD -> DHP + 3 PI | 3.1.3.1 |
| 249 | ALPL, HOPS, TNSALP | AHTD -> DHP + 3 PI | 3.1.3.1 |
| 250 | ALPP | AHTD -> DHP + 3 PI | 3.1.3.1 |
| 251 | ALPPL2 | AHTD -> DHP + 3 PI | 3.1.3.1 |

TABLE 1-continued

| Locus ID | Gene Ab. | Reaction Stoichiometry | E.C. |
|---|---|---|---|
| 439 | ASNA1, ARSA-I | | 3.6.1.16 |
| 8694 | DGAT, ARGP1 | DAGLY + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> TAGLY + ACP | 2.3.1.20 |
| 3989 | LIPB | | 3.1.1.3 |
| 3990 | LIPC, HL | | 3.1.1.3 |
| 5406 | PNLIP | | 3.1.1.3 |
| 5407 | PNLIPRP1, PLRP1 | | 3.1.1.3 |
| 5408 | PNLIPRP2, PLRP2 | | 3.1.1.3 |
| 8513 | LIPF, HGL, HLAL | | 3.1.1.3 |
| 4023 | LPL, LIPD | | 3.1.1.34 |
| 8443 | GNPAT, DHAPAT, DAP-AT | | 2.3.1.42 |
| 8540 | AGPS, ADAP-S, ADAS, ADHAPS, ADPS, ALDHPSY | | 2.5.1.26 |
| 4186 | MDCR, MDS, LIS1 | | 3.1.1.47 |
| 5048 | PAFAH1B1, LIS1, MDCR, PAFAH | | 3.1.1.47 |
| 5049 | PAFAH1B2 | | 3.1.1.47 |
| 5050 | PAFAH1B3 | | 3.1.1.47 |
| 5051 | PAFAH2, HSD-PLA2 | | 3.1.1.47 |
| 7941 | PLA2G7, PAFAH, LDL-PLA2 | | 3.1.1.47 |
| 8.2 Inositol phosphate metabolism PATH:hsa00562 | | | |
| 5290 | PIK3CA | ATP + PINS -> ADP + PINSP | 2.7.1.137 |
| 5291 | PIK3CB, PIK3C1 | ATP + PINS -> ADP + PINSP | 2.7.1.137 |
| 5293 | PIK3CD | ATP + PINS -> ADP + PINSP | 2.7.1.137 |
| 5294 | PIK3CG | ATP + PINS -> ADP + PINSP | 2.7.1.137 |
| 5297 | PIK4CA, PI4K-ALPHA | ATP + PINS -> ADP + PINS4P | 2.7.1.67 |
| 5305 | PIP5K2A | PINS4P + ATP -> D45PI + ADP | 2.7.1.68 |
| 5330 | PLCB2 | D45PI -> TPI + DAGLY | 3.1.4.11 |
| 5331 | PLCB3 | D45PI -> TPI + DAGLY | 3.1.4.11 |
| 5333 | PLCD1 | D45PI -> TPI + DAGLY | 3.1.4.11 |
| 5335 | PLCG1, PLC1 | D45PI -> TPI + DAGLY | 3.1.4.11 |
| 5336 | PLCG2 | D45PI -> TPI + DAGLY | 3.1.4.11 |
| 3612 | IMPA1, IMPA | MI1P -> MYOI + PI | 3.1.3.25 |
| 3613 | IMPA2 | MI1P -> MYOI + PI | 3.1.3.25 |
| 3628 | INPP1 | | 3.1.3.57 |
| 3632 | INPP5A | | |
| 3633 | INPP5B | | 3.1.3.56 |
| 3636 | INPPL1, SHIP2 | | 3.1.3.56 |
| 4952 | OCRL, LOCR, OCRL1, INPP5F | | 3.1.3.56 |
| 8867 | SYNJ1, INPP5G | | 3.1.3.56 |
| 3706 | ITPKA | | 2.7.1.127 |
| 51477 | ISYNA1 | G6P -> MI1P | 5.5.1.4 |
| 3631 | INPP4A, INPP4 | | 3.1.3.66 |
| 8821 | INPP4B | | 3.1.3.66 |
| 8.3 Sphingophospholipid biosynthesis PATH:hsa00570 | | | |
| 6609 | SMPD1, NPD | | 3.1.4.12 |
| 8.4 Phospholipid degradation PATH:hsa00580 | | | |
| 1178 | CLC | | 3.1.1.5 |
| 5321 | PLA2G4A, CPLA2-ALPHA, PLA2G4 | | 3.1.1.5 |
| 8.5 Sphingoglycolipid metabolism PATH:hsa00600 | | | |
| 10558 | SPTLC1, LCB1, SPTI | PALCOA + SER -> COA + DHSPH + CO2 | 2.3.1.50 |
| 9517 | SPTLC2, KIAA0526, LCB2 | PALCOA + SER -> COA + DHSPH + CO2 | 2.3.1.50 |
| 427 | ASAH, AC, PHP32 | | 3.5.1.23 |
| 7357 | UGCG, GCS | | 2.4.1.80 |
| 2629 | GBA, GLUC | | 3.2.1.45 |
| 2583 | GALGT, GALNACT | | 2.4.1.92 |
| 6489 | SIAT8A, SIAT8, ST8SIA-I | | 2.4.99.8 |
| 6481 | SIAT2 | | 2.4.99.2 |
| 4668 | NAGA, D22S674, GALB | | 3.2.1.49 |
| 9514 | CST | | 2.8.2.11 |
| 410 | ARSA, MLD | | 3.1.6.8 |
| 8.6 Blood group glycolipid biosynthesis - lact series PATH:hsa00601 | | | |
| 28 | ABO | | 2.4.1.40 |
| | | | 2.4.1.37 |
| 2525 | FUT3, LE | | 2.4.1.65 |
| 2527 | FUT5, FUC-TV | | 2.4.1.65 |
| 2528 | FUT6 | | 2.4.1.65 |
| 2523 | FUT1, H, HH | | 2.4.1.69 |
| 2524 | FUT2, SE | | 2.4.1.69 |
| 8.7 Blood group glycolipid biosynthesis - neolact series PATH:hsa00602 | | | |
| 2651 | GCNT2, IGNT, NACGT1, NAGCT1 | | 2.4.1.150 |
| 8.8 Prostaglandin and leukotriene metabolism PATH:hsa00590 | | | |
| 239 | ALOX12, LOG12 | | 1.13.11.31 |
| 246 | ALOX15 | | 1.13.11.33 |
| 240 | ALOX5 | | 1.13.11.34 |
| 4056 | LTC4S | | 2.5.1.37 |
| 4048 | LTA4H | | 3.3.2.6 |
| 4051 | CYP4F3, CYP4F, LTB4H | | 1.14.13.30 |

TABLE 1-continued

| Locus ID | Gene Ab. | Reaction Stoichiometry | E.C. |
|---|---|---|---|
| 8529 | CYP4F2 | | 1.14.13.30 |
| 5742 | PTGS1, PGHS-1 | | 1.14.99.1 |
| 5743 | PTGS2, COX-2, COX2 | | 1.14.99.1 |
| 27306 | PGDS | | 5.3.99.2 |
| 5730 | PTGDS | | 5.3.99.2 |
| 5740 | PTGIS, CYP8, PGIS | | 5.3.99.4 |
| 6916 | TBXAS1, CYP5 | | 5.3.99.5 |
| 873 | CBR1, CBR | | 1.1.1.184 |
| | | | 1.1.1.189 |
| | | | 1.1.1.197 |
| 874 | CBR3 | | 1.1.1.184 |

9. Metabolism of Cofactors and Vitamins
9.2 Riboflavin metabolism PATH:hsa00740

| Locus ID | Gene Ab. | Reaction Stoichiometry | E.C. |
|---|---|---|---|
| 52 | ACP1 | | 3.1.3.48 |
| | | FMN -> RIBOFLAV + PI | 3.1.3.2 |
| 53 | ACP2 | FMN -> RIBOFLAV + PI | 3.1.3.2 |
| 54 | ACP5, TRAP | FMN -> RIBOFLAV + PI | 3.1.3.2 |
| 55 | ACPP, PAP | FMN -> RIBOFLAV + PI | 3.1.3.2 |

9.3 Vitamin B6 metabolism PATH:hsa00750

| Locus ID | Gene Ab. | Reaction Stoichiometry | E.C. |
|---|---|---|---|
| 8566 | PDXK, PKH, PNK | PYRDX + ATP -> P5P + ADP | 2.7.1.35 |
| | | PDLA + ATP -> PDLA5P + ADP | |
| | | PL + ATP -> PL5P + ADP | |

9.4 Nicotinate and nicotinamide metabolism PATH:hsa00760

| Locus ID | Gene Ab. | Reaction Stoichiometry | E.C. |
|---|---|---|---|
| 23475 | QPRT | QA + PRPP -> NAMN + CO2 + PPI | 2.4.2.19 |
| 4837 | NNMT | | 2.1.1.1 |
| 683 | BST1, CD157 | NAD -> NAM + ADPRIB | 3.2.2.5 |
| 952 | CD38 | NAD -> NAM + ADPRIB | 3.2.2.5 |
| 23530 | NNT | | 1.6.1.2 |

9.5 Pantothenate and CoA biosynthesis PATH:hsa00770
9.6 Biotin metabolism PATH:hsa00780

| Locus ID | Gene Ab. | Reaction Stoichiometry | E.C. |
|---|---|---|---|
| 3141 | HLCS, HCS | | 6.3.4.— |
| | | | 6.3.4.9 |
| | | | 6.3.4.10 |
| | | | 6.3.4.11 |
| | | | 6.3.4.15 |
| 686 | BTD | | 3.5.1.12 |

9.7 Folate biosynthesis PATH:hsa00790

| Locus ID | Gene Ab. | Reaction Stoichiometry | E.C. |
|---|---|---|---|
| 2643 | GCH1, DYT5, GCH, GTPCH1 | GTP -> FOR + AHTD | 3.5.4.16 |
| 1719 | DHFR | DHF + NADPH -> NADP + THF | 1.5.1.3 |
| 2356 | FPGS | THF + ATP + GLU <-> ADP + PI + THFG | 6.3.2.17 |
| 8836 | GGH, GH | | 3.4.19.9 |
| 5805 | PTS | | 4.6.1.10 |
| 6697 | SPR | | 1.1.1.153 |
| 5860 | QDPR, DHPR, PKU2 | NADPH + DHBP -> NADP + THBP | 1.6.99.7 |

9.8 One carbon pool by folate PATH:hsa00670

| Locus ID | Gene Ab. | Reaction Stoichiometry | E.C. |
|---|---|---|---|
| 10840 | FTHFD | | 1.5.1.6 |
| 10588 | MTHFS | ATP + FTHF -> ADP + PI + MTHF | 6.3.3.2 |

9.10 Porphyrin and chlorophyll metabolism PATH:hsa00860

| Locus ID | Gene Ab. | Reaction Stoichiometry | E.C. |
|---|---|---|---|
| 210 | ALAD | 2 ALAV -> PBG | 4.2.1.24 |
| 3145 | HMBS, PBGD, UPS | 4 PBG -> HMB + 4 NH3 | 4.3.1.8 |
| 7390 | UROS | HMB -> UPRG | 4.2.1.75 |
| 7389 | UROD | UPRG -> 4 CO2 + CPP | 4.1.1.37 |
| 1371 | CPO, CPX | O2 + CPP -> 2 CO2 + PPHG | 1.3.3.3 |
| 5498 | PPOX, PPO | O2 + PPHGm -> PPIXm | 1.3.3.4 |
| 2235 | FECH, FCE | PPIXm -> PTHm | 4.99.1.1 |
| 3162 | HMOX1, HO-1 | | 1.14.99.3 |
| 3163 | HMOX2, HO-2 | | 1.14.99.3 |
| 644 | BLVRA, BLVR | | 1.3.1.24 |
| 645 | BLVRB, FLR | | 1.3.1.24 |
| | | | 1.6.99.1 |
| 2232 | FDXR, ADXR | | 1.18.1.2 |
| 3052 | HCCS, CCHL | | 4.4.1.17 |
| 1356 | CP | | 1.16.3.1 |

9.11 Ubiquinone biosynthesis PATH:hsa00130

| Locus ID | Gene Ab. | Reaction Stoichiometry | E.C. |
|---|---|---|---|
| 4938 | OAS1, IFI-4, OIAS | | 2.7.7.— |
| 4939 | OAS2, P69 | | 2.7.7.— |
| 5557 | PRIM1 | | 2.7.7.— |
| 5558 | PRIM2A, PRIM2 | | 2.7.7.— |
| 5559 | PRIM2B, PRIM2 | | 2.7.7.— |
| 7015 | TERT, EST2, TCS1, TP2, TRT | | 2.7.7.— |
| 8638 | OASL, TRIP14 | | 2.7.7.— |

10. Metabolism of Other Substances
10.1 Terpenoid biosynthesis PATH:hsa00900
10.2 Flavonoids, stilbene and lignin biosynthesis PATH:hsa00940
10.3 Alkaloid biosynthesis I PATH:hsa00950
10.4 Alkaloid biosynthesis II PATH:hsa00960
10.6 Streptomycin biosynthesis PATH:hsa00521
10.7 Erythromycin biosynthesis PATH:hsa00522

TABLE 1-continued

| Locus ID | Gene Ab. | Reaction Stoichiometry | E.C. |
|---|---|---|---|
| 10.8 Tetracycline biosynthesis PATH:hsa00253 | | | |
| 10.14 gamma-Hexachlorocyclohexane degradation PATH:hsa00361 | | | |
| 5444 | PON1, ESA, PON | | 3.1.8.1 |
| | | | 3.1.1.2 |
| 5445 | PON2 | | 3.1.1.2 |
| | | | 3.1.8.1 |
| 10.18 1,2-Dichloroethane degradation PATH:hsa00631 | | | |
| 10.20 Tetrachloroethene degradation PATH:hsa00625 | | | |
| 2052 | EPHX1, EPHX, MEH | | 3.3.2.3 |
| 2053 | EPHX2 | | 3.3.2.3 |
| 10.21 Styrene degradation PATH:hsa00643 | | | |
| 11. Transcription (condensed) | | | |
| 11.1 RNA polymerase PATH:hsa03020 | | | |
| 11.2 Transcription factors PATH:hsa03022 | | | |
| 12. Translation (condensed) | | | |
| 12.1 Ribosome PATH:hsa03010 | | | |
| 12.2 Translation factors PATH:hsa03012 | | | |
| 1915 | EEF1A1, EF1A, ALPHA, EEF-1, EEF1A | | 3.6.1.48 |
| 1917 | EEF1A2, EF1A | | 3.6.1.48 |
| 1938 | EEF2, EF2, EEF-2 | | 3.6.1.48 |
| 12.3 Aminoacyl-tRNA biosynthesis PATH:hsa00970 | | | |
| 13. Sorting and Degradation (condensed) | | | |
| 13.1 Protein export PATH:hsa03060 | | | |
| 23478 | SPC18 | | 3.4.21.89 |
| 13.4 Proteasome PATH:hsa03050 | | | |
| 5687 | PSMA6, IOTA, PROS27 | | 3.4.99.46 |
| 5683 | PSMA2, HC3, MU, PMSA2, PSC2 | | 3.4.99.46 |
| 5685 | PSMA4, HC9 | | 3.4.99.46 |
| 5688 | PSMA7, XAPC7 | | 3.4.99.46 |
| 5686 | PSMA5, ZETA, PSC5 | | 3.4.99.46 |
| 5682 | PSMA1, HC2, NU, PROS30 | | 3.4.99.46 |
| 5684 | PSMA3, HC8 | | 3.4.99.46 |
| 5698 | PSMB9, LMP2, RING12 | | 3.4.99.46 |
| 5695 | PSMB7, Z | | 3.4.99.46 |
| 5691 | PSMB3, HC10-II | | 3.4.99.46 |
| 5690 | PSMB2, HC7-I | | 3.4.99.46 |
| 5693 | PSMB5, LMPX, MB1 | | 3.4.99.46 |
| 5689 | PSMB1, HC5, PMSB1 | | 3.4.99.46 |
| 5692 | PSMB4, HN3, PROS26 | | 3.4.99.46 |
| 14. Replication and Repair | | | |
| 14.1 DNA polymerase PATH:hsa03030 | | | |
| 14.2 Replication Complex PATH:hsa03032 | | | |
| 23626 | SPO11 | | 5.99.1.3 |
| 7153 | TOP2A, TOP2 | | 5.99.1.3 |
| 7155 | TOP2B | | 5.99.1.3 |
| 7156 | TOP3A, TOP3 | | 5.99.1.2 |
| 8940 | TOP3B | | 5.99.1.2 |
| 22. Enzyme Complex | | | |
| 22.1 Electron Transport System, Complex I PATH:hsa03100 | | | |
| 22.2 Electron Transport System, Complex II PATH:hsa03150 | | | |
| 22.3 Electron Transport System, Complex III PATH:hsa03140 | | | |
| 22.4 Electron Transport System, Complex IV PATH:hsa03130 | | | |
| 22.5 ATP Synthase PATH:hsa03110 | | | |
| 22.8 ATPases PATH:hsa03230 | | | |
| 23. Unassigned | | | |
| 23.1 Enzymes | | | |
| 5538 | PPT1, CLN1, PPT, INCL | C160ACP + H2O -> C160 + ACP | 3.1.2.22 |
| 23.2 Non-enzymes | | | |
| 22934 | RPIA, RPI | RL5P <-> R5P | 5.3.1.6 |
| 5250 | SLC25A3, PHC | PI + H <-> Hm + PIm | |
| 6576 | | CIT + MALm <-> CITm + MAL | |
| 51166 | LOC51166 | AADP + AKG -> GLU + KADP | 2.6.1.39 |
| 5625 | PRODH | PRO + FAD -> P5C + FADH2 | 1.5.3.— |
| 6517 | SLC2A4, GLUT4 | GLCxt -> GLC | |
| 6513 | SLC2A1, GLUT1, GLUT | GLCxt -> GLC | |
| 26275 | HIBCH, HIBYL-COA-H | HIBCOAm + H2Om -> HIBm + COAm | 3.1.2.4 |
| 23305 | KIAA0837, ACS2, LACS5, LACS2 | C160 + COA + ATP -> AMP + PPI + C160COA | |
| 8611 | PPAP2A, PAP-2A | PA + H2O -> DAGLY + PI | |
| 8612 | PPAP2C, PAP-2C | PA + H2O -> DAGLY + PI | |
| 8613 | PPAP2B, PAP-2B | PA + H2O -> DAGLY + PI | |
| 56994 | LOC56994 | CDPCHO + DAGLY -> PC + CMP | |
| 10400 | PEMT, PEMT2 | SAM + PE -> SAH + PMME | |
| 5833 | PCYT2, ET | PETHM + CTP -> CDPETN + PPI | |
| 10390 | CEPT1 | CDPETN + DAGLY <-> CMP + PE | |

TABLE 1-continued

| Locus ID | Gene Ab. | Reaction Stoichiometry | E.C. |
|---|---|---|---|
| 8394 | PIP5K1A | PINS4P + ATP -> D45PI + ADP | |
| 8395 | PIP5K1B, STM7, MSS4 | PINS4P + ATP -> D45PI + ADP | |
| 8396 | PIP5K2B | PINS4P + ATP -> D45PI + ADP | |
| 23396 | PIP5K1C, KIAA0589, PIP5K-GAMMA | PINS4P + ATP -> D45PI + ADP | |
| 24. Our own reactions which need to be found in KEGG | | | |
| | | GL3P <-> GL3Pm | |
| | | T3P2 <-> T3P2m | |
| | | PYR <-> PYRm + Hm | |
| | | ADP + ATPm + PI + H -> Hm + ADPm + ATP + PIm | |
| | | AKG + MALm <-> AKGm + MAL | |
| | | ASPm + GLU + H -> Hm + GLUm + ASP | |
| | | GDP + GTPm + PI + H -> Hm + GDPm + GTP + PIm | |
| | | C160Axt + FABP -> C160FP + ALBxt | |
| | | C160FP -> C160 + FABP | |
| | | C180Axt + FABP -> C180FP + ALBxt | |
| | | C180FP -> C180 + FABP | |
| | | C161Axt + FABP -> C161FP + ALBxt | |
| | | C161FP -> C161 + FABP | |
| | | C181Axt + FABP -> C181FP + ALBxt | |
| | | C181FP -> C181 + FABP | |
| | | C182Axt + FABP -> C182FP + ALBxt | |
| | | C182FP -> C182 + FABP | |
| | | C204Axt + FABP -> C204FP + ALBxt | |
| | | C204FP -> C204 + FABP | |
| | | O2xt -> O2 | |
| | | O2 <-> O2m | |
| | | ACTACm + SUCCOAm -> SUCCm + AACCOAm | |
| | | 3HB -> 3HBm | |
| | | MGCOAm + H2Om -> H3MCOAm | 4.2.1.18 |
| | | OMVAL -> OMVALm | |
| | | OIVAL -> OIVALm | |
| | | OICAP -> OICAPm | |
| | | C160CAR <-> C160CARm | |
| | | CAR <-> CARm | |
| | | DMMCOAm -> LMMCOAm | 5.1.99.1 |
| amino acid metabolism | | | |
| | | THR -> NH3 + H2O + OBUT | 4.2.1.16 |
| | | THR + NAD -> CO2 + NADH + AMA | 1.1.1.103 |
| | | THR + NAD + COA -> NADH + ACCOA + GLY | |
| | | AASA + NAD -> NADH + AADP | 1.2.1.31 |
| | | FKYN + H2O -> FOR + KYN | 3.5.1.9 |
| | | CMUSA -> CO2 + AM6SA | 4.1.1.45 |
| | | AM6SA + NAD -> AMUCO + NADH | 1.2.1.32 |
| | | AMUCO + NADPH -> KADP + NADP + NH4 | 1.5.1.— |
| | | CYSS + AKG <-> GLU + SPYR | |
| | | URO + H2O -> 4I5P | 4.2.1.49 |
| | | 4I5P + H2O -> FIGLU | 3.5.2.7 |
| | | GLU <-> GLUm + Hm | |
| | | ORN + Hm -> ORNm | |
| | | ORN + Hm + CITRm <-> CITR + ORNm | |
| | | GLU + ATP + NADPH -> NADP + ADP + PI + GLUGSAL | |
| | | GLYAm + ATPm -> ADPm + 2PGm | |
| | | AM6SA -> PIC | |
| | | SPYR + H2O -> H2SO3 + PYR | |
| | | P5C <-> GLUGSAL | |
| fatty acid synthesis | | | |
| | | MALCOA + ACP <-> MALACP + COA | 2.3.1.39 |
| | | ACCOA + ACP <-> ACACP + COA | |
| | | ACACP + 4 MALACP + 8 NADPH -> 8 NADP + C100ACP + 4 CO2 + 4 ACP | |
| | | ACACP + 5 MALACP + 10 NADPH -> 10 NADP + C120ACP + 5 CO2 + 5 ACP | |
| | | ACACP + 6 MALACP + 12 NADPH -> 12 NADP + C140ACP + 6 CO2 + 6 ACP | |
| | | ACACP + 6 MALACP + 11 NADPH -> 11 NADP + C141ACP + 6 CO2 + 6 ACP | |
| | | ACACP + 7 MALACP + 14 NADPH -> 14 NADP + C160ACP + 7 CO2 + 7 ACP | |
| | | ACACP + 7 MALACP + 13 NADPH -> 13 NADP + C161ACP + 7 CO2 + 7 ACP | |
| | | ACACP + 8 MALACP + 16 NADPH -> 16 NADP + C180ACP + 8 CO2 + 8 ACP | |
| | | ACACP + 8 MALACP + 15 NADPH -> 15 NADP + C181ACP + 8 CO2 + 8 ACP | |

TABLE 1-continued

| Locus ID | Gene Ab. | Reaction Stoichiometry | E.C. |
|---|---|---|---|
| | | ACACP + 8 MALACP + 14 NADPH -> 14 NADP + C182ACP + 8 CO2 + 8 ACP | |
| | | C160COA + CAR -> C160CAR + COA | |
| | | C160CARm + COAm -> C160COAm + CARm | |
| | fatty acid degredation | | |
| | | GL3P + 0.017 C100ACP + 0.062 C120ACP + 0.1 C140ACP + 0.27 C160ACP + 0.169 C161ACP + 0.055 C180ACP + 0.235 C181ACP + 0.093 C182ACP -> AGL3P + ACP | |
| | | TAGLYm + 3 H2Om -> GLm + 3 C160m | |
| | Phospholipid metabolism | | |
| | | SAM + PMME -> SAH + PDME | |
| | | PDME + SAM -> PC + SAH | |
| | | PE + SER <-> PS + ETHM | |
| | Muscle contraction | | |
| | | MYOACT + ATP -> MYOATP + ACTIN | |
| | | MYOATP + ACTIN -> MYOADPAC | |
| | | MYOADPAC -> ADP + PI + MYOACT + CONTRACT | |

TABLE 2

// Homo Sapiens Core Metabolic Network //

// Glycolysis //

−1 GLC −1 ATP +1 G6P +1 ADP 0 HK1
−1 G6P −1 H2O +1 GLC +1 PI 0 G6PC
−1 G6P +1 F6P 0 GPIR
−1 F6P −1 ATP +1 FDP +1 ADP 0 PFKL
−1 FDP −1 H2O +1 F6P +1 PI 0 FBP1
−1 FDP +1 T3P2 +1 T3P1 0 ALDOAR
−1 T3P2 +1 T3P1 0 TPI1R
−1 T3P1 −1 PI −1 NAD +1 NADH +1 13PDG 0 GAPDR
−1 13PDG −1 ADP +1 3PG +1 ATP 0 PGK1R
−1 13PDG +1 23PDG 0 PGAM1
−1 23PDG −1 H2O +1 3PG +1 PI 0 PGAM2
−1 3PG +1 2PG 0 PGAM3R
−1 2PG +1 PEP +1 H2O 0 ENO1R
−1 PEP −1 ADP +1 PYR +1 ATP 0 PKLR
−1 PYRm −1 COAm −1 NADm +1 NADHm +1 CO2m +1 ACCOAm 0 PDHA1
−1 NAD −1 LAC +1 PYR +1 NADH 0 LDHAR
−1 G1P +1 G6P 0 PGM1R

// TCA //

−1 ACCOAm −1 OAm −1 H2Om +1 COAm +1 CITm 0 CS
−1 CIT +1 ICIT 0 ACO1R
−1 CITm +1 ICITm 0 ACO2R
−1 ICIT −1 NADP +1 NADPH +1 CO2 +1 AKG 0 IDH1
−1 ICITm −1 NADPm +1 NADPHm +1 CO2m +1 AKGm 0 IDH2
−1 ICITm −1 NADm +1 CO2m +1 NADHm +1 AKGm 0 IDH3A
−1 AKGm −1 NADm −1 COAm +1 CO2m +1 NADHm +1 SUCCOAm 0 OGDH
−1 GTPm −1 SUCCm −1 COAm +1 GDPm +1 PIm +1 SUCCOAm 0 SUCLG1R
−1 ATPm −1 SUCCm −1 COAm +1 ADPm +1 PIm +1 SUCCOAm 0 SUCLA2R
−1 FUMm −1 H2Om +1 MALm 0 FHR
−1 MAL −1 NAD +1 NADH +1 OA 0 MDH1R
−1 MALm −1 NADm +1 NADHm +1 OAm 0 MDH2R
−1 PYRm −1 ATPm −1 CO2m +1 ADPm +1 OAm +1 PIm 0 PC
−1 OA −1 GTP +1 PEP +1 GDP +1 CO2 0 PCK1
−1 OAm −1 GTPm +1 PEPm +1 GDPm +1 CO2m 0 PCK2
−1 ATP −1 CIT −1 COA −1 H2O +1 ADP +1 PI +1 ACCOA +1 OA 0 ACLY

// PPP //

−1 G6P −1 NADP +1 D6PGL +1 NADPH 0 G6PDR
−1 D6PGL −1 H2O +1 D6PGC 0 PGLS
−1 D6PGC −1 NADP +1 NADPH +1 CO2 +1 RL5P 0 PGD
−1 RL5P +1 X5P 0 RPER

−1 R5P −1 X5P +1 T3P1 +1 S7P 0 TKT1R
−1 X5P −1 E4P +1 F6P +1 T3P1 0 TKT2R
−1 T3P1 −1 S7P +1 E4P +1 F6P 0 TALDO1R
−1 RL5P +1 R5P 0 RPIAR

// Glycogen //

−1 G1P −1 UTP +1 UDPG +1 PPI 0 UGP1
−1 UDPG +1 UDP +1 GLYCOGEN 0 GYS1
−1 GLYCOGEN −1 PI +1 G1P 0 GBE1

// ETS //

−1 MALm −1 NADPm +1 CO2m +1 NADPHm +1 PYRm 0 ME3
−1 MALm −1 NADm +1 CO2m +1 NADHm +1 PYRm 0 ME2
−1 MAL −1 NADP +1 CO2 +1 NADPH +1 PYR 0 ME1
−1 NADHm −1 Qm −4 Hm +1 QH2m +1 NADm +4 H 0 MTND1
−1 SUCCm −1 FADm +1 FUMm +1 FADH2m 0 SDHC1R
−1 FADH2m −1 Qm +1 FADm +1 QH2m 0 SDHC2R
−1 O2m −4 FEROm −4 Hm +4 FERIm +2 H2Om +4 H 0 UQCRFS1
−1 QH2m −2 FERIm −4 Hm +1 Qm +2 FEROm +4 H 0 COX5BL4
−1 ADPm −1 PIm −3 H +1 ATPm +3 Hm +1 H2Om 0 MTAT
−1 ADP −1 ATPm −1 PI −1 H +1 Hm +1 ADPm +1 ATP +1 PIm 0 ATPMC
−1 GDP −1 GTPm −1 PI −1 H +1 Hm +1 GDPm +1 GTP +1 PIm 0 GTPMC
−1 PPI +2 PI 0 PP
−1 ACCOA −1 ATP −1 CO2 +1 MALCOA +1 ADP +1 PI 0 ACACAR
−1 GDP −1 ATP +1 GTP +1 ADP 0 GOT3R

// Transporters //

−1 CIT −1 MALm +1 CITm +1 MAL 0 CITMCR
−1 PYR −1 H +1 PYRm +1 Hm 0 PYRMCR

// Glycerol Phosphate Shuttle //

−1 GL3Pm −1 FADm +1 T3P2m +1 FADH2m 0 GPD2
−1 T3P2 −1 NADH +1 GL3P +1 NAD 0 GPD1
−1 GL3P +1 GL3Pm 0 GL3PMCR
−1 T3P2 +1 T3P2m 0 T3P2MCR

// Malate/Aspartate Shuttle //

−1 OAm −1 GLUm +1 ASPm +1 AKGm 0 GOT1R
−1 ASP −1 AKG +1 OA +1 GLU 0 GOT2R
−1 AKG −1 MALm +1 AKGm +1 MAL 0 MALMCR
−1 ASPm −1 GLU −1 H +1 Hm +1 GLUm +1 ASP 0 ASPMC

// Exchange Fluxes //

+1 GLC 0 GLCexR
+1 PYR 0 PYRexR
+1 CO2 0 CO2exR
+1 O2 0 O2exR
+1 PI 0 PIexR
+1 H2O 0 H2OexR
+1 LAC 0 LACexR
+1 CO2m 0 CO2min

TABLE 2-continued

// Homo Sapiens Core Metabolic Network //

```
−1 CO2m 0 CO2mout
+1 O2m 0 O2min
−1 O2m 0 O2mout
+1 H2Om 0 H2Omin
−1 H2Om 0 H2Omout
+1 PIm 0 PImin
−1 PIm 0 PImout
// Output //

−1 ATP +1 ADP +1 PI 0 Output
0.0 end
end E 0
max
1 Output
0 end
0 GLCexR 1
−1000 PYRexR 0
−1000 LACexR 0
0 end 0
rev. rxn 33
nonrev. rxn 31
total rxn 64
matrix columns 97
unique enzymes 52
```

TABLE 3

| Abbrev. | Reaction | Rxn Name |
|---|---|---|
| Glycolysis | | |
| HK1 | GLC + ATP -> G6P + ADP | HK1 |
| G6PC, G6PT | G6P + H2O -> GLC + PI | G6PC |
| GPI | G6P <-> F6P | GPI |
| PFKL | F6P + ATP -> FDP + ADP | PFKL |
| FBP1, FBP | FDP + H2O -> F6P + PI | FBP1 |
| ALDOA | FDP <-> T3P2 + T3P1 | ALDOA |
| TPI1 | T3P2 <-> T3P1 | TPI1 |
| GAPD, GAPDH | T3P1 + PI + NAD <-> NADH + 13PDG | GAPD |
| PGK1, PGKA | 13PDG + ADP <-> 3PG + ATP | PGK1 |
| PGAM1, PGAMA | 13PDG <-> 23PDG | PGAM1 |
|  | 23PDG + H2O -> 3PG + PI | PGAM2 |
|  | 3PG <-> 2PG | PGAM3 |
| ENO1, PPH, ENO1L1 | 2PG <-> PEP + H2O | ENO1 |
| PKLR, PK1 | PEP + ADP -> PYR + ATP | PKLR |
| PDHA1, PHE1A, PDHA | PYRm + COAm + NADm -> + NADHm + CO2m + ACCOAm | PDHA1 |
| LDHA, LDH1 | NAD + LAC <-> PYR + NADH | LDHA |
| PGM1 | G1P <-> G6P | PGM1 |
| TCA | | |
| CS | ACCOAm + OAm + H2Om -> COAm + CITm | CS |
| ACO1, IREB1, IRP1 | CIT <-> ICIT | ACO1 |
| ACO2 | CITm <-> ICITm | ACO2 |
| IDH1 | ICIT + NADP -> NADPH + CO2 + AKG | IDH1 |
| IDH2 | ICITm + NADPm -> NADPHm + CO2m + AKGm | IDH2 |
| IDH3A | ICITm + NADm -> CO2m + NADHm + AKGm | IDH3A |
| OGDH | AKGm + NADm + COAm -> CO2m + NADHm + SUCCOAm | OGDH |
| SUCLG1, SUCLA1 | GTPm + SUCCm + COAm <-> GDPm + PIm + SUCCOAm | SUCLG1 |
| SUCLA2 | ATPm + SUCCm + COAm <-> ADPm + PIm + SUCCOAm | SUCLA2 |
| FH | FUMm + H2Om <-> MALm | FH |
| MDH1 | MAL + NAD <-> NADH + OA | MDH1 |
| MDH2 | MALm + NADm <-> NADHm + OAm | MDH2 |
| PC, PCB | PYRm + ATPm + CO2m -> ADPm + OAm + PIm | PC |
| ACLY, ATPCL, CLATP | ATP + CIT + COA + H2O -> ADP + PI + ACCOA + OA | ACLY |
| PCK1 | OA + GTP -> PEP + GDP + CO2 | PCK1 |
| PPP | | |
| G6PD, G6PD1 | G6P + NADP <-> D6PGL + NADPH | G6PD |
| PGLS, 6PGL | D6PGL + H2O -> D6PGC | PGLS |
| PGD | D6PGC + NADP -> NADPH + CO2 + RL5P | PGD |
| RPE | RL5P <-> X5P | RPE |
| TKT | R5P + X5P <-> T3P1 + S7P | TKT1 |
|  | X5P + E4P <-> F6P + T3P1 | TKT2 |
| TALDO1 | T3P1 + S7P <-> E4P + F6P | TALDO1 |
| UGP1 | G1P + UTP -> UDPG + PPI | UGP1 |
| ACACA, ACAC, ACC | ACCOA + ATP + CO2 <-> MALCOA + ADP + PI + H | ACACA |
| ETS | | |
| ME3 | MALm + NADPm -> CO2m + NADPHm + PYRm | ME3 |
| MTND1 | NADHm + Qm + 4 Hm -> QH2m + NADm + 4 H | MTND1 |
| SDHC | SUCCm + FADm <-> FUMm + FADH2m | SDHC1 |
|  | FADH2m + Qm <-> FADm + QH2m | SDHC2 |
| UQCRFS1, RIS1 | O2m + 4 FEROm + 4 Hm -> 4 FERIm + 2 H2Om + 4 H | UQCRFS1 |
| COX5BL4 | QH2m + 2 FERIm + 4 Hm -> Qm + 2 FEROm + 4 H | COX5BL4 |
| MTATP6 | ADPm + PIm + 3 H -> ATPm + 3 Hm + H2Om | MTAT |
| PP, SID6-8061 | PPI -> 2 PI | PP |

TABLE 3-continued

| Abbrev. | Reaction | Rxn Name |
|---|---|---|
| Malate Aspartate shunttle | | |
| GOT1 | OAm + GLUm <-> ASPm + AKGm | GOT1 |
| GOT2 | OA + GLU <-> ASP + AKG | GOT2 |
| | GDP + ATP <-> GTP + ADP | GOT3 |
| Glycogen | | |
| GBE1 | GLYCOGEN + PI -> G1P | GBE1 |
| GYS1, GYS | UDPG -> UDP + GLYCOGEN | GYS1 |
| Glycerol Phosphate Shunttle | | |
| GPD2 | GL3Pm + FADm -> T3P2m + FADH2m | GPD2 |
| GPD1 | T3P2 + NADH -> GL3P + NAD | GPD1 |
| RPIA, RPI | RL5P <-> R5P | RPIA |
| Mitochondria Transport | CIT + MALm <-> CITm + MAL | CITMC |
| | GL3P <-> GL3Pm | GL3PMC |
| | T3P2 <-> T3P2m | T3P2MC |
| | PYR <-> PYRm + Hm | PYRMC |
| | ADP + ATPm + PI + H -> Hm + ADPm + ATP + PIm | ATPMC |
| | AKG + MALm <-> AKGm + MAL | MALMC |
| | ASPm + GLU + H -> Hm + GLUm + ASP | ASPMC |
| | GDP + GTPm + PI + H -> Hm + GDPm + GTP + PIm | GTPMC |

TABLE 4

Metabolic Reaction for Muscle Cells

| Reaction | | Rxt Name |
|---|---|---|
| GLC + ATP -> G6P + ADP | 0 | HK1 |
| G6P <-> F6P | 0 | GPI |
| F6P + ATP -> FDP + ADP | 0 | PFKL1 |
| FDP + H2O -> F6P + PI | 0 | FBP1 |
| FDP <-> T3P2 + T3P1 | 0 | ALDOA |
| T3P2 <-> T3P1 | 0 | TPI1 |
| T3P1 + PI + NAD <-> NADH + 13PDG | 0 | GAPD |
| 13PDG + ADP <-> 3PG + ATP | 0 | PGK1 |
| 3PG <-> 2PG | 0 | PGAM3 |
| 2PG <-> PEP + H2O | 0 | ENO1 |
| PEP + ADP -> PYR + ATP | 0 | PK1 |
| PYRm + COAm + NADm -> + NADHm + CO2m + ACCOAm | 0 | PDHA1 |
| NAD + LAC <-> PYR + NADH | 0 | LDHA |
| G1P <-> G6P | 0 | PGM1 |
| ACCOAm + OAm + H2Om -> COAm + CITm | 0 | CS |
| CIT <-> ICIT | 0 | ACO1 |
| CITm <-> ICITm | 0 | ACO2 |
| ICIT + NADP -> NADPH + CO2 + AKG | 0 | IDH1 |
| ICITm + NADPm -> NADPHm + CO2m + AKGm | 0 | IDH2 |
| ICITm + NADm -> CO2m + NADHm + AKGm | 0 | IDH3A |
| AKGm + NADm + COAm -> CO2m + NADHm + SUCCOAm | 0 | OGDH |
| GTPm + SUCCm + COAm <-> GDPm + PIm + SUCCOAm | 0 | SUCLG1 |
| ATPm + SUCCm + COAm <-> ADPm + PIm + SUCCOAm | 0 | SUCLA2 |
| FUMm + H2Om <-> MALm | 0 | FH |
| MAL + NAD <-> NADH + OA | 0 | MDH1 |
| MALm + NADm <-> NADHm + OAm | 0 | MDH2 |
| PYRm + ATPm + CO2m -> ADPm + OAm + PIm | 0 | PC |
| ATP + CIT + COA + H2O -> ADP + PI + ACCOA + OA | 0 | ACLY |
| OA + GTP -> PEP + GDP + CO2 | 0 | PCK1 |
| OAm + GTPm -> PEPm + GDPm + CO2m | 0 | PCK2 |
| G6P + NADP <-> D6PGL + NADPH | 0 | G6PD |
| D6PGL + H2O -> D6PGC | 0 | H6PD |
| D6PGC + NADP -> NADPH + CO2 + RL5P | 0 | PGD |
| RL5P <-> X5P | 0 | RPE |
| R5P + X5P <-> T3P1 + S7P | 0 | TKT1 |
| X5P + E4P <-> F6P + T3P1 | 0 | TKT2 |
| T3P1 + S7P <-> E4P + F6P | 0 | TALDO1 |
| RL5P <-> R5P | 0 | RPIA |
| G1P + UTP -> UDPG + PPI | 0 | UGP1 |
| GLYCOGEN + PI -> G1P | 0 | GBE1 |
| UDPG -> UDP + GLYCOGEN | 0 | GYS1 |
| MALm + NADm -> CO2m + NADHm + PYRm | 0 | ME2 |
| MALm + NADPm -> CO2m + NADPHm + PYRm | 0 | ME3 |
| MAL + NADP -> CO2 + NADPH + PYR | 0 | HUMNDME |
| NADHm + Qm + 4 Hm -> QH2m + NADm + 4 H | 0 | MTND1 |
| SUCCm + FADm <-> FUMm + FADH2m | 0 | SDHC1 |

TABLE 4-continued

Metabolic Reaction for Muscle Cells

| Reaction | | Rxt Name |
|---|---|---|
| FADH2m + Qm <-> FADm + QH2m | 0 | SDHC2 |
| O2m + 4 FEROm + 4 Hm -> 4 FERIm + 2 H2Om + 4 H | 0 | UQCRFS1 |
| QH2m + 2 FERIm + 4 Hm -> Qm + 2 FEROm + 4 H | 0 | COX5BL4 |
| ADPm + PIm + 3 H -> ATPm + 3 Hm + H2Om | 0 | MTAT1 |
| ADP + ATPm + PI + H -> Hm + ADPm + ATP + PIm | 0 | ATPMC |
| GDP + GTPm + PI + H -> Hm + GDPm + GTP + PIm | 0 | GTPMC |
| PPI -> 2 PI | 0 | PP |
| GDP + ATP <-> GTP + ADP | 0 | NME1 |
| ACCOA + ATP + CO2 <-> MALCOA + ADP + PI + H | 0 | ACACA |
| MALCOA + ACP <-> MALACP + COA | 0 | FAS1_1 |
| ACCOA + ACP <-> ACACP + COA | 0 | FAS1_2 |
| ACACP + 4 MALACP + 8 NADPH -> 8 NADP + C100ACP + 4 CO2 + 4 ACP | 0 | C100SY |
| ACACP + 5 MALACP + 10 NADPH -> 10 NADP + C120ACP + 5 CO2 + 5 ACP | 0 | C120SY |
| ACACP + 6 MALACP + 12 NADPH -> 12 NADP + C140ACP + 6 CO2 + 6 ACP | 0 | C140SY |
| ACACP + 6 MALACP + 11 NADPH -> 11 NADP + C141ACP + 6 CO2 + 6 ACP | 0 | C141SY |
| ACACP + 7 MALACP + 14 NADPH -> 14 NADP + C160ACP + 7 CO2 + 7 ACP | 0 | C160SY |
| ACACP + 7 MALACP + 13 NADPH -> 13 NADP + C161ACP + 7 CO2 + 7 ACP | 0 | C161SY |
| ACACP + 8 MALACP + 16 NADPH -> 16 NADP + C180ACP + 8 CO2 + 8 ACP | 0 | C180SY |
| ACACP + 8 MALACP + 15 NADPH -> 15 NADP + C181ACP + 8 CO2 + 8 ACP | 0 | C181SY |
| ACACP + 8 MALACP + 14 NADPH -> 14 NADP + C182ACP + 8 CO2 + 8 ACP | 0 | C182SY |
| C160ACP + H2O -> C160 + ACP | 0 | PPT1 |
| C160 + COA + ATP -> AMP + PPI + C160COA | 0 | KIAA |
| C160COA + CAR -> C160CAR + COA | 0 | C160CA |
| C160CARm + COAm -> C160COAm + CARm | 0 | C160CB |
| C160CARm + COAm + FADm + NADm -> FADH2m + NADHm + C140COAM + ACCOAM | 0 | HADHA |
| C140COAm + 7 COAm + 7 FADm + 7 NADm -> 7 FADH2m + 7 NADHm + 7 ACCOAm | 0 | HADH2 |
| TAGLYm + 3 H2Om -> GLm + 3 C160m | 0 | TAGRXN |
| GL3P + 0.017 C100ACP + 0.062 C120ACP + 0.1 C140ACP + 0.27 C160ACP + 0.169 C161ACP + 0.055 C180ACP + 0.235 C181ACP + 0.093 C182ACP -> AGL3P + ACP | 0 | GAT1 |
| AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | 0 | AGPAT1 |
| ATP + CHO -> ADP + PCHO | 0 | CHKLT1 |
| PCHO + CTP -> CDPCHO + PPI | 0 | PCYT1A |
| CDPCHO + DAGLY -> PC + CMP | 0 | LOC |
| SAM + PE -> SAH + PMME | 0 | PEMT |
| SAM + PMME -> SAH + PDME | 0 | MFPS |
| PDME + SAM -> PC + SAH | 0 | PNMNM |
| G6P -> MI1P | 0 | ISYNA1 |
| MI1P -> MYOI + PI | 0 | IMPA1 |
| PA + CTP <-> CDPDG + PPI | 0 | CDS1 |
| CDPDG + MYOI -> CMP + PINS | 0 | PIS |
| ATP + PINS -> ADP + PINSP | 0 | PIK3CA |
| ATP + PINS -> ADP + PINS4P | 0 | PIK4CA |
| PINS4P + ATP -> D45PI + ADP | 0 | PIP5K1 |
| D45PI -> TPI + DAGLY | 0 | PLCB2 |
| PA + H2O -> DAGLY + PI | 0 | PPAP2A |
| DAGLY + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> TAGLY + ACP | 0 | DGAT |
| CDPDG + SER <-> CMP + PS | 0 | PTDS |
| CDPETN + DAGLY <-> CMP + PE | 0 | CEPT1 |
| PE + SER <-> PS + ETHM | 0 | PESER |
| ATP + ETHM -> ADP + PETHM | 0 | EKI1 |
| PETHM + CTP -> CDPETN + PPI | 0 | PCYT2 |
| PS -> PE + CO2 | 0 | PISD |
| 3HBm + NADm -> NADHm + Hm + ACTACm | 0 | BDH |
| ACTACm + SUCCOAm -> SUCCm + AACOAm | 0 | 3OCT |
| THF + SER <-> GLY + METTHF | 0 | SHMT1 |
| THFm + SERm <-> GLYm + METTHFm | 0 | SHMT2 |
| SERm + PYRm <-> ALAm + 3HPm | 0 | AGXT |
| 3PG + NAD <-> NADH + PHP | 0 | PHGDH |
| PHP + GLU <-> AKG + 3PSER | 0 | PSA |
| 3PSER + H2O -> PI + SER | 0 | PSPH |
| 3HPm + NADHm -> NADm + GLYAm | 0 | GLYD |
| SER -> PYR + NH3 + H2O | 0 | SDS |

TABLE 4-continued

Metabolic Reaction for Muscle Cells

| Reaction | | Rxt Name |
|---|---|---|
| GLYAm + ATPm -> ADPm + 2PGm | 0 | GLTK |
| PYR + GLU <-> AKG + ALA | 0 | GPT |
| GLUm + CO2m + 2 ATPm -> 2 ADPm + 2 PIm + CAPm | 0 | CPS1 |
| AKGm + NADHm + NH3m <-> NADm + H2Om + GLUm | 0 | GLUD1 |
| AKGm + NADPHm + NH3m <-> NADPm + H2Om + GLUm | 0 | GLUD2 |
| GLUm + NH3m + ATPm -> GLNm + ADPm + PIm | 0 | GLUL |
| ASPm + ATPm + GLNm -> GLUm + ASNm + AMPm + PPIm | 0 | ASNS |
| ORN + AKG <-> GLUGSAL + GLU | 0 | OAT |
| GLU <-> GLUm + Hm | 0 | GLUMT |
| GLU + ATP + NADPH -> NADP + ADP + PI + GLUGSAL | 0 | P5CS |
| GLUP + NADH -> NAD + PI + GLUGSAL | 0 | PYCS |
| P5C <-> GLUGSAL | 0 | SPTC |
| HIS -> NH3 + URO | 0 | HAL |
| URO + H2O -> 4I5P | 0 | UROH |
| 4I5P + H2O -> FIGLU | 0 | IMPR |
| FIGLU + THF -> NFTHF + GLU | 0 | FTCD |
| MET + ATP + H2O -> PPI + PI + SAM | 0 | MAT1A |
| SAM + DNA -> SAH + DNA5MC | 0 | DNMT1 |
| SAH + H2O -> HCYS + ADN | 0 | AHCYL1 |
| HCYS + MTHF -> THF + MET | 0 | MTR |
| SER + HCYS -> LLCT + H2O | 0 | CBS |
| LLCT + H2O -> CYS + HSER | 0 | CTH1 |
| OBUT + NH3 <-> HSER | 0 | CTH2 |
| CYS + O2 <-> CYSS | 0 | CDO1 |
| CYSS + AKG <-> GLU + SPYR | 0 | CYSAT |
| SPYR + H2O -> H2SO3 + PYR | 0 | SPTB |
| LYS + NADPH + AKG -> NADP + H2O + SAC | 0 | LKR1 |
| SAC + H2O + NAD -> GLU + NADH + AASA | 0 | LKR2 |
| AASA + NAD -> NADH + AADP | 0 | 2ASD |
| AADP + AKG -> GLU + KADP | 0 | LOC5 |
| TRP + O2 -> FKYN | 0 | TDO2 |
| FKYN + H2O -> FOR + KYN | 0 | KYNF |
| KYN + NADPH + O2 -> HKYN + NADP + H2O | 0 | KMO |
| HKYN + H2O -> HAN + ALA | 0 | KYNU2 |
| HAN + O2 -> CMUSA | 0 | HAAO |
| CMUSA -> CO2 + AM6SA | 0 | ACSD |
| AM6SA -> PIC | 0 | SPTA |
| AM6SA + NAD -> AMUCO + NADH | 0 | AMSD |
| AMUCO + NADPH -> KADP + NADP + NH4 | 0 | 2AMR |
| ARG -> ORN + UREA | 0 | ARG2 |
| ORN + Hm -> ORNm | 0 | ORNMT |
| ORN + Hm + CITRm <-> CITR + ORNm | 0 | ORNCITT |
| ORNm + CAPm -> CITRm + Pim + Hm | 0 | OTC |
| CITR + ASP + ATP <-> AMP + PPI + ARGSUCC | 0 | ASS |
| ARGSUCC -> FUM + ARG | 0 | ASL |
| PRO + FAD -> P5C + FADH2 | 0 | PRODH |
| P5C + NADPH -> PRO + NADP | 0 | PYCR1 |
| THR -> NH3 + H2O + OBUT | 0 | WTDH |
| THR + NAD -> CO2 + NADH + AMA | 0 | TDH |
| AMA + H2O + FAD -> NH3 + FADH2 + MTHGXL | 0 | MAOA |
| GLYm + THFm + NADm <-> METTHFm + NADHm + CO2m + NH3m | 0 | AMT |
| PHE + THBP + O2 -> TYR + DHBP + H2O | 0 | PAH |
| NADPH + DHBP -> NADP + THBP | 0 | QDPR |
| AKG + TYR -> HPHPYR + GLU | 0 | TAT |
| HPHPYR + O2 -> HGTS + CO2 | 0 | HPD |
| HGTS + O2 -> MACA | 0 | HGD |
| MACA -> FACA | 0 | GSTZ1 |
| FACA + H2O -> FUM + ACA | 0 | FAH |
| AKG + ILE -> OMVAL + GLU | 0 | BCAT1A |
| OMVALm + COAm + NADm -> MBCOAm + NADHm + CO2m | 0 | BCKDHAA |
| MBCOAm + FADm -> MCCOAm + FADH2m | 0 | ACADMA |
| MCCOAm + H2Om -> MHVCOAm | 0 | ECHS1B |
| MHVCOAm + NADm -> MAACOAm + NADHm | 0 | EHHADHA |
| MAACOAm -> ACCOAm + PROPCOAm | 0 | ACAA2 |
| 2 ACCOAm <-> COAm + AACCOAm | 0 | ACATm1 |
| AKG + VAL -> OIVAL + GLU | 0 | BCAT1B |
| OIVALm + COAm + NADm -> IBCOAm + NADHm + CO2m | 0 | BCKDHAB |
| IBCOAm + FADm -> MACOAm + FADH2m | 0 | ACADSB |
| MACOAm + H2Om -> HIBCOAm | 0 | EHHADHC |
| HIBCOAm + H2Om -> HIBm + COAm | 0 | HIBCHA |
| HIBm + NADm -> MMAm + NADHm | 0 | EHHADHB |
| MMAm + COAm + NADm -> NADHm + CO2m + PROPCOAm | 0 | MMSDH |
| PROPCOAm + CO2m + ATPm -> ADPm + PIm + DMMCOAm | 0 | PCCA |
| DMMCOAm -> LMMCOAm | 0 | HIBCHF |
| LMMCOAm -> SUCCOAm | 0 | MUT |
| AKG + LEU -> OICAP + GLU | 0 | BCAT1C |

TABLE 4-continued

Metabolic Reaction for Muscle Cells

| Reaction | | Rxt Name |
|---|---|---|
| OICAPm + COAm + NADm -> IVCOAm + NADHm + CO2m | 0 | BCKDHAC |
| OICAPm + COAm + NADH -> IVCOAm + NADHm + CO2m | 0 | BCKDHBC |
| OICAPm + COAm + NADHm -> IVCOAm + NADHm + CO2m | 0 | DBTC |
| IVCOAm + FADm -> MCRCOAm + FADH2m | 0 | IVD |
| MCRCOAm + ATPm + CO2m + H2Om -> MGCOAm + ADPm + Pim | 0 | MCCC1 |
| MGCOAm + H2Om -> H3MCOAm | 0 | HIBCHB |
| H3MCOAm -> ACCOAm + ACTACm | 0 | HMGCL |
| MYOACT + ATP -> MYOATP + ACTIN | 0 | MYOSA |
| MYOATP + ACTIN -> MYOADPAC | 0 | MYOSB |
| MYOADPAC -> ADP + PI + MYOACT + CONTRACT | 0 | MYOSC |
| PCRE + ADP -> CRE + ATP | 0 | CREATA |
| AMP + H2O -> PI + ADN | 0 | CREATB |
| ATP + AMP <-> 2 ADP | 0 | CREATC |
| O2 <-> O2m | 0 | O2MT |
| 3HB -> 3HBm | 0 | HBMT |
| CIT + MALm <-> CITm + MAL | 0 | CITMC |
| PYR <-> PYRm + Hm | 0 | PYRMC |
| C160CAR + COAm -> C160COAm + CAR | 0 | C160CM |
| OMVAL -> OMVALm | 0 | HIBCHC |
| OIVAL -> OIVALm | 0 | HIBCHD |
| OICAP -> OICAPm | 0 | HIBCHE |
| GL <-> GLm | 0 | GLMT |
| GL3Pm + FADm -> T3P2m + FADH2m | 0 | GPD2 |
| T3P2 + NADH <-> GL3P + NAD | 0 | GPD1 |
| GL3P <-> GL3Pm | 0 | GL3PMC |
| T3P2 <-> T3P2m | 0 | T3P2MC |
| OAm + GLUm <-> ASPm + AKGm | 0 | GOT1 |
| OA + GLU <-> ASP + AKG | 0 | GOT2 |
| AKG + MALm <-> AKGm + MAL | 0 | MALMC |
| ASPm + GLU + H -> Hm + GLUm + ASP | 0 | ASPMC |
| GLCxt -> GLC | 0 | GLUT4 |
| O2xt -> O2 | 0 | O2UP |
| C160Axt + FABP -> C160FP + ALBxt | 0 | FAT1 |
| C160FP -> C160 + FABP | 0 | FAT2 |
| C180Axt + FABP -> C180FP + ALBxt | 0 | FAT3 |
| C180FP -> C180 + FABP | 0 | FAT4 |
| C161Axt + FABP -> C161FP + ALBxt | 0 | FAT5 |
| C161FP -> C161 + FABP | 0 | FAT6 |
| C181Axt + FABP -> C181FP + ALBxt | 0 | FAT7 |
| C181FP -> C181 + FABP | 0 | FAT8 |
| C182Axt + FABP -> C182FP + ALBxt | 0 | FAT9 |
| C182FP -> C182 + FABP | 0 | FAT10 |
| C204Axt + FABP -> C204FP + ALBxt | 0 | FAT11 |
| C204FP -> C204 + FABP | 0 | FAT12 |
| PYRxt + HEXT <-> PYR + H | 0 | PYRUP |
| LACxt + HEXT <-> LAC + HEXT | 0 | LACUP |
| H <-> HEXT | 0 | HextUP |
| CO2 <-> CO2m | 0 | CO2MT |
| H2O <-> H2Om | 0 | H2OMT |
| ATP + AC + COA -> AMP + PPI + ACCOA | 0 | FLJ2 |
| C160CAR <-> C160CARm | 0 | C160MT |
| CARm <-> CAR | 0 | CARMT |
| CO2xt <-> CO2 | 0 | CO2UP |
| H2Oxt <-> H2O | 0 | H2OUP |
| PIxt + HEXT <-> HEXT + PI | 0 | PIUP |
| <-> GLCxt | 0 | GLCexR |
| <-> PYRxt | 0 | PYRexR |
| <-> CO2xt | 0 | CO2exR |
| <-> O2xt | 0 | O2exR |
| <-> PIxt | 0 | PIexR |
| <-> H2Oxt | 0 | H2OexR |
| <-> LACxt | 0 | LACexR |
| <-> C160Axt | 0 | C160AexR |
| <-> C161Axt | 0 | C161AexR |
| <-> C180Axt | 0 | C180AexR |
| <-> C181Axt | 0 | C181AexR |
| <-> C182Axt | 0 | C182AexR |
| <-> C204Axt | 0 | C204AexR |
| <-> ALBxt | 0 | ALBexR |
| <-> 3HB | 0 | HBexR |
| <-> GLYCOGEN | 0 | GLYex |
| <-> PCRE | 0 | PCREex |
| <-> TAGLYm | 0 | TAGmex |
| <-> ILE | 0 | ILEex |
| <-> VAL | 0 | VALex |
| <-> CRE | 0 | CREex |

TABLE 4-continued

Metabolic Reaction for Muscle Cells

| Reaction | | Rxt Name |
|---|---|---|
| <-> ADN | 0 | ADNex |
| <-> PI | 0 | Plex |

TABLE 5

Human Cell Types

Keratinizing epithelial cells

Epidermal keratinocyte (differentiating epidermal cell)
Epidermal basal cell (stem cell)
Keratinocyte of fingernails and toenails
Nail bed basal cell (stem cell)
Medullary hair shaft cell
Cortical hair shaft cell
Cuticular hair shaft cell
Cuticular hair root sheath cell
Hair root sheath cell of Huxley's layer
Hair root sheath cell of Henle's layer
External hair root sheath cell
Hair matrix cell (stem cell)
Wet stratified barrier epithelial cells Surface epithelial cell of stratified squamous epithelium of cornea, tongue, oral cavity, esophagus, anal canal, distal urethra and vagina
basal cell (stem cell) of epithelia of cornea, tongue, oral cavity, esophagus, anal canal, distal urethra and vagina
Urinary epithelium cell (lining urinary bladder and urinary ducts)
Exocrine secretory epithelial cells Salivary gland mucous cell (polysaccharide-rich secretion)
Salivary gland serous cell (glycoprotein enzyme-rich secretion)
Von Ebner's gland cell in tongue (washes taste buds)
Mammary gland cell (milk secretion)
Lacrimal gland cell (tear secretion)
Ceruminous gland cell in ear (wax secretion)
Eccrine sweat gland dark cell (glycoprotein secretion)
Eccrine sweat gland clear cell (small molecule secretion)
Apocrine sweat gland cell (odoriferous secretion, sex-hormone sensitive)
Gland of Moll cell in eyelid (specialized sweat gland)
Sebaceous gland cell (lipid-rich sebum secretion)
Bowman's gland cell in nose (washes olfactory epithelium)
Brunner's gland cell in duodenum (enzymes and alkaline mucus)
Seminal vesicle cell (secretes seminal fluid components, including fructose for swimming sperm)
Prostate gland cell (secretes seminal fluid components)
Bulbourethral gland cell (mucus secretion)
Bartholin's gland cell (vaginal lubricant secretion)
Gland of Littre cell (mucus secretion)
Uterus endometrium cell (carbohydrate secretion)
Isolated goblet cell of respiratory and digestive tracts (mucus secretion)
Stomach lining mucous cell (mucus secretion)
Gastric gland zymogenic cell (pepsinogen secretion)
Gastric gland oxyntic cell (hydrogen chloride secretion)
Pancreatic acinar cell (bicarbonate and digestive enzyme secretion)
Paneth cell of small intestine (lysozyme secretion)
Type II pneumocyte of lung (surfactant secretion)
Clara cell of lung
Hormone secreting cells Anterior pituitary cells
Somatotropes
Lactotropes
Thyrotropes
Gonadotropes
Corticotropes
Intermediate pituitary cell, secreting melanocyte-stimulating hormone
Magnocellular neurosecretory cells
secreting oxytocin
secreting vasopressin
Gut and respiratory tract cells secreting serotonin
secreting endorphin
secreting somatostatin

TABLE 5-continued

Human Cell Types secreting gastrin
secreting secretin
secreting cholecystokinin
secreting insulin
secreting glucagon
secreting bombesin
Thyroid gland cells
thyroid epithelial cell
parafollicular cell
Parathyroid gland cells
Parathyroid chief cell
oxyphil cell
Adrenal gland cells
chromaffin cells
secreting steroid hormones (mineralcorticoids and gluco corticoids)
Leydig cell of testes secreting testosterone
Theca interna cell of ovarian follicle secreting estrogen
Corpus luteum cell of ruptured ovarian follicle secreting progesterone
Kidney juxtaglomerular apparatus cell (renin secretion)
Macula densa cell of kidney
Peripolar cell of kidney
Mesangial cell of kidney
Epithelial absorptive cells (Gut, Exocrine Glands and Urogenital Tract)

Intestinal brush border cell (with microvilli)
Exocrine gland striated duct cell
Gall bladder epithelial cell
Kidney proximal tubule brush border cell
Kidney distal tubule cell
Ductulus efferens nonciliated cell
Epididymal principal cell
Epididymal basal cell
Metabolism and storage cells Hepatocyte (liver cell)
White fat cell
Brown fat cell
Liver lipocyte
Barrier function cells (Lung, Gut, Exocrine Glands and Urogenital Tract)

Type I pneumocyte (lining air space of lung)
Pancreatic duct cell (centroacinar cell)
Nonstriated duct cell (of sweat gland, salivary gland, mammary gland, etc.)
Kidney glomerulus parietal cell
Kidney glomerulus podocyte
Loop of Henle thin segment cell (in kidney)
Kidney collecting duct cell
Duct cell (of seminal vesicle, prostate gland, etc.)
Epithelial cells lining closed internal body cavities Blood vessel and lymphatic vascular endothelial fenestrated cell
Blood vessel and lymphatic vascular endothelial continuous cell
Blood vessel and lymphatic vascular endothelial splenic cell
Synovial cell (lining joint cavities, hyaluronic acid secretion)
Serosal cell (lining peritoneal, pleural, and pericardial cavities)
Squamous cell (lining perilymphatic space of ear)
Squamous cell (lining endolymphatic space of ear)
Columnar cell of endolymphatic sac with microvilli (lining endolymphatic space of ear)
Columnar cell of endolymphatic sac without microvilli (lining endolymphatic space of ear)
Dark cell (lining endolymphatic space of ear)
Vestibular membrane cell (lining endolymphatic space of ear)
Stria vascularis basal cell (lining endolymphatic space of ear)
Stria vascularis marginal cell (lining endolymphatic space of ear)
Cell of Claudius (lining endolymphatic space of ear)
Cell of Boettcher (lining endolymphatic space of ear)
Choroid plexus cell (cerebrospinal fluid secretion)
Pia-arachnoid squamous cell
Pigmented ciliary epithelium cell of eye
Nonpigmented ciliary epithelium cell of eye
Corneal endothelial cell
Ciliated cells with propulsive function Respiratory tract ciliated cell
Oviduct ciliated cell (in female)
Uterine endometrial ciliated cell (in female)
Rete testis cilated cell (in male)
Ductulus efferens ciliated cell (in male)
Ciliated ependymal cell of central nervous system (lining brain cavities)

TABLE 5-continued

Human Cell Types

Extracellular matrix secretion cells

Ameloblast epithelial cell (tooth enamel secretion)
Planum semilunatum epithelial cell of vestibular apparatus of ear (proteoglycan secretion)
Organ of Corti interdental epithelial cell (secreting tectorial membrane covering hair cells)
Loose connective tissue fibroblasts
Corneal fibroblasts
Tendon fibroblasts
Bone marrow reticular tissue fibroblasts
Other nonepithelial fibroblasts
Blood capillary pericyte
Nucleus pulposus cell of intervertebral disc
Cementoblast/cementocyte (tooth root bonelike cementum secretion)
Odontoblast/odontocyte (tooth dentin secretion)
Hyaline cartilage chondrocyte
Fibrocartilage chondrocyte
Elastic cartilage chondrocyte
Osteoblast/osteocyte
Osteoprogenitor cell (stem cell of osteoblasts)
Hyalocyte of vitreous body of eye
Stellate cell of perilymphatic space of ear Contractile cells Red skeletal muscle cell (slow)
White skeletal muscle cell (fast)
Intermediate skeletal muscle cell
nuclear bag cell of Muscle spindle
nuclear chain cell of Muscle spindle
Satellite cell (stem cell)
Ordinary heart muscle cell
Nodal heart muscle cell
Purkinje fiber cell
Smooth muscle cell (various types)
Myoepithelial cell of iris
Myoepithelial cell of exocrine glands
Red Blood Cell Blood and immune system cells Erythrocyte (red blood cell)
Megakaryocyte (platelet precursor)
Monocyte
Connective tissue macrophage (various types)
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Mast cell
Helper T cell
Suppressor T cell
Cytotoxic T cell
B cells
Natural killer cell
Reticulocyte
Stem cells and committed progenitors for the blood and immune system (various types)

Sensory transducer cells

Photoreceptor rod cell of eye
Photoreceptor blue-sensitive cone cell of eye
Photoreceptor green-sensitive cone cell of eye
Photoreceptor red-sensitive cone cell of eye
Auditory inner hair cell of organ of Corti
Auditory outer hair cell of organ of Corti
Type I hair cell of vestibular apparatus of ear (acceleration and gravity)
Type II hair cell of vestibular apparatus of ear (acceleration and gravity)
Type I taste bud cell
Olfactory receptor neuron
Basal cell of olfactory epithelium (stem cell for olfactory neurons)
Type I carotid body cell (blood pH sensor)
Type II carotid body cell (blood pH sensor)
Merkel cell of epidermis (touch sensor)
Touch-sensitive primary sensory neurons (various types)
Cold-sensitive primary sensory neurons
Heat-sensitive primary sensory neurons
Pain-sensitive primary sensory neurons (various types)
Proprioceptive primary sensory neurons (various types)

TABLE 5-continued

Human Cell Types

Autonomic neuron cells

Cholinergic neural cell (various types)
Adrenergic neural cell (various types)
Peptidergic neural cell (various types)
Sense organ and peripheral neuron supporting cells Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Type I taste bud supporting cell
Olfactory epithelium supporting cell
Schwann cell
Satellite cell (encapsulating peripheral nerve cell bodies)
Enteric glial cell
Central nervous system neurons and glial cells Neuron cells (large variety of types, still poorly classified)
Astrocyte (various types)
Oligodendrocyte
Lens cells Anterior lens epithelial cell
Crystallin-containing lens fiber cell
Pigment cells Melanocyte
Retinal pigmented epithelial cell
Germ cells Oogonium/Oocyte
Spermatid
Spermatocyte
Spermatogonium cell (stem cell for spermatocyte)
Spermatozoon
Nurse cells Ovarian follicle cell
Sertoli cell (in testis)
Thymus epithelial cell

TABLE 6

Human Tissues

Epithelial Tissue
    Unilaminar (simple) epithelia
        Squamous
        Cuboidal
        Columnar
        Sensory
        Myoepitheliocyte
    Multilaminar eipithelia
        Replacing or stratified squamous epithelia
        Stratified cuboidal and columnar eipithelia
    Urothelium (transitional epithelium)
        Seminiferous eipthelium
    Glands
        Exocrine glands
            Ducts and Tubules
        Endocrine glands
Nervous Tissue
    Neurons
        Multipolar Neurons in CNS
    Nerves
        Nerves of the PNS
    Receptors
        Miessner's and Pacinian Corpuscles TABLE 6-continued

```
Connective Tissues
    Fluid Connective Tissues
        Lymph
        Blood
    Connective Tissues Proper
        Loose Connective Tissues
            Areolar
            Loose Connective Tissues and Inflammation
            Adipose
            Reticular
        Dense Connective Tissues
            Regular(collagen)
            Irregular(collagen)
            Regular(elastic)
    Supportive Connective Tissues
        Osseous Tissue
            Compact
            Cancellous
        Cartilage
            Hyaline
            Elastic
            Fibrocartilage
Muscle Tissue
    Non-striated
        Smooth Muscle
    Striated
        Skeletal Muscle
        Cardiac Muscle
```

| Systems | Major Structures | Functions |
|---|---|---|
| Skeletal | Bones, cartilage, tendons, ligaments, and joints | provides structure; supports and protects internal organs |
| Muscular | Muscles (skeletal, cardiac, and smooth) | provides structure; supports and moves trunk and limbs; moves substances through body |
| Integumentary | Skin, hair nails, breast | protects against pathogens; helps regulate body temperature |
| Circulatory | Heart, blood vessels, blood | transports nutrients and wastes to and from all body tissues |
| Respiratory | Trachea, air passages, lungs | carries air into and out of lungs, where gases (oxygen and carbon dioxide) are exchanged |
| Immune | Lymph nodes and vessels, white blood cells | provides protection against infection and disease |
| Digestive | Mouth, esophagus, stomach, liver, pancreas, duodenum, jejunum, ileum, caecum, rectum, gallbladder, pancreas, small and large intestines | stores and digests food; absorbs nutrients; eliminates waste |
| Excretory and Urinary | Kidneys, ureters, bladder, urethra | eliminate waste; maintains water and chemical balance |
| Nervous | Brain, spinal cord, nerves, sense organs, receptors, dorsal root ganglion | controls and coordinates body movements and senses; controls consciousness and creativity; helps monitor and maintain other body systems |
| Endocrine | Endocrine glands, pineal gland, pituitary gland, adrenal gland, thyroid gland, and hormones | maintain homeostasis; regulates metabolism, water and mineral balance, growth and sexual development, and reproduction |
| Lymphatic | Lymph nodes, spleen, lymph vessels | cleans and returns tissue fluid to the blood and destroys pathogens that enter the body |
| Reproductive | Ovaries, uterus, fallopian tube, mammary glands (in females), vas deferens, prostate, testes (in males), umbilical cord, placenta | produce gametes and offspring |

TABLE 7

Cells of the Liver

Hepatocytes
Perisinusoidal (Ito) cells
Endotheliocytes
Macrophages (Kupffer cells)
Lymphocytes (pit cells)

TABLE 7-continued

Cells of the Liver

Cells of the biliary tree
Cuboidal epitheliocytes
Columnar epitheliocytes
Connective tissue cells

TABLE 15

Adipocyte-myocyte reactions

| Reaction Abbreviation | Reaction Name | Equation | Subsystem | Protein Classification |
|---|---|---|---|---|
| G6PASEer_ac | glucose-6-phosphatase | [f]: g6p + h2o --> glc-D + pi | Glycolysis/Gluconeogenesis | EC-3.1.3.9 |
| G6PASEer_mc | glucose-6-phosphatase | [u]: g6p + h2o --> glc-D + pi | Glycolysis/Gluconeogenesis | EC-3.1.3.9 |
| PFK26_ac | 6-phosphofructo-2-kinase | [a]: atp + f6p --> adp + f26bp + h | Glycolysis/Gluconeogenesis | EC-2.7.1.105 |

TABLE 15-continued

Adipocyte-myocyte reactions

| Reaction Abbreviation | Reaction Name | Equation | Subsystem | Protein Classification |
|---|---|---|---|---|
| PGI__ac | glucose-6-phosphate isomerase | [a]: g6p <==> f6p | Glycolysis/Gluconeogenesis | EC-5.3.1.9 |
| PGK__ac | phosphoglycerate kinase | [a]: 13dpg + adp <==> 3pg + atp | Glycolysis/Gluconeogenesis | EC-2.7.2.3 |
| PGM__ac | phosphoglycerate mutase | [a]: 3pg <==> 2pg | Glycolysis/Gluconeogenesis | EC-5.4.2.1 |
| PYK__ac | pyruvate kinase | [a]: adp + h + pep --> atp + pyr | Glycolysis/Gluconeogenesis | EC-2.7.1.40 |
| TPI__ac | triose-phosphate isomerase | [a]: dhap <==> g3p | Glycolysis/Gluconeogenesis | EC-5.3.1.1 |
| ACONTm__ac | Aconitate hydratase | [b]: cit <==> icit | Central Metabolism | EC-4.2.1.3 |
| ACONTm__mc | Aconitate hydratase | [z]: cit <==> icit | Central Metabolism | EC-4.2.1.3 |
| AKGDm__ac | 2-oxoglutarate dehydrogenase, mitochondrial | [b]: akg + coa + nad --> co2 + nadh + succoa | Central Metabolism | |
| AKGDm__mc | 2-oxoglutarate dehydrogenase, mitochondrial | [z]: akg + coa + nad --> co2 + nadh + succoa | Central Metabolism | |
| CITL2__ac | Citrate lyase (ATP-requiring) | [a]: atp + cit + coa --> accoa + adp + oaa + pi | Central Metabolism | EC-4.1.3.8 |
| CITL2__mc | Citrate lyase (ATP-requiring) | [y]: atp + cit + coa --> accoa + adp + oaa + pi | Central Metabolism | EC-4.1.3.8 |
| CSm__ac | citrate synthase | [b]: accoa + h2o + oaa --> cit + coa + h | Central Metabolism | EC-4.1.3.7 |
| CSm__mc | citrate synthase | [z]: accoa + h2o + oaa --> cit + coa + h | Central Metabolism | EC-4.1.3.7 |
| ENO__ac | enolase | [a]: 2pg <==> h2o + pep | Central Metabolism | EC-4.2.1.11 |
| ENO__mc | enolase | [y]: 2pg <==> h2o + pep | Central Metabolism | EC-4.2.1.11 |
| FBA__ac | fructose-bisphosphate aldolase | [a]: fdp <==> dhap + g3p | Central Metabolism | EC-4.1.2.13 |
| FBA__mc | fructose-bisphosphate aldolase | [y]: fdp <==> dhap + g3p | Central Metabolism | EC-4.1.2.13 |
| F8P26__ac | Fructose-2,6-bisphosphate 2-phosphatase | [a]: f26bp + h2o --> f6p + pi | Central Metabolism | EC-3.1.3.46 |
| FBP26__mc | Fructose-2,6-bisphosphate 2-phosphatase | [y]: f26bp + h2o --> f6p + pi | Central Metabolism | EC-3.1.3.46 |
| FBP__ac | fructose-bisphosphatase | [a]: fdp + h2o --> f6p + pi | Central Metabolism | EC-3.1.3.11 |
| FBP__mc | fructose-bisphosphatase | [y]: fdp + h2o --> f6p + pi | Central Metabolism | EC-3.1.3.11 |
| FUMm__ac | fumarase, mitochondrial | [b]: fum + h2o <==> mal-L | Central Metabolism | EC-4.2.1.2 |
| FUMm__mc | fumarase, mitochondrial | [z]: fum + h2o <==> mal-L | Central Metabolism | EC-4.2.1.2 |
| G3PD1__ac | glycerol-3-phosphate dehydrogenase (NAD), adipocyte | [a]: glyc3p + nad <==> dhap + h + nadh | Central Metabolism | EC-1.1.1.94 |
| G3PD__mc | Glycerol-3-phosphate dehydrogenase (NAD) | [y]: dhap + h + nadh --> glyc3p + nad | Central Metabolism | EC-1.1.1.8 |
| G3PDm__ac | glycerol-3-phosphate dehydrogenase | [b]: fad + glyc3p --> dhap + fadh2 | Central Metabolism | EC-1.1.99.5 |
| G3PDm__mc | glycerol-3-phosphate dehydrogenase | [z]: fad + glyc3p --> dhap + fadh2 | Central Metabolism | EC-1.1.99.5 |
| G6PDH__ac | glucose 6-phosphate dehydrogenase | [a]: g6p + nadp --> 6pgl + h + nadph | Central Metabolism | EC-1.1.1.49 |
| G6PDH__mc | glucose 6-phosphate dehydrogenase | [y]: g6p + nadp --> 6pgl + h + nadph | Central Metabolism | EC-1.1.1.49 |
| GAPD__ac | glyceraldehyde-3-phosphate dehydrogenase (NAD) | [a]: g3p + nad + pi <==> 13dpg + h + nadh | Central Metabolism | EC-1.2.1.12 |
| GAPD__mc | glyceraldehyde-3-phosphate dehydrogenase (NAD) | [y]: g3p + nad + pi <==> 13dpg + h + nadh | Central Metabolism | EC-1.2.1.12 |
| GL3Ptm__ac | glycerol-3-phosphate transport, adipocyte mitochondrial | glyc3p[a] <==> glyc3p[b] | Central Metabolism | |
| GLCP__ac | glycogen phosphorylase | [a]: glycogen + pi --> g1p | Central Metabolism | EC-2.4.1.1 |
| HCO3Em__ac | HCO3 equilibration reaction, mitochondrial | [b]: co2 + h2o <==> h + hco3 | Central Metabolism | EC-4.2.1.1 |
| HCO3Em__mc | HCO3 equilibration reaction, mitochondrial | [z]: co2 + h2o <==> h + hco3 | Central Metabolism | EC-4.2.1.1 |
| HEX1__ac | hexokinase (D-glucose:ATP) | [a]: atp + glc-D --> adp + g6p + h | Central Metabolism | EC-2.7.1.2 |
| HEX1__mc | hexokinase (D-glucose:ATP) | [y]: atp + glc-D --> adp + g6p + h | Central Metabolism | EC-2.7.1.2 |
| ICDHxm__ac | Isocitrate dehydrogenase (NAD+) | [b]: icit + nad --> akg + co2 + nadh | Central Metabolism | EC-1.1.1.41 |
| ICDHxm__mc | Isocitrate dehydrogenase (NAD+) | [z]: icit + nad --> akg + co2 + nadh | Central Metabolism | EC-1.1.1.41 |

TABLE 15-continued

Adipocyte-myocyte reactions

| Reaction Abbreviation | Reaction Name | Equation | Subsystem | Protein Classification |
|---|---|---|---|---|
| ICDHym_ac | Isocitrate dehydrogenase (NADP+) | [b]: icit + nadp --> akg + co2 + nadph | Central Metabolism | EC-1.1.1.42 |
| ICDHym_mc | Isocitrate dehydrogenase (NADP+) | [z]: icit + nadp --> akg + co2 + nadph | Central Metabolism | EC-1.1.1.42 |
| LDH_L_mc | L-lactate dehydrogenase | [y]: lac-L + nad <==> h + nadh + pyr | Central Metabolism | EC-1.1.1.27 |
| MDH_ac | malate dehydrogenase | [a]: mal-L + nad <==> h + nadh + oaa | Central Metabolism | EC-1.1.1.37 |
| MDH_mc | malate dehydrogenase | [y]: mal-L + nad <==> h + nadh + oaa | Central Metabolism | EC-1.1.1.37 |
| MDHm_ac | malate dehydrogenase, mitochondrial | [b]: mal-L + nad <==> h + nadh + oaa | Central Metabolism | EC-1.1.1.37 |
| MDHm_mc | malate dehydrogenase, mitochondrial | [z]: mal-L + nad <==> h + nadh + oaa | Central Metabolism | EC-1.1.1.37 |
| ME1m_ac | malic enzyme (NAD), mitochondrial | [b]: mal-L + nad --> co2 + nadh + pyr | Central Metabolism | EC-1.1.1.38 |
| ME1m_mc | malic enzyme (NAD), mitochondrial | [z]: mal-L + nad --> co2 + nadh + pyr | Central Metabolism | EC-1.1.1.38 |
| ME2_ac | malic enzyme (NADP) | [a]: mal-L + nadp --> co2 + nadph + pyr | Central Metabolism | EC-1.1.1.40 |
| ME2_mc | malic enzyme (NADP) | [y]: mal-L + nadp --> co2 + nadph + pyr | Central Metabolism | EC-1.1.1.40 |
| ME2m_ac | malic enzyme (NADP), mitochondrial | [b]: mal-L + nadp --> co2 + nadph + pyr | Central Metabolism | EC-1.1.1.40 |
| ME2m_mc | malic enzyme (NADP), mitochondrial | [z]: mal-L + nadp --> co2 + nadph + pyr | Central Metabolism | EC-1.1.1.40 |
| PCm_mc | pyruvate carboxylase, mitochondrial | [z]: atp + hco3 + pyr --> adp + h + oaa + pi | Central Metabolism | EC-6.4.1.1 |
| PDHm_mc | pyruvate dehydrogenase, mitochondrial | [z]: coa + nad + pyr --> accoa + co2 + nadh | Central Metabolism | EC-1.2.1.51 |
| PFK26_mc | 6-phosphofructo-2-kinase | [y]: atp + f6p --> adp + f26bp + h | Central Metabolism | EC-2.7.1.105 |
| PFK_ac | phosphofructokinase | [a]: atp + f6p --> adp + fdp + h | Central Metabolism | EC-2.7.1.11 |
| PFK_mc | phosphofructokinase | [y]: atp + f6p --> adp + fdp + h | Central Metabolism | EC-2.7.1.11 |
| PGDH_mc | phosphogluconate dehydrogenase | [y]: 6pgc + nadp --> co2 + nadph + ru5p-D | Central Metabolism | EC-1.1.1.44 |
| PGI_mc | glucose-6-phosphate isomerase | [y]: g6p <==> f6p | Central Metabolism | EC-5.3.1.9 |
| PGK_mc | phosphoglycerate kinase | [y]: 13dpg + adp <==> 3pg + atp | Central Metabolism | EC-2.7.2.3 |
| PGL_mc | 6-phosphogluconolactonase | [y]: 6pgl + h2o --> 6pgc + h | Central Metabolism | EC-3.1.1.31 |
| PGM_mc | phosphoglycerate mutase | [y]: 3pg <==> 2pg | Central Metabolism | EC-5.4.2.1 |
| PPA_ac | inorganic diphosphatase | [a]: h2o + ppi --> h + (2) pi | Central Metabolism | EC-3.6.1.1 |
| PPA_mc | inorganic diphosphatase | [y]: h2o + ppi --> h + (2) pi | Central Metabolism | EC-3.6.1.1 |
| PPCKG_ac | phosphoenolpyruvate carboxykinase (GTP) | [a]: gtp + oaa --> co2 + gdp + pep | Central Metabolism | EC-4.1.1.32 |
| PPCKG_mc | phosphoenolpyruvate carboxykinase (GTP) | [y]: gtp + oaa --> co2 + gdp + pep | Central Metabolism | EC-4.1.1.32 |
| PYK_mc | pyruvate kinase | [y]: adp + h + pep --> atp + pyr | Central Metabolism | EC-2.7.1.40 |
| RPE_mc | ribulose 5-phosphate 3-epimerase | [y]: ru5p-D <==> xu5p-D | Central Metabolism | EC-5.1.3.1 |
| RPI_mc | ribose-5-phosphate isomerase | [y]: r5p <==> ru5p-D | Central Metabolism | EC-5.3.1.6 |
| SUCD1m_mc | succinate dehydrogenase | [z]: succ + ubq <==> fum + qh2 | Central Metabolism | EC-1.3.5.1 |
| SUCD3m_mc | succinate dehydrogenase cytochrome b | [z]: fadh2 + ubq <==> fad + qh2 | Central Metabolism | |
| SUCOASAm_mc | Succinate—CoA ligase (ADP-forming) | [z]: atp + coa + succ <==> adp + pi + succoa | Central Metabolism | EC-6.2.1.4 |
| SUCOASGm_mc | Succinate—CoA ligase (GDP-forming) | [z]: coa + gtp + succ <==> gdp + pi + succoa | Central Metabolism | EC-6.2.1.4 |
| TAL_mc | transaldolase | [y]: g3p + s7p <==> e4p + f6p | Central Metabolism | EC-2.2.1.2 |
| TKT1_mc | transketolase | [y]: r5p + xu5p-D <==> g3p + s7p | Central Metabolism | EC-2.2.1.1 |
| TKT2_mc | transketolase | [y]: e4p + xu5p-D <==> f6p + g3p | Central Metabolism | EC-2.2.1.1 |
| TPI_mc | triose-phosphate isomerase | [y]: dhap <==> g3p | Central Metabolism | EC-5.3.1.1 |
| SUCOASAm_ac | Succinate—CoA ligase (ADP-forming) | [b]: atp + coa + succ <==> adp + pi + succoa | Citrate Cycle (TCA) | EC-6.2.1.4 |
| SUCOASGm_ac | Succinate—CoA ligase (GDP-forming) | [b]: coa + gtp + succ <==> gdp + pi + succoa | Citrate Cycle (TCA) | EC-6.2.1.4 |
| PGDH_ac | phosphogluconate dehydrogenase | [a]: 6pgc + nadp --> co2 + nadph + ru5p-D | Pentose Phosphate Cycle | EC-1.1.1.44 |
| PGL_ac | 6-phosphogluconolactonase | [a]: 6pgl + h2o --> 6pgc + h | Pentose Phosphate Cycle | EC-3.1.1.31 |
| RPE_ac | ribulose 5-phosphate 3-epimerase | [a]: ru5p-D <==> xu5p-D | Pentose Phosphate Cycle | EC-5.1.3.1 |
| RPI_ac | ribose-5-phosphate isomerase | [a]: r5p <==> ru5p-D | Pentose Phosphate Cycle | EC-5.3.1.6 |
| TAL_ac | transaldolase | [a]: g3p + s7p <==> e4p + f6p | Pentose Phosphate Cycle | EC-2.2.1.2 |
| TKT1_ac | transketolase | [a]: r5p + xu5p-D <==> g3p + s7p | Pentose Phosphate Cycle | EC-2.2.1.1 |

TABLE 15-continued

Adipocyte-myocyte reactions

| Reaction Abbreviation | Reaction Name | Equation | Subsystem | Protein Classification |
|---|---|---|---|---|
| TKT2_ac | transketolase | [a]: e4p + xu5p-D <==> f6p + g3p | Pentose Phosphate Cycle | EC-2.2.1.1 |
| PCm_ac | pyruvate carboxylase, mitochondrial | [b]: atp + hco3 + pyr --> adp + h + oaa + pi | Pyruvate metabolism | EC-6.4.1.1 |
| PDHm_ac | pyruvate dehydrogenase, mitochondrial | [b]: coa + nad + pyr --> accoa + co2 + nadh | Pyruvate metabolism | EC-1.2.1.51 |
| ATPM_ac | ATP maintenance requirment | [a]: atp + h2o --> adp + h + pi | Energy Metabolism | |
| ATPM_mc | ATP maintenance requirment | [y]: atp + h2o --> adp + h + pi | Energy Metabolism | |
| ATPS4m_ac | ATP synthase, adipocyte mitochondrial | adp[b] + (4) h[a] + pi[b] --> atp[b] + (3) h[b] + h2o[b] | Energy Metabolism | EC-3.6.1.14, |
| ATPS4m_mc | ATP synthase, myocyte mitochondrial | adp[z] + (4) h[y] + pi[z] --> atp[z] + (3) h[z] + h2o[y] | Energy Metabolism | EC-3.6.1.14, |
| ATPSis_ac | ATPase, adipocyte cytosolic | atp[a] + h2o[a] --> adp[a] + h[i] + pi[a] | Energy Metabolism | EC-3.6.3.6, |
| ATPSis_mc | ATPase, myocyte cytosolic | atp[y] + h2o[y] --> adp[y] + h[c] + pi[y] | Energy Metabolism | EC-3.6.3.6, |
| CREATK_mc | creatine kinase, myocyte cytosol | [y]: atp + creat <==> adp + creatp | Energy Metabolism | EC-2.7.3.2 |
| CREATPD_mc | creatine phosphate dephosphorylation, spontaneous | [y]: creatp --> crtn + h + pi | Energy Metabolism | |
| CYOO4m_ac | cytochrome c oxidase (adipocyte mitochondrial 4 protons) | (4) focytc[b] + (8) h[b] + o2[b] --> (4) ficytc[b] + (4) h[a] + (2) h2o[b] | Energy Metabolism | EC-1.9.3.1, |
| CYOO4m_mc | cytochrome c oxidase (myocyte mitochondrial 4 protons) | (4) focytc[z] + (8) h[z] + o2[z] --> (4) ficytc[z] + (4) h[y] + (2) h2o[z] | Energy Metabolism | EC-1.9.3.1, |
| CYOR4m_ac | ubiquinol cytochrome c reductase, adipocyte | (2) ficytc[b] + (2) h[b] + qh2[b] --> (2) focytc[b] + (4) h[a] + ubq[b] | Energy Metabolism | EC-1.10.2.2, |
| CYOR4m_mc | ubiquinol cytochrome c reductase, myocyte | (2) ficytc[z] + (2) h[z] + qh2[z] --> (2) focytc[z] + (4) h[y] + ubq[z] | Energy Metabolism | EC-1.10.2.2, |
| NADH4m_mc | NADH dehydrogenase, mitochondrial | (5) h[z] + nadh[z] + ubq[z] --> (4) h[y] + nad[z] + qh2[z] | Energy Metabolism | EC-1.6.99.3, |
| NADH4m_ac | NADH dehydrogenase, adipocyte mitochondrial | (5) h[b] + nadh[b] + ubq[b] --> (4) h[a] + nad[b] + qh2[b] | Oxidative phosphorylation | EC-1.6.99.3, |
| SUCD1m_ac | succinate dehydrogenase | [b]: succ + ubq <==> fum + qh2 | Oxidative phosphorylation | EC-1.3.5.1 |
| SUCD3m_ac | succinate dehydrogenase cytochrome b | [b]: fadh2 + ubq <==> fad + qh2 | Oxidative phosphorylation | |
| GALUi_ac | UTP-glucose-1-phosphate uridylyltransferase (irreversible) | [a]: g1p + h + utp --> ppi + udpg | Galactose metabolism | EC-2.7.7.9 |
| PGMT_ac | phosphoglucomutase | [a]: g1p <==> g6p | Galactose metabolism | EC-5.4.2.2 |
| GALUi_mc | UTP-glucose-1-phosphate uridylyltransferase (irreversible) | [y]: g1p + h + utp --> ppi + udpg | Carbohydrate Metabolism | EC-2.7.7.9 |
| GLCP_mc | glycogen phosphorylase | [y]: glycogen + pi --> g1p | Carbohydrate Metabolism | EC-2.4.1.1 |
| GLYGS_ac | glycogen synthase (UDPGlc) | [a]: udpg --> glycogen + h + udp | Carbohydrate Metabolism | EC-2.4.1.11 |
| GLYGS_mc | glycogen synthase (UDPGlc) | [y]: udpg --> glycogen + h + udp | Carbohydrate Metabolism | EC-2.4.1.11 |
| PGMT_mc | phosphoglucomutase | [y]: g1p <==> g6p | Carbohydrate Metabolism | EC-5.4.2.2 |
| ACACT10m_ac | acetyl-CoA C-acyltransferase, adipocyte mitochondrial | [b]: 2maacoa + coa --> accoa + ppcoa | Amino Acid Metabolism | EC-2.3.1.16 |
| ACOAD3m_ac | acyl-CoA dehydrogenase, adipocyte mitochondrial | [b]: 2mbcoa + fad <==> 2mb2coa + fadh2 | Amino Acid Metabolism | EC-1.3.99.3 |
| ASPO_D_ac | D-aspartate oxidase | [a]: asp-D + h2o + o2 --> h + h2o2 + nh3 + oaa | Amino Acid Metabolism | EC-1.4.3.16 |
| ASPR_ac | aspartase racemase, adipocyte cytosolic | [a]: asp-D <==> asp-L | Amino Acid Metabolism | EC-5.1.1.13 |
| ASPTA1_ac | aspartate transaminase | [a]: akg + asp-L <==> glu-L + oaa | Amino Acid Metabolism | EC-2.6.1.1 |
| ASPTA1_mc | aspartate transaminase | [y]: akg + asp-L <==> glu-L + oaa | Amino Acid Metabolism | EC-2.6.1.1 |
| ASPTA1m_ac | aspartate transaminase, mitochondrial | [b]: akg + asp-L <==> glu-L + oaa | Amino Acid Metabolism | EC-2.6.1.1 |
| ASPTA1m_mc | aspartate transaminase, mitochondrial | [z]: akg + asp-L <==> glu-L + oaa | Amino Acid Metabolism | EC-2.6.1.1 |
| ECOAH3m_ac | enoyl-CoA hydratase, adipocyte mitochondrial | [b]: 2mb2coa + h2o <==> 3hmbcoa | Amino Acid Metabolism | EC-4.2.1.17 |

TABLE 15-continued

Adipocyte-myocyte reactions

| Reaction Abbreviation | Reaction Name | Equation | Subsystem | Protein Classification |
|---|---|---|---|---|
| HACD8m__ac | 3-hydroxyacyl-CoA dehydrogenase (2-Methylacetoacetyl-CoA), adipocyte mitochondrial | [b]: 3hmbcoa + nad <==> 2maacoa + h + nadh | Amino Acid Metabolism | EC-1.1.1.35 |
| ILETA__ac | isoleucine transaminase, adipocyte cytosolic | [a]: akg + ile-L <==> 3mop + glu-L | Amino Acid Metabolism | EC-2.6.1.42 |
| MOBD3m__ac | 3-Methyl-2-oxobutanoate dehydrogenase, adipocyte mitochondrial | [b]: 3mop + coa + nad --> 2mbcoa + co2 + nadh | Amino Acid Metabolism | |
| CSNAT__mc | carnitine O-acetyltransferase, myocyte cytosol | [y]: accoa + crn --> acrn + coa | Carnitine Shuttle | EC-2.3.1.7 |
| CSNATifm__mc | carnitine O-aceyltransferase, forward reaction, myocyte mitochondrial | [z]: acrn + coa --> accoa + crn | Carnitine Shuttle | EC-2.3.1.7 |
| PPS__ac | propionyl-CoA synthetase, adipocyte cytosolic | [a]: atp + coa + ppa <==> amp + ppcoa + ppi | Propanoate Metabolism | EC-6.2.1.1 |
| PPSm__ac | propionyl-CoA synthetase, adipocyte mitochondrial | [b]: atp + coa + ppa <==> amp + ppcoa + ppi | Propanoate Metabolism | EC-6.2.1.1 |
| ACACT10m__mc | acetyl-CoA C-acyltransferase (octanoyl-CoA) | [z]: accoa + occoa <==> 3odcoa + coa | Fatty Acid Degradation | EC-2.3.1.16 |
| ACACT11m__mc | acetyl-CoA C-acyltransferase (nonanoyl-CoA) | [z]: accoa + nncoa <==> 3oedcoa + coa | Fatty Acid Degradation | EC-2.3.1.16 |
| ACACT12m__mc | acetyl-CoA C-acyltransferase (decanoyl-CoA) | [z]: accoa + dccoa <==> 3oddcoa + coa | Fatty Acid Degradation | EC-2.3.1.16 |
| ACACT13m__mc | acetyl-CoA C-acyltransferase (endecanoyl-CoA) | [z]: accoa + edcoa <==> 3otrdcoa + coa | Fatty Acid Degradation | EC-2.3.1.16 |
| ACACT145m__mc | acetyl-CoA C-acyltransferase (dodecenoyl-CoA C12:1CoA, n-3) | [z]: accoa + cis-dd2coa <==> 3otdecoa5 + coa | Fatty Acid Degradation | EC-2.3.1.16 |
| ACACT14m__mc | acetyl-CoA C-acyltransferase (dodecanoyl-CoA) | [z]: accoa + ddcoa <==> 3otdcoa + coa | Fatty Acid Degradation | EC-2.3.1.16 |
| ACACT15m__mc | acetyl-CoA C-acyltransferase (tridecanoyl-CoA) | [z]: accoa + trdcoa <==> 3opdcoa + coa | Fatty Acid Degradation | EC-2.3.1.16 |
| ACACT167m__mc | acetyl-CoA C-acyltransferase (tetradecenoyl-CoA C14:1CoA, n-5) | [z]: accoa + tdecoa5 <==> 3ohdecoa7 + coa | Fatty Acid Degradation | EC-2.3.1.16 |
| ACACT16m__mc | acetyl-CoA C-acyltransferase (tetradecanoyl-CoA) | [z]: accoa + tdcoa <==> 3ohdcoa + coa | Fatty Acid Degradation | EC-2.3.1.16 |
| ACACT189m__mc | acetyl-CoA C-acyltransferase (hexadecenoyl-CoA C16:1CoA, n-7) | [z]: accoa + hdcoa7 <==> 3oodcecoa9 + coa | Fatty Acid Degradation | EC-2.3.1.16 |
| ACACT18m__mc | acetyl-CoA C-acyltransferase (palmitoyl-CoA C16:0CoA) | [z]: accoa + pmtcoa <==> 3oodcoa + coa | Fatty Acid Degradation | EC-2.3.1.16 |
| ACACT20m__mc | acetyl-CoA C-acyltransferase (octadecanoyl-CoA C18:0CoA) | [z]: accoa + strcoa <==> 3oescoa + coa | Fatty Acid Degradation | EC-2.3.1.16 |
| ACACT22p__mc | acetyl-CoA C-acyltransferase (eicosanoyl-CoA C20:0CoA) | [w]: accoa + ecsacoa <==> 3odscoa + coa | Fatty Acid Degradation | EC-2.3.1.16 |
| ACACT4m__mc | acetyl-CoA C-acyltransferase (acetyl-CoA) | [z]: (2) accoa <==> aacoa + coa | Fatty Acid Degradation | EC-2.3.1.16 |
| ACACT5m__mc | acetyl-CoA C-acyltransferase (propanoyl CoA) | [z]: accoa + ppcoa <==> 3optcoa + coa | Fatty Acid Degradation | EC-2.3.1.16 |
| ACACT6m__mc | acetyl-CoA C-acyltransferase (butanoyl-CoA) | [z]: accoa + btcoa <==> 3ohcoa + coa | Fatty Acid Degradation | EC-2.3.1.16 |

TABLE 15-continued

Adipocyte-myocyte reactions

| Reaction Abbreviation | Reaction Name | Equation | Subsystem | Protein Classification |
|---|---|---|---|---|
| ACACT7m__mc | acetyl-CoA C-acyltransferase (pentanoyl-CoA) | [z]: accoa + ptcoa <==> 3ohpcoa + coa | Fatty Acid Degradation | EC-2.3.1.16 |
| ACACT8m__mc | acetyl-CoA C-acyltransferase (hexanoyl-CoA) | [z]: accoa + hxcoa <==> 3oocoa + coa | Fatty Acid Degradation | EC-2.3.1.16 |
| ACACT9m__mc | acetyl-CoA C-acyltransferase (heptanoyl-CoA) | [z]: accoa + hpcoa <==> 3onncoa + coa | Fatty Acid Degradation | EC-2.3.1.16 |
| ACOAD10m__mc | acyl-CoA dehydrogenase (decanoyl-CoA C10:0CoA) | [z]: dccoa + fad <==> dc2coa + fadh2 | Fatty Acid Degradation | EC-1.3.99.13 |
| ACOAD11m__mc | acyl-CoA dehydrogenase (endecanoyl-CoA) | [z]: edcoa + fad <==> ed2coa + fadh2 | Fatty Acid Degradation | EC-1.3.99.13 |
| ACOAD12m__mc | acyl-CoA dehydrogenase (dodecanoyl-CoA C12:0CoA) | [z]: ddcoa + fad <==> fadh2 + trans-dd2coa | Fatty Acid Degradation | EC-1.3.99.13 |
| ACOAD13m__mc | acyl-CoA dehydrogenase (tridecanoyl-CoA) | [z]: fad + trdcoa <==> fadh2 + trd2coa | Fatty Acid Degradation | EC-1.3.99.13 |
| ACOAD145m__mc | acyl-CoA dehydrogenase (tetradecenoyl-CoA, C14:1CoA, n-5) | [z]: fad + tdecoa5 <==> fadh2 + tde2coa5 | Fatty Acid Degradation | EC-1.3.99.13 |
| ACOAD14m__mc | acyl-CoA dehydrogenase (tetradecanoyl-CoA) | [z]: fad + tdcoa <==> fadh2 + td2coa | Fatty Acid Degradation | EC-1.3.99.13 |
| ACOAD15m__mc | acyl-CoA dehydrogenase (pentadecanoyl-CoA) | [z]: fad + pdcoa <==> fadh2 + pd2coa | Fatty Acid Degradation | EC-1.3.99.13 |
| ACOAD167m__mc | acyl-CoA dehydrogenase (hexadecenoyl-CoA, C16:1CoA, n-7) | [z]: fad + hdcoa7 <==> fadh2 + hde2coa7 | Fatty Acid Degradation | EC-1.3.99.13 |
| ACOAD16m__mc | acyl-CoA dehydrogenase (hexadecanoyl-CoA C16:0CoA) | [z]: fad + pmtcoa <==> fadh2 + hdd2coa | Fatty Acid Degradation | EC-1.3.99.13 |
| ACOAD189m__mc | acyl-CoA dehydrogenase (octadecenoyl-CoA, C18:1CoA, n-9) | [z]: fad + odecoa9 <==> fadh2 + ode2coa9 | Fatty Acid Degradation | EC-1.3.99.13 |
| ACOAD18m__mc | acyl-CoA dehydrogenase (Stearyl-CoA, C18:0CoA) | [z]: fad + strcoa <==> fadh2 + od2coa | Fatty Acid Degradation | EC-1.3.99.13 |
| ACOAD20m__mc | acyl-CoA dehydrogenase (eicosanoyl-CoA, C20:0CoA) | [z]: ecsacoa + fad <==> es2coa + fadh2 | Fatty Acid Degradation | EC-1.3.99.13 |
| ACOAD22p__mc | acyl-CoA dehydrogenase (docosanoyl-CoA, C22:0CoA) | [w]: dcsacoa + fad <==> ds2coa + fadh2 | Fatty Acid Degradation | EC-1.3.99.13 |
| ACOAD4m__mc | acyl-CoA dehydrogenase (butanoyl-CoA C4:0CoA) | [z]: btcoa + fad <==> b2coa + fadh2 | Fatty Acid Degradation | EC-1.3.99.13 |
| ACOAD5m__mc | acyl-CoA dehydrogenase (pentanoyl-CoA) | [z]: fad + ptcoa <==> fadh2 + pt2coa | Fatty Acid Degradation | EC-1.3.99.13 |
| ACOAD6m__mc | acyl-CoA dehydrogenase (hexanoyl-CoA C8:0CoA) | [z]: fad + hxcoa <==> fadh2 + hx2coa | Fatty Acid Degradation | EC-1.3.99.13 |
| ACOAD7m__mc | acyl-CoA dehydrogenase (heptanoyl-CoA) | [z]: fad + hpcoa <==> fadh2 + hp2coa | Fatty Acid Degradation | EC-1.3.99.13 |
| ACOAD8m__mc | acyl-CoA dehydrogenase (octanoyl-CoA C8:0CoA) | [z]: fad + occoa <==> fadh2 + oc2coa | Fatty Acid Degradation | EC-1.3.99.13 |
| ACOAD9m__mc | acyl-CoA dehydrogenase (nonanoyl-CoA) | [z]: fad + nncoa <==> fadh2 + nn2coa | Fatty Acid Degradation | EC-1.3.99.13 |
| CRNDST__mc | carnitine docosanoyltransferase, myocyte | [y]: crn + dcsacoa --> coa + dcsacrn | Fatty Acid Degradation | EC-2.3.1.21 |
| CRNDSTp__mc | carnitine docosanoyltransferase II, myocyte | coa[w] + dcsacrn[y] <==> crn[y] + dcsacoa[w] | Fatty Acid Degradation | |
| CRNDT__mc | carnitine dodecanoyltransferase, myocyte | [y]: crn + ddcoa <==> coa + ddcrn | Fatty Acid Degradation | EC-2.3.1.21 |
| CRNDTm__mc | carnitine dodecanoyltransferase II, myocyte | coa[z] + ddcrn[y] <==> crn[y] + ddcoa[z] | Fatty Acid Degradation | |
| CRNET__mc | carnitine eicosanoyltransferase, myocyte | [y]: crn + ecsacoa <==> coa + ecsacrn | Fatty Acid Degradation | EC-2.3.1.21 |
| CRNETm__mc | carnitine eicosanoyltransferase II, myocyte | coa[z] + ecsacrn[y] <==> crn[y] + ecsacoa[z] | Fatty Acid Degradation | |
| CRNETp__mc | carnitine eicosanoyltransferase II, myocyte | coa[w] + ecsacrn[y] <==> crn[y] + ecsacoa[w] | Fatty Acid Degradation | |

TABLE 15-continued

Adipocyte-myocyte reactions

| Reaction Abbreviation | Reaction Name | Equation | Subsystem | Protein Classification |
|---|---|---|---|---|
| CRNODET_mc | carnitine 9-cis-octadecenoyltransferase, myocyte | [y]: crn + odecoa9 <==> coa + odecrn9 | Fatty Acid Degradation | EC-2.3.1.21 |
| CRNOT_mc | carnitine octadecanoyltransferase, myocyte | [y]: crn + strcoa <==> coa + strcrn | Fatty Acid Degradation | EC-2.3.1.21 |
| CRNOTm_mc | carnitine octadecanoyltransferase II, myocyte | coa[z] + strcrn[y] <==> crn[y] + strcoa[z] | Fatty Acid Degradation | |
| CRNPTDT_mc | carnitine pentadecanoyltransferase, myocyte | [y]: crn + pdcoa <==> coa + pdcrn | Fatty Acid Degradation | EC-2.3.1.21 |
| CRNPT_mc | carnitine O-palmitoyltransferase, myocyte | [y]: crn + pmtcoa --> coa + pmtcrn | Fatty Acid Degradation | EC-2.3.1.21 |
| CRNPTm_mc | carnitine O-palmitoyltransferase II, myocyte | coa[z] + pmtcrn[y] --> crn[y] + pmtcoa[z] | Fatty Acid Degradation | |
| CRNTT_mc | carnitine tetradecanoyltransferase, myocyte | [y]: crn + tdcoa <==> coa + tdcrn | Fatty Acid Degradation | EC-2.3.1.21 |
| CRNTTm_mc | carnitine tetradecanoyltransferase II, myocyte | coa[z] + tdcrn[y] <==> crn[y] + tdcoa[z] | Fatty Acid Degradation | |
| DDCIm_mc | dodecenoyl-CoA D-isomerase, myocyte mitochondrial | [z]: cis-dd2coa <==> trans-dd2coa | Fatty Acid Degradation | EC-5.3.3.8 |
| ECOAH10m_mc | 3-hydroxyacyl-CoA dehydratase (3-hydroxydecanoyl-CoA) | [z]: 3hdcoa <==> dc2coa + h2o | Fatty Acid Degradation | EC-4.2.1.17 |
| ECOAH11m_mc | 3-hydroxyacyl-CoA dehydratase (3-hydroxyendecanoyl-CoA) | [z]: 3hedcoa <==> ed2coa + h2o | Fatty Acid Degradation | EC-4.2.1.17 |
| ECOAH12m_mc | 3-hydroxyacyl-CoA dehydratase (3-hydroxydodecanoyl-CoA) | [z]: 3hddcoa <==> h2o + trans-dd2coa | Fatty Acid Degradation | EC-4.2.1.17 |
| ECOAH13m_mc | 3-hydroxyacyl-CoA dehydratase (3-hydroxytridecanoyl-CoA) | [z]: 3htrdcoa <==> h2o + trd2coa | Fatty Acid Degradation | EC-4.2.1.17 |
| ECOAH145m_mc | 3-hydroxyacyl-CoA dehydratase (3-hydroxytetradecenoyl-CoA, C14:1CoA, n-5) | [z]: 3htdecoa5 <==> h2o + tde2coa5 | Fatty Acid Degradation | EC-4.2.1.17 |
| ECOAH14m_mc | 3-hydroxyacyl-CoA dehydratase (3-hydroxytetradecanoyl-CoA) | [z]: 3htdcoa <==> h2o + td2coa | Fatty Acid Degradation | EC-4.2.1.17 |
| ECOAH15m_mc | 3-hydroxyacyl-CoA dehydratase (3-hydroxypentadecanoyl-CoA) | [z]: 3hpdcoa <==> h2o + pd2coa | Fatty Acid Degradation | EC-4.2.1.17 |
| ECOAH167m_mc | 3-hydroxyacyl-CoA dehydratase (3-hydroxyhexadecenoyl-CoA, C16:1CoA, n-7) | [z]: 3hhdecoa7 <==> h2o + hde2coa7 | Fatty Acid Degradation | EC-4.2.1.17 |
| ECOAH16m_mc | 3-hydroxyacyl-CoA dehydratase (3-hydroxyhexadecanoyl-CoA) | [z]: 3hhdcoa <==> h2o + hdd2coa | Fatty Acid Degradation | EC-4.2.1.17 |
| ECOAH189m_mc | 3-hydroxyacyl-CoA dehydratase (3-hydroxyoctadecenoyl-CoA, C18:1CoA, n-9) | [z]: 3hodecoa9 <==> h2o + ode2coa9 | Fatty Acid Degradation | EC-4.2.1.17 |
| ECOAH18m_mc | 3-hydroxyacyl-CoA dehydratase (3-hydroxyoctadecanoyl-CoA, C18:0CoA) | [z]: 3hodcoa <==> h2o + od2coa | Fatty Acid Degradation | EC-4.2.1.17 |
| ECOAH20m_mc | 3-hydroxyacyl-CoA dehydratase (3-hydroxyeicosanoyl-CoA, C18:0CoA) | [z]: 3hescoa <==> es2coa + h2o | Fatty Acid Degradation | EC-4.2.1.17 |
| ECOAH22p_mc | 3-hydroxyacyl-CoA dehydratase (3-hydroxydocosanoyl-CoA, C18:0CoA) | [w]: 3hdscoa <==> ds2coa + h2o | Fatty Acid Degradation | EC-4.2.1.17 |

TABLE 15-continued

Adipocyte-myocyte reactions

| Reaction Abbreviation | Reaction Name | Equation | Subsystem | Protein Classification |
|---|---|---|---|---|
| ECOAH4m_mc | 3-hydroxyacyl-CoA dehydratase (3-hydroxybutanoyl-CoA) | [z]: 3hbycoa <==> b2coa + h2o | Fatty Acid Degradation | EC-4.2.1.17 |
| ECOAH5m_mc | 3-hydroxyacyl-CoA dehydratase (3-hydroxypentanoyl-CoA) | [z]: 3hptcoa <==> h2o + pt2coa | Fatty Acid Degradation | EC-4.2.1.17 |
| ECOAH6m_mc | 3-hydroxyacyl-CoA dehydratase (3-hydroxyhexanoyl-CoA) | [z]: 3hhcoa <==> h2o + hx2coa | Fatty Acid Degradation | EC-4.2.1.17 |
| ECOAH7m_mc | 3-hydroxyacyl-CoA dehydratase (3-hydroxyheptanoyl-CoA) | [z]: 3hhpcoa <==> h2o + hp2coa | Fatty Acid Degradation | EC-4.2.1.17 |
| ECOAH8m_mc | 3-hydroxyacyl-CoA dehydratase (3-hydroxyoctanoyl-CoA) | [z]: 3hocoa <==> h2o + oc2coa | Fatty Acid Degradation | EC-4.2.1.17 |
| ECOAH9m_mc | 3-hydroxyacyl-CoA dehydratase (3-hydroxynonanoyl-CoA) | [z]: 3hnncoa <==> h2o + nn2coa | Fatty Acid Degradation | EC-4.2.1.17 |
| HACD10m_mc | 3-hydroxyacyl-CoA dehydrogenase (3-oxodecanoyl-CoA) | [z]: 3odcoa + h + nadh <==> 3hdcoa + nad | Fatty Acid Degradation | EC-1.1.1.35 |
| HACD11m_mc | 3-hydroxyacyl-CoA dehydrogenase (3-oxoendecanoyl-CoA) | [z]: 3oedcoa + h + nadh <==> 3hedcoa + nad | Fatty Acid Degradation | EC-1.1.1.35 |
| HACD12m_mc | 3-hydroxyacyl-CoA dehydrogenase (3-oxododecanoyl-CoA) | [z]: 3oddcoa + h + nadh <==> 3hddcoa + nad | Fatty Acid Degradation | EC-1.1.1.35 |
| HACD13m_mc | 3-hydroxyacyl-CoA dehydrogenase (3-oxotridecanoyl-CoA) | [z]: 3otrdcoa + h + nadh <==> 3htrdcoa + nad | Fatty Acid Degradation | EC-1.1.1.35 |
| HACD145m_mc | 3-hydroxyacyl-CoA dehydrogenase (3-oxotetradecenoyl-CoA C14:1CoA, n-5) | [z]: 3otdecoa5 + h + nadh <==> 3htdecoa5 + nad | Fatty Acid Degradation | EC-1.1.1.35 |
| HACD14m_mc | 3-hydroxyacyl-CoA dehydrogenase (3-oxotetradecanoyl-CoA) | [z]: 3otdcoa + h + nadh <==> 3htdcoa + nad | Fatty Acid Degradation | EC-1.1.1.35 |
| HACD15m_mc | 3-hydroxyacyl-CoA dehydrogenase (3-oxopentadecanoyl-CoA) | [z]: 3opdcoa + h + nadh <==> 3hpdcoa + nad | Fatty Acid Degradation | EC-1.1.1.35 |
| HACD167m_mc | 3-hydroxyacyl-CoA dehydrogenase (3-oxohexadecenoyl-CoA C16:1CoA, n-7) | [z]: 3ohdecoa7 + h + nadh <==> 3hhdecoa7 + nad | Fatty Acid Degradation | EC-1.1.1.35 |
| HACD16m_mc | 3-hydroxyacyl-CoA dehydrogenase (3-oxohexadecanoyl-CoA) | [z]: 3ohdcoa + h + nadh <==> 3hhdcoa + nad | Fatty Acid Degradation | EC-1.1.1.35 |
| HACD189m_mc | 3-hydroxyacyl-CoA dehydrogenase (3-oxooctadecenoyl-CoA C18:1CoA, n-9) | [z]: 3oodcecoa9 + h + nadh <==> 3hodecoa9 + nad | Fatty Acid Degradation | EC-1.1.1.35 |
| HACD18m_mc | 3-hydroxyacyl-CoA dehydrogenase (3-oxooctadecanoyl-CoA C18:0CoA) | [z]: 3oodcoa + h + nadh <==> 3hodcoa + nad | Fatty Acid Degradation | EC-1.1.1.35 |
| HACD20m_mc | 3-hydroxyacyl-CoA dehydrogenase (3-oxoeicosanoyl-CoA C18:0CoA) | [z]: 3oescoa + h + nadh <==> 3hescoa + nad | Fatty Acid Degradation | EC-1.1.1.35 |
| HACD22p_mc | 3-hydroxyacyl-CoA dehydrogenase (3-oxodocosanoyl-CoA C18:0CoA) | [w]: 3odscoa + h + nadh <==> 3hdscoa + nad | Fatty Acid Degradation | EC-1.1.1.35 |
| HACD4m_mc | 3-hydroxyacyl-CoA dehydrogenase (3-oxobutanoyl-CoA) | [z]: aacoa + h + nadh <==> 3hbycoa + nad | Fatty Acid Degradation | EC-1.1.1.35 |
| HACD5m_mc | 3-hydroxyacyl-CoA dehydrogenase (3-oxopentanoyl-CoA) | [z]: 3optcoa + h + nadh <==> 3hptcoa + nad | Fatty Acid Degradation | EC-1.1.1.35 |
| HACD6m_mc | 3-hydroxyacyl-CoA dehydrogenase (3-oxohexanoyl-CoA) | [z]: 3ohcoa + h + nadh <==> 3hhcoa + nad | Fatty Acid Degradation | EC-1.1.1.35 |
| HACD7m_mc | 3-hydroxyacyl-CoA dehydrogenase (3-oxoheptanoyl-CoA) | [z]: 3ohpcoa + h + nadh <==> 3hhpcoa + nad | Fatty Acid Degradation | EC-1.1.1.35 |

TABLE 15-continued

Adipocyte-myocyte reactions

| Reaction Abbreviation | Reaction Name | Equation | Subsystem | Protein Classification |
|---|---|---|---|---|
| HACD8m__mc | 3-hydroxyacyl-CoA dehydrogenase (3-oxooctanoyl-CoA) | [z]: 3oocoa + h + nadh <==> 3hocoa + nad | Fatty Acid Degradation | EC-1.1.1.35 |
| HACD9m__mc | 3-hydroxyacyl-CoA dehydrogenase (3-oxononanoyl-CoA) | [z]: 3onncoa + h + nadh <==> 3hnncoa + nad | Fatty Acid Degradation | EC-1.1.1.35 |
| MMEm__mc | methylmalonyl-CoA epimerase, myocyte mitochondrial | [z]: mmcoa-S <==> mmcoa-R | Fatty Acid Degradation | EC-5.1.99.1 |
| MMMm__mc | R-methylmalonyl-CoA mutase, myocyte mitochondrial | [z]: mmcoa-R --> succoa | Fatty Acid Degradation | EC-5.4.99.2 |
| PPCOACm__mc | Propionyl-CoA carboxylase, myocyte mitochondrial | [z]: atp + hco3 + ppcoa --> adp + h + mmcoa-S + pi | Fatty Acid Degradation | EC-6.4.1.3 |
| FACOAL120__mc | fatty-acid—CoA ligase (dodecanoate, C12:0), myocyte | [y]: atp + coa + ddca <==> amp + ddcoa + ppi | Fatty Acid Metabolism | EC-6.2.1.3 |
| FACOAL140__mc | fatty-acid—CoA ligase (tetradecanoate, C14:0), myocyte | [y]: atp + coa + ttdca <==> amp + ppi + tdcoa | Fatty Acid Metabolism | EC-6.2.1.3 |
| FACOAL150__mc | fatty-acid—CoA ligase (pentadecanoate, C15:0), myocyte | [y]: atp + coa + ptdca <==> amp + pdcoa + ppi | Fatty Acid Metabolism | EC-6.2.1.3 |
| FACOAL160__mc | fatty-acid—CoA ligase (hexadecanoate, C16:0), myocyte | [y]: atp + coa + hdca <==> amp + pmtcoa + ppi | Fatty Acid Metabolism | EC-6.2.1.3 |
| FACOAL180__mc | fatty-acid—CoA ligase (octadecanoate, C28:0), myocyte | [y]: atp + coa + ocdca <==> amp + ppi + strcoa | Fatty Acid Metabolism | EC-6.2.1.3 |
| FACOAL181_9__mc | fatty-acid—CoA ligase (octadecenoate, C18:1 n-9), myocyte | [y]: atp + coa + ocdcea9 <==> amp + odecoa9 + ppi | Fatty Acid Metabolism | EC-6.2.1.3 |
| FACOAL200__mc | fatty-acid—CoA ligase (eicosanoate, C20:0), myocyte | [y]: atp + coa + ecsa <==> amp + ecsacoa + ppi | Fatty Acid Metabolism | EC-6.2.1.3 |
| ACCOAC__ac | acetyl-CoA carboxylase | [a]: accoa + atp + hco3 --> adp + h + malcoa + pi | Fatty Acid Synthesis | EC-6.4.1.2 |
| AGAT__ac__HS__ub | unbalanced 1-Acyl-glycerol-3-phosphate acyltransferase, adipocyte cytosol, Homo sapiens specific | [a]: 1ag3p__HS + (0.00032) dcsacoa + (0.00698) ddcoa + (0.00024) dsecoa11 + (0.00056) dsecoa9 + (0.00172) dshcoa3 + (0.00163) dspcoa3 + (0.00016) dspcoa6 + (0.00182) ecsacoa + (0.00272) esdcoa6 + (0.00035) esdcoa9 + (0.00148) esecoa11 + (0.00026) esecoa7 + (0.00732) esecoa9 + (0.00036) espcoa3 + (0.00027) estcoa3 + (0.0023) estcoa6 + (0.00027) ettcoa3 + (0.00311) ettcoa6 + (0.02985) hdcoa7 + (0.00582) hdcoa9 + (0.00295) hpdcoa8 + (0.15761) ocdycacoa6 + (0.00499) odcoa3 + (0.00039) odcoa6 + (0.0026) odecoa5 + (0.01831) odecoa7 + (0.39309) odecoa9 + (0.00138) osttcoa6 + (0.00375) pdcoa + (0.24351) pmtcoa + (0.06379) strcoa + (0.03728) tdcoa + (0.00244) tdecoa5 + (0.00037) tdecoa7 --> coa + pa__HS | Fatty Acid Synthesis | |
| DESAT141_5__ac | Myristicoyl-CoA desaturase (n-C14:0CoA -> C14:1CoA, n-5), adipocyte | [a]: h + nadph + o2 + tdcoa --> (2) h2o + nadp + tdecoa5 | Fatty Acid Synthesis | EC-1.14.19.1 |
| DESAT141_7__ac | Myristicoyl-CoA desaturase (n-C14:0CoA -> C14:1CoA, n-7), adipocyte | [a]: h + nadph + o2 + tdcoa --> (2) h2o + nadp + tdecoa7 | Fatty Acid Synthesis | EC-1.14.19.1 |
| DESAT161_7__ac | Palmitoyl-CoA desaturase (n-C16:0CoA -> C16:1CoA, n-7), adipocyte | [a]: h + nadph + o2 + pmtcoa --> (2) h2o + hdcoa7 + nadp | Fatty Acid Synthesis | EC-1.14.19.1 |
| DESAT161_9__ac | Palmitoyl-CoA desaturase (n-C16:0CoA -> C16:1CoA, n-9), adipocyte | [a]: h + nadph + o2 + pmtcoa --> (2) h2o + hdcoa9 + nadp | Fatty Acid Synthesis | EC-1.14.19.1 |

TABLE 15-continued

Adipocyte-myocyte reactions

| Reaction Abbreviation | Reaction Name | Equation | Subsystem | Protein Classification |
|---|---|---|---|---|
| DESAT171__8__ac | Palmitoyl-CoA desaturase (n-C17:0CoA -> C17:1CoA, n-8), adipocyte | [a]: h + hpdcoa + nadph + o2 --> (2) h2o + hpdcoa8 + nadp | Fatty Acid Synthesis | EC-1.14.19.1 |
| DESAT181__5__ac | stearoyl-CoA desaturase (n-C18:0CoA -> C18:1CoA, n-5), adipocyte | [a]: h + nadph + o2 + strcoa --> (2) h2o + nadp + odecoa5 | Fatty Acid Synthesis | EC-1.14.19.1 |
| DESAT181__7__ac | stearoyl-CoA desaturase (n-C18:0CoA -> C18:1CoA, n-7), adipocyte | [a]: h + nadph + o2 + strcoa --> (2) h2o + nadp + odecoa7 | Fatty Acid Synthesis | EC-1.14.19.1 |
| DESAT181__9__ac | stearoyl-CoA desaturase (n-C18:0CoA -> C18:1CoA, n-9), adipocyte | [a]: h + nadph + o2 + strcoa --> (2) h2o + nadp + odecoa9 | Fatty Acid Synthesis | EC-1.14.19.1 |
| DESAT201__11__ac | stearoyl-CoA desaturase (n-C20:0CoA -> C20:1CoA, n-11), adipocyte | [a]: ecsacoa + h + nadph + o2 --> esecoa11 + (2) h2o + nadp | Fatty Acid Synthesis | EC-1.14.19.1 |
| DESAT201__7__ac | stearoyl-CoA desaturase (n-C20:0CoA -> C20:1CoA, n-7), adipocyte | [a]: ecsacoa + h + nadph + o2 --> esecoa7 + (2) h2o + nadp | Fatty Acid Synthesis | EC-1.14.19.1 |
| DESAT201__9__ac | stearoyl-CoA desaturase (n-C20:0CoA -> C20:1CoA, n-9), adipocyte | [a]: ecsacoa + h + nadph + o2 --> esecoa9 + h2o + nadp | Fatty Acid Synthesis | EC-1.14.19.1 |
| DESAT202__9__ac | stearoyl-CoA desaturase (lumped: n-C20:0CoA -> C20:2CoA, n-9), adipocyte | [a]: ecsacoa + (2) h + (2) nadph + (2) o2 --> esdcoa9 + (4) h2o + (2) nadp | Fatty Acid Synthesis | EC-1.14.19.1 |
| DESAT221__11__ac | stearoyl-CoA desaturase (n-C22:0CoA -> C22:1CoA, n-11), adipocyte | [a]: dcsacoa + h + nadph + o2 --> dsecoa11 + (2) h2o + nadp | Fatty Acid Synthesis | EC-1.14.19.1 |
| DESAT221__9__ac | stearoyl-CoA desaturase (n-C22:0CoA -> C22:1CoA, n-9), adipocyte | [a]: dcsacoa + h + nadph + o2 --> dsecoa9 + (2) h2o + nadp | Fatty Acid Synthesis | EC-1.14.19.1 |
| FACOAL120__ac | fatty-acid—CoA ligase (dodecanoate, C12:0), adipocyte | [a]: atp + coa + ddca <==> amp + ddcoa + ppi | Fatty Acid Synthesis | EC-6.2.1.3 |
| FACOAL140__ac | fatty-acid—CoA ligase (tetradecanoate, C14:0), adipocyte | [a]: atp + coa + ttdca <==> amp + ppi + tdcoa | Fatty Acid Synthesis | EC-6.2.1.3 |
| FACOAL141__5__ac | fatty-acid—CoA ligase (tetradecenoate, C14:1 n-5), adipocyte | [a]: atp + coa + ttdcea5 <==> amp + ppi + tdecoa5 | Fatty Acid Synthesis | EC-6.2.1.3 |
| FACOAL141__7__ac | fatty-acid—CoA ligase (tetradecenoate, C14:1 n-7), adipocyte | [a]: atp + coa + ttdcea7 <==> amp + ppi + tdecoa7 | Fatty Acid Synthesis | EC-6.2.1.3 |
| FACOAL150__ac | fatty-acid—CoA ligase (heptadecanoate, C15:0), adipocyte | [a]: atp + coa + ptdca <==> amp + pdcoa + ppi | Fatty Acid Synthesis | EC-6.2.1.3 |
| FACOAL160__ac | fatty-acid—CoA ligase (hexadecanoate, C16:0), adipocyte | [a]: atp + coa + hdca <==> amp + pmtcoa + ppi | Fatty Acid Synthesis | EC-6.2.1.3 |
| FACOAL161__7__ac | fatty-acid—CoA ligase (hexadecenoate, C16:1 n-7), adipocyte | [a]: atp + coa + hdcea7 <==> amp + hdcoa7 + ppi | Fatty Acid Synthesis | EC-6.2.1.3 |
| FACOAL161__9__ac | fatty-acid—CoA ligase (hexadecenoate, C16:1 n-9), adipocyte | [a]: atp + coa + hdcea9 <==> amp + hdcoa9 + ppi | Fatty Acid Synthesis | EC-6.2.1.3 |
| FACOAL170__ac | fatty-acid—CoA ligase (heptadecanoate, C17:0), adipocyte | [a]: atp + coa + hpdca <==> amp + hpdcoa + ppi | Fatty Acid Synthesis | EC-6.2.1.3 |
| FACOAL171__8__ac | fatty-acid—CoA ligase (heptadecenoate, C17:1 n-8), adipocyte | [a]: atp + coa + hpdcea8 <==> amp + hpdcoa8 + ppi | Fatty Acid Synthesis | EC-6.2.1.3 |
| FACOAL180__ac | fatty-acid—CoA ligase (octadecanoate, C18:0), adipocyte | [a]: atp + coa + ocdca <==> amp + ppi + strcoa | Fatty Acid Synthesis | EC-6.2.1.3 |
| FACOAL181__5__ac | fatty-acid—CoA ligase (octadecenoate, C18:1 n-5), adipocyte | [a]: atp + coa + ocdcea5 <==> amp + odecoa5 + ppi | Fatty Acid Synthesis | EC-6.2.1.3 |
| FACOAL181__7__ac | fatty-acid—CoA ligase (octadecenoate, C18:1 n-7), adipocyte | [a]: atp + coa + ocdcea7 <==> amp + odecoa7 + ppi | Fatty Acid Synthesis | EC-6.2.1.3 |
| FACOAL181__9__ac | fatty-acid—CoA ligase (octadecenoate, C18:1 n-9), adipocyte | [a]: atp + coa + ocdcea9 <==> amp + odecoa9 + ppi | Fatty Acid Synthesis | EC-6.2.1.3 |

TABLE 15-continued

Adipocyte-myocyte reactions

| Reaction Abbreviation | Reaction Name | Equation | Subsystem | Protein Classification |
|---|---|---|---|---|
| FACOAL182_6_ac | fatty-acid—CoA ligase (octadecadienoate, C18:2 n-6), adipocyte | [a]: atp + coa + ocddea6 <==> amp + ocdycacoa6 + ppi | Fatty Acid Synthesis | EC-6.2.1.3 |
| FACOAL183_3_ac | fatty-acid—CoA ligase (octadecadienoate, C18:3 n-3), adipocyte | [a]: atp + coa + ocdctra3 <==> amp + odcoa3 + ppi | Fatty Acid Synthesis | EC-6.2.1.3 |
| FACOAL183_6_ac | fatty-acid—CoA ligase (octadecadienoate, C18:3 n-6), adipocyte | [a]: atp + coa + ocdctra6 <==> amp + odcoa6 + ppi | Fatty Acid Synthesis | EC-6.2.1.3 |
| FACOAL200_ac | fatty-acid—CoA ligase (eicosanoate, C20:0), adipocyte | [a]: atp + coa + ecsa <==> amp + ecsacoa + ppi | Fatty Acid Synthesis | EC-6.2.1.3 |
| FACOAL201_11_ac | fatty-acid—CoA ligase (eicosenoate, C20:1 n-11), adipocyte | [a]: atp + coa + ecsea11 <==> amp + esecoa11 + ppi | Fatty Acid Synthesis | EC-6.2.1.3 |
| FACOAL201_7_ac | fatty-acid—CoA ligase (eicosenoate, C20:1 n-7), adipocyte | [a]: atp + coa + ecsea7 <==> amp + esecoa7 + ppi | Fatty Acid Synthesis | EC-6.2.1.3 |
| FACOAL201_9_ac | fatty-acid—CoA ligase (eicosenoate, C20:1 n-9), adipocyte | [a]: atp + coa + ecsea9 <==> amp + esecoa9 + ppi | Fatty Acid Synthesis | EC-6.2.1.3 |
| FACOAL202_6_ac | fatty-acid—CoA ligase (eicosadienoate, C20:2 n-6), adipocyte | [a]: atp + coa + ecsdea6 <==> amp + esdcoa6 + ppi | Fatty Acid Synthesis | EC-6.2.1.3 |
| FACOAL202_9_ac | fatty-acid—CoA ligase (eicosadienoate, C20:2 n-9), adipocyte | [a]: atp + coa + ecsdea9 <==> amp + esdcoa9 + ppi | Fatty Acid Synthesis | EC-6.2.1.3 |
| FACOAL203_3_ac | fatty-acid—CoA ligase (eicosatrienoate, C20:3 n-6), adipocyte | [a]: atp + coa + ecstea3 <==> amp + estcoa3 + ppi | Fatty Acid Synthesis | EC-6.2.1.3 |
| FACOAL203_6_ac | fatty-acid—CoA ligase (eicosatrienoate, C20:3 n-6), adipocyte | [a]: atp + coa + ecstea6 <==> amp + estcoa6 + ppi | Fatty Acid Synthesis | EC-6.2.1.3 |
| FACOAL204_3_ac | fatty-acid—CoA ligase (eicosatetraenoate, C20:4 n-3), adipocyte | [a]: atp + coa + ecsttea3 <==> amp + ettcoa3 + ppi | Fatty Acid Synthesis | EC-6.2.1.3 |
| FACOAL204_6_ac | fatty-acid—CoA ligase (eicosatetraenoate, C20:4 n-6), adipocyte | [a]: atp + coa + ecsttea6 <==> amp + ettcoa6 + ppi | Fatty Acid Synthesis | EC-6.2.1.3 |
| FACOAL205_3_ac | fatty-acid—CoA ligase (eicosapentaenoate, C20:5 n-3), adipocyte | [a]: atp + coa + ecspea3 <==> amp + espcoa3 + ppi | Fatty Acid Synthesis | EC-6.2.1.3 |
| FACOAL220_ac | fatty-acid—CoA ligase (docosanoate, C22:0), adipocyte | [a]: atp + coa + dcsa <==> amp + dcsacoa + ppi | Fatty Acid Synthesis | EC-6.2.1.3 |
| FACOAL221_11_ac | fatty-acid—CoA ligase (docosenoate, C22:1 n-11), adipocyte | [a]: atp + coa + dcsea11 <==> amp + dsecoa11 + ppi | Fatty Acid Synthesis | EC-6.2.1.3 |
| FACOAL221_9_ac | fatty-acid—CoA ligase (docosenoate, C22:1 n-9), adipocyte | [a]: atp + coa + dcsea9 <==> amp + dsecoa9 + ppi | Fatty Acid Synthesis | EC-6.2.1.3 |
| FACOAL224_6_ac | fatty-acid—CoA ligase (ocosatetraenoate, C22:4 n-6), adipocyte | [a]: atp + coa + ocsttea6 <==> amp + osttcoa6 + ppi | Fatty Acid Synthesis | EC-6.2.1.3 |
| FACOAL225_3_ac | fatty-acid—CoA ligase (docosapentaenoate, C22:5 n-3), adipocyte | [a]: atp + coa + dcspea3 <==> amp + dspcoa3 + ppi | Fatty Acid Synthesis | EC-6.2.1.3 |
| FACOAL225_6_ac | fatty-acid—CoA ligase (docosapentaenoate, C22:5 n-6), adipocyte | [a]: atp + coa + dcspea6 <==> amp + dspcoa6 + ppi | Fatty Acid Synthesis | EC-6.2.1.3 |
| FACOAL226_6_ac | fatty-acid—CoA ligase (docosahexaenoate, C22:6 n-6), adipocyte | [a]: atp + coa + dcshea3 <==> amp + dshcoa3 + ppi | Fatty Acid Synthesis | EC-6.2.1.3 |
| FAS100_ac | fatty acid synthase (n-C10:0), adipocyte | [a]: (3) h + malcoa + (2) nadph + octa --> co2 + coa + dca + h2o + (2) nadp | Fatty Acid Synthesis | EC-2.3.1.85 |
| FAS120_ac | fatty acid synthase (n-C12:0), adipocyte | [a]: dca + (3) h + malcoa + (2) nadph --> co2 + coa + ddca + h2o + (2) nadp | Fatty Acid Synthesis | EC-2.3.1.85 |
| FAS140_ac | fatty acid synthase (n-C14:0), adipocyte | [a]: ddca + (3) h + malcoa + (2) nadph --> co2 + coa + h2o + (2) nadp + ttdca | Fatty Acid Synthesis | EC-2.3.1.85 |
| FAS150_ac | fatty acid synthase (C15:0), adipocyte cytosol | [a]: (17) h + (6) malcoa + (12) nadph + ppcoa --> (6) co2 + (7) coa + (5) h2o + (12) nadp + ptdca | Fatty Acid Synthesis | |

TABLE 15-continued

Adipocyte-myocyte reactions

| Reaction Abbreviation | Reaction Name | Equation | Subsystem | Protein Classification |
|---|---|---|---|---|
| FAS160_ac | fatty acid synthase (n-C16:0), adipocyte | [a]: (3) h + malcoa + (2) nadph + ttdca --> co2 + coa + h2o + hdca + (2) nadp | Fatty Acid Synthesis | EC-2.3.1.85 |
| FAS170_ac | fatty acid synthase (C17:0), adipocyte cytosol | [a]: (3) h + malcoa + (2) nadph + ptdca --> co2 + coa + h2o + hpdca + (2) nadp | Fatty Acid Synthesis | |
| FAS180_ac | fatty acid synthase (n-C18:0), adipocyte | [a]: (3) h + hdca + malcoa + (2) nadph --> co2 + coa + h2o + (2) nadp + ocdca | Fatty Acid Synthesis | EC-2.3.1.85 |
| FAS200_ac | fatty acid synthase (n-C20:0), adipocyte | [a]: (3) h + malcoa + (2) nadph + ocdca --> co2 + coa + ecsa + h2o + (2) nadp | Fatty Acid Synthesis | EC-2.3.1.85 |
| FAS220_ac | fatty acid synthase (n-C22:0), adipocyte | [a]: ecsa + (3) h + malcoa + (2) nadph --> co2 + coa + dcsa + h2o + (2) nadp | Fatty Acid Synthesis | EC-2.3.1.85 |
| FAS80_L_ac | fatty acid synthase (n-C8:0), lumped reaction, adipocyte | [a]: accoa + (8) h + (3) malcoa + (6) nadph --> (3) co2 + (4) coa + (2) h2o + (6) nadp + octa | Fatty Acid Synthesis | EC-23.1.85 |
| GAT1_ac_HS_ub | unbalanced glycerol 3-phosphate acyltransferase (glycerol 3-phosphate), adipocyte cytosol, Homo sapiens specific | [a]: (0.00032) dcsacoa + (0.00698) ddcoa + (0.00024) dsecoa11 + (0.00056) dsecoa9 + (0.00172) dshcoa3 + (0.00163) dspcoa3 + (0.00016) dspcoa6 + (0.00182) ecsacoa + (0.00272) esdcoa6 + (0.00035) esdcoa9 + (0.00148) esecoa11 + (0.00026) esecoa7 + (0.00732) esecoa9 + (0.00036) espcoa3 + (0.00027) estcoa3 + (0.0023) estcoa6 + (0.00027) ettcoa3 + (0.00311) ettcoa6 + glyc3p + (0.02985) hdcoa7 + (0.00582) hdcoa9 + (0.00295) hpdcoa8 + (0.15761) ocdycacoa6 + (0.00499) odcoa3 + (0.00039) odcoa6 + (0.0026) odecoa5 + (0.01831) odecoa7 + (0.39309) odecoa9 + (0.00138) osttcoa6 + (0.00375) pdcoa + (0.24351) pmtcoa + (0.06379) strcoa + (0.03728) tdcoa + (0.00244) tdecoa5 + (0.00037) tdecoa7 --> 1ag3p_HS + coa | Fatty Acid Synthesis | |
| 12DGRH_ac_HS_ub | unbalanced diacylglycerol hydrolase, adipocyte cytosol, Homo sapiens specific | [a]: 12dgr_HS + h2o --> (0.00032) dcsa + (0.00024) dcsea11 + (0.00056) dcsea9 + (0.00172) dcshea3 + (0.00163) dcspea3 + (0.00016) dcspea6 + (0.00698) ddca + (0.00182) ecsa + (0.00272) ecsdea6 + (0.00035) ecsdea9 + (0.00148) ecsea11 + (0.00026) ecsea7 + (0.00732) ecsea9 + (0.00036) ecspea3 + (0.00027) ecstea3 + (0.0023) ecstea6 + (0.00027) ecsttea3 + (0.00311) ecsttea6 + h + (0.24351) hdca + (0.02985) hdcea7 + (0.00582) hdcea9 + (0.00295) hpdcea8 + mglyc_HS + (0.06379) ocdca + (0.0026) ocdcea5 + (0.01831) ocdcea7 + (0.39309) ocdcea9 + (0.00499) ocdctra3 + (0.00039) ocdctra6 + (0.15761) ocddea6 + (0.00138) ocsttea6 + (0.00375) ptdca + (0.03728) ttdca + (0.00244) ttdcea5 + (0.00037) ttdcea7 | Triglycerol Degradation | EC-3.1.1.3 |
| MGLYCH_ac_HS_ub | unbalanced monoglycerol hydrolase, adipocyte cytosol, Homo sapiens specific | [a]: h2o + mglyc_HS --> (0.00032) dcsa + (0.00024) dcsea11 + (0.00056) dcsea9 + (0.00172) dcshea3 + (0.00163) dcspea3 + (0.00016) dcspea6 + (0.00698) ddca + (0.00182) ecsa + (0.00272) ecsdea6 + (0.00035) ecsdea9 + (0.00148) ecsea11 + (0.00026) ecsea7 + (0.00732) ecsea9 + (0.00036) | Triglycerol Degradation | EC-3.1.1.3 |

TABLE 15-continued

Adipocyte-myocyte reactions

| Reaction Abbreviation | Reaction Name | Equation | Subsystem | Protein Classification |
|---|---|---|---|---|
| | | ecspea3 + (0.00027) ecstea3 + (0.0023) ecstea6 + (0.00027) ecsttea3 + (0.00311) ecsttea6 + glyc + h + (0.24351) hdca + (0.02985) hdcea7 + (0.00582) hdcea9 + (0.00295) hpdcea8 + (0.06379) ocdca + (0.0026) ocdcea5 + (0.01831) ocdcea7 + (0.39309) ocdcea9 + (0.00499) ocdctra3 + (0.00039) ocdctra6 + (0.15761) ocddea6 + (0.00138) ocsttea6 + (0.00375) ptdca + (0.03728) ttdca + (0.00244) ttdcea5 + (0.00037) ttdcea7 | | |
| TRIGH_ac_HS_ub | unbalanced triacylglycerol hydrolase, adipocyte cytosol, Homo sapiens specific | [a]: h2o + triglyc_HS --> 12dgr_HS + (0.00032) dcsa + (0.00024) dcsea11 + (0.00056) dcsea9 + (0.00172) dcshea3 + (0.00163) dcspea3 + (0.00016) dcspea6 + (0.00698) ddca + (0.00182) ecsa + (0.00272) ecsdea6 + (0.00035) ecsdea9 + (0.00148) ecsea11 + (0.00026) ecsea7 + (0.00732) ecsea9 + (0.00036) ecspea3 + (0.00027) ecstea3 + (0.0023) ecstea6 + (0.00027) ecsttea3 + (0.00311) ecsttea6 + h + (0.24351) hdca + (0.02985) hdcea7 + (0.00582) hdcea9 + (0.00295) hpdcea8 + (0.06379) ocdca + (0.0026) ocdcea5 + (0.01831) ocdcea7 + (0.39309) ocdcea9 + (0.00499) ocdctra3 + (0.00039) ocdctra6 + (0.15761) ocddea6 + (0.00138) ocsttea6 + (0.00375) ptdca + (0.03728) ttdca + (0.00244) ttdcea5 + (0.00037) ttdcea7 | Triglycerol Degradation | EC-3.1.1.3 |
| DAGPYP_ac_HS_ub | unbalanced diacylglycerol pyrophosphate phosphatase, adipocyte cytosol, Homo sapiens specific | [a]: h2o + pa_HS --> 12dgr_HS + pi | Triglycerol Synthesis | EC-3.1.3.4 |
| TRIGS_ac_HS_ub | unbalanced triglycerol synthesis, adipocyte cytosol, Homo sapiens specific | [a]: 12dgr_HS + (0.00032) dcsacoa + (0.00698) ddcoa + (0.00024) dsecoa11 + (0.00056) dsecoa9 + (0.00172) dshcoa3 + (0.00163) dspcoa3 + (0.00016) dspcoa6 + (0.00182) ecsacoa + (0.00272) esdcoa6 + (0.00035) esdcoa9 + (0.00148) esecoa11 + (0.00026) esecoa7 + (0.00732) esecoa9 + (0.00036) espcoa3 + (0.00027) estcoa3 + (0.0023) estcoa6 + (0.00027) ettcoa3 + (0.00311) ettcoa6 + (0.02985) hdcoa7 + (0.00582) hdcoa9 + (0.00295) hpdcoa8 + (0.15761) ocdycacoa6 + (0.00499) odcoa3 + (0.00039) odcoa6 + (0.0026) odecoa5 + (0.01831) odecoa7 + (0.39309) odecoa9 + (0.00138) osttcoa6 + (0.00375) pdcoa + (0.24351) pmtcoa + (0.06379) strcoa + (0.03728) tdcoa + (0.00244) tdecoa5 + (0.00037) tdecoa7 --> coa + triglyc_HS | Triglycerol Synthesis | |
| NDPK1_ac | nucleoside-diphosphate kinase (ATP:GDP) | [a]: atp + gdp <==> adp + gtp | Nucleotide Metabolism | EC-2.7.4.6 |
| NDPK1_mc | nucleoside-diphosphate kinase (ATP:GDP) | [y]: atp + gdp <==> adp + gtp | Nucleotide Metabolism | EC-2.7.4.6 |
| ADK1_mc | adenylate kinase, myocyte cytosolic | [y]: amp + atp <==> (2) adp | Nucleotide Salvage Pathways | EC-2.7.4.3 |

TABLE 15-continued

Adipocyte-myocyte reactions

| Reaction Abbreviation | Reaction Name | Equation | Subsystem | Protein Classification |
|---|---|---|---|---|
| NTPP6m_ac | Nucleoside triphosphate pyrophosphorylase (atp), adipocyte mitochondrial | [b]: atp + h2o --> amp + h + ppi | Nucleotide Salvage Pathways | |
| ADK1_ac | adenylate kinase, adipocyte cytosolic | [a]: amp + atp <==> (2) adp | Nucleotide Savage Pathway | EC-2.7.4.3 |
| CAT_ac | catalase, adipocyte cytosolic | [a]: (2) h2o2 --> (2) h2o + o2 | Other | EC-1.11.1.6 |
| HCO3E_ac | carbonate dehydratase (HCO3 equilibration reaction), adipocyte cytosolic | [a]: co2 + h2o <==> h + hco3 | Other | EC-4.2.1.1 |
| HCO3E_mc | carbonate dehydratase (HCO3 equilibration reaction), myocyte cytosolic | [y]: co2 + h2o <==> h + hco3 | Other | EC-4.2.1.1 |
| HCO3Ei | carbonate dehydratase (HCO3 equilibration reaction), intra-organism | [i]: co2 + h2o <==> h + hco3 | Other | EC-4.2.1.1 |
| NH4DIS_ac | nh4 Dissociation | [a]: nh4 <==> h + nh3 | Other | |
| CONTRACTION_mc | muscle contraction, myocyte cytosol | [y]: myoactinADPPi --> adp + myoactin + pi | Contraction | |
| MYOADPPIA_mc | myosin-ADP-Pi attachment, myocyte cytosol | [y]: actin + myosinADPPi --> myoactinADPPi | Contraction | |
| MYOSINATPB_mc | mysosin ATP binding, myocyte cytosol | [y]: atp + myoactin --> actin + myosinATP | Contraction | |
| MYOSINATPH_mc | myosin-ATP hydrolysis, myocyte cytosol | [y]: h2o + myosinATP --> h + myosinADPPi | Contraction | |
| CREATt2is_mc | Creatine Na+ symporter, myocyte cytosol | creat[i] + na1[c] <==> creat[y] + na1[y] | Transport | |
| CRTNtis_mc | creatinine transport, myocyte cytosol | crtn[i] <==> crtn[y] | Transport | |
| Clt_xo | chlorideion transport out via diffusion | cl[e] --> cl[i] | Transport | |
| DCSAtis_ac | docosanoate (C22:0) adipocyte transport | dcsa[a] --> dcsa[i] | Transport | |
| DCSEA11tis_ac | docosenoate (C22:1, n-11) adipocyte transport | dcsea11[a] --> dcsea11[i] | Transport | |
| DCSEA9tis_ac | docosenoate (C22:1, n-9) adipocyte transport | dcsea9[a] --> dcsea9[i] | Transport | |
| DCSHEA3t | docosahexaenoate (C22:6, n-3) transport | dcshea3[e] <==> dcshea3[i] | Transport | |
| DCSHEA3tis_ac | docosahexaenoate (C22:6, n-3) adipocyte transport | dcshea3[i] <==> dcshea3[a] | Transport | |
| DCSPEA3t | Docosapentaenoate (C22:5, n-3) transport | dcspea3[e] <==> dcspea3[i] | Transport | |
| DCSPEA3tis_ac | Docosapentaenoate (C22:5, n-3) adipocyte transport | dcspea3[i] <==> dcspea3[a] | Transport | |
| DCSPEA6t | Docosapentaenoate (C22:5, n-6) transport | dcspea6[e] <==> dcspea6[i] | Transport | |
| DCSPEA6tis_ac | Docosapentaenoate (C22:5, n-6) adipocyte transport | dcspea6[i] <==> dcspea6[a] | Transport | |
| DDCAtis_ac | dodecanoate (C12:0) adipocyte transport | ddca[a] --> ddca[i] | Transport | |
| DDCAtis_mc | dodecanoate (C12:0) myocyte transport | ddca[i] --> ddca[y] | Transport | |
| ECSAtis_ac | eicosanoate (C20:0) adipocyte transport | ecsa[a] --> ecsa[i] | Transport | |
| ECSDEA6t | Eicosadienoate (C20:2, n-6) transport | ecsdea6[e] <==> ecsdea6[i] | Transport | |
| ECSDEA6tis_ac | Eicosadienoate (C20:2, n-6) adipocyte transport | ecsdea6[i] <==> ecsdea6[a] | Transport | |
| ECSDEA9tis_ac | eicosadienoate (C20:2, n-9) adipocyte transport | ecsdea9[a] --> ecsdea9[i] | Transport | |
| ECSEA11tis_ac | eicosenoate (C20:1, n-11) adipocyte transport | ecsea11[a] --> ecsea11[i] | Transport | |
| ECSEA7tis_ac | eicosenoate (C20:1, n-7) adipocyte transport | ecsea7[a] --> ecsea7[i] | Transport | |
| ECSEA9tis_ac | eicosenoate (C20:1, n-9) adipocyte transport | ecsea9[a] --> ecsea9[i] | Transport | |
| ECSFAtis_mc | eicosanoate transport (n-C20:0) | ecsa[i] <==> ecsa[y] | Transport | |

TABLE 15-continued

Adipocyte-myocyte reactions

| Reaction Abbreviation | Reaction Name | Equation | Subsystem | Protein Classification |
|---|---|---|---|---|
| ECSPEA3t | Eicosapentaenoate (C20:5, n-3) transport | ecspea3[e] <==> ecspea3[i] | Transport | |
| ECSPEA3tis_ac | Eicosapentaenoate (C20:5, n-3) adipocyte transport | ecspea3[i] <==> ecspea3[a] | Transport | |
| ECSTEA3t | Eicosatrienoate (C20:3, n-3) transport | ecstea3[e] <==> ecstea3[i] | Transport | |
| ECSTEA3tis_ac | Eicosatrienoate (C20:3, n-3) adipocyte transport | ecstea3[i] <==> ecstea3[a] | Transport | |
| ECSTEA6t | Eicosatrienoate (C20:3, n-6) transport | ecstea6[e] <==> ecstea6[i] | Transport | |
| ECSTEA6tis_ac | Eicosatrienoate (C20:3, n-6) adipocyte transport | ecstea6[i] <==> ecstea6[a] | Transport | |
| ECSTTEA3t | Eicosatetraenoate (C20:4, n-3) transport | ecsttea3[e] <==> ecsttea3[i] | Transport | |
| ECSTTEA3tis_ac | Eicosatetraenoate (C20:4, n-3) adipocyte transport | ecsttea3[i] <==> ecsttea3[a] | Transport | |
| ECSTTEA6t | Eicosatetraenoate (C20:4, n-6) transport | ecsttea6[e] <==> ecsttea6[i] | Transport | |
| ECSTTEA6tis_ac | Eicosatetraenoate (C20:4, n-6) adipocyte transport | ecsttea6[i] <==> ecsttea6[a] | Transport | |
| GLYCt6is_ac | glycerol transport in/out via symporter, adipocyte | glyc[a] + h[a] <==> glyc[i] + h[i] | Transport | |
| HCO3t2 | HCO3 transport out via diffusion | hco3[e] <==> hco3[i] | Transport | |
| HDCAtis_ac | hexadecanoate (C16:0) adipocyte transport | hdca[a] --> hdca[i] | Transport | |
| HDCAtis_mc | hexadecanoate (C16:0) myocyte transport | hdca[i] --> hdca[y] | Transport | |
| HDCEA7tis_ac | hexadecenoate (C16:1, n-7) adipocyte transport | hdcea7[a] --> hdcea7[i] | Transport | |
| HDCEA9tis_ac | hexadecenoate (C16:1, n-9) adipocyte transport | hdcea9[a] --> hdcea9[i] | Transport | |
| HPDCEA8tis_ac | heptadecenoate (C17:1, n-8) adipocyte transport | hpdcea8[a] --> hpdcea8[i] | Transport | |
| ILEtis_ac | L-isoeucine transport in/out via proton symport, adipocyte | h[i] + ile-L[i] <==> h[a] + ile-L[a] | Transport | TC-2.A.26 |
| NAt | sodium transport in/out via proton antiport (one H+) | h[i] + na1[e] <==> h[e] + na1[i] | Transport | TC-2.A.36 |
| NAtis_mc | sodium transport in/out via the non-selective cation channel | na1[i] <==> na1[y] | Transport | TC-1.A.15 |
| NH4CLt_xo | ammonium chloride transport | cl[i] + nh4[i] <==> cl[e] + nh4[e] | Transport | |
| NH4tis_ac | ammonia transport via diffusion, adipocyte cytosolic | nh4[i] <==> nh4[a] | Transport | |
| OCDCAtis_ac | octadecanoate (C18:0) adipocyte transport | ocdca[a] --> ocdca[i] | Transport | |
| OCDCAtis_mc | octadecanoate (C18:0) myocyte transport | ocdca[i] --> ocdca[y] | Transport | |
| OCDCEA5tis_ac | octadecenoate (C18:1, n-5) adipocyte transport | ocdcea5[a] --> ocdcea5[i] | Transport | |
| OCDCEA7tis_ac | octadecenoate (C18:1, n-7) adipocyte transport | ocdcea7[a] --> ocdcea7[i] | Transport | |
| OCDCEA9tis_ac | octadecenoate (C18:1, n-9) adipocyte transport | ocdcea9[a] --> ocdcea9[i] | Transport | |
| OCDCEA9tis_mc | octadecenoate (C18:1, n-9) myocyte transport | ocdcea9[i] --> ocdcea9[y] | Transport | |
| OCDCTRA3t | Octadecatrienoate (C18:3, n-3) transport | ocdctra3[e] <==> ocdctra3[i] | Transport | |
| OCDCTRA3tis_ac | Octadecatrienoate (C18:3, n-3) adipocyte transport | ocdctra3[i] <==> ocdctra3[a] | Transport | |
| OCDCTRA6t | Octadecatrienoate (C18:3, n-6) transport | ocdctra6[e] <==> ocdctra6[i] | Transport | |
| OCDCTRA6tis_ac | Octadecatrienoate (C18:3, n-6) adipocyte transport | ocdctra6[i] <==> ocdctra6[a] | Transport | |
| OCDDEA6t | Octadecadienoate (C18:2, n-6) transport | ocddea6[e] <==> ocddea6[i] | Transport | |
| OCDDEA6tis_ac | Octadecadienoate (C18:2, n-6) adipocyte transport | ocddea6[i] <==> ocddea6[a] | Transport | |
| OCSTTEA6t | Ocosatetraenoate (C22:4, n-6) transport | ocsttea6[e] <==> ocsttea6[i] | Transport | |

TABLE 15-continued

Adipocyte-myocyte reactions

| Reaction Abbreviation | Reaction Name | Equation | Subsystem | Protein Classification |
|---|---|---|---|---|
| OCSTTEA6tis__ac | Ocosatetraenoate (C22:4, n-6) adipocyte transport | ocsttea6[i] <==> ocsttea6[a] | Transport | |
| PIt2__xo | phosphate transport in via proton symport | h[e] + pi[e] <==> h[i] + pi[i] | Transport | |
| PTDCAtis__ac | pentadecanoate (C15:0) adipocyte transport | ptdca[a] --> ptdca[i] | Transport | |
| PTDCAtis__mc | pentadecanoate (C15:0) myocyte transport | ptdca[i] --> ptdca[y] | Transport | |
| TTDCAtis__ac | tetradecanoate (C14:0) adipocyte transport | ttdca[a] --> ttdca[i] | Transport | |
| TTDCAtis__mc | tetradecanoate (C14:0) myocyte transport | ttdca[i] --> ttdcat[y] | Transport | |
| TTDCEA5tis__ac | tetradecenoate (C14:1, n-5) adipocyte transport | ttdcea5[a] --> ttdcea5[i] | Transport | |
| TTDCEA7tis__ac | tetradecenoate (C14:1, n-7) adipocyte transport | ttdcea7[a] --> ttdcea7[i] | Transport | |
| G6Pter__ac | glucose 6-phosphate adipocyte endoplasmic reticular transport via diffusion | g6p[a] <==> g6p[f] | Transport, Endoplasmic Reticular | |
| G6Pter__mc | glucose 6-phosphate myocyte endoplasmic reticular transport via diffusion | g6p[y] <==> g6p[u] | Transport, Endoplasmic Reticular | |
| GLCter__ac | glucose transport, endoplasmic reticulum | glc-D[a] <==> glc-D[f] | Transport, Endoplasmic Reticular | |
| GLCter__mc | glucose transport, endoplasmic reticulum | glc-D[y] <==> glc-D[u] | Transport, Endoplasmic Reticular | |
| CO2t__xo | CO2 transport via diffusion | co2[e] <==> co2[i] | Transport, Extracellular | |
| CO2tis__ac | CO2 adipocyte transport out via diffusion | co2[i] <==> co2[a] | Transport, Extracellular | |
| CO2tis__mc | CO2 myocyte transport out via diffusion | co2[i] <==> co2[y] | Transport, Extracellular | |
| CRTNt | creatinine transport | crtn[i] <==> crtn[e] | Transport, Extracellular | |
| GLCt1__xo | glucose transport (uniport: facilitated diffusion), intra-organism | glc-D[e] <==> glc-D[i] | Transport, Extracellular | |
| GLCt1is__ac | glucose transport into adipocyte (uniport: facilitated diffusion) | glc-D[i] <==> glc-D[a] | Transport, Extracellular | |
| GLCt1is__mc | glucose transport into myocyte (uniport: facilitated diffusion) | glc-D[i] <==> glc-D[y] | Transport, Extracellular | |
| H2Ot5__xo | H2O transport via diffusion | h2o[e] <==> h2o[i] | Transport, Extracellular | |
| H2Ot5is__ac | H2O transport into adipocyte via diffusion | h2o[i] <==> h2o[a] | Transport, Extracellular | |
| H2Ot5is__mc | H2O transport into myocyte via diffusion | h2o[i] <==> h2o[y] | Transport, Extracellular | |
| ILEt | L-isoeucine transport in/out via proton symport | h[e] + ile-L[e] <==> h[i] + ile-L[i] | Transport, Extracellular | TC-2.A.26 |
| L-LACt2__xo | L-lactate transport via proton symport | h[e] + lac-L[e] <==> h[i] + lac-L[i] | Transport, Extracellular | |
| L-LACt2is__mc | L-lactate reversible transport into myocyte via proton symport | h[i] + lac-L[i] <==> h[y] + lac-L[y] | Transport, Extracellular | |
| O2t__xo | O2 transport via diffusion | o2[e] <==> o2[i] | Transport, Extracellular | |
| O2tis__ac | O2 transport into adipocyte via diffusion | o2[i] <==> o2[a] | Transport, Extracellular | |
| O2tis__mc | O2 transport into myocyte via diffusion | o2[i] <==> o2[y] | Transport, Extracellular | |
| PIt2__xo [deleted Aug. 26, 2004 01:34:57 PM] | phosphate transport in via proton symport | h[e] + pi[e] --> h[i] + pi[i] | Transport, Extracellular | |
| PIt6is__ac | phosphate transport in/out of adipocyte via proton symporter | h[i] + pi[i] <==> h[a] + pi[a] | Transport, Extracellular | TC-2.A.20 |
| PIt6is__mc | phosphate transport in/out of myocyte via proton symporter | h[i] + pi[i] <==> h[y] + pi[y] | Transport, Extracellular | TC-2.A.20 |
| 3MOPtm__ac | 3-Methyl-2-oxopentanoate transport, diffusion, adipocyte mitochondrial | 3mop[a] <==> 3mop[b] | Transport, Mitochondrial | |

TABLE 15-continued

Adipocyte-myocyte reactions

| Reaction Abbreviation | Reaction Name | Equation | Subsystem | Protein Classification |
|---|---|---|---|---|
| ATP/ADPtm__ac | ATP/ADP transport, adipocyte mitochondrial | adp[a] + atp[b] <==> adp[b] + atp[a] | Transport, Mitochondrial | |
| ATP/ADPtm__mc | ATP/ADP transport, myocyte mitochondrial | adp[y] + atp[z] <==> adp[z] + atp[y] | Transport, Mitochondrial | |
| CITtam__ac | citrate transport, adipocyte mitochondrial | cit[a] + mal-L[b] <==> cit[b] + mal-L[a] | Transport, Mitochondrial | |
| CITtam__mc | citrate transport, myocyte mitochondrial | cit[y] + mal-L[z] <==> cit[z] + mal-L[y] | Transport, Mitochondrial | |
| CO2tm__ac | CO2 transport (diffusion), adipocyte mitochondrial | co2[a] <==> co2[b] | Transport, Mitochondrial | |
| CO2tm__mc | CO2 transport (diffusion), myocyte mitochondrial | co2[y] <==> co2[z] | Transport, Mitochondrial | |
| CRNCARtm__mc | carnitine-acetylcarnithine carrier, myocyte mitochondrial | acrn[y] + crn[z] --> acrn[z] + crn[y] | Transport, Mitochondrial | |
| CRNODETm__mc | carnitine 9-cis-octadecenoyltransferase II, myocyte | coa[z] + odecrn9[y] <==> crn[y] + odecoa9[z] | Transport, Mitochondrial | |
| CRNPTDTm__mc | carnitine pentadecanoyltransferase II, myocyte | coa[z] + pdcrn[y] <==> crn[y] + pdcoa[z] | Transport, Mitochondrial | |
| DHAP1tm__ac | dihydroxyacetone phosphate transport, adipocyte mitochondrial | dhap[a] <==> dhap[b] | Transport, Mitochondrial | |
| DHAP1tm__mc | dihydroxyacetone phosphate transport, myocyte mitochondrial | dhap[y] <==> dhap[z] | Transport, Mitochondrial | |
| GACm__ac | glutamate aspartate carrier, adipocyte cytosolic/mitochondrial | asp-L[b] + glu-L[a] + h[a] --> asp-L[a] + glu-L[b] + h[b] | Transport, Mitochondrial | |
| GACm__mc | glutamate aspartate carrier, myocyte cytosolic/mitochondrial | asp-L[z] + glu-L[y] + h[y] --> asp-L[y] + glu-L[z] + h[z] | Transport, Mitochondrial | |
| GL3Ptm__mc | glycerol-3-phosphate transport, myocyte mitochondrial | glyc3p[y] <==> glyc3p[z] | Transport, Mitochondrial | |
| GTPt3m__ac | GTP/GDP transporter, adipocyte mitochondrial | gdp[b] + gtp[a] + h[a] --> gdp[a] + gtp[b] + h[b] | Transport, Mitochondrial | |
| GTPt3m__mc | GTP/GDP transporter, myocyte mitochondrial | gdp[z] + gtp[y] + h[y] --> gdp[y] + gtp[z] + h[z] | Transport, Mitochondrial | |
| H2Otm__ac | H2O transport, adipocyte mitochondrial | h2o[a] <==> h2o[b] | Transport, Mitochondrial | |
| H2Otm__mc | H2O transport, myocyte mitochondrial | h2o[y] <==> h2o[z] | Transport, Mitochondrial | |
| MALAKGtm__ac | malate-alphaketoglutarate transporter, adipocyte mitochondria | akg[b] + mal-L[a] --> akg[a] + mal-L[b] | Transport, Mitochondrial | |
| MALAKGtm__mc | malate-alphaketoglutarate transporter, myocyte mitochondria | akg[z] + mal-L[y] --> akg[y] + mal-L[z] | Transport, Mitochondrial | |
| O2trm__ac | O2 transport into adipocyte mitochondria (diffusion) | o2[a] <==> o2[b] | Transport, Mitochondrial | |
| O2trm__mc | O2 transport into myocyte mitochondria (diffusion) | o2[y] <==> o2[z] | Transport, Mitochondrial | |
| Pltm__ac | phosphate transporter, adipocyte mitochondrial | h[a] + pi[a] <==> h[b] + pi[b] | Transport, Mitochondrial | |
| Pltm__mc | phosphate transporter, myocyte mitochondrial | h[y] + pi[y] <==> h[z] + pi[z] | Transport, Mitochondrial | |
| PPAtm__ac | propionate transport in/out via proton symport, adipocyte | h[a] + ppa[a] <==> h[b] + ppa[b] | Transport, Mitochondrial | TC-2.A.20 |
| PYRtm__ac | pyruvate transport, adipocyte mitochondrial | h[a] + pyr[a] <==> h[b] + pyr[b] | Transport, Mitochondrial | |
| PYRtm__mc | pyruvate transport, myocyte mitochondrial | h[y] + pyr[y] <==> h[z] + pyr[z] | Transport, Mitochondrial | |
| CRNCARtp__mc | carnitine-acetylcarnithine carrier, myocyte peroxixome | acrn[y] + crn[w] <==> acrn[w] + crn[y] | Transport, Peroxisomal | |

What is claimed is:

1. A computer readable medium or media having stored thereon computer-implemented instructions causing a processor to generate an output describing a physiological function of a first cell and a second cell that interact with one another via an intercellular space by performing steps comprising:

(a) providing a first stoichiometric matrix having rows and columns of elements that correspond to stoichiometric coefficients of a plurality of first reactions within a first naturally occurring biochemical network within the first cell, each of said reactions comprising a reactant identified as a substrate of the reaction and a reactant identified as a product of the reaction, wherein a stoichiometric coefficient of the first stoichiometric matrix relates said substrate and said product;

(b) providing a second stoichiometric matrix having rows and columns of elements that correspond to stoichiometric coefficients of a plurality of second reactions within a second naturally occurring biochemical network within the second cell, each of said reactions comprising a reactant identified as a substrate of the reaction and a reactant identified as a product of the reaction, wherein a stoichiometric coefficient of the second stoichiometric matrix relates said substrate and said product;

(c) providing a third stoichiometric matrix having rows and columns of elements that correspond to stoichiometric coefficients of a plurality of intercellular reactions relating to an interaction between said first and second cells via a third naturally occurring biochemical network within the intercellular space, each of said intercellular reactions comprising a reactant identified as a substrate of the reaction and a reactant identified as a product of the reaction, wherein a stoichiometric coefficient of the third stoichiometric matrix relates said substrate and said product;

(d) providing a constraint set for said plurality of reactions for said first, second, and third stoichiometric matrices, the constraint set specifying an upper or lower boundary of flux through each of the reactions described in the first, second, and third stoichiometric matrices;

(e) defining an objective function to be a linear combination of fluxes through the reactions described in the first, second, and third stoichiometric matrices that relates to a physiological function of said first and second cells;

(f) determining at least one flux distribution for said plurality of first, second, and intercellular reactions across said first cell, said second cell, and said intercellular space by (i) identifying a plurality of flux vectors that each satisfies the first, second, and third stoichiometric matrices and satisfies the constraint set and (ii) identifying at least one linear combination of the identified flux vectors that minimizes or maximizes the objective function, wherein said at least one flux distribution is predictive of a physiological function of said first and second cells; and (g) providing output to a user of said at least one flux distribution determined in step (f).

2. The computer readable medium or media of claim 1, further comprising instructions causing the processor to provide one or more fourth stoichiometric matrices, each fourth stoichiometric matrix having rows and columns of elements that correspond to stoichiometric coefficients of a plurality of reactions within one or more third cells within a multicellular organism, each of said reactions comprising a reactant identified as a substrate of the reaction and a reactant identified as a product of the reaction, wherein a stoichiometric coefficient of the one or more fourth stoichiometric matrices relates said substrate and said product.

3. The computer readable medium or media of claim 2, wherein said one or more fourth stoichiometric matrices comprises a plurality of stoichiometric matrices.

4. The computer readable medium or media of claim 3, wherein said plurality of stoichiometric matrices comprise a stoichiometric matrix for a plurality of different cells.

5. The computer readable medium or media of claim 2, wherein said plurality of stoichiometric matrices comprise a stoichiometric matrix for a plurality of different cell types.

6. The computer readable medium or media of claim 4 or 5, wherein said one or more third cells comprise at least 4 cells, 5 cells, 6 cells, 7 cells, 8 cells, 9 cells, 10 cells, 100cells, 1000 cells, 5000 cells, 10,000 cells or more.

7. The computer readable medium or media of claim 1, wherein said first and second cells comprise eukaryotic cells.

8. The computer readable medium or media of claim 1, wherein said first and second cells comprise prokaryotic cells.

9. The computer readable medium or media of claim 7, wherein said first and second eukaryotic cells comprise cells of the same tissue or organ.

10. The computer readable medium or media of claim 7, wherein said first and second eukaryotic cells comprise cells of different tissues or organs.

11. The computer readable medium or media of claim 1, wherein at least one of said reactions is annotated to indicate an associated gene.

12. The computer readable medium or media of claim 11, further comprising a gene database having information characterizing said associated gene.

13. The computer readable medium or media of claim 1, wherein at least one reaction within said plurality of first reactions, said plurality of second reactions, or said plurality of intercellular reactions is a regulated reaction.

14. The computer readable medium or media of claim 13, wherein said constraint set includes a variable constraint for said regulated reaction.

15. The computer readable medium or media of claim 1, wherein said plurality of intercellular reactions comprise one or more reactions performed in the hematopoietic system, urine, connective tissue, contractile system, lymphatic system, respiratory system or renal system.

16. The computer readable medium or media of claim 15, wherein said intercellular reactions comprise a reactant or reactions selected from the group consisting of a bicarbonate buffer system, an ammonia buffer system, a hormone, a signaling molecule, a vitamin, a mineral or a combination thereof.

17. The computer readable medium or media of claim 1, wherein said first or second cell is selected from a mammary gland cell, hepatocyte, white fat cell, brown fat cell, liver lipocyte, red skeletal muscle cell, white skeletal muscle cell, intermediate skeletal muscle cell, smooth muscle cell, red blood cell, adipocyte, monocyte, reticulocyte, fibroblast, neuronal cell epithelial cell or a cell set forth in Table 5.

18. The computer readable medium or media of claim 1, wherein said physiological function is selected from metabolite yield, ATP yield, biomass demand, growth, triacylglycerol storage, muscle contraction, milk secretion and oxygen transport capacity.

19. The computer readable medium or media of claim 1, wherein at least one reactant within said plurality of first reactions, said plurality of second reactions, or said plurality of intercellular reactions or at least one reaction within said plurality of first reactions, said plurality of second reactions, or said plurality of intercellular reactions is annotated with an assignment to a subsystem or compartment.

20. The computer readable medium or media of claim 19, wherein a first substrate or product in said plurality of reactions is assigned to a first compartment and a second substrate or product in said plurality of reactions is assigned to a second compartment.

21. The computer readable medium or media of claim 12, wherein a plurality of reactions is annotated to indicate a plurality of associated genes and wherein said gene database comprises information characterizing said plurality of associated genes.

22. A computer readable medium or media having stored thereon computer-implemented instructions causing a processor to generate an output describing a physiological function of a plurality of first cells and a plurality of second cells that interact with one another via an intercellular space by performing steps comprising:
  (a) providing a plurality of first stoichiometric matrices having rows and columns of elements that correspond to stoichiometric coefficients of a plurality of first reactions within a plurality of first naturally occurring biochemical networks within the plurality of first cells within a multicellular organism, each of said first reactions comprising a reactant identified as a substrate of the reaction and a reactant identified as a product of the reaction, wherein a stoichiometric coefficient of the stoichiometric matrix relates said substrate and said product;
  (b) providing a plurality of second stoichiometric matrices having rows and columns of elements that correspond to stoichiometric coefficients of a plurality of second reactions within a plurality of second naturally occurring biochemical networks within the plurality of second cells within said multicellular organism, each of said second reactions comprising a reactant identified as a substrate of the reaction and a reactant identified as a product of the reaction, wherein a stoichiometric coefficient of the stoichiometric matrix relates said substrate and said product;
  (c) providing a plurality of third stoichiometric matrices having rows and columns of elements that correspond to stoichiometric coefficients of a plurality of intercellular reactions relating to interactions between the plurality of first and second cells within said multicellular organism via a plurality of third naturally occurring biochemical networks within the intercellular space, each of said intercellular reactions comprising a reactant identified as a substrate of the reaction and a reactant identified as a product of the reaction, wherein a stoichiometric coefficient of the stoichiometric matrix relates said substrate and said product;
  (d) providing a constraint set for said plurality of reactions for said pluralities of first, second and third stoichiometric matrices, the constraint set specifying an upper or lower boundary of flux through each of the reactions described in the pluralities of first, second, and third stoichiometric matrices;
  (e) defining an objective function to be a linear combination of fluxes through the reactions described in the pluralities of first, second, and third stoichiometric matrices that relates to a physiological function of said multicellular organism;
  (f) determining at least one flux distribution for said pluralities of first, second, and intercellular reactions across said plurality of first cells, said plurality of second cells and said plurality of intercellular spaces by (i) identifying a plurality of flux vectors that each satisfies the pluralities of first, second, and third stoichiometric matrices and satisfies the constraint set and (ii) identifying at least one linear combination of the identified flux vectors within said multicellular organism that minimizes or maximizes the objective function, wherein said at least one flux distribution is predictive of a physiological function of said multicellular organism; and
  (g) providing output to a user of said at least one flux distribution determined in step (f).

23. The computer readable medium or media of claim 22, further comprising a plurality of fourth stoichiometric matrices, each of said plurality of fourth stoichiometric matrices having rows and columns of elements that correspond to stoichiometric coefficients of a plurality of reactions within a plurality of third cells within a multicellular organism, each of said reactions comprising a reactant identified as a substrate of the reaction and a reactant identified as a product of the reaction, wherein a stoichiometric coefficient of the plurality of fourth stoichiometric matrices relates said substrate and said product.

24. The computer readable medium or media of claim 23, wherein said plurality of first through fourth stoichiometric matrices comprise stoichiometric matrices for a plurality of different cells.

25. The computer readable medium or media of claim 23, wherein said plurality of first through fourth stoichiometric matrices comprise stoichiometric matrices for a plurality of different cell types.

26. The computer readable medium or media of claim 24 or 25, wherein said one or more third cells comprise at least 4 cells, 5 cells, 6 cells, 7 cells, 8 cells, 9 cells, 10 cells, 100 cells, 1000 cells, 5000 cells, 10,000 cells or more.

27. A computer implemented method for predicting a physiological function of a first cell and second cell that interact with one another via an intercellular space in a multicellular organism, comprising:
  (a) providing on a computer a first stoichiometric matrix having rows and columns of elements that correspond to stoichiometric coefficients of a plurality of first reactions within a first naturally occurring biochemical network within the first cell, each of said reactions comprising a reactant identified as a substrate of the reaction and a reactant identified as a product of the reaction, wherein a stoichiometric coefficient of the first stoichiometric matrix relates said substrate and said product;
  (b) providing on a computer a second stoichiometric matrix having rows and columns of elements that correspond to stoichiometric coefficients of a plurality of second reactions within a second naturally occurring biochemical network within the second cell, each of said reactions comprising a reactant identified as a substrate of the reaction and a reactant identified as a product of the reaction, wherein a stoichiometric coefficient of the second stoichiometric matrix relates said substrate and said product;
  (c) providing on a computer a third stoichiometric matrix having rows and columns of elements that correspond to stoichiometric coefficients of a plurality of intercellular reactions relating to an interaction between said first and second cells via a third naturally occurring biochemical network within the intercellular space, each of said intercellular reactions comprising a reactant identified as a substrate of the reaction and a reactant identified as a product of the reaction, wherein a stoichiometric coefficient of the third stoichiometric matrix relates said substrate and said product;

(d) providing a constraint set for said plurality of reactions for said first, second and third stoichiometric matrices, the constraint set specifying an upper or lower boundary of flux through each of the reactions described in the first, second, and third stoichiometric matrices;

(e) defining an objective function to be a linear combination of fluxes through the reactions described in the first, second, and third stoichiometric matrices that relates to a physiological function of said first and second cells;

(f) determining at least one flux distribution for said plurality of first, second, and intercellular reactions across said first cell, said second cell and said intercellular space by (i) identifying a plurality of flux vectors that each satisfies the first, second, and third stoichiometric matrices and satisfies the constraint set and (ii) identifying at least one linear combination of the identified flux vectors that minimizes or maximizes the objective function, wherein said at least one flux distribution is predictive of a physiological function of said first and second cells; and (g) providing output to a user of said at least one flux distribution determined in step (f).

28. The method of claim 27, further comprising one or more fourth stoichiometric matrices, each fourth stoichiometric matrix having rows and columns of elements that correspond to stoichiometric coefficients of a plurality of reactions within one or more third cells within a multicellular organism, each of said reactions comprising a reactant identified as a substrate of the reaction and a reactant identified as a product of the reaction, wherein a stoichiometric coefficient of the one or more fourth stoichiometric matrices relates said substrate and said product.

29. The method of claim 28, wherein said one or more fourth stoichiometric matrices comprises a plurality of stoichiometric matrices.

30. The method of claim 29, wherein said plurality of stoichiometric matrices comprise a stoichiometric matrix for a plurality of different cells.

31. The method of claim 29, wherein said plurality of stoichiometric matrices comprise a stoichiometric matrix for a plurality of different cell types.

32. The method of claim 30 or 31, wherein said one or more third cells comprise at least 4 cells, 5 cells, 6 cells, 7 cells, 8 cells, 9 cells, 10 cells, 100 cells, 1000 cells, 5000 cells, 10,000 cells or more.

33. The method of claim 27, wherein said first and second cells comprise eukaryotic cells.

34. The method of claim 27, wherein said first and second cells comprise prokaryotic cells.

35. The method of claim 33, wherein said first and second eukaryotic cells comprise cells of the same tissue or organ.

36. The method of claim 33, wherein said first and second eukaryotic cells comprise cells of different tissues or organs.

37. The method of claim 27, wherein at least one of said reactions is annotated to indicate an associated gene.

38. The method of claim 27, further comprising a gene database having information characterizing said associated gene.

39. The method of claim 27, wherein at least one of said reactions is a regulated reaction.

40. The method of claim 39, wherein said constraint set includes a variable constraint for said regulated reaction.

41. The method of claim 27, wherein said at least one intercellular reaction comprises one or more reactions performed in the hematopoietic system, urine, connective tissue, contractile system, lymphatic system, respiratory system or renal system.

42. The method of claim 41, wherein said intercellular reactions comprise a reactant or reactions selected from the group consisting of a bicarbonate buffer system, an ammonia buffer system, a hormone, a signaling molecule, a vitamin, a mineral or a combination thereof.

43. The method of claim 27, wherein said first or second cell is selected from a mammary gland cell, hepatocyte, white fat cell, brown fat cell, liver lipocyte, red skeletal muscle cell, white skeletal muscle cell, intermediate skeletal muscle cell, smooth muscle cell, red blood cell, adipocyte, monocyte, reticulocyte, fibroblast, neuronal cell epithelial cell or a cell set forth in Table 5.

44. The method of claim 27, wherein said physiological function is selected from metabolite yield, ATP yield, biomass demand, growth, triacylglycerol storage, muscle contraction, milk secretion and oxygen transport capacity.

45. The method of claim 27, wherein at least one reactant within said plurality of first reactions, said plurality of second reactions, or said plurality of intercellular reactions or at least one reaction within said plurality of first reactions, said plurality of second reactions, or said plurality of intercellular reactions is annotated with an assignment to a subsystem or compartment.

46. The method of claim 45, wherein a first substrate or product in said plurality of reactions is assigned to a first compartment and a second substrate or product in said plurality of reactions is assigned to a second compartment.

47. The method of claim 38, wherein a plurality of reactions is annotated to indicate a plurality of associated genes and wherein said gene database comprises information characterizing said plurality of associated genes.

* * * * *